US012048281B2

(12) United States Patent
Mankin et al.

(10) Patent No.: US 12,048,281 B2
(45) **Date of Patent: *Jul. 30, 2024**

(54) METHOD FOR TREATING POST-EMERGENT RICE

(71) Applicant: BASF SE, Ludwigshafen (DE)

(72) Inventors: Scots Llewellyn Mankin, Raleigh, NC (US); Leon Neuteboom, Morrisville, NC (US); Sherry R. Whitt, Raleigh, NC (US); Ulrich Schoefl, Apex, NC (US); Haiping Hong, Cary, NC (US); Allan Wenck, Durham, NC (US); Dale R. Carlson, Apex, NC (US); John A. McElver, Durham, NC (US); Jill M. Stevenson-Paulik, Cary, NC (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/111,058

(22) Filed: Dec. 3, 2020

(65) Prior Publication Data

US 2021/0153448 A1 May 27, 2021
US 2023/0404009 A9 Dec. 21, 2023

Related U.S. Application Data

(60) Division of application No. 15/395,832, filed on Dec. 30, 2016, now Pat. No. 11,096,345, which is a continuation-in-part of application No. 15/156,671, filed on May 17, 2016, and a continuation-in-part of application No. 14/357,691, filed as application No. PCT/US2012/064831 on Nov. 13, 2012, now Pat. No. 9,540,627, and a continuation of application No. 13/393,780, filed as application No. PCT/US2010/047571 on Sep. 1, 2010, now abandoned.

(60) Provisional application No. 61/559,618, filed on Nov. 14, 2011, provisional application No. 61/365,298, filed on Jul. 16, 2010, provisional application No. 61/238,906, filed on Sep. 1, 2009.

(51) Int. Cl.

| | |
|---|---|
| ***C12N 15/82*** | (2006.01) |
| ***A01H 5/10*** | (2018.01) |
| ***A01H 6/46*** | (2018.01) |
| ***A01N 39/02*** | (2006.01) |
| ***A01N 43/40*** | (2006.01) |
| *A01N 43/60* | (2006.01) |

(52) U.S. Cl.
CPC ............. *A01H 6/4636* (2018.05); *A01H 5/10* (2013.01); *A01N 39/02* (2013.01); *A01N 43/40* (2013.01); *C12N 15/8274* (2013.01); *A01N 43/60* (2013.01)

(58) Field of Classification Search
CPC .................................................. C12N 15/8274
See application file for complete search history.

(56) References Cited

U.S. PATENT DOCUMENTS

| | | | | |
|---|---|---|---|---|
| 5,162,602 | A | 11/1992 | Somers et al. | |
| 5,290,696 | A | 3/1994 | Somers et al. | |
| 5,801,233 | A | 9/1998 | Haselkorn et al. | |
| 5,910,626 | A | 6/1999 | Haselkorn et al. | |
| 5,925,805 | A | 7/1999 | Ohlrogge et al. | |
| 6,027,945 | A | 2/2000 | Smith et al. | |
| 6,069,298 | A | 5/2000 | Gengenbach et al. | |
| 6,281,168 | B1 | 8/2001 | Shaner et al. | |
| 6,306,636 | B1 | 10/2001 | Haselkorn et al. | |
| 6,368,800 | B1 | 4/2002 | Smith et al. | |
| 2003/0236208 | A1 | 12/2003 | Kmiec et al. | |
| 2004/0123343 | A1 | 6/2004 | La Rosa et al. | |
| 2006/0039943 | A1 | 2/2006 | Applebaum et al. | |
| 2007/0074303 | A1 | 3/2007 | McCutchen et al. | |
| 2008/0234130 | A1 | 9/2008 | McCutchen et al. | |
| 2008/0256668 | A1 | 10/2008 | Beetham et al. | |
| 2009/0093366 | A1* | 4/2009 | Wright ............... | C12N 15/8209 800/300 |
| 2010/0048405 | A1 | 2/2010 | Raymer et al. | |
| 2011/0214196 | A1 | 9/2011 | Raymer et al. | |
| 2013/0023416 | A1 | 1/2013 | Hinga et al. | |
| 2013/0111618 | A1 | 5/2013 | Mankin et al. | |

(Continued)

FOREIGN PATENT DOCUMENTS

| | | |
|---|---|---|
| CN | 102083303 A | 6/2011 |
| CN | 102905516 A | 1/2013 |

(Continued)

OTHER PUBLICATIONS

Maneechote, Chanya, S. Jamjod, and B. Rerkasem. "Controlling invasive wild rice with ACCase-inhibiting herbicides." Proceedings of the 4th International Crop Science Congress, Brisbane, Australia. 2004. (Year: 2004).*

Anyszka, Zbigniew, and A. Dobrzanski. "The response of snap bean and barnyard grass [*Echinochloa crus-galli*] on quizalofop-P-tefuryl." Vegetable Crops Research Bulletin 51 (1999): 95-102. (Year: 1999).*

Till, Bradley J., et al. "Discovery of chemically induced mutations in rice by TILLING." BMC plant biology 7.1 (2007): 19. (Year: 2007).*

(Continued)

*Primary Examiner* — Weihua Fan
(74) *Attorney, Agent, or Firm* — Lowenstein Sandler LLP

(57) ABSTRACT

The present disclosure provides a method for treating rice. The method comprises the steps of: providing a domestic rice crop plant and at least one ACCase-inhibiting aryloxyphenoxypropanoate herbicide selected from the group consisting of quizalofop or an ester thereof, haloxyfop, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence; thereby creating a treated rice plant; and growing the resulting treated rice plant.

20 Claims, 46 Drawing Sheets

Specification includes a Sequence Listing.

(56) References Cited

U.S. PATENT DOCUMENTS

| | | | | |
|---|---|---|---|---|
| 2014/0045686 | A1 | 2/2014 | Mankin et al. | |
| 2015/0038331 | A1* | 2/2015 | Hinga ............ | C12Y 604/01002 800/300 |
| 2016/0108423 | A1 | 4/2016 | Mankin et al. | |
| 2016/0244780 | A1 | 8/2016 | Mankin et al. | |
| 2016/0251677 | A1 | 9/2016 | Mankin et al. | |
| 2017/0275645 | A1 | 9/2017 | Mankin et al. | |

FOREIGN PATENT DOCUMENTS

| | | | |
|---|---|---|---|
| EP | 0374753 | A2 | 6/1990 |
| EP | 0374853 | A1 | 6/1990 |
| EP | 0427529 | A1 | 5/1991 |
| EP | 0451878 | A1 | 10/1991 |
| EP | 2473024 | A2 | 7/2012 |
| JP | 2013-526833 | | 7/2012 |
| JP | 2013526833 | A | 6/2013 |
| WO | 1993/007278 | | 4/1993 |
| WO | 93007278 | A1 | 4/1993 |
| WO | 9534656 | A1 | 12/1995 |
| WO | 9854330 | A1 | 12/1998 |
| WO | 0192512 | A2 | 12/2001 |
| WO | 02015701 | A2 | 2/2002 |
| WO | 03018810 | A2 | 3/2003 |
| WO | 03052073 | A2 | 6/2003 |
| WO | 2005123946 | A1 | 12/2005 |
| WO | 2008089061 | A2 | 7/2008 |
| WO | 2009056333 | A2 | 5/2009 |
| WO | 2011028832 | A2 | 3/2011 |
| WO | 2011028836 | A2 | 3/2011 |

OTHER PUBLICATIONS

Baldwin, John L., et al. "Effect of growth stage and application site on tolerance of rice (*Oryza sativa*) to haloxyfop." Weed technology 10.2 (1996): 268-272. (Year: 1996).*

Noldin, JosÉ A., et al. "Red rice (*Oryza sativa*) biology. II. Ecotype sensitivity to herbicides." Weed Technology (1999): 19-24. (Year: 1999).*

Joachimiak et al., "Wheat cytosolic acetyl-CoA carboxylase complements an ACC1 null mutation in yeast," Proc. Natl. Acad. Sci. USA, vol. 94, pp. 9990-9995, Sep. 1997.

Liu et al., "Single-site mutations in the carboxyltransferase domain of plastid acetyl-CoA carboxylase confer resistance to grass-specific herbicides," PNAS, Feb. 27, 2007, vol. 104 no. 9, pp. 3627-3632.

Marshall et at, "Allelic mutations in acetyl-coenzyme A carboxylase confer herbicide tolerance in maize," Theor. Appl. Genet, 1992, Voi. 83, pp. 435-442.

Neve et at, "High survival frequencies at low herbicide use rates in populations of Lolium rigidum result in rapid evolution of herbicide resistance," Heredity, 2005, vol. 95, pp. 485-492.

Nikolau et at, "Plant biotin-containing carboxylases," Archives of Biochemistry and Biophysics, vol. 414, 2003, pp. 211-222.

Nikolskaya et al,, "Herbicide sensitivity determinant of wheat plastid acetyl-CoA carboxylase is located in a 400-amino acid fragment of the carboxyltransferase domain," PNAS, Dec. 7, 1999, vol. 96 No. 25, pp. 14647-14651.

Parker et al., "Selection and Characterization of Sethoxydim-Tolerant Maize Tissue Cultures," Plant Physiol., 1990, vol. 92, pp. 1220-1225.

Podkowlnski et al., "Expression of Cytosolic and Plastid Acetyl-Coenzyme A Carboxylase Genes in Young Wheat Plants," Plant Physiology, Feb. 2003, vol. 131, pp. 763-772.

Shivrain et al., "Gene flow between Clearfield(TM) rice and red rice," Crop Protection, vol. 26, 2007, pp. 349-356.

Tal et al., "Molecular characterization and inheritance of resistance to ACCase-inhibiting herbicides in Lolium rigidum," Pest Manag. Sci., Mar. 15, 2004, vol. 60, pp. 1013-1018.

Yu et al., "Diversity of Acetyl-Coenzyme A Carboxylase Mutations in Resistant Lolium Populations: Evaluation Using Clethodim," Plant Physiology, Oct. 2007, vol. 145, pp. 547-558.

Zagnitko et al., "An isoleucine/leucine residue in the carboxyltransferase domain of acetyl-CoA carboxylase is critical for interaction with aryloxyphenoxypropionate and cyclohexanedione inhibitors," PNAS, Jun. 5, 2001, vol. 98 No. 12, pp. 6617-6622.

Roesler et al., "Targeting of the *Arabidopsis* Homomeric Acetyl-Coenzyme A Carboxylase to Plastids of Rapeseeds," Plant Physiol., 1997, vol. 113, pp. 75-81.

Zhu et al., "Computational Simulations of the Interactions between Acetyl-Coenzye-A Carboxylase and Clodinafop: Resistance Mechanism Due to Active and Nonactive Site Mutations," J. Chem. Inf. Model., 2009, vol. 29, pp. 1936-1943.

International Preliminary Report on Patentability, International Application No. PCT/US2010/047571, dated Mar. 6, 2012.

Liu et al., Proc. Natl. Acad. Sol. (2007) 104:3627-3632.

Maneechote, Chanya, S. Jamjod, and B. Rerkasem. "Controlling invasive wild rice with ACCase-inhibiting herbicides." Proceedings of the 4th International Crop Science Congress, Brisbane, Australia. 2004. (Year: 2004).

Griffin, James L., and John B. Baker. "Tolerance of rice (*Oryza sativa*) cultivars to fenoxaprop, sethoxydim, and haloxyfop." Weed Science 38.6 (1990): 528-531. (Year: 1990).

Okuzaki, A., and K. Toriyama. "Chimeric RNA/DNA oligonucleotide-directed gene targeting in rice." Plant cell reports 22.7 (2004): 509-512. (Year: 2004).

Delye, Christophe, Annick Matejicek, and Severine Michel. "Cross-resistance patterns to ACCase-inhibiting herbicides conferred by mutant ACCase isoforms in *Alopecurus myosuroides* Huds.(black-grass), re-examined at the recommended herbicide field rate." Pest management science 64.11 (2008): 1179-1186. (Year: 2008).

O'Sullivan, P. A., WH Vanden Born, and H. A. Friesen. "Influence of herbicides for broad-leaved weeds and adjuvants with dichlorfop methyl on wild oat control." Canadian Journal of Plant Science 57.1 (1977): 117-125. (Year: 1977).

Maneechote, Chanya, et al. "Resistance to ACCase-inhibiting herbicides in sprangletop (*Leptochloa chinensis*)." Weed science 53.3 (2005): 290-295. (Year: 2005).

"Extended European Search Report issued in European Application No. 10814446.0", dated Jun. 6, 2013, 14 pages.

"Extended European Search Report issued in European Application No. 16202167.9", dated Mar. 16, 2017, 9 pages.

"International Search Report issued in International Application No. PCT/US2010/047571", dated May 18, 2011,4 pages.

Ashley, Jr., James Elton, "Evaluation of Weed Control and Crop Tolerance With Postemergence Herbicides in Sethoxydim-Tolerant Corn", Thesis submitted to Virginia Polytechnic Institute, Apr. 27, 1998, 4 pages.

Balgheim, et al., "Resistance to ACCase inhibiting herbicides is due to target-site modification in a biotype of Alopecurus myosuroides Huds", The BCPC International Congress-Crop Science & Technology, 2005, pp. 155-162.

Buell, C. Robin, "Poaceae Genomes: Going from Unattainable to Becoming a Model Glade for Comparative Plant Genomics", Plant Physiology, vol. 149, Issue 1, Jan. 2009, pp. 111-116.

Callan, "In Vitro Selection for and Biochemical Analysis of Sethoxydim-Tolerant winter Wheat (*Triticum aestivum* L. )", In partial fulfillment of the requirements for the Degree of Doctor of Philosophy, Colorado State University, Fort Collins, Colorado, Fall, 1996, 30 pages.

Carlson, et al., "Tissue Culture Selection System in Poa Pratensis", NCWSS Proceedings, vol. 45, 1990, Abstract, 1 page.

Christoffers, et al., "An Isoleucine to Leucine Mutation in Acetyl-CoA Carboxylase Confers Herbicide Resistance In Wild Oat", Genome, National Research Council Canada, vol. 45, Issue 6, Jan. 1, 2002, pp. 1049-1056.

Delye, et al., "An isoleucine-leucine substitution in chloroplastic acetyl-CoA carboxylase from green foxtail (*Setaria viridis* L. Beauv.) is responsible for resistance to the cyclohexanedione herbicide sethoxydim", Planta. vol. 214, Issue 3, Jan. 2002, pp. 421-427.

Delye, et al., "Molecular Bases for Sensitivity to Acetyl-Coenzyme A Carboxylase Inhibitors in Black-Grass", Plant Physiology, vol. 137, Mar. 2005, pp. 794-806.

Delye, et al., "PCR-based detection of resistance to acetyl-CoA Carboxylase-inhibitor herbicides in black-grass (*Alopecurus myosuroides*

(56) References Cited

OTHER PUBLICATIONS

Huds) and ryegrass (*Lolium rigidum* Gaud)", Pest Management Science, vol. 58, Issue 5, May 2002, pp. 474-478.
Delye, et al., "SNP markers for black-grass (*Alopecurus myosuroides* Huds) genotypes resistant to acetyl CoA-carboxylase inhibiting herbicides", Theoretical and Applied Genetics, vol. 104, Issue 6-7, May 2002, pp. 1114-1120.
Delye, et al., "Universal' primers for PCR-sequencing of grass chloroplastic acetyl-CoA carboxylase domains involved in resistance to herbicides", Weed Research, vol. 45, 2005, pp. 323-330.
Heckart, Douglas Lee, "Obtaining Sethoxydim Resistance in Seashore Paspalum (*Paspalum vaginatum*)", A Thesis Submitted to the Graduate Faculty of the University of Georgia in Partial Fulfillment of the Requirements for the Degree, Athens, GA, 2009, 51 pages.
Herbert, et al., "Susceptibilities of Different Test Systems from Maize (*Zea mays*), Poa annua, and Festuca rubrato Herbicides that Inhibit the Enzyme Acetyl-Coenzyme A Carboxylase", Pesticide Biochemistry and Physiology, vol. 55, Issue 2, Jun. 1996, pp. 129-139.
Hiei, et al., "Agrobacterium-mediated Transformation of Rice Using Immature Embryos or Calli Induced from Mature Seed", Nature Protocols, vol. 3, No. 5, Apr. 17, 2008, pp. 824-834.
Jain, S.M., "Tissue culture-derived variation in crop improvement", Euphytica, vol. 118, Issue 2, Mar. 2001, pp. 153-166.
Joachimiak, et al., "Wheat cytosolic acetyl-CoA carboxylase complements an ACC1 null mutation in yeast", Proceeding of the National Academy Science, Plant Biology, vol. 94, Sep. 1997, pp. 9990-9995.
JP Ruiz-Santaella, et al., "Basis of selectivity of cyhalofop-butyl in *Oryza sativa* L.", Planta, vol. 223, Issue 2, Jan. 2006, pp. 191-199.
JP Ruiz-Santaella, et al., "Detection of a new mutation of glycine to serine in the ACCase of a Resistant Biotype of Phalaris Paradoxa", Weed Science Sec. Am. Abstr. 46:93, 2006 (New York: WSSA 2006 Annual Meeting, Abstract, 1 page.
JP Ruiz-Santaella, et al., "Is it possible to detect *Echinochloa* spp. tolerance to ACCase- inhibiting herbicides using a simple quick tolerance test?", Commun. Agric. Appl. Biol. ScL, vol. 68, (4 Pt A), 2003, pp. 331-334.
Kellogg, Elizabeth A., "The Evolutionary History of Ehrhartoideae, Oryzeae, and *Oryza*", Rice, vol. 2, Issue 1, Mar. 2009, pp. 1-14.
Liu, et al., "Single-site mutations in the carboxyltransferase domain of plastid acetyl-CoA carboxylase confer resistance to grass-specific herbicides", PNAS, vol. 104, Issue 9, Feb. 2007, pp. 3627-3632.
Madoka, et al., "Chloroplast Transformation with Modified accD Operon Increases Acetyl-CoA Carboxylase and Causes Extension of Leaf Longevity and Increase in Seed Yield in Tobacco", Plant and Cell Physiology, vol. 43, Issue 12, Dec. 15, 2002, pp. 1518-1525.
Marshall, et al., "Allelic mutations in acetyl-coenzyme A carboxylase confer herbicide tolerance in maize", Theoretical and Applied Genetics, vol. 83, Issue 4, Feb. 1992, pp. 435-442.
Mathews, et al., "Phylogenetic Structure in the Grass Family (Poaceae): Evidence From the Nuclear Gene Phytochrome B", American Journal of Botany 87(1), 2000, pp. 96-107.
Menchari, et al., "Fitness costs associated with three mutant acetyl-coenzyme A carboxylase alleles endowing herbicide resistance in black-grass *Alopecurus myosuroides*", Journal of Applied Ecology, vol. 45, Issue 3, Jun. 2008, pp. 939-947.
Neve, et al., "High survival frequencies at low herbicide use rates in populations of Lolium rigidum result in rapid evolution of herbicide resistance", Heredity, vol. 95, Jul. 2005, pp. 485-492.
Nikolau, et al., "Plant biotin-containing carboxylases", Archives of Biochemistry and Biophysics, vol. 414, Issue 2, Jun. 15, 2003, pp. 211-222.
Nikolskaya, et al., "Herbicide sensitivity determinant of wheat plastid acetyl-CoA carboxylase is located in a 400-amino acid fragment of the carboxyltransferase domain", PNAS, vol. 96 No. 25, Dec. 7, 1999, pp. 14647-14651.
Parker, et al., "Dominant mutations causing alterations in acetyl-coenzyme A carboxylase confer tolerance to cyclohexanedione and aryloxyphenoxypropionate herbicides in maize", Proceedings of the National Academy of Science, vol. 87, Sep. 1990, pp. 7175-7179.
Parker, et al., "Selection and Characterization of Sethoxydim-Tolerant Maize Tissue Cultures", Plant Physiology, vol. 92, 1990, pp. 1220-1225.
Podkowinski, et al., "Expression of Cytosolic and Plastid Acetyl-Coenzyme A Carboxylase Genes in Young Wheat Plants", Plant Physiology, vol. 131, Feb. 2003, pp. 763-772.
Rafael De Prado, et al., "Resistance to ACCase inhibitor herbicides in a green foxtail (*Setaria viridis*) biotype in Europe", Weed Science, vol. 52, No. 4, Jul.-Aug. 2004, pp. 506-512.
Roesler, et al., "Targeting of the *Arabidopsis* Homomeric Acetyl-Coenzyme A Carboxylase to Plastids of Rapeseeds", Plant Physiology, vol. 113, Issue 1, Jan. 1997, pp. 75-81.
"Genotyping Sethoxydim Resistant Maize: A method for the detection of the ACC1-11781 (Am)L allele in *Zea mays*", BASF internal manual.
Buell, C. Robin, "Poaceae Genomes: Going from Unattainable to Becoming a Model Glade for Comparative Plant Genomics", Plant Physiology, vol. 149, Issue 1, Jan. 2009, pp. HI-116.
Christoffers, et al., "An Isoleucine to Leucine Mutation in Acetyl-CoA Carboxylas Confers Herbicide Resistance In Wild Oat", Genome, National Research Council Canada, vol. 45, Issue 6, Jan. 1, 2002, pp. 1049-1056.
Herbert, et al., "Susceptibilities of Different Test Systems from Maize (*Zea mays*), Pea annua, and Festuca rubrato Herbicides that Inhibit the Enzyme Acetyl-Coenzyme A Carboxylase", Pesticide Biochemistry and Physiology, vol. 55, Issue 2, Jun. 1996, pp. 129-139.
Hiei, et al., "Agrobacterium-mediated Transformation of Rice Using Immature Embryos or Call Induced from Mature Seed", Nature Protocols, vol. 3, No. 5, Apr. 17, 2008, pp. 824-834.
Maneechote et al., "Controlling invasive wild rice with ACCase-inhibiting herbicides." Proceedings of the 4th International Crop Science Congress, Brisbane, Australia. 2004. (Year: 2004).
Xiang, et al., "A different mechanism for the inhibition of the carboxyltransferase domain of acetyl-coenzyme A carboxylase by tepraloxydim", PNAS, vol. 106, No. 49, December 8. 2009, pp. 20723-20727.
Ferrero et al, (1999) Crop Protection 18:245-251.
Beversdorf et al., Weed Science, 1987, 35: 9-11.
BoA Decision T 0210/02.
BoA Decision T 0488/16.
BoA Decision T 0939/92.
Bradley et al., Weed Science, 2001, 49: 477-484.
Datta, Biotech and Gen. Engineering Reviews, 2002, 19:338-354.
Laha et al., Rice Genetics Newsletter 20, 2003: 88-91.
Mulwa et al., African Journal of Biotechnology, 2006, 5(5): 396-404.
Notice from the EPO concerning the staying proceedings due to referral G 2/21, Official Journal EPO, 2021, A87.
Ruiz-Santaella et al., WSSA Abstract, 2006.
USDA Determination of Nonregulated Status for Glufosinate Tolerant Rice (Liberty Link@Rice), dated Apr. 27, 1999.
Vidal et al., Plant Weed, 2006, 24(3); English Abstract.
Yu, et al., "The Genomes of *Oryza sativa*: A History of Duplications", PLoS Biology, vol. 3, Issue 2, e38, Feb. 2005, pp. 0266-0281.
Zagnitko, et al., "An isoleucine/leucine residue in the carboxyltransferase domain of acetyl-CoA carboxylase is critical for interaction with aryloxyphenoxypropionate and cyclohexanedione inhibitors", PNAS, vol. 98, No. 12, Jun. 5, 2001, pp. 6617-6622.
Zhang, et al., "The molecular bases for resistance to acetyl co-enzyme A carboxylase (ACCase) inhibiting herbicides in two target-based resistant biotypes of annual ryegrass (*Lolium rigidum*)", Planta., vol. 223, Issue 3, Feb. 2006, pp. 550-557.
Zhu, et al., "Computational Simulations of the Interactions between Acetyl-Coenzyme-A Carboxylase and Clodinafop: Resistance Mechanism Due to Active and Non active Site Mutations", Journal of Chemical Information and Modeling, vol. 49, No. 8, Jul. 13, 2009, pp. 1936-1943.
Georges, F. and Ray H., GM Crops and Food 2017, 8:1-12, pp. 2-6.

(56) References Cited

OTHER PUBLICATIONS

Custers, R., Emerging Topics in Life Sciences (2017), Portland Press, "The regulatory status of gene-edited agricultural products in the EU and beyond" pp. 1-9.
Sprink, T. et al., "Regulatory hurdles for genome editing: process- vs. product-based approaches in different regulatory contexts." Plant Cell Rep 2016, 35: 1493-1506.
EU Directive 2001/18/EC, Official Journal of the European Communities (Apr. 17, 2001 ):L106/1-38.
M. Lusser & E. Rodriguez-Cerezo "Comparative Regulatory Approaches for New Plant Breeding Techniques," presented Jun. 26, 2012 at the 16th ICABR Conference, Ravello, Italy.
M. Lusser et al., "Deployment of new biotechnologies in plant breeding," Nature Biotechnology 30(3):231-239 (2012); Abstract.
BIO Product Launch Stewardship Policy of May 21, 2007.
CropLife International (CLI) Product Launch Stewardship Guidance of 2008.
Excellence Through Stewardship (ETS) Guide for Product Launch of Biotechnology-Derived Plant Products of 2009; 13 pages.
Diclofop Methyl herbicide directions for use, Cheminova Australia Pty Ltd, pp. 1-4.
Aramo, Tepraloxydim herbicide directions for use, BASF (2015), pp. 1-8.
BASF, "Segment Herbicide" pp. 1-2, 2008. APN 08-14-002-0051.
Gressel, et al., "A strategy to provide long-term control of weedy rice while mitigating herbicide resistance transgene flow, and its potential use for other crops with related weeds," Wiley Interscience, Apr. 14, 2009. DOI 10.1002/ps. 1754 pp. 723-731.
Johnson, et al., "Managing the potential for developing herbicide-resistant weeds in herbicide-tolerant rice" Weed Science, pp. 551-557.
Valverde, et al., "Status and Management of Grass-Weed Herbicide Resistance in Latin America," Weed Technology 2007 21:310-323.
Zhu, et al., "Engineering herbicide-resistant maize using chimeric RNA/DNA oligonucleotides." Nature Biotechnology vol. 18 May 2000, pp. 555-558.
U.S. Department of Agriculture, Agricultural Resource Management Survey: U.S. Rice Industry. Jan. 2015, No. 2015-02, pp. 1-4.
K. Johnson et al., "Managing the potential for developing herbicide-resistant weeds in herbicide-tolerant rice," at p. 556 in J.E. Hill & B. Hardy (eds ), Proceedings of the Second Temperate Rice Conference (Int. Rice Res. Inst.) (2002).
Page 37 in "Implementing Integrated Weed Management for Herbicide Tolerant Crops" (CropLife International, Feb. 2012; https://croplife.org/wp-content/uploads/2014/04/Implementing-Integrated-Weed-Management-for-Herbicide-Tolerant-Crops.pdf.
J.W. Heiser (U. Missouri—Weed Science), Rice News (Sep. 5, 2014), in AgFax (http://agfax.com/2014/09/05/rice-herbicide-tolerant-provisia-highlighted-missouri-delta-center-field-day/).
Khush, G.S., Plant Mol. Biol., 1997, 35:25-34.
EMBL Accession No. EAY97401, Submitted on Sep. 12, 2003.
Delye et al, Pest Management Science, 2008 64:1179-1186.
Delye et al, Plant Physiol (2003) 132:1716-1723.
Collavo, A., PhD Dissertation, University of Padova, Jan. 2008.
Okuzaki et al, "Chimeric RNA/DNA oligonucleotide-directed gene targeting in rice," Plant Cell Reports, 22:7, 2004, 509-512.
Rutger et al, Crop Science, 2005, 45:1170-1171.
UniProt Accession No. A2Y2U1, integrated into database Mar. 20, 2007.
Suzuki et al, Mol. Genet. Genomics, 2008, 279:213-223.
Heong, Kong Luen, and M.M. Escalada, eds. Pest Management of rice farmers in Asia, Int. Rice Res. Inst, 1997.
Till, et al, "Discovery of chemically induced mutations in rice by TILLLING." BMC Plant Biology 7.1, 2007, 19.
Hongle, et al, "Mutations of codon position 1991 of acetyl-CoA carboxylase confer resistance to ACCase-inhibiting herbicides in Japanese foxtail (*Alopecurus japonicas*)." Pest Management Science 70.12, 2014, 1894-1901.
Delye et al, WEed Res. (2005) 45:323-330.
Delye, Weed Science (2005) 56:728-746.
Okuzaki et al. Plant Cell Rep. (2004) 22:509-512.
UniProt Accession No. A2Y2U1, integrated into the database on Mar. 20, 2007.
Liu et al, Proc. Natl. Acad. Sci. (2007) 104:3627-3632.
Powles, et al., Resistance and World Grains, CRC Press (2001), Boca Raton Florida, pp. 31-33.
Beetham et al., "A Toold for Functional Plant Genomics: Chimeric RNA/DNA Oligonucleotides Cause In Vivo Gene-Specific Mutations," Proc Natl Acad Sci USA, vol. 96, pp. 8774-8778, 1999.
Chugh, A. and Eudes, F., "Study of Uptake of Cell Penetrating Peptides and Their Cargoes in Permeabilized Wheat Immature Embryos," FEBS J. vol. 275, pp. 2403-2414, 2008.
Getz et al., "Improved Method for High Efficiency Transformation of Intact Yeast Cells," Nuci Acids Res, vol. 20, p. 1425, 1992.
Hasslacher et al., "Acetyl-CoA Carboxylase from Yeast is an Essential Enzyme and is Regulated by Factors that Control Phospholipid Metabolism," J Biol Chem, vol. 268, No. 15, pp. 10946-10952, 1993.
Mumberg et al., "Yeast Vectors for the Controlled Expression of Heterologous Proteins in Different Genetic Backgrounds," Gene, vol. 156, pp. 119-122, 1995.
Schneiter et al., A Yeast Acetyl Coenzyme A Caboxylase Mutant Links Very-Long-Chain Fatty Acid Synthesis to the Structure and Function of the Nuclear Membrane-Pore Complex, Mol Cell Biol, vol. 16, pp. 7161-7172, 1996.
Ruiter, et al., "Spontaneous Mutation Frequency in Plant Obscures the Effect of Chimeraplasty", Plant Molecular Biology, vol. 53, Nov. 2003, pp. 715-729.
Maneechote, Chanya, et al. "Resistance to ACCase-inhibiting herbicides in sprangletop (*Leptochloa chinensis*)." Weed science 53 (2005): 290-295. (Year: 2005).
Shivrain, et al., "Gene flow between Clearfield™ rice and red rice", Crop Protection, vol. 26, Issue 3, Mar. 2007, pp. 349-356.
Somers, David A., "Chapter 11: Aryloxyphenoxypropionate- and Cyclohexanedione-Resistant Crops", Herbicide-Resistant Crops: Agricultural, Environmental, Economic, Regulatory and Technical Aspects, CRC Press, Inc., 1996, pp. 175-188.
Xiang, et al., "A different mechanism for the inhibition of the carboxyltransferase domain of acetyl-coenzyme A carboxylase by tepraloxydim", PNAS, vol. 106, No. 49, Dec. 8, 2009, pp. 20723-20727.
Tal, et al., "Molecular characterization and inheritance of resistance to ACCase-inhibiting herbicides in Lolium rigidum", Pest Management Science, vol. 60, Issue 10, Oct. 2004, pp. 1013-1018.
Tate, Trent Matthew, "Characterization of acetyl coenzyme A inhibitor resistance in turfgrass and grassy weeds", A Thesis Submitted to the Graduate Faculty of The University of Georgia in Partial Fulfillment of the Requirements for the Degree, Dec. 2012, 64 pages.
White, et al., "Differences in the molecular basis of resistance to the cyclohexanedione herbicide sethoxydim in Lolium multiflorum", Weed Research, vol. 45, Issue 6, Dec. 2005,pp. 440-448.
Yu, et al., "Diversity of Acetyl-Coenzyme A Carboxylase Mutations in Resistant Lolium Populations: Evaluation Using Clethodim", Plant Physiology, vol. 145, Issue 2, Oct. 2007, pp. 547-558.
K. Johnson et al., "Managing the potential for developing herbicide-resistant weeds in herbicide-tolerant rice," at p. 556 n J.E. Hill & B. Hardy (eds), Proceedings of the Second Temperate Rice Conference (Int. Rice Res Inst.) (2002).
J.W. Heiser (U. Missouri—Weed Science), Rice News (Sep. 5, 2014), in AgFax (http:/agfax.com/2014/09/05/ice-herbicide-tolerant-pro visia-highlighted-missouri-delta-center-field-day/).
Delye et al, Pest Manag. Sol (2008) 64:1179-1186.
Beetham et al., "A Tool for Functional Plant Genomics: Chimeric RNA/DNA Oligonucleotides Cause In Vivo Gene-Specific Mutations," Proc Natl Acad Sci USA, vol. 96, pp. 8774-8778, 1999.
Delye et al., "An Isoleucine Residue Within the Carboxyltransferase Domain of Multidomain Acetyl-Coenzyme A Carboxylase is a Major Determinant of Sensitivity to Aryloxyphenoxypropionate but not to Cyclohexanedione Inhibitors," Plant Physiol, vol. 132, pp. 1716-1723, 2003.

(56) References Cited

OTHER PUBLICATIONS

Delye et al., "Molecular Bases for Sensitivity to Acetyl-Coenzyme A Carboxylase Inhibitors in Black-Grass," Plant Physiol, vol. 137, pp. 794-806, 2005.
Gietz et al., "Improved Method for High Efficiency Transformation of Intact Yeast Cells," Nucl Acids Res, vol. 20, p. 1425, 1992.
Joachimiak et al., "Wheat Cytosolic Acetyl-CoA Carboxylase Complements an ACC1 Null Mutation in Yeast," Proc Natl Acad Sci USA, vol. 94, No. 18, pp. 9990-9995, 1997.
Liu et al., "Single-Site Mutations in the Carboxyltransferase Domain of Plastid Acetyl-CoA Carboxylase Confer Resistance to Grass-Specific Herbicides," Proc Natl Acad Sci USA, vol. 104, No. 9, pp. 3627-3632, 2007.
Nikolau et al., "Plant Biotin-Containing Carboxylases," Arch Biochem Biophys, vol. 414, pp. 211-222, 2003.
Nikolskaya et al., "Herbicide Sensitivity Determinant of Wheat Plastid Acetyl-CoA Carboxylase is Located in a 400-Amino Acid Fragment of the Carboxyltransferase Domain," Proc Natl Acad Sci USA, vol. 96, No. 25, pp. 14647-14651, 1999.
Podkowinski et al., Expression of Cytosolic and Plastid Acetyl-Coenzyme A Carboxylase Genes in Young Wheat Plants, Plant Physiol, vol. 131, No. 2, pp. 763-772, 2003.
Schneiter et al., A Yeast Acetyl Coenzyme A Carboxylase Mutant Links Very-Long-Chain Fatty Acid Synthesis to the Structure and Function of the Nuclear Membrane-Pore Complex, Mol Cell Biol, vol. 16, pp. 7161-7172, 1996.
Shivrain et al., Gene Flow Between Clearfield® Rice and Red Rice, Crop Protection, vol. 26, pp. 349-356, 2007.
Somers, D.A., "Aryloxyphenoxypropionate and Cyclohexanedione-Resistant Crops," In: Duke SO (Editor), Herbicide-Resistant Crops Agricultural, Environmental, Economic, Regulatory and Technical Aspects, CRC Press, New York, pp. 175-187, 1996.
Varanasi, A.V., "Assessment of Acetyl-CoA Carboxylase Mutations Using Partial Gene Replacement in Yeast," Proquest Dissertations and Theses: the Science and Engineering Collection, 2008.
International Search Report and Written Opinion for application No. PCT/US2012/064831, filed Nov. 13, 2012.
International Preliminary Report on Patentability for application No. PCT/US2012/064831, filed Nov. 13, 2012.
Rafael De Prado et al., "Resistance to ACCase inhibitor herbicides in a green foxtail (*Setaria viridis*) biotype in Europe", Weed Science, vol. 52: 506-512 (2004).
Song Xiang eta!., "A different mechanism for the inhibition of the carboxyltransferase domain of acetyl-coenzyme A carboxylase by tepraloxydim", PNAS, vol. 106, No. 49, pp. 20723-20727, Dec. 8, 2009.
Delye, Weed Science (2005) 53:728-746.
JP Ruiz-Santaella et al., "Is it possible to detect *Echinochioa* spp. tolerance to ACCaseinhibiting herbicides using a simple quick tolerance test?," Commun. Agric. Appl. Biol. Sci. 68(4, pt.A):331-34 (2003).
JP Ruiz-Santaella et al., "Basis of selectivity of cyhalofop-butyl in *Oryza saliva* L.," Planta 223(2):191-99 (Jan. 2006) (ePub Sep. 14, 2005).
A. Okuzaki et al., "Chimeric RNA/DNA Oligonucleotide-Directed Gene Targeting In Rice", Plant Cell Rep Laboratory of Plant Breeding and Genetics, Tohoku University, Sendai, Japan, (2004) 22:509-512.
Delye, "Weed resistance to acetyl coenzyme A carboxylase inhibitors: an update," Weed Science, vol. 53, No. 5, Sep. 2005, pp. 728-746.
Delye et al., "PCR-based detection of resistance to acetyl-CoA carboxylase-inhibiting herbicides in black-grass (*Alopercurus myosuroides* Huds) and ryegrass (*Lolium rigidum* Gaud)," Pest Management Science, vol. 58, No. 5, May 2002, pp. 474-478.
Delye et al., "An isoleucine-leucine substitution in chloroplastic acetyl-CoA carboxylase from green foxtail (*Setaria viridis* L. Beauv.) is responsible for resistance to the cyclohexanedione herbicide sethoxydium," Planta, vol. 214, No. 3, Jan. 1, 2002, pp. 421-427.
Delye et al., "SNP markers for black-grass (*Alopecurus myosuroides* Huds.) genotypes resistant to acetyl CoA-carboxylase inhibiting herbiddes," Theoretical and Applied Genetics, vol. 104, No. 6-7, May 1, 2002, pp. 1114-1120.
Christoffers et al., "An Isoleucine to 1-23 Leucine Mutation in Acetyl-CoA Carboxylase Confers Herbicide Resistance In Wild Oat," Genome, National Research Council Canada, vol. 45, No. 6,Jan. 1, 2002.
Menchari et al., "Fitness costs associated with three mutant acetyl-coenzyme A carboxylase alleles endowing herbicide resistance in black-grass *Alopecurus myosuroides*," Journal of Applied Ecology, vol. 45, No. 3, Jun. 2008, pp. 939-947.
Tate, "Characterization of Acetyl Coenzyme A Inhibitor Resistance in Turfgrass and Grassy Weeds," A Thesis Submitted to the Graduate Faculty of the University of Georgia in Partial Fulfillment of the Requirements for the Degree, 2012.
Somers, "Chapter 11: Aryloxyphenoxypropionate- and Cyclohexanedione-Resistant Crops," Herbicide-Resistant Crops: Agricultural, Environmental, Economic, Regulatory and Technical Aspects, CRC Press, Inc., 1996, pp. 175-188.
Callan, In Vitro Selection for and Biochemical Analysis of Sethoxydim-Tolerant Winter Wheat (*Triticum aestivum* L), In partial fulfillment of the requirements for the Degree of Doctor of Philosophy, Colorado State University, Fort Collins, Colorado, Fall 1996.
Carlson et al., "Tissue Culture Selection System in Poa Pratensis," NCWSS Proceedings, vol. 45, p. 11, 1990.
White et al., "Differences in the molecular basis of resistance to the cyclohexanedione herbicide sethoxydim in Lolium multiflorum," Weed Research 45(6), pp. 440-448, Dec. 2005.
Zhang et al., "The molecular bases for resistance to acetyl co-enzyme A carboxylase (ACCase) inhibiting herbicides in WO target-based resistant biotypes of annual ryegrass (*Lolium rigidum*)," Planta 223(3), pp. 550-557, Feb. 2006.
Collavo, "Resistance to graminicides in monocotyledons weeds: Case studies of *Lolium* spp. and Phalaris paradoxa in Italy," 2008 (Ph.D. Thesis, U. Padua/Padova).
Ruiz-Santaella et al., "Detection of a new mutation of glycine to serine in the ACCase of a resistant biotype of Phalaris paradoxa," Weed Sci. Soc. Am. Abstr. 46:93 (2006) (New York: WSSA 2006 Annual Meeting, Abstracts).
Makoda, Yuka, et al., "Chloroplast Transformation with Modified accD Operon Increases Acetyl-CoA Carboxylase and Causes Extension of Leaf Longevity and Increase in Seed Yield in Tobacco", 43(12): 1518-1525 (2002), Genesis Research Inst, Inc., Japan.
Heckart, Obtaining Sethoxydim Resistance in Seashore Paspalum (*Paspalum vaginatum*), A Thesis Submitted to the Graduate Faculty of the University of Georgia in Partial Fulfillment of the Requirements for the Degree, Athens, GA, 2009.
Heckart et al., "Obtaining Sethoxydim Resistance in Seashore Paspalum," Crop Science, vol. 50, Nov.-Dec. 2010, pp. 2632-2640.
Herbert et al., "Susceptibilities of Different Test Systems from Maine (*Zea mays*), Poa annua, and Festuca rubra to Herbicides that Inhibit the Enzyme Acetyl-Coenzyme A Carboxylase," Pesticide Biochemistery and Physiology, No. 55, pp. 129-139, 1996.
Buell, Poaceae Genomes: Going from Unattainable to Becoming a Model Clade for Comparative Plant Genomics, Plant Physiology, Jan. 2009, vol. 149, pp. 111-116.
Kellogg, "The Evolutionary History of Ehrhartoideae, Oryzeae, and *Oryza*," Rice, Jan. 8, 2009, vol. 2, pp. 1-14.
Mathews et al., "Phylogenetic Structure in the Grass Family (Poaceae): Evidence From the Nuclear Gene Phytochrome B," American Journal of Botany 87(1), pp. 96-107, 2000.
Ashley, Jr., "Evaluation of Weed Control and Crop Tolerance With Postemergence Herbicides in Sethoxydim-Tolerant Corn," Thesis submitted to Virginia Polytechnic Institute, Apr. 27, 1998.
Delye et al., "An Isoleucine Residue within the Carboxyl-Transferase Domain of Multidomain Acetyl-Coenzyme A Carboxylase Is a Major Determinant of Sensitivity to Aryloxyphenoxypropionate But Not to Cydohexanedione Inhibitors," Plant Physiology, Jul. 2003, vol. 132, pp. 1716-1723.
Delye et al., "Molecular Bases for Sensitivity to Acetyl-Coenzyme A Carboxylase Inhibitors in Black-Grass," Plant Physiology, Mar. 2005, vol. 137, pp. 794-806.

(56) References Cited

OTHER PUBLICATIONS

Delye et al., "Cross-resistance patterns to ACCase-inhibiting herbicides conferred by mutant ACCase isoforms in *Alopecurus myosuroides* Huds. (black-grass), re-examined at the recommended herbicide field rate," Pest Manag. Sci,, 2008.
Hiei et al., "Agrobacterium-mediated transformation of rice using immature embryos or calli induced from mature seed," Nature Protocols, 2008, vol. 3 No. 5, pp. 824-834.
Tong et al., Systematic Genetic Analysis with Ordered Arrays of Yeast Deletion Mutants, Science, vol. 294, No. 5550, pp. 2364-2368, 2001.
Tong, A.H.Y. and Boone, C., "Synthetic Genetic Array Analysis in *Saccharomyces cerevisiae*," Methods Mol Biol, vol. 313, pp. 171-192, 2006.
Lancaster, Zachary D., Jason K. Norsworthy, and Robert C. Scott. "Evaluation of quizalofop-resistant rice for Arkansas rice production systems." International Journal of Agronomy 2018 (2018). (Year: 2018).
Won, Ok Jae, et al. "Identification of Herbicide-Resistant Barnyardgrass (Echinochloa crus-galli var. crus-galli) Biotypes in Korea." Weed & Turfgrass Science 3.2 (2014): 110-113 . (Year: 2014).

* cited by examiner

FIGURE 5

```
   1 MGSTHLPIVG FNASTTPSLS TLRQINSAAA AFQSSSPSRS SKKKSRRVKS IRDDGDGSVP
  61 DPAGHGQSIR QGLAGIIDLP KEGASAPDVD ISHGSEDHKA SYQMNGILNE SHNGRHASLS
 121 KVYEFCTELG GKTPIHSVLV ANNGMAAAKF MRSVRTWAND TFGSEKAIQL IAMATPEDMR
 181 INAEHIRIAD QFVEVPGGTN NNNYANVQLI VEIAERTGVS AVWPGWGHAS ENPELPDALT
 241 AKGIVFLGPP ASSMNALGDK VGSALIAQAA GVPTLAWSGS HVEIPLELCL DSIPEEMYRK
 301 ACVTTADEAV ASCQMIGYPA MIKASWGGGG KGIRKVNNDD EVKALFKQVQ GEVPGSPIFI
 361 MRLASQSRHL EVQLLCDEYG NVAALHSRDC SVQRRHQKII EEGPVTVAPR ETVKELEQAA
 421 RRLAKAVGYV GAATVEYLYS METGEYYFLE LNPRLQVEHP VTESIAEVNL PAAQVAVGMG
 481 IPLWQIPEIR RFYGMDNGGG YDIWRKTAAL ATPFNFDEVD SQWPKGHCVA VRITSENPDD
 541 GFKPTGGKVK EISFKSKPNV WGYFSVKSGG GIHEFADSQF GHVFAYGETR SAAITSMSLA
 601 LKEIQIRGEI HTNVDYTVDL LNAPDFRENT IHTGWLDTRI AMRVQAERPP WYISVVGGAL
 661 YKTITTNAET VSEYVSYLIK GQIPPKHISL VHSTISLNIE ESKYTIEIVR SGQGSYRLRL
 721 NGSLIEANVQ TLCDGGLLMQ LDGNSHVIYA EEEAGGTRLL IDGKTCLLQN DHDPSRLLAE
 781 TPCKLLRFLI ADGAHVDADV PYAEVEVMKM CMPLLSPAAG VINVLLSEGQ AMQAGDLIAR
 841 LDLDDPSAVK RAEPFEGSFP EMSLPIAASG QVHKRCAASL NAARMVLAGY DHAANKVVQD
 901 LVWCLDTPAL PFLQWEELMS VLATRLPRRL KSELEGKYNE YKLNVDHVKI KDFPTEMLRE
 961 TIEENLACVS EKEMVTIERL VDPLMSLLKS YEGGRESHAH FIVKSLFEEY LSVEELFSDG
1021 IQSDVIERLR LQYSKDLQKV VDIVLSHQGV RNKTKLILAL MEKLVYPNPA AYRDQLIRFS
1081 SLNHKRYYKL ALKASELLEQ TKLSELRTSI ARNLSALDMF TEEKADFSLQ DRKLAINESM
1141 GDLVTAPLPV EDALVSLFDC TDQTLQQRVI QTYISRLYQP QLVKDSIQLK YQDSGVIALW
1201 EFTEGNHEKR LGAMVILKSL ESVSTAIGAA LKDASHYASS AGNTVHIALL DADTQLNTTE
1261 DSGDNDQAQD KMDKLSFVLK QDVVMADLRA ADVKVVSCIV QRDGAIMPMR RTFLLSEEKL
1321 CYEEEPILRH VEPPLSALLE LDKLKVKGYN EMKYTPSRDR QWHIYTLRNT ENPKMLHRVF
1381 FRTLVRQPSA GNRFTSDHIT DVEVGHAEEP LSFTSSSILK SLKIAKEELE LHAIRTGHSH
1441 MYLCILKEQK LLDLVPVSGN TVVDVGQDEA TACSLLKEMA LKIHELVGAR MHHLSVCQWE
1501 VKLKLVSDGP ASGSWRVVTT NVTGHTCTVD IYREVEDTES QKLVYHSTAL SSGPLHGVAL
1561 NTSYQPLSVI DLKRCSARNN KTTYCYDFPL TFEAAVQKSW SNISSENNQC YVKATELVFA
1621 EKNGSWGTPI IPMQRAAGLN DIGMVAWILD MSTPEFPSGR QIIVIANDIT FRAGSFGPRE
1681 DAFFEAVTNL ACEKKLPLIY LAANSGARIG IADEVKSCFR VGWTDDSSPE RGFRYIYMTD
1741 EDHDRIGSSV IAHKMQLDSG EIRWVIDSVV GKEDGLGVEN IHGSAAIASA YSRAYEETFT
1801 LTFVTGRTVG IGAYLARLGI RCIQRIDQPI ILTGFSALNK LLGREVYSSH MQLGGPKIMA
1861 TNGVVHLTVP DDLEGVSNIL RWLSYVPANI GGPLPITKSL DPIDRPVAYI PENTCDPRAA
1921 ISGIDDSQGK WLGGMFDKDS FVETFEGWAK TVVTGRAKLG GIPVGVIAVE TQTMMQLVPA
1981 DPGQPDSHER SVPRAGQVWF PDSATKTAQA MLDFNREGLP LFILANWRGF SGGQRDLFEG
2041 ILQAGSTIVE NLRTYNQPAF VYIPKAAELR GGAWVVIDSK INPDRIECYA ERTAKGNVLE
2101 PQGLIEIKFR SEELKECMGR LDPELIDLKA RLQGANGSLS DGESLQKSIE ARKKQLLPLY
2161 TQIAVRFAEL HDTSLRMAAK GVIRKVVDWE DSRSFFYKRL RRRLSEDVLA KEIRGVIGEK
2221 FPHKSAIELI KKWYLASEAA AAGSTDWDDD DAFVAWRENP ENYKEYIKEL RAQRVSRLLS
2281 DVAGSSSDLQ ALPQGLSMLL DKMDPSKRAQ FIEEVMKVLK
```

FIGURE 6

```
   1 ATGGGATCCA CACATCTGCC CATTGTCGGG TTTAATGCAT CCACAACACC ATCGCTATCC
  61 ACTCTTCGCC AGATAAACTC AGCTGCTGCT GCATTCCAAT CTTCGTCCCC TTCAAGGTCA
 121 TCCAAGAAGA AAAGCCGACG TGTTAAGTCA ATAAGGGATG ATGGCGATGG AAGCGTGCCA
 181 GACCCTGCAG GCCATGGCCA GTCTATTCGC CAAGGTCTCG CTGGCATCAT CGACCTCCCA
 241 AAGGAGGGCG CATCAGCTCC AGATGTGGAC ATTTCACATG GGTCTGAAGA CCACAAGGCC
 301 TCCTACCAAA TGAATGGGAT ACTGAATGAA TCACATAACG GGAGGCACGC CTCTCTGTCT
 361 AAAGTTTATG AATTTTGCAC GGAATTGGGT GGAAAAACAC CAATTCACAG TGTATTAGTC
 421 GCCAACAATG GAATGGCAGC AGCTAAGTTC ATGCGGAGTG TCCGGACATG GGCTAATGAT
 481 ACATTTGGGT CAGAGAAGGC GATTCAGTTG ATAGCTATGG CAACTCCGGA AGACATGAGA
 541 ATAAATGCAG AGCACATTAG AATTGCTGAT CAGTTTGTTG AAGTACCTGG TGGAACAAAC
 601 AATAACAACT ATGCAAATGT CCAACTCATA GTGGAGATAG CAGAGAGAAC TGGTGTCTCC
 661 GCCGTTTGGC CTGGTTGGGG CCATGCATCT GAGAATCCTG AACTTCCAGA TGCACTAACT
 721 GCAAAAGGAA TTGTTTTTCT TGGGCCACCA GCATCATCAA TGAACGCACT AGGCGACAAG
 781 GTTGGTTCAG CTCTCATTGC TCAAGCAGCA GGGGTTCCCA CTCTTGCTTG GAGTGGATCA
 841 CATGTGGAAA TTCCATTAGA ACTTTGTTTG GACTCGATAC CTGAGGAGAT GTATAGGAAA
 901 GCCTGTGTTA CAACCGCTGA TGAAGCAGTT GCAAGTTGTC AGATGATTGG TTACCCTGCC
 961 ATGATCAAGG CATCCTGGGG TGGTGGTGGT AAAGGGATTA GAAAGGTTAA TAATGATGAC
1021 GAGGTGAAAG CACTGTTTAA GCAAGTACAG GGTGAAGTTC CTGGCTCCCC GATATTTATC
1081 ATGAGACTTG CATCTCAGAG TCGTCATCTT GAAGTCCAGC TGCTTTGTGA TGAATATGGC
1141 AATGTAGCAG CACTTCACAG TCGTGATTGC AGTGTGCAAC GACGACACCA AAAGATTATC
1201 GAGGAAGGAC CAGTTACTGT TGCTCCTCGT GAAACAGTGA AAGAGCTAGA GCAAGCAGCA
1261 AGGAGGCTTG CTAAGGCCGT GGGTTACGTC GGTGCTGCTA CTGTTGAATA TCTCTACAGC
1321 ATGGAGACTG GTGAATACTA TTTTCTGGAG CTTAATCCAC GGTTGCAGGT TGAGCACCCA
1381 GTCACCGAGT CGATAGCTGA AGTAAATTTG CCTGCAGCCC AAGTTGCAGT TGGGATGGGT
1441 ATACCCCTTT GGCAGATTCC AGAGATCAGA CGTTTCTACG GAATGGACAA TGGAGGAGGC
1501 TATGATATTT GGAGGAAAAC AGCAGCTCTC GCTACTCCAT TCAACTTTGA TGAAGTAGAT
1561 TCTCAATGGC CGAAGGGTCA TTGTGTGGCA GTTAGGATAA CCAGTGAGAA TCCAGATGAT
1621 GGATTCAAGC CTACTGGTGG AAAAGTAAAG GAGATAAGTT TTAAAAGTAA GCCAAATGTC
1681 TGGGGATATT TCTCAGTTAA GTCTGGTGGA GGCATTCATG AATTTGCGGA TTCTCAGTTT
1741 GGACACGTTT TTGCCTATGG AGAGACTAGA TCAGCAGCAA TAACCAGCAT GTCTCTTGCA
1801 CTAAAAGAGA TTCAAATTCG TGGAGAAATT CATACAAACG TTGATTACAC GGTTGATCTC
1861 TTGAATGCCC CAGACTTCAG AGAAAACACG ATCCATACCG GTTGGCTGGA TACCAGAATA
1921 GCTATGCGTG TTCAAGCTGA GAGGCCTCCC TGGTATATTT CAGTGGTTGG AGGAGCTCTA
1981 TATAAAACAA TAACCACCAA TGCGGAGACC GTTTCTGAAT ATGTTAGCTA TCTCATCAAG
2041 GGTCAGATTC CACCAAAGCA CATATCCCTT GTCCATTCAA CTATTTCTTT GAATATAGAG
2101 GAAAGCAAAT ATACAATTGA GATTGTGAGG AGTGGACAGG GTAGCTACAG ATTGAGACTG
2161 AATGGATCAC TTATTGAAGC CAATGTACAA ACATTATGTG ATGGAGGCCT TTTAATGCAG
2221 CTGGATGGAA ATAGCCATGT TATTTATGCT GAAGAAGAAG CGGGTGGTAC ACGGCTTCTT
2281 ATTGATGGAA AAACATGCTT GCTACAGAAT GACCATGATC CGTCAAGGTT ATTAGCTGAG
2341 ACACCCTGCA AACTTCTTCG TTTCTTGATT GCCGATGGTG CTCATGTTGA TGCTGATGTA
2401 CCATACGCGG AAGTTGAGGT TATGAAGATG TGCATGCCCC TCTTGTCGCC TGCTGCTGGT
2461 GTCATTAATG TTTTGTTGTC TGAGGGCCAG GCGATGCAGG CTGGTGATCT TATAGCGAGA
2521 CTTGATCTCG ATGACCCTTC TGCTGTGAAG AGAGCCGAGC CATTTGAAGG ATCTTTTCCA
2581 GAAATGAGCC TTCCTATTGC TGCTTCTGGC CAAGTTCACA AAAGATGTGC TGCAAGTTTG
2641 AACGCTGCTC GAATGGTCCT TGCAGGATAT GACCATGCGG CCAACAAAGT TGTGCAAGAT
2701 TTGGTATGGT GCCTTGATAC ACCTGCTCTT CCTTTCCTAC AATGGGAAGA GCTTATGTCT
2761 GTTTTAGCAA CTAGACTTCC AAGACGTCTT AAGAGCGAGT TGGAGGGCAA ATACAATGAA
2821 TACAAGTTAA ATGTTGACCA TGTGAAGATC AAGGATTTCC CTACCGAGAT GCTTAGAGAG
2881 ACAATCGAGG AAAATCTTGC ATGTGTTTCC GAGAAGGAAA TGGTGACAAT TGAGAGGCTT
2941 GTTGACCCTC TGATGAGCCT GCTGAAGTCA TACGAGGGTG GGAGAGAAAG CCATGCCCAC
```

FIGURE 6 (continued)

```
3001 TTTATTGTCA AGTCCCTTTT TGAGGAGTAT CTCTCGGTTG AGGAACTATT CAGTGATGGC
3061 ATTCAGTCTG ACGTGATTGA ACGCCTGCGC CTACAATATA GTAAAGACCT CCAGAAGGTT
3121 GTAGACATTG TTTTGTCTCA CCAGGGTGTG AGAAACAAAA CAAAGCTGAT ACTCGCGCTC
3181 ATGGAGAAAC TGGTCTATCC AAACCCTGCT GCCTACAGAG ATCAGTTGAT TCGCTTTTCT
3241 TCCCTCAACC ATAAAAGATA TTATAAGTTG GCTCTTAAAG CTAGTGAACT TCTTGAACAA
3301 ACCAAGCTCA GCGAACTCCG CACAAGCATT GCAAGGAACC TTTCAGCGCT GGATATGTTC
3361 ACCGAGGAAA AGGCAGATTT CTCCTTGCAA GACAGAAAAT TGGCCATTAA TGAGAGCATG
3421 GGAGATTTAG TCACTGCCCC ACTGCCAGTT GAAGATGCAC TTGTTTCTTT GTTTGATTGT
3481 ACTGATCAAA CTCTTCAGCA GAGAGTGATT CAGACATACA TATCTCGATT ATACCAGCCT
3541 CAACTTGTGA AGGATAGCAT CCAGCTGAAA TATCAGGATT CTGGTGTTAT TGCTTTATGG
3601 GAATTCACTG AAGGAAATCA TGAGAAGAGA TTGGGTGCTA TGGTTATCCT GAAGTCACTA
3661 GAATCTGTGT CAACAGCCAT TGGAGCTGCT CTAAAGGATG CATCACATTA TGCAAGCTCT
3721 GCGGGCAACA CGGTGCATAT TGCTTTGTTG GATGCTGATA CCCAACTGAA TACAACTGAA
3781 GATAGTGGTG ATAATGACCA AGCTCAAGAC AAGATGGATA AACTTTCTTT TGTACTGAAA
3841 CAAGATGTTG TCATGGCTGA TCTACGTGCT GCTGATGTCA AGGTTGTTAG TTGCATTGTT
3901 CAAAGAGATG GAGCAATCAT GCCTATGCGC CGTACCTTCC TCTTGTCAGA GGAAAAACTT
3961 TGTTACGAGG AAGAGCCGAT TCTTCGGCAT GTGGAGCCTC CACTTTCTGC ACTTCTTGAG
4021 TTGGATAAAT TGAAAGTGAA AGGATACAAT GAGATGAAGT ATACACCGTC ACGTGATCGT
4081 CAGTGGCATA TATACACACT TAGAAATACT GAAAATCCAA AAATGCTGCA CAGGGTATTT
4141 TTCCGAACAC TTGTCAGACA ACCCAGTGCA GGCAACAGGT TTACATCAGA CCATATCACT
4201 GATGTTGAAG TAGGACACGC AGAGGAACCT CTTTCATTTA CTTCAAGCAG CATATTAAAA
4261 TCGTTGAAGA TTGCTAAAGA AGAATTGGAG CTTCACGCGA TCAGGACTGG CCATTCTCAT
4321 ATGTACTTGT GCATATTGAA AGAGCAAAAG CTTCTTGACC TTGTTCCTGT TTCAGGGAAC
4381 ACTGTTGTGG ATGTTGGTCA AGATGAAGCT ACTGCATGCT CTCTTTTGAA AGAAATGGCT
4441 TTAAAGATAC ATGAACTTGT TGGTGCAAGA ATGCATCATC TTTCTGTATG CCAGTGGGAA
4501 GTGAAACTTA AGTTGGTGAG CGATGGGCCT GCCAGTGGTA GCTGGAGAGT TGTAACAACC
4561 AATGTTACTG GTCACACCTG CACTGTGGAT ATCTACCGGG AGGTCGAAGA TACAGAATCA
4621 CAGAAACTAG TATACCACTC CACCGCATTG TCATCTGGTC CTTTGCATGG TGTTGCACTG
4681 AATACTTCGT ATCAGCCTTT GAGTGTTATT GATTTAAAAC GTTGCTCTGC CAGGAACAAC
4741 AAAACTACAT ACTGCTATGA TTTTCCATTG ACATTTGAAG CTGCAGTGCA GAAGTCGTGG
4801 TCTAACATTT CCAGTGAAAA CAACCAATGT TATGTTAAAG CGACAGAGCT TGTGTTTGCT
4861 GAAAAGAATG GGTCGTGGGG CACTCCTATA ATTCCTATGC AGCGTGCTGC TGGGCTGAAT
4921 GACATTGGTA TGGTAGCCTG GATCTTGGAC ATGTCCACTC CTGAATTTCC CAGCGGCAGA
4981 CAGATCATTG TTATCGCAAA TGATATTACA TTTAGAGCTG GATCATTTGG CCCAAGGGAA
5041 GATGCATTTT TCGAAGCTGT AACCAACCTG GCTTGTGAGA AGAAGCTTCC ACTTATCTAC
5101 TTGGCTGCAA ACTCTGGTGC TCGGATTGGC ATTGCTGATG AAGTAAAATC TTGCTTCCGT
5161 GTTGGATGGA CTGATGATAG CAGCCCTGAA CGTGGATTTA GGTACATTTA TATGACTGAC
5221 GAAGACCATG ATCGTATTGG CTCTTCAGTT ATAGCACACA AGATGCAGCT AGATAGTGGC
5281 GAGATCAGGT GGGTTATTGA TTCTGTTGTG GGAAAAGAGG ATGGACTAGG TGTGGAGAAC
5341 ATACATGGAA GTGCTGCTAT TGCCAGTGCC TATTCTAGGG CGTACGAGGA GACATTTACA
5401 CTTACATTCG TTACTGGACG AACTGTTGGA ATCGGAGCCT ATCTTGCTCG ACTTGGCATA
5461 CGGTGCATAC AGCGTATTGA CCAGCCCATT ATTTTGACCG GGTTTTCTGC CCTGAACAAG
5521 CTTCTTGGGC GGGAGGTGTA CAGCTCCCAC ATGCAGTTGG GTGGTCCCAA AATCATGGCG
5581 ACGAATGGTG TTGTCCATCT GACTGTTCCA GATGACCTTG AAGGTGTTTC TAATATATTG
5641 AGGTGGCTCA GCTATGTTCC TGCAAACATT GGTGGACCTC TTCCTATTAC AAAATCTTTG
5701 GACCCAATAG ACAGACCCGT TGCATACATC CCTGAGAATA CATGTGATCC TCGTGCAGCC
5761 ATCAGTGGCA TTGATGACAG CCAAGGGAAA TGGTTGGGTG GCATGTTTGA CAAAGACAGT
5821 TTTGTGGAGA CATTTGAAGG ATGGGCGAAG ACAGTAGTTA CTGGCAGAGC AAAACTTGGA
5881 GGGATTCCTG TTGGTGTTAT AGCTGTGGAG ACACAGACCA TGATGCAGCT CGTCCCCGCT
5941 GATCCAGGCC AGCCTGATTC CCACGAGCGG TCTGTTCCTC GTGCTGGGCA AGTTTGGTTT
6001 CCAGATTCTG CTACCAAGAC AGCGCAGGCG ATGTTGGACT TCAACCGTGA AGGATTACCT
6061 CTGTTCATAC TTGCTAACTG GAGAGGCTTC TCTGGAGGGC AAAGAGATCT TTTTGAAGGA
6121 ATTCTGCAGG CTGGGTCAAC AATTGTTGAG AACCTTAGGA CATACAATCA GCCTGCCTTT
6181 GTATATATCC CCAAGGCTGC AGAGCTACGT GGAGGAGCCT GGGTCGTGAT TGATAGCAAG
```

FIGURE 6 (continued)

```
6241 ATAAACCCAG ATCGCATCGA GTGCTATGCT GAGAGGACTG CAAAGGGTAA TGTTCTCGAA
6301 CCTCAAGGGT TGATTGAGAT CAAGTTCAGG TCAGAGGAAC TCAAAGAATG CATGGGTAGG
6361 CTTGATCCAG AATTGATAGA TCTGAAAGCA AGACTCCAGG GAGCAAATGG AAGCCTATCT
6421 GATGGAGAAT CCCTTCAGAA GAGCATAGAA GCTCGGAAGA AACAGTTGCT GCCTCTGTAC
6481 ACCCAAATCG CGGTACGTTT TGCGGAATTG CACGACACTT CCCTTAGAAT GGCTGCTAAA
6541 GGTGTGATCA GGAAAGTTGT AGACTGGGAA GACTCTCGGT CTTTCTTCTA CAAGAGATTA
6601 CGGAGGAGGC TATCCGAGGA CGTTCTGGCA AAGGAGATTA GAGGTGTAAT TGGTGAGAAG
6661 TTTCCTCACA AATCAGCGAT CGAGCTGATC AAGAAATGGT ACTTGGCTTC TGAGGCAGCT
6721 GCAGCAGGAA GCACCGACTG GGATGACGAC GATGCTTTTG TCGCCTGGAG GGAGAACCCT
6781 GAAAACTATA AGGAGTATAT CAAAGAGCTT AGGGCTCAAA GGGTATCTCG GTTGCTCTCA
6841 GATGTTGCAG GCTCCAGTTC GGATTTACAA GCCTTGCCGC AGGGTCTTTC CATGCTACTA
6901 GATAAGATGG ATCCCTCTAA GAGAGCACAG TTTATCGAGG AGGTCATGAA GGTCCTGAAA
6961 TGA
```

FIGURE 7A

**>*Oryza sativa* Plastidic ACCase genomic sequence**

ATGACATCCACACATGTGGCGACATTGGGAGTTGGTGCCCAGGCACCTCCTCGTCACCAGAAAAAGTCAGCTGG
CACTGCATTTGTATCATCTGGGTCATCAAGACCCTCATACCGAAAGAATGGTCAGCGTACTCGGTCACTTAGGG
AAGAAAGCAATGGAGGAGTGTCTGATTCCAAAAAGCTTAACCACTCTATTCGCCAAGGTGACCACTAGCTACTT
TACATATGCTATAATTTGTGCCAAACATAAACATGCAATGGCTGCTATTATTTAAACGTTAATGTTGAAATAGC
TGCTATAGGATACAGCAAAAATATATAATTGACTGGGCAAGATGCAACAATTGTTTTTCACTAAAGTTAGTTAT
CTTTTGCTGTAAAAGACAACTGTTTTTTACATAAAATGGTATTAATAACCTTGTAATATTCAATGCAACATGTT
CTCAAGTAAAAAAAAACATTGCCTGGTTGTATAAGCAAATGTGTCGTTGTAGACATCTTATTAAACCTTTTTGT
GATATCTATTACCGTAGGGAACAGGGGAGCTGTTTAAATCTGTTATCATAGAGTAATATGAGAAAAGTGGATTG
TGCGACTTTGGCATGTATACCTGCTCAATTTCAAATATATGTCTATGTGCAGGTCTTGCTGGCATCATTGACCT
CCCAAATGACGCAGCTTCAGAAGTTGATATTTCACAGTAAGGACTTTATATTTTATAATAATTATTATATAATT
TTCTGACATGTTTTGAGAACCTCAAAACATGTGATTGCACCTTCCTTTTTTATGTCTGGTTCAGAAACTGATAA
GTTTTGACAGTGTTTAGGATGGATCTTTGATGCGCACAGTGCTTTCTAATGTTTTCATTTTTGAAAGTAATGTT
TTAGGAAGAAATATCTGATTAAATTTATACTTTATCTTTACAAAAGTCAAATGCGTTCTGTATCAATTGCGGTT
TGTAATATGGCAAGAACATGCTTTCAGAATTTGTTCATACAATGCTTTCTTTCTATTATTATGTAGAACAAATA
CCTAATACTTTGTTCACCTTTTATAGTGGACACCTCTCACAGCTTTTTCAGTAAGTGATGCAATTTTGTACATT
TGTAAGATGTGTTCCAGAAACCTTTTCTCCTGCAATTCTAATGTACCCACTCAAACTGGTATCACCAAAGATCT
CCATCTGATTGAAAAAAAGCTGCGTGAAGTATGCTTATTTATGCTAACCATACATGATTTATACTGTTTTATAG
TACAATGCTTATTTATGCTAACCATACATAATTTTATTCTGTTTTCTAGTACATTATTTGTGCCCCTGACCATA
AATGATCCTTTCTTTTACAGTGGTTCCGAAGATCCCAGGGGGCCTACGGTCCCAGGTTCCTACCAAATGAATGG
GATTATCAATGAAACACATAATGGGAGGCATGCTTCAGTCTCCAAGGTTGTTGAGTTTTGTACGGCACTTGGTG
GCAAAACACCAATTCACAGTGTATTAGTGGCCAACAATGGAATGGCAGCAGCTAAGTTCATGCGGAGTGTCCGA
ACATGGGCTAATGATACTTTTGGATCAGAGAAGGCAATTCAGCTGATAGCTATGGCAACTCCGGAGGATCTGAG
GATAAATGCAGAGCACATCAGAATTGCCGATCAATTTGTAGAGGTACCTGGTGGAACAAACAACAACAACTATG
CAAATGTCCAACTCATAGTGGAGGTTAGTTCAGCTCATCCCTCAACACAACATTTTCGTTTCTATTTAAGTTAG
GGAAAAATCTCTACGACCCTCCAATTTCTGAACATCCAATTTTCACCATCAACTGCAATCACAGATAGCAGAGA
GAACAGGTGTTTCTGCTGTTTGGCCTGGTTGGGGTCATGCATCTGAGAATCCTGAACTTCCAGATGCGCTGACT
GCAAAAGGAATTGTTTTTCTTGGGCCACCAGCATCATCAATGCATGCATTAGGAGACAAGGTTGGCTCAGCTCT
CATTGCTCAAGCAGCTGGAGTTCCAACACTTGCTTGGAGTGGATCACATGTGAGCCTTGTCTTCTCTTTTTTAG
CTTATCATCTTATCTTTTCGGTGATGCATTATCCCAATGACACTAAACCATAGGTGGAAGTTCCTCTGGAGTGT
TGCTTGGACTCAATACCTGATGAGATGTATAGAAAAGCTTGTGTTACTACCACAGAGGAAGCAGTTGCAAGTTG
TCAGGTGGTTGGTTATCCTGCCATGATTAAGGCATCTTGGGGTGGTGGTGGTAAAGGAATAAGGAAGGTTTGTT
CTTCTTGTAGTTATCAAGAGATTGTTTGGATTGCAAGTGTTTAGTGCCCATAGTTAACTCTGGTCTTTCTAACA
TGAGTAACTCAACTTTCTTGCAGGTTCATAATGATGATGAGGTTAGGACATTATTTAAGCAAGTTCAAGGCGAA
GTACCTGGTTCCCCAATATTTATCATGAGGCTAGCTGCTCAGGTGGGGCCTTTTATGGAAGTTACACCTTTTCC
CTTAATGTTGAGTTATTCCGGAGTTATTATGGTTATGTTCTGTATGTTTGATCTGTAAATTATTGAAATTCACC
TCCATTGGTTCTCCAGATTAGCAGACCTACAATTCTACATATGGTTTATACTTTATAAATACTAGGATTTAGGG
ATCTTCATATAGTTTATACATGGTATTTAGATTTCATTTGTAACCCTATTGAAGACATCCTGATTGTTGTCTTA
TGTAGAGTCGACATCTTGAAGTTCAGTTGCTTTGTGATCAATATGGCAACGTAGCAGCACTTCACAGTCGAGAT
TGCAGTGTACAACGGCGACACCAAAAGGTCTGCTGTCTCAGTTAAATCACCCCTCTGAATGATCTACTTCTTGC
CTGCTGCGTTGGTCAGAGGAATAATGGTTGTATTCTACTGAACAGATAATCGAGGAAGGACCAGTTACTGTTGC
TCCTCGTGAGACTGTGAAAGAGCTTGAGCAGGCAGCACGGAGGCTTGCTAAAGCTGTGGGTTATGTTGGTGCTG
CTACTGTTGAATACCTTTACAGCATGGAAACTGGTGAATATTATTTTCTGGAACTTAATCCACGGCTACAGGTC
GGCTCCTTTGACATTCTTCAGGAATTAATTTCTGTTGACCACATGATTTACATTGTCAAATGGTCTCACAGGTT
GAGCATCCTGTCACTGAGTGGATAGCTGAAGTAAATTTGCCTGCGGCTCAAGTTGCTGTTGGAATGGGTATACC
CCTTTGGCAGATTCCAGGTAATGCTTCTTCATTTAGTTCCTGCTCTTTGTTAATTGAATGAGCTCTTATACAGA
CCATGAGACACATTCTACTGTTAATTCATAGTATCCCCTGACTTGTTAGTGTTAGAGATACAGAGATGTATCAC

FIGURE 7A (continued)

AAATTCATTGTATCTCCTCAAGGACTGTAAAAATCCTATAATTAAATTTCTGAAAATTTGTTCTTTTAAGCAGA
AAAAAAATCTCTAAATTATCTCCCTGTATACAGAGATCAGGCGCTTCTACGGAATGAACCATGGAGGAGGCTAT
GACCTTTGGAGGAAAACAGCAGCTCTAGCGACTCCATTTAACTTTGATGAAGTAGATTCTAAATGGCCAAAAGG
CCACTGCGTAGCTGTTAGAATAACTAGCGAGGATCCAGATGATGGGTTTAAGCCTACTGGTGGAAAAGTAAAGG
TGCGGTTTCCTGATGTTAGGTGTATGAATTGAACACATTGCTATATTGCAGCTAGTGAAATGACTGGATCATGG
TTCTCTTATTTTCAGGAGATAAGTTTCAAGAGTAAACCAAATGTTTGGGCCTATTTCTCAGTAAAGGTAGTCCT
CAATATTGTTGCACTGCCACATTATTTGAGTTGTCCTAACAATTGTGCTGCAATTGTTAGTTTTCAACTATTTG
TTGTTCTGTTTGGTTGACTGGTACCCTCTCTTTGCAGTCTGGTGGAGGCATCCATGAATTCGCTGATTCTCAGT
TCGGTATGTAAAGTTAAAAGAGTAATATTGTCTTTGCTATTTATGTTTGTCCTCACTTTTAAAAGATATTGCCT
TCCATTACAGGACATGTTTTTGCGTATGGAACTACTAGATCGGCAGCAATAACTACCATGGCTCTTGCACTAAA
AGAGGTTCAAATTCGTGGAGAAATTCATTCAAACGTAGACTACACAGTTGACCTATTAAATGTAAGGACTAAAT
ATCTGCTTATTGAACCTTGCTTTTTGGTTCCCTAATGCCATTTTAGTCTGGCTACTGAAGAACTTATCCATCAT
GCCATTTCTGTTATCTTAAATTCAGGCCTCAGATTTTAGAGAAAATAAGATTCATACTGGTTGGCTGGATACCA
GGATAGCCATGCGTGTTCAAGCTGAGAGGCCTCCATGGTATATTTCAGTCGTTGGAGGGGCTTTATATGTAAGA
CAAACTATGCCACTCATTAGCATTTATGTGAAGCAAATGCGGAAAACATGATCAATATGTCGTCTTATTTAAAT
TTATTTATTTTTGTGCTGCAGAAAACAGTAACTGCCAACACGGCCACTGTTTCTGATTATGTTGGTTATCTTAC
CAAGGGCCAGATTCCACCAAAGGTACTATTCTGTTTTTTCAGGATATGAATGCTGTTTGAATGTGAAAACCATT
GACCATAAATCCTTGTTTGCAGCATATATCCCTTGTCTATACGACTGTTGCTTTGAATATAGATGGGAAAAAAT
ATACAGTAAGTGTGACATTCTTAATGGGGAAACTTAATTTGTTGTAAATAATCAATATCATATTGACTCGTGTA
TGCTGCATCATAGATCGATACTGTGAGGAGTGGACATGGTAGCTACAGATTGCGAATGAATGGATCAACGGTTG
ACGCAAATGTACAAATATTATGTGATGGTGGGCTTTTAATGCAGGTAATATCTTCTTCCTAGTTAAAGAAGATA
TATCTTGTTCAAAGAATTCTGATTATTGATCTTTTAATGTTTTCAGCTGGATGGAAACAGCCATGTAATTTATG
CTGAAGAAGAGGCCAGTGGTACACGACTTCTTATTGATGGAAAGACATGCATGTTACAGGTAATGATAGCCTTG
TTCTTTTTAGTTCTAGTCACGGTGTTTGCTTGCTATTTGTTGTATCTATTTAATGCATTCACTAATTACTATAT
TAGTTTGCATCATCAAGTTAAAATGGAACTTCTTTCTTGCAGAATGACCATGACCCATCAAAGTTATTAGCTGA
GACACCATGCAAACTTCTTCGTTTCTTGGTTGCTGATGGTGCTCATGTTGATGCTGATGTACCATATGCGGAAG
TTGAGGTTATGAAGATGTGCATGCCCCTCTTATCACCCGCTTCTGGTGTCATACATGTTGTAATGTCTGAGGGC
CAAGCAATGCAGGTACATTCCTACATTCCATTCATTGTGCTGTGCTGACATGAACATTTCAAGTAAATACCTGT
AACTTGTTTATTATTCTAGGCTGGTGATCTTATAGCTAGGCTGGATCTTGATGACCCTTCTGCTGTTAAGAGAG
CTGAGCCGTTCGAAGATACTTTTCCACAAATGGGTCTCCCTATTGCTGCTTCTGGCCAAGTTCACAAATTATGT
GCTGCAAGTCTGAATGCTTGTCGAATGATCCTTGCGGGGTATGAGCATGATATTGACAAGGTAAACATCATGTC
CTCTTGTTTTTTCTTTTGTTTATCATGCATTCTTATGTTCATCATGTCCTCTGGCAAATCTAGATTCCGCTGTC
GTTTCACACAGATTTTTCTCATTCTCATAATGGTGCCAAACATAAATATGCTGCTATATTCATCAATGTTTTCA
CTCGATTTCTAATTTTGCTTTTGAGTTTTAAACTTTAGTACAATCCATATCTAATCTCCTTTGGCAACAGTGAA
TCCATTATATATATTTTTATTAAACTGCTTTCTTTTTCAGGTTGTGCCAGAGTTGGTATACTGCCTAGACACTC
CGGAGCTTCCTTTCCTGCAGTGGGAGGAGCTTATGTCTGTTTTAGCAACTAGACTTCCAAGAAATCTTAAAAGT
GAGGTATATTATGGTTGACAAGATAGCTAGTCTCATGCTCTAAGGACTTGTACATTTCGCCACATAGGTTAATT
TTCCATATCAAGTTCTAATGTACGATATAAAAGTAGTACTGGCCTAAAACAGTATTGGTGGTTGACTATCTTTG
TTGTGTAAGATCAAGTATTTCTTTTTCATGCTTAGTTTGTCAATACTTCACATTTATCACTGACTTGTCGAGCT
AAATGAGATTTTATTTGATTTCTGTGCTCCATTATTTTTGTATATATATATATATATATTTAACTATGACTATATG
TTATGCCTCAAACGTTTCAAACTCTTTCAGTTGGAGGGCAAATATGAGGAATACAAAGTAAAATTTGACTCTGG
GATAATCAATGATTTCCCTGCCAATATGCTACGAGTGATAATTGAGGTCAGTTATTCAATTTGTTGTGATAATC
ACTGCCTTAACTGTTCGTTCTTTTAACAAGCGGTTTTATAGGAAAATCTTGCATGTGGTTCTGAGAAGGAGAAG
GCTACAAATGAGAGGCTTGTTGAGCCTCTTATGAGCCTACTGAAGTCATATGAGGGTGGAGAGAAAGTCATGC
TCACTTTGTTGTCAAGTCCCTTTTTGAGGAGTATCTCTATGTTGAAGAATTGTTCAGTGATGGAATTCAGGTTA
ACTTACCTATTCGCATTAAACAAATCATCAGTTGTTTTATGATAAAGTCAAAATGTTTATATTTCCCATTCTTC
TGTGGATCAAATATATCACGGACATGATATAGTTTCCTTAGGCTATATAATGGTTCTTCATCAAATAATATTGC
AGGAAACAGTATAGCAAACTATTTGTATATACTCGAGATGGAAATTGTTAGAAACATCATTGACTAAATCTGTC
CTTTGTTACGCTGTTTTTGTAGTCTGATGTGATTGAGCGTCTGCGCCTTCAACATAGTAAAGACCTACAGAAGG
TCGTAGACATTGTGTTGTCCCACCAGGTAAATTTCTTCATGGTCTGATGACTTCACTGCGAATGGTTACTGAAC
TGTCTTCTTGTTCTGACAATGTGACTTTTCTTTGTAGAGTGTTAGAAATAAAACTAAGCTGATACTAAAACTCA
TGGAGAGTCTGGTCTATCCAAATCCTGCTGCCTACAGGGATCAATTGATTCGCTTTTCTTCCCTTAATCACAAA
GCGTATTACAAGGTGACCAGGATAAACATAAATAAACGTGAATTTTTCAATGACCTTTTCTTCTGACATCTGAA
TCTGATGAATTTCTTGCATATTAATACAGTTGGCACTTAAAGCTAGTGAACTTCTTGAACAAACAAAACTTAGT

FIGURE 7A (continued)

GAGCTCCGTGCAAGAATAGCAAGGAGCCTTTCAGAGCTGGAGATGTTTACTGAGGAAAGCAAGGGTCTCTCCAT
GCATAAGCGAGAAATTGCCATTAAGGAGAGCATGGAAGATTTAGTCACTGCTCCACTGCCAGTTGAAGATGCGC
TCATTTCTTTATTTGATTGTAGTGATACAACTGTTCAACAGAGAGTGATTGAGACTTATATAGCTCGATTATAC
CAGGTATGAGAAGAAAGACCTTTTGAAATTATTTATATTAACATATCCTAGTAAAACAGCATGCTCATCATTTC
TTAAAAAAAGTTTACAGCACCTGATGTTTGGTTACTGACCGCATCATTAAAATAAAGTTACTTGTTGTGGAGAG
ATGTATTTTGGAACTTGTGGCACATGCAGTAACATGCTACTGCTCGATATGTTTGCTAACTTGACAACAATATT
TTTCAGCCTCATCTTGTAAAGGACAGTATCAAAATGAAATGGATAGAATCGGGTGTTATTGCTTTATGGGAATT
TCCTGAAGGGCATTTTGATGCAAGAAATGGAGGAGCGGTTCTTGGTGACAAAAGATGGGGTGCCATGGTCATTG
TCAAGTCTCTTGAATCACTTTCAATGGCCATTAGATTTGCACTAAAGGAGACATCACACTACACTAGCTCTGAG
GGCAATATGATGCATATTGCTTTGTTGGGTGCTGATAATAAGATGCATATAATTCAAGAAAGGTATGTTCATAT
GCTATGTTGGTGCTGAAATAGTTATATATGTAGTTAGCTGGTGGAGTTCTGGTAATTAACCTATCCCATTGTTC
AGTGGTGATGATGCTGACAGAATAGCCAAACTTCCCTTGATACTAAAGGATAATGTAACCGATCTGCATGCCTC
TGGTGTGAAAACAATAAGTTTCATTGTTCAAAGAGATGAAGCACGGATGACAATGCGTCGTACCTTCCTTTGGT
CTGATGAAAAGCTTTCTTATGAGGAAGAGCCAATTCTCCGGCATGTGGAACCTCCTCTTTCTGCACTTCTTGAG
TTGGTACGTGATATCATCAAAATGATAATGTTTTGGTATGGCATTGATTATCTTCTATGCTCTTTGTATTTATT
CAGCCTATTGTGGATACAGGACAAGTTGAAAGTGAAAGGATACAATGAAATGAAGTATACCCCATCACGGGATC
GTCAATGGCATATCTACACACTTAGAAATACTGAAAACCCCAAAATGTTGCACCGGGTATTTTTCCGAACCCTT
GTCAGGCAACCCAGTGTATCCAACAAGTTTTCTTCGGGCCAGATTGGTGACATGGAAGTTGGGAGTGCTGAAGA
ACCTCTGTCATTTACATCAACCAGCATATTAAGATCTTTGATGACTGCTATAGAGGAATTGGAGCTTCACGCAA
TTAGAACTGGCCATTCACACATGTATTTGCATGTATTGAAAGAACAAAAGCTTCTTGATCTTGTTCCAGTTTCA
GGGTAAGTGCGCATATTTCTTTTTGGGAACATATGCTTGCTTATGAGGTTGGTCTTCTCAATGATCTTCTTATC
TTACTCAGGAATACAGTTTTGGATGTTGGTCAAGATGAAGCTACTGCATATTCACTTTTAAAAGAAATGGCTAT
GAAGATACATGAACTTGTTGGTGCAAGAATGCACCATCTTTCTGTATGCCAATGGGAAGTGAAACTTAAGTTGG
ACTGCGATGGTCCTGCCAGTGGTACCTGGAGGATTGTAACAACCAATGTTACTAGTCACACTTGCACTGTGGAT
GTAAGTTTAATCCTCTAGCATTTTGTTTTCTTTGGAAAAGCATGTGATTTTAAGCCGGCTGGTCCTCATACCCA
GACCTAGTGATCTTTATATAGTGTAGACATTTTTCTAACTGCTTTTAATTGTTTTAGATCTACCGTGAGATGGA
AGATAAAGAATCACGGAAGTTAGTATACCATCCCGCCACTCCGGCGGCTGGTCCTCTGCATGGTGTGGCACTGA
ATAATCCATATCAGCCTTTGAGTGTCATTGATCTCAAACGCTGTTCTGCTAGGAATAATAGAACTACATACTGC
TATGATTTTCCACTGGTGAGTTGACTGCTCCCTTATATTCAATGCATTACCATAGCAAATTCATATTCGTTCAT
GTTGTCAAAATAAGCCGATGAAAATTCAAAACTGTAGGCATTTGAAACTGCAGTGAGGAAGTCATGGTCCTCTA
GTACCTCTGGTGCTTCTAAAGGTGTTGAAAATGCCCAATGTTATGTTAAAGCTACAGAGTTGGTATTTGCGGAC
AAACATGGGTCATGGGGCACTCCTTTAGTTCAAATGGACCGGCCTGCTGGGCTCAATGACATTGGTATGGTAGC
TTGGACCTTGAAGATGTCCACTCCTGAATTTCCTAGTGGTAGGGAGATTATTGTTGTTGCAAATGATATTACGT
TCAGAGCTGGATCATTTGGCCCAAGGGAAGATGCATTTTTTGAAGCTGTTACCAACCTAGCCTGTGAGAAGAAA
CTTCCTCTTATTTATTTGGCAGCAAATTCTGGTGCTCGAATTGGCATAGCAGATGAAGTGAAATCTTGCTTCCG
TGTTGGGTGGTCTGATGATGGCAGCCCTGAACGTGGGTTTCAGTACATTTATCTAAGCGAAGAAGACTATGCTC
GTATTGGCACTTCTGTCATAGCACATAAGATGCAGCTAGACAGTGGTGAAATTAGGTGGGTTATTGATTCTGTT
GTGGGCAAGGAAGATGGACTTGGTGTGGAGAATATACATGGAAGTGCTGCTATTGCCAGTGCTTATTCTAGGGC
ATATAAGGAGACATTTACACTTACATTTGTGACTGGAAGAACTGTTGGAATAGGAGCTTATCTTGCTCGACTTG
GCATCCGGTGCATACAGCGTCTTGACCAGCCTATTATTCTTACAGGCTATTCTGCACTGAACAAGCTTCTTGGG
CGGGAAGTGTACAGCTCCCACATGCAGTTGGGTGGTCCCAAAATCATGGCAACTAATGGTGTTGTCCATCTTAC
TGTTTCAGATGACCTTGAAGGCGTTTCTAATATATTGAGGTGGCTCAGTTATGTTCCTGCCTACATTGGTGGAC
CACTTCCAGTAACAACACCGTTGGACCCACCGGACAGACCTGTTGCATACATTCCTGAGAACTCGTGTGATCCT
CGAGCGGCTATCCGTGGTGTTGATGACAGCCAAGGGAAATGGTTAGGTGGTATGTTTGATAAAGACAGCTTTGT
GGAAACATTTGAAGGTTGGGCTAAGACAGTGGTTACTGGCAGAGCAAAGCTTGGTGGAATTCCAGTGGGTGTGA
TAGCTGTGGAGACTCAGACCATGATGCAAACTATCCCTGCTGACCCTGGTCAGCTTGATTCCCGTGAGCAATCT
GTTCCTCGTGCTGGACAAGTGTGGTTTCCAGATTCTGCAACCAAGACTGCGCAGGCATTGCTGGACTTCAACCG
TGAAGGATTACCTCTGTTCATCCTCGCTAACTGGAGAGGCTTCTCTGGTGGACAAAGAGATCTTTTTGAAGGAA
TTCTTCAGGCTGGCTCGACTATTGTTGAGAACCTTAGGACATACAATCAGCCTGCCTTTGTCTACATTCCCATG
GCTGCAGAGCTACGAGGAGGGGCTTGGGTTGTGGTTGATAGCAAGATAAACCCAGACCGCATTGAGTGCTATGC
TGAGAGGACTGCAAAAGGCAATGTTCTGGAACCGCAAGGGTTAATTGAGATCAAGTTCAGGTCAGAGGAACTCC
AGGATTGCATGAGTCGGCTTGACCCAACATTAATTGATCTGAAAGCAAAACTCGAAGTAGCAAATAAAAATGGA
AGTGCTGACACAAAATCGCTTCAAGAAAATATAGAAGCTCGAACAAAACAGTTGATGCCTCTATATACTCAGAT
TGCGATACGGTTTGCTGAATTGCATGATACATCCCTCAGAATGGCTGCGAAAGGTGTGATTAAGAAAGTTGTGG

FIGURE 7A (continued)

ACTGGGAAGAATCACGATCTTTCTTCTATAAGAGATTACGGAGGAGGATCTCTGAGGATGTTCTTGCAAAAGAA
ATTAGAGCTGTAGCAGGTGAGCAGTTTTCCCACCAACCAGCAATCGAGCTGATCAAGAAATGGTATTCAGCTTC
ACATGCAGCTGAATGGGATGATGACGATGCTTTTGTTGCTTGGATGGATAACCCTGAAAACTACAAGGATTATA
TTCAATATCTTAAGGCTCAAAGAGTATCCCAATCCCTCTCAAGTCTTTCAGATTCCAGCTCAGATTTGCAAGCC
CTGCCACAGGGTCTTTCCATGTTACTAGATAAGGTAATTAGCTTACTGATGCTTATATAAATTCTTTTTCATTA
CATATGGCTGGAGAACTATCTAATCAAATAATGATTATAATTCCAATCGTTCTTTTTATGCCATTATGATCTTC
TGAAATTTCCTTCTTTGGACACTTATTCAGATGGATCCCTCTAGAAGAGCTCAACTTGTTGAAGAAATCAGGAA
GGTCCTTGGTTGA

FIGURE 7B

**>*Oryza sativa* Plastidic ACCase protein coding sequence**

ATGACATCCACACATGTGGCGACATTGGGAGTTGGTGCCCAGGCACCTCCTCGTCACCAGAAAAAGTCAGCTGG
CACTGCATTTGTATCATCTGGGTCATCAAGACCCTCATACCGAAAGAATGGTCAGCGTACTCGGTCACTTAGGG
AAGAAAGCAATGGAGGAGTGTCTGATTCCAAAAAGCTTAACCACTCTATTCGCCAAGGTCTTGCTGGCATCATT
GACCTCCCAAATGACGCAGCTTCAGAAGTTGATATTTCACATGGTTCCGAAGATCCCAGGGGGCCTACGGTCCC
AGGTTCCTACCAAATGAATGGGATTATCAATGAAACACATAATGGGAGGCATGCTTCAGTCTCCAAGGTTGTTG
AGTTTTGTACGGCACTTGGTGGCAAAACACCAATTCACAGTGTATTAGTGGCCAACAATGGAATGGCAGCAGCT
AAGTTCATGCGGAGTGTCCGAACATGGGCTAATGATACTTTTGGATCAGAGAAGGCAATTCAGCTGATAGCTAT
GGCAACTCCGGAGGATCTGAGGATAAATGCAGAGCACATCAGAATTGCCGATCAATTTGTAGAGGTACCTGGTG
GAACAAACAACAACAACTATGCAAATGTCCAACTCATAGTGGAGATAGCAGAGAGAACAGGTGTTTCTGCTGTT
TGGCCTGGTTGGGGTCATGCATCTGAGAATCCTGAACTTCCAGATGCGCTGACTGCAAAAGGAATTGTTTTTCT
TGGGCCACCAGCATCATCAATGCATGCATTAGGAGACAAGGTTGGCTCAGCTCTCATTGCTCAAGCAGCTGGAG
TTCCAACACTTGCTTGGAGTGGATCACATGTGGAAGTTCCTCTGGAGTGTTGCTTGGACTCAATACCTGATGAG
ATGTATAGAAAAGCTTGTGTTACTACCACAGAGGAAGCAGTTGCAAGTTGTCAGGTGGTTGGTTATCCTGCCAT
GATTAAGGCATCTTGGGGTGGTGGTGGTAAAGGAATAAGGAAGGTTCATAATGATGATGAGGTTAGGACATTAT
TTAAGCAAGTTCAAGGCGAAGTACCTGGTTCCCCAATATTTATCATGAGGCTAGCTGCTCAGAGTCGACATCTT
GAAGTTCAGTTGCTTTGTGATCAATATGGCAACGTAGCAGCACTTCACAGTCGAGATTGCAGTGTACAACGGCG
ACACCAAAAGATAATCGAGGAAGGACCAGTTACTGTTGCTCCTCGTGAGACTGTGAAAGAGCTTGAGCAGGCAG
CACGGAGGCTTGCTAAAGCTGTGGGTTATGTTGGTGCTGCTACTGTTGAATACCTTTACAGCATGGAAACTGGT
GAATATTATTTTCTGGAACTTAATCCACGGCTACAGGTTGAGCATCCTGTCACTGAGTGGATAGCTGAAGTAAA
TTTGCCTGCGGCTCAAGTTGCTGTTGGAATGGGTATACCCCTTTGGCAGATTCCAGAGATCAGGCGCTTCTACG
GAATGAACCATGGAGGAGGCTATGACCTTTGGAGGAAAACAGCAGCTCTAGCGACTCCATTTAACTTTGATGAA
GTAGATTCTAAATGGCCAAAAGGCCACTGCGTAGCTGTTAGAATAACTAGCGAGGATCCAGATGATGGGTTTAA
GCCTACTGGTGGAAAAGTAAAGGAGATAAGTTTCAAGAGTAAACCAAATGTTTGGGCCTATTTCTCAGTAAAGT
CTGGTGGAGGCATCCATGAATTCGCTGATTCTCAGTTCGGACATGTTTTTGCGTATGGAACTACTAGATCGGCA
GCAATAACTACCATGGCTCTTGCACTAAAAGAGGTTCAAATTCGTGGAGAAATTCATTCAAACGTAGACTACAC
AGTTGACCTATTAAATGCCTCAGATTTTAGAGAAAATAAGATTCATACTGGTTGGCTGGATACCAGGATAGCCA
TGCGTGTTCAAGCTGAGAGGCCTCCATGGTATATTTCAGTCGTTGGAGGGGCTTTATATAAAACAGTAACTGCC
AACACGGCCACTGTTTCTGATTATGTTGGTTATCTTACCAAGGGCCAGATTCCACCAAAGCATATATCCCTTGT
CTATACGACTGTTGCTTTGAATATAGATGGGAAAAAATATACAATCGATACTGTGAGGAGTGGACATGGTAGCT
ACAGATTGCGAATGAATGGATCAACGGTTGACGCAAATGTACAAATATTATGTGATGGTGGGCTTTTAATGCAG
CTGGATGGAAACAGCCATGTAATTTATGCTGAAGAAGAGGCCAGTGGTACACGACTTCTTATTGATGGAAAGAC
ATGCATGTTACAGAATGACCATGACCCATCAAAGTTATTAGCTGAGACACCATGCAAACTTCTTCGTTTCTTGG
TTGCTGATGGTGCTCATGTTGATGCTGATGTACCATATGCGGAAGTTGAGGTTATGAAGATGTGCATGCCCCTC
TTATCACCCGCTTCTGGTGTCATACATGTTGTAATGTCTGAGGGCCAAGCAATGCAGGCTGGTGATCTTATAGC
TAGGCTGGATCTTGATGACCCTTCTGCTGTTAAGAGAGCTGAGCCGTTCGAAGATACTTTTCCACAAATGGGTC
TCCCTATTGCTGCTTCTGGCCAAGTTCACAAATTATGTGCTGCAAGTCTGAATGCTTGTCGAATGATCCTTGCG
GGGTATGAGCATGATATTGACAAGGTTGTGCCAGAGTTGGTATACTGCCTAGACACTCCGGAGCTTCCTTTCCT
GCAGTGGGAGGAGCTTATGTCTGTTTTAGCAACTAGACTTCCAAGAAATCTTAAAAGTGAGTTGGAGGGCAAAT
ATGAGGAATACAAAGTAAAATTTGACTCTGGGATAATCAATGATTTCCCTGCCAATATGCTACGAGTGATAATT
GAGGAAAATCTTGCATGTGGTTCTGAGAAGGAGAAGGCTACAAATGAGAGGCTTGTTGAGCCTCTTATGAGCCT
ACTGAAGTCATATGAGGGTGGGAGAGAAAGTCATGCTCACTTTGTTGTCAAGTCCCTTTTTGAGGAGTATCTCT
ATGTTGAAGAATTGTTCAGTGATGGAATTCAGTCTGATGTGATTGAGCGTCTGCGCCTTCAACATAGTAAAGAC
CTACAGAAGGTCGTAGACATTGTGTTGTCCCACCAGAGTGTTAGAAATAAAACTAAGCTGATACTAAAACTCAT
GGAGAGTCTGGTCTATCCAAATCCTGCTGCCTACAGGGATCAATTGATTCGCTTTTCTTCCCTTAATCACAAAG
CGTATTACAAGTTGGCACTTAAAGCTAGTGAACTTCTTGAACAAACAAAACTTAGTGAGCTCCGTGCAAGAATA
GCAAGGAGCCTTTCAGAGCTGGAGATGTTTACTGAGGAAAGCAAGGGTCTCTCCATGCATAAGCGAGAAATTGC

FIGURE 7B (continued)

CATTAAGGAGAGCATGGAAGATTTAGTCACTGCTCCACTGCCAGTTGAAGATGCGCTCATTTCTTTATTTGATT
GTAGTGATACAACTGTTCAACAGAGAGTGATTGAGACTTATATAGCTCGATTATACCAGCCTCATCTTGTAAAG
GACAGTATCAAAATGAAATGGATAGAATCGGGTGTTATTGCTTTATGGGAATTTCCTGAAGGGCATTTTGATGC
AAGAAATGGAGGAGCGGTTCTTGGTGACAAAAGATGGGGTGCCATGGTCATTGTCAAGTCTCTTGAATCACTTT
CAATGGCCATTAGATTTGCACTAAAGGAGACATCACACTACACTAGCTCTGAGGGCAATATGATGCATATTGCT
TTGTTGGGTGCTGATAATAAGATGCATATAATTCAAGAAAGTGGTGATGATGCTGACAGAATAGCCAAACTTCC
CTTGATACTAAAGGATAATGTAACCGATCTGCATGCCTCTGGTGTGAAAACAATAAGTTTCATTGTTCAAAGAG
ATGAAGCACGGATGACAATGCGTCGTACCTTCCTTTGGTCTGATGAAAAGCTTTCTTATGAGGAAGAGCCAATT
CTCCGGCATGTGGAACCTCCTCTTTCTGCACTTCTTGAGTTGGACAAGTTGAAAGTGAAAGGATACAATGAAAT
GAAGTATACCCCATCACGGGATCGTCAATGGCATATCTACACACTTAGAAATACTGAAAACCCCAAAATGTTGC
ACCGGGTATTTTTCCGAACCCTTGTCAGGCAACCCAGTGTATCCAACAAGTTTTCTTCGGGCCAGATTGGTGAC
ATGGAAGTTGGGAGTGCTGAAGAACCTCTGTCATTTACATCAACCAGCATATTAAGATCTTTGATGACTGCTAT
AGAGGAATTGGAGCTTCACGCAATTAGAACTGGCCATTCACACATGTATTTGCATGTATTGAAAGAACAAAAGC
TTCTTGATCTTGTTCCAGTTTCAGGGAATACAGTTTTGGATGTTGGTCAAGATGAAGCTACTGCATATTCACTT
TTAAAAGAAATGGCTATGAAGATACATGAACTTGTTGGTGCAAGAATGCACCATCTTTCTGTATGCCAATGGGA
AGTGAAACTTAAGTTGGACTGCGATGGTCCTGCCAGTGGTACCTGGAGGATTGTAACAACCAATGTTACTAGTC
ACACTTGCACTGTGGATATCTACCGTGAGATGGAAGATAAAGAATCACGGAAGTTAGTATACCATCCCGCCACT
CCGGCGGCTGGTCCTCTGCATGGTGTGGCACTGAATAATCCATATCAGCCTTTGAGTGTCATTGATCTCAAACG
CTGTTCTGCTAGGAATAATAGAACTACATACTGCTATGATTTTCCACTGGCATTTGAAACTGCAGTGAGGAAGT
CATGGTCCTCTAGTACCTCTGGTGCTTCTAAAGGTGTTGAAAATGCCCAATGTTATGTTAAAGCTACAGAGTTG
GTATTTGCGGACAAACATGGGTCATGGGGCACTCCTTTAGTTCAAATGGACCGGCCTGCTGGGCTCAATGACAT
TGGTATGGTAGCTTGGACCTTGAAGATGTCCACTCCTGAATTTCCTAGTGGTAGGGAGATTATTGTTGTTGCAA
ATGATATTACGTTCAGAGCTGGATCATTTGGCCCAAGGGAAGATGCATTTTTTGAAGCTGTTACCAACCTAGCC
TGTGAGAAGAAACTTCCTCTTATTTATTTGGCAGCAAATTCTGGTGCTCGAATTGGCATAGCAGATGAAGTGAA
ATCTTGCTTCCGTGTTGGGTGGTCTGATGATGGCAGCCCTGAACGTGGGTTTCAGTACATTTATCTAAGCGAAG
AAGACTATGCTCGTATTGGCACTTCTGTCATAGCACATAAGATGCAGCTAGACAGTGGTGAAATTAGGTGGGTT
ATTGATTCTGTTGTGGGCAAGGAAGATGGACTTGGTGTGGAGAATATACATGGAAGTGCTGCTATTGCCAGTGC
TTATTCTAGGGCATATAAGGAGACATTTACACTTACATTTGTGACTGGAAGAACTGTTGGAATAGGAGCTTATC
TTGCTCGACTTGGCATCCGGTGCATACAGCGTCTTGACCAGCCTATTATTCTTACAGGCTATTCTGCACTGAAC
AAGCTTCTTGGGCGGGAAGTGTACAGCTCCCACATGCAGTTGGGTGGTCCCAAAATCATGGCAACTAATGGTGT
TGTCCATCTTACTGTTTCAGATGACCTTGAAGGCGTTTCTAATATATTGAGGTGGCTCAGTTATGTTCCTGCCT
ACATTGGTGGACCACTTCCAGTAACAACACCGTTGGACCCACCGGACAGACCTGTTGCATACATTCCTGAGAAC
TCGTGTGATCCTCGAGCGGCTATCCGTGGTGTTGATGACAGCCAAGGGAAATGGTTAGGTGGTATGTTTGATAA
AGACAGCTTTGTGGAAACATTTGAAGGTTGGGCTAAGACAGTGGTTACTGGCAGAGCAAAGCTTGGTGGAATTC
CAGTGGGTGTGATAGCTGTGGAGACTCAGACCATGATGCAAACTATCCCTGCTGACCCTGGTCAGCTTGATTCC
CGTGAGCAATCTGTTCCTCGTGCTGGACAAGTGTGGTTTCCAGATTCTGCAACCAAGACTGCGCAGGCATTGCT
GGACTTCAACCGTGAAGGATTACCTCTGTTCATCCTCGCTAACTGGAGAGGCTTCTCTGGTGGACAAAGAGATC
TTTTTGAAGGAATTCTTCAGGCTGGCTCGACTATTGTTGAGAACCTTAGGACATACAATCAGCCTGCCTTTGTC
TACATTCCCATGGCTGCAGAGCTACGAGGAGGGGCTTGGGTTGTGGTTGATAGCAAGATAAACCCAGACCGCAT
TGAGTGCTATGCTGAGAGGACTGCAAAAGGCAATGTTCTGGAACCGCAAGGGTTAATTGAGATCAAGTTCAGGT
CAGAGGAACTCCAGGATTGCATGAGTCGGCTTGACCCAACATTAATTGATCTGAAAGCAAAACTCGAAGTAGCA
AATAAAAATGGAAGTGCTGACACAAAATCGCTTCAAGAAAATATAGAAGCTCGAACAAAACAGTTGATGCCTCT
ATATACTCAGATTGCGATACGGTTTGCTGAATTGCATGATACATCCCTCAGAATGGCTGCGAAAGGTGTGATTA
AGAAAGTTGTGGACTGGGAAGAATCACGATCTTTCTTCTATAAGAGATTACGGAGGAGGATCTCTGAGGATGTT
CTTGCAAAAGAAATTAGAGCTGTAGCAGGTGAGCAGTTTTCCCACCAACCAGCAATCGAGCTGATCAAGAAATG
GTATTCAGCTTCACATGCAGCTGAATGGGATGATGACGATGCTTTTGTTGCTTGGATGGATAACCCTGAAAACT
ACAAGGATTATATTCAATATCTTAAGGCTCAAAGAGTATCCCAATCCCTCTCAAGTCTTTCAGATTCCAGCTCA
GATTTGCAAGCCCTGCCACAGGGTCTTTCCATGTTACTAGATAAGATGGATCCCTCTAGAAGAGCTCAACTTGT
TGAAGAAATCAGGAAGGTCCTTGGTTGA

FIGURE 7C

**>*Oryza sativa* Plastidic ACCase protein**

MTSTHVATLGVGAQAPPRHQKKSAGTAFVSSGSSRPSYRKNGQRTRSLREESNGGVSDSKKLNHSIRQGLAGII
DLPNDAASEVDISHGSEDPRGPTVPGSYQMNGIINETHNGRHASVSKVVEFCTALGGKTPIHSVLVANNGMAAA
KFMRSVRTWANDTFGSEKAIQLIAMATPEDLRINAEHIRIADQFVEVPGGTNNNNYANVQLIVEIAERTGVSAV
WPGWGHASENPELPDALTAKGIVFLGPPASSMHALGDKVGSALIAQAAGVPTLAWSGSHVEVPLECCLDSIPDE
MYRKACVTTTEEAVASCQVVGYPAMIKASWGGGGKGIRKVHNDDEVRTLFKQVQGEVPGSPIFIMRLAAQSRHL
EVQLLCDQYGNVAALHSRDCSVQRRHQKIIEEGPVTVAPRETVKELEQAARRLAKAVGYVGAATVEYLYSMETG
EYYFLELNPRLQVEHPVTEWIAEVNLPAAQVAVGMGIPLWQIPEIRRFYGMNHGGGYDLWRKTAALATPFNFDE
VDSKWPKGHCVAVRITSEDPDDGFKPTGGKVKEISFKSKPNVWAYFSVKSGGGIHEFADSQFGHVFAYGTTRSA
AITTMALALKEVQIRGEIHSNVDYTVDLLNASDFRENKIHTGWLDTRIAMRVQAERPPWYISVVGGALYKTVTA
NTATVSDYVGYLTKGQIPPKHISLVYTTVALNIDGKKYTIDTVRSGHGSYRLRMNGSTVDANVQILCDGGLLMQ
LDGNSHVIYAEEEASGTRLLIDGKTCMLQNDHDPSKLLAETPCKLLRFLVADGAHVDADVPYAEVEVMKMCMPL
LSPASGVIHVVMSEGQAMQAGDLIARLDLDDPSAVKRAEPFEDTFPQMGLPIAASGQVHKLCAASLNACRMILA
GYEHDIDKVVPELVYCLDTPELPFLQWEELMSVLATRLPRNLKSELEGKYEEYKVKFDSGIINDFPANMLRVII
EENLACGSEKEKATNERLVEPLMSLLKSYEGGRESHAHFVVKSLFEEYLYVEELFSDGIQSDVIERLRLQHSKD
LQKVVDIVLSHQSVRNKTKLILKLMESLVYPNPAAYRDQLIRFSSLNHKAYYKLALKASELLEQTKLSELRARI
ARSLSELEMFTEESKGLSMHKREIAIKESMEDLVTAPLPVEDALISLFDCSDTTVQQRVIETYIARLYQPHLVK
DSIKMKWIESGVIALWEFPEGHFDARNGGAVLGDKRWGAMVIVKSLESLSMAIRFALKETSHYTSSEGNMMHIA
LLGADNKMHIIQESGDDADRIAKLPLILKDNVTDLHASGVKTISFIVQRDEARMTMRRTFLWSDEKLSYEEEPI
LRHVEPPLSALLELDKLKVKGYNEMKYTPSRDRQWHIYTLRNTENPKMLHRVFFRTLVRQPSVSNKFSSGQIGD
MEVGSAEEPLSFTSTSILRSLMTAIEELELHAIRTGHSHMYLHVLKEQKLLDLVPVSGNTVLDVGQDEATAYSL
LKEMAMKIHELVGARMHHLSVCQWEVKLKLDCDGPASGTWRIVTTNVTSHTCTVDIYREMEDKESRKLVYHPAT
PAAGPLHGVALNNPYQPLSVIDLKRCSARNNRTTYCYDFPLAFETAVRKSWSSSTSGASKGVENAQCYVKATEL
VFADKHGSWGTPLVQMDRPAGLNDIGMVAWTLKMSTPEFPSGREIIVVANDITFRAGSFGPREDAFFEAVTNLA
CEKKLPLIYLAANSGARIGIADEVKSCFRVGWSDDGSPERGFQYIYLSEEDYARIGTSVIAHKMQLDSGEIRWV
IDSVVGKEDGLGVENIHGSAAIASAYSRAYKETFTLTFVTGRTVGIGAYLARLGIRCIQRLDQPIILTGYSALN
KLLGREVYSSHMQLGGPKIMATNGVVHLTVSDDLEGVSNILRWLSYVPAYIGGPLPVTTPLDPPDRPVAYIPEN
SCDPRAAIRGVDDSQGKWLGGMFDKDSFVETFEGWAKTVVTGRAKLGGIPVGVIAVETQTMMQTIPADPGQLDS
REQSVPRAGQVWFPDSATKTAQALLDFNREGLPLFILANWRGFSGGQRDLFEGILQAGSTIVENLRTYNQPAFV
YIPMAAELRGGAWVVVDSKINPDRIECYAERTAKGNVLEPQGLIEIKFRSEELQDCMSRLDPTLIDLKAKLEVA
NKNGSADTKSLQENIEARTKQLMPLYTQIAIRFAELHDTSLRMAAKGVIKKVVDWEESRSFFYKRLRRRISEDV
LAKEIRAVAGEQFSHQPAIELIKKWYSASHAAEWDDDDAFVAWMDNPENYKDYIQYLKAQRVSQSLSSLSDSSS
DLQALPQGLSMLLDKMDPSRRAQLVEEIRKVLG*

FIGURE 8A

>AY312172_Zea mays

ATGTCACAGCTTGGATTAGCCGCAGCTGCCTCAAAGGCCTTGCCACTACTCCCTAATCGCCAGAGAAGTTCAGCTGG
GACTACATTCTCATCATCTTCATTATCGAGGCCCTTAAACAGAAGGAAAAGCCGTACTCGTTCACTCCGTGATGGCG
GAGATGGGGTATCAGATGCCAAAAAGCACAGCCAGTCTGTTCGTCAAGGTCTTGCTGGCATTATCGACCTCCCAAGT
GAGGCACCTTCCGAAGTGGATATTTCACATGGATCTGAGGATCCTAGGGGGCCAACAGATTCTTATCAAATGAATGG
GATTATCAATGAAACACATAATGGAAGACATGCCTCAGTGTCCAAGGTTGTTGAATTTTGTGCGGCACTAGGTGGCA
AAACACCAATTCACAGTATATTAGTGGCCAACAATGGAATGGCAGCAGCAAAATTTATGAGGAGTGTCCGGACATGG
GCTAATGATACTTTTGGATCTGAGAAGGCAATTCAACTCATAGCTATGGCAACTCCGGAAGACATGAGGATAAATGC
AGAACACATTAGAATTGCTGACCAATTCGTAGAGGTGCCTGGTGGAACAAACAATAATAACTACGCCAATGTTCAAC
TCATAGTGGAGATGGCACAAAAACTAGGTGTTTCTGCTGTTTGGCCTGGTTGGGGTCATGCTTCTGAGAATCCTGAA
CTGCCAGATGCATTGACCGCAAAAGGGATCGTTTTTCTTGGCCCACCTGCATCATCAATGAATGCTTTGGGAGATAA
GGTCGGCTCAGCTCTCATTGCTCAAGCAGCCGGGGTCCCAACTCTTGCTCGGAGTGGATCACATGTTGAAGTTCCAT
TAGAGTGCTGCTTAGACGCGATACCTGAGGAGATGTATAGAAAAGCTTGCGTTACTACCACAGAGGAAGCAGTTGCA
AGTTGTCAAGTGGTTGGTTATCCTGCCATGATTAAGGCATCCTGGGGAGGTGGTGGTAAAGGAATAAGAAAGGTTCA
TAATGATGATGAGGTTAGAGCGCTGTTTAAGCAAGTACAAGGTGAAGTCCCTGGCTCCCCAATATTTGTCATGAGGC
TTGCATCCCAGAGTCGGCATCTTGAAGTTCAGTTGCTTTGTGATCAATATGGTAATGTAGCAGCACTTCACAGTCGT
GATTGCAGTGTGCAACGGCGACACCAGAAGATTATTGAAGAAGGTCCAGTTACTGTTGCTCCTCGTGAGACAGTTAA
AGCACTTGAGCAGGCAGCAAGGAGGCTTGCTAAGGCTGTGGGTTATGTTGGTGCTGCTACTGTTGAGTATCTTTACA
GCATGGAAACTGGAGACTACTATTTTCTGGAACTTAATCCCCGACTACAGGTTGAGCATCCAGTCACCGAGTGGATA
GCTGAAGTAAATCTGCCTGCAGCTCAAGTTGCTGTTGGAATGGGCATACCTCTTTGGCAGATTCCAGAAATCAGACG
TTTCTATGGAATGGACTATGGAGGAGGGTATGACATTTGGAGGAAAACAGCAGCTCTTGCTACACCATTTAATTTTG
ATGAAGTAGATTCTCAATGGCCAAAGGGCCATTGTGTAGCAGTTAGAATTACTAGTGAGGACCCAGATGATGGTTTC
AAACCTACTGGTGGAAAGTGAAGGAGATAAGTTTTAAAAGCAAGCCTAATGTTTGGGCCTACTTCTCAGTAAAGTC
TGGTGGAGGCATTCATGAATTTGCTGATTCTCAGTTCGGACATGTTTTTGCATATGGGCTCTCTAGATCAGCAGCAA
TAACAAACATGACTCTTGCATTAAAAGAGATTCAAATTCGTGGAGAAATTCATTCAAATGTTGATTACACAGTTGAC
CTCTTAAATGCTTCAGACTTTAGAGAAAACAAGATTCATACTGGTTGGCTCGACACCAGAATAGCTATGCGTGTTCA
AGCTGAGAGGCCCCCATGGTATATTTCAGTGGTTGGAGGTGCTTTATATAAAACAGTAACCACCAATGCAGCCACTG
TTTCTGAATATGTTAGTTATCTCACCAAGGGCCAGATTCCACCAAAGCATATATCCCTTGTCAATTCTACAGTTAAT
TTGAATATAGAAGGGAGCAAATACACAATTGAAACTGTAAGGACTGGACATGGTAGCTACAGGTTGAGAATGAATGA
TTCAACAGTTGAAGCGAATGTACAATCTTTATGTGATGGTGGCCTCTTAATGCAGTTGGATGGAAACAGCCATGTAA
TTTATGCAGAAGAAGAAGCTGGTGGTACACGGCTTCAGATTGATGGAAAGACATGTTTATTGCAGAATGACCATGAT
CCATCAAAGTTATTAGCTGAGACACCCTGCAAACTTCTTCGTTTCTTGGTTGCTGATGGTGCTCATGTTGATGCGGA
TGTACCATACGCGGAAGTTGAGGTTATGAAGATGTGCATGCCTCTCTTGTCACCTGCTTCTGGTGTCATTCATTGTA
TGATGTCTGAGGGCCAGGCATTGCAGGCTGGTGATCTTATAGCAAGGTTGGATCTTGATGACCCTTCTGCTGTGAAA
AGAGCTGAGCCATTTGATGGAATATTTCCACAAATGGAGCTCCCTGTTGCTGTCTCTAGTCAAGTACACAAAAGATA
TGCTGCAAGTTTGAATGCTGCTCGAATGGTCCTTGCAGGATATGAGCACAATATTAATGAAGTCGTTCAAGATTTGG
TATGCTGCCTGGACAACCCTGAGCTTCCTTTCCTACAGTGGGATGAACTTATGTCTGTTCTAGCAACGAGGCTTCCA
AGAAATCTCAAGAGTGAGTTAGAGGATAAATACAAGGAATACAAGTTGAATTTTTACCATGGAAAAAACGAGGACTT
TCCATCCAAGTTGCTAAGAGACATCATTGAGGAAAATCTTTCTTATGGTTCAGAGAAGGAAAAGGCTACAAATGAGA
GGCTTGTTGAGCCTCTTATGAACCTACTGAAGTCATATGAGGGTGGGAGAGAGAGCCATGCACATTTTGTTGTCAAG
TCTCTTTTCGAGGAGTATCTTACAGTGGAAGAACTTTTTAGTGATGGCATTCAGTCTGACGTGATTGAAACATTGCG
GCATCAGCACAGTAAAGACCTGCAGAAGGTTGTAGACATTGTGTTGTCTCACCAGGGTGTGAGGAACAAAGCTAAGC
TTGTAACGGCACTTATGGAAAAGCTGGTTTATCCAAATCCTGGTGGTTACAGGGATCTGTTAGTTCGCTTTTCTTCC
CTCAATCATAAAAGATATTATAAGTTGGCCCTTAAAGCAAGTGAACTTCTTGAACAAACCAAACTAAGTGAACTCCG
TGCAAGCGTTGCAAGAAGCCTTTCGGATCTGGGGATGCATAAGGGAGAAATGAGTATTAAGGATAACATGGAAGATT
TAGTCTCTGCCCCATTACCTGTTGAAGATGCTCTGATTTCTTTGTTTGATTACAGTGATCGAACTGTTCAGCAGAAA
GTGATTGAGACATACATATCACGATTGTACCAGCCTCATCTTGTAAAGGATAGCATCCAAATGAAATTCAAGGAATC
TGGTGCTATTACTTTTTGGGAATTTTATGAAGGGCATGTTGATACTAGAAATGGACATGGGGCTATTATTGGTGGGA
AGCGATGGGGTGCCATGGTCGTTCTCAAATCACTTGAATCTGCGTCAACAGCCATTGTGGCTGCATTAAAGGATTCG
GCACAGTTCAACAGCTCTGAGGGCAACATGATGCACATTGCATTATTGAGTGCTGAAAATGAAAGTAATATAAGTGG
AATAAGCAGTGATGATCAAGCTCAACATAAGATGGAAAAGCTTAGCAAGATACTGAAGGATACTAGCGTTGCAAGTG
ATCTCCAAGCTGCTGGTTTGAAGGTTATAAGTTGCATTGTTCAAAGAGATGAAGCTCGCATGCCAATGCGCCACACA

FIGURE 8A (continued)

TTCCTCTGGTTGGATGACAAGAGTTGTTATGAAGAAGAGCAGATTCTCCGGCATGTGGAGCCTCCCCTCTCTACACT
TCTTGAATTGGATAAGTTGAAGGTGAAAGGATACAATGAAATGAAGTATACTCCTTCGCGTGACCGCCAATGGCATA
TCTACACACTAAGAAATACTGAAAACCCCAAAATGTTGCATAGGGTGTTTTTCCGAACTATTGTCAGGCAACCCAAT
GCAGGCAACAAGTTTACATCGGCTCAGATCAGCGACGCTGAAGTAGGATGTCCCGAAGAATCTCTTTCATTTACATC
AAATAGCATCTTAAGATCATTGATGACTGCTATTGAAGAATTAGAGCTTCATGCAATTAGGACAGGTCATTCTCACA
TGTATTTGTGCATACTGAAAGAGCAAAAGCTTCTTGACCTCATTCCATTTTCAGGGAGTACAATTGTTGATGTTGGC
CAAGATGAAGCTACCGCTTGTTCACTTTTAAAATCAATGGCTTTGAAGATACATGAGCTTGTTGGTGCAAGGATGCA
TCATCTGTCTGTATGCCAGTGGGAGGTGAAACTCAAGTTGGACTGTGATGGCCCTGCAAGTGGTACCTGGAGAGTTG
TAACTACAAATGTTACTGGTCACACCTGCACCATTGATATATACCGAGAAGTGGAGGAAATAGAATCGCAGAAGTTA
GTGTACCATTCAGCCACTTCGTCAGCTGGACCATTGCATGGTGTTGCACTGAATAATCCATATCAACCTTTGAGTGT
GATTGATCTAAAGCGCTGCTCTGCTAGGAACAACAGAACAACATATTGCTATGATTTTCCGCTGGCCTTTGAAACTG
CACTGCAGAAGTCATGGCAGTCCAATGGCTCTACTGTTTCTGAAGGCAATGAAAATAGTAAATCCTACGTGAAGGCA
ACTGAGCTAGTGTTTGCTGAAAAACATGGGTCCTGGGGCACTCCTATAATTCCGATGGAACGCCCTGCTGGGCTCAA
CGACATTGGTATGGTCGCTTGGATCATGGAGATGTCAACACCTGAATTTCCCAATGGCAGGCAGATTATTGTTGTAG
CAAATGATATCACTTTCAGAGCTGGATCATTTGGCCCAAGGGAAGATGCATTTTTTGAAACTGTCACTAACCTGGCT
TGCGAAAGGAAACTTCCTCTTATATACTTGGCAGCAAACTCTGGTGCTAGGATTGGCATAGCTGATGAAGTAAAATC
TTGCTTCCGTGTTGGATGGTCTGACGAAGGCAGTCCTGAACGAGGGTTTCAGTACATCTATCTGACTGAAGAAGACT
ATGCTCGCATTAGCTCTTCTGTTATAGCACATAAGCTGGAGCTAGATAGTGGTGAAATTAGGTGGATTATTGACTCT
GTTGTGGGCAAGGAGGATGGGCTTGGTGTCGAGAACATACATGGAAGTGCTGCTATTGCCAGTGCTTATTCTAGGGC
ATATGAGGAGACATTTACACTTACATTTGTGACTGGGCGGACTGTAGGAATAGGAGCTTATCTTGCTCGACTTGGTA
TACGGTGCATACAGCGTCTTGACCAGCCTATTATTTTAACAGGGTTTTCTGCCCTGAACAAGCTCCTTGGGCGGGAA
GTGTACAGCTCCCACATGCAGCTTGGTGGTCCTAAGATCATGGCGACTAATGGTGTTGTCCACCTCACTGTTCCAGA
TGACCTTGAAGGTGTTTCCAATATATTGAGGTGGCTCAGCTATGTTCCTGCAAACATTGGTGGACCTCTTCCTATTA
CCAAACCTCTGGACCCTCCAGACAGACCTGTTGCTTACATCCCTGAGAACACATGCGATCCACGTGCAGCTATCTGT
GGTGTAGATGACAGCCAAGGGAAATGGTTGGGTGGTATGTTTGACAAAGACAGCTTTGTGGAGACATTTGAAGGATG
GGCAAAAACAGTGGTTACTGGCAGAGCAAAGCTTGGAGGAATTCCTGTGGGCGTCATAGCTGTGGAGACACAGACCA
TGATGCAGATCATCCCTGCTGATCCAGGTCAGCTTGATTCCCATGAGCGATCTGTCCCTCGTGCTGGACAAGTGTGG
TTCCCAGATTCTGCAACCAAGACCGCTCAGGCATTATTAGACTTCAACCGTGAAGGATTGCCTCTGTTCATCCTGGC
TAATTGGAGAGGCTTCTCTGGTGGACAAAGAGATCTCTTTGAAGGAATTCTTCAGGCTGGGTCAACAATTGTCGAGA
ACCTTAGGACATCTAATCAGCCTGCTTTTGTGTACATTCCTATGGCTGGAGAGCTTCGTGGAGGAGCTTGGGTTGTG
GTCGATAGCAAAATAAATCCAGACCGCATTGAGTGTTATGCTGAAAGGACTGCCAAAGGTAATGTTCTCGAACCTCA
AGGGTTAATTGAAATCAAGTTCAGGTCAGAGGAACTCCAAGACTGTATGGGTAGGCTTGACCCAGAGTTGATAAATC
TGAAAGCAAAACTCCAAGATGTAAATCATGGAAATGGAAGTCTACCAGACATAGAAGGGATTCGGAAGAGTATAGAA
GCACGTACGAAACAGTTGCTGCCTTTATATACCCAGATTGCAATACGGTTTGCTGAATTGCATGATACTTCCCTAAG
AATGGCAGCTAAAGGTGTGATTAAGAAAGTTGTAGACTGGGAAGAATCACGCTCGTTCTTCTATAAAAGGCTACGGA
GGAGGATCGCAGAAGATGTTCTTGCAAAAGAAATAAGGCAGATAGTCGGTGATAAATTTACGCACCAATTAGCAATG
GAGCTCATCAAGGAATGGTACCTTGCTTCTCAGGCCACAACAGGAAGCACTGGATGGGATGACGATGATGCTTTTGT
TGCCTGGAAGGACAGTCCTGAAAACTACAAGGGGCATATCCAAAAGCTTAGGGCTCAAAAAGTGTCTCATTCGCTCT
CTGATCTTGCTGACTCCAGTTCAGATCTGCAAGCATTCTCGCAGGGTCTTTCTACGCTATTAGATAAGATGGATCCC
TCTCAGAGAGCGAAGTTTGTTCAGGAAGTCAAGAAGGTCCTTGATTGA

FIGURE 8B

>AAP78897_Zea mays

MSQLGLAAAASKALPLLPNRQRSSAGTTFSSSSLSRPLNRRKSRTRSLRDGGDGVSDAKKHSQSVRQGLAGIID
LPSEAPSEVDISHGSEDPRGPTDSYQMNGIINETHNGRHASVSKVVEFCAALGGKTPIHSILVANNGMAAAKFM
RSVRTWANDTFGSEKAIQLIAMATPEDMRINAEHIRIADQFVEVPGGTNNNNYANVQLIVEMAQKLGVSAVWPG
WGHASENPELPDALTAKGIVFLGPPASSMNALGDKVGSALIAQAAGVPTLARSGSHVEVPLECCLDAIPEEMYR
KACVTTTEEAVASCQVVGYPAMIKASWGGGGKGIRKVHNDDEVRALFKQVQGEVPGSPIFVMRLASQSRHLEVQ
LLCDQYGNVAALHSRDCSVQRRHQKIIEEGPVTVAPRETVKALEQAARRLAKAVGYVGAATVEYLYSMETGDYY
FLELNPRLQVEHPVTEWIAEVNLPAAQVAVGMGIPLWQIPEIRRFYGMDYGGGYDIWRKTAALATPFNFDEVDS
QWPKGHCVAVRITSEDPDDGFKPTGGKVKEISFKSKPNVWAYFSVKSGGGIHEFADSQFGHVFAYGLSRSAAIT
NMTLALKEIQIRGEIHSNVDYTVDLLNASDFRENKIHTGWLDTRIAMRVQAERPPWYISVVGGALYKTVTTNAA
TVSEYVSYLTKGQIPPKHISLVNSTVNLNIEGSKYTIETVRTGHGSYRLRMNDSTVEANVQSLCDGGLLMQLDG
NSHVIYAEEEAGGTRLQIDGKTCLLQNDHDPSKLLAETPCKLLRFLVADGAHVDADVPYAEVEVMKMCMPLLSP
ASGVIHCMMSEGQALQAGDLIARLDLDDPSAVKRAEPFDGIFPQMELPVAVSSQVHKRYAASLNAARMVLAGYE
HNINEVVQDLVCCLDNPELPFLQWDELMSVLATRLPRNLKSELEDKYKEYKLNFYHGKNEDFPSKLLRDIIEEN
LSYGSEKEKATNERLVEPLMNLLKSYEGGRESHAHFVVKSLFEEYLTVEELFSDGIQSDVIETLRHQHSKDLQK
VVDIVLSHQGVRNKAKLVTALMEKLVYPNPGGYRDLLVRFSSLNHKRYYKLALKASELLEQTKLSELRASVARS
LSDLGMHKGEMSIKDNMEDLVSAPLPVEDALISLFDYSDRTVQQKVIETYISRLYQPHLVKDSIQMKFKESGAI
TFWEFYEGHVDTRNGHGAIIGGKRWGAMVVLKSLESASTAIVAALKDSAQFNSSEGNMMHIALLSAENESNISG
ISSDDQAQHKMEKLSKILKDTSVASDLQAAGLKVISCIVQRDEARMPMRHTFLWLDDKSCYEEEQILRHVEPPL
STLLELDKLKVKGYNEMKYTPSRDRQWHIYTLRNTENPKMLHRVFFRTIVRQPNAGNKFTSAQISDAEVGCPEE
SLSFTSNSILRSLMTAIEELELHAIRTGHSHMYLCILKEQKLLDLIPFSGSTIVDVGQDEATACSLLKSMALKI
HELVGARMHHLSVCQWEVKLKLDCDGPASGTWRVVTTNVTGHTCTIDIYREVEEIESQKLVYHSATSSAGPLHG
VALNNPYQPLSVIDLKRCSARNNRTTYCYDFPLAFETALQKSWQSNGSTVSEGNENSKSYVKATELVFAEKHGS
WGTPIIPMERPAGLNDIGMVAWIMEMSTPEFPNGRQIIVVANDITFRAGSFGPREDAFFETVTNLACERKLPLI
YLAANSGARIGIADEVKSCFRVGWSDEGSPERGFQYIYLTEEDYARISSSVIAHKLELDSGEIRWIIDSVVGKE
DGLGVENIHGSAAIASAYSRAYEETFTLTFVTGRTVGIGAYLARLGIRCIQRLDQPIILTGFSALNKLLGREVY
SSHMQLGGPKIMATNGVVHLTVPDDLEGVSNILRWLSYVPANIGGPLPITKPLDPPDRPVAYIPENTCDPRAAI
CGVDDSQGKWLGGMFDKDSFVETFEGWAKTVVTGRAKLGGIPVGVIAVETQTMMQIIPADPGQLDSHERSVPRA
GQVWFPDSATKTAQALLDFNREGLPLFILANWRGFSGGQRDLFEGILQAGSTIVENLRTSNQPAFVYIPMAGEL
RGGAWVVVDSKINPDRIECYAERTAKGNVLEPQGLIEIKFRSEELQDCMGRLDPELINLKAKLQDVNHGNGSLP
DIEGIRKSIEARTKQLLPLYTQIAIRFAELHDTSLRMAAKGVIKKVVDWEESRSFFYKRLRRRIAEDVLAKEIR
QIVGDKFTHQLAMELIKEWYLASQATTGSTGWDDDDAFVAWKDSPENYKGHIQKLRAQKVSHSLSDLADSSSDL
QAFSQGLSTLLDKMDPSQRAKFVQEVKKVLD

FIGURE 9A

>AY312171_Zea mays

ATGTCACAGCTTGGATTAGCCGCAGCTGCCTCAAAGGCCTTGCCACTACTCCCTAATCGCCAGAGAAGTTCAGCTGG
GACTACATTCTCATCATCTTCATTATCGAGGCCCTTAAACAGAAGGAAAAGCCGTACTCGTTCACTCCGTGATGGCG
GAGATGGGGTATCAGATGCCAAAAAGCACAGCCAGTCTGTTCGTCAAGGTCTTGCTGGCATTATCGACCTCCCAAGT
GAGGCACCTTCCGAAGTGGATATTTCACATGGATCTGAGGATCCTAGGGGGCCAACAGATTCTTATCAAATGAATGG
GATTATCAATGAAACACATAATGGAAGACATGCCTCAGTGTCCAAGGTTGTTGAATTTTGTGCGGCACTAGGTGGCA
AAACACCAATTCACAGTATATTAGTGGCCAACAATGGAATGGCAGCAGCAAAATTTATGAGGAGTGTCCGGACATGG
GCTAATGATACTTTTGGATCTGAGAAGGCAATTCAACTCATAGCTATGGCAACTCCGGAAGACATGAGGATAAATGC
AGAACACATTAGAATTGCTGACCAATTCGTAGAGGTGCCTGGTGGAACAAACAATAATAACTACGCCAATGTTCAAC
TCATAGTGGAGATGGCACAAAAACTAGGTGTTTCTGCTGTTTGGCCTGGTTGGGGTCATGCTTCTGAGAATCCTGAA
CTGCCAGATGCATTGACCGCAAAAGGGATCGTTTTTCTTGGCCCACCTGCATCATCAATGAATGCTTTGGGAGATAA
GGTCGGCTCAGCTCTCATTGCTCAAGCAGCCGGGGTCCCAACTCTTGCTTGGAGTGGATCACATGTTGAAGTTCCAT
TAGAGTGCTGCTTAGACGCGATACCTGAGGAGATGTATAGAAAAGCTTGCGTTACTACCACAGAGGAAGCAGTTGCA
AGTTGTCAAGTGGTTGGTTATCCTGCCATGATTAAGGCATCCTGGGGAGGTGGTGGTAAAGGAATAAGAAAGGTTCA
TAATGATGATGAGGTTAGAGCGCTGTTTAAGCAAGTACAAGGTGAAGTCCCTGGCTCCCCAATATTTGTCATGAGGC
TTGCATCCCAGAGTCGGCATCTTGAAGTTCAGTTGCTTTGTGATCAATATGGTAATGTAGCAGCACTTCACAGTCGT
GATTGCAGTGTGCAACGGCGACACCAGAAGATTATTGAAGAAGGTCCAGTTACTGTTGCTCCTCGTGAGACAGTTAA
AGCACTTGAGCAGGCAGCAAGGAGGCTTGCTAAGGCTGTGGGTTATGTTGGTGCTGCTACTGTTGAGTATCTTTACA
GCATGGAAACTGGAGACTACTATTTTCTGGAACTTAATCCCCGACTACAGGTTGAGCATCCAGTCACCGAGTGGATA
GCTGAAGTAAATCTGCCTGCAGCTCAAGTTGCTGTTGGAATGGGCATACCTCTTTGGCAGATTCCAGAAATCAGACG
TTTCTATGGAATGGACTATGGAGGAGGGTATGACATTTGGAGGAAAACAGCAGCTCTTGCTACACCATTTAATTTTG
ATGAAGTAGATTCTCAATGGCCAAAGGGCCATTGTGTAGCAGTTAGAATTACTAGTGAGGACCCAGATGATGGTTTC
AAACCTACTGGTGGGAAAGTGAAGGAGATAAGTTTTAAAAGCAAGCCTAATGTTTGGGCCTACTTCTCAGTAAAGTC
TGGTGGAGGCATTCATGAATTTGCTGATTCTCAGTTCGGACATGTTTTTGCATATGGGCTCTCTAGATCAGCAGCAA
TAACAAACATGACTCTTGCATTAAAAGAGATTCAAATTCGTGGAGAAATTCATTCAAATGTTGATTACACAGTTGAC
CTCTTAAATGCTTCAGACTTTAGAGAAAACAAGATTCATACTGGTTGGCTCGACACCAGAATAGCTATGCGTGTTCA
AGCTGAGAGGCCCCCATGGTATATTTCAGTGGTTGGGGGTGCTTTATATAAAACAGTAACCACCAATGCAGCCACTG
TTTCTGAATATGTTAGTTATCTCACCAAGGGCCAGATTCCACCAAAGCATATATCCCTTGTCAATTCTACAGTTAAT
TTGAATATAGAAGGGAGCAAATACACAATTGAAACTGTAAGGACTGGACATGGTAGCTACAGGTTGAGAATGAATGA
TTCAACAGTTGAAGCGAATGTACAATCTTTATGTGATGGTGGCCTCTTAATGCAGTTGGATGGAAACAGCCATGTAA
TTTATGCAGAAGAAGAAGCTGGTGGTACACGGCTTCAGATTGATGGAAAGACATGTTTATTGCAGAATGACCATGAT
CCATCAAAGTTATTAGCTGAGACACCCTGCAAACTTCTTCGTTTCTTGGTTGCTGATGGTGCTCATGTTGATGCGGA
TGTACCATACGCGGAAGTTGAGGTTATGAAGATGTGCATGCCTCTCTTGTCGCCTGCTTCTGGTGTCATTCATTGTA
TGATGTCTGAGGGCCAGGCATTGCAGGCTGGTGATCTTATAGCAAGGTTGGATCTTGATGACCCTTCTGCTGTGAAA
AGAGCTGAGCCATTTGATGGAATATTTCCACAAATGGAGCTCCCTGTTGCTGTCTCTAGTCAAGTACACAAAAGATA
TGCTGCAAGTTTGAATGCTGCTCGAATGGTCCTTGCAGGATATGAGCACAATATTAATGAAGTCGTTCAAGATTTGG
TATGCTGCCTGGACAACCCTGAGCTTCCTTTCCTACAGTGGGATGAACTTATGTCTGTTCTAGCAACGAGGCTTCCA
AGAAATCTCAAGAGTGAGTTAGAGGATAAATACAAGGAATACAAGTTGAATTTTTACCATGGAAAAAACGAGGACTT
TCCATCCAAGTTGCTAAGAGACATCATTGAGGAAAATCTTTCTTATGGTTCAGAGAAGGAAAAGGCTACAAATGAGA
GGCTTGTTGAGCCTCTTATGAACCTACTGAAGTCATATGAGGGTGGGAGAGAGAGCCATGCACATTTTGTTGTCAAG
TCTCTTTTCGAGGAGTATCTTACAGTGGAAGAACTTTTTAGTGATGGCATTCAGTCTGACGTGATTGAAACATTGCG
GCATCAGCACAGTAAAGACCTGCAGAAGGTTGTAGACATTGTGTTGTCTCACCAGGGTGTGAGGAACAAAGCTAAGC
TTGTAACGGCACTTATGGAAAAGCTGGTTTATCCAAATCCTGGTGGTTACAGGGATCTGTTAGTTCGCTTTTCTTCC
CTCAATCATAAAAGATATTATAAGTTGGCCCTTAAAGCAAGTGAACTTCTTGAACAAACCAAACTAAGTGAACTCCG
TGCAAGCGTTGCAAGAAGCCTTTCGGATCTGGGGATGCATAAGGGAGAAATGAGTATTAAGGATAACATGGAAGATT
TAGTCTCTGCCCCATTACCTGTTGAAGATGCTCTGATTTCTTTGTTTGATTACAGTGATCGAACTGTTCAGCAGAAA
GTGATTGAGACATACATATCACGATTGTACCAGCCTCATCTTGTAAAGGATAGCATCCAAATGAAATTCAAGGAATC
TGGTGCTATTACTTTTTGGGAATTTTATGAAGGGCATGTTGATACTAGAAATGGACATGGGGCTATTATTGGTGGGA
AGCGATGGGGTGCCATGGTCGTTCTCAAATCACTTGAATCTGCGTCAACAGCCATTGTGGCTGCATTAAAGGATTCG
GCACAGTTCAACAGCTCTGAGGGCAACATGATGCACATTGCATTATTGAGTGCTGAAAATGAAAGTAATATAAGTGG
AATAAGTGATGATCAAGCTCAACATAAGATGGAAAAGCTTAGCAAGATACTGAAGGATACTAGCGTTGCAAGTGATC
TCCAAGCTGCTGGTTTGAAGGTTATAAGTTGCATTGTTCAAAGAGATGAAGCTCGCATGCCAATGCGCCACACATTC
CTCTGGTTGGATGACAAGAGTTGTTATGAAGAAGAGCAGATTCTCCGGCATGTGGAGCCTCCCCTCTCTACACTTCT

FIGURE 9A (continued)

```
TGAATTGGATAAGTTGAAGGTGAAAGGATACAATGAAATGAAGTATACTCCTTCGCGTGACCGCCAATGGCATATCT
ACACACTAAGAAATACTGAAAACCCCAAAATGTTGCATAGGGTGTTTTTCCGAACTATTGTCAGGCAACCCAATGCA
GGCAACAAGTTTACATCGGCTCAGATCAGCGACGCTGAAGTAGGATGTCCCGAAGAATCTCTTTCATTTACATCAAA
TAGCATCTTAAGATCATTGATGACTGCTATTGAAGAATTAGAGCTTCATGCAATTAGGACAGGTCATTCTCACATGT
ATTTGTGCATACTGAAAGAGCAAAAGCTTCTTGACCTCATTCCATTTTCAGGGAGTACAATTGTTGATGTTGGCCAA
GATGAAGCTACCGCTTGTTCACTTTTAAAATCAATGGCTTTGAAGATACATGAGCTTGTTGGTGCAAGGATGCATCA
TCTGTCTGTATGCCAGTGGGAGGTGAAACTCAAGTTGGACTGTGATGGCCCTGCAAGTGGTACCTGGAGAGTTGTAA
CTACAAATGTTACTGGTCACACCTGCACCATTGATATATACCGAGAAGTGGAGGAAATAGAATCGCAGAAGTTAGTG
TACCATTCAGCCACTTCGTCAGCTGGACCATTGCATGGTGTTGCACTGAATAATCCATATCAACCTTTGAGTGTGAT
TGATCTAAAGCGCTGCTCTGCTAGGAACAACAGAACAACATATTGCTATGATTTTCCGCTGGCCTTTGAAACTGCAC
TGCAGAAGTCATGGCAGACCAATGGCTCTACTGTTTCTGAAGGCAATGAAAATAGTAAATCCTACGTGAAGGCAACT
GAGCTAGTGTTTGCTGAAAAACATGGGTCCTGGGGCACTCCTATAATTCCGATGGAACGCCCTGCTGGGCTCAACGA
CATTGGTATGGTCGCTTGGATCATGGAGATGTCAACACCTGAATTTCCCAATGGCAGGCAGATTATTGTTGTAGCAA
ATGATATCACTTTCAGAGCTGGATCATTTGGCCCAAGGGAAGATGCATTTTTTGAAACTGTCACTAACCTGGCTTGC
GAAAGGAAACTTCCTCTTATATACTTGGCAGCAAACTCTGGTGCTAGGATTGGCATAGCTGATGAAGTAAAATCTTG
CTTCCGTGTTGGATGGTCTGACGAAGGCAGTCCTGAACGAGGGTTTCAGTACATCTATCTGACTGAAGAAGACTATG
CTCGCATTAGCTCTTCTGTTATAGCACATAAGCTGGAGCTAGATAGTGGTGAAATTAGGTGGATTATTGACTCTGTT
GTGGGCAAGGAGGATGGGCTTGGTGTCGAGAACATACATGGAAGTGCTGCTATTGCCAGTGCTTATTCTAGGGCATA
TGAGGAGACATTTACACTTACATTTGTGACTGGGCGGACTGTAGGAATAGGAGCTTATCTTGCTCGACTTGGTATAC
GGTGCATACAGCGTCTTGACCAGCCTATTATTTTAACAGGGTTTTCTGCCCTGAACAAGCTCCTTGGGCGGGAAGTG
TACAGCTCCCACATGCAGCTTGGTGGTCCTAAGATCATGGCGACTAATGGTGTTGTCCACCTCACTGTTCCAGATGA
CCTTGAAGGTGTTTCCAATATATTGAGGTGGCTCAGCTATGTTCCTGCAAACATTGGTGGACCTCTTCCTATTACCA
AACCTCTGGACCCTCCAGACAGACCTGTTGCTTACATCCCTGAGAACACATGCGATCCACGTGCAGCTATCTGTGGT
GTAGATGACAGCCAAGGGAAATGGTTGGGTGGTATGTTTGACAAAGACAGCTTTGTGGAGACATTTGAAGGATGGGC
AAAAACAGTGGTTACTGGCAGAGCAAAGCTTGGAGGAATTCCTGTGGGCGTCATAGCTGTGGAGACACAGACCATGA
TGCAGATCATCCCTGCTGATCCAGGTCAGCTTGATTCCCATGAGCGATCTGTCCCTCGTGCTGGACAAGTGTGGTTC
CCAGATTCTGCAACCAAGACCGCTCAGGCATTATTAGACTTCAACCGTGAAGGATTGCCTCTGTTCATCCTGGCTAA
TTGGAGAGGCTTCTCTGGTGGACAAAGAGATCTCTTTGAAGGAATTCTTCAGGCTGGGTCAACAATTGTCGAGAACC
TTAGGACATATAATCAGCCTGCTTTTGTGTACATTCCTATGGCTGGAGAGCTTCGTGGAGGAGCTTGGGTTGTGGTC
GATAGCAAAATAAATCCAGACCGCATTGAGTGTTATGCTGAAAGGACTGCCAAAGGTAATGTTCTCGAACCTCAAGG
GTTAATTGAAATCAAGTTCAGGTCAGAGGAACTCCAAGACTGTATGGGTAGGCTTGACCCAGAGTTGATAAATCTGA
AAGCAAAACTCCAAGATGTAAATCATGGAAATGGAAGTCTACCAGACATAGAAGGGATTCGGAAGAGTATAGAAGCA
CGTACGAAACAGTTGCTGCCTTTATATACCCAGATTGCAATACGGTTTGCTGAATTGCATGATACTTCCCTAAGAAT
GGCAGCTAAAGGTGTGATTAAGAAAGTTGTAGACTGGGAAGAATCACGCTCGTTCTTCTATAAAAGGCTACGGAGGA
GGATCGCAGAAGATGTTCTTGCAAAAGAAATAAGGCAGATAGTCGGTGATAAATTTACGCACCAATTAGCAATGGAG
CTCATCAAGGAATGGTACCTTGCTTCTCAGGCCACAACAGGAAGCACTGGATGGGATGACGATGATGCTTTTGTTGC
CTGGAAGGACAGTCCTGAAAACTACAAGGGGCATATCCAAAAGCTTAGGGCTCAAAAAGTGTCTCATTCGCTCTCTG
ATCTTGCTGACTCCAGTTCAGATCTGCAAGCATTCTCGCAGGGTCTTTCTACGCTATTAGATAAGATGGATCCCTCT
CAGAGAGCGAAGTTTGTTCAGGAAGTCAAGAAGGTCCTTGATTGA
```

FIGURE 9B

>AAP78896_Zea mays

MSQLGLAAAASKALPLLPNRQRSSAGTTFSSSSLSRPLNRRKSRTRSLRDGGDGVSDAKKHSQSVRQGLAGIID
LPSEAPSEVDISHGSEDPRGPTDSYQMNGIINETHNGRHASVSKVVEFCAALGGKTPIHSILVANNGMAAAKFM
RSVRTWANDTFGSEKAIQLIAMATPEDMRINAEHIRIADQFVEVPGGTNNNNYANVQLIVEMAQKLGVSAVWPG
WGHASENPELPDALTAKGIVFLGPPASSMNALGDKVGSALIAQAAGVPTLAWSGSHVEVPLECCLDAIPEEMYR
KACVTTTEEAVASCQVVGYPAMIKASWGGGGKGIRKVHNDDEVRALFKQVQGEVPGSPIFVMRLASQSRHLEVQ
LLCDQYGNVAALHSRDCSVQRRHQKIIEEGPVTVAPRETVKALEQAARRLAKAVGYVGAATVEYLYSMETGDYY
FLELNPRLQVEHPVTEWIAEVNLPAAQVAVGMGIPLWQIPEIRRFYGMDYGGGYDIWRKTAALATPFNFDEVDS
QWPKGHCVAVRITSEDPDDGFKPTGGKVKEISFKSKPNVWAYFSVKSGGGIHEFADSQFGHVFAYGLSRSAAIT
NMTLALKEIQIRGEIHSNVDYTVDLLNASDFRENKIHTGWLDTRIAMRVQAERPPWYISVVGGALYKTVTTNAA
TVSEYVSYLTKGQIPPKHISLVNSTVNLNIEGSKYTIETVRTGHGSYRLRMNDSTVEANVQSLCDGGLLMQLDG
NSHVIYAEEEAGGTRLQIDGKTCLLQNDHDPSKLLAETPCKLLRFLVADGAHVDADVPYAEVEVMKMCMPLLSP
ASGVIHCMMSEGQALQAGDLIARLDLDDPSAVKRAEPFDGIFPQMELPVAVSSQVHKRYAASLNAARMVLAGYE
HNINEVVQDLVCCLDNPELPFLQWDELMSVLATRLPRNLKSELEDKYKEYKLNFYHGKNEDFPSKLLRDIIEEN
LSYGSEKEKATNERLVEPLMNLLKSYEGGRESHAHFVVKSLFEEYLTVEELFSDGIQSDVIETLRHQHSKDLQK
VVDIVLSHQGVRNKAKLVTALMEKLVYPNPGGYRDLLVRFSSLNHKRYYKLALKASELLEQTKLSELRASVARS
LSDLGMHKGEMSIKDNMEDLVSAPLPVEDALISLFDYSDRTVQQKVIETYISRLYQPHLVKDSIQMKFKESGAI
TFWEFYEGHVDTRNGHGAIIGGKRWGAMVVLKSLESASTAIVAALKDSAQFNSSEGNMMHIALLSAENESNISG
ISDDQAQHKMEKLSKILKDTSVASDLQAAGLKVISCIVQRDEARMPMRHTFLWLDDKSCYEEEQILRHVEPPLS
TLLELDKLKVKGYNEMKYTPSRDRQWHIYTLRNTENPKMLHRVFFRTIVRQPNAGNKFTSAQISDAEVGCPEES
LSFTSNSILRSLMTAIEELELHAIRTGHSHMYLCILKEQKLLDLIPFSGSTIVDVGQDEATACSLLKSMALKIH
ELVGARMHHLSVCQWEVKLKLDCDGPASGTWRVVTTNVTGHTCTIDIYREVEEIESQKLVYHSATSSAGPLHGV
ALNNPYQPLSVIDLKRCSARNNRTTYCYDFPLAFETALQKSWQTNGSTVSEGNENSKSYVKATELVFAEKHGSW
GTPIIPMERPAGLNDIGMVAWIMEMSTPEFPNGRQIIVVANDITFRAGSFGPREDAFFETVTNLACERKLPLIY
LAANSGARIGIADEVKSCFRVGWSDEGSPERGFQYIYLTEEDYARISSSVIAHKLELDSGEIRWIIDSVVGKED
GLGVENIHGSAAIASAYSRAYEETFTLTFVTGRTVGIGAYLARLGIRCIQRLDQPIILTGFSALNKLLGREVYS
SHMQLGGPKIMATNGVVHLTVPDDLEGVSNILRWLSYVPANIGGPLPITKPLDPPDRPVAYIPENTCDPRAAIC
GVDDSQGKWLGGMFDKDSFVETFEGWAKTVVTGRAKLGGIPVGVIAVETQTMMQIIPADPGQLDSHERSVPRAG
QVWFPDSATKTAQALLDFNREGLPLFILANWRGFSGGQRDLFEGILQAGSTIVENLRTYNQPAFVYIPMAGELR
GGAWVVVDSKINPDRIECYAERTAKGNVLEPQGLIEIKFRSEELQDCMGRLDPELINLKAKLQDVNHGNGSLPD
IEGIRKSIEARTKQLLPLYTQIAIRFAELHDTSLRMAAKGVIKKVVDWEESRSFFYKRLRRRIAEDVLAKEIRQ
IVGDKFTHQLAMELIKEWYLASQATTGSTGWDDDDAFVAWKDSPENYKGHIQKLRAQKVSHSLSDLADSSSDLQ
AFSQGLSTLLDKMDPSQRAKFVQEVKKVLD

FIGURE 10A

>AF029895_Triticum aestivum

ATGGGATCCACACATTTGCCCATTGTCGGCCTTAATGCCTCGACAACACCATCGCTATCCACTATTCGCCCGGTAAA
TTCAGCCGGTGCTGCATTCCAACCATCTGCCCCTTCTAGAACCTCCAAGAAGAAAAGTCGTCGTGTTCAGTCATTAA
GGGATGGAGGCGATGGAGGCGTGTCAGACCCTAACCAGTCTATTCGCCAAGGTCTTGCCGGCATCATTGACCTCCCA
AAGGAGGGCACATCAGCTCCGGAAGTGGATATTTCACATGGGTCCGAAGAACCCAGGGGCTCCTACCAAATGAATGG
GATACTGAATGAAGCACATAATGGGAGGCATGCTTCGCTGTCTAAGGTTGTCGAATTTTGTATGGCATTGGGCGGCA
AAACACCAATTCACAGTGTATTAGTTGCGAACAATGGAATGGCAGCAGCTAAGTTCATGCGGAGTGTCCGAACATGG
GCTAATGAAACATTTGGGTCAGAGAAGGCAATTCAGTTGATAGCTATGGCTACTCCAGAAGACATGAGGATAAATGC
AGAGCACATTAGAATTGCTGATCAATTTGTTGAAGTACCCGGTGGAACAAACAATAACAACTATGCAAATGTCCAAC
TCATAGTGGAGATAGCAGTGAGAACCGGTGTTTCTGCTGTTTGGCCTGGTTGGGGCCATGCATCTGAGAATCCTGAA
CTTCCAGATGCACTAAATGCAAACGGAATTGTTTTTCTTGGGCCACCATCATCATCAATGAACGCACTAGGTGACAA
GGTTGGTTCAGCTCTCATTGCTCAAGCAGCAGGGGTTCCGACTCTTCCTTGGAGTGGATCACAGGTGGAAATTCCAT
TAGAAGTTTGTTTGGACTCGATACCCGCGGAGATGTATAGGAAAGCTTGTGTTAGTACTACGGAGGAAGCACTTGCG
AGTTGTCAGATGATTGGGTATCCCGCCATGATTAAAGCATCATGGGGTGGTGGTGGTAAAGGGATCCGAAAGGTTAA
TAATGACGATGATGTCAGAGCACTGTTTAAGCAAGTGCAAGGTGAAGTTCCTGGCTCCCCAATATTTATCATGAGAC
TTGCATCTCAGAGTCGACATCTTGAAGTTCAGTTGCTTTGTGATCAATATGGCAATGTAGCTGCGCTTCACAGTCGT
GACTGCAGTGTGCAACGGCGACACCAAAAGATTATTGAGGAAGGACCAGTTACTGTTGCTCCTCGCGAGACAGTGAA
AGAGCTAGAGCAAGCAGCAAGGAGGCTTGCTAAGGCTGTGGGTTATGTTGGTGCTGCTACTGTTGAATATCTCTACA
GCATGGAGACTGGTGAATACTATTTTCTGGAACTTAATCCACGGTTGCAGGTTGAGCATCCAGTCACCGAGTGGATA
GCTGAAGTAAACTTGCCTGCAGCTCAAGTTGCAGTTGGAATGGGTATACCCCTTTGGCAGGTTCCAGAGATCAGACG
TTTCTATGGAATGGACAATGGAGGAGGCTATGACATTTGGAGGAAAACAGCAGCTCTTGCTACTCCATTTAACTTCG
ATGAAGTGGATTCTCAATGGCCAAAGGGTCATTGTGTAGCAGTTAGGATAACCAGTGAGGATCCAGATGACGGATTC
AAGCCTACCGGTGGAAAAGTAAAGGAGATCAGTTTTAAAAGCAAGCCAAATGTTTGGGCCTATTTCTCTGTTAAGTC
CGGTGGAGGCATTCATGAATTTGCTGATTCTCAGTTTGGACATGTTTTTGCATATGGAGTGTCTAGAGCAGCAGCAA
TAACCAACATGTCTCTTGCGCTAAAAGAGATTCAAATTCGTGGAGAAATTCATTCAAATGTTGATTACACAGTTGAT
CTCTTGAATGCCTCAGACTTCAAAGAAAACAGGATTCATACTGGCTGGCTGGATAACAGAATAGCAATGCGAGTCCA
AGCTGAGAGACCTCCGTGGTATATTTCAGTGGTTGGAGGAGCTCTATATAAAACAATAACGAGCAACACAGACACTG
TTTCTGAATATGTTAGCTATCTCGTCAAGGGTCAGATTCCACCGAAGCATATATCCCTTGTCCATTCAACTGTTTCT
TTGAATATAGAGGAAAGCAAATATACAATTGAAACTATAAGGAGCGGACAGGGTAGCTACAGATTGCGAATGAATGG
ATCAGTTATTGAAGCAAATGTCCAAACATTATGTGATGGTGGACTTTTAATGCAGTTGGATGGAAACAGCCATGTAA
TTTATGCTGAAGAAGAGGCCGGTGGTACACGGCTTCTAATTGATGGAAAGACATGCTTGTTACAGAATGATCACGAT
CCTTCAAGGTTATTAGCTGAGACACCCTGCAAACTTCTTCGTTTCTTGGTTGCCGATGGTGCTCATGTTGAAGCTGA
TGTACCATATGCGGAAGTTGAGGTTATGAAGATGTGCATGCCCCTCTTGTCACCTGCTGCTGGTGTCATTAATGTTT
TGTTGTCTGAGGGCCAGCCTATGCAGGCTGGTGATCTTATAGCAAGACTTGATCTTGATGACCCTTCTGCTGTGAAG
AGAGCTGAGCCATTTAACGGATCTTTCCCAGAAATGAGCCTTCCTATTGCTGCTTCTGGCCAAGTTCACAAAAGATG
TGCCACAAGCTTGAATGCTGCTCGGATGGTCCTTGCAGGATATGATCACCCGATCAACAAAGTTGTACAAGATCTGG
TATCCTGTCTAGATGCTCCTGAGCTTCCTTTCCTACAATGGGAAGAGCTTATGTCTGTTTTAGCAACTAGACTTCCA
AGGCTTCTTAAGAGCGAGTTGGAGGGTAAATACAGTGAATATAAGTTAAATGTTGGCCATGGGAAGAGCAAGGATTT
CCCTTCCAAGATGCTAAGAGAGATAATCGAGGAAAATCTTGCACATGGTTCTGAGAAGGAAATTGCTACAAATGAGA
GGCTTGTTGAGCCTCTTATGAGCCTACTGAAGTCATATGAGGGTGGCAGAGAAAGCCATGCACACTTTATTGTGAAG
TCCCTTTTCGAGGACTATCTCTCGGTTGAGGAACTATTCAGTGATGGCATTCAGTCTGATGTGATTGAACGCCTGCG
CCAACAACATAGTAAAGATCTCCAGAAGGTTGTAGACATTGTGTTGTCTCACCAGGGTGTGAGAAACAAAACTAAGC
TGATACTAACACTCATGGAGAAACTGGTCTATCCAAACCCTGCTGTCTACAAGGATCAGTTGACTCGCTTTTCCTCC
CTCAATCACAAAAGATATTATAAGTTGGCCCTTAAAGCTAGCGAGCTTCTTGAACAAACCAAGCTTAGTGAGCTCCG
CACAAGCATTGCAAGGAGCCTTTCAGAACTTGAGATGTTTACTGAAGAAAGGACGGCCATTAGTGAGATCATGGGAG
ATTTAGTGACTGCCCCACTGCCAGTTGAAGATGCACTGGTTTCTTTGTTTGATTGTAGTGATCAAACTCTTCAGCAG
AGGGTGATCGAGACGTACATATCTCGATTATACCAGCCTCATCTTGTCAAGGATAGTATCCAGCTGAAATATCAGGA
ATCTGGTGTTATTGCTTTATGGGAATTCGCTGAAGCGCATTCAGAGAAGAGATTGGGTGCTATGGTTATTGTGAAGT
CGTTAGAATCTGTATCAGCAGCAATTGGAGCTGCACTAAAGGGTACATCACGCTATGCAAGCTCTGAGGGTAACATA
ATGCATATTGCTTTATTGGGTGCTGATAATCAAATGCATGGAACTGAAGACAGTGGTGATAACGATCAAGCTCAAGT
CAGGATAGACAAACTTTCTGCGACACTGGAACAAAATACTGTCACAGCTGATCTCCGTGCTGCTGGTGTGAAGGTTA

FIGURE 10A (continued)

TTAGTTGCATTGTTCAAAGGGATGGAGCACTCATGCCTATGCGCCATACCTTCCTCTTGTCGGATGAAAAGCTTTGT
TATGAGGAAGAGCCGGTTCTCCGGCATGTGGAGCCTCCTCTTTCTGCTCTTCTTGAGTTGGGTAAGTTGAAAGTGAA
AGGATACAATGAGGTGAAGTATACACCGTCACGTGATCGTCAGTGGAACATATACACACTTAGAAATACAGAGAACC
CCAAAATGTTGCACAGGGTGTTTTTCCGAACTCTTGTCAGGCAACCCGGTGCTTCCAACAAATTCACATCAGGCAAC
ATCAGTGATGTTGAAGTGGGAGGAGCTGAGGAATCTCTTTCATTTACATCGAGCAGCATATTAAGATCGCTGATGAC
TGCTATAGAAGAGTTGGAGCTTCACGCGATTAGGACAGGTCACTCTCATATGTTTTTGTGCATATTGAAAGAGCAAA
AGCTTCTTGATCTTGTTCCCGTTTCAGGGAACAAAGTTGTGGATATTGGCCAAGATGAAGCTACTGCATGCTTGCTT
CTGAAAGAAATGGCTCTACAGATACATGAACTTGTGGGTGCAAGGATGCATCATCTTTCTGTATGCCAATGGGAGGT
GAAACTTAAGTTGGACAGCGATGGGCCTGCCAGTGGTACCTGGAGAGTTGTAACAACCAATGTTACTAGTCACACCT
GCACTGTGGATATCTACCGTGAGGTCGAAGATACAGAATCACAGAAACTAGTGTACCACTCTGCTCCATCGTCATCT
GGTCCTTTGCATGGCGTTGCACTGAATACTCCATATCAGCCTTTGAGTGTTATTGATCTGAAACGTTGCTCCGCTAG
AAATAACAGAACTACATACTGCTATGATTTTCCGTTGGCATTTGAAACTGCAGTGCAGAAGTCATGGTCTAACATTT
CTAGTGACACTAACCGATGTTATGTTAAAGCGACGGAGCTGGTGTTTGCTCACAAGAACGGGTCATGGGGCACTCCT
GTAATTCCTATGGAGCGTCCTGCTGGGCTCAATGACATTGGTATGGTAGCTTGGATCTTGGACATGTCCACTCCTGA
ATATCCCAATGGCAGGCAGATTGTTGTCATCGCAAATGATATTACTTTTAGAGCTGGATCGTTTGGTCCAAGGGAAG
ATGCATTTTTTGAAACTGTTACCAACCTAGCTTGTGAGAGGAAGCTTCCTCTCATCTACTTGGCAGCAAACTCTGGT
GCTCGGATCGGCATAGCAGATGAAGTAAAATCTTGCTTCCGTGTTGGATGGTCTGATGATGGCAGCCCTGAACGTGG
GTTTCAATATATTTATCTGACTGAAGAAGACCATGCTCGTATTAGCGCTTCTGTTATAGCGCACAAGATGCAGCTTG
ATAATGGTGAAATTAGGTGGGTTATTGATTCTGTTGTAGGGAAGGAGGATGGGCTAGGTGTGGAGAACATACATGGA
AGTGCTGCTATTGCCAGTGCCTATTCTAGGGCCTATGAGGAGACATTTACGCTTACATTTGTGACTGGAAGGACTGT
TGGAATAGGAGCATATCTTGCTCGACTTGGCATACGGTGCATACAGCGTACTGACCAGCCCATTATCCTAACTGGGT
TCTCTGCCTTGAACAAGCTTCTTGGCCGGGAAGTTTACAGCTCCCACATGCAGTTGGGTGGCCCCAAAATTATGGCG
ACAAACGGTGTTGTCCATCTGACAGTTTCAGATGACCTTGAAGGTGTATCTAATATATTGAGGTGGCTCAGCTATGT
TCCTGCCAACATTGGTGGACCTCTTCCTATTACAAAATCTTTGGACCCACCTGACAGACCCGTTGCTTACATCCCTG
AGAATACATGCGATCCTCGTGCTGCCATCAGTGGCATTGATGATAGCCAAGGGAAATGGTTGGGGGGCATGTTCGAC
AAAGACAGTTTTGTGGAGACATTTGAAGGATGGGCGAAGTCAGTTGTTACTGGCAGAGCGAAACTCGGAGGGATTCC
GGTGGGTGTTATAGCTGTGGAGACACAGACTATGATGCAGCTCATCCCTGCTGATCCAGGCCAGCTTGATTCCCATG
AGCGATCTGTTCCTCGTGCTGGGCAAGTCTGGTTTCCAGATTCAGCTACTAAGACAGCGCAGGCAATGCTGGACTTC
AACCGTGAAGGATTACCTCTGTTCATCCTTGCTAACTGGAGAGGCTTCTCTGGTGGACAAAGAGATCTTTTTGAAGG
AATCCTTCAGGCTGGGTCAACAATTGTTGAGAACCTTAGGACATACAATCAGCCTGCCTTTGTATATATCCCCAAGG
CTGCAGAGCTACGTGGAGGGGCTTGGGTCGTGATTGATAGCAAGATAAATCCAGATCGCATTGAGTTCTATGCTGAG
AGGACTGCAAAGGGCAATGTTCTCGAACCTCAAGGGTTGATCGAGATCAAGTTCAGGTCAGAGGAACTCCAAGAGTG
CATGGGTAGGCTTGATCCAGAATTGATAAATCTGAAGGCAAAGCTCCAGGGAGTAAAGCATGAAAATGGAAGTCTAC
CTGAGTCAGAATCCCTTCAGAAGAGCATAGAAGCCCGGAAGAAACAGTTGTTGCCTTTGTATACTCAAATTGCGGTA
CGGTTCGCTGAATTGCATGACACTTCCCTTAGAATGGCTGCTAAGGGTGTGATTAAGAAGGTTGTAGACTGGGAAGA
TTCTAGGTCGTTCTTCTACAAGAGATTACGGAGGAGGATATCCGAGGATGTTCTTGCGAAGGAAATTAGAGGTGTAA
GTGGCAAGCAGTTTTCTCACCAATCGGCAATCGAGCTGATCCAGAAATGGTACTTGGCCTCTAAGGGAGCTGAAACA
GGAAGCACTGAATGGGATGATGACGATGCTTTTGTTGCCTGGAGGGAAAACCCTGAAAACTACCAGGAGTATATCAA
AGAACTCAGGGCTCAAAGGGTATCTCAGTTGCTCTCAGATGTTGCAGACTCCAGTCCAGATCTAGAAGCCTTGCCAC
AGGGTCTTTCTATGCTATTAGAGAAGATGGATCCCTCAAGGAGAGCACAGTTTGTTGAGGAAGTCAAGAAAGTCCTT
AAATGA

FIGURE 10B

>AAC39330_Triticum aestivum

MGSTHLPIVGLNASTTPSLSTIRPVNSAGAAFQPSAPSRTSKKKSRRVQSLRDGGDGGVSDPNQSIRQGLAGII
DLPKEGTSAPEVDISHGSEEPRGSYQMNGILNEAHNGRHASLSKVVEFCMALGGKTPIHSVLVANNGMAAAKFM
RSVRTWANETFGSEKAIQLIAMATPEDMRINAEHIRIADQFVEVPGGTNNNNYANVQLIVEIAVRTGVSAVWPG
WGHASENPELPDALNANGIVFLGPPSSSMNALGDKVGSALIAQAAGVPTLPWSGSQVEIPLEVCLDSIPAEMYR
KACVSTTEEALASCQMIGYPAMIKASWGGGGKGIRKVNNDDDVRALFKQVQGEVPGSPIFIMRLASQSRHLEVQ
LLCDQYGNVAALHSRDCSVQRRHQKIIEEGPVTVAPRETVKELEQAARRLAKAVGYVGAATVEYLYSMETGEYY
FLELNPRLQVEHPVTEWIAEVNLPAAQVAVGMGIPLWQVPEIRRFYGMDNGGGYDIWRKTAALATPFNFDEVDS
QWPKGHCVAVRITSEDPDDGFKPTGGKVKEISFKSKPNVWAYFSVKSGGGIHEFADSQFGHVFAYGVSRAAAIT
NMSLALKEIQIRGEIHSNVDYTVDLLNASDFKENRIHTGWLDNRIAMRVQAERPPWYISVVGGALYKTITSNTD
TVSEYVSYLVKGQIPPKHISLVHSTVSLNIEESKYTIETIRSGQGSYRLRMNGSVIEANVQTLCDGGLLMQLDG
NSHVIYAEEEAGGTRLLIDGKTCLLQNDHDPSRLLAETPCKLLRFLVADGAHVEADVPYAEVEVMKMCMPLLSP
AAGVINVLLSEGQPMQAGDLIARLDLDDPSAVKRAEPFNGSFPEMSLPIAASGQVHKRCATSLNAARMVLAGYD
HPINKVVQDLVSCLDAPELPFLQWEELMSVLATRLPRLLKSELEGKYSEYKLNVGHGKSKDFPSKMLREIIEEN
LAHGSEKEIATNERLVEPLMSLLKSYEGGRESHAHFIVKSLFEDYLSVEELFSDGIQSDVIERLRQQHSKDLQK
VVDIVLSHQGVRNKTKLILTLMEKLVYPNPAVYKDQLTRFSSLNHKRYYKLALKASELLEQTKLSELRTSIARS
LSELEMFTEERTAISEIMGDLVTAPLPVEDALVSLFDCSDQTLQQRVIETYISRLYQPHLVKDSIQLKYQESGV
IALWEFAEAHSEKRLGAMVIVKSLESVSAAIGAALKGTSRYASSEGNIMHIALLGADNQMHGTEDSGDNDQAQV
RIDKLSATLEQNTVTADLRAAGVKVISCIVQRDGALMPMRHTFLLSDEKLCYEEEPVLRHVEPPLSALLELGKL
KVKGYNEVKYTPSRDRQWNIYTLRNTENPKMLHRVFFRTLVRQPGASNKFTSGNISDVEVGGAEESLSFTSSSI
LRSLMTAIEELELHAIRTGHSHMFLCILKEQKLLDLVPVSGNKVVDIGQDEATACLLLKEMALQIHELVGARMH
HLSVCQWEVKLKLDSDGPASGTWRVVTTNVTSHTCTVDIYREVEDTESQKLVYHSAPSSSGPLHGVALNTPYQP
LSVIDLKRCSARNNRTTYCYDFPLAFETAVQKSWSNISSDTNRCYVKATELVFAHKNGSWGTPVIPMERPAGLN
DIGMVAWILDMSTPEYPNGRQIVVIANDITFRAGSFGPREDAFFETVTNLACERKLPLIYLAANSGARIGIADE
VKSCFRVGWSDDGSPERGFQYIYLTEEDHARISASVIAHKMQLDNGEIRWVIDSVVGKEDGLGVENIHGSAAIA
SAYSRAYEETFTLTFVTGRTVGIGAYLARLGIRCIQRTDQPIILTGFSALNKLLGREVYSSHMQLGGPKIMATN
GVVHLTVSDDLEGVSNILRWLSYVPANIGGPLPITKSLDPPDRPVAYIPENTCDPRAAISGIDDSQGKWLGGMF
DKDSFVETFEGWAKSVVTGRAKLGGIPVGVIAVETQTMMQLIPADPGQLDSHERSVPRAGQVWFPDSATKTAQA
MLDFNREGLPLFILANWRGFSGGQRDLFEGILQAGSTIVENLRTYNQPAFVYIPKAAELRGGAWVVIDSKINPD
RIEFYAERTAKGNVLEPQGLIEIKFRSEELQECMGRLDPELINLKAKLQGVKHENGSLPESESLQKSIEARKKQ
LLPLYTQIAVRFAELHDTSLRMAAKGVIKKVVDWEDSRSFFYKRLRRRISEDVLAKEIRGVSGKQFSHQSAIEL
IQKWYLASKGAETGSTEWDDDDAFVAWRENPENYQEYIKELRAQRVSQLLSDVADSSPDLEALPQGLSMLLEKM
DPSRRAQFVEEVKKVLK

FIGURE 11A

>AY219174_Setaria italica (foxtail millet)

ATGTCGCAACTTGGATTAGCTGCAGCTGCCTCAAAGGCGCTGCCACTACTTCCTAATCGCCATAGAACTTCAGCTGG
AACTACATTCCCATCACCTGTATCATCGCGGCCCTCAAACCGAAGGAAAAGCCGCACTCGTTCACTTCGTGATGGAG
GAGATGGGGTATCAGATGCCAAAAAGCACAACCAGTCTGTCCGTCAAGGTCTTGCTGGCATCATCGACCTCCCAAAT
GAGGCAACATCGGAAGTGGATATTTCTCATGGATCCGAGGATCCCAGGGGGCCAACCGATTCATATCAAATGAATGG
GATTGTAAGTGAAGCACATAATGGCAGACATGCCTCAGTGTCCAAGGTTGTTGAATTTTGTGCGGCGCTAGGTGGCA
AAACACCAATTCACAGTATACTAGTGGCCAACAATGGAATGGCAGCAGCAAAGTTCATGAGGAGTGTCCGGACATGG
GCTAATGATACTTTTGGATCGGAGAAGGCGATTCAGCTCATAGCTATGGCAACTCCAGAAGACATGAGGATAAATGC
AGAACACATTAGAATTGCTGATCAATTTGTGGAGGTGCCTGGTGGAACAAACAATAACAACTATGCAAATGTTCAAC
TCATAGTGGAGGTAGCAGAAAGAATAGGTGTTTCTGCTGTTTGGCCTGGTTGGGGTCATGCTTCTGAGAATCCTGAA
CTTCCAGATGCATTGACCGCAAAAGGAGTTGTTTTCCTTGGGCCACCTGCGGCATCAATGAATGCATTGGGAGATAA
GGTCGGTTCAGCTCTCATTGCTCAAGCAGCTGGGGTCCCGACCCTTTCGTGGAGTGGATCACATGTTGAAGTTCCAT
TAGAGTGCTGCTTAGATGCGATACCTGAGGAAATGTATAGAAAAGCTTGTGTTACTACCACAGAAGAAGCTGTTGCG
AGTTGTCAGGTGGTTGGTTATCCTGCCATGATTAAGGCATCCTGGGGAGGTGGTGGTAAAGGAATAAGAAAGGTTCA
TAATGACGATGAGGTTAGAGCACTGTTTAAGCAAGTACAAGGTGAAGTCCCTGGCTCCCCAATATTTATCATGAGGC
TTGCATCCCAGAGTCGTCATCTTGAAGTTCAGTTGCTTTGTGATCAATATGGCAATGTGGCAGCACTTCACAGTCGT
GATTGCAGTGTGCAACGGCGACACCAAAAGATTATTGAGGAAGGCCCAGTTACTGTTGCTCCTCGTGAGACAGTTAA
AGCGCTTGAGCAGGCAGCAAGGAGGCTTGCTAAGGCTGTGGGTTATGTTGGTGCTGCTACTGTTGAATACCTTTACA
GCATGGAGACTGGGGAATACTATTTTCTGGAGCTTAATCCCAGATTACAGGTCGAGCATCCAGTCACTGAGTGGATT
GCTGAAGTAAATCTTCCTGCAGCTCAAGTTGCAGTTGGAATGGGCATACCTCTTTGGCAGATTCCAGAAATCAGACG
TTTCGATGGAATGGACTATGGAGGAGGATATGACATTTGGAGGAAAACAGCAGCTCTTGCCACACCATTTAATTTTG
ATGAAGTAGATTCTCAATGGCCAAAGGGCCATTGTGTAGCAGTTAGAATTACTAGCGAGGATCCAGATGATGGTTTC
AAACCTACTGGTGGGAAAGTGAAGGAGATAAGTTTTAAAAGCAAGCCTAATGTTTGGGCCTACTTCTCAGTAAAGTC
TGGTGGAGGCATTCATGAATTTGTTGATTCTCAGTTTGGGCATGTTTTTGCATATGGGCTCTCTAGATCAGCAGCAA
TAACGAACATGGCTCTTGCATTAAAAGAGATTCAAATTCGTGGAGAAATTCATTCAAATGTTGATTACACAGTTGAT
CTCTTAAATGCTTCAGACTTCAGAGAAAATAAGATTCATACTGGCTGGCTTGATACCAGAATAGCTATGCGTGTTCA
AGCTGAGAGGCCCCCATGGTATATTTCAGTGGTTGGAGGAGCTCTATATAAAACAGTAACTGCCAATGCAGCCACTG
TTTCTGATTATGTCAGTTATCTCACCAAGGGCCAGATTCCACCAAAGCATATATCCCTTGTCAGTTCAACAGTTAAT
CTGAATATCGAAGGGAGCAAATACACAGTTGAAACTGTAAGGACTGGACATGGTAGCTACAGATTACGAATGAATGA
TTCAGCAATTGAAGCGAATGTACAATCCTTATGTGATGGAGGCCTCTTAATGCAGTTGGATGGAAATAGCCATGTAA
TTTACGCGGAAGAAGAAGCTGGTGGTACACGACTTCTGATTGATGGAAAGACATGCTTGTTACAGAATGATCATGAT
CCATCAAAGTTATTAGCTGAGACACCCTGCAAACTTCTTCGGTTCTTGGTTGCTGATGGTGCCCATGTTGATGCTGA
TGTACCATATGCGGAAGTTGAGGTTATGAAAATGTGCATGCCTCTCTTGTCGCCTGCTTCTGGTGTCATTCATGTTA
TGATGTCTGAGGGCCAGGCATTGCAGGCTGGTGATCTTATAGCAAGGCTGGATCTTGATGACCCTTCTGCTGTGAAA
AGAGCTGAACCATTTCATGGAATATTTCCACAAATGGACCTTCCTGTTGCTGCCTCTAGCCAAGTACACAAAAGATA
TGCTGCAAGTTGGAATGCTGCTCGAATGGTCCTTGCAGGATACGAGCATAATATCAATGAAGTTGTACAAGATTTGG
TATGCTGCCTGGATGATCCCGAGCTTCCCTTCCTACAGTGGGATGAACTTATGTCAGTTCTAGCAACTAGGCTTCCA
AGAAATCTTAAGAGTGAGTTAGAGGATAAATACATGGAATACAAGTTGAACTTTTACCATGGGAAAAACAAGGACTT
CCCGTCCAAGCTGCTGAGAGACATCATTGAGGCAAATCTTGCATATGGTTCAGAGAAGGAAAAAGCTACGAATGAGA
GGCTTATTGAGCCTCTTATGAGCCTACTTAAGTCATATGAGGGTGGGAGAGAAAGCCATGCTCATTTTGTTGTCAAG
TCCCTTTTCAAGGAGTACCTTGCTGTGGAAGAACTTTTCAGTGATGGGATTCAGTCTGATGTGATTGAAACCCTGCG
TCATCAGCACAGTAAAGACTTGCAGAAGGTTGTAGACATTGTGTTGTCTCACCAGGGTGTGAGGAACAAAGCTAAGC
TTGTAACAGCACTTATGGAAAAGCTGGTTTATCCAAATCCTGCTGCTTACAGGGATCTGTTGGTTCGCTTTTCTTCA
CTCAATCATAAAAGATATTATAAGTTGGCCCTTAAAGCAAGCGAACTTCTTGAACAAACTAAACTAAGTGAACTCCG
TGCAAGCATCGCAAGAAGCCTTTCTGATCTGGGGATGCATAAGGGAGAAATGACTATTGAAGATAGCATGGAAGATT
TAGTCTCTGCCCCATTACCTGTCGAAGATGCACTTATTTCTTTGTTTGATTACAGTGATCCAACTGTTCAGCAGAAA
GTGATCGAGACATACATATCTCGATTGTATCAGCCTCTTCTTGTGAAAGATAGCATCCAAGTGAAATTTAAGGAATC
TGGTGCCTTTGCTTTATGGGAATTTTCTGAAGGGCATGTTGATACTAAAAATGGACAAGGGACCGTTCTTGGTCGAA
CAAGATGGGGTGCCATGGTAGCTGTCAAATCAGTTGAATCTGCACGAACAGCCATTGTAGCTGCATTAAAGGATTCG
GCACAGCATGCCAGCTCTGAGGGCAACATGATGCACATTGCCTTATTGAGTGCTGAAAATGAAAATAATATCAGTGA
TGATCAAGCTCAACATAGGATGGAAAAACTTAACAAGATACTCAAGGATACTAGTGTCGCAAATGATCTTCGAGCTG
CTGGTTTGAAGGTTATAAGTTGCATTGTTCAAAGAGATGAAGCACGCATGCCAATGCGCCACACATTACTCTGGTCA
GATGAAAAGAGTTGTTATGAGGAAGAGCAGATTCTTCGGCATGTGGAGCCTCCCCTCTCCATGCTTCTTGAAATGGA

FIGURE 11A (continued)

TAAGTTGAAAGTGAAAGGATACAATGAAATGAAGTATACTCCATCACGTGATCGTCAATGGCATATCTACACACTAA
GAAATACTGAAAACCCCAAAATGTTGCATAGGGTATTTTTCCGAACTATTGTCAGGCAACCCAATGCAGGCAACAAG
TTTATATCAGCCCAAATTGGCGACACTGAAGTAGGAGGTCCTGAGGAATCTTTGTCATTTACATCTAATAGCATTTT
AAGAGCCTTGATGACTGCTATTGAAGAATTAGAGCTTCATGCAATTAGGACTGATCATTCTCACATGTATTTGTGCA
TATTGAAAGAACAAAAGCTTCTTGATCTCATTCCGTTTTCAGGGAGCACAATCGTCGATGTTGTCCAAGACGAAGCT
ACTGCTTGTTCACTTTTAAAATCAATGGCTTTGAAGATACACGAACTTGTTGGTGCACAGATGCATCATCTTTCTGT
ATGCCAGTGGGAGGTGAAACTCAAGTTGTACTGCGATGGGCCTGCCAGTGGCACCTGGAGAGTTGTAACTACAAATG
TTACTAGTCACACTTGCACCGTTGATATCTACCGGGAAGTGGAAGATACTGAATCGCAGAAGTTAGTATACCATTCA
GCTTCTCCGTCAGCTAGTCCTTTGCATGGTGTGGCCCTGGATAATCCGTATCAACCTTTGAGTGTCATTGATCTAAA
ACACTGCTCTGCTAGGAACAACAGAACTACATATTGCTATGATTTTCCACTGGCATTTGAAACTGCCCTGCAGAAGT
CATGGCAGTCCAATGGCTCCAGTGTTTCTGAAGGCAGTGAAAATAGTAGGTCTTATGTGAAAGCAACAGAGCTGGTG
TTTGCTGAAAAACATGGGTCCTGGGGCACTCCTATAATTTCCATGGAGCGTCCCGCTGGGCTCAATGACATTGGCAT
GGTAGCTTGGATCTTAGAGATGTCCACTCCTGAATTTCCCAATGGCAGGCAGATTATTGTCATAGCAAATGATATTA
CTTTCAGAGCTGGATCATTTGGCCCAAGGGAAGATGCGTTTTTTGAAGCTGTCACGAACCTGGCCTGCGAGAGGAAG
CTTCCTCTTATATACTTGGCAGCAAACTCCGGTGCTAGGATTGGCATAGCCGATGAAGTGAAATCTTGCTTCCGTGT
TGGGTGGTCCGATGAAGGCAGCCCTGAACGGGGTTTTCAGTACATTTATCTGACTGACGAAGACTATGCCCGTATTA
GCTTGTCTGTTATAGCACACAAGCTGCAGCTGGATAATGGTGAAATTAGGTGGATTATTGACTCTGTTGTGGGCAAG
GAGGATGGGCTTGGTGTTGAGAATATACATGGAAGTGCTGCTATTGCCAGTGCTTATTCTAGGGCATATGAGGAGAC
ATTTACACTTACATTTGTGACTGGGCGGACTGTTGGAATAGGAGCATATCTTGCTCGGCTCGGTATACGGTGCATAC
AGCGTCTTGACCAGCCTATTATTTTAACTGGGTTTTCTGCCCTGAACAAGCTTCTTGGGCGGGAAGTGTACAGCTCC
CACATGCAGTTGGGTGGTCCTAAGATCATGGCGACCAATGGTGTTGTCCACTTGACTGTTTCAGATGACCTTGAAGG
TGTTTCCAATATATTGAGGTGGCTCAGCTATGTTCCTGCCAACATTGGTGGACCTCTTCCTATTACAAAACCTTTGG
ACCCACCAGACAGACCTGTTGCATACATCCCTGAGAACACATGTGATCCGCGCGCAGCCATTCGTGGTGTAGATGAC
AGCCAAGGGAAATGGTTGGGTGGTATGTTTGACAAAGACAGCTTTGTCGAGACATTTGAAGGATGGGCGAAAACAGT
GGTTACGGGCAGAGCAAAGCTTGGAGGAATTCCTGTTGGCGTCATAGCTGTGGAGACACAAACCATGATGCAGCTTA
TCCCTGCTGATCCAGGCCAGCTTGATTCCCATGAGCGATCTGTTCCTCGGGCTGGACAAGTGTGGTTCCCAGATTCT
GCAACCAAGACAGCTCAGGCATTGTTGGACTTCAACCGTGAAGGATTGCCGCTGTTCATCCTTGCTAACTGGAGAGG
ATTCTCTGGTGGACAAAGAGATCTGTTTGAAGGAATTCTTCAGGCTGGGTCAACAATTGTTGAGAACCTTAGGACAT
ACAATCAGCCTGCTTTTGTCTACATTCCTATGGCTGGAGAGCTGCGTGGAGGAGCTTGGGTTGTGGTTGATAGCAAA
ATAAATCCAGACCGAATTGAGTGTTATGCTGAGAGGACTGCTAAAGGCAATGTTCTGGAACCTCAAGGGTTAATTGA
AATCAAATTCAGATCAGAGGAGCTCCAAGACTGTATGGGTAGGCTTGACCCAGGGTTGATAAATCTGAAAGCAAAAC
TCCAAGGTGCAAAGCTTGGAAATGGAAGCCTAACAGATGTAGAATCCCTTCAGAAGAGTATAGATGCTCGTACGAAA
CAGTTGTTGCCTTTATACACCCAGATTGCAATACGGTTTGCTGAATTGCATGATACTTCCCTCAGAATGGCAGCTAA
AGGTGTGATTAAGAAAGTTGTAGATTGGGAAGAATCACGTTCTTTCTTCTACAGAAGGCTACGGAGGAGGATCTCTG
AAGATGTTCTTGCAAAAGAAATAAGAGGAATAGCTGGTGACCACTTCACTCACCAATCAGCAGTTGAGCTGATCAAG
GAATGGTACTTGGCTTCTCAAGCCACAACAGGAAGCACTGAATGGGATGATGATGATGCTTTTGTTGCCTGGAAGGA
GAATCCTGAAAACTATAAGGGATATATCCAAGAGTTAAGGGCTCAAAAGGTGTCTCAGTCGCTCTCCGATCTTGCAG
ACTCCAGTTCAGATCTAGAAGCATTCTCACAGGGTCTTTCCACATTATTAGATAAGATGGATCCCTCTCAGAGAGCC
AAGTTCATTCAGGAAGTCAAGAAGGTCCTGGGTTGA

FIGURE 11B

>AAO62902_Setaria italica (foxtail millet)

MSQLGLAAAASKALPLLPNRHRTSAGTTFPSPVSSRPSNRRKSRTRSLRDGGDGVSDAKKHNQSVRQGLAGIID
LPNEATSEVDISHGSEDPRGPTDSYQMNGIVSEAHNGRHASVSKVVEFCAALGGKTPIHSILVANNGMAAAKFM
RSVRTWANDTFGSEKAIQLIAMATPEDMRINAEHIRIADQFVEVPGGTNNNNYANVQLIVEVAERIGVSAVWPG
WGHASENPELPDALTAKGVVFLGPPAASMNALGDKVGSALIAQAAGVPTLSWSGSHVEVPLECCLDAIPEEMYR
KACVTTTEEAVASCQVVGYPAMIKASWGGGGKGIRKVHNDDEVRALFKQVQGEVPGSPIFIMRLASQSRHLEVQ
LLCDQYGNVAALHSRDCSVQRRHQKIIEEGPVTVAPRETVKALEQAARRLAKAVGYVGAATVEYLYSMETGEYY
FLELNPRLQVEHPVTEWIAEVNLPAAQVAVGMGIPLWQIPEIRRFDGMDYGGGYDIWRKTAALATPFNFDEVDS
QWPKGHCVAVRITSEDPDDGFKPTGGKVKEISFKSKPNVWAYFSVKSGGGIHEFVDSQFGHVFAYGLSRSAAIT
NMALALKEIQIRGEIHSNVDYTVDLLNASDFRENKIHTGWLDTRIAMRVQAERPPWYISVVGGALYKTVTANAA
TVSDYVSYLTKGQIPPKHISLVSSTVNLNIEGSKYTVETVRTGHGSYRLRMNDSAIEANVQSLCDGGLLMQLDG
NSHVIYAEEEAGGTRLLIDGKTCLLQNDHDPSKLLAETPCKLLRFLVADGAHVDADVPYAEVEVMKMCMPLLSP
ASGVIHVMMSEGQALQAGDLIARLDLDDPSAVKRAEPFHGIFPQMDLPVAASSQVHKRYAASWNAARMVLAGYE
HNINEVVQDLVCCLDDPELPFLQWDELMSVLATRLPRNLKSELEDKYMEYKLNFYHGKNKDFPSKLLRDIIEAN
LAYGSEKEKATNERLIEPLMSLLKSYEGGRESHAHFVVKSLFKEYLAVEELFSDGIQSDVIETLRHQHSKDLQK
VVDIVLSHQGVRNKAKLVTALMEKLVYPNPAAYRDLLVRFSSLNHKRYYKLALKASELLEQTKLSELRASIARS
LSDLGMHKGEMTIEDSMEDLVSAPLPVEDALISLFDYSDPTVQQKVIETYISRLYQPLLVKDSIQVKFKESGAF
ALWEFSEGHVDTKNGQGTVLGRTRWGAMVAVKSVESARTAIVAALKDSAQHASSEGNMMHIALLSAENENNISD
DQAQHRMEKLNKILKDTSVANDLRAAGLKVISCIVQRDEARMPMRHTLLWSDEKSCYEEEQILRHVEPPLSMLL
EMDKLKVKGYNEMKYTPSRDRQWHIYTLRNTENPKMLHRVFFRTIVRQPNAGNKFISAQIGDTEVGGPEESLSF
TSNSILRALMTAIEELELHAIRTDHSHMYLCILKEQKLLDLIPFSGSTIVDVVQDEATACSLLKSMALKIHELV
GAQMHHLSVCQWEVKLKLYCDGPASGTWRVVTTNVTSHTCTVDIYREVEDTESQKLVYHSASPSASPLHGVALD
NPYQPLSVIDLKHCSARNNRTTYCYDFPLAFETALQKSWQSNGSSVSEGSENSRSYVKATELVFAEKHGSWGTP
IISMERPAGLNDIGMVAWILEMSTPEFPNGRQIIVIANDITFRAGSFGPREDAFFEAVTNLACERKLPLIYLAA
NSGARIGIADEVKSCFRVGWSDEGSPERGFQYIYLTDEDYARISLSVIAHKLQLDNGEIRWIIDSVVGKEDGLG
VENIHGSAAIASAYSRAYEETFTLTFVTGRTVGIGAYLARLGIRCIQRLDQPIILTGFSALNKLLGREVYSSHM
QLGGPKIMATNGVVHLTVSDDLEGVSNILRWLSYVPANIGGPLPITKPLDPPDRPVAYIPENTCDPRAAIRGVD
DSQGKWLGGMFDKDSFVETFEGWAKTVVTGRAKLGGIPVGVIAVETQTMMQLIPADPGQLDSHERSVPRAGQVW
FPDSATKTAQALLDFNREGLPLFILANWRGFSGGQRDLFEGILQAGSTIVENLRTYNQPAFVYIPMAGELRGGA
WVVVDSKINPDRIECYAERTAKGNVLEPQGLIEIKFRSEELQDCMGRLDPGLINLKAKLQGAKLGNGSLTDVES
LQKSIDARTKQLLPLYTQIAIRFAELHDTSLRMAAKGVIKKVVDWEESRSFFYRRLRRRISEDVLAKEIRGIAG
DHFTHQSAVELIKEWYLASQATTGSTEWDDDDAFVAWKENPENYKGYIQELRAQKVSQSLSDLADSSSDLEAFS
QGLSTLLDKMDPSQRAKFIQEVKKVLG

FIGURE 12A

>AY219175_Setaria italica (foxtail millet)

atgtcgcaacttggattagctgcagctgcctcaaaggcgctgccactacttcctaatcgccatagaacttcagctgg
aactacattcccatcacctgtatcatcgcggccctcaaaccgaaggaaaagccgcactcgttcacttcgtgatggag
gagatggggtatcagatgccaaaaagcacaaccagtctgtccgtcaaggtcttgctggcatcatcgacctcccaaat
gaggcaacatcggaagtggatatttctcatggatccgaggatcccaggggccaaccgattcatatcaaatgaatgg
gattgtaaatgaagcacataatggcagacatgcctcagtgtccaaggttgttgaattttgtgcggcgctaggtggca
aaacaccaattcacagtatactagtggccaacaatggaatggcagcagcaaagttcatgaggagtgtccggacatgg
gctaatgatactttggatcggagaaggcgattcagctcatagctatggcaactccagaagacatgaggataaatgc
agaacacattagaattgctgatcaatttgtagaggtgcctggtggaacaaacaataacaactatgcaaatgttcaac
tcatagtggaggtagcagaaagaataggtgtttctgctgtttggcctggttggggtcatgcttctgagaatcctgaa
cttccagatgcattgaccgcaaaaggaattgttttccttgggccacctgcggcatcaatgaatgcattgggagataa
ggtcggttcagctctcattgctcaagcagctggggtcccgaccctttcgtggagtggatcacatgttgaagttccat
tagagtgctgcttagatgcgatacctgaggaaatgtatagaaaagcttgtgttactaccacagaagaagctgttgcg
agttgtcaggtggttggttatcctgccatgattaaggcatcctggggaggtggtggtaaaggaataagaaaggttca
taatgacgatgaggttagagcactgtttaagcaagtacaaggtgaagtccctggctccccaatatttatcatgaggc
ttgcatcccagagtcgtcatcttgaagttcagttgctttgtgatcaatatggcaatgtggcagcacttcacagtcgt
gattgcagtgtgcaacggcgacaccaaaagattattgaggaaggcccagttactgttgctcctcgtgagacagttaa
agcgcttgagcaggcagcaaggaggcttgctaaggctgtgggttatgttggtgctgctactgttgaatacctttaca
gcatggagactggggaatactattttctggagcttaatcccagattacaggtcgagcatccagtcactgagtggatt
gctgaagtaaatcttcctgcagctcaagttgcagttggaatgggcatacctctttggcagattccagaaatcagacg
tttctatggaatggactatggaggaggatatgacatttggaggaaaacagcagctcttgccacaccatttaatttg
atgaagtagattctcaatggccaaagggccattgtgtagcagttagaattactagcgaggatccagatgatggtttc
aaacctactggtgggaaagtgaaggagataagttttaaaagcaagcctaatgtttggcctacttctcagtaaagtc
tggtggaggcattcatgaatttgctgattctcagtttgggcatgtttttgcatatgggctctctagatcagcagcaa
taacgaacatggctcttgcattaaaagagattcaaattcgtggagaaattcattcaaatgttgattacacagttgat
ctcttaaatgcttcagacttcagagaaaataagattcatactggctggcttgataccagaatagctatgcgtgttca
agctgagaggcccccatggtatatttcagtggttggaggagctctatataaaacagtaactgccaatgcagccactg
tttctgattatgtcagttatctcaccaagggccagattccaccaaagcatatatcccttgtcagttcaacagttaat
ctgaatatcgaagggagcaaatacacagttgaaactgtaaggactggacatggtagctacagattacgaatgaatga
ttcagcaattgaagcgaatgtacaatctttatgtgatggaggcctcttaatgcagttggatggaaatagccatgtaa
tttacgcggaagaagaagctggtggtacacgacttctgattgatggaaagacatgcttgttacagaatgatcatgat
ccatcaaagttattagctgagacaccctgcaaacttcttcggttcttggttgctgatggtgctcatgttgatgctga
tgtaccatatgcggaagttgaggttatgaaaatgtgcatgcctctcttgtcgcctgcttctggtgtcattcatgtta
tgatgtctgagggccaggcattgcaggctggtgatcttatagcaaggctggatcttgatgacccttctgctgtgaaa
agagctgaaccatttcatggaatatttccacaaatggaccttcctgttgctgcctctagccaagtacacaaaagata
tgctgcaagtttgaatgctgctcgaatggtccttgcaggatacgagcataatatcaatgaagttgtacaagatttgg
tatgctgcctggatgatcccgagcttcccttcctacagtgggatgaacttatgtcagttctagcaactaggcttcca
agaaatcttaagagtgagttagaggataaatacatggaatacaagttgaacttttaccatgggaaaaacaaggactt
cccgtccaagctgctgagagacatcattgaggcaaatcttgcatatggttcagagaaggaaaaagctacgaatgaga
ggcttattgagcctcttatgagcctacttaagtcatatgagggtggagagaaagccatgctcatttgttgtcaag
tccctttcaaggagtaccttgctgtggaagaacttttcagtgatgggattcagtctgatgtgattgaaaccctgcg
tcatcagcacagtaaagacttgcagaaggttgtagacattgtgttgtctcaccagggtgtgaggaacaaagctaagc
ttgtaacagcacttatggaaaagctggtttatccaaatcctgctgcttacagggatctgttggttcgcttttcttca
ctcaatcataaaagatattataagttggcccttaaagcaagcgaacttcttgaacaaactaaactaagtgaactccg
tgcaagcatcgcaagaagcctttctgatctggggatgcataagggagaaatgactattgaagatagcatggaagatt
tagtctctgccccattacctgtcgaagatgcacttatttctttgtttgattacagtgatccaactgttcagcagaaa
gtgatcgagacatacatatctcgattgtatcagcctcttcttgtgaaagatagcatccaagtgaaatttaaggaatc
tggtgcctttgctttatgggaattttctgaagggcatgttgatactaaaaatggacaagggaccgttcttggtcgaa
caagatggggtgccatggtagctgtcaaatcagttgaatctgcacgaacagccattgtagctgcattaaaggattcg
gcacagcatgccagctctgagggcaacatgatgcacattgccttattgagtgctgaaaatgaaaataatatcagtga
tgatcaagctcaacataggatggaaaaacttaacaagatactcaaggatactagtgtcgcaaatgatcttcgagctg
ctggtttgaaggttataagttgcattgttcaaagagatgaagcacgcatgccaatgcgccacacattactctggtca
gatgaaaagagttgttatgaggaagagcagattcttcggcatgtggagcctcccctctccatgcttcttgaaatgga

FIGURE 12A (continued)

taagttgaaagtgaaaggatacaatgaaatgaagtatactccatcacgtgatcgtcaatggcatatctacacactaa
gaaatactgaaaaccccaaaatgttgcatagggtatttttccgaactattgtcaggcaacccaatgcaggcaacaag
tttatatcagcccaaattggcgacactgaagtaggaggtcctgaggaatctttgtcatttacatctaatagcatttt
aagagccttgatgactgctattgaagaattagagcttcatgcaattaggactggtcattctcacatgtatttgtgca
tattgaaagaacaaaagcttcttgatctcattccgttttcagggagcacaatcgtcgatgttggccaagacgaagct
actgcttgttcacttttaaaatcaatggctttgaagatacacgaacttgttggtgcacagatgcatcatctttctgt
atgccagtgggaggtgaaactcaagttgtactgcgatgggcctgccagtggcacctggagagttgtaactacaaatg
ttactagtcacacttgcaccattgatatctaccgggaagtggaagatactgaatcgcagaagttagtataccattca
gcttctccgtcagctagtcctttgcatggtgtggccctggataatccgtatcaacctttgagtgtcattgatctaaa
acgctgctctgctaggaacaacagaactacatattgctatgattttccactggcatttgaaactgccctgcagaagt
catggcagtccaatggctccagtgtttctgaaggcagtgaaaatagtaggtcttatgtgaaagcaacagagctggtg
tttgctgaaaaacatgggtcctggggcactcctataatttccatggagcgtcccgctgggctcaatgacattggcat
ggtagcttggatcttagagatgtccactcctgaatttcccaatggcaggcagattattgtcatagcaaatgatatta
ctttcagagctggatcatttggcccaagggaagatgcgtttttttgaagctgtcacgaacctggcctgcgagaggaag
cttcctcttatatacttggcagcaaactccggtgctaggattggcatagccgatgaagtgaaatcttgcttccgtgt
tgggtggtccgatgaaggcagccctgaacggggttttcagtacatttatctgactgacgaagactatgcccgtatta
gcttgtctgttatagcacacaagctgcagctggataatggtgaaattaggtggattattgactctgttgtgggcaag
gaggatgggcttggtgttgagaatctacatggaagtgctgctattgccagtgcttattctagggcatatgaggagac
atttacacttacatttgtgactgggcggactgttggaataggagcatatctcgctcggctcggtatacggtgcatac
agcgtcttgaccagcctattattttaactgggttttctgccctgaacaagcttcttgggcgggaagtgtacagctcc
cacatgcagttgggtggtcctaagatcatggcgaccaatggtgttgtccacttgactgtttcagatgaccttgaagg
tgtttccaatatattgaggtggctcagctatgttcctgccaacattggtggacctcttcctattacaaaacctttgg
acccaccagacagacctgttgcatacatccctgagaacacatgtgatccgcgcgcagccattcgtggtgtagatgac
agccaagggaaatggttgggtggtatgtttgacaaagacagctttgtcgagacatttgaaggatgggcgaaaacagt
ggttacgggcagagcaaagcttggaggaattcctgttggtgtcatagctgtggagacacaaaccatgatgcagctta
tccctgctgatccaggccagcttgattcccatgagcgatctgttcctcgggctggacaagtgtggttcccagattct
gcaaccaagacagctcaggcattgttggacttcaaccgtgaaggattgccgctgttcatccttgctaactggagagg
attctctggtggacaaagagatctgtttgaaggaattcttcaggctgggtcaacaattgttgagaaccttaggacat
acaatcagcctgcttttgtctacattcctatggctggagagctgcgtggaggagcttgggttgtggttgatagcaaa
ataaatccagaccgaattgagtgttatgctgagaggactgctaaaggcaatgttcttgaacctcaagggttaattga
aatcaaattcagatcagaggagctccaagactgtatgggtaggcttgacccagagttgataaatctgaaagcaaaac
tccaaggtgcaaagcttggaaatggaagcctaacagatgtagaatcccttcagaagagtatagatgctcgtacgaaa
cagttgttgcctttatacacccagattgcaatacggtttgctgaattgcatgatacttccctcagaatggcagctaa
aggtgtgattaagaaagttgtagattgggaagaatcacgttctttcttctacagaaggctacggaggaggatctctg
aagatgttcttgcaaaagaaataagaggaatagctggtgaccacttcactcaccaatcagcagttgagctgatcaag
gaatggtacttggcttctcaagccacaacaggaagcactgaatgggatgatgatgatgcttttgttgcctggaagga
gaatcctgaaaactataagggatatatccaagagttaagggctcaaaaggtgtctcagtcgctctccgatcttgcag
actccagttcagatctagaagcattctcacagggtctttccacattattagataagatggatccctctcagagagcc
aagttcattcaggaagtcaagaaggtcctgggttga

FIGURE 12B

>AAO62903_Setaria italica (foxtail millet)

MSQLGLAAAASKALPLLPNRHRTSAGTTFPSPVSSRPSNRRKSRTRSLRDGGDGVSDAKKHNQSVRQGLAGIID
LPNEATSEVDISHGSEDPRGPTDSYQMNGIVNEAHNGRHASVSKVVEFCAALGGKTPIHSILVANNGMAAAKFM
RSVRTWANDTFGSEKAIQLIAMATPEDMRINAEHIRIADQFVEVPGGTNNNNYANVQLIVEVAERIGVSAVWPG
WGHASENPELPDALTAKGIVFLGPPAASMNALGDKVGSALIAQAAGVPTLSWSGSHVEVPLECCLDAIPEEMYR
KACVTTTEEAVASCQVVGYPAMIKASWGGGGKGIRKVHNDDEVRALFKQVQGEVPGSPIFIMRLASQSRHLEVQ
LLCDQYGNVAALHSRDCSVQRRHQKIIEEGPVTVAPRETVKALEQAARRLAKAVGYVGAATVEYLYSMETGEYY
FLELNPRLQVEHPVTEWIAEVNLPAAQVAVGMGIPLWQIPEIRRFYGMDYGGGYDIWRKTAALATPFNFDEVDS
QWPKGHCVAVRITSEDPDDGFKPTGGKVKEISFKSKPNVWAYFSVKSGGGIHEFADSQFGHVFAYGLSRSAAIT
NMALALKEIQIRGEIHSNVDYTVDLLNASDFRENKIHTGWLDTRIAMRVQAERPPWYISVVGGALYKTVTANAA
TVSDYVSYLTKGQIPPKHISLVSSTVNLNIEGSKYTVETVRTGHGSYRLRMNDSAIEANVQSLCDGGLLMQLDG
NSHVIYAEEEAGGTRLLIDGKTCLLQNDHDPSKLLAETPCKLLRFLVADGAHVDADVPYAEVEVMKMCMPLLSP
ASGVIHVMMSEGQALQAGDLIARLDLDDPSAVKRAEPFHGIFPQMDLPVAASSQVHKRYAASLNAARMVLAGYE
HNINEVVQDLVCCLDDPELPFLQWDELMSVLATRLPRNLKSELEDKYMEYKLNFYHGKNKDFPSKLLRDIIEAN
LAYGSEKEKATNERLIEPLMSLLKSYEGGRESHAHFVVKSLFKEYLAVEELFSDGIQSDVIETLRHQHSKDLQK
VVDIVLSHQGVRNKAKLVTALMEKLVYPNPAAYRDLLVRFSSLNHKRYYKLALKASELLEQTKLSELRASIARS
LSDLGMHKGEMTIEDSMEDLVSAPLPVEDALISLFDYSDPTVQQKVIETYISRLYQPLLVKDSIQVKFKESGAF
ALWEFSEGHVDTKNGQGTVLGRTRWGAMVAVKSVESARTAIVAALKDSAQHASSEGNMMHIALLSAENENNISD
DQAQHRMEKLNKILKDTSVANDLRAAGLKVISCIVQRDEARMPMRHTLLWSDEKSCYEEEQILRHVEPPLSMLL
EMDKLKVKGYNEMKYTPSRDRQWHIYTLRNTENPKMLHRVFFRTIVRQPNAGNKFISAQIGDTEVGGPEESLSF
TSNSILRALMTAIEELELHAIRTGHSHMYLCILKEQKLLDLIPFSGSTIVDVGQDEATACSLLKSMALKIHELV
GAQMHHLSVCQWEVKLKLYCDGPASGTWRVVTTNVTSHTCTIDIYREVEDTESQKLVYHSASPSASPLHGVALD
NPYQPLSVIDLKRCSARNNRTTYCYDFPLAFETALQKSWQSNGSSVSEGSENSRSYVKATELVFAEKHGSWGTP
IISMERPAGLNDIGMVAWILEMSTPEFPNGRQIIVIANDITFRAGSFGPREDAFFEAVTNLACERKLPLIYLAA
NSGARIGIADEVKSCFRVGWSDEGSPERGFQYIYLTDEDYARISLSVIAHKLQLDNGEIRWIIDSVVGKEDGLG
VENLHGSAAIASAYSRAYEETFTLTFVTGRTVGIGAYLARLGIRCIQRLDQPIILTGFSALNKLLGREVYSSHM
QLGGPKIMATNGVVHLTVSDDLEGVSNILRWLSYVPANIGGPLPITKPLDPPDRPVAYIPENTCDPRAAIRGVD
DSQGKWLGGMFDKDSFVETFEGWAKTVVTGRAKLGGIPVGVIAVETQTMMQLIPADPGQLDSHERSVPRAGQVW
FPDSATKTAQALLDFNREGLPLFILANWRGFSGGQRDLFEGILQAGSTIVENLRTYNQPAFVYIPMAGELRGGA
WVVVDSKINPDRIECYAERTAKGNVLEPQGLIEIKFRSEELQDCMGRLDPELINLKAKLQGAKLGNGSLTDVES
LQKSIDARTKQLLPLYTQIAIRFAELHDTSLRMAAKGVIKKVVDWEESRSFFYRRLRRRISEDVLAKEIRGIAG
DHFTHQSAVELIKEWYLASQATTGSTEWDDDDAFVAWKENPENYKGYIQELRAQKVSQSLSDLADSSSDLEAFS
QGLSTLLDKMDPSQRAKFIQEVKKVLG

FIGURE 13A

>AF294805_Setaria italica (foxtail millet)

ATGTCGCAACTTGGATTAGCTGCAGCTGCCTCAAAGGCGCTGCCACTACTTCCTAATCGCCATAGAACTTCAGCTGG
AACTACATTCCCATCACCTGTATCATCGCGGCCCTCAAACCGAAGGAAAAGCCGCACTCGTTCACTTCGTGATGGAG
GAGATGGGGTATCAGATGCCAAAAAGCACAACCAGTCTGTCCGTCAAGGTCTTGCTGGCATCATCGACCTCCCAAAT
GAGGCAACATCGGAAGTGGATATTTCTCATGGATCCGAGGATCCCAGGGGGCCAACCGATTCATATCAAATGAATGG
GATTGTAAATGAAGCACATAATGGCAGACATGCCTCAGTGTCCAAGGTTGTTGAATTTTGTGCGGCGCTAGGTGGCA
AAACACCAATTCACAGTATACTAGTGGCCAACAATGGAATGGCAGCAGCAAAGTTCATGAGGAGTGTCCGGACATGG
GCTAATGATACTTTTGGATCGGAGAAGGCGATTCAGCTCATAGCTATGGCAACTCCAGAAGACATGAGGATAAATGC
AGAACACATTAGAATTGCTGATCAATTTGTAGAGGTGCCTGGTGGAACAAACAATAACAACTATGCAAATGTTCAAC
TCATAGTGGAGGTAGCAGAAAGAATAGGTGTTTCTGCTGTTTGGCCTGGTTGGGGTCATGCTTCTGAGAATCCTGAA
CTTCCAGATGCATTGACCGCAAAAGGAATTGTTTTCCTTGGGCCACCTGCGGCATCAATGAATGCATTGGGAGATAA
GGTCGGTTCAGCTCTCATTGCTCAAGCAGCTGGGGTCCCGACCCTTTCGTGGAGTGGATCACATGTTGAAGTTCCAT
TAGAGTGCTGCTTAGATGCGATACCTGAGGAAATGTATAGAAAAGCTTGTGTTACTACCACAGAAGAAGCTGTTGCG
AGTTGTCAGGTGGTTGGTTATCCTGCCATGATTAAGGCATCCTGGGGAGGTGGTGGTAAAGGAATAAGAAAGGTTCA
TAATGACGATGAGGTTAGAGCACTGTTTAAGCAAGTACAAGGTGAAGTCCCTGGCTCCCCAATATTTATCATGAGGC
TTGCATCCCAGAGTCGTCATCTTGAAGTTCAGTTGCTTTGTGATCAATATGGCAATGTGGCAGCACTTCACAGTCGT
GATTGCAGTGTGCAACGGCGACACCAAAAGATTATTGAGGAAGGCCCAGTTACTGTTGCTCCTCGTGAGACAGTTAA
AGCGCTTGAGCAGGCAGCAAGGAGGCTTGCTAAGGCTGTGGGTTATGTTGGTGCTGCTACTGTTGAATACCTTTACA
GCATGGAGACTGGGGAATACTATTTTCTGGAGCTTAATCCCAGATTACAGGTCGAGCATCCAGTCACTGAGTGGATT
GCTGAAGTAAATCTTCCTGCAGCTCAAGTTGCAGTTGGAATGGGCATACCTCTTTGGCAGATTCCAGAAATCAGACG
TTTCTATGGAATGGACTATGGAGGAGGATATGACATTTGGAGGAAAACAGCAGCTCTTGCCACACCATTTAATTTG
ATGAAGTAGATTCTCAATGGCCAAAGGGCCATTGTGTAGCAGTTAGAATTACTAGCGAGGATCCAGATGATGGTTTC
AAACCTACTGGTGGGAAAGTGAAGGAGATAAGTTTTAAAAGCAAGCCTAATGTTTGGGCCTACTTCTCAGTAAAGTC
TGGTGGAGGCATTCATGAATTTGCTGATTCTCAGTTTGGGCATGTTTTTGCATATGGGCTCTCTAGATCAGCAGCAA
TAACGAACATGGCTCTTGCATTAAAAGAGATTCAAATTCGTGGAGAAATTCATTCAAATGTTGATTACACAGTTGAT
CTCTTAAATGCTTCAGACTTCAGAGAAAATAAGATTCATACTGGCTGGCTTGATACCAGAATAGCTATGCGTGTTCA
AGCTGAGAGGCCCCCATGGTATATTTCAGTGGTTGGAGGAGCTCTATATAAAACAGTAACTGCCAATGCAGCCACTG
TTTCTGATTATGTCAGTTATCTCACCAAGGGCCAGATTCCACCAAAGCATATATCCCTTGTCAGTTCAACAGTTAAT
CTGAATATCGAAGGGAGCAAATACACAGTTGAAACTGTAAGGACTGGACATGGTAGCTACAGATTACGAATGAATGA
TTCAGCAATTGAAGCGAATGTACAATCTTTATGTGATGGAGGCCTCTTAATGCAGTTGGATGGAAATAGCCATGTAA
TTTACGCGGAAGAAGAAGCTGGTGGTACACGACTTCTGATTGATGGAAAGACATGCTTGTTACAGAATGATCATGAT
CCATCAAAGTTATTAGCTGAGACACCCTGCAAACTTCTTCGGTTCTTGGTTGCTGATGGTGCTCATGTTGATGCTGA
TGTACCATATGCGGAAGTTGAGGTTATGAAAATGTGCATGCCTCTCTTGTCGCCTGCTTCTGGTGTCATTCATGTTA
TGATGTCTGAGGGCCAGGCATTGCAGGCTGGTGATCTTATAGCAAGGCTGGATCTTGATGACCCTTCTGCTGTGAAA
AGAGCTGAACCATTTCATGGAATATTTCCACAAATGGACCTTCCTGTTGCTGCCTCTAGCCAAGTACACAAAAGATA
TGCTGCAAGTTTGAATGCTGCTCGAATGGTCCTTGCAGGATACGAGCATAATATCAATGAAGTTGTACAAGATTTGG
TATGCTGCCTGGATGATCCCGAGCTTCCCTTCCTACAGTGGGATGAACTTATGTCAGTTCTAGCAACTAGGCTTCCA
AGAAATCTTAAGAGTGAGTTAGAGGATAAATACATGGAATACAAGTTGAACTTTTACCATGGGAAAAACAAGGACTT
CCCGTCCAAGCTGCTGAGAGACATCATTGAGGCAAATCTTGCATATGGTTCAGAGAAGGAAAAAGCTACGAATGAGA
GGCTTATTGAGCCTCTTATGAGCCTACTTAAGTCATATGAGGGTGGGAGAGAAAGCCATGCTCATTTTGTTGTCAAG
TCCCTTTTCAAGGAGTACCTTGCTGTGGAAGAACTTTTCAGTGATGGGATTCAGTCTGATGTGATTGAAACCCTGCG
TCATCAGCACAGTAAAGACTTGCAGAAGGTTGTAGACATTGTGTTGTCTCACCAGGGTGTGAGGAACAAAGCTAAGC
TTGTAACAGCACTTATGGAAAAGCTGGTTTATCCAAATCCTGCTGCTTACAGGGATCTGTTGGTTCGCTTTTCTTCA
CTCAATCATAAAAGATATTATAAGTTGGCCCTTAAAGCAAGCGAACTTCTTGAACAAACTAAACTAAGTGAACTCCG
TGCAAGCATCGCAAGAAGCCTTTCTGATCTGGGGATGCATAAGGGAGAAATGACTATTGAAGATAGCATGGAAGATT
TAGTCTCTGCCCCATTACCTGTCGAAGATGCACTTATTTCTTTGTTTGATTACAGTGATCCAACTGTTCAGCAGAAA
GTGATCGAGACATACATATCTCGATTGTATCAGCCTCTTCTTGTGAAAGATAGCATCCAAGTGAAATTTAAGGAATC
TGGTGCCTTTGCTTTATGGGAATTTTCTGAAGGGCATGTTGATACTAAAAATGGACAAGGGACCGTTCTTGGTCGAA
CAAGATGGGGTGCCATGGTAGCTGTCAAATCAGTTGAATCTGCACGAACAGCCATTGTAGCTGCATTAAAGGATTCG
GCACAGCATGCCAGCTCTGAGGGCAACATGATGCACATTGCCTTATTGAGTGCTGAAAATGAAAATAATATCAGTGA
TGATCAAGCTCAACATAGGATGGAAAAACTTAACAAGATACTCAAGGATACTAGTGTCGCAAATGATCTTCGAGCTG
CTGGTTTGAAGGTTATAAGTTGCATTGTTCAAAGAGATGAAGCACGCATGCCAATGCGCCACACATTACTCTGGTCA

FIGURE 13A (continued)

GATGAAAAGAGTTGTTATGAGGAAGAGCAGATTCTTCGGCATGTGGAGCCTCCCCTCTCCATGCTTCTTGAAATGGA
TAAGTTGAAAGTGAAAGGATACAATGAAATGAAGTATACTCCATCACGTGATCGTCAATGGCATATCTACACACTAA
GAAATACTGAAAACCCCAAAATGTTGCATAGGGTATTTTTCCGAACTATTGTCAGGCAACCCAATGCAGGCAACAAG
TTTATATCAGCCCAAATTGGCGACACTGAAGTAGGAGGTCCTGAGGAATCTTTGTCATTTACATCTAATAGCATTTT
AAGAGCCTTGATGACTGCTATTGAAGAATTAGAGCTTCATGCAATTAGGACTGGTCATTCTCACATGTATTTGTGCA
TATTGAAAGAACAAAAGCTTCTTGATCTCATTCCGTTTTCAGGGAGCACAATCGTCGATGTTGGCCAAGACGAAGCT
ACTGCTTGTTCACTTTTAAAATCAATGGCTTTGAAGATACACGAACTTGTTGGTGCACAGATGCATCATCTTTCTGT
ATGCCAGTGGGAGGTGAAACTCAAGTTGTACTGCGATGGGCCTGCCAGTGGCACCTGGAGAGTTGTAACTACAAATG
TTACTAGTCACACTTGCACCGTTGATATCTACCGGGAAGTGGAAGATACTGAATCGCAGAAGTTAGTATACCATTCA
GCTTCTCCGTCAGCTAGTCCTTTGCATGGTGTGGCCCTGGATAATCCGTATCAACCTTTGAGTGTCATTGATCTAAA
ACGCTGCTCTGCTAGGAACAACAGAACTACATATTGCTATGATTTTCCACTGGCATTTGAAACTGCCCTGCAGAAGT
CATGGCAGTCCAATGGCTCCAGTGTTTCTGAAGGCAGTGAAAATAGTAGGTCTTATGTGAAAGCAACAGAGCTGGTG
TTTGCTGAAAAACATGGGTCCTGGGGCACTCCTATAATTTCCATGGAGCGTCCCGCTGGGCTCAATGACATTGGCAT
GGTAGCTTGGATCTTAGAGATGTCCACTCCTGAATTTCCCAATGGCAGGCAGATTATTGTCATAGCAAATGATATTA
CTTTCAGAGCTGGATCATTTGGCCCAAGGGAAGATGCGTTTTTTGAAGCTGTCACGAACCTGGCCTGCGAGAGGAAG
CTTCCTCTTATATACTTGGCAGCAAACTCCGGTGCTAGGATTGGCATAGCCGATGAAGTGAAATCTTGCTTCCGTGT
TGGGTGGTCCGATGAAGGCAGCCCTGAACGGGGTTTTCAGTACATTTATCTGACTGACGAAGACTATGCCCGTATTA
GCTTGTCTGTTATAGCACACAAGCTGCAGCTGGATAATGGTGAAATTAGGTGGATTATTGACTCTGTTGTGGGCAAG
GAGGATGGGCTTGGTGTTGAGAATATACATGGAAGTGCTGCTATTGCCAGTGCTTATTCTAGGGCATATGAGGAGAC
ATTTACACTTACATTTGTGACTGGGCGGACTGTTGGAATAGGAGCATATCTTGCTCGGCTCGGTATACGGTGCATAC
AGCGTCTTGACCAGCCTATTATTTTAACTGGGTTTTCTGCCCTGAACAAGCTTCTTGGGCGGGAAGTGTACAGCTCC
CACATGCAGTTGGGTGGTCCTAAGATCATGGCGACCAATGGTGTTGTCCACTTGACTGTTTCAGATGACCTTGAAGG
TGTTTCCAATATATTGAGGTGGCTCAGCTATGTTCCTGCCAACATTGGTGGACCTCTTCCTATTACAAAACCTTTGG
ACCCACCAGACAGACCTGTTGCATACATCCCTGAGAACACATGTGATCCGCGCGCAGCCATTCGTGGTGTAGATGAC
AGCCAAGGGAAATGGTTGGGTGGTATGTTTGACAAAGACAGCTTTGTCGAGACATTTGAAGGATGGGCGAAAACAGT
GGTTACGGGCAGAGCAAAGCTTGGAGGAATTCCTGTTGGTGTCATAGCTGTGGAGACACAAACCATGATGCAGCTTA
TCCCTGCTGATCCAGGCCAGCTTGATTCCCATGAGCGATCTGTTCCTCGGGCTGGACAAGTGTGGTTCCCAGATTCT
GCAACCAAGACAGCTCAGGCATTGTTGGACTTCAACCGTGAAGGATTGCCGCTGTTCATCCTTGCTAACTGGAGAGG
ATTCTCTGGTGGACAAAGAGATCTGTTTGAAGGAATTCTTCAGGCTGGGTCAACAATTGTTGAGAACCTTAGGACAT
ACAATCAGCCTGCTTTTGTCTACATTCCTATGGCTGGAGAGCTGCGTGGAGGAGCTTGGGTTGTGGTTGATAGCAAA
ATAAATCCAGACCGAATTGAGTGTTATGCTGAGAGGACTGCTAAAGGCAATGTTCTGGAACCTCAAGGGTTAATTGA
AATCAAATTCAGATCAGAGGAGCTCCAAGACTGTATGGGTAGGCTTGACCCAGAGTTGATAAATCTGAAAGCAAAAC
TCCAAGGTGCAAAGCTTGGAAATGGAAGCCTAACAGATGTAGAATCCCTTCAGAAGAGTATAGATGCTCGTACGAAA
CAGTTGTTGCCTTTATACACCCAGATTGCAATACGGTTTGCTGAATTGCATGATACTTCCCTCAGAATGGCAGCTAA
AGGTGTGATTAAGAAAGTTGTAGATTGGGAAGAATTACGTTCTTTCTTCTACAGAAGGCTACGGAGGAGGATCTCTG
AAGATGTTCTTGCAAAAGAAATAAGAGGAATAGCTGGTGACCACTTCACTCACCAATCAGCAGTTGAGCTGATCAAG
GAATGGTACTTGGCTTCTCAAGCCACAACAGGAAGCACTGAATGGGATGATGATGATGCTTTTGTTGCCTGGAAGGA
GAATCCTGAAAACTATAAGGGATATATCCAAGAGTTAAGGGCTCAAAAGGTGTCTCAGTCGCTCTCCGATCTTGCAG
ACTCCAGTTCAGATCTAGAAGCATTCTCACAGGGTCTTTCCACATTATTAGATAAGATGGATCCCTCTCAGAGAGCC
AAGTTCATTCAGGAAGTCAAGAAGGTCCTGGGTTGA

FIGURE 13B

>AAL02056_Setaria italica (foxtail millet)

MSQLGLAAAASKALPLLPNRHRTSAGTTFPSPVSSRPSNRRKSRTRSLRDGGDGVSDAKKHNQSVRQGLAGIID
LPNEATSEVDISHGSEDPRGPTDSYQMNGIVNEAHNGRHASVSKVVEFCAALGGKTPIHSILVANNGMAAAKFM
RSVRTWANDTFGSEKAIQLIAMATPEDMRINAEHIRIADQFVEVPGGTNNNNYANVQLIVEVAERIGVSAVWPG
WGHASENPELPDALTAKGIVFLGPPAASMNALGDKVGSALIAQAAGVPTLSWSGSHVEVPLECCLDAIPEEMYR
KACVTTTEEAVASCQVVGYPAMIKASWGGGGKGIRKVHNDDEVRALFKQVQGEVPGSPIFIMRLASQSRHLEVQ
LLCDQYGNVAALHSRDCSVQRRHQKIIEEGPVTVAPRETVKALEQAARRLAKAVGYVGAATVEYLYSMETGEYY
FLELNPRLQVEHPVTEWIAEVNLPAAQVAVGMGIPLWQIPEIRRFYGMDYGGGYDIWRKTAALATPFNFDEVDS
QWPKGHCVAVRITSEDPDDGFKPTGGKVKEISFKSKPNVWAYFSVKSGGGIHEFADSQFGHVFAYGLSRSAAIT
NMALALKEIQIRGEIHSNVDYTVDLLNASDFRENKIHTGWLDTRIAMRVQAERPPWYISVVGGALYKTVTANAA
TVSDYVSYLTKGQIPPKHISLVSSTVNLNIEGSKYTVETVRTGHGSYRLRMNDSAIEANVQSLCDGGLLMQLDG
NSHVIYAEEEAGGTRLLIDGKTCLLQNDHDPSKLLAETPCKLLRFLVADGAHVDADVPYAEVEVMKMCMPLLSP
ASGVIHVMMSEGQALQAGDLIARLDLDDPSAVKRAEPFHGIFPQMDLPVAASSQVHKRYAASLNAARMVLAGYE
HNINEVVQDLVCCLDDPELPFLQWDELMSVLATRLPRNLKSELEDKYMEYKLNFYHGKNKDFPSKLLRDIIEAN
LAYGSEKEKATNERLIEPLMSLLKSYEGGRESHAHFVVKSLFKEYLAVEELFSDGIQSDVIETLRHQHSKDLQK
VVDIVLSHQGVRNKAKLVTALMEKLVYPNPAAYRDLLVRFSSLNHKRYYKLALKASELLEQTKLSELRASIARS
LSDLGMHKGEMTIEDSMEDLVSAPLPVEDALISLFDYSDPTVQQKVIETYISRLYQPLLVKDSIQVKFKESGAF
ALWEFSEGHVDTKNGQGTVLGRTRWGAMVAVKSVESARTAIVAALKDSAQHASSEGNMMHIALLSAENENNISD
DQAQHRMEKLNKILKDTSVANDLRAAGLKVISCIVQRDEARMPMRHTLLWSDEKSCYEEEQILRHVEPPLSMLL
EMDKLKVKGYNEMKYTPSRDRQWHIYTLRNTENPKMLHRVFFRTIVRQPNAGNKFISAQIGDTEVGGPEESLSF
TSNSILRALMTAIEELELHAIRTGHSHMYLCILKEQKLLDLIPFSGSTIVDVGQDEATACSLLKSMALKIHELV
GAQMHHLSVCQWEVKLKLYCDGPASGTWRVVTTNVTSHTCTVDIYREVEDTESQKLVYHSASPSASPLHGVALD
NPYQPLSVIDLKRCSARNNRTTYCYDFPLAFETALQKSWQSNGSSVSEGSENSRSYVKATELVFAEKHGSWGTP
IISMERPAGLNDIGMVAWILEMSTPEFPNGRQIIVIANDITFRAGSFGPREDAFFEAVTNLACERKLPLIYLAA
NSGARIGIADEVKSCFRVGWSDEGSPERGFQYIYLTDEDYARISLSVIAHKLQLDNGEIRWIIDSVVGKEDGLG
VENIHGSAAIASAYSRAYEETFTLTFVTGRTVGIGAYLARLGIRCIQRLDQPIILTGFSALNKLLGREVYSSHM
QLGGPKIMATNGVVHLTVSDDLEGVSNILRWLSYVPANIGGPLPITKPLDPPDRPVAYIPENTCDPRAAIRGVD
DSQGKWLGGMFDKDSFVETFEGWAKTVVTGRAKLGGIPVGVIAVETQTMMQLIPADPGQLDSHERSVPRAGQVW
FPDSATKTAQALLDFNREGLPLFILANWRGFSGGQRDLFEGILQAGSTIVENLRTYNQPAFVYIPMAGELRGGA
WVVVDSKINPDRIECYAERTAKGNVLEPQGLIEIKFRSEELQDCMGRLDPELINLKAKLQGAKLGNGSLTDVES
LQKSIDARTKQLLPLYTQIAIRFAELHDTSLRMAAKGVIKKVVDWEELRSFFYRRLRRRISEDVLAKEIRGIAG
DHFTHQSAVELIKEWYLASQATTGSTEWDDDDAFVAWKENPENYKGYIQELRAQKVSQSLSDLADSSSDLEAFS
QGLSTLLDKMDPSQRAKFIQEVKKVLG

FIGURE 14A

>AJ310767_Alopecurus myosuroides (black-grass)

ATGGGATCCACACATCTGCCCATTGTCGGGTTTAATGCATCCACAACACCATCGCTATCCACTCTTCGCCAGATAAA
CTCAGCTGCTGCTGCATTCCAATCTTCGTCCCCTTCAAGGTCATCCAAGAAGAAAAGCCGACGTGTTAAGTCAATAA
GGGATGATGGCGATGGAAGCGTGCCAGACCCTGCAGGCCATGGCCAGTCTATTCGCCAAGGTCTCGCTGGCATCATC
GACCTCCCAAAGGAGGGCGCATCAGCTCCAGATGTGGACATTTCACATGGGTCTGAAGACCACAAGGCCTCCTACCA
AATGAATGGGATACTGAATGAATCACATAACGGGAGGCACGCCTCTCTGTCTAAAGTTTATGAATTTTGCACGGAAT
TGGGTGGAAAAACACCAATTCACAGTGTATTAGTCGCCAACAATGGAATGGCAGCAGCTAAGTTCATGCGGAGTGTC
CGGACATGGGCTAATGATACATTTGGGTCAGAGAAGGCGATTCAGTTGATAGCTATGGCAACTCCGGAAGACATGAG
AATAAATGCAGAGCACATTAGAATTGCTGATCAGTTTGTTGAAGTACCTGGTGGAACAAACAATAACAACTATGCAA
ATGTCCAACTCATAGTGGAGATAGCAGAGAGAACTGGTGTCTCCGCCGTTTGGCCTGGTTGGGGCCATGCATCTGAG
AATCCTGAACTTCCAGATGCACTAACTGCAAAAGGAATTGTTTTTCTTGGGCCACCAGCATCATCAATGAACGCACT
AGGCGACAAGGTTGGTTCAGCTCTCATTGCTCAAGCAGCAGGGGTTCCCACTCTTGCTTGGAGTGGATCACATGTGG
AAATTCCATTAGAACTTTGTTTGGACTCGATACCTGAGGAGATGTATAGGAAAGCCTGTGTTACAACCGCTGATGAA
GCAGTTGCAAGTTGTCAGATGATTGGTTACCCTGCCATGATCAAGGCATCCTGGGGTGGTGGTGGTAAAGGGATTAG
AAAGGTTAATAATGATGACGAGGTGAAAGCACTGTTTAAGCAAGTACAGGGTGAAGTTCCTGGCTCCCCGATATTTA
TCATGAGACTTGCATCTCAGAGTCGTCATCTTGAAGTCCAGCTGCTTTGTGATGAATATGGCAATGTAGCAGCACTT
CACAGTCGTGATTGCAGTGTGCAACGACGACACCAAAAGATTATCGAGGAAGGACCAGTTACTGTTGCTCCTCGTGA
AACAGTGAAAGAGCTAGAGCAAGCAGCAAGGAGGCTTGCTAAGGCCGTGGGTTACGTCGGTGCTGCTACTGTTGAAT
ATCTCTACAGCATGGAGACTGGTGAATACTATTTTCTGGAGCTTAATCCACGGTTGCAGGTTGAGCACCCAGTCACC
GAGTCGATAGCTGAAGTAAATTTGCCTGCAGCCCAAGTTGCAGTTGGGATGGGTATACCCCTTTGGCAGATTCCAGA
GATCAGACGTTTCTACGGAATGGACAATGGAGGAGGCTATGATATTTGGAGGAAAACAGCAGCTCTCGCTACTCCAT
TCAACTTTGATGAAGTAGATTCTCAATGGCCGAAGGGTCATTGTGTGGCAGTTAGGATAACCAGTGAGAATCCAGAT
GATGGATTCAAGCCTACTGGTGGAAAAGTAAAGGAGATAAGTTTTAAAAGTAAGCCAAATGTCTGGGGATATTTCTC
AGTTAAGTCTGGTGGAGGCATTCATGAATTTGCGGATTCTCAGTTTGGACACGTTTTTGCCTATGGAGAGACTAGAT
CAGCAGCAATAACCAGCATGTCTCTTGCACTAAAAGAGATTCAAATTCGTGGAGAAATTCATACAAACGTTGATTAC
ACGGTTGATCTCTTGAATGCCCCAGACTTCAGAGAAAACACGATCCATACCGGTTGGCTGGATACCAGAATAGCTAT
GCGTGTTCAAGCTGAGAGGCCTCCCTGGTATATTTCAGTGGTTGGAGGAGCTCTATATAAAACAATAACCACCAATG
CGGAGACCGTTTCTGAATATGTTAGCTATCTCATCAAGGGTCAGATTCCACCAAAGCACATATCCCTTGTCCATTCA
ACTATTTCTTTGAATATAGAGGAAAGCAAATATACAATTGAGATTGTGAGGAGTGGACAGGGTAGCTACAGATTGAG
ACTGAATGGATCACTTATTGAAGCCAATGTACAAACATTATGTGATGGAGGCCTTTTAATGCAGCTGGATGGAAATA
GCCATGTTATTTATGCTGAAGAAGAAGCGGGTGGTACACGGCTTCTTATTGATGGAAAAACATGCTTGCTACAGAAT
GACCATGATCCGTCAAGGTTATTAGCTGAGACACCCTGCAAACTTCTTCGTTTCTTGATTGCCGATGGTGCTCATGT
TGATGCTGATGTACCATACGCGGAAGTTGAGGTTATGAAGATGTGCATGCCCCTCTTGTCGCCTGCTGCTGGTGTCA
TTAATGTTTTGTTGTCTGAGGGCCAGGCGATGCAGGCTGGTGATCTTATAGCGAGACTTGATCTCGATGACCCTTCT
GCTGTGAAGAGAGCCGAGCCATTTGAAGGATCTTTTCCAGAAATGAGCCTTCCTATTGCTGCTTCTGGCCAAGTTCA
CAAAAGATGTGCTGCAAGTTTGAACGCTGCTCGAATGGTCCTTGCAGGATATGACCATGCGGCCAACAAAGTTGTGC
AAGATTTGGTATGGTGCCTTGATACACCTGCTCTTCCTTTCCTACAATGGGAAGAGCTTATGTCTGTTTTAGCAACT
AGACTTCCAAGACGTCTTAAGAGCGAGTTGGAGGGCAAATACAATGAATACAAGTTAAATGTTGACCATGTGAAGAT
CAAGGATTTCCCTACCGAGATGCTTAGAGAGACAATCGAGGAAAATCTTGCATGTGTTTCCGAGAAGGAAATGGTGA
CAATTGAGAGGCTTGTTGACCCTCTGATGAGCCTGCTGAAGTCATACGAGGGTGGGAGAGAAAGCCATGCCCACTTT
ATTGTCAAGTCCCTTTTTGAGGAGTATCTCTCGGTTGAGGAACTATTCAGTGATGGCATTCAGTCTGACGTGATTGA
ACGCCTGCGCCTACAATATAGTAAAGACCTCCAGAAGGTTGTAGACATTGTTTTGTCTCACCAGGGTGTGAGAAACA
AAACAAAGCTGATACTCGCGCTCATGGAGAAACTGGTCTATCCAAACCCTGCTGCCTACAGAGATCAGTTGATTCGC
TTTTCTTCCCTCAACCATAAAAGATATTATAAGTTGGCTCTTAAAGCTAGTGAACTTCTTGAACAAACCAAGCTCAG
CGAACTCCGCACAAGCATTGCAAGGAACCTTTCAGCGCTGGATATGTTCACCGAGGAAAAGGCAGATTTCTCCTTGC
AAGACAGAAAATTGGCCATTAATGAGAGCATGGGAGATTTAGTCACTGCCCCACTGCCAGTTGAAGATGCACTTGTT
TCTTTGTTTGATTGTACTGATCAAACTCTTCAGCAGAGAGTGATTCAGACATACATATCTCGATTATACCAGCCTCA
ACTTGTGAAGGATAGCATCCAGCTGAAATATCAGGATTCTGGTGTTATTGCTTTATGGGAATTCACTGAAGGAAATC
ATGAGAAGAGATTGGGTGCTATGGTTATCCTGAAGTCACTAGAATCTGTGTCAACAGCCATTGGAGCTGCTCTAAAG
GATGCATCACATTATGCAAGCTCTGCGGGCAACACGGTGCATATTGCTTTGTTGGATGCTGATACCCAACTGAATAC
AACTGAAGATAGTGGTGATAATGACCAAGCTCAAGACAAGATGGATAAACTTTCTTTTGTACTGAAACAAGATGTTG
TCATGGCTGATCTACGTGCTGCTGATGTCAAGGTTGTTAGTTGCATTGTTCAAAGAGATGGAGCAATCATGCCTATG
CGCCGTACCTTCCTCTTGTCAGAGGAAAAACTTTGTTACGAGGAAGAGCCGATTCTTCGGCATGTGGAGCCTCCACT

FIGURE 14A (continued)

TTCTGCACTTCTTGAGTTGGATAAATTGAAAGTGAAAGGATACAATGAGATGAAGTATACACCGTCACGTGATCGTC
AGTGGCATATATACACACTTAGAAATACTGAAAATCCAAAAATGCTGCACAGGGTATTTTTCCGAACACTTGTCAGA
CAACCCAGTGCAGGCAACAGGTTTACATCAGACCATATCACTGATGTTGAAGTAGGACACGCAGAGGAACCTCTTTC
ATTTACTTCAAGCAGCATATTAAAATCGTTGAAGATTGCTAAAGAAGAATTGGAGCTTCACGCGATCAGGACTGGCC
ATTCTCATATGTACTTGTGCATATTGAAAGAGCAAAAGCTTCTTGACCTTGTTCCTGTTTCAGGGAACACTGTTGTG
GATGTTGGTCAAGATGAAGCTACTGCATGCTCTCTTTTGAAAGAAATGGCTTTAAAGATACATGAACTTGTTGGTGC
AAGAATGCATCATCTTTCTGTATGCCAGTGGGAAGTGAAACTTAAGTTGGTGAGCGATGGGCCTGCCAGTGGTAGCT
GGAGAGTTGTAACAACCAATGTTACTGGTCACACCTGCACTGTGGATATCTACCGGGAGGTCGAAGATACAGAATCA
CAGAAACTAGTATACCACTCCACCGCATTGTCATCTGGTCCTTTGCATGGTGTTGCACTGAATACTTCGTATCAGCC
TTTGAGTGTTATTGATTTAAAACGTTGCTCTGCCAGGAACAACAAAACTACATACTGCTATGATTTTCCATTGACAT
TTGAAGCTGCAGTGCAGAAGTCGTGGTCTAACATTTCCAGTGAAAACAACCAATGTTATGTTAAAGCGACAGAGCTT
GTGTTTGCTGAAAAGAATGGGTCGTGGGGCACTCCTATAATTCCTATGCAGCGTGCTGCTGGGCTGAATGACATTGG
TATGGTAGCCTGGATCTTGGACATGTCCACTCCTGAATTTCCCAGCGGCAGACAGATCATTGTTATCGCAAATGATA
TTACATTTAGAGCTGGATCATTTGGCCCAAGGGAAGATGCATTTTTCGAAGCTGTAACCAACCTGGCTTGTGAGAAG
AAGCTTCCACTTATCTACTTGGCTGCAAACTCTGGTGCTCGGATTGGCATTGCTGATGAAGTAAAATCTTGCTTCCG
TGTTGGATGGACTGATGATAGCAGCCCTGAACGTGGATTTAGGTACATTTATATGACTGACGAAGACCATGATCGTA
TTGGCTCTTCAGTTATAGCACACAAGATGCAGCTAGATAGTGGCGAGATCAGGTGGGTTATTGATTCTGTTGTGGGA
AAAGAGGATGGACTAGGTGTGGAGAACATACATGGAAGTGCTGCTATTGCCAGTGCCTATTCTAGGGCGTACGAGGA
GACATTTACACTTACATTCGTTACTGGACGAACTGTTGGAATCGGAGCCTATCTTGCTCGACTTGGCATACGGTGCA
TACAGCGTATTGACCAGCCCATTATTTTGACCGGGTTTTCTGCCCTGAACAAGCTTCTTGGGCGGGAGGTGTACAGC
TCCCACATGCAGTTGGGTGGTCCCAAAATCATGGCGACGAATGGTGTTGTCCATCTGACTGTTCCAGATGACCTTGA
AGGTGTTTCTAATATATTGAGGTGGCTCAGCTATGTTCCTGCAAACATTGGTGGACCTCTTCCTATTACAAAATCTT
TGGACCCAATAGACAGACCCGTTGCATACATCCCTGAGAATACATGTGATCCTCGTGCAGCCATCAGTGGCATTGAT
GACAGCCAAGGGAAATGGTTGGGTGGCATGTTTGACAAAGACAGTTTTGTGGAGACATTTGAAGGATGGGCGAAGAC
AGTAGTTACTGGCAGAGCAAAACTTGGAGGGATTCCTGTTGGTGTTATAGCTGTGGAGACACAGACCATGATGCAGC
TCGTCCCCGCTGATCCAGGCCAGCCTGATTCCCACGAGCGGTCTGTTCCTCGTGCTGGGCAAGTTTGGTTTCCAGAT
TCTGCTACCAAGACAGCGCAGGCGATGTTGGACTTCAACCGTGAAGGATTACCTCTGTTCATACTTGCTAACTGGAG
AGGCTTCTCTGGAGGGCAAAGAGATCTTTTTGAAGGAATTCTGCAGGCTGGGTCAACAATTGTTGAGAACCTTAGGA
CATACAATCAGCCTGCCTTTGTATATATCCCCAAGGCTGCAGAGCTACGTGGAGGAGCCTGGGTCGTGATTGATAGC
AAGATAAACCCAGATCGCATCGAGTGCTATGCTGAGAGGACTGCAAAGGGTAATGTTCTCGAACCTCAAGGGTTGAT
TGAGATCAAGTTCAGGTCAGAGGAACTCAAAGAATGCATGGGTAGGCTTGATCCAGAATTGATAGATCTGAAAGCAA
GACTCCAGGGAGCAAATGGAAGCCTATCTGATGGAGAATCCCTTCAGAAGAGCATAGAAGCTCGGAAGAAACAGTTG
CTGCCTCTGTACACCCAAATCGCGGTACGTTTTGCGGAATTGCACGACACTTCCCTTAGAATGGCTGCTAAAGGTGT
GATCAGGAAAGTTGTAGACTGGGAAGACTCTCGGTCTTTCTTCTACAAGAGATTACGGAGGAGGCTATCCGAGGACG
TTCTGGCAAAGGAGATTAGAGGTGTAATTGGTGAGAAGTTTCCTCACAAATCAGCGATCGAGCTGATCAAGAAATGG
TACTTGGCTTCTGAGGCAGCTGCAGCAGGAAGCACCGACTGGGATGACGACGATGCTTTTGTCGCCTGGAGGGAGAA
CCCTGAAAACTATAAGGAGTATATCAAAGAGCTTAGGGCTCAAAGGGTATCTCGGTTGCTCTCAGATGTTGCAGGCT
CCAGTTCGGATTTACAAGCCTTGCCGCAGGGTCTTTCCATGCTACTAGATAAGATGGATCCCTCTAAGAGAGCACAG
TTTATCGAGGAGGTCATGAAGGTCCTGAAATGA

FIGURE 14B

>CAC84161_Alopecurus myosuroides (black-grass)

MGSTHLPIVGFNASTTPSLSTLRQINSAAAAFQSSSPSRSSKKKSRRVKSIRDDGDGSVPDPAGHGQSIRQGLA
GIIDLPKEGASAPDVDISHGSEDHKASYQMNGILNESHNGRHASLSKVYEFCTELGGKTPIHSVLVANNGMAAA
KFMRSVRTWANDTFGSEKAIQLIAMATPEDMRINAEHIRIADQFVEVPGGTNNNNYANVQLIVEIAERTGVSAV
WPGWGHASENPELPDALTAKGIVFLGPPASSMNALGDKVGSALIAQAAGVPTLAWSGSHVEIPLELCLDSIPEE
MYRKACVTTADEAVASCQMIGYPAMIKASWGGGGKGIRKVNNDDEVKALFKQVQGEVPGSPIFIMRLASQSRHL
EVQLLCDEYGNVAALHSRDCSVQRRHQKIIEEGPVTVAPRETVKELEQAARRLAKAVGYVGAATVEYLYSMETG
EYYFLELNPRLQVEHPVTESIAEVNLPAAQVAVGMGIPLWQIPEIRRFYGMDNGGGYDIWRKTAALATPFNFDE
VDSQWPKGHCVAVRITSENPDDGFKPTGGKVKEISFKSKPNVWGYFSVKSGGGIHEFADSQFGHVFAYGETRSA
AITSMSLALKEIQIRGEIHTNVDYTVDLLNAPDFRENTIHTGWLDTRIAMRVQAERPPWYISVVGGALYKTITT
NAETVSEYVSYLIKGQIPPKHISLVHSTISLNIEESKYTIEIVRSGQGSYRLRLNGSLIEANVQTLCDGGLLMQ
LDGNSHVIYAEEEAGGTRLLIDGKTCLLQNDHDPSRLLAETPCKLLRFLIADGAHVDADVPYAEVEVMKMCMPL
LSPAAGVINVLLSEGQAMQAGDLIARLDLDDPSAVKRAEPFEGSFPEMSLPIAASGQVHKRCAASLNAARMVLA
GYDHAANKVVQDLVWCLDTPALPFLQWEELMSVLATRLPRRLKSELEGKYNEYKLNVDHVKIKDFPTEMLRETI
EENLACVSEKEMVTIERLVDPLMSLLKSYEGGRESHAHFIVKSLFEEYLSVEELFSDGIQSDVIERLRLQYSKD
LQKVVDIVLSHQGVRNKTKLILALMEKLVYPNPAAYRDQLIRFSSLNHKRYYKLALKASELLEQTKLSELRTSI
ARNLSALDMFTEEKADFSLQDRKLAINESMGDLVTAPLPVEDALVSLFDCTDQTLQQRVIQTYISRLYQPQLVK
DSIQLKYQDSGVIALWEFTEGNHEKRLGAMVILKSLESVSTAIGAALKDASHYASSAGNTVHIALLDADTQLNT
TEDSGDNDQAQDKMDKLSFVLKQDVVMADLRAADVKVVSCIVQRDGAIMPMRRTFLLSEEKLCYEEEPILRHVE
PPLSALLELDKLKVKGYNEMKYTPSRDRQWHIYTLRNTENPKMLHRVFFRTLVRQPSAGNRFTSDHITDVEVGH
AEEPLSFTSSSILKSLKIAKEELELHAIRTGHSHMYLCILKEQKLLDLVPVSGNTVVDVGQDEATACSLLKEMA
LKIHELVGARMHHLSVCQWEVKLKLVSDGPASGSWRVVTTNVTGHTCTVDIYREVEDTESQKLVYHSTALSSGP
LHGVALNTSYQPLSVIDLKRCSARNNKTTYCYDFPLTFEAAVQKSWSNISSENNQCYVKATELVFAEKNGSWGT
PIIPMQRAAGLNDIGMVAWILDMSTPEFPSGRQIIVIANDITFRAGSFGPREDAFFEAVTNLACEKKLPLIYLA
ANSGARIGIADEVKSCFRVGWTDDSSPERGFRYIYMTDEDHDRIGSSVIAHKMQLDSGEIRWVIDSVVGKEDGL
GVENIHGSAAIASAYSRAYEETFTLTFVTGRTVGIGAYLARLGIRCIQRIDQPIILTGFSALNKLLGREVYSSH
MQLGGPKIMATNGVVHLTVPDDLEGVSNILRWLSYVPANIGGPLPITKSLDPIDRPVAYIPENTCDPRAAISGI
DDSQGKWLGGMFDKDSFVETFEGWAKTVVTGRAKLGGIPVGVIAVETQTMMQLVPADPGQPDSHERSVPRAGQV
WFPDSATKTAQAMLDFNREGLPLFILANWRGFSGGQRDLFEGILQAGSTIVENLRTYNQPAFVYIPKAAELRGG
AWVVIDSKINPDRIECYAERTAKGNVLEPQGLIEIKFRSEELKECMGRLDPELIDLKARLQGANGSLSDGESLQ
KSIEARKKQLLPLYTQIAVRFAELHDTSLRMAAKGVIRKVVDWEDSRSFFYKRLRRRLSEDVLAKEIRGVIGEK
FPHKSAIELIKKWYLASEAAAAGSTDWDDDDAFVAWRENPENYKEYIKELRAQRVSRLLSDVAGSSSDLQALPQ
GLSMLLDKMDPSKRAQFIEEVMKVLK

FIGURE 15A

>EU660897_Aegilops tauschii (jointed goatgrass)

ATGGGATCCACACATTTGCCCATTGTCGGCCTTAATGCCTCGACAACACCATCGCTATCCACTATTCGCCCGGTAAA
TTCAGCCGGTGCTGCATTCCAACCATCTGCCCCTTCTAGAACCTCCAAGAAGAAAAGTCGTCGTGTTCAGTCATTAA
GGGATGGAGGCGATGGAGGCGTGTCAGACCCTAACCAGTCTATTCGCCAAGGTCTTGCCGGCATCATTGACCTCCCA
AAGGAGGGCACATCAGCTCCGGAAGTGGATATTTCACATGGGTCCGAAGAACCCAGGGGCTCCTACCAAATGAATGG
GATACTGAATGAAGCACATAATGGGAGGCATGCTTCGCTGTCTAAGGTTGTCGAATTTTGTATGGCATTGGGCGGCA
AAACACCAATTCATAGTGTATTAGTTGCGAACAATGGAATGGCAGCAGCTAAGTTCATGCGGAGTGTCCGAACATGG
GCTAATGAAACATTTGGGTCAGAGAAGGCAATTCAGTTGATAGCTATGGCTACTCCAGAAGACATGAGGATAAATGC
AGAGCACATTAGAATTGCTGATCAATTTGTTGAAGTACCCGGTGGAACAAACAATAACAACTATGCAAATGTCCAAC
TCATAGTGGAGATAGCAGTGAGAACCGGTGTTTCTGCTGTTTGGCCTGGTTGGGGCCATGCATCTGAGAATCCTGAA
CTTCCAGATGCACTAAATGCAAACGGAATTGTTTTTCTTGGGCCACCATCATCATCAATGAACGCACTAGGTGACAA
GGTTGGTTCAGCTCTCATTGCTCAAGCAGCAGGGGTTCCGACTCTTCCTTGGAGTGGATCACAGGTGGAAATTCCAT
TAGAAGTTTGTTTGGACTCGATACCTGCGGATATGTATAGGAAAGCTTGTGTTAGTACTACGGAGGAAGCACTTGCG
AGTTGTCAGATGATTGGGTATCCAGCCATGATTAAAGCATCATGGGGTGGTGGTGGTAAAGGGATCCGAAAGGTTAA
TAACGACGATGATGTCAGAGCACTGTTTAAGCAAGTGCAAGGTGAAGTTCCTGGCTCCCCAATATTTATCATGAGAC
TTGCATCTCAGAGTCGACATCTTGAAGTTCAGTTGCTTTGTGATCAATATGGCAATGTAGCTGCGCTTCACAGTCGT
GACTGCAGTGTGCAACGGCGACACCAAAAGATTATTGAGGAAGGACCAGTTACTGTTGCTCCTCGCGAGACAGTGAA
AGAGCTAGAGCAAGCAGCAAGGAGGCTTGCTAAGGCTGTGGGTTATGTTGGTGCTGCTACTGTTGAATATCTCTACA
GCATGGAGACTGGTGAATACTATTTTCTGGAACTTAATCCACGGTTGCAGGTTGAGCATCCAGTCACCGAGTGGATA
GCTGAAGTAAACTTGCCTGCAGCTCAAGTTGCAGTTGGAATGGGTATACCCCTTTGGCAGGTTCCAGAGATCAGACG
TTTCTATGGAATGGACAATGGAGGAGGCTATGACATTTGGAGGAAAACAGCAGCTCTTGCTACCCCATTTAACTTTG
ATGAAGTGGATTCTCAATGGCCAAAGGGTCATTGTGTAGCAGTTAGGATAACCAGTGAGGATCCAGATGACGGATTC
AAGCCTACCGGTGGAAAAGTAAAGGAGATCAGTTTTAAAAGCAAGCCAAATGTTTGGGCCTATTTCTCTGTTAAGTC
CGGTGGAGGCATTCATGAATTTGCTGATTCTCAGTTTGGACATGTTTTTGCATATGGAGTGTCTAGAGCAGCAGCAA
TAACCAACATGTCTCTTGCGCTAAAAGAGATTCAAATTCGTGGAGAAATTCATTCAAATGTTGATTACACAGTTGAT
CTCTTGAATGCCTCAGACTTCAAAGAAAACAGGATTCATACTGGCTGGCTGGATAACAGAATAGCAATGCGAGTCCA
AGCTGAGAGACCTCCGTGGTATATTTCAGTGGTTGGAGGAGCTCTATATAAAACAATAACGAGCAACACAGACACTG
TTTCTGAATATGTTAGCTATCTCGTCAAGGGTCAGATTCCACCGAAGCATATATCCCTTGTCCATTCAACTGTTTCT
TTGAATATAGAGGAAAGCAAATATACAATTGAAACTATAAGGAGCGGACAGGGTAGCTACAGATTGCGAATGAATGG
ATCAGTTATTGAAGCAAATGTCCAAACATTATGTGATGGTGGACTTTTAATGCAGTTGGATGGAAACAGCCATGTAA
TTTATGCTGAAGAAGAGGCCGGTGGTACACGGCTTCTAATTGATGGAAAGACATGCTTGTTACAGAATGATCACGAT
CCTTCAAGGTTATTAGCTGAGACACCCTGCAAACTTCTTCGTTTCTTGGTTGCCGATGGTGCTCATGTTGAAGCTGA
TGTACCATATGCGGAAGTTGAGGTTATGAAGATGTGCATGCCCCTCTTGTCACCTGCTGCTGGTGTCATTAATGTTT
TGTTGTCTGAGGGCCAGCCTATGCAGGCTGGTGATCTTATAGCAAGACTTGATCTTGATGACCCTTCTGCTGTGAAG
AGAGCTGAGCCGTTTAACGGATCTTTCCCAGAAATGAGCCTTCCTATTGCTGCTTCTGGCCAAGTTCACAAAAGATG
TGCCACAAGCTTGAATGCTGCTCGGATGGTCCTTGCAGGATATGATCACCCGATCAACAAAGTTGTACAAGATCTGG
TATCCTGTCTAGATGCTCCTGAGCTTCCTTTCCTACAATGGGAAGAGCTTATGTCTGTTTTAGCAACTAGACTTCCA
AGGCTTCTTAAGAGCGAGTTGGAGGGTAAATACAGTGAATATAAGTTAAATGTTGGCCATGGAAAGAGCAAGGATTT
CCCTTCCAAGATGCTAAGAGAGATAATCGAGGAAAATCTTGCACATGGTTCTGAGAAGGAAATTGCTACAAATGAGA
GGCTTGTTGAGCCTCTTATGAGCCTACTGAAGTCATATGAGGGTGGCAGAGAAAGCCATGCACACTTTATTGTGAAG
TCCCTTTTCGAGGACTATCTCTCGGTTGAGGAACTATTCAGTGATGGCATTCAGTCTGATGTGATTGAACGCCTGCG
CCAACAACATAGTAAAGATCTCCAGAAGGTTGTAGACATTGTGTTGTCTCACCAGGGTGTGAGAAACAAAACTAAGC
TGATACTAACACTCATGGAGAAACTGGTCTATCCAAACCCTGCTGCCTACAAGGATCAGTTGACTCGCTTTTCCTCC
CTCAATCACAAAAGATATTATAAGTTGGCCCTTAAAGCTAGCGAGCTTCTTGAACAAACCAAGCTTAGTGAGCTCCG
CACAAGCATTGCAAGGAGCCTTTCAGAACTTGAGATGTTTACTGAAGAAAGGACGGCCATTAGTGAGATCATGGGAG
ATTTAGTGACTGCCCCACTGCCAGTTGAAGATGCACTGGTTTCTTTGTTTGATTGTAGTGATCAAACTCTTCAGCAG
AGGGTGATCGAGACGTACATATCTCGATTATACCAGCCTCATCTTGTCAAGGATAGTATCCAGCTGAAATATCAGGA
ATCTGGTGTTATTGCTTTATGGGAATTCGCTGAAGCGCATTCAGAGAAGAGATTGGGTGCTATGGTTATTGTGAAGT
CGTTAGAATCTGTATCAGCAGCAATTGGAGCTGCACTAAAGGGTACATCACGCTATGCAAGCTCTGAGGGTAACATA
ATGCATATTGCTTTATTGGGTGCTGATAATCAAATGCATGGAACTGAAGACAGTGGTGATAACGATCAAGCTCAAGT
CAGGATAGACAAACTTTCTGCGACACTGGAACAAAATACTGTCACAGCTGATCTCCGTGCTGCTGGTGTGAAGGTTA
TTAGTTGCATTGTTCAAAGGGATGGAGCACTCATGCCTATGCGCCATACCTTCCTCTTGTCGGATGAAAAGCTTTGT
TATGAGGAAGAGCCGGTTCTCCGGCATGTGGAGCCTCCTCTTTCTGCTCTTCTTGAGTTGGGTAAGTTGAAAGTGAA

FIGURE 15A (continued)

AGGATACAATGAGGTGAAGTATACACCGTCACGTGATCGTCAGTGGAACATATACACACTTAGAAATACAGAGAACC
CCAAAATGTTGCACAGGGTGTTTTTCCGAACTCTTGTCAGGCAACCCGGTGCTTCCAACAAATTCACATCAGGCAAC
ATCAGTGATGTTGAAGTGGGAGGAGCTGAGGAATCTCTTTCATTTACATCGAGCAGCATATTAAGATCGCTGATGAC
TGCTATAGAAGAGTTGGAGCTTCACGCGATTAGGACAGGTCACTCTCATATGTTTTTGTGCATATTGAAAGAGCAAA
AGCTTCTTGATCTTGTTCCCGTTTCAGGGAACAAAGTTGTGGATATTGGCCAAGATGAAGCTACTGCATGCTTGCTT
CTGAAAGAAATGGCTCTACAGATACATGAACTTGTGGGTGCAAGGATGCATCATCTTTCTGTATGCCAATGGGAGGT
GAAACTTAAGTTGGACAGCGATGGGCCTGCCAGTGGTACCTGGAGAGTTGTAACAACCAATGTTACTAGTCACACCT
GCACTGTGGATATCTACCGTGAGGTTGAAGATACAGAATCACAGAAACTAGTGTACCACTCTGCTCCATCGTCATCT
GGTCCTTTGCATGGCGTTGCACTGAATACTCCATATCAGCCTTTGAGTGTTATTGATCTGAAACGTTGCTCCGCTAG
AAATAACAGAACTACATACTGCTATGATTTTCCGTTGGCATTTGAAACTGCAGTGCAGAAGTCATGGTCTAACATTT
CTAGTGACACTAACCGATGTTATGTTAAAGCGACGGAGCTGGTGTTTGCTCACAAGAACGGGTCATGGGGCACTCCT
GTAATTCCTATGGAGCGTCCTGCTGGGCTCAATGACATTGGTATGGTAGCTTGGATCTTGGACATGTCCACTCCTGA
ATATCCCAATGGCAGGCAGATTGTTGTCATCGCAAATGATATTACTTTTAGAGCTGGATCGTTTGGTCCAAGGGAAG
ATGCATTTTTTGAAACTGTTACCAACCTAGCTTGTGAGAGGAAGCTTCCTCTCATCTACTTGGCAGCAAACTCTGGT
GCTCGGATCGGCATAGCAGATGAAGTAAAATCTTGCTTCCGTGTTGGATGGTCTGATGATGGCAGCCCTGAACGTGG
GTTTCAATATATTTATCTGACTGAAGAAGACCATGCTCGTATTAGCGCTTCTGTTATAGCGCACAAGATGCAGCTTG
ATAATGGTGAAATTAGGTGGGTTATTGATTCTGTTGTAGGGAAGGAGGATGGGCTAGGTGTGGAGAACATACATGGA
AGTGCTGCTATTGCCAGTGCCTATTCTAGGGCCTATGAGGAGACATTTACGCTTACATTTGTGACTGGAAGGACTGT
TGGAATAGGAGCATATCTTGCTCGACTTGGCATACGGTGCATTCAGCGTACTGACCAGCCCATTATCCTAACTGGGT
TCTCTGCCTTGAACAAGCTTCTTGGCCGGGAAGTGTACAGCTCCCACATGCAGTTGGGTGGCCCCAAAATTATGGCC
ACAAACGGTGTTGTCCATCTGACAGTTTCAGATGACCTTGAAGGTGTATCTAATATATTGAGGTGGCTCAGCTATGT
TCCTGCCAACATTGGTGGACCTCTTCCTATTACAAAATCTTTGGACCCACCTGACAGACCCGTTGCTTACATCCCTG
AGAATACATGTGATCCTCGTGCAGCCATCAGTGGCATTGATGATAGCCAAGGGAAATGGTTGGGGGGTATGTTCGAC
AAAGACAGTTTTGTGGAGACATTTGAAGGATGGGCGAAGTCAGTAGTTACTGGCAGAGCGAAACTCGGAGGGATTCC
GGTGGGTGTTATAGCTGTGGAGACACAGACTATGATGCAGCTCATCCCTGCTGATCCAGGTCAGCTTGATTCCCATG
AGCGGTCTGTTCCTCGTGCTGGGCAAGTCTGGTTTCCAGATTCAGCTACTAAGACAGCGCAGGCAATGCTGGACTTC
AACCGTGAAGGATTACCTCTGTTCATCCTTGCTAACTGGAGAGGCTTCTCTGGTGGGCAAAGAGATCTTTTTGAAGG
AATCCTTCAGGCTGGGTCAACAATTGTTGAGAACCTTAGGACATACAATCAGCCTGCCTTTGTATATATCCCCAAGG
CTGCAGAGCTACGTGGAGGGGCTTGGGTCGTGATTGATAGCAAGATAAATCCAGATCGCATTGAGTTCTATGCTGAG
AGGACTGCAAAGGGCAATGTTCTTGAACCTCAAGGGTTGATTGAGATCAAGTTCAGGTCAGAGGAACTCCAAGAGTG
CATGGGCAGGCTTGACCCAGAATTGATAAATTTGAAGGCAAAACTCCTGGGAGCAAAGCATGAAAATGGAAGTCTAT
CTGAGTCAGAATCCCTTCAGAAGAGCATAGAAGCCCGGAAGAAACAGTTGTTGCCTTTGTATACTCAAATTGCGGTA
CGGTTCGCTGAATTGCATGACACTTCCCTTAGAATGGCTGCTAAGGGTGTGATTAAGAAGGTTGTAGACTGGGAAGA
TTCTAGGTCTTTCTTCTACAAGAGATTACGGAGGAGGATATCCGAGGATGTTCTTGCAAAGGAAATTAGAGGTGTAA
GTGGCAAGCAGTTTTCTCACCAATCGGCAATCGAGCTGATCCAGAAATGGTACTTGGCCTCTAAGGGAGCTGAAACG
GGAAACACTGAATGGGATGATGACGATGCTTTTGTTGCCTGGAGGGAAAACCCTGAAAACTACCAGGAGTATATCAA
AGAACTCAGGGCTCAAAGGGTATCTCAGTTGCTCTCAGATGTTGCAGACTCCAGTCCAGATCTAGAAGCCTTGCCAC
AGGGTCTTTCTATGCTACTAGAGAAGATGGATCCCTCAAGGAGAGCACAGTTTGTTGAGGAAGTCAAGAAGGCCCTT
AAATGA

FIGURE 15B

>EU660897_Aegilops tauschii (jointed goatgrass)

MGSTHLPIVGLNASTTPSLSTIRPVNSAGAAFQPSAPSRTSKKKSRRVQSLRDGGDGGVSDPNQSIRQGLAGII
DLPKEGTSAPEVDISHGSEEPRGSYQMNGILNEAHNGRHASLSKVVEFCMALGGKTPIHSVLVANNGMAAAKFM
RSVRTWANETFGSEKAIQLIAMATPEDMRINAEHIRIADQFVEVPGGTNNNNYANVQLIVEIAVRTGVSAVWPG
WGHASENPELPDALNANGIVFLGPPSSSMNALGDKVGSALIAQAAGVPTLPWSGSQVEIPLEVCLDSIPADMYR
KACVSTTEEALASCQMIGYPAMIKASWGGGGKGIRKVNNDDDVRALFKQVQGEVPGSPIFIMRLASQSRHLEVQ
LLCDQYGNVAALHSRDCSVQRRHQKIIEEGPVTVAPRETVKELEQAARRLAKAVGYVGAATVEYLYSMETGEYY
FLELNPRLQVEHPVTEWIAEVNLPAAQVAVGMGIPLWQVPEIRRFYGMDNGGGYDIWRKTAALATPFNFDEVDS
QWPKGHCVAVRITSEDPDDGFKPTGGKVKEISFKSKPNVWAYFSVKSGGGIHEFADSQFGHVFAYGVSRAAAIT
NMSLALKEIQIRGEIHSNVDYTVDLLNASDFKENRIHTGWLDNRIAMRVQAERPPWYISVVGGALYKTITSNTD
TVSEYVSYLVKGQIPPKHISLVHSTVSLNIEESKYTIETIRSGQGSYRLRMNGSVIEANVQTLCDGGLLMQLDG
NSHVIYAEEEAGGTRLLIDGKTCLLQNDHDPSRLLAETPCKLLRFLVADGAHVEADVPYAEVEVMKMCMPLLSP
AAGVINVLLSEGQPMQAGDLIARLDLDDPSAVKRAEPFNGSFPEMSLPIAASGQVHKRCATSLNAARMVLAGYD
HPINKVVQDLVSCLDAPELPFLQWEELMSVLATRLPRLLKSELEGKYSEYKLNVGHGKSKDFPSKMLREIIEEN
LAHGSEKEIATNERLVEPLMSLLKSYEGGRESHAHFIVKSLFEDYLSVEELFSDGIQSDVIERLRQQHSKDLQK
VVDIVLSHQGVRNKTKLILTLMEKLVYPNPAAYKDQLTRFSSLNHKRYYKLALKASELLEQTKLSELRTSIARS
LSELEMFTEERTAISEIMGDLVTAPLPVEDALVSLFDCSDQTLQQRVIETYISRLYQPHLVKDSIQLKYQESGV
IALWEFAEAHSEKRLGAMVIVKSLESVSAAIGAALKGTSRYASSEGNIMHIALLGADNQMHGTEDSGDNDQAQV
RIDKLSATLEQNTVTADLRAAGVKVISCIVQRDGALMPMRHTFLLSDEKLCYEEEPVLRHVEPPLSALLELGKL
KVKGYNEVKYTPSRDRQWNIYTLRNTENPKMLHRVFFRTLVRQPGASNKFTSGNISDVEVGGAEESLSFTSSSI
LRSLMTAIEELELHAIRTGHSHMFLCILKEQKLLDLVPVSGNKVVDIGQDEATACLLLKEMALQIHELVGARMH
HLSVCQWEVKLKLDSDGPASGTWRVVTTNVTSHTCTVDIYREVEDTESQKLVYHSAPSSSGPLHGVALNTPYQP
LSVIDLKRCSARNNRTTYCYDFPLAFETAVQKSWSNISSDTNRCYVKATELVFAHKNGSWGTPVIPMERPAGLN
DIGMVAWILDMSTPEYPNGRQIVVIANDITFRAGSFGPREDAFFETVTNLACERKLPLIYLAANSGARIGIADE
VKSCFRVGWSDDGSPERGFQYIYLTEEDHARISASVIAHKMQLDNGEIRWVIDSVVGKEDGLGVENIHGSAAIA
SAYSRAYEETFTLTFVTGRTVGIGAYLARLGIRCIQRTDQPIILTGFSALNKLLGREVYSSHMQLGGPKIMATN
GVVHLTVSDDLEGVSNILRWLSYVPANIGGPLPITKSLDPPDRPVAYIPENTCDPRAAISGIDDSQGKWLGGMF
DKDSFVETFEGWAKSVVTGRAKLGGIPVGVIAVETQTMMQLIPADPGQLDSHERSVPRAGQVWFPDSATKTAQA
MLDFNREGLPLFILANWRGFSGGQRDLFEGILQAGSTIVENLRTYNQPAFVYIPKAAELRGGAWVVIDSKINPD
RIEFYAERTAKGNVLEPQGLIEIKFRSEELQECMGRLDPELINLKAKLLGAKHENGSLSESESLQKSIEARKKQ
LLPLYTQIAVRFAELHDTSLRMAAKGVIKKVVDWEDSRSFFYKRLRRRISEDVLAKEIRGVSGKQFSHQSAIEL
IQKWYLASKGAETGNTEWDDDDAFVAWRENPENYQEYIKELRAQRVSQLLSDVADSSPDLEALPQGLSMLLEKM
DPSRRAQFVEEVKKALK

FIGURE 16

| ACCase Mutation | Selections Agent | #exp | # ies | # Putative events | Putative TE | # Confirmed events | Confirmed TE | % escapes |
|---|---|---|---|---|---|---|---|---|
| RLM185 | pursuit | 2 | 27 | 15 | 56% | 14 | 52% | 4% |
| | cycloxydim | 2 | 29 | 0 | 0% | 0 | 0% | 0% |
| | tepraloxydim | 2 | 29 | 0 | 0% | 0 | 0% | 0% |
| I1781L | pursuit | 2 | 40 | 22 | 55% | 21 | 53% | 3% |
| | cycloxydim | 2 | 50 | 16 | 32% | 15 | 30% | 2% |
| | tepraloxydim | 2 | 50 | 0 | 0% | 0 | 0% | 0% |
| I1781L, W2027C | pursuit | 2 | 40 | 10 | 25% | 9 | 23% | 3% |
| | cycloxydim | 2 | 50 | 20 | 40% | 20 | 40% | 0% |
| | tepraloxydim | 2 | 50 | 11 | 22% | 11 | 22% | 0% |
| I1781L, I2041N | pursuit | 2 | 40 | 10 | 25% | 9 | 23% | 3% |
| | cycloxydim | 2 | 50 | 12 | 24% | 12 | 24% | 0% |
| | tepraloxydim | 2 | 50 | 14 | 28% | 14 | 28% | 0% |
| I1781A | pursuit | 2 | 35 | 16 | 46% | 14 | 40% | 6% |
| | cycloxydim | 2 | 50 | 0 | 0% | 0 | 0% | 0% |
| | tepraloxydim | 2 | 50 | 0 | 0% | 0 | 0% | 0% |
| Wild Type | pursuit | 2 | 30 | 16 | 53% | 15 | 50% | 3% |
| | cycloxydim | 2 | 50 | 0 | 0% | 0 | 0% | 0% |
| | tepraloxydim | 2 | 50 | 0 | 0% | 0 | 0% | 0% |

Figure 18

1MGSTHLPIVG FNASTTPSLS TLRQINSAAA AFQSSSPSRS SKKKSRRVKS IRDDGDGSVP
61 DPAGHGQSIR QGLAGIIDLP KEGASAPDVD ISHGSEDHKA SYQMNGILNE SHNGRHASLS
121 KVYEFCTELG GKTPIHSVLV ANNGMAAAKF MRSVRTWAND TFGSEKAIQL IAMATPEDMR
181 INAEHIRIAD QFVEVPGGTN NNNYANVQLI VEIAERTGVS AVWPGWGHAS ENPELPDALT
241 AKGIVFLGPP ASSMNALGDK VGSALIAQAA GVPTLAWSGS HVEIPLELCL DSIPEEMYRK
301 ACVTTADEAV ASCQMIGYPA MIKASWGGGG KGIRKVNNDD EVKALFKQVQ GEVPGSPIFI
361 MRLASQSRHL EVQLLCDEYG NVAALHSRDC SVQRRHQKII EEGPVTVAPR ETVKELEQAA
421 RRLAKAVGYV GAATVEYLYS METGEYYFLE LNPRLQVEHP VTESIAEVNL PAAQVAVGMG
481 IPLWQIPEIR RFYGMDNGGG YDIWRKTAAL ATPFNFDEVD SQWPKGHCVA VRITSENPDD
541 GFKPTGGKVK EISFKSKPNV WGYFSVKSGG GIHEFADSQF GHVFAYGETR SAAITSMSLA
601 LKEIQIRGEI HTNVDYTVDL LNAPDFRENT IHTGWLDTRI AMRVQAERPP WYISVVGGAL
661 YKTITTNAET VSEYVSYLIK GQIPPKHISL VHSTISLNIE ESKYTIEIVR SGQGSYRLRL
721 NGSLIEANVQ TLCDGGLLMQ LDGNSHVIYA EEEAGGTRLL IDGKTCLLQN DHDPSRLLAE
781 TPCKLLRFLI ADGAHVDADV PYAEVEVMKM CMPLLSPAAG VINVLLSEGQ AMQAGDLIAR
841 LDLDDPSAVK RAEPFEGSFP EMSLPIAASG QVHKRCAASL NAARMVLAGY DHAANKVVQD
901 LVWCLDTPAL PFLQWEELMS VLATRLPRRL KSELEGKYNE YKLNVDHVKI KDFPTEMLRE
961 TIEENLACVS EKEMVTIERL VDPLMSLLKS YEGGRESHAH FIVKSLFEEY LSVEELFSDG
1021 IQSDVIERLR LQYSKDLQKV VDIVLSHQGV RNKTKLILAL MEKLVYPNPA AYRDQLIRFS
1081 SLNHKRYYKL ALKASELLEQ TKLSELRTSI ARNLSALDMF TEEKADFSLQ DRKLAINESM
1141 GDLVTAPLPV EDALVSLFDC TDQTLQQRVI QTYISRLYQP QLVKDSIQLK YQDSGVIALW
1201 EFTEGNHEKR LGAMVILKSL ESVSTAIGAA LKDASHYASS AGNTVHIALL DADTQLNTTE
1261 DSGDNDQAQD KMDKLSFVLK QDVVMADLRA ADVKVVSCIV QRDGAIMPMR RTFLLSEEKL
1321 CYEEEPILRH VEPPLSALLE LDKLKVKGYN EMKYTPSRDR QWHIYTLRNT ENPKMLHRVF
1381 FRTLVRQPSA GNRFTSDHIT DVEVGHAEEP LSFTSSSILK SLKIAKEELE LHAIRTGHSH
1441 MYLCILKEQK LLDLVPVSGN TVVDVGQDEA TACSLLKEMA LKIHELVGAR MHHLSVCQWE
1501 VKLKLVSDGP ASGSWRVVTT NVTGHTCTVD IYREVEDTES QKLVYHSTAL SSGPLHGVAL
1561 NTSYQPLSVI DLKRCSARNN KTTYCYDFPL TFEAAVQKSW SNISSENNQC YVKATELVFA
1621 EKNGSWGTPI IPMQRAAGLN DIGMVAWILD MSTPEFPSGR QIIVIANDIT FRAGSFGPRE
1681 DAFFEAVTNL ACEKKLPLIY LAANSGARIG IADEVKSCFR VGWTDDSSPE RGFRYIYMTD
1741 EDHDRIGSSV IAHKMQLDSG EIRWVIDSVV GKEDGLGVEN IHGSAAIASA YSRAYEETFT
1801 LTFVTGRTVG IGAYLARLGI RCIQRIDQPI ILTGFSALNK LLGREVYSSH MQLGGPKIMA
1861 TNGVVHLTVP DDLEGVSNIL RWLSYVPANI GGPLPITKSL DPIDRPVAYI PENTCDPRAA
1921 ISGIDDSQGK WLGGMFDKDS FVETFEGWAK TVVTGRAKLG GIPVGVIAVE TQTMMQLVPA
1981 DPGQPDSHER SVPRAGQVWF PDSATKTAQA MLDFNREGLP LFILANWRGF SGGQRDLFEG
2041 ILQAGSTIVE NLRTYNQPAF VYIPKAAELR GGAWVVIDSK INPDRIECYA ERTAKGNVLE
2101 PQGLIEIKFR SEELKECMGR LDPELIDLKA RLQGANGSLS DGESLQKSIE ARKKQLLPLY
2161 TQIAVRFAEL HDTSLRMAAK GVIRKVVDWE DSRSFFYKRL RRRLSEDVLA KEIRGVIGEK
2221 FPHKSAIELI KKWYLASEAA AAGSTDWDDD DAFVAWRENP ENYKEYIKEL RAQRVSRLLS
2281 DVAGSSSDLQ ALPQGLSMLL DKMDPSKRAQ FIEEVMKVLK

Figure 19

```
                                     1                                                         60
          AmACCI [CAC84161]    (1)   MGSTHLPIVGFNASTTPSLSTLRQINSAAAAFQSSSPSRSSKKKSRRVKSIRDDGDGSVP
OsIACCI [BGIOSIBCE018385]    (1)   MTSTHVATLGVGAQAPPRHQ---KKSAGTAFVSSGSSRPSYRKNGQRTRSLREESNGGVS
        OsJACCI [EAZ33685]    (1)   MTSTHVATLGVGAQAPPRHQ---KKSAGTAFVSSGSSRPSYRKNGQRTRSLREESNGGVS

                                     61                                                       120
          AmACCI [CAC84161]   (61)   DPAGHGQSIRQGLAGIIDLPKEGASAPDVDISHGSEDHKA------SYQMNGILNESHNGR
OsIACCI [BGIOSIBCE018385]   (58)   DSKKLNHSIRQGLAGIIDLPNDAAS--EVDISHGSEDPRGPTVPGSYQMNGIINETHNGR
        OsJACCI [EAZ33685]   (58)   DSKKLNHSIRQGLAGIIDLPNDAAS--EVDISHGSEDPRGPTVPGSYQMNGIINETHNGR

                                     121                                                      180
          AmACCI [CAC84161]  (116)   HASLSKVYEFCTELGGKTPIHSVLVANNGMAAAKFMRSVRTWANDTFGSEKAIQLIAMAT
OsIACCI [BGIOSIBCE018385]  (116)   HASVSKVVEFCTALGGKTPIHSVLVANNGMAAAKFMRSVRTWANDTFGSEKAIQLIAMAT
        OsJACCI [EAZ33685]  (116)   HASVSKVVEFCTALGGKTPIHSVLVANNGMAAAKFMRSVRTWANDTFGSEKAIQLIAMAT

                                     181                                                      240
          AmACCI [CAC84161]  (176)   PEDMRINAEHIRIADQFVEVPGGTNNNNYANVQLIVEIAERTGVSAVWPGWGHASENPEL
OsIACCI [BGIOSIBCE018385]  (176)   PEDLRINAEHIRIADQFVEVPGGTNNNNYANVQLIVEIAERTGVSAVWPGWGHASENPEL
        OsJACCI [EAZ33685]  (176)   PEDLRINAEHIRIADQFVEVPGGTNNNNYANVQLIVEIAERTGVSAVWPGWGHASENPEL

                                     241                                                      300
          AmACCI [CAC84161]  (236)   PDALTAKGIVFLGPPASSMNALGDKVGSALIAQAAGVPTLAWSGSHVEIPLELCLDSIPE
OsIACCI [BGIOSIBCE018385]  (236)   PDALTAKGIVFLGPPASSMHALGDKVGSALIAQAAGVPTLAWSGSHVEVPLECCLDSIPD
        OsJACCI [EAZ33685]  (236)   PDALTAKGIVFLGPPASSMHALGDKVGSALIAQAAGVPTLAWSGSHVEVPLECCLDSIPD

                                     301                                                      360
          AmACCI [CAC84161]  (296)   EMYRKACVTTADEAVASCQMIGYPAMIKASWGGGGKGIRKVNNDDEVKALFKQVQGEVPG
OsIACCI [BGIOSIBCE018385]  (296)   EMYRKACVTTTEEAVASCQVVGYPAMIKASWGGGGKGIRKVHNDDEVRTLFKQVQGEVPG
        OsJACCI [EAZ33685]  (296)   EMYRKACVTTTEEAVASCQVVGYPAMIKASWGGGGKGIRKVHNDDEVRTLFKQVQGEVPG

                                     361                                                      420
          AmACCI [CAC84161]  (356)   SPIFIMRLASQSRHLEVQLLCDEYGNVAALHSRDCSVQRRHQKIIEEGPVTVAPRETVKE
OsIACCI [BGIOSIBCE018385]  (356)   SPIFIMRLAAQSRHLEVQLLCDQYGNVAALHSRDCSVQRRHQKIIEEGPVTVAPRETVKE
        OsJACCI [EAZ33685]  (356)   SPIFIMRLAAQSRHLEVQLLCDQYGNVAALHSRDCSVQRRHQKIIEEGPVTVAPRETVKE

                                     421                                                      480
          AmACCI [CAC84161]  (416)   LEQAARRLAKAVGYVGAATVEYLYSMETGEYYFLELNPRLQVEHPVTESIAEVNLPAAQV
OsIACCI [BGIOSIBCE018385]  (416)   LEQAARRLAKAVGYVGAATVEYLYSMETGEYYFLELNPRLQVEHPVTEWIAEVNLPAAQV
        OsJACCI [EAZ33685]  (416)   LEQAARRLAKAVGYVGAATVEYLYSMETGEYYFLELNPRLQVEHPVTEWIAEVNLPAAQV

                                     481                                                      540
          AmACCI [CAC84161]  (476)   AVGMGIPLWQIPEIRRFYGMDNGGGYDIWRKTAALATPFNFDEVDSQWPKGHCVAVRITS
OsIACCI [BGIOSIBCE018385]  (476)   AVGMGIPLWQIPEIRRFYGMNHGGGYDLWRKTAALATPFNFDEVDSKWPKGHCVAVRITS
        OsJACCI [EAZ33685]  (476)   AVGMGIPLWQIPEIRRFYGMNHGGGYDLWRKTAALATPFNFDEVDSKWPKGHCVAVRITS

                                     541                                                      600
          AmACCI [CAC84161]  (536)   ENPDDGFKPTGGKVKEISFKSKPNVWGYFSVKSGGGIHEFADSQFGHVFAYGETRSAAIT
OsIACCI [BGIOSIBCE018385]  (536)   EDPDDGFKPTGGKVKEISFKSKPNVWAYFSVKSGGGIHEFADSQFGHVFAYGTTRSAAIT
        OsJACCI [EAZ33685]  (536)   EDPDDGFKPTGGKVKEISFKSKPNVWAYFSVKSGGGIHEFADSQFGHVFAYGTTRSAAIT

                                     601                                                      660
          AmACCI [CAC84161]  (596)   SMSLALKEIQIRGEIHTNVDYTVDLLNAPDFRENTIHTGWLDTRIAMRVQAERPPWYISV
OsIACCI [BGIOSIBCE018385]  (596)   TMALALKEVQIRGEIHSNVDYTVDLLNASDFRENKIHTGWLDTRIAMRVQAERPPWYISV
        OsJACCI [EAZ33685]  (596)   TMALALKEVQIRGEIHSNVDYTVDLLNASDFRENKIHTGWLDTRIAMRVQAERPPWYISV

                                     661                                                      720
          AmACCI [CAC84161]  (656)   VGGALYKTITTNAETVSEYVSYLIKGQIPPKHISLVHSTISLNIEESKYTIEIVRSGQGS
OsIACCI [BGIOSIBCE018385]  (656)   VGGALYKTVTANTATVSDYVGYLTKGQIPPKHISLVYTTVALNIDGKKYTIDTVRSGHGS
        OsJACCI [EAZ33685]  (656)   VGGALYKTVTANTATVSDYVGYLTKGQIPPKHISLVYTTVALNIDGKKYTIDTVRSGHGS

                                     721                                                      780
          AmACCI [CAC84161]  (716)   YRLRLNGSLIEANVQTLCDGGLLMQLDGNSHVIYAEEEAGGTRLLIDGKTCLLQNDHDPS
OsIACCI [BGIOSIBCE018385]  (716)   YRLRMNGSTVDANVQILCDGGLLMQLDGNSHVIYAEEEASGTRLLIDGKTCMLQNDHDPS
        OsJACCI [EAZ33685]  (716)   YRLRMNGSTVDANVQILCDGGLLMQLDGNSHVIYAEEEASGTRLLIDGKTCMLQNDHDPS

                                     781                                                      840
          AmACCI [CAC84161]  (776)   RLLAETPCKLLRFLIADGAHVDADVPYAEVEVMKMCMPLLSPAAGVINVLLSEGQAMQAG
OsIACCI [BGIOSIBCE018385]  (776)   KLLAETPCKLLRFLVADGAHVDADVPYAEVEVMKMCMPLLSPASGVIHVVMSEGQAMQAG
```

Figure 19 (continued)

```
          OsJACCI [EAZ33685]  (776)  KLLAETPCKLLRFLVADGAHVDADVPYAEVEVMKMCMPLLSPASGVIHVVMSEGQAMQAG

                                     841                                                       900
           AmACCI [CAC84161]  (836)  DLIARLDLDDPSAVKRAEPFEGSFPEMSLPIAASGQVHKRCAASLNAARMVLAGYDHAAN
   OsIACCI [BGIOSIBCE018385]  (836)  DLIARLDLDDPSAVKRAEPFEDTFPQMGLPIAASGQVHKLCAASLNACRMILAGYEHDID
          OsJACCI [EAZ33685]  (836)  DLIARLDLDDPSAVKRAEPFEDTFPQMGLPIAASGQVHKLCAASLNACRMILAGYEHDID

                                     901                                                       960
           AmACCI [CAC84161]  (896)  KVVQDLVWCLDTPALPFLQWEELMSVLATRLPRRLKSELEGKYNEYKLNVDHVKIKDFPT
   OsIACCI [BGIOSIBCE018385]  (896)  KVVPELVYCLDTPELPFLQWEELMSVLATRLPRNLKSELEGKYEEYKVKFDSGIINDFPA
          OsJACCI [EAZ33685]  (896)  KVVPELVYCLDTPELPFLQWEELMSVLATRLPRNLKSELEGKYEEYKVKFDSGIINDFPA

                                     961                                                      1020
           AmACCI [CAC84161]  (956)  EMLRETIEENLACVSEKEMVTIERLVDPLMSLLKSYEGGRESHAHFIVKSLFEEYLSVEE
   OsIACCI [BGIOSIBCE018385]  (956)  NMLRVIIEENLACGSEKEKATNERLVEPLMSLLKSYEGGRESHAHFVVKSLFEEYLYVEE
          OsJACCI [EAZ33685]  (956)  NMLRVIIEENLACGSEKEKATNERLVEPLMSLLKSYEGGRESHAHFVVKSLFEEYLYVEE

                                     1021                                                     1080
           AmACCI [CAC84161] (1016)  LFSDGIQSDVIERLRLQYSKDLQKVVDIVLSHQGVRNKTKLILALMEKLVYPNPAAYRDQ
   OsIACCI [BGIOSIBCE018385] (1016)  LFSDGIQSDVIERLRLQHSKDLQKVVDIVLSHQSVRNKTKLILKLMESLVYPNPAAYRDQ
          OsJACCI [EAZ33685] (1016)  LFSDGIQSDVIERLRLQHSKDLQKVVDIVLSHQSVRNKTKLILKLMESLVYPNPAAYRDQ

                                     1081                                                     1140
           AmACCI [CAC84161] (1076)  LIRFSSLNHKRYYKLALKASELLEQTKLSELRTSIARNLSALDMFTEEKADFSLQDRKLA
   OsIACCI [BGIOSIBCE018385] (1076)  LIRFSSLNHKAYYKLALKASELLEQTKLSELRARIARSLSELEMFTEESKGLSMHKREIA
          OsJACCI [EAZ33685] (1076)  LIRFSSLNHKAYYKLALKASELLEQTKLSELRARIARSLSELEMFTEESKGLSMHKREIA

                                     1141                                                     1200
           AmACCI [CAC84161] (1136)  INESMGDLVTAPLPVEDALVSLFDCTDQTLQQRVIQTYISRLYQPQLVKDSIQLKYQDSG
   OsIACCI [BGIOSIBCE018385] (1136)  IKESMEDLVTAPLPVEDALISLFDCSDTTVQQRVIETYIARLYQPHLVKDSIKMKWIESG
          OsJACCI [EAZ33685] (1136)  IKESMEDLVTAPLPVEDALISLFDCSDTTVQQRVIETYIARLYQPHLVKDSIKMKWIESG

                                     1201                                                     1260
           AmACCI [CAC84161] (1196)  VIALWEFTEGNHEKR----------LGAMVILKSLESVSTAIGAALKDASHYASSAGNTV
   OsIACCI [BGIOSIBCE018385] (1196)  VIALWEFPEGHFDARNGGAVLGDKRWGAMVIVKSLESLSMAIRFALKETSHYTSSEGNMM
          OsJACCI [EAZ33685] (1196)  VIALWEFPEGHFDARNGGAVLGDKRWGAMVIVKSLESLSMAIRFALKETSHYTSSEGNMM

                                     1261                                                     1320
           AmACCI [CAC84161] (1246)  HIALLDADTQLNTTEDSGDNDQAQDKMDKLSFVLKQDVVMADLRAADVKVVSCIVQRDGA
   OsIACCI [BGIOSIBCE018385] (1256)  HIALLGADNKMHIIQESG---DDADRIAKLPLILKDN--VTDLHASGVKTISFIVQRDEA
          OsJACCI [EAZ33685] (1256)  HIALLGADNKMHIIQESG---DDADRIAKLPLILKDN--VTDLHASGVKTISFIVQRDEA

                                     1321                                                     1380
           AmACCI [CAC84161] (1306)  IMPMRRTFLLSEEKLCYEEEPILRHVEPPLSALLELDKLKVKGYNEMKYTPSRDRQWHIY
   OsIACCI [BGIOSIBCE018385] (1311)  RMTMRRTFLWSDEKLSYEEEPILRHVEPPLSALLELDKLKVKGYNEMKYTPSRDRQWHIY
          OsJACCI [EAZ33685] (1311)  RMTMRRTFLWSDEKLSYEEEPILRHVEPPLSALLELDKLKVKGYNEMKYTPSRDRQWHIY

                                     1381                                                     1440
           AmACCI [CAC84161] (1366)  TLRNTENPKMLHRVFFRTLVRQPSAGNRFTSDHITDVEVGHAEEPLSFTSSSILKSLKIA
   OsIACCI [BGIOSIBCE018385] (1371)  TLRNTENPKMLHRVFFRTLVRQPSVSNKFSSGQIGDMEVGSAEEPLSFTSTSILRSLMTA
          OsJACCI [EAZ33685] (1371)  TLRNTENPKMLHRVFFRTLVRQPSVSNKFSSGQIGDMEVGSAEEPLSFTSTSILRSLMTA

                                     1441                                                     1500
           AmACCI [CAC84161] (1426)  KEELELHAIRTGHSHMYLCILKEQKLLDLVPVSGNTVVDVGQDEATACSLLKEMALKIHE
   OsIACCI [BGIOSIBCE018385] (1431)  IEELELHAIRTGHSHMYLHVLKEQKLLDLVPVSGNTVLDVGQDEATAYSLLKEMAMKIHE
          OsJACCI [EAZ33685] (1431)  IEELELHAIRTGHSHMYLHVLKEQKLLDLVPVSGNTVLDVGQDEATAYSLLKEMAMKIHE

                                     1501                                                     1560
           AmACCI [CAC84161] (1486)  LVGARMHHLSVCQWEVKLKLVSDGPASGSWRVVTTNVTGHTCTVDIYREVEDTESQKLVY
   OsIACCI [BGIOSIBCE018385] (1491)  LVGARMHHLSVCQWEVKLKLDCDGPASGTWRIVTTNVTSHTCTVDIYREMEDKESRKLVY
          OsJACCI [EAZ33685] (1491)  LVGARMHHLSVCQWEVKLKLDCDGPASGTWRIVTTNVTSHTCTVDIYREMEDKESRKLVY

                                     1561                                                     1620
           AmACCI [CAC84161] (1546)  HSTALSSGPLHGVALNTSYQPLSVIDLKRCSARNNKTTYCYDFPLTFEAAVQKSWSNISS
   OsIACCI [BGIOSIBCE018385] (1551)  HPATPAAGPLHGVALNNPYQPLSVIDLKRCSARNNRTTYCYDFPLAFETAVRKSWSSSTS
          OsJACCI [EAZ33685] (1551)  HPATPAAGPLHGVALNNPYQPLSVIDLKRCSARNNRTTYCYDFPLAFETAVRKSWSSSTS

                                     1621                                                     1680
```

Figure 19 (continued)

```
     AmACCI [CAC84161] (1606)  -------ENNQCYVKATELVFAEKNGSWGTPIIPMQRAAGLNDIGMVAWILDMSTPEFPSG
OsIACCI [BGIOSIBCE018385] (1611)  GASKGVENAQCYVKATELVFADKHGSWGTPLVQMDRPAGLNDIGMVAWTLKMSTPEFPSG
     OsJACCI [EAZ33685] (1611)  GASKGVENAQCYVKATELVFADKHGSWGTPLVQMDRPAGLNDIGMVAWTLKMSTPEFPSG

                                1681                                                     1740
     AmACCI [CAC84161] (1660)  RQIIVIANDITFRAGSFGPREDAFFEAVTNLACEKKLPLIYLAANSGARIGIADEVKSCF
OsIACCI [BGIOSIBCE018385] (1671)  REIIVVANDITFRAGSFGPREDAFFEAVTNLACEKKLPLIYLAANSGARIGIADEVKSCF
     OsJACCI [EAZ33685] (1658)  REIIVVANDITFRAGSFGPREDAFFEAVTNLACEKKLPLIYLAANSGARIGIADEVKSCF

                                1741                                                     1800
     AmACCI [CAC84161] (1720)  RVGWTDDSSPERGFRYIYMTDEDHDRIGSSVIAHKMQLDSGEIRWVIDSVVGKEDGLGVE
OsIACCI [BGIOSIBCE018385] (1731)  RVGWSDDGSPERGFQYIYLSEEDYARIGTSVIAHKMQLDSGEIRWVIDSVVGKEDGLGVE
     OsJACCI [EAZ33685] (1718)  RVGWSDDGSPERGFQYIYLSEEDYARIGTSVIAHKMQLDSGEIRWVIDSVVGKEDGLGVE

                                1801                                                     1860
     AmACCI [CAC84161] (1780)  NIHGSAAIASAYSRAYEETFTLTFVTGRTVGIGAYLARLGIRCIQRIDQPIILTGFSALN
OsIACCI [BGIOSIBCE018385] (1791)  NIHGSAAIASAYSRAYKETFTLTFVTGRTVGIGAYLARLGIRCIQRLDQPIILTGYSALN
     OsJACCI [EAZ33685] (1778)  NIHGSAAIASAYSRAYKETFTLTFVTGRTVGIGAYLARLGIRCIQRLDQPIILTGYSALN

                                1861                                                     1920
     AmACCI [CAC84161] (1840)  KLLGREVYSSHMQLGGPKIMATNGVVHLTVPDDLEGVSNILRWLSYVPANIGGPLPITKS
OsIACCI [BGIOSIBCE018385] (1851)  KLLGREVYSSHMQLGGPKIMATNGVVHLTVSDDLEGVSNILRWLSYVPAYIGGPLPVTTP
     OsJACCI [EAZ33685] (1838)  KLLGREVYSSHMQLGGPKIMATNGVVHLTVSDDLEGVSNILRWLSYVPAYIGGPLPVTTP

                                1921                                                     1980
     AmACCI [CAC84161] (1900)  LDPIDRPVAYIPENTCDPRAAISGIDDSQGKWLGGMFDKDSFVETFEGWAKTVVTGRAKL
OsIACCI [BGIOSIBCE018385] (1911)  LDPPDRPVAYIPENSCDPRAAIRGVDDSQGKWLGGMFDKDSFVETFEGWAKTVVTGRAKL
     OsJACCI [EAZ33685] (1898)  LDPPDRPVAYIPENSCDPRAAIRGVDDSQGKWLGGMFDKDSFVETFEGWAKTVVTGRAKL

                                1981                                                     2040
     AmACCI [CAC84161] (1960)  GGIPVGVIAVETQTMMQLVPADPGQPDSHERSVPRAGQVWFPDSATKTAQAMLDFNREGL
OsIACCI [BGIOSIBCE018385] (1971)  GGIPVGVIAVETQTMMQTIPADPGQLDSREQSVPRAGQVWFPDSATKTAQALLDFNREGL
     OsJACCI [EAZ33685] (1958)  GGIPVGVIAVETQTMMQTIPADPGQLDSREQSVPRAGQVWFPDSATKTAQALLDFNREGL

                                2041                                                     2100
     AmACCI [CAC84161] (2020)  PLFILANWRGFSGGQRDLFEGILQAGSTIVENLRTYNQPAFVYIPKAAELRGGAWVVIDS
OsIACCI [BGIOSIBCE018385] (2031)  PLFILANWRGFSGGQRDLFEGILQAGSTIVENLRTYNQPAFVYIPMAAELRGGAWVVVDS
     OsJACCI [EAZ33685] (2018)  PLFILANWRGFSGGQRDLFEGILQAGSTIVENLRTYNQPAFVYIPMAAELRGGAWVVVDS

                                2101                                                     2160
     AmACCI [CAC84161] (2080)  KINPDRIECYAERTAKGNVLEPQGLIEIKFRSEELKECMGRLDPELIDLKARLQGAN-GS
OsIACCI [BGIOSIBCE018385] (2091)  KINPDRIECYAERTAKGNVLEPQGLIEIKFRSEELQDCMSRLDPTLIDLKAKLEVANKNG
     OsJACCI [EAZ33685] (2078)  KINPDRIECYAERTAKGNVLEPQGLIEIKFRSEELQDCMSRLDPTLIDLKAKLEVANKNG

                                2161                                                     2220
     AmACCI [CAC84161] (2139)  LSDGESLQKSIEARKKQLLPLYTQIAVRFAELHDTSLRMAAKGVIRKVVDWEDSRSFFYK
OsIACCI [BGIOSIBCE018385] (2151)  SADTKSLQENIEARTKQLMPLYTQIAIRFAELHDTSLRMAAKGVIKKVVDWEESRSFFYK
     OsJACCI [EAZ33685] (2138)  SADTKSLQENIEARTKQLMPLYTQIAIRFAELHDTSLRMAAKGVIKKVVDWEESRSFFYK

                                2221                                                     2280
     AmACCI [CAC84161] (2199)  RLRRRLSEDVLAKEIRGVIGEKFPHKSAIELIKKWYLASEAAAAGSTDWDDDDAFVAWRE
OsIACCI [BGIOSIBCE018385] (2111)  RLRRRISEDVLAKEIRAVAGEQFSHQPAIELIKKWYSASHAA-----EWDDDDAFVAWMD
     OsJACCI [EAZ33685] (2198)  RLRRRISEDVLAKEIRAVAGEQFSHQPAIELIKKWYSASHAA-----EWDDDDAFVAWMD

                                2281                                                     2340
     AmACCI [CAC84161] (2259)  NPENYKEYIKELRAQRVSRLLSDVAGSSSDLQALPQGLSMLLDKMDPSKRAQFIEEVMKV
OsIACCI [BGIOSIBCE018385] (2266)  NPENYKDYIQYLKAQRVSQSLSSLSDSSSDLQALPQGLSMLLDKMDPSRRAQLVEEIRKV
     OsJACCI [EAZ33685] (2253)  NPENYKDYIQYLKAQRVSQSLSSLSDSSSDLQALPQGLSMLLDKMDPSRRAQLVEEIRKV

                                2341
     AmACCI [CAC84161] (2319)  LK
OsIACCI [BGIOSIBCE018385] (2326)  LG
     OsJACCI [EAZ33685] (2313)  LG
```

METHOD FOR TREATING POST-EMERGENT RICE

RELATED APPLICATIONS

This application is a division of U.S. application Ser. No. 15/395,832, filed Dec. 30, 2016, which is a Continuation-in-Part of U.S. application Ser. No. 14/357,691, filed on May 12, 2014 now U.S. Pat. No. 9,540,627 issued Jan. 10, 2017, which is a 35 U.S.C. 371 National Stage entry of PCT/US12/64831, filed on Nov. 13, 2012, which claims the benefit of U.S. Provisional Application Ser. No. 61/559,618, filed on Nov. 14, 2011, all of which are hereby incorporated herein in their entirety by reference. U.S. application Ser. No. 15/395,832 also is a Continuation-in-Part of U.S. application Ser. No. 15/156,671, filed May 17, 2016, which is a continuation of U.S. application Ser. No. 13/393,780, filed Jan. 7, 2013, which is a 35 U.S.C. 371 National Stage entry of PCT/US10/47571, filed on Sep. 1, 2010, which claims the benefit of U.S. Provisional Application Ser. No. 61/365,298, filed Jul. 16, 2009, and 61/238,906, filed Sep. 1, 2009, all of which are hereby incorporated herein in their entirety by reference.

FIELD

The present disclosure generally relates to treatment of domestic rice crop plants for the control of weeds.

BACKGROUND

Rice is one of the most important food crops in the world, particularly in Asia. Rice is a cereal grain produced by plants in the genus *Oryza*. The two most frequently cultivated species are *Oryza sativa* and *Oryza glaberrima*, with *O. sativa* being the most frequently cultivated domestic rice. In addition to the two domestic species, the genus *Oryza* contains more than 20 wild species. One of these wild species, *Oryza rufipogon* ("red rice" also referred to as *Oryza sativa* subsp. *rufipogon*) presents a major problem in commercial cultivation. Red rice produces red coated seeds. After harvest, rice seeds are milled to remove their hull. After milling, domestic rice is white while wild red rice appears discolored. The presence of discolored seeds reduces the value of the rice crop. Since red rice belongs to the same species as cultivated rice (*Oryza sativa*), their genetic makeup is very similar. This genetic similarity has made herbicidal control of red rice difficult.

Domestic rice tolerant to imidazolinone herbicides have been developed and are currently marketed under the tradename CLEARFIELD●. Imidazolinone herbicides inhibit a plant's acetohydroxyacid synthase (AHAS) enzyme. When cultivating CLEARFIELD● rice, it is possible to control red rice and other weeds by application of imidazolinone herbicides. Unfortunately, imidazolinone herbicide-tolerant red rice and weeds have developed.

Acetyl-Coenzyme A carboxylase (ACCase; EC 6.4.1.2) enzymes synthesize malonyl-CoA as the start of the de novo fatty acid synthesis pathway in plant chloroplasts. ACCase in grass chloroplasts is a multifunctional, nuclear-genome-encoded, very large, single polypeptide, transported into the plastid via an N-terminal transit peptide. The active form in grass chloroplasts is a homomeric protein, likely a homodimer.

ACCase enzymes in grasses are inhibited by three classes of herbicidal active ingredients. The two most prevalent classes are aryloxyphenoxypropanoates ("FOPs") and cyclohexanediones ("DIMs"). In addition to these two classes, a third class phenylpyrazolines ("DENs") has been described.

A number of ACCase-inhibitor-tolerance (AIT) mutations have been found in monocot weed species exhibiting tolerance toward one or more DIM or FOP herbicides. Further, an AIT maize has been marketed by BASF. All such mutations are found in the carboxyltransferase domain of the ACCase enzyme, and these appear to be located in a substrate binding pocket, altering access to the catalytic site.

DIMs and FOPs are important herbicides and it would be advantageous if rice could be provided that exhibits tolerance to these classes of herbicide. Currently, these classes of herbicide are of limited value in rice agriculture. In some cases, herbicide-tolerance-inducing mutations create a severe fitness penalty in the tolerant plant. Therefore, there remains a need in the art for an AIT rice that also exhibits no fitness penalty. This need and others are met by the present invention.

SUMMARY

One aspect of the present disclosure relates to a method for treating rice. The method comprises the steps of: providing a domestic rice crop plant and at least one ACCase-inhibiting aryloxyphenoxypropanoate herbicide selected from the group consisting of quizalofop or an ester thereof, haloxyfop, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence; thereby creating a treated rice plant; and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

In still other embodiments, the aryloxyphenoxypropanoate herbicide is quizalofop or an ester thereof. In some further embodiments, the effective amount of quizalofop or an ester thereof is at least 14 g AI/Ha.

In even other embodiments, the aryloxyphenoxypropanoate herbicide is fluazifop or an ester thereof. In some further embodiments, the effective amount of fluazifop or an ester thereof is at least 56 g AI/Ha.

In some other embodiments, the aryloxyphenoxypropanoate herbicide is clodinafop or clodinafop-propargyl. In some further embodiments, the effective amount of clodinafop or clodinafop-propargyl is at least 11 g AI/Ha.

In still other embodiments, the aryloxyphenoxypropanoate herbicide is diclofop or diclofop-methyl. In some further embodiments, the effective amount of diclofop or diclofop-methyl is at least 226 g AI/Ha.

In some embodiments, the effective amount is effective for killing a weed of the genus *Echinochloa*. In some further embodiments, the weed of the genus *Echinochloa* is selected from the group consisting of *Echinochloa colona, Echinochloa crus-galli, Echinochloa crus-pavonis, Echinochloa oryzicola*, and *Echinochloa oryzoides*.

In other embodiments, the effective amount is effective for killing a weed of the genus *Leptochloa*. In some further embodiments, the weed of the genus *Leptochloa* is selected from the group consisting of *Leptochloa chinensis, Leptochloa fascicularis, Leptochloa panacea*, and *Leptochloa panicoides*.

In some embodiments, the method further comprises providing at least one cyclohexanedione herbicide and applying an effective amount thereof to the domestic rice crop plant.

Another aspect of the present disclosure relates to a method for treating rice comprising providing a domestic rice crop plant and at least one ACCase-inhibiting aryloxyphenoxypropanoate herbicide selected from the group consisting of quizalofop or an ester thereof, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence, wherein said effective amount is 0.5× of an amount that causes both at least about 90% phytotoxicity in wild type *Echinochloa crus-galli* and more than 10% phytotoxicity in wild-type *Oryza sativa*; thereby creating a treated rice plant, and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

BRIEF DESCRIPTION OF THE DRAWINGS

The present disclosure can be better understood by reference to the following drawings. The drawings are merely exemplary to illustrate certain features that may be used singularly or in combination with other features and the aspects of the present disclosure should not be limited to the embodiments shown.

FIG. 5 provides the amino acid sequence of acetyl-coenzyme A carboxylase from *Alopecurus myosuroides* (GenBank accession number CAC84161) (SEQ ID NO. 24).

FIG. 6 provides the mRNA encoding acetyl-coenzyme A carboxylase from *Alopecurus myosuroides* (GenBank accession number AJ310767 region: 157..7119).

FIG. 7A provides the genomic nucleotide sequence for *Oryza sativa Indica* & *Japonica* acetyl-Coenzyme A carboxylase gene (SEQ ID NO:5).

FIG. 7B provides the nucleotide sequence encoding *Oryza sativa Indica* & *Japonica* acetyl-Coenzyme A carboxylase (SEQ ID NO:6).

FIG. 7C provides the amino acid sequence of *Oryza sativa Indica* acetyl-Coenzyme A carboxylase (SEQ ID NO:3).

FIG. 8A provides the nucleotide sequence encoding *Zea mays* acetyl-Coenzyme A carboxylase (SEQ ID NO:11).

FIG. 8B provides the amino acid sequence of *Zea mays* acetyl-Coenzyme A carboxylase (SEQ ID NO:12).

FIG. 9A provides the nucleotide sequence encoding *Zea mays* acetyl-Coenzyme A carboxylase (SEQ ID NO:13).

FIG. 9B provides the amino acid sequence of *Zea mays* acetyl-Coenzyme A carboxylase (SEQ ID NO:14).

FIG. 10A provides the nucleotide sequence encoding *Triticum aestivum* acetyl-Coenzyme A carboxylase (SEQ ID NO:15).

FIG. 10B provides the amino acid sequence of *Triticum aestivum* acetyl-Coenzyme A carboxylase (SEQ ID NO:16).

FIG. 11A provides the nucleotide sequence encoding *Setaria italica* acetyl-Coenzyme A carboxylase (SEQ ID NO:17).

FIG. 11B provides the amino acid sequence of *Setaria italica* acetyl-Coenzyme A carboxylase (SEQ ID NO:18).

FIG. 12A provides the nucleotide sequence encoding *Setaria italica* acetyl-Coenzyme A carboxylase (SEQ ID NO:19).

FIG. 12B provides the amino acid sequence of *Setaria italica* acetyl-Coenzyme A carboxylase (SEQ ID NO:20).

FIG. 13A provides the nucleotide sequence encoding *Setaria italica* acetyl-Coenzyme A carboxylase (SEQ ID NO:21).

FIG. 13B provides the amino acid sequence of *Setaria italica* acetyl-Coenzyme A carboxylase (SEQ ID NO:22).

FIG. 14A provides the nucleotide sequence encoding *Alopecurus myosuroides* acetyl-Coenzyme A carboxylase (SEQ ID NO:23).

FIG. 14B provides the amino acid sequence of *Alopecurus myosuroides* acetyl-Coenzyme A carboxylase (SEQ ID NO:24).

FIG. 15A provides the nucleotide sequence encoding *Aegilops tauschii* acetyl-Coenzyme A carboxylase (SEQ ID NO:25).

FIG. 15B provides the amino acid sequence of *Aegilops tauschii* acetyl-Coenzyme A carboxylase (SEQ ID NO:26).

FIG. 16 provides a comparison of single and double mutants.

FIG. 18 provides *Alopecurus myosuroides* acetyl-Coenzyme A carboxylase amino acid sequence (GenBank accession no. CAC84161) (SEQ ID NO. 24). Amino acids that may be altered in the acetyl-Coenzyme A carboxylase enzymes of the disclosure are indicated in bold double underline.

FIG. 19 provides amino acid sequence of wild-type *Oryza sativa* acetyl-Coenzyme A carboxylases (SEQ ID NOs. 2, 3) aligned with *Alopecurus myosuroides* acetyl-Coenzyme A carboxylase (SEQ ID NO. 24) with some critical residues denoted.

DETAILED DESCRIPTION

Figures 1, 1A, 1B, 1C:
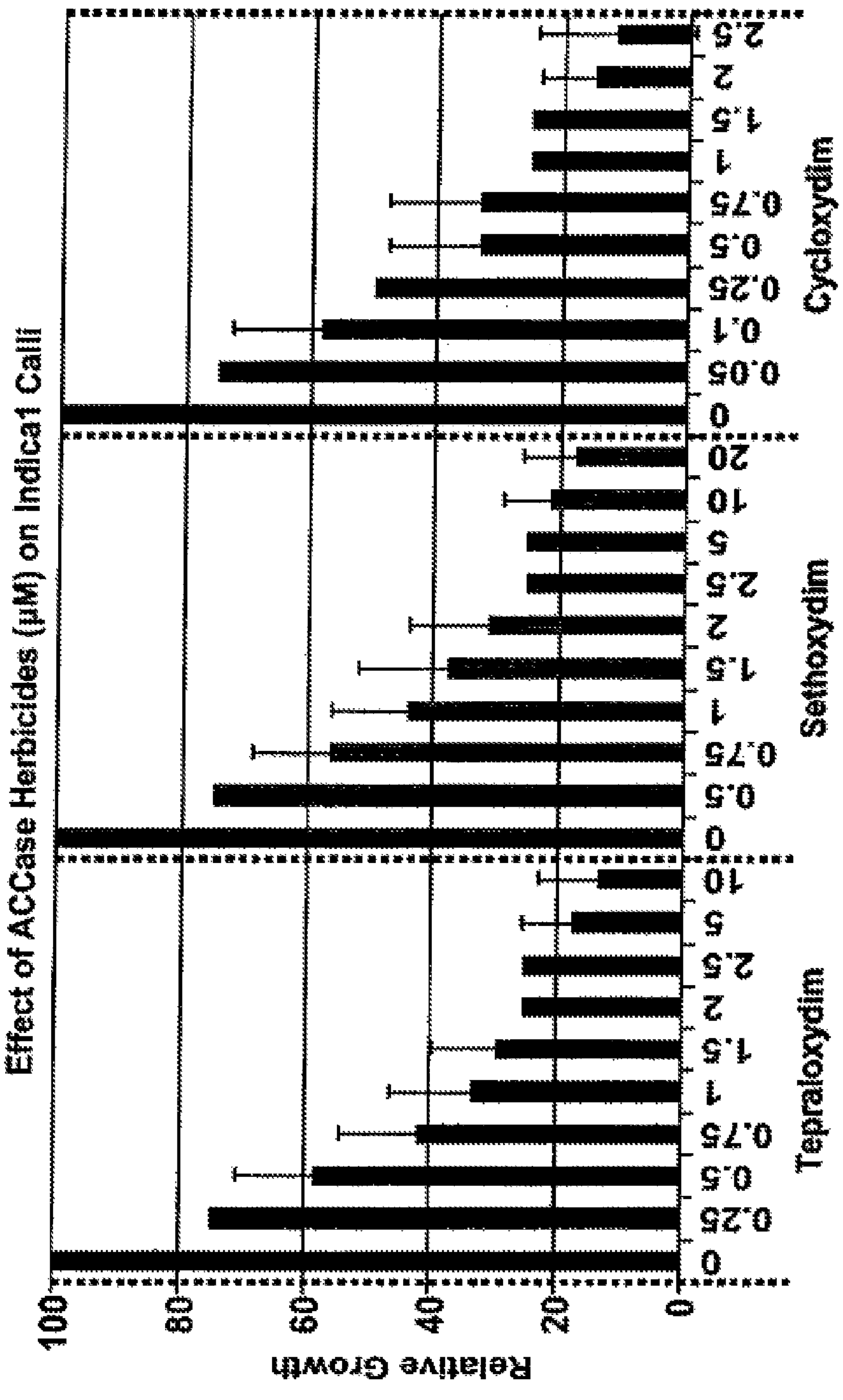
FIG. 1 is a bar graph showing relative growth rice calli derived from *Oryza sativa* subsp. *indica* grown in the presence of difference selection levels of herbicide.
FIG. 1A shows the results obtained with tepraloxydim.
FIG. 1B shows the results obtained with sethoxydim.
FIG. 1C shows the results obtained with cycloxydim.

The following detailed description is presented to enable any person skilled in the art to make and use the objectives of the present disclosure. For purposes of explanation, specific nomenclature is set forth to provide a thorough understanding of the objectives of the present disclosure. However, it will be apparent to one skilled in the art that these specific details are not required to practice the objectives of the present disclosure. Descriptions of specific applications are provided only as representative examples. The presently claimed disclosure is not intended to be limited to the embodiments shown, but is to be accorded the widest possible scope consistent with the principles and features disclosed herein.

Definitions

As used herein, "tolerant" or "herbicide-tolerant" indicates a plant or portion thereof capable of growing in the presence of an amount of herbicide that normally causes growth inhibition in a non-tolerant (e.g., a wild-type) plant or portion thereof. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant.

As used herein, "recombinant" refers to an organism having genetic material from different sources.

As used herein, "mutagenized" refers to an organism having an altered genetic material as compared to the genetic material of a corresponding wild-type organism, wherein the alterations in genetic material were induced and/or selected by human action. Examples of human action that can be used to produce a mutagenized organism include, but are not limited to, tissue culture of plant cells (e.g., calli) in sub-lethal concentrations of herbicides (e.g., acetyl-Coenzyme A carboxylase inhibitors such as cycloxydim or sethoxydim), treatment of plant cells with a chemical mutagen and subsequent selection with herbicides (e.g., acetyl-Coenzyme A carboxylase inhibitors such as cycloxydim or sethoxydim); or by treatment of plant cells with x-rays and subsequent selection with herbicides (e.g., acetyl-Coenzyme A carboxylase inhibitors such as cycloxydim or sethoxydim). Any method known in the art may be used to induce mutations. Methods of inducing mutations may induce mutations in random positions in the genetic material or may induce mutations in specific locations in the genetic material (i.e., may be directed mutagenesis techniques).

As used herein, a "genetically modified organism" (GMO) is an organism whose genetic characteristics have been altered by insertion of genetic material from another source organism or progeny thereof that retain the inserted genetic material. The source organism may be of a different type of organism (e.g., a GMO plant may contain bacterial genetic material) or from the same type of organism (e.g., a GMO plant may contain genetic material from another plant). As used herein, recombinant and GMO are considered synonyms and indicate the presence of genetic material from a different source whereas mutagenized indicates altered genetic material from a corresponding wild-type organism but no genetic material from another source organism.

As used herein, "wild-type" or "corresponding wild-type plant" means the typical form of an organism or its genetic material, as it normally occurs, as distinguished from mutagenized and/or recombinant forms.

For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope.

As used herein in regard to herbicides useful in various embodiments hereof, terms such as auxinic herbicide, AHAS inhibitor, acetyl-Coenzyme A carboxylase (ACCase) inhibitor, PPO inhibitor, EPSPS inhibitor, imidazolinone, sulfonylurea, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

When used in reference to a particular mutant enzyme or polypeptide, terms such as herbicide tolerant (HT) and herbicide tolerance refer to the ability of such enzyme or polypeptide to perform its physiological activity in the presence of an amount of an herbicide A.I. that would normally inactivate or inhibit the activity of the wild-type (non-mutant) version of said enzyme or polypeptide. For example, when used specifically in regard to an AHAS enzyme, or AHASL polypeptide, it refers specifically to the ability to tolerate an AHAS-inhibitor. Classes of AHAS-inhibitors include sulfonylureas, imidazolinones, triazolopyrimidines, sulfonylaminocarbonyltriazolinones, and pyrimidinyloxy[thio]benzoates.

As used herein, "descendant" refers to any generation plant.

As used herein, "progeny" refers to a first generation plant.

As used herein, an "effective amount" refers to the amount of an herbicide required to achieve at least about 65% phytotoxicity of conventional rice (e.g., red rice) in field applications. In some embodiments, an effective amount may be further defined as an amount of an herbicide required to achieve at least about 70, 75, 80, 85, 90, 95 or 99% phytotoxicity of conventional rice (e.g., red rice) in field applications. In other embodiments, an effective amount may be further defined as an amount of an herbicide required to achieve at least about 65, 70, 75, 80, 85, 90, 95 or 99% phytotoxicity of *Echinochloa* or *Leptochloa* species weeds in field applications. Typically, an effective amount for post-emergent application will be at least 0.5× the standard application rate of a given herbicide. 1× rates of herbicides listed herein are within the knowledge of one of ordinary skill in the art and it understood herein that for any herbicide not having a published 1× application rate, a 1× rate is one that causes at least 90% phytotoxicity in *Echinochloa crus-galli.*

As used herein, the amino acid numbering, and the associated DNA sequence numbering are based on the numbering of the ACCase in *Alopercurus myosuroides* (blackgrass) (Genbank CAC84161.1) and denoted with an (Am). The reference positions cited within are intended to correspond to the actual recited positional equivalent in the ACCase of *Alopercurus myosuroides.*

As used herein, a "non-selective" or "rice-non-selective" ACCase-inhibiting herbicide relates to an herbicide of the DIM or FOP class that, at a given rate of application, of active ingredient causes both at least about 90% phytotoxicity in *Echinochloa crus-galli* and more than 10% phytotoxicity in domestic rice (*Oryza sativa*). Conversely, "selective" means any ACCase-inhibiting DIM or FOP herbicide that, at a given rate of application causes both at least 90% phytotoxicity in *Echinochloa crus-galli* and not more than 10% phytotoxicity in domestic rice (*Oryza sativa*).

As used herein, the terms "post-emergence" and "postemergent" refer to a time period encompassing the post-germination emergence of a seedling through the soil surface to the maturity of the plant.

As used herein in regard to mutant or mutagenized nucleic acids that encode herbicide-tolerant ACCase enzymes, the term "endogenous non-transfected" is defined to mean:

(1) that the nucleic acid is endogenous to the respective cell, seed, plant, or plant part and (2) that its nucleotide sequence is "non-transfected" in that (a) it contains herbicide-tolerance mutation(s) produced randomly by a technique involving no step of introducing exogenous nucleic acid(s) or nucleic acid analog(s), into a plant cell or into other plant material, and (b) it contains no mutation(s) produced by a technique involving a step of introducing exogenous nucleic acid(s) or nucleic acid analog(s), into a plant cell or into other plant material.

Thus, techniques useful to produce such "non-transfected" nucleic acid sequences, as defined herein, include, e.g., traditional chemical mutagenesis using a chemical (i.e. non-nucleic-acid- or -analog-containing) mutagen, tissue culture mutagenesis involving somaclonal variation, radiation exposure, and other techniques for inducing mutations in endogenous plant gene(s) in a random or non-directed manner.

Accordingly, as defined herein, "endogenous non-transfected" nucleic acids exclude both those mutant or mutagenized nucleic acids whose mutation-containing sequences have resulted without an applied technique and those that were produced by use of a technique involving introduction into a plant cell or into other plant material of an exogenous nucleic acid or nucleic acid analog, whether per se or as part of a heteromolecular construct or complex. Examples of techniques excluded under this definition include: genetic engineering, oligonucleotide-directed mutagenesis, DNA mismatch-repair oligonucleotide-based mutagenesis, and other mutation-producing processes in which exogenous nucleic acid (or nucleic acid analog) has been transiently or stably introduced into a plant cell or other plant material.

As used in this definition of "endogenous non-transfected," the term "non-transfected" is analogous to the term "non-infected" used to describe a physician's patient who, not having been infected with or exposed to a pathogen, is not a carrier of it. Thus, by analogy, a "non-transfected" nucleic acid is one that is not a carrier of any "transfection product," i.e. of any mutation caused by a technique involving transient or stable introduction of exogenous nucleic acid or its analog.

One aspect of the present disclosure relates to a method for treating rice. The method comprises the steps of: providing a domestic rice crop plant and at least one ACCase-inhibiting aryloxyphenoxypropanoate herbicide selected from the group consisting of quizalofop or an ester thereof, haloxyfop, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence; thereby creating a treated rice plant; and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

In still other embodiments, the aryloxyphenoxypropanoate herbicide is quizalofop or an ester thereof. The 1× application rate for quizalofop or an ester thereof is 28 g AI/ha. In some further embodiments, an effective amount of quizalofop or an ester thereof is at least 14 g AI/Ha.

In even other embodiments, the aryloxyphenoxypropanoate herbicide is fluazifop or an ester thereof. The 1× application rate for fluazifop or an ester thereof is 112 g AI/ha. In some further embodiments, an effective amount of fluazifop or an ester thereof is at least 56 g AI/Ha.

In some other embodiments, the aryloxyphenoxypropanoate herbicide is clodinafop or clodinafop-propargyl. The 1× application rate for clodinafop or clodinafop-propargyl is 22 g AI/ha. In some further embodiments, an effective amount of clodinafop or clodinafop-propargyl is at least 11 g AI/Ha.

In still other embodiments, the aryloxyphenoxypropanoate herbicide is diclofop or diclofop-methyl. The 1× application rate for diclofop or diclofop-methyl is 452 g AI/ha. In some further embodiments, an effective amount of diclofop or diclofop-methyl is at least 226 g AI/Ha.

In some embodiments, the effective amount is effective for killing a weed of the genus *Echinochloa*. In some further embodiments, the weed of the genus *Echinochloa* is selected from the group consisting of *Echinochloa colona, Echinochloa crus-galli, Echinochloa crus-pavonis, Echinochloa oryzicola*, and *Echinochloa oryzoides*.

In other embodiments, the effective amount is effective for killing a weed of the genus *Leptochloa*. In some further embodiments, the weed of the genus *Leptochloa* is selected from the group consisting of *Leptochloa chinensis, Leptochloa fascicularis, Leptochloa panacea*, and *Leptochloa panicoides*.

In some embodiments, the method further comprises providing at least one cyclohexanedione herbicide and applying an effective amount thereof to the domestic rice crop plant.

Another aspect of the present disclosure relates to a method for treating rice comprising providing a domestic rice crop plant and at least one ACCase-inhibiting aryloxyphenoxypropanoate herbicide selected from the group consisting of quizalofop or an ester thereof, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence, wherein said effective amount is 0.5× of an amount that causes both at least about 90% phytotoxicity in wild type *Echinochloa crus-galli* and more than 10% phytotoxicity in wild-type *Oryza sativa*; thereby creating a treated rice plant, and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

Yet another aspect of the present disclosure relates to a method for treating rice comprising providing a domestic rice crop plant and at least one rice-non-selective ACCase-inhibiting aryloxyphenoxypropanoate herbicide selected from the group consisting of quizalofop or an ester thereof, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence, wherein said effective amount is at least 0.5× of an amount that causes both at least about 90% phytotoxicity in wild type *Echinochloa crus-galli* and more than 10% phytotoxicity in wild-type *Oryza sativa*; thereby creating a treated rice plant, and growing the resulting treated rice plant.

In some embodiments, said effective amount is at least 0.5× and less than 1× of an amount that causes both at least about 90% phytotoxicity in wild type *Echinochloa crus-galli* and more than 10% phytotoxicity in wild-type *Oryza sativa*; thereby creating a treated rice plant.

In other embodiments, said effective amount is at least 0.5× and less than 0.95× of an amount that causes both at least about 90% phytotoxicity in wild type *Echinochloa crus-galli* and more than 10% phytotoxicity in wild-type *Oryza sativa*; thereby creating a treated rice plant.

In still other embodiments, said effective amount is at least 0.5× and less than 0.9× of an amount that causes both at least about 90% phytotoxicity in wild type *Echinochloa crus-galli* and more than 10% phytotoxicity in wild-type *Oryza sativa*; thereby creating a treated rice plant.

In yet other embodiments, said effective amount is at least 0.5× and less than 0.85× of an amount that causes both at least about 900% phytotoxicity in wild type *Echinochloa crus-galli* and more than 10% phytotoxicity in wild-type *Oryza sativa*; thereby creating a treated rice plant.

In even other embodiments, said effective amount is at least 0.5× and less than 0.8× of an amount that causes both at least about 90% phytotoxicity in wild type *Echinochloa crus-galli* and more than 10% phytotoxicity in wild-type *Oryza sativa*; thereby creating a treated rice plant.

In still even other embodiments, said effective amount is at least 0.5× and less than 0.75× of an amount that causes both at least about 90% phytotoxicity in wild type *Echinochloa crus-galli* and more than 10% phytotoxicity in wild-type *Oryza sativa*; thereby creating a treated rice plant.

In some embodiments, postemergent application of herbicides in the present methods can take place at the time of seedling emergence. In some embodiments, postemergent application of herbicides in the present methods can take place at the 2-, 3-, and/or 4-leaf stage. In some embodiments, postemergent application of herbicides in the present methods can take place at the 1st, 2nd, 3rd, and/or 4th tiller stage. In some embodiments, postemergent application of herbicides in the present methods can take place at the panicle initiation and/or panicle differentiation stage. In some embodiments, postemergent application of herbicides in the present methods can take place at the 2-, 3-, and/or 4-leaf stage. In some embodiments, postemergent application of herbicides in the present methods can take place at the heading, milk, or dough stages. In some embodiments, postemergent application of herbicides in the present methods can take place on mature plants.

Plants

The present disclosure provides herbicide-tolerant monocotyledonous plants of the grass family Poaceae. The family Poaceae may be divided into two major clades, the clade containing the subfamilies Bambusoideae, Ehrhartoideae, and Pooideae (the BEP clade) and the clade containing the subfamilies Panicoideae, Arundinoideae, Chloridoideae, Centothecoideae, Micrairoideae, Aristidoideae, and Danthonioideae (the PACCMAD clade). The subfamily Bambusoideae includes tribe Oryzeae. The present disclosure relates to plants of the BEP clade, in particular plants of the subfamilies Bambusoideae and Ehrhartoideae. Plants of the disclosure are typically tolerant to at least one herbicide that inhibits acetyl-Coenzyme A carboxylase activity as a result of expressing an acetyl-Coenzyme A carboxylase enzyme as described below. The BET clade includes subfamilies Bambusoideae. Ehrhartoideae, and group Triticodae and no other subfamily Pooideae groups. BET crop plants are plants grown for food or forage that are members of BET subclade, for example barley, corn, etc.

The present disclosure also provides commercially important herbicide-tolerant monocots, including Sugarcane (*Saccharum* spp.), as well as Turfgrasses, e.g., *Poa pratensis* (Bluegrass), *Agrostis* spp. (Bentgrass), *Lolium* spp. (Ryegrasses), *Festuca* spp. (Fescues), *Zoysia* spp. (*Zoysia* grass), *Cynodon* spp. (Bermudagrass), *Stenotaphrum secundatum* (St. Augustine grass), *Paspalum* spp. (Bahiagrass), *Eremochloa ophiuroides* (Centipedegrass), *Axonopus* spp. (Carpetgrass), *Bouteloua dactyloides* (Buffalograss), and *Bouteloua* var. spp. (Grama grass).

In one embodiment, the present disclosure provides herbicide-tolerant plants of the Bambusoideae subfamily. Such plants are typically tolerant to one or more herbicides that inhibit acetyl-Coenzyme A carboxylase activity. Examples of herbicide-tolerant plants of the subfamily Bambusoideae include, but are not limited to, those of the genera *Arundinaria, Bambusa, Chusquea, Guadua*, and *Shibataea.*

In one embodiment, the present disclosure provides herbicide-tolerant plants of the Ehrhartoideae subfamily. Such plants are typically tolerant to one or more herbicides that inhibit acetyl-Coenzyme A carboxylase activity. Examples of herbicide-tolerant plants of the subfamily Ehrhartoideae include, but are not limited to, those of the genera *Erharta, Leersia, Microlaena, Oryza*, and *Zizania.*

In one embodiment, the present disclosure provides herbicide-tolerant plants of the Pooideae subfamily. Such plants are typically tolerant to one or more herbicides that inhibit acetyl-Coenzyme A carboxylase activity. Examples of herbicide-tolerant plants of the subfamily Ehrhartoideae include, but are not limited to, those of the genera *Triticeae, Aveneae*, and *Poeae.*

In one embodiment, herbicide-tolerant plants of the disclosure are rice plants. Two species of rice are most frequently cultivated, *Oryza sativa* and *Oryza glaberrima.* Numerous subspecies of *Oryza sativa* are commercially important including *Oryza sativa* subsp. *indica, Oryza sativa* subsp. *japonica, Oryza sativa* subsp. *javanica, Oryza sativa* subsp. *glutinosa* (glutinous rice), *Oryza sativa Aromatica* group (e.g., basmati), and *Oryza sativa* (Floating rice group). The present disclosure encompasses herbicide-tolerant plants in all of the aforementioned species and subspecies.

In addition to being able to tolerate herbicides that inhibit acetyl-Coenzyme A carboxylase activity, plants of the disclosure may also be able to tolerate herbicides that work on other physiological processes. For example, plants of the disclosure may be tolerant to acetyl-Coenzyme A carboxylase inhibitors and also tolerant to other herbicides, for example, enzyme inhibitors. Examples of other enzyme inhibitors to which plants of the disclosure may be tolerant include, but are not limited to, inhibitors of 5-enolpyruvylshikimate-3-phosphate synthase (EPSPS) such as glyphosate, inhibitors of acetohydroxyacid synthase (AHAS) such as imidazolinones, sulfonylureas and sulfonamide herbicides, and inhibitors of glutamine synthase such as glufosinate. In addition to enzyme inhibitors, plants of the disclosure may also be tolerant of herbicides having other modes of action, for example, auxinic herbicides such as 2,4-D or dicamba, chlorophyll/carotenoid pigment inhibitors such as hydroxyphenylpyruvate dioxygenase (HPPD) inhibitors or phytoene desaturase (PDS) inhibitors, protoporphyrinogen-IX oxidase inhibitors, cell membrane destroyers, photosynthetic inhibitors such as bromoxynil or ioxynil, cell division inhibitors, root inhibitors, shoot inhibitors, and combinations thereof. Thus, plants of the disclosure tolerant to acetyl-Coenzyme A carboxylase inhibitors can be made resistant to multiple classes of herbicides.

For example, plants of the present disclosure are tolerant to acetyl-Coenzyme A carboxylase inhibitors, such as "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden), in some embodiments, may be auxinic-herbicide tolerant, tolerant to EPSPS inhibitors, such as glyphosate; to PPO inhibitors, such as pyrimidinedione, such as saflufenacil, triazolinone, such as sulfentrazone, carfentrazone, flumioxazin, diphenylethers, such as acifluorfen, fomesafen, lactofen, oxyfluorfen, N-phenylphthalamides, such as flumiclorac, CGA-248757, and/or to GS inhibitors, such as glufosinate. In addition to these classes of inhibitors, plants of the disclosure tolerant to acetyl-Coenzyme A carboxylase inhibitors may also be tolerant to herbicides having other modes of action, for example, chlorophyll/carotenoid pigment inhibitors, cell membrane disruptors, photosynthesis inhibitors, cell division inhibitors, root inhibitors, shoot inhibitors, and combinations thereof. Such tolerance traits may be expressed, e.g., as mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or cytochrome P450 (CYP450) proteins having an herbicide-degrading activity. Plants tolerant to acetyl-Coenzyme A carboxylase inhibitors hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, plants are also covered that, in addition to being able to tolerate herbicides that inhibit acetyl-Coenzyme A carboxylase activity, are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present disclosure these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (*Coeloptera*), two-winged insects (*Diptera*), and moths (*Lepidoptera*) and to nematodes (*Nematoda*).

Furthermore, in one embodiment, plants are also covered that are, e.g., by the use of recombinant DNA techniques and/or by breeding and/or otherwise selected for such traits, able to synthesize one or more proteins to increase the resistance or tolerance of those plants to bacterial, viral or fungal pathogens. The methods for producing such genetically modified plants are generally known to the person skilled in the art. The plants produced as described herein can also be stacked with other traits including, but not limited to, disease resistance, enhanced mineral profile, enhanced vitamin profile, enhanced oil profile (e.g., high oleic acid content), amino acid profile (e.g, high lysine corn), and other trait types known in the art.

Furthermore, in one embodiment, plants are also covered that are, e.g., by the use of recombinant DNA techniques and/or by breeding and/or by other means of selection, able to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, in one embodiment, plants are also covered that contain, e.g., by the use of recombinant DNA techniques and/or by breeding and/or by other means of selection, a modified amount of substances of content or new substances of content, specifically to improve human or animal nutrition. Furthermore, plants are also covered that contain by the use of recombinant DNA techniques a modified amount of substances of content or new substances of content, specifically to improve raw material production.

Furthermore, in some embodiments, plants of the disclosure are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, plants of the disclosure tolerant to acetyl-Coenzyme A carboxylase inhibitors, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), 1-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, 1,2'-disinapoyl-2-feruloylgentiobiose, 3-O-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, plants of the disclosure tolerant to acetyl-Coenzyme A carboxylase inhibitors, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g., genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla.

In other embodiments, plants of the disclosure tolerant to acetyl-Coenzyme A carboxylase inhibitors, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

The present disclosure also encompasses progeny of the plants of the disclosure as well as seeds derived from the herbicide-tolerant plants of the disclosure and cells derived from the herbicide-tolerant plants of the invention.

In various embodiments, plants hereof can be used to produce plant products. Thus, a method for preparing a descendant seed comprises planting a seed of a capable of producing a plant hereof, growing the resulting plant, and harvesting descendant seed thereof. In some embodiments, such a method can further comprise applying an ACCase-inhibiting herbicide composition to the resulting plant. Similarly, a method for producing a derived product from a plant hereof can comprise processing a plant part thereof to obtain a derived product. In some embodiments, such a method can be used to obtain a derived product that is any of, e.g., fodder, feed, seed meal, oil, or seed-treatment-coated seeds. Seeds, treated seeds, and other plant products obtained by such methods are useful products that can be commercialized.

In various embodiments, the present disclosure provides production of food products, consumer products, industrial products, and veterinary products from any of the plants described herein.

Acetyl-Coenzyme A Carboxylase Enzymes

The present disclosure provides plants expressing acetyl-Coenzyme A carboxylase enzymes with amino acid sequences that differ from the amino acid sequence of the acetyl-Coenzyme A carboxylase enzyme found in the corresponding wild-type plant. For ease of understanding, the amino acid numbering system used herein will be the numbering system used for the acetyl-Coenzyme A carboxylase from *Alopecurus myosuroides* [Huds.] (also referred to as black grass). The mRNA sequence encoding the *A. myosuroides* acetyl-Coenzyme A carboxylase is available at GenBank accession number AJ310767 and the protein sequence is available at GenBank accession no. CAC84161 both of which are specifically incorporated herein by reference. The number of the amino acid referred to will be followed with (Am) to indicate the amino acid in the *Alopecurus myosuroides* sequence to which the amino acid corresponds. FIG. 18 provides *Alopecurus myosuroides* acetyl-Coenzyme A carboxylase amino acid sequence (GenBank accession no. CAC84161). Amino acids that may be altered in the acetyl-Coenzyme A carboxylase enzymes of the disclosure are indicated in bold double underline, and FIG. 19 depicts the amino acid sequence of wild-type *Oryza sativa* acetyl-Coenzyme A carboxylases aligned with *Alopecurus myosuroides* acetyl-Coenzyme A carboxylase with some critical residues denoted.

In one embodiment, an acetyl-Coenzyme A carboxylase of the present disclosure differs from the corresponding wild-type acetyl-Coenzyme A carboxylase at amino acid position 1,781(Am). Wild-type *A. myosuroides* acetyl-Coenzyme A carboxylase has an isoleucine at position 1,781 (Am) (I1781). The 1,781(Am) ACCase mutants of the disclosure will have an amino acid other than isoleucine at this position. Suitable examples of amino acids that may be found at this position in the acetyl-Coenzyme A carboxylase enzymes of the disclosure include, but are not limited to, leucine (I1781L), valine (I1781V), threonine (I1781T) and alanine (I1781A). In one embodiment, an acetyl-Coenzyme A carboxylase enzyme of the disclosure will have a leucine at position 1,781(Am).

In one embodiment, an acetyl-Coenzyme A carboxylase of the present disclosure differs from the corresponding wild-type acetyl-Coenzyme A carboxylase at amino acid position 1,785(Am). Wild-type *A. myosuroides* acetyl-Coenzyme A carboxylase has an alanine at position 1,785(Am) (A1785). The 1,785(Am) ACCase mutants of the disclosure will have an amino acid other than alanine at this position. Suitable examples of amino acids that may be found at this position in the acetyl-Coenzyme A carboxylase enzymes of the disclosure include, but are not limited to, glycine (A1785G). In one embodiment, an acetyl-Coenzyme A carboxylase enzyme of the disclosure will have a glycine at position 1,785(Am).

In one embodiment, an acetyl-Coenzyme A carboxylase of the present disclosure differs from the corresponding wild-type acetyl-Coenzyme A carboxylase at amino acid position 1,786(Am). Wild-type *A. myosuroides* acetyl-Coenzyme A carboxylase has an alanine at position 1,786(Am) (A1786). The 1,786(Am) ACCase mutants of the disclosure will have an amino acid other than alanine at this position. Suitable examples of amino acids that may be found at this position in the acetyl-Coenzyme A carboxylase enzymes of the disclosure include, but are not limited to, proline (A1786P). In one embodiment, an acetyl-Coenzyme A carboxylase enzyme of the disclosure will have a proline at position 1,786(Am).

In one embodiment, an acetyl-Coenzyme A carboxylase of the present disclosure differs from the corresponding wild-type acetyl-Coenzyme A carboxylase at amino acid position 1,811(Am). Wild-type *A. myosuroides* acetyl-Coenzyme A carboxylase has an isoleucine at position 1,811 (Am) (I1811). The 1,811(Am) ACCase mutants of the disclosure will have an amino acid other than isoleucine at this position. Suitable examples of amino acids that may be found at this position in the acetyl-Coenzyme A carboxylase enzymes of the disclosure include, but are not limited to, asparagine (I1811N). In one embodiment, an acetyl-Coenzyme A carboxylase enzyme of the disclosure will have an asparagine at position 1,811(Am).

In one embodiment, an acetyl-Coenzyme A carboxylase of the present disclosure differs from the corresponding wild-type acetyl-Coenzyme A carboxylase at amino acid position 1,824(Am). Wild-type *A. myosuroides* acetyl-Coenzyme A carboxylase has a glutamine at position 1,824 (Am) (Q1824). The 1,824(Am) ACCase mutants of the disclosure will have an amino acid other than glutamine at this position. Suitable examples of amino acids that may be found at this position in the acetyl-Coenzyme A carboxylase enzymes of the disclosure include, but are not limited to, proline (Q1824P). In one embodiment, an acetyl-Coenzyme A carboxylase enzyme of the disclosure will have a proline at position 1,824(Am).

In one embodiment, an acetyl-Coenzyme A carboxylase of the present disclosure differs from the corresponding wild-type acetyl-Coenzyme A carboxylase at amino acid position 1,864(Am). Wild-type *A. myosuroides* acetyl-Coenzyme A carboxylase has a valine at position 1,864(Am) (V1864). The 1,864(Am) ACCase mutants of the disclosure will have an amino acid other than valine at this position. Suitable examples of amino acids that may be found at this position in the acetyl-Coenzyme A carboxylase enzymes of the disclosure include, but are not limited to, phenylalanine (V1864F). In one embodiment, an acetyl-Coenzyme A carboxylase enzyme of the disclosure will have a phenylalanine at position 1,864(Am).

In one embodiment, an acetyl-Coenzyme A carboxylase of the present disclosure differs from the corresponding wild-type acetyl-Coenzyme A carboxylase at amino acid position 1,999(Am). Wild-type *A. myosuroides* acetyl-Coenzyme A carboxylase has a tryptophan at position 1,999 (Am) (W1999). The 1,999(Am) ACCase mutants of the disclosure will have an amino acid other than tryptophan at this position. Suitable examples of amino acids that may be found at this position in the acetyl-Coenzyme A carboxylase enzymes of the disclosure include, but are not limited to, cysteine (W1999C) and glycine (W1999G). In one embodiment, an acetyl-Coenzyme A carboxylase enzyme of the disclosure will have a glycine at position 1,999(Am).

In one embodiment, an acetyl-Coenzyme A carboxylase of the present disclosure differs from the corresponding wild-type acetyl-Coenzyme A carboxylase at amino acid position 2,027(Am). Wild-type *A. myosuroides* acetyl-Coenzyme A carboxylase has a tryptophan at position 2,027 (Am)(W2027). The 2,027(Am) ACCase mutants of the disclosure will have an amino acid other than tryptophan at this position. Suitable examples of amino acids that may be found at this position in the acetyl-Coenzyme A carboxylase enzymes of the disclosure include, but are not limited to, cysteine (W2027C) and arginine (W2027R). In one embodiment, an acetyl-Coenzyme A carboxylase enzyme of the disclosure will have a cysteine at position 2,027(Am).

In one embodiment, an acetyl-Coenzyme A carboxylase of the present disclosure differs from the corresponding wild-type acetyl-Coenzyme A carboxylase at amino acid position 2,039(Am). Wild-type *A. myosuroides* acetyl-Coenzyme A carboxylase has a glutamic acid at position 2,039(Am) (E2039). The 2,039(Am) ACCase mutants of the disclosure will have an amino acid other than glutamic acid at this position. Suitable examples of amino acids that may be found at this position in the acetyl-Coenzyme A carboxylase enzymes of the disclosure include, but are not limited to, glycine (E2039G). In one embodiment, an acetyl-Coenzyme A carboxylase enzyme of the disclosure will have an glycine at position 2,039(Am).

In one embodiment, an acetyl-Coenzyme A carboxylase of the present disclosure differs from the corresponding wild-type acetyl-Coenzyme A carboxylase at amino acid position 2,041(Am). Wild-type *A. myosuroides* acetyl-Coenzyme A carboxylase has an isoleucine at position 2,041 (Am) (12041). The 2,041(Am) ACCase mutants of the disclosure will have an amino acid other than isoleucine at this position. Suitable examples of amino acids that may be found at this position in the acetyl-Coenzyme A carboxylase enzymes of the disclosure include, but are not limited to, asparagine (12041N), or valine (12041V). In one embodiment, an acetyl-Coenzyme A carboxylase enzyme of the disclosure will have an asparagine at position 2,041(Am).

In one embodiment, an acetyl-Coenzyme A carboxylase of the present disclosure differs from the corresponding wild-type acetyl-Coenzyme A carboxylase at amino acid position 2,049(Am). Wild-type *A. myosuroides* acetyl-Coenzyme A carboxylase has an valine at position 2,049(Am) (V2049). The 2,049(Am) ACCase mutants of the disclosure will have an amino acid other than valine at this position. Suitable examples of amino acids that may be found at this position in the acetyl-Coenzyme A carboxylase enzymes of the disclosure include, but are not limited to, phenylalanine (V2049F), isoleucine (V20491) and leucine (V2049L). In one embodiment, an acetyl-Coenzyme A carboxylase enzyme of the disclosure will have an phenylalanine at position 2,049(Am).

In one embodiment, an acetyl-Coenzyme A carboxylase of the present disclosure differs from the corresponding wild-type acetyl-Coenzyme A carboxylase at amino acid position 2,059(Am). Wild-type *A. myosuroides* acetyl-Coenzyme A carboxylase has an alanine at position 2,059(Am) (A2059). The 2,059(Am) ACCase mutants of the disclosure will have an amino acid other than an alanine at this position. Suitable examples of amino acids that may be found at this position in the acetyl-Coenzyme A carboxylase enzymes of the disclosure include, but are not limited to, valine (A2059V). In one embodiment, an acetyl-Coenzyme A carboxylase enzyme of the disclosure will have a valine at position 2,059(Am).

In one embodiment, an acetyl-Coenzyme A carboxylase of the present disclosure differs from the corresponding wild-type acetyl-Coenzyme A carboxylase at amino acid position 2074(Am). Wild-type *A. myosuroides* acetyl-Coenzyme A carboxylase has a tryptophan at position 2074(Am) (W2074). The 2,074(Am) ACCase mutants of the disclosure will have an amino acid other than tryptophan at this position. Suitable examples of amino acids that may be found at this position in the acetyl-Coenzyme A carboxylase enzymes of the disclosure include, but are not limited to, leucine (W2074L). In one embodiment, an acetyl-Coenzyme A carboxylase enzyme of the disclosure will have a leucine at 2074(Am).

In one embodiment, an acetyl-Coenzyme A carboxylase of the present disclosure differs from the corresponding wild-type acetyl-Coenzyme A carboxylase at amino acid position 2,075(Am). Wild-type *A. myosuroides* acetyl-Coenzyme A carboxylase has a valine at position 2,075(Am) (V2075). The 2,075(Am) ACCase mutants of the disclosure will have an amino acid other than valine at this position. Suitable examples of amino acids that may be found at this position in the acetyl-Coenzyme A carboxylase enzymes of the disclosure include, but are not limited to, methionine (V2075M), leucine (V2075L) and isoleucine (V2075I). In one embodiment, an acetyl-Coenzyme A carboxylase enzyme of the disclosure will have a leucine at position 2,075(Am). In some embodiments, an acetyl-Coenzyme A carboxylase enzyme of the disclosure will have a valine at position 2075(Am) and an additional valine immediately after position 2075(Am) and before the valine at position 2076(Am), i.e., may have three consecutive valines where the wild-type enzyme has two.

In one embodiment, an acetyl-Coenzyme A carboxylase of the present disclosure differs from the corresponding wild-type acetyl-Coenzyme A carboxylase at amino acid position 2,078(Am). Wild-type *A. myosuroides* acetyl-Coenzyme A carboxylase has an aspartate at position 2,078 (Am) (D2078). The 2,078(Am) ACCase mutants of the disclosure will have an amino acid other than aspartate at this position. Suitable examples of amino acids that may be found at this position in the acetyl-Coenzyme A carboxylase enzymes of the disclosure include, but are not limited to, lysine (D2,078K), glycine (D2078G), or threonine (D2078T). In one embodiment, an acetyl-Coenzyme A carboxylase enzyme of the disclosure will have a glycine at position 2,078(Am).

In one embodiment, an acetyl-Coenzyme A carboxylase of the present disclosure differs from the corresponding wild-type acetyl-Coenzyme A carboxylase at amino acid position 2,079(Am). Wild-type *A. myosuroides* acetyl-Coenzyme A carboxylase has a serine at position 2,079(Am) (S2079). The 2,079(Am) ACCase mutants of the disclosure will have an amino acid other than serine at this position. Suitable examples of amino acids that may be found at this position in the acetyl-Coenzyme A carboxylase enzymes of the disclosure include, but are not limited to, phenylalanine (S2079F). In one embodiment, an acetyl-Coenzyme A carboxylase enzyme of the disclosure will have a phenylalanine at position 2,079(Am).

In one embodiment, an acetyl-Coenzyme A carboxylase of the present disclosure differs from the corresponding wild-type acetyl-Coenzyme A carboxylase at amino acid position 2,080(Am). Wild-type *A. myosuroides* acetyl-Coenzyme A carboxylase has a lysine at position 2,080(Am) (K2080). The 2,080(Am) ACCase mutants of the disclosure will have an amino acid other than lysine at this position. Suitable examples of amino acids that may be found at this position in the acetyl-Coenzyme A carboxylase enzymes of the disclosure include, but are not limited to, glutamic acid (K2080E). In one embodiment, an acetyl-Coenzyme A carboxylase enzyme of the disclosure will have a glutamic acid at position 2,080(Am). In another embodiment, acetyl-Coenzyme A carboxylase enzymes of the disclosure will typically have a deletion of this position (A2080).

In one embodiment, an acetyl-Coenzyme A carboxylase of the present disclosure differs from the corresponding wild-type acetyl-Coenzyme A carboxylase at amino acid position 2,081(Am). Wild-type *A. myosuroides* acetyl-Coenzyme A carboxylase has a isoleucine at position 2,081 (Am) (I2081). The 2,081(Am) ACCase mutants of the disclosure will have an amino acid other than isoleucine at this position. In one embodiment, acetyl-Coenzyme A carboxylase enzymes of the disclosure will typically have a deletion of this position (Δ2081).

In one embodiment, an acetyl-Coenzyme A carboxylase of the present disclosure differs from the corresponding wild-type acetyl-Coenzyme A carboxylase at amino acid position 2,088(Am). Wild-type *A. myosuroides* acetyl-Coenzyme A carboxylase has a cysteine at position 2,088(Am) (C2088). The 2,088(Am) ACCase mutants of the disclosure will have an amino acid other than cysteine at this position. Suitable examples of amino acids that may be found at this position in the acetyl-Coenzyme A carboxylase enzymes of the disclosure include, but are not limited to, arginine (C2088R), tryptophan (C2088W), phenylalanine (C2088F), glycine (C2088G), histidine (C2088H), lysine (C2088K), serine (C2088S), threonine (C2088T), leucine (C2088L) or valine (C2088V). In one embodiment, an acetyl-Coenzyme A carboxylase enzyme of the disclosure will have an arginine at position 2,088(Am).

In one embodiment, an acetyl-Coenzyme A carboxylase of the present disclosure differs from the corresponding wild-type acetyl-Coenzyme A carboxylase at amino acid position 2,095(Am). Wild-type *A. myosuroides* acetyl-Coenzyme A carboxylase has a lysine at position 2,095(Am) (K2095). The 2,095(Am) ACCase mutants of the disclosure will have an amino acid other than lysine at this position. Suitable examples of amino acids that may be found at this position in the acetyl-Coenzyme A carboxylase enzymes of the disclosure include, but are not limited to, glutamic acid (K2095E). In one embodiment, an acetyl-Coenzyme A carboxylase enzyme of the disclosure will have a glutamic acid at position 2,095(Am).

In one embodiment, an acetyl-Coenzyme A carboxylase of the present disclosure differs from the corresponding wild-type acetyl-Coenzyme A carboxylase at amino acid position 2,096(Am). Wild-type *A. myosuroides* acetyl-Coenzyme A carboxylase has a glycine at position 2,096(Am) (G2096). The 2,096(Am) ACCase mutants of the disclosure will have an amino acid other than glycine at this position. Suitable examples of amino acids that may be found at this position in the acetyl-Coenzyme A carboxylase enzymes of the disclosure include, but are not limited to, alanine (G2096A), or serine (G2096S). In one embodiment, an acetyl-Coenzyme A carboxylase enzyme of the disclosure will have an alanine at position 2,096(Am).

In one embodiment, an acetyl-Coenzyme A carboxylase of the present disclosure differs from the corresponding wild-type acetyl-Coenzyme A carboxylase at amino acid position 2,098(Am). Wild-type *A. myosuroides* acetyl-Coenzyme A carboxylase has a valine at position 2,098(Am) (V2098). The 2,098(Am) ACCase mutants of the disclosure will have an amino acid other than valine at this position. Suitable examples of amino acids that may be found at this position in the acetyl-Coenzyme A carboxylase enzymes of the disclosure include, but are not limited to, alanine (V2098A), glycine (V2098G), proline (V2098P), histidine (V2098H), serine (V2098S) or cysteine (V2098C). In one embodiment, an acetyl-Coenzyme A carboxylase enzyme of the disclosure will have an alanine at position 2,098(Am).

In one embodiment, the present disclosure encompasses acetyl-Coenzyme A carboxylase of an herbicide-tolerant plant of the disclosure which differs from the acetyl-Coenzyme A carboxylase of the corresponding wild-type plant at only one of the following positions: 1,781(Am), 1,785(Am), 1,786(Am), 1,811(Am), 1,824(Am), 1,864(Am), 1,999 (Am), 2,027(Am), 2,039(Am), 2,041(Am), 2,049(Am), 2,059(Am), 2,074(Am), 2,075(Am), 2,078(Am), 2,079 (Am), 2,080(Am), 2,081(Am), 2,088(Am), 2,095(Am), 2,096(Am), or 2,098(Am). In one embodiment the acetyl-Coenzyme A carboxylase of an herbicide-tolerant plant of the disclosure will differ at only one of the following positions: 2,078(Am), 2,088(Am), or 2,075(Am). In a preferred embodiment the acetyl-Coenzyme A carboxylase of an herbicide-tolerant plant of the disclosure will differ at only one of the following positions: 2,039(Am), 2,059(Am), 2,080(Am), or 2,095(Am). In a more preferred embodiment the acetyl-Coenzyme A carboxylase of a herbicide-tolerant plant of the disclosure will differ at only one of the following positions: 1,785(Am), 1,786(Am), 1,811(Am), 1,824(Am), 1,864(Am), 2,041(Am), 2,049(Am), 2,074(Am), 2,079 (Am), 2,081(Am), 2,096(Am), or 2,098(Am). In a most preferred embodiment the acetyl-Coenzyme A carboxylase of an herbicide-tolerant plant of the disclosure will differ at only one of the following positions: 1,781(Am), 1,999(Am), 2,027(Am), 2,041(Am), or 2,096(Am).

In one embodiment, Acetyl-Coenzyme A carboxylase enzymes of the disclosure will have only one of the following substitutions: an isoleucine at position 2,075(Am), glycine at position 2,078(Am), or arginine at position 2,088 (Am). In a preferred embodiment. Acetyl-Coenzyme A carboxylase enzymes of the disclosure will have only one of the following substitutions: a glycine at position 2,039(Am), valine at position 2,059(Am), methionine at position 2,075 (Am), duplication of position 2,075(Am) (i.e., an insertion of valine between 2,074(Am) and 2,075(Am), or an insertion of valine between position 2,075(Am) and 2,076(Am)), deletion of amino acid position 2,080(Am), glutamic acid at position 2,080(Am), deletion of position 2,081(Am), or glutamic acid at position 2,095(Am). In a more preferred embodiment, Acetyl-Coenzyme A carboxylase enzymes of the disclosure will have only one of the following substitutions: a glycine at position 1,785(Am), a proline at position 1,786(Am), an asparagine at position 1,811(Am), a leucine at position 2,075(Am), a methionine at position 2,075(Am), a threnonine at position 2,078(Am), a deletion at position 2,080(Am), a deletion at position 2,081(Am), a tryptophan, phenylalanine, glycine, histidine, lysine, leucine, serine, threonine, or valine at position 2,088(Am), a serine at position 2,096(Am), an alanine at position 2,096(Am), an alanine at position 2,098(Am), a glycine at position 2,098 (Am), an histidine at position 2,098(Am), a proline at position 2,098(Am), or a serine at position 2,098(Am). In a most preferred embodiment, Acetyl-Coenzyme A carboxylase enzymes of the disclosure will have only one of the following substitutions: a leucine at position 1,781(Am), a threonine at position 1,781(Am), a valine at position 1,781 (Am), an alanine at position 1,781(Am), a glycine at position 1,999(Am), a cysteine or arginine at position 2,027(Am), an arginine at position 2,027(Am), an asparagine at position 2,041(Am), a valine at position 2,041(Am), an alanine at position 2,096(Am), and a serine at position 2,096(Am).

In one embodiment, nucleic acids encoding Acetyl-Coenzyme A carboxylase polypeptide having only one of the following substitutions: isoleucine at position 2,075(Am), glycine at position 2,078(Am), or arginine at position 2,088 (Am) are used transgenically. In another embodiment, a monocot plant cell is transformed with an expression vector construct comprising the nucleic acid encoding Acetyl-Coenzyme A carboxylase polypeptide having only one of the following substitutions: isoleucine at position 2,075(Am), glycine at position 2,078(Am), or arginine at position 2,088 (Am).

In one embodiment, the present disclosure provides rice plants comprising nucleic acids encoding Acetyl-Coenzyme A carboxylase polypeptides having a substitution at only one amino acid position as described above.

In one embodiment, the present disclosure provides BEP clade plants comprising nucleic acids encoding Acetyl-Coenzyme A carboxylase polypeptides having a substitution at only one amino acid position as described above.

In one embodiment, the present disclosure provides BET subclade plants comprising nucleic acids encoding Acetyl-Coenzyme A carboxylase polypeptides having a substitution at only one amino acid position as described above.

In one embodiment, the present disclosure provides BET crop plants comprising nucleic acids encoding Acetyl-Coenzyme A carboxylase polypeptides having a substitution at only one amino acid position as described above.

In one embodiment, the present disclosure provides monocot plants comprising nucleic acids encoding Acetyl-Coenzyme A carboxylase polypeptides having a substitution at only one amino acid position as described above.

In one embodiment, the present disclosure provides monocot plants comprising nucleic acids encoding Acetyl-Coenzyme A carboxylase polypeptides having a substitution at amino acid position 1,781(Am), wherein the amino acid at position 1,781(Am) differs from that of wild type and is not leucine.

In one embodiment, the present disclosure provides monocot plants comprising nucleic acids encoding Acetyl-Coenzyme A carboxylase polypeptides having a substitution at amino acid position 1,999(Am), wherein the amino acid at position 1,999(Am) differs from that of wild type and is not cysteine.

In one embodiment, the present disclosure provides monocot plants comprising nucleic acids encoding Acetyl-Coenzyme A carboxylase polypeptides having a substitution at amino acid position 2,027 (Am), wherein the amino acid at position 2,027(Am) differs from that of wild type and is not cysteine.

In one embodiment, the present disclosure provides monocot plants comprising nucleic acids encoding Acetyl-Coenzyme A carboxylase polypeptides having a substitution at amino acid position 2,041(Am), wherein the amino acid at position 2,041(Am) differs from that of wild type and is not valine or asparagine.

In one embodiment, the present disclosure provides monocot plants comprising nucleic acids encoding Acetyl-Coenzyme A carboxylase polypeptides having a substitution at amino acid position 2,096(Am), wherein the amino acid at position 2,096(Am) differs from that of wild type and is not alanine.

The present disclosure also provides acetyl-Coenzyme A carboxylase enzymes with an amino acid sequence that differs in more than one amino acid position from that of the acetyl-Coenzyme A carboxylase enzyme found in the corresponding wild-type plant. For example, an acetyl-Coenzyme A carboxylase of the present disclosure may differ in 2, 3, 4, 5, 6, or 7 positions from that of the acetyl-Coenzyme A carboxylase enzyme found in the corresponding wild-type plant.

In one embodiment, an acetyl-Coenzyme A carboxylase of the present disclosure differs from the corresponding wild-type acetyl-Coenzyme A carboxylase at amino acid position 1,781(Am) and at one or more additional amino acid positions. Acetyl-Coenzyme A carboxylase enzymes of the present disclosure will typically have a leucine, a threonine, a valine, or an alanine at position 1,781(Am). In addition, enzymes of this embodiment will also comprise one or more of a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine, or an additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine tryptophan, phenylalanine, glycine, histidine, lysine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a leucine, a threonine, a valine, or an alanine at position 1,781(Am) and a glycine at position 1,785(Am). In one embodiment, an acetyl-Coenzyme A carboxylase of the present disclosure will have a leucine, a threonine, a valine, or an alanine at position 1,781(Am) and a proline at position 1,786(Am). In one embodiment, an acetyl-Coenzyme A carboxylase of the present disclosure will have a leucine, a threonine, a valine, or an alanine at position 1,781(Am) and an asparagine at position 1,811(Am). In one embodiment, an acetyl-Coenzyme A carboxylase of the present disclosure will have a leucine, a threonine, a valine, or an alanine at position 1,781(Am) and a proline at position 1824(Am) In one embodiment, an acetyl-Coenzyme A carboxylase of the present disclosure will have a leucine, a threonine, a valine, or an alanine at position 1,781(Am) and a phenylalanine at position 1864(Am). In one embodiment, an acetyl-Coenzyme A carboxylase of the present disclosure will have a leucine, a threonine, a valine, or an alanine at position 1,781(Am) and a cysteine or glycine at position 1,999(Am). In one embodiment, an acetyl-Coenzyme A carboxylase of the present disclosure will have a leucine, a threonine, a valine, or an alanine at position 1,781(Am) and a cysteine or an arginine at position 2,027(Am). In one embodiment, an acetyl-Coenzyme A carboxylase of the present disclosure will have a leucine, a threonine, a valine, or an alanine at position 1,781(Am) and a glycine at position 2039(Am). In one embodiment, an acetyl-Coenzyme A carboxylase of the present disclosure will have a leucine, a threonine, a valine, or an alanine at position 1,781(Am) and an asparagine at position 2,041(Am). In one embodiment, an acetyl-Coenzyme A carboxylase of the present disclosure will have a leucine, a threonine, a valine, or an alanine at position 1,781(Am) and a phenylalanine, leucine or isoleucine at position 2,049(Am). In one embodiment, an acetyl-Coenzyme A carboxylase of the present disclosure will have a leucine, a threonine, a valine, or an alanine at position 1,781(Am) and a valine at position 2059(Am). In one embodiment, an acetyl-Coenzyme A carboxylase of the present disclosure will have a leucine, a threonine, a valine, or an alanine at position 1,781(Am) and a leucine at position 2,074(Am). In one embodiment, an acetyl-Coenzyme A carboxylase of the present disclosure will have a leucine, a threonine, a valine, or an alanine at position 1,781(Am) and a leucine, isoleucine methionine, or additional valine at position 2,075(Am). In one embodiment, an acetyl-Coenzyme A carboxylase of the present disclosure will have a leucine, a threonine, a valine, or an alanine at position 1,781(Am) and a glycine or threonine at position 2,078 (Am). In one embodiment, an acetyl-Coenzyme A carboxylase of the present disclosure will have a leucine, a threonine, a valine, or an alanine at position 1,781(Am) and a phenylalanine at position 2079(Am). In one embodiment, an acetyl-Coenzyme A carboxylase of the present disclosure will have a leucine, a threonine, a valine, or an alanine at position 1,781(Am) and a glutamic acid or a deletion at position 2080(Am). In one embodiment, an acetyl-Coenzyme A carboxylase of the present disclosure will have a leucine, a threonine, a valine, or an alanine at position 1,781(Am) and a deletion at position 2081(Am). In one embodiment, an acetyl-Coenzyme A carboxylase of the present disclosure will have a leucine, a threonine, a valine, or an alanine at position 1,781(Am) and an arginine, tryptophan, phenylalanine, glycine, histidine, lysine, serine, threonine, or valine at position 2,088(Am). In one embodiment, an acetyl-Coenzyme A carboxylase of the present disclosure will have a leucine, a threonine, a valine, or an alanine at position 1,781(Am) and a glutamic acid at position 2,095(Am). In one embodiment, an acetyl-Coenzyme A carboxylase of the present disclosure will have a leucine, a threonine, a valine, or an alanine at position 1,781(Am) and an alanine or serine at position 2,096(Am). In one embodiment, an acetyl-Coenzyme A carboxylase of the present disclosure will have a leucine, a threonine, a valine, or an alanine at position 1,781(Am) and an alanine, glycine, proline, histidine, cysteine, or serine at position 2,098(Am). In one embodiment, an acetyl-Coenzyme A carboxylase of the present disclosure will have a leucine, a threonine, a valine, or an alanine at position 1,781(Am), a cysteine or arginine at position 2,027(Am), and an asparagine at position 2,041(Am). In one embodiment, an acetyl-Coenzyme A carboxylase of the present disclosure will have a leucine, a threonine, a valine, or an alanine at position 1,781(Am), a cysteine or arginine at position 2,027(Am), an asparagine at position 2,041(Am), and an alanine at position 2,096(Am).

In one embodiment, an acetyl-Coenzyme A carboxylase of the present disclosure differs from the corresponding wild-type acetyl-Coenzyme A carboxylase at amino acid position 1,785(Am) and at one or more additional amino acid positions. Acetyl-Coenzyme A carboxylase enzymes of the disclosure will typically have a glycine at position 1,785(Am). In addition, enzymes of this embodiment will also comprise one or more of a leucine, threonine, a valine, or alanine at position 1,781(Am), a proline at position 1,786(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a glycine at position 1,785(4n) and a leucine, a threonine, a valine, or an alanine at position 1,781(Am). In one embodiment, an acetyl-Coenzyme A carboxylase of the present disclosure will have a glycine at position 1,785(Am) and a proline at position 1,786(Am). In one embodiment, an acetyl-Coenzyme A carboxylase of the present disclosure will have a glycine at position 1,785(Am) and an asparagine at position 1,811(Am). In one embodiment, an acetyl-Coenzyme A carboxylase of the present disclosure will have a glycine at position 1,785(Am) and a proline at position 1,824(Am). In one embodiment, an acetyl-Coenzyme A carboxylase of the present disclosure will have a glycine at position 1,785(Am) and a phenylalanine at position 1,864(Am). In one embodiment, an acetyl-Coenzyme A carboxylase of the present disclosure will have a glycine at position 1,785(Am) and a cysteine or glycine at position 1,999(Am). In one embodiment, an acetyl-Coenzyme A carboxylase of the present disclosure will have a glycine at position 1,785(Am) and a cysteine or an arginine at position 2,027(Am). In one embodiment, an acetyl-Coenzyme A carboxylase of the present disclosure will have a glycine at position 1,785(Am) and a glycine at position 2,039(Am). In one embodiment, an acetyl-Coenzyme A carboxylase of the present disclosure will have a glycine at position 1,785(Am) and an asparagine at position 2,041 (Am). In one embodiment, an acetyl-Coenzyme A carboxylase of the present disclosure will have a glycine at position 1,785(Am) and a phenylalanine, isoleucine or leucine at position 2,049(Am). In one embodiment, an acetyl-Coenzyme A carboxylase of the present disclosure will have a glycine at position 1,785(Am) and a valine at position 2,059(Am). In one embodiment, an acetyl-Coenzyme A carboxylase of the present disclosure will have a glycine at position 1,785(Am) and a leucine at position 2,074(Am). In one embodiment, an acetyl-Coenzyme A carboxylase of the present disclosure will have a glycine at position 1,785(Am) and a leucine, isoleucine, methionine or additional valine at position 2,075(Am). In one embodiment, an acetyl-Coenzyme A carboxylase of the present disclosure will have a glycine at position 1,785(Am) and a glycine or threonine at position 2,078(Am). In one embodiment, an acetyl-Coenzyme A carboxylase of the present disclosure will have a glycine at position 1,785(Am) and a phenylalanine at position 2,079(Am). In one embodiment, an acetyl-Coenzyme A carboxylase of the present disclosure will have a glycine at position 1,785(Am) and a glutamic acid or deletion at position 2,080(Am). In one embodiment, an acetyl-Coenzyme A carboxylase of the present disclosure will have a glycine at position 1,785(Am) and a deletion at position 2,081(Am). In one embodiment, an acetyl-Coenzyme A carboxylase of the present disclosure will have a glycine at position 1,785(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a glycine at position 1,785(Am) and a glutamic acid at position 2,095(Am). In one embodiment, an acetyl-Coenzyme A carboxylase of the present disclosure will have a glycine at position 1,785(Am) and an alanine or serine at position 2,096(Am). In one embodiment, an acetyl-Coenzyme A carboxylase of the present disclosure will have a glycine at position 1,785(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,786(Am) and at one or more additional amino acid positions. Acetyl-Coenzyme A carboxylase enzymes of the disclosure will typically have a proline at position 1,786(Am). In addition, enzymes of this embodiment will also comprise one or more of a leucine, threonine, a valine, or alanine at position 1,781(Am), a glycine at position 1,785(Am), an asparagine at position 1,811 (Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid or deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095 (Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a proline at position 1,786(Am) and a leucine, a threonine, a valine, or an alanine at position 1,781(Am). In one embodiment, an acetyl-Coenzyme A carboxylase of the present disclosure will have a proline at position 1,786(Am) and a glycine at position 1,785(Am). In one embodiment, an acetyl-Coenzyme A carboxylase of the present disclosure will have a proline at position 1,786(Am) and an asparagine at position 1,811(Am). In one embodiment, an acetyl-Coenzyme A carboxylase of the present disclosure will have a proline at position 1,786(Am) and a proline at position 1,824(Am). In one embodiment, an acetyl-Coenzyme A carboxylase of the present disclosure will have a proline at position 1,786(Am) and phenylalanine at position 1,864 (Am). In one embodiment, an acetyl-Coenzyme A carboxylase of the present disclosure will have a proline at position 1,786(Am) and a cysteine or glycine at position 1,999(Am). In one embodiment, an acetyl-Coenzyme A carboxylase of the present disclosure will have a proline at position 1,786 (Am) and a cysteine or an arginine at position 2,027(Am). In one embodiment, an acetyl-Coenzyme A carboxylase of the present disclosure will have a proline at position 1,786(Am) and a glycine at position 2,039(Am). In one embodiment, an acetyl-Coenzyme A carboxylase of the present disclosure will have a proline at position 1,786(Am) and an asparagine at position 2,041(Am). In one embodiment, an acetyl-Coenzyme A carboxylase of the present disclosure will have a proline at position 1,786(Am) and phenylalanine, isoleucine or leucine at position 2,049(Am) In one embodiment, an acetyl-Coenzyme A carboxylase of the present disclosure will have a proline at position 1,786(Am) and a valine at position 2,059(Am). In one embodiment, an acetyl-Coenzyme A carboxylase of the present disclosure will have a proline at position 1,786(Am) and a leucine at position 2,074(Am). In one embodiment, an acetyl-Coenzyme A carboxylase of the present disclosure will have a proline at position 1,786(Am) and a leucine, isoleucine, methionine or additional valine at position 2,075(Am). In one embodiment, an acetyl-Coenzyme A carboxylase of the present disclosure will have a proline at position 1,786(Am) and a glycine or threonine at position 2,078(Am). In one embodiment, an acetyl-Coenzyme A carboxylase of the present disclosure will have a proline at position 1,786(Am) and a phenylalanine at position 2,079(Am). In one embodiment, an acetyl-Coenzyme A carboxylase of the present disclosure will have a proline at position 1,786(Am) and a glutamic acid or deletion at position 2,080(Am). In one embodiment, an acetyl-Coenzyme A carboxylase of the present disclosure will have a proline at position 1,786(Am) and a deletion at position 2,081(Am). In one embodiment, an acetyl-Coenzyme A carboxylase of the present disclosure will have a proline at position 1,786(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a proline at position 1,786(Am) and a glutamic acid at position 2,095(Am). In one embodiment, an acetyl-Coenzyme A carboxylase of the present disclosure will have a proline at position 1,786(Am) and an alanine or serine at position 2,096(Am). In one embodiment, an acetyl-Coenzyme A carboxylase of the present disclosure will have a proline at position 1,786(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,811(Am) and at one or more additional amino acid positions. Acetyl-Coenzyme A carboxylase enzymes of the disclosure will typically have an asparagine at position 1,811(Am). In addition, enzymes of this embodiment will also comprise one or more of a leucine, threonine, a valine, or alanine at position 1,781(Am), a glycine at position 1,785(Am), a proline at position 1,786(Am), a proline at position 1,824(Am), a phenylalanine at position 1,864(Am), a cysteine or glycine at position 1,999(Am), a cysteine or arginine at position 2,027(Am), a glycine at position 2,039 (Am), an asparagine at position 2,041(Am), a a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078 (Am), a phenylalanine at position 2,079(Am), a glutamic acid at position 2,080(Am), a deletion at position 2,080 (Am), a deletion at position 2,081(4n), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have an asparagine at position 1,811(Am) and a leucine, a threonine, a valine, or an alanine at position 1,781(Am). In one embodiment, an acetyl-Coenzyme A carboxylase of the present disclosure will have an asparagine at position 1,811 (Am) and a glycine at position 1,785(Am). In one embodiment, an acetyl-Coenzyme A carboxylase of the present disclosure will have an asparagine at position 1,811(Am) and a proline at position 1,786(Am). In one embodiment, an acetyl-Coenzyme A carboxylase of the present disclosure will have an asparagine at position 1,811(Am) and a proline at position 1,824(Am) In one embodiment, an acetyl-Coenzyme A carboxylase of the present disclosure will have an asparagine at position 1,811(Am) and phenylalanine at position 1,864(Am). In one embodiment, an acetyl-Coenzyme A carboxylase of the present disclosure will have an asparagine at position 1,811(Am) and a cysteine or glycine at position 1,999(Am). In one embodiment, an acetyl-Coenzyme A carboxylase of the present disclosure will have an asparagine at position 1,811(Am) and a cysteine or an arginine at position 2,027(Am). In one embodiment, an acetyl-Coenzyme A carboxylase of the present disclosure will have an asparagine at position 1,811(Am) and a glycine at position 2,039(Am). In one embodiment, an acetyl-Coenzyme A carboxylase of the present disclosure will have an asparagine at position 1,811(Am) and an asparagine at position 2,041(Am). In one embodiment, an acetyl-Coenzyme A carboxylase of the present disclosure will have an asparagine at position 1,811(Am) and phenylalanine, isoleucine or leucine at position 2,049(Am). In one embodiment, an acetyl-Coenzyme A carboxylase of the present disclosure will have an asparagine at position 1,811(Am) and a valine at position 2,059(Am). In one embodiment, an acetyl-Coenzyme A carboxylase of the present disclosure will have an asparagine at position 1,811(Am) and a leucine at position 2,074(Am). In one embodiment, an acetyl-Coenzyme A carboxylase of the present disclosure will have an asparagine at position 1,811(Am) and a leucine, isoleucine, methionine or additional valine at position 2,075(Am). In one embodiment, an acetyl-Coenzyme A carboxylase of the present disclosure will have an asparagine at position 1,811 (Am) and a glycine or threonine at position 2,078(Am). In one embodiment, an acetyl-Coenzyme A carboxylase of the present disclosure will have an asparagine at position 1,811 (Am) and a phenylalanine at position 2,079(Am). In one embodiment, an acetyl-Coenzyme A carboxylase of the present disclosure will have an asparagine at position 1,811 (Am) and a glutamic acid or deletion at position 2,080(Am). In one embodiment, an acetyl-Coenzyme A carboxylase of the present disclosure will have an asparagine at position 1,811(Am) and a deletion at position 2,081(Am). In one embodiment, an acetyl-Coenzyme A carboxylase of the present disclosure will have an asparagine at position 1,811 (Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have an asparagine at position 1,811(Am) and a glutamic acid at position 2,095(Am). In one embodiment, an acetyl-Coenzyme A carboxylase of the present disclosure will have an asparagine at position 1,811(Am) and an alanine or serine at position 2,096(Am). In one embodiment, an acetyl-Coenzyme A carboxylase of the present disclosure will have an asparagine at position 1,811(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,824(Am) and at one or more additional amino acid positions. Acetyl-Coenzyme A carboxylase enzymes of the disclosure will typically have a proline at position 1,824(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,864(Am) and at one or more additional amino acid positions. Acetyl-Coenzyme A carboxylase enzymes of the disclosure will typically have a phenylalanine at position 1,864(Am). In addition, enzymes of this embodiment will also comprise one or more of a leucine, threonine, a valine, or alanine at position 1,781(Am), a glycine at position 1,785(Am), a proline at position 1,786(4n), an asparagine at position 1,811(Am), a proline at position 1,824(Am), a cysteine or glycine at position 1,999(Am), a cysteine or arginine at position 2,027(Am), a glycine at position 2,039 (Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,999(Am) and at one or more additional amino acid positions. Acetyl-Coenzyme A carboxylase enzymes of the disclosure will typically have a cysteine or glycine at position 1,999(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075 (Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a cysteine or glycine at position 1,999(Am) and a leucine, a threonine, a valine, or an alanine at position 1,781(Am). In one embodiment, an acetyl-Coenzyme A carboxylase of the present disclosure will have a cysteine or glycine at position 1,999(Am) and a glycine at position 1,785(Am). In one embodiment, an acetyl-Coenzyme A carboxylase of the present disclosure will have a cysteine or glycine at position 1,999(Am) and a proline at position 1,786(Am). In one embodiment, an acetyl-Coenzyme A carboxylase of the present disclosure will have a cysteine or glycine at position 1,999(Am) and have an asparagine at position 1,811(Am). In one embodiment, an acetyl-Coenzyme A carboxylase of the present disclosure will have a cysteine or glycine at position 1,999(Am) and a proline at position 1,824(Am). In one embodiment, an acetyl-Coenzyme A carboxylase of the present disclosure will have a cysteine or glycine at position 1,999(Am) and phenylalanine at position 1,864(Am). In one embodiment, an acetyl-Coenzyme A carboxylase of the present disclosure will have a cysteine or glycine at position 1,999(Am) and a cysteine or an arginine at position 2,027(Am). In one embodiment, an acetyl-Coenzyme A carboxylase of the present disclosure will have a cysteine or glycine at position 1,999(Am) and a glycine at position 2,039(Am). In one embodiment, an acetyl-Coenzyme A carboxylase of the present disclosure will have a cysteine or glycine at position 1,999(Am) and an asparagine at position 2,041(Am). In one embodiment, an acetyl-Coenzyme A carboxylase of the present disclosure will have a cysteine or glycine at position 1,999(Am) and a phenylalanine, isoleucine or leucine at position 2,049(Am). In one embodiment, an acetyl-Coenzyme A carboxylase of the present disclosure will have a cysteine or glycine at position 1,999(Am) and a cysteine or a valine at position 2,059(Am). In one embodiment, an acetyl-Coenzyme A carboxylase of the present disclosure will have a cysteine or glycine at position 1,999(Am) and a leucine at position 2,074(Am). In one embodiment, an acetyl-Coenzyme A carboxylase of the present disclosure will have a cysteine or glycine at position 1,999(Am) and a leucine, isoleucine, methionine or additional valine at position 2,075(Am). In one embodiment, an acetyl-Coenzyme A carboxylase of the present disclosure will have a cysteine or glycine at position 1,999(Am) and a glycine or threonine at position 2,078 (Am). In one embodiment, an acetyl-Coenzyme A carboxylase of the present disclosure will have a cysteine or glycine at position 1,999(Am) and a phenylalanine at position 2,079 (Am). In one embodiment, an acetyl-Coenzyme A carboxylase of the present disclosure will have a cysteine or glycine at position 1,999(Am) and a glutamic acid or deletion at position 2,080(Am). In one embodiment, an acetyl-Coenzyme A carboxylase of the present disclosure will have a cysteine or glycine at position 1,999(Am) and a deletion at position 2,081(Am). In one embodiment, an acetyl-Coenzyme A carboxylase of the present disclosure will have a cysteine or glycine at position 1,999(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a cysteine or glycine at position 1,999(Am) and a glutamic acid at position 2,095(Am). In one embodiment, an acetyl-Coenzyme A carboxylase of the present disclosure will have a cysteine or glycine at position 1,999(Am) and an alanine or serine at position 2,096(Am). In one embodiment, an acetyl-Coenzyme A carboxylase of the present disclosure will have a cysteine or glycine at position 1,999(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,027(Am) and at one or more additional amino acid positions. Acetyl-Coenzyme A carboxylase enzymes of the disclosure will typically have a cysteine or arginine at position 2,027(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a cysteine or arginine at position 2,027(Am) and a leucine, a threonine, a valine, or an alanine at position 1,781(Am). In one embodiment, an acetyl-Coenzyme A carboxylase of the present disclosure will have a cysteine or arginine at position 2,027(Am) and a glycine at position 1,785(Am). In one embodiment, an acetyl-Coenzyme A carboxylase of the present disclosure will have a cysteine or arginine at position 2,027(Am) and a proline at position 1,786(Am). In one embodiment, an acetyl-Coenzyme A carboxylase of the present disclosure will have a cysteine or arginine at position 2,027(Am) and have an asparagine at position 1,811(Am). In one embodiment, an acetyl-Coenzyme A carboxylase of the present disclosure will have a cysteine or arginine at position 2,027(Am) and have a proline at position 1,824(Am). In one embodiment, an acetyl-Coenzyme A carboxylase of the present disclosure will have a cysteine or arginine at position 2,027(Am) and have a phenylalanine at position 1,864(Am) In one embodiment, an acetyl-Coenzyme A carboxylase of the present disclosure will have a cysteine or arginine at position 2,027(Am) and a cysteine or glycine at position 1,999(Am). In one embodiment, an acetyl-Coenzyme A carboxylase of the present disclosure will have a cysteine or arginine at position 2,027(Am) and have a glycine at position 2,039 (Am). In one embodiment, an acetyl-Coenzyme A carboxylase of the present disclosure will have a cysteine or arginine at position 2,027(Am) and an asparagine at position 2,041 (Am). In one embodiment, an acetyl-Coenzyme A carboxylase of the present disclosure will have a cysteine or arginine at position 2,027(Am) and a phenylalanine, isoleucine or leucine at position 2,049(Am). In one embodiment, an acetyl-Coenzyme A carboxylase of the present disclosure will have a cysteine or arginine at position 2,027(Am) and have a valine at position 2,059(Am). In one embodiment, an acetyl-Coenzyme A carboxylase of the present disclosure will have a cysteine or arginine at position 2,027(Am) and a leucine at position 2,074(Am). In one embodiment, an acetyl-Coenzyme A carboxylase of the present disclosure will have a cysteine or arginine at position 2,027(Am) and a leucine, isoleucine, methionine or additional valine at position 2,075(Am). In one embodiment, an acetyl-Coenzyme A carboxylase of the present disclosure will have a cysteine or arginine at position 2,027(Am) and a glycine or threonine at position 2,078(Am). In one embodiment, an acetyl-Coenzyme A carboxylase of the present disclosure will have a cysteine or arginine at position 2,027(Am) and a phenylalanine at position 2,079(Am). In one embodiment, an acetyl-Coenzyme A carboxylase of the present disclosure will have a cysteine or arginine at position 2,027(Am) and a glutamic acid or deletion at position 2,080(Am). In one embodiment, an acetyl-Coenzyme A carboxylase of the present disclosure will have a cysteine or arginine at position 2,027(Am) and a deletion at position 2,081(Am). In one embodiment, an acetyl-Coenzyme A carboxylase of the present disclosure will have a cysteine or arginine at position 2,027(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a cysteine or arginine at position 2,027(Am) and a glutamic acid at position 2,095(Am). In one embodiment, an acetyl-Coenzyme A carboxylase of the present disclosure will have a cysteine or arginine at position 2,027(Am) and an alanine or serine at position 2,096(Am). In one embodiment, an acetyl-Coenzyme A carboxylase of the present disclosure will have a cysteine or arginine at position 2,027(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,039(Am) and at one or more additional amino acid positions. Acetyl-Coenzyme A carboxylase enzymes of the disclosure will typically have a glycine at position 2,039(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,041(Am) and at one or more additional amino acid positions. Acetyl-Coenzyme A carboxylase enzymes of the disclosure will typically have an asparagine at position 2,041(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811 (Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081 (Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine or serine at position 2,098(Am). In one embodiment, an acetyl-Coenzyme A carboxylase of the present disclosure will have an asparagine at position 2,041(Am) and a leucine, a threonine, a valine, or an alanine at position 1,781(Am). In one embodiment, an acetyl-Coenzyme A carboxylase of the present disclosure will have an asparagine at position 2,041(Am)

and a glycine at position 1,785(Am). In one embodiment, an acetyl-Coenzyme A carboxylase of the present disclosure will have an asparagine at position 2,041(Am) and a proline at position 1,786(Am). In one embodiment, an acetyl-Coenzyme A carboxylase of the present disclosure will have an asparagine at position 2,041(Am) and have an asparagine at position 1,811(Am). In one embodiment, an acetyl-Coenzyme A carboxylase of the present disclosure will have an asparagine at position 2,041(Am) and a proline at position 1824(Am). In one embodiment, an acetyl-Coenzyme A carboxylase of the present disclosure will have an asparagine at position 2,041(Am) and a phenylalanine at position 1864(Am). In one embodiment, an acetyl-Coenzyme A carboxylase of the present disclosure will have an asparagine at position 2,041(Am) and a cysteine or glycine at position 1,999(Am). In one embodiment, an acetyl-Coenzyme A carboxylase of the present disclosure will have an asparagine at position 2,041(Am) and a cysteine or arginine at position 2,027(Am). In one embodiment, an acetyl-Coenzyme A carboxylase of the present disclosure will have an asparagine at position 2,041(Am) and a glycine at position 2039(Am). In one embodiment, an acetyl-Coenzyme A carboxylase of the present disclosure will have an asparagine at position 2,041(Ami) and an asparagine at position 2,041(Am). In one embodiment, an acetyl-Coenzyme A carboxylase of the present disclosure will have an asparagine at position 2,041(Am) and a phenylalanine, isoleucine or leucine at position 2,049(Am) In one embodiment, an acetyl-Coenzyme A carboxylase of the present disclosure will have an asparagine at position 2,041(Am) and a valine at position 2,059(Am). In one embodiment, an acetyl-Coenzyme A carboxylase of the present disclosure will have an asparagine at position 2,041(Am) and a leucine at position 2,074(Am). In one embodiment, an acetyl-Coenzyme A carboxylase of the present disclosure will have an asparagine at position 2,041(Am) and a leucine, isoleucine, methionine or additional valine at position 2,075(Am). In one embodiment, an acetyl-Coenzyme A carboxylase of the present disclosure will have an asparagine at position 2,041 (Am) and a glycine or threonine at position 2,078(Am). In one embodiment, an acetyl-Coenzyme A carboxylase of the present disclosure will have an asparagine at position 2,041 (Am) and a phenylalanine at position 2079(Am). In one embodiment, an acetyl-Coenzyme A carboxylase of the present disclosure will have an asparagine at position 2,041 (Am) and a glutamic acid or a deletion at position 2080 (Am). In one embodiment, an acetyl-Coenzyme A carboxylase of the present disclosure will have an asparagine at position 2,041(Am) and a deletion at position 2081(Am). In one embodiment, an acetyl-Coenzyme A carboxylase of the present disclosure will have an isoleucine at position 2,041 (Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have an isoleucine at position 2,041(Am) and a glutamic acid at position 2,095(Am). In one embodiment, an acetyl-Coenzyme A carboxylase of the present disclosure will have an isoleucine at position 2,041(Am) and an alanine or serine at position 2,096(Am). In one embodiment, an acetyl-Coenzyme A carboxylase of the present disclosure will have an isoleucine at position 2,041(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,049(Am) and at one or more additional amino acid positions. Acetyl-Coenzyme A carboxylase enzymes of the disclosure will typically have a phenylalanine, isoleucine or leucine at position 2,049(Am). In addition, enzymes of this embodiment will also comprise one or more of a leucine, threonine, a valine, or alanine at position 1,781 (Am), a glycine at position 1,785(Am), a proline at position 1,786(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a valine at position 2,059(Am), a leucine at position 2,074(Am), a leucine, isoleucine, methionine or additional valine at position 2,075(Am), a glycine or threonine at position 2,078 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Ar), an alanine or serine at position 2,096(Am), and an alanine, glycine, proline, histidine, cysteine, or serine at position 2,098(Am). In one embodiment, an acetyl-Coenzyme A carboxylase of the present disclosure will have a phenylalanine, isoleucine or leucine at position 2,049(Am) and a leucine, a threonine, a valine, or an alanine at position 1,781(Am). In one embodiment, an acetyl-Coenzyme A carboxylase of the present disclosure will have a phenylalanine, isoleucine or leucine at position 2,049(Am) and a glycine at position 1,785(Am). In one embodiment, an acetyl-Coenzyme A carboxylase of the present disclosure will have a phenylalanine, isoleucine or leucine at position 2,049(Am) and a proline at position 1,786(Am). In one embodiment, an acetyl-Coenzyme A carboxylase of the present disclosure will have a phenylalanine, isoleucine or leucine at position 2,049(Am) and have an asparagine at position 1,811(Am). In one embodiment, an acetyl-Coenzyme A carboxylase of the present disclosure will have a phenylalanine, isoleucine or leucine at position 2,049(Am) and a proline at position 1824(Am). In one embodiment, an acetyl-Coenzyme A carboxylase of the present disclosure will have a phenylalanine, isoleucine or leucine at position 2,049(Am) and a phenylalanine at position 1864(Am). In one embodiment, an acetyl-Coenzyme A carboxylase of the present disclosure will have a phenylalanine, isoleucine or leucine at position 2,049(Am) and a cysteine or glycine at position 1,999(Am). In one embodiment, an acetyl-Coenzyme A carboxylase of the present disclosure will have a phenylalanine, isoleucine or leucine at position 2,049(Am) and a cysteine or an arginine at position 2,027(Am). In one embodiment, an acetyl-Coenzyme A carboxylase of the present disclosure will have a phenylalanine, isoleucine or leucine at position 2,049(Am) and a glycine at position 2039(Am). In one embodiment, an acetyl-Coenzyme A carboxylase of the present disclosure will have a phenylalanine, isoleucine or leucine at position 2,049(Am) and an asparagine at position 2,041(Am). In one embodiment, an acetyl-Coenzyme A carboxylase of the present disclosure will have a phenylalanine, isoleucine or leucine at position 2,049(Am) and a valine at position 2059(Am). In one embodiment, an acetyl-Coenzyme A carboxylase of the present disclosure will have a phenylalanine, isoleucine or leucine at position 2,049(Am) and a leucine at position 2,074(Am). In one embodiment, an acetyl-Coenzyme A carboxylase of the present disclosure will have a phenylalanine, isoleucine or leucine at position 2,049(Am) and a leucine, isoleucine methionine, or additional valine at position 2,075(Am). In one embodiment, an acetyl-Coenzyme A carboxylase of the present disclosure will have a phenylalanine, isoleucine or leucine at position 2,049(Am) and a glycine or threonine at position 2,078 (Am). In one embodiment, an acetyl-Coenzyme A carboxylase of the present disclosure will have a phenylalanine, isoleucine or leucine at position 2,049(Am) and a phenylalanine at position 2079(Am). In one embodiment, an acetyl-Coenzyme A carboxylase of the present disclosure will have a phenylalanine, isoleucine or leucine at position 2,049(Am) and a glutamic acid or a deletion at position 2080(Am). In one embodiment, an acetyl-Coenzyme A carboxylase of the present disclosure will have a phenylalanine, isoleucine or leucine at position 2,049(Am) and a deletion at position 2081(Am). In one embodiment, an acetyl-Coenzyme A carboxylase of the present disclosure will have a phenylalanine, isoleucine or leucine at position 2,049(Am) and an arginine, tryptophan, phenylalanine, glycine, histidine, lysine, serine, threonine, or valine at position 2,088(Am). In one embodiment, an acetyl-Coenzyme A carboxylase of the present disclosure will have a phenylalanine, isoleucine or leucine at position 2,049(Am) and a glutamic acid at position 2,095(Am). In one embodiment, an acetyl-Coenzyme A carboxylase of the present disclosure will have a phenylalanine, isoleucine or leucine at position 2,049(Am) and an alanine or serine at position 2,096(Am). In one embodiment, an acetyl-Coenzyme A carboxylase of the present disclosure will have a phenylalanine, isoleucine or leucine at position 2,049(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,059(Am) and at one or more additional amino acid positions. Acetyl-Coenzyme A carboxylase enzymes of the disclosure will typically have a valine at position 2,059 (Am). In addition, enzymes of this embodiment will also comprise one or more of a leucine, threonine, a valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine or tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,074(Am) and at one or more additional amino acid positions. Acetyl-Coenzyme A carboxylase enzymes of the disclosure will typically have a leucine at position 2,074(Am). In addition, enzymes of this embodiment will also comprise one or more of a leucine, threonine, a valine, or alanine at position 1,781(Am), a glycine at position 1,785(4n), a proline at position 1,786(4n), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a leucine at position 2,074(Am) and a leucine, a threonine, a valine, or an alanine at position 1,781(Am). In one embodiment, an acetyl-Coenzyme A carboxylase of the present disclosure will have a leucine at position 2,074(Am) and a glycine at position 1,785(Am). In one embodiment, an acetyl-Coenzyme A carboxylase of the present disclosure will have a leucine at position 2,074(Am) and a proline at position 1,786(Am). In one embodiment, an acetyl-Coenzyme A carboxylase of the present disclosure will have a leucine at position 2,074(Am) and have an asparagine at position 1,811(Am). In one embodiment, an acetyl-Coenzyme A carboxylase of the present disclosure will have a leucine at position 2,074(Am) and a proline at position 1824(Am). In one embodiment, an acetyl-Coenzyme A carboxylase of the present disclosure will have a leucine at position 2,074(Am) and a phenylalanine at position 1864(Am). In one embodiment, an acetyl-Coenzyme A carboxylase of the present disclosure will have a leucine at position 2,074(Am) and a cysteine or glycine at position 1,999(Am). In one embodiment, an acetyl-Coenzyme A carboxylase of the present disclosure will have a leucine at position 2,074(Am) and a cysteine or an arginine at position 2,027(Am). In one embodiment, an acetyl-Coenzyme A carboxylase of the present disclosure will have a leucine at position 2,074(Am) and a glycine at position 2039(Am). In one embodiment, an acetyl-Coenzyme A carboxylase of the present disclosure will have a leucine at position 2,074(Am) and an asparagine at position 2,041(Am). In one embodiment, an acetyl-Coenzyme A carboxylase of the present disclosure will have a leucine at position 2,074(Am) and a phenylalanine, leucine or isoleucine at position 2,049(Am). In one embodiment, an acetyl-Coenzyme A carboxylase of the present disclosure will have a leucine at position 2,074 (Am) and a valine at position 2059(Am). In one embodiment, an acetyl-Coenzyme A carboxylase of the present disclosure will have a leucine at position 2,074(Am) and a leucine, isoleucine methionine, or additional valine at position 2,075(Am). In one embodiment, an acetyl-Coenzyme A carboxylase of the present disclosure will have a leucine at position 2,074(Am) and a glycine or threonine at position 2,078(Am). In one embodiment, an acetyl-Coenzyme A carboxylase of the present disclosure will have a leucine at position 2,074(Am) and a phenylalanine at position 2079 (Am). In one embodiment, an acetyl-Coenzyme A carboxylase of the present disclosure will have a leucine at position 2,074(Am) and a glutamic acid or a deletion at position 2080(Am). In one embodiment, an acetyl-Coenzyme A carboxylase of the present disclosure will have a leucine at position 2,074(Am) and a deletion at position 2081(Am). In one embodiment, an acetyl-Coenzyme A carboxylase of the present disclosure will have a leucine at position 2,074(Am) and an arginine, tryptophan, phenylalanine, glycine, histidine, lysine, serine, threonine, or valine at position 2,088 (Am). In one embodiment, an acetyl-Coenzyme A carboxylase of the present disclosure will have a leucine at position 2,074(Am) and a glutamic acid at position 2,095(Am). In one embodiment, an acetyl-Coenzyme A carboxylase of the present disclosure will have a leucine at position 2,074(Am) and an alanine or serine at position 2,096(Am) In one embodiment, an acetyl-Coenzyme A carboxylase of the present disclosure will have a leucine at position 2,074(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,075(Am) and at one or more additional amino acid positions. Acetyl-Coenzyme A carboxylase enzymes of the disclosure will typically have a leucine, isoleucine, methionine or additional valine at position 2,075(Am). In addition, enzymes of this embodiment will also comprise one or more of a leucine, threonine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a leucine, isoleucine, methionine or additional valine at position 2,075(Am) and a leucine, a threonine, a valine, or an alanine at position 1,781(Am). In one embodiment, an acetyl-Coenzyme A carboxylase of the present disclosure will have a leucine, isoleucine, methionine or additional valine at position 2,075(Am) and a glycine at position 1,785(Am). In one embodiment, an acetyl-Coenzyme A carboxylase of the present disclosure will have a leucine, isoleucine, methionine or additional valine at position 2,075(Am) and a proline at position 1,786(Am). In one embodiment, an acetyl-Coenzyme A carboxylase of the present disclosure will have a leucine, isoleucine, methionine or additional valine at position 2,075(Am) and have an asparagine at position 1,811(Am). In one embodiment, an acetyl-Coenzyme A carboxylase of the present disclosure will have a leucine, isoleucine, methionine or additional valine at position 2,075(Am) and a cysteine or glycine at position 1,999(Am). In one embodiment, an acetyl-Coenzyme A carboxylase of the present disclosure will have a leucine, isoleucine, methionine or additional valine at position 2,075(Am) and a cysteine or arginine at position 2,027 (Am). In one embodiment, an acetyl-Coenzyme A carboxylase of the present disclosure will have a leucine, isoleucine, methionine or additional valine at position 2,075(Am) and an isoleucine at position 2,041(Am). In one embodiment, an acetyl-Coenzyme A carboxylase of the present disclosure will have a leucine, isoleucine, methionine or additional valine at position 2,075(Am) and a phenylalanine, isoleucine or leucine at position 2,049(Am). In one embodiment, an acetyl-Coenzyme A carboxylase of the present disclosure will have a leucine, isoleucine, methionine or additional valine at position 2,075(Am) and a leucine at position 2,074(Am). In one embodiment, an acetyl-Coenzyme A carboxylase of the present disclosure will have a leucine, isoleucine, methionine or additional valine at position 2,075 (Am) and a glycine or threonine at position 2,078(Am). In one embodiment, an acetyl-Coenzyme A carboxylase of the present disclosure will have a leucine, isoleucine, methionine or additional valine at position 2,075(Am) and an arginine or tryptophan, phenylalanine, glycine, histidine, lysine, leucine, serine, threonine, or valine at position 2,088 (Am). In one embodiment, an acetyl-Coenzyme A carboxylase of the present disclosure will have a leucine, isoleucine, methionine or additional valine at position 2,075(Am) and an alanine or serine at position 2,096(Am). In one embodiment, an acetyl-Coenzyme A carboxylase of the present disclosure will have a leucine, isoleucine, methionine or additional valine at position 2,075(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,078(Am) and at one or more additional amino acid positions. Acetyl-Coenzyme A carboxylase enzymes of the disclosure will typically have a glycine or threonine at position 2,078(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine or serine at position 2,098(Am). In one embodiment, an acetyl-Coenzyme A carboxylase of the present disclosure will have a glycine or threonine at position 2,078(Am) and a leucine, a threonine or an alanine at position 1,781(Am). In one embodiment, an acetyl-Coenzyme A carboxylase of the present disclosure will have a glycine or threonine at position 2,078(Am) and a glycine at position 1,785(Am). In one embodiment, an acetyl-Coenzyme A carboxylase of the present disclosure will have a glycine or threonine at position 2,078(Am) and a proline at position 1,786(Am). In one embodiment, an acetyl-Coenzyme A carboxylase of the present disclosure will have a glycine or threonine at position 2,078(Am) and an asparagine at position 1,811(Am). In one embodiment, an acetyl-Coenzyme A carboxylase of the present disclosure will have a glycine or threonine at position 2,078(Am) and a cysteine or glycine at position 1,999(Am). In one embodiment, an acetyl-Coenzyme A carboxylase of the present disclosure will have a glycine or threonine at position 2,078(Am) and a cysteine or arginine at position 2,027(Am). In one embodiment, an acetyl-Coenzyme A carboxylase of the present disclosure will have a glycine or threonine at position 2,078(Am) and an isoleucine at position 2,041(Am). In one embodiment, an acetyl-Coenzyme A carboxylase of the present disclosure will have a glycine or threonine at position 2,078(Am) and a phenylalanine, isoleucine or leucine at position 2,049(Am). In one embodiment, an acetyl-Coenzyme A carboxylase of the present disclosure will have a glycine or threonine at position 2,078(Am) and a leucine at position 2,074(Am). In one embodiment, an acetyl-Coenzyme A carboxylase of the present disclosure will have a glycine or threonine at position 2,078(Am) and a leucine, isoleucine, methionine or additional valine at position 2,075 (Am). In one embodiment, an acetyl-Coenzyme A carboxylase of the present disclosure will have a glycine or threonine at position 2,078(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a glycine or threonine at position 2,078(Am) and an alanine or serine at position 2,096(Am) In one embodiment, an acetyl-Coenzyme A carboxylase of the present disclosure will have a glycine or threonine at position 2,078(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,079(Am) and at one or more additional amino acid positions. Acetyl-Coenzyme A carboxylase enzymes of the disclosure will typically have a phenylalanine at position 2,079(Am). In addition, enzymes of this embodiment will also comprise one or more of a leucine, threonine, valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,080(Am) and at one or more additional amino acid positions. Acetyl-Coenzyme A carboxylase enzymes of the disclosure will typically have a glutamic acid or a deletion at position 2,080(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075 (Am), a glycine or threonine at position 2,078(Am), a phenylalanine at position 2,079(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,081(Am) and at one or more additional amino acid positions. Acetyl-Coenzyme A carboxylase enzymes of the disclosure will typically have a deletion at position 2,081(Am). In addition, enzymes of this embodiment will also comprise one or more of a leucine, threonine, valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080 (Am), a deletion at position 2,080(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,088(Am) and at one or more additional amino acid positions. Acetyl-Coenzyme A carboxylase enzymes of the disclosure will typically have an arginine, tryptophan, phenylalanine, glycine, histidine, lysine, leucine, serine, threonine, or valine at position 2,088(Am). In addition, enzymes of this embodiment will also comprise one or more of a leucine, threonine, valine, or alanine at position 1,781 (Am), a glycine at position 1,785(Am), a proline at position 1,786(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a leucine, a threonine, valine, or an alanine at position 1,781(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a glycine at position 1,785(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a proline at position 1,786(Am). In one embodiment, an acetyl-Coenzyme A carboxylase of the present disclosure will have an arginine, tryptophan, phenylalanine, glycine, histidine, lysine, leucine, serine, threonine, or valine at position 2,088 (Am) and an asparagine at position 1,811(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a cysteine or glycine at position 1,999(Am). In one embodiment, an acetyl-Coenzyme A carboxylase of the present disclosure will have an arginine or tryptophan, phenylalanine, glycine, histidine, lysine, leucine, serine, threonine, or valine at position 2,088(Am) and a cysteine or arginine at position 2,027(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an isoleucine at position 2,041(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a phenylalanine, isoleucine or leucine at position 2,049(Am). In one embodiment, an acetyl-Coenzyme A carboxylase of the present disclosure will have an arginine, tryptophan, phenylalanine, glycine, histidine, lysine, leucine, serine, threonine, or valine at position 2,088 (Am) and a leucine at position 2,074(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a leucine, isoleucine, methionine or additional valine at position 2,075(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a glycine or threonine at position 2,078(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an alanine or serine at position 2,096(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,095(Am) and at one or more additional amino acid positions. Acetyl-Coenzyme A carboxylase enzymes of the disclosure will typically have a glutamic acid at position 2,095(Am). In addition, enzymes of this embodiment will also comprise one or more of a leucine, threonine, valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080 (Am), a deletion at position 2,080(Am), a deletion at position 2,081(Am), an arginine or tryptophan, phenylalanine, glycine, histidine, lysine, leucine, serine, threonine, or valine at position 2,088(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,096(Am) and at one or more additional amino acid positions. Acetyl-Coenzyme A carboxylase enzymes of the disclosure will typically have an alanine or serine at position 2,096(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080 (Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095 (Am), and an alanine, glycine, proline, histidine, cysteine, or serine at position 2,098(Am). In one embodiment, an acetyl-Coenzyme A carboxylase of the present disclosure will have an alanine or serine at position 2,096(Am) and a leucine, a threonine or an alanine at position 1,781(Am). In one embodiment, an acetyl-Coenzyme A carboxylase of the present disclosure will have an alanine or serine at position 2,096(Am) and a glycine at position 1,785(Am). In one embodiment, an acetyl-Coenzyme A carboxylase of the present disclosure will have an alanine or serine at position 2,096(Am) and a proline at position 1,786(Am). In one embodiment, an acetyl-Coenzyme A carboxylase of the present disclosure will have an alanine or serine at position 2,096(Am) and an asparagine at position 1,811(Am). In one embodiment, an acetyl-Coenzyme A carboxylase of the present disclosure will have an alanine or serine at position 2,096(Am) and a cysteine or glycine at position 1,999(Am). In one embodiment, an acetyl-Coenzyme A carboxylase of the present disclosure will have an alanine or serine at position 2,096(Am) and a cysteine or arginine at position 2,027(Am). In one embodiment, an acetyl-Coenzyme A carboxylase of the present disclosure will have an alanine or serine at position 2,096(Am) and an isoleucine at position 2,041(Am). In one embodiment, an acetyl-Coenzyme A carboxylase of the present disclosure will have an alanine or serine at position 2,096(Am) and a phenylalanine, isoleucine or leucine at position 2,049(Am). In one embodiment, an acetyl-Coenzyme A carboxylase of the present disclosure will have an alanine or serine at position 2,096(Am) and a leucine at position 2,074(Am). In one embodiment, an acetyl-Coenzyme A carboxylase of the present disclosure will have an alanine or serine at position 2,096(Am) and a leucine, isoleucine, methionine or additional valine at position 2,075(Am). In one embodiment, an acetyl-Coenzyme A carboxylase of the present disclosure will have an alanine or serine at position 2,096(Am) and a glycine or threonine at position 2,078(Am). In one embodiment, an acetyl-Coenzyme A carboxylase of the present disclosure will have an alanine or serine at position 2,096(Am) and an an arginine, tryptophan, phenylalanine, glycine, histidine, lysine, leucine, serine, threonine, or valine at position 2,088(Am). In one embodiment, an acetyl-Coenzyme A carboxylase of the present disclosure will have an alanine or serine at position 2,096(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,098(Am) and at one or more additional amino acid positions. Acetyl-Coenzyme A carboxylase enzymes of the disclosure will typically have an alanine, glycine, proline, histidine, cysteine, or serine at position 2,098(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081 (Am), an arginine, tryptophan, phenylalanine, glycine, histidine, lysine, leucine, serine, threonine, or valine at position 2,088(Am), a glutamic acid at position 2,095(Am), and an alanine or serine at position 2,096(Am). In one embodiment, an acetyl-Coenzyme A carboxylase of the present disclosure will have an alanine, glycine, proline, histidine, cysteine, or serine at position 2,098(Am) and a leucine, a threonine, valine, or an alanine at position 1,781(Am). In one embodiment, an acetyl-Coenzyme A carboxylase of the present disclosure will have an alanine, glycine, proline, histidine, cysteine, or serine at position 2,098(Am) and a glycine at position 1,785(Am). In one embodiment, an acetyl-Coenzyme A carboxylase of the present disclosure will have an alanine, glycine, proline, histidine, cysteine, or serine at position 2,098(Am) and a proline at position 1,786(Am). In one embodiment, an acetyl-Coenzyme A carboxylase of the present disclosure will have an alanine, glycine, proline, histidine, cysteine, or serine at position 2,098(Am) and an asparagine at position 1,811(Am). In one embodiment, an acetyl-Coenzyme A carboxylase of the present disclosure will have an alanine, glycine, proline, histidine, cysteine, or serine at position 2,098(Am) and a cysteine or glycine at position 1,999(Am). In one embodiment, an acetyl-Coenzyme A carboxylase of the present disclosure will have an alanine, glycine, proline, histidine, cysteine, or serine at position 2,098(Am) and a cysteine or arginine at position 2,027(Am). In one embodiment, an acetyl-Coenzyme A carboxylase of the present disclosure will have an alanine, glycine, proline, histidine, cysteine, or serine at position 2,098(Am) and an isoleucine at position 2,041(Am). In one embodiment, an acetyl-Coenzyme A carboxylase of the present disclosure will have an alanine, glycine, proline, histidine, cysteine, or serine at position 2,098(Am) and a phenylalanine, isoleucine or leucine at position 2,049(Am). In one embodiment, an acetyl-Coenzyme A carboxylase of the present disclosure will have an alanine, glycine, proline, histidine, cysteine, or serine at position 2,098(Am) and a leucine at position 2,074(Am). In one embodiment, an acetyl-Coenzyme A carboxylase of the present disclosure will have an alanine, glycine, proline, histidine, cysteine, or serine at position 2,098(0.4m) and a leucine, isoleucine, methionine or additional valine at position 2,075(Am). In one embodiment, an acetyl-Coenzyme A carboxylase of the present disclosure will have an alanine, glycine, proline, histidine, cysteine, or serine at position 2,098(Am) and a glycine or threonine at position 2,078(Am). In one embodiment, an acetyl-Coenzyme A carboxylase of the present disclosure will have an alanine, glycine, proline, histidine, cysteine, or serine at position 2,098(Am) and an arginine or tryptophan, phenylalanine, glycine, histidine, lysine, leucine, serine, threonine, or valine at position 2,088(Am). In one embodiment, an acetyl-Coenzyme A carboxylase of the present disclosure will have an alanine, glycine, proline, histidine, cysteine, or serine at position 2,098(Am) and an alanine or serine at position 2,096(Am).

In one embodiment, the disclosure includes acetyl-Coenzyme A carboxylases having an isoleucine at position 2,075 (Am) and a glycine at position 1,999(Am); acetyl-Coenzyme A carboxylases having a methionine at position 2,075 (Am) and a glutamic acid at position 2,080(Am); acetyl-Coenzyme A carboxylases having a methionine at position 2,075(Am) and a glutamic acid at position 2,095(Am); acetyl-Coenzyme A carboxylases having a glycine at position 2,078(Am) and a valine at position 2,041(Am); acetyl-Coenzyme A carboxylases having a glycine at position 2,078(Am) and a glycine at position 2,039(Am); acetyl-Coenzyme A carboxylases having a glycine at position 2,078(Am) and an alanine at position 2,049(Am); acetyl-Coenzyme A carboxylases having a glycine at position 2,078(Am) and a cysteine at position 2,049(Am); acetyl-Coenzyme A carboxylases having a glycine at position 2,078(Am) and a serine at position 2,049(Am); acetyl-Coenzyme A carboxylases having a glycine at position 2,078(Am) and a threonine at position 2,049(Am); acetyl-Coenzyme A carboxylases having a glycine at position 2,078(Am) and a valine at position 2,059(Am); acetyl-Coenzyme A carboxylases having a glycine at position 2,078(Am) and a phenylalanine at position 2,079(Am), acetyl-Coenzyme A carboxylases having a glycine at position 2,078(Am) and a proline at position at position 2,079 (Am); and acetyl-Coenzyme A carboxylases having a glycine at position 2,078(Am) and a glycine at position 2,088 (Am).

In a preferred embodiment, the disclosure includes acetyl-Coenzyme A carboxylases having a leucine at position 1,781(Am) and a proline at position 1,824(Am); acetyl-Coenzyme A carboxylases having a leucine at position 1,781(Am) and an arginine at position 2027(Am); and acetyl-Coenzyme A carboxylases having a glycine at position 2,078(Am) and a proline at position 1,824(Am).

In a more preferred embodiment, the disclosure includes acetyl-Coenzyme A carboxylases having a leucine at position 1,781(Am) and a phenylalanine at position 2,049(Am), acetyl-Coenzyme A carboxylases having an alanine at position 2,098(Am) and a leucine at position 2,049(Am); acetyl-Coenzyme A carboxylases having an alanine at position 2,098(Am) and a histidine at position 2088(Am); acetyl- Coenzyme A carboxylases having an alanine at position 2,098(Am) and a phenylalanine at position 2,088(Am); acetyl-Coenzyme A carboxylases having an alanine at position 2,098(Am) and a lysine at position 2,088(Am); acetyl-Coenzyme A carboxylases having an alanine at position 2,098(Am) and a leucine at position 2,088(Am); acetyl-Coenzyme A carboxylases having an alanine at position 2,098(Am) and a threonine at position 2,088(Am); acetyl-Coenzyme A carboxylases having a glycine at position 2,098(Am) and a glycine at position 2,088(Am); acetyl-Coenzyme A carboxylases having a glycine at position 2,098(Am) and a histidine at position 2,088(Am); acetyl-Coenzyme A carboxylases having a glycine at position 2,098(Am) and leucine at position 2,088(Am); acetyl-Coenzyme A carboxylases having a glycine at position 2,098 (Am) and a serine at position 2,088(Am); acetyl-Coenzyme A carboxylases having a glycine at position 2,098(Am) and threonine at position 2,088(Am); acetyl-Coenzyme A carboxylases having a glycine at position 2,098(Am) and a valine at position 2,088(Am); acetyl-Coenzyme A carboxylases having a cysteine at position 2,098(Am) and a tryptophan at position 2088(Am); acetyl-Coenzyme A carboxylases having a serine at position 2,098(Am) and a tryptophan at position 2088(Am); and acetyl-Coenzyme A carboxylases having a deletion at position 2,080(Am) and a deletion at position 2081(Am).

In a most preferred embodiment, the disclosure includes acetyl-Coenzyme A carboxylases having a leucine at position 1,781(Am) and a asparagine at position 2,041(Am); acetyl-Coenzyme A carboxylases having a leucine at position 1,781(Am) and a cysteine at position 2,027(Am); acetyl-Coenzyme A carboxylases having a leucine at position 1,781(Am) and a leucine at position 2,075(Am); acetyl-Coenzyme A carboxylases having a leucine at position 1,781(Am) and a phenylalanine at position 1,864(Am); acetyl-Coenzyme A carboxylases having a leucine at position 1,781(Am) and an alanine at position 2098(Am); acetyl-Coenzyme A carboxylases having a leucine at position 1,781(Am) and a glycine at position 2,098(Am); acetyl-Coenzyme A carboxylases having a leucine at position 1,781(Am) and a duplication 2,075(Am); acetyl-Coenzyme A carboxylases having a glycine at position 1,999(Am) and a phenylalanine at position 1,864(Am); acetyl-Coenzyme A carboxylases having a glycine at position 1,999(Am) and isoleucine at position 2,049(Am); acetyl-Coenzyme A carboxylases having a glycine at position 1,999(Am) and leucine at position 2,075(Am); and acetyl-Coenzyme A carboxylases having a glycine at position 1,999(Am) and alanine at position 2,098(Am).

Nucleic Acid Molecules

The present disclosure also encompasses nucleic acid molecules that encode all or a portion of the acetyl-Coenzyme A carboxylase enzymes described above. Nucleic acid molecules of the disclosure may comprise a nucleic acid sequence encoding an amino acid sequence comprising a modified version of one or both of SEQ ID NOs: 2 and 3, wherein the sequence is modified such that the encoded protein comprises one or more of the following: the amino acid at position 1,781(Am) is leucine, threonine, valine, or alanine; the amino acid at position 1,785(Am) is glycine; the amino acid at position 1,786(Am) is proline; the amino acid at position 1,811(Am) is asparagine; the amino acid at position 1,824(Am) is proline; the amino acid at position 1,864(Am) is phenylalanine; the amino acid at position 1,999(Am) is cysteine or glycine; the amino acid at position 2,027(Am) is cysteine or arginine; the amino acid at position 2,039(Am) is glycine; the amino acid at position 2,041(Am) is asparagine; the amino acid at position 2049(Am) is phenylalanine, isoleucine or leucine; the amino acid at position 2,059(Am) is valine; the amino acid at position 2,074(Am) is leucine; the amino acid at position 2,075(Am) is leucine, isoleucine, methionine or additional valine; the amino acid at position 2,078(Am) is glycine, or threonine; the amino acid at position 2,079(Am) is phenylalnine; the amino acid at position 2,080(Am) is glutamic acid; the amino acid at position 2,080(Am) is deleted; the amino acid at position 2,081(Am) is deleted; the amino acid at position 2,088(Am) is arginine, tryptophan, phenylalanine, glycine, histidine, lysine, leucine, serine, threonine, or valine; the amino acid at position 2,095(Am) is glutamic acid; the amino acid at position 2,096(Am) is alanine, or serine; or the amino acid at position 2,098(Am) is alanine, glycine, proline, histidine, or serine, as well as nucleic acid molecules complementary to all or a portion of the coding sequences. In some embodiments, a nucleic acid molecule of the disclosure may encode an acetyl-Coenzyme A carboxylase having multiple differences from the wild type acetyl-Coenzyme A carboxylase as described above.

In one embodiment, the present disclosure encompasses a nucleic acid molecule encoding an acetyl-Coenzyme A carboxylase which differs from the acetyl-Coenzyme A carboxylase of the corresponding wild-type plant at only one of the following positions: 1,781(Am), 1,785(Am), 1,786 (Am), 1,811(Am), 1,824(Am), 1,864(Am), 1,999(Am), 2,027(Am), 2,039(Am), 2,041(Am), 2,049(Am), 2,059 (Am), 2,074(Am), 2,075(Am), 2,078(Am), 2,079(Am), 2,080(Am), 2,081 (Am), 2,088(Am), 2,095(Am), 2,096 (Am), or 2,098(Am). In one embodiment the acetyl-Coenzyme A carboxylase of an herbicide-tolerant plant of the disclosure will differ at only one of the following positions: 2,078(Am), 2,088(Am), or 2,075(Am). In a preferred embodiment the acetyl-Coenzyme A carboxylase of an herbicide-tolerant plant of the disclosure will differ at only one of the following positions: 2,039(Am), 2,059(Am), 2,080 (Am), or 2,095(Am). In a more preferred embodiment the acetyl-Coenzyme A carboxylase of an herbicide-tolerant plant of the disclosure will differ at only one of the following positions: 1,785(Am), 1,786(Am), 1,811(Am), 1,824(Am), 1,864(Am), 2,041(Am), 2,049(Am), 2,074(Am), 2,079 (Am), 2,081(Am), 2,096(Am), or 2,098(Am). In a most preferred embodiment the acetyl-Coenzyme A carboxylase of an herbicide-tolerant plant of the disclosure will differ at only one of the following positions: 1,781(Am), 1,999(Am), 2,027(Am), 2,041(Am), or 2,096(Am).

In one embodiment, the present disclosure encompasses a nucleic acid molecule encoding an acetyl-Coenzyme A carboxylase having only one of the following substitutions: isoleucine at position 2,075(Am), glycine at position 2,078 (Am), or arginine at position 2,088(Am). In a preferred embodiment, the present disclosure encompasses a nucleic acid molecule encoding an acetyl-Coenzyme A carboxylase having only one of the following substitutions: glycine at position 2,039(Am), valine at position 2,059(Am), methionine at position 2,075(Am), duplication of position 2,075 (Am) (i.e., an insertion of valine between 2,074(Am) and 2,075(Am), or an insertion of valine between position 2,075 (Am) and 2,076(Am), deletion of amino acid position 2,088 (Am), glutamic acid at position 2,080(Am), deletion of position 2,088(Am), or glutamic acid at position 2,095(Am). In a more preferred embodiment, the present disclosure encompasses a nucleic acid molecule encoding an acetyl-Coenzyme A carboxylase having only one of the following substitutions: a glycine at position 1,785(Am), a proline at position 1,786(Am), an asparagine at position 1,811(Am), a leucine at position 2,075(Am), a methionine at position 2,075(Am), a threnonine at position 2,078(Am), a deletion at position 2,080(Am), a deletion at position 2,081(Am), a tryptophan at position 2,088(Am), a serine at position 2,096 (Am), an alanine at position 2,096(Am), an alanine at position 2,098(Am), a glycine at position 2,098(Am), an histidine at position 2,098(Am), a proline at position 2,098 (Am), or a serine at position 2,098(Am). In a most preferred embodiment, the present disclosure encompasses a nucleic acid molecule encoding an acetyl-Coenzyme A carboxylase having only one of the following substitutions: a leucine at position 1,781(Am), a threonine at position 1,781(Am), a valine at position 1,781(Am), an alanine at position 1,781 (Am), a glycine at position 1,999(Am), a cysteine at position 2,027(Am), an arginine at position 2,027(Am), an asparagine at position 2,041(Am), a valine at position 2,041(Am), an alanine at position 2,096(Am), and a serine at position 2,096(Am).

In one embodiment, a nucleic acid molecule of the disclosure may encode an acetyl-Coenzyme A carboxylase comprising a leucine, threonine, valine, or an alanine at position 1,781(Am) and a cysteine or glycine at position 1,999(Am). In one embodiment, a nucleic acid molecule of the disclosure may encode an acetyl-Coenzyme A carboxylase comprising a leucine, threonine, valine, or an alanine at position 1,781(Am) and a cysteine or arginine at position 2,027(Am). In one embodiment, a nucleic acid molecule of the disclosure may encode an acetyl-Coenzyme A carboxylase comprising a leucine, threonine, valine, or an alanine at position 1,781(Am) and an asparagine at position 2,041 (Am). In one embodiment, a nucleic acid molecule of the disclosure may encode an acetyl-Coenzyme A carboxylase comprising a leucine, threonine, valine, or an alanine at position 1,781(Am) and a phenylalanine, isoleucine or leucine at position 2,049(Am). In one embodiment, a nucleic acid molecule of the disclosure may encode an acetyl-Coenzyme A carboxylase comprising a leucine, threonine, valine, or an alanine at position 1,781(Am) and a leucine or isoleucine at position 2,075(Am). In one embodiment, a nucleic acid molecule of the disclosure may encode an acetyl-Coenzyme A carboxylase comprising a leucine, threonine, valine, or an alanine at position 1,781(Am) and a glycine at position 2,078(Am). In one embodiment, a nucleic acid molecule of the disclosure may encode an acetyl-Coenzyme A carboxylase comprising a leucine, threonine, valine, or an alanine at position 1,781(Am) and an arginine at position 2,088(Am). In one embodiment, a nucleic acid molecule of the disclosure may encode an acetyl-Coenzyme A carboxylase comprising a leucine, threonine, valine, or an alanine at position 1,781(Am) and an alanine at position 2,096(Am). In one embodiment, a nucleic acid molecule of the disclosure may encode an acetyl-Coenzyme A carboxylase comprising a leucine, threonine, valine, or an alanine at position 1,781(Am) and an alanine at position 2,098(Am). In one embodiment, a nucleic acid molecule of the disclosure may encode an acetyl-Coenzyme A carboxylase comprising a leucine, threonine, valine, or an alanine at position 1,781(Am), a cysteine at position 2,027 (Am), and an asparagine at position 2,041(Am). In one embodiment, a nucleic acid molecule of the disclosure may encode an acetyl-Coenzyme A carboxylase comprising a leucine, threonine, valine, or an alanine at position 1,781 (Am), a cysteine at position 2,027(Am), an asparagine at position 2,041(Am), and an alanine at position 2,096(Am).

In one embodiment, the disclosure includes a nucleic acid molecule encoding an acetyl-Coenzyme A carboxylase having an isoleucine at position 2,075(Am) and a glycine at position 1,999(Am); a nucleic acid molecule encoding an acetyl-Coenzyme A carboxylase having a methionine at position 2,075(Am) and a glutamic acid at position 2,080 (Am); a nucleic acid molecule encoding an acetyl-Coenzyme A carboxylase having a methionine at position 2,075 (Am) and a glutamic acid at position 2,095(Am); a nucleic acid molecule encoding an acetyl-Coenzyme A carboxylase having a glycine at position 2,078(Am) and a valine at position 2,041(Am); a nucleic acid molecule encoding an acetyl-Coenzyme A carboxylase having a glycine at position 2,078(Am) and a glycine at position 2,039(Am); a nucleic acid molecule encoding an acetyl-Coenzyme A carboxylase having a glycine at position 2,078(Am) and an alanine at position 2,049(Am); a nucleic acid molecule encoding an acetyl-Coenzyme A carboxylase having a glycine at position 2,078(Am) and a cysteine at position 2,049(Am); a nucleic acid molecule encoding an acetyl-Coenzyme A carboxylase having a glycine at position 2,078(Am) and a serine at position 2,049(Am); a nucleic acid molecule encoding an acetyl-Coenzyme A carboxylase having a glycine at position 2,078(Am) and a threonine at position 2,049(Am); a nucleic acid molecule encoding an acetyl-Coenzyme A carboxylase having a glycine at position 2,078(Am) and a valine at position 2,059(Am); a nucleic acid molecule encoding an acetyl-Coenzyme A carboxylase having a glycine at position 2,078(Am) and a phenylalanine at position 2,079(Am); a nucleic acid molecule encoding an acetyl-Coenzyme A carboxylase having a glycine at position 2,078(Am) and a proline at position at position 2,079(Am); or a nucleic acid molecule encoding an acetyl-Coenzyme A carboxylase having a glycine at position 2,078(Am) and a glycine at position 2,088(Am).

In a preferred embodiment, the disclosure includes a nucleic acid molecule encoding an acetyl-Coenzyme A carboxylase having a leucine at position 1,781(Am) and a proline at position 1,824(Am); a nucleic acid molecule encoding an acetyl-Coenzyme A carboxylase having a leucine at position 1,781(Am) and an arginine at position 2027(Am); or a nucleic acid molecule encoding an acetyl-Coenzyme A carboxylase having a glycine at position 2,078 (Am) and a proline at position 1,824(Am).

In a more preferred embodiment, the disclosure includes a nucleic acid molecule encoding an acetyl-Coenzyme A carboxylase having a leucine at position 1,781(Am) and a phenylalanine at position 2,049(Am); a nucleic acid molecule encoding an acetyl-Coenzyme A carboxylase having an alanine at position 2,098(Am) and a leucine at position 2,049(Am); a nucleic acid molecule encoding an acetyl-Coenzyme A carboxylase having an alanine at position 2,098(Am) and a histidine at position 2088(Am); a nucleic acid molecule encoding an acetyl-Coenzyme A carboxylase having an alanine at position 2,098(Am) and a phenylalanine at position 2,088(Am); a nucleic acid molecule encoding an acetyl-Coenzyme A carboxylase having an alanine at position 2,098(Am) and a lysine at position 2,088(Am); a nucleic acid molecule encoding an acetyl-Coenzyme A carboxylase having an alanine at position 2,098(Am) and a leucine at position 2,088(Am); a nucleic acid molecule encoding an acetyl-Coenzyme A carboxylase having an alanine at position 2,098(Am) and a threonine at position 2,088(Am); a nucleic acid molecule encoding an acetyl-Coenzyme A carboxylase having a glycine at position 2,098 (Am) and a glycine at position 2,088(Am); a nucleic acid molecule encoding an acetyl-Coenzyme A carboxylase having a glycine at position 2,098(Am) and a histidine at position 2,088(Am); a nucleic acid molecule encoding an acetyl-Coenzyme A carboxylase having a glycine at position 2,098(Am) and leucine at position 2,088(Am); a nucleic acid molecule encoding an acetyl-Coenzyme A carboxylase having a glycine at position 2,098(Am) and a serine at position 2,088(Am); a nucleic acid molecule encoding an acetyl-Coenzyme A carboxylase having a glycine at position 2,098 (Am) and threonine at position 2,088(Am); a nucleic acid molecule encoding an acetyl-Coenzyme A carboxylase having a glycine at position 2,098(Am) and a valine at position 2,088(Am); a nucleic acid molecule encoding an acetyl-Coenzyme A carboxylase having a cysteine at position 2,098(Am) and a tryptophan at position 2088(Am); a nucleic acid molecule encoding an acetyl-Coenzyme A carboxylase having a serine at position 2,098(Am) and a tryptophan at position 2088(Am); or a nucleic acid molecule encoding an acetyl-Coenzyme A carboxylase having a deletion at position 2,080(Am) and a deletion at position 2081(Am).

In a most preferred embodiment, the disclosure includes a nucleic acid molecule encoding an acetyl-Coenzyme A carboxylase having a leucine at position 1,781(Am) and a asparagine at position 2,041(Am), a nucleic acid molecule encoding an acetyl-Coenzyme A carboxylase having a leucine at position 1,781(Am) and a cysteine at position 2,027 (Am), a nucleic acid molecule encoding an acetyl-Coenzyme A carboxylase having a leucine at position 1,781(Am) and a leucine at position 2,075(Am); a nucleic acid molecule encoding an acetyl-Coenzyme A carboxylase having a leucine at position 1,781(Am) and a phenylalanine at position 1,864(Am); a nucleic acid molecule encoding an acetyl-Coenzyme A carboxylase having a leucine at position 1,781 (Am) and an alanine at position 2098(Am); a nucleic acid molecule encoding an acetyl-Coenzyme A carboxylase having a leucine at position 1,781(Am) and a glycine at position 2,098(Am); a nucleic acid molecule encoding an acetyl-Coenzyme A carboxylase having a leucine at position 1,781 (Am) and a duplication 2,075(Am); a nucleic acid molecule encoding an acetyl-Coenzyme A carboxylase having a glycine at position 1,999(Am) and a phenylalanine at position 1,864(Am); a nucleic acid molecule encoding an acetyl-Coenzyme A carboxylase having a glycine at position 1,999 (Am) and isoleucine at position 2,049(Am); a nucleic acid molecule encoding an acetyl-Coenzyme A carboxylase having a glycine at position 1,999(Am) and leucine at position 2,075(Am); or a nucleic acid molecule encoding an acetyl-Coenzyme A carboxylase having a glycine at position 1,999 (Am) and alanine at position 2,098(Am).

In one embodiment, the disclosure provides rice plants comprising nucleic acids encoding Acetyl-Coenzyme A carboxylase polypeptide having one or more substitutions as described above.

In one embodiment, the disclosure provides BEP clade plants comprising nucleic acids encoding Acetyl-Coenzyme A carboxylase polypeptide having one or more substitutions as described above.

In one embodiment, the disclosure provides BET subclade plant comprising nucleic acids encoding Acetyl-Coenzyme A carboxylase polypeptide having one or more substitutions as described above.

In one embodiment, the disclosure provides BET crop plants comprising nucleic acids encoding Acetyl-Coenzyme A carboxylase polypeptide having one or more substitutions as described above.

In one embodiment, the disclosure provides monocot plants comprising nucleic acids encoding Acetyl-Coenzyme A carboxylase polypeptide having one or more substitutions as described above.

A nucleic acid molecule of the disclosure may be DNA, derived from genomic DNA or cDNA, or RNA A nucleic acid molecule of the disclosure may be naturally occurring or may be synthetic. A nucleic acid molecule of the disclosure may be isolated, recombinant and/or mutagenized.

In one embodiment, a nucleic acid molecule of the disclosure encodes an acetyl-Coenzyme A carboxylase enzyme in which the amino acid at position 1,781(Am) is leucine or alanine or is complementary to such a nucleic acid molecule. Such nucleic acid molecules include, but are not limited to, genomic DNA that serves as a template for a primary RNA transcription, a plasmid molecule encoding the acetyl-Coenzyme A carboxylase, as well as an mRNA encoding such an acetyl-Coenzyme A carboxylase.

Nucleic acid molecules of the disclosure may comprise non-coding sequences, which may or may not be transcribed. Non-coding sequences that may be included in the nucleic acid molecules of the disclosure include, but are not limited to, 5' and 3' UTRs, polyadenylation signals and regulatory sequences that control gene expression (e.g., promoters). Nucleic acid molecules of the disclosure may also comprise sequences encoding transit peptides, protease cleavage sites, covalent modification sites and the like. In one embodiment, nucleic acid molecules of the disclosure encode a chloroplast transit peptide sequence in addition to a sequence encoding an acetyl-Coenzyme A carboxylase enzyme.

In another embodiment, nucleic acid molecules of the disclosure may encode an acetyl-Coenzyme A carboxylase enzyme having at least 50%, 60%, 70%, 75%, 80%, 85%, 90%, 95% or more sequence identity to a modified version of one or both of SEQ ID NOs: 2 and 3, wherein the sequence is modified such that the encoded protein comprises one or more of the following: the amino acid at position 1,781(Am) is leucine, threonine, valine, or alanine; the amino acid at position 1,785(Am) is glycine; the amino acid at position 1,786(Am) is proline; the amino acid at position 1,811(Am) is asparagine; the amino acid at position 1,824(Am) is proline; the amino acid at position 1,864(Am) is phenylalanine; the amino acid at position 1,999(Am) is cysteine or glycine; the amino acid at position 2,027(Am) is cysteine or arginine; the amino acid at position 2,039(Am) is glycine; the amino acid at position 2,041(Am) is asparagine; the amino acid at position 2049(Am) is phenylalanine, leucine or isoleucine; the amino acid at position 2,059(Am) is valine; the amino acid at position 2,074(Am) is leucine; the amino acid at position 2,075(Am) is leucine, isoleucine or methionine or an additional valine; the amino acid at position 2,078(Am) is glycine, or threonine; the amino acid at position 2,079(Am) is phenylalnine; the amino acid at position 2,080(Am) is glutamic acid; the amino acid at position 2,080(Am) is deleted; the amino acid at position 2,081(Am) is deleted; the amino acid at position 2,088(Am) is arginine, tryptophan, phenylalanine, glycine, histidine, lysine, leucine, serine, threonine, or valine; the amino acid at position 2,095(Am) is glutamic acid; the amino acid at position 2,096(Am) is alanine, or serine; or the amino acid at position 2,098(Am) is alanine, glycine, proline, histidine, or serine, as well as nucleic acid molecules complementary to all or a portion of the coding sequences.

As used herein, "percent (%) sequence identity" is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program BLAST available at http://blast.ncbi.nlm.nih.gov/Blast.cgi with search parameters set to default values.

The present disclosure also encompasses nucleic acid molecules that hybridize to nucleic acid molecules encoding acetyl-Coenzyme A carboxylase of the present disclosure as well as nucleic acid molecules that hybridize to the reverse complement of nucleic acid molecules encoding an acetyl-Coenzyme A carboxylase of the present disclosure. In one embodiment, nucleic acid molecules of the disclosure comprise nucleic acid molecules that hybridize to a nucleic acid molecule encoding one or more of a modified version of one or both of SEQ ID NOs: 2 and 3, wherein the sequence is modified such that the encoded protein comprises one or more of the following: the amino acid at position 1,781(Am) is leucine, threonine, valine, or alanine; the amino acid at position 1,785(Am) is glycine; the amino acid at position 1,786(Am) is proline; the amino acid at position 1,811(Am) is asparagine; the amino acid at position 1,824(Am) is proline; the amino acid at position 1,864(Am) is phenylalanine; the amino acid at position 1,999(Am) is cysteine or glycine; the amino acid at position 2,027(Am) is cysteine or arginine; the amino acid at position 2,039(Am) is glycine; the amino acid at position 2,041(Am) is asparagine; the amino acid at position 2049(Am) is phenylalanine, isoleucine or leucine; the amino acid at position 2,059(Am) is valine; the amino acid at position 2,074(Am) is leucine; the amino acid at position 2,075(Am) is leucine, isoleucine or methionine or an additional valine; the amino acid at position 2,078(Am) is glycine, or threonine; the amino acid at position 2,079(Am) is phenylalnine; the amino acid at position 2,080(Am) is glutamic acid; the amino acid at position 2,080(Am) is deleted; the amino acid at position 2,081(Am) is deleted; the amino acid at position 2,088(Am) is arginine, tryptophan, phenylalanine, glycine, histidine, lysine, leucine, serine, threonine, or valine; the amino acid at position 2,095(Am) is glutamic acid; the amino acid at position 2,096(Am) is alanine, or serine; or the amino acid at position 2,098(Am) is alanine, glycine, proline, histidine, or serine, as well as nucleic acid molecules complementary to all or a portion of the coding sequences, or the reverse complement of such nucleic acid molecules under stringent conditions. The stringency of hybridization can be controlled by temperature, ionic strength, pH, and the presence of denaturing agents such as formamide during hybridization and washing. Stringent conditions that may be used include those defined in *Current Protocols in Molecular Biology*, Vol. 1, Chap. 2.10, John Wiley & Sons, Publishers (1994) and Sambrook et al., *Molecular Cloning*, Cold Spring Harbor (1989) which are specifically incorporated herein as they relate to teaching stringent conditions.

Any of the mutants described above in a plasmid with a combination of the gene of interest can be used in transformation.

In one embodiment, the present disclosure provides expression vectors comprising nucleic acid molecules encoding any of the ACCase mutants described above.

In one embodiment, the present disclosure provides for the use of mutant ACCase nucleic acids and proteins encoded by such mutant ACCase nucleic acids as described above as selectable markers.

In one embodiment, nucleic acid molecules of the disclosure encompass oligonucleotides that may be used as hybridization probes, sequencing primers, and/or PCR primers. Such oligonucleotides may be used, for example, to determine a codon sequence at a particular position in a nucleic acid molecule encoding an acetyl-Coenzyme A carboxylase, for example, by allele specific PCR. Such oligonucleotides may be from about 15 to about 30, from about 20 to about 30, or from about 20-25 nucleotides in length.

Test for Double Mutant ACCase Genes "DBLM Assay":

(1) In a test population (of, e.g., at least 12 and preferably at least 20) whole rice plants containing 1 or 2 copies of a transgenic ACCase gene encoding an at-least-double-mutant ACCase (i.e. 1 min. and 2 max. chromosomal insertions of the transgenic ACCase gene to be tested), wherein the rice plants are T0 ("T-zero") regenerants and in parallel with a control population of such plants to be used as untreated check plants;

(2) Application to the test population at 200 L/ha spray volume of a composition comprising Tepraloxydim (AI) and 1% Crop Oil Concentrate (COC), to provide an AI application rate equivalent to 50 g/ha of Tepraloxydim (AI);

(3) Determining a phytotoxicity score for each test and check plant, based on a traditional plant injury rating system (e.g., evaluating visual evidence of herbicide burn, leaf morphology changes, wilt, yellowing, and other morphological characteristics, preferably according to a typical, at least-5-level injury rating scale);

(4) Analyzing the collected data to determine whether at least 75% of the plants in the test population exhibit an average phytotoxicity, i.e. increase in injury relative to check plants, of less than 10%, and (5) Identifying a positive result so determined as demonstrating that the double-mutant ACCase provides an acceptable AIT.

Herbicides

The present disclosure provides plants, e.g., rice plants, that are tolerant of concentrations of herbicide that normally inhibit the growth of wild-type plants. The plants are typically resistant to herbicides that interfere with acetyl-Coenzyme A carboxylase activity. Any herbicide that inhibits acetyl-Coenzyme A carboxylase activity can be used in conjunction with the plants of the invention. Suitable examples include, but are not limited to, cyclohexanedione herbicides, aryloxyphenoxy propionate herbicides, and phenylpyrazole herbicides. In some methods of controlling weeds and/or growing herbicide-tolerant plants, at least one herbicide is selected from the group consisting of sethoxydim, cycloxydim, tepraloxydim, haloxyfop, haloxyfop-P or a derivative of any of these herbicides.

Table 1 provides a list of cyclohexanedione herbicides (DIMs, also referred to as: cyclohexene oxime cyclohexanedione oxime; and CHD) that interfere with acetyl-Coenzyme A carboxylase activity and may be used in conjunction with the herbicide-tolerant plants of the invention. One skilled in the art will recognize that other herbicides in this class exist and may be used in conjunction with the herbicide-tolerant plants of the invention. Also included in Table 1 is a list of aryloxyphenoxy propionate herbicides (also referred to as aryloxyphenoxy propanoate; aryloxyphenoxyalkanoate; oxyphenoxy; APP; AOPP; APA; APPA; FOP, note that these are sometime written with the suffix '-oic') that interfere with acetyl-Coenzyme A carboxylase activity and may be used in conjunction with the herbicide-tolerant plants of the invention. One skilled in the art will recognize that other herbicides in this class exist and may be used in conjunction with the herbicide-tolerant plants of the invention.

TABLE 1

| ACCase Inhibitor | Class | Company | Examples of Synonyms and Trade Names |
|---|---|---|---|
| alloxydim | DIM | BASF | Fervin, Kusagard, NP-48Na, BAS 9021H, Carbodimedon, Zizalon |
| butroxydim | DIM | Syngenta | Falcon, ICI-A0500, Butroxydim |
| clethodim | DIM | Valent | Select, Prism, Centurion, RE-45601, Motsa |
| Clodinafop-propargyl | FOP | Syngenta | Discover, Topik, CGA 184 927 |
| clofop | FOP | | Fenofibric Acid, Alopex |
| cloproxydim | FOP | | |
| chlorazifop | FOP | | |
| cycloxydim | DIM | BASF | Focus, Laser, Stratos, BAS 517H |
| cyhalofop-butyl | FOP | Dow | Clincher, XDE 537, DEH 112, Barnstorm |
| diclofop-methyl | FOP | Bayer | Hoegrass, Hoelon, Illoxan, HOE 23408, Dichlorfop, Illoxan |
| fenoxaprop-P-ethyl | FOP | Bayer | Super Whip, Option Super, Exel Super, HOE-46360, Aclaim, Puma S. Fusion |
| fenthiaprop | FOP | | Taifun; Joker |
| fluazifop-P-butyl | FOP | Syngenta | Fusilade, Fusilade 2000, Fusilade DX, ICI-A 0009, ICI-A 0005, SL-236, IH-773B, TF-1169, Fusion |
| haloxyfop-etotyl | FOP | Dow | Gallant, DOWCO 453EE |
| haloxyfop-methyl | FOP | Dow | Verdict, DOWCO 453ME |
| haloxyfop-P-methyl | FOP | Dow | Edge, DE 535 |
| isoxapyrifop | FOP | | |
| Metamifop | FOP | Dongbu | NA |
| pinoxaden | DEN | Syngenta | Axial |
| profoxydim | DIM | BASF | Aura, Tetris, BAS 625H, Clefoxydim |
| propaquizafop | FOP | Syngenta | Agil, Shogun, Ro 17-3664, Correct |
| quizalofop-P-ethyl | FOP | DuPont | Assure, Assure II, DPX-Y6202-3, Targa Super, NC-302, Quizafop |
| quizalofop-P-tefuryl | | Uniroyal | Pantera, UBI C4874 |
| sethoxydim | DIM | BASF | Poast, Poast Plus, NABU, Fervinal, NP-55, Sertin, BAS 562H, Cyethoxydim, Rezult |
| tepraloxydim | DIM | BASF | BAS 620H, Aramo, Caloxydim |
| tralkoxydim | DIM | Syngenta | Achieve, Splendor, ICI-A0604, Tralkoxydime, Tralkoxidym |
| trifop | FOP | | |

In addition to the herbicides listed above, other ACCase-inhibitors can be used in conjunction with the herbicide-tolerant plants of the invention. For example, ACCase-inhibiting herbicides of the phenylpyrazole class, also known as DENs, can be used. An exemplary DEN is pinoxaden, which is a phenylpyrazoline-type member of this class. Herbicide compositions containing pinoxaden are sold under the brands Axial and Traxos.

The herbicidal compositions hereof comprising one or more acetyl-Coenzyme A carboxylase-inhibiting herbicides, and optionally other agronomic A.I.(s), e.g., one or more sulfonylureas (SUs) selected from the group consisting of amidosulfuron, flupyrsulfuron, foramsulfuron, imazosulfuron, iodosulfuron, mesosulfuron, nicosulfuron, thifensulfuron, and tribenuron, agronomically acceptable salts and esters thereof, or one or more imidazolinones selected from the group of imazamox, imazethapyr, imazapyr, imazapic, combinations thereof, and their agriculturally suitable salts and esters, can be used in any agronomically acceptable format. For example, these can be formulated as ready-to-spray aqueous solutions, powders, suspensions; as concentrated or highly concentrated aqueous, oily or other solutions, suspensions or dispersions; as emulsions, oil dispersions, pastes, dusts, granules, or other broadcastable formats. The herbicide compositions can be applied by any means known in the art, including, for example, spraying, atomizing, dusting, spreading, watering, seed treatment, or co-planting in admixture with the seed. The use forms depend on the intended purpose; in any case, they should ensure the finest possible distribution of the active ingredients according to the invention.

In other embodiments, where the optional A.I. includes an herbicide from a different class to which the plant(s) hereof would normally be susceptible, the plant to be used is selected from among those that further comprise a trait of tolerance to such herbicide. Such further tolerance traits can be provided to the plant by any method known in the art, e.g., including techniques of traditional breeding to obtain a tolerance trait gene by hybridization or introgression, of mutagenesis, and/or of transformation. Such plants can be described as having "stacked" traits.

In addition, any of the above acetyl-Coenzyme A carboxylase-inhibiting herbicides can be combined with one or more herbicides of another class, for example, any of the acetohydroxyacid synthase-inhibiting herbicides, EPSP synthase-inhibiting herbicides, glutamine synthase-inhibiting herbicides, lipid- or pigment-biosynthesis inhibitor herbicides, cell-membrane disruptor herbicides, photosynthesis or respiration inhibitor herbicides, or growth regulator or growth inhibitor herbicides known in the art. Non-limiting examples include those recited in Weed Science Society of America's *Herbicide Handbook*, 9th Edition edited by S. A. Senseman, copy right 2007. An herbicidal composition herein can contain one or more agricultural active ingredient (s) selected from the agriculturally-acceptable fungicides, strobilurin fungicides, insecticides (including nematicides), miticides, and molluscicides. Non-limiting examples include those recited in 2009 Crop Protection Reference (www.greenbook.net), Vance Publications.

In one embodiment of the invention, any of the above acetyl-Coenzyme A carboxylase-inhibiting herbicides are combined with herbicides which exhibit low damage to rice, whereby the rice tolerance to such herbicides may optionally be a result of genetic modifications of the crop plants. Examples of such herbicides are the acetohydroxyacid synthase-inhibiting herbicides imazamethabenz, imazamox, imazapic, imazapyr, imazaquin, imazethapyr, azimsulfuron, bensulfuron, chlorimuron, cyclosulfamuron, ethoxysulfuron, flucetosulfuron, halosulfuron, imazosulfuron, metsulfuron, orthosulfamuron, propyrisulfuron, pyrazosulfuron, bispyribac, pyrimisulfan or penoxsulam, the EPSP synthase-inhibiting herbicides glyphosate or sulfosate, the glutamine synthase-inhibiting herbicides glufosinate, glufosinate-P or bialaphos, the lipid biosynthesis inhibitor herbicides benfuresate, molinate or thiobencarb, the photosynthesis inhibitor herbicides bentazon, paraquat, prometryn or propanil, the bleacher herbicides benzobicyclone, clomazone or tefuryltrione, the auxin herbicides 2,4-D, fluroxypyr, MCPA, quinclorac, quinmerac or triclopyr, the microtubule inhibitor herbicide pendimethalin, the VLCFA inhibitor herbicides anilofos, butachlor, fentrazamide, ipfencarbazone, mefenacet, pretilachlor, acetochlor, metolachlor or S-metolachlor or the protoporphyrinogen-IX-oxidase inhibitor herbicides carfentrazone, oxadiazon, oxyfluorfen, pyraclonil or saflufenacil.

In one embodiment of the invention, any of the above acetyl-Coenzyme A carboxylase-inhibiting herbicides are combined with herbicides which exhibit low damage to cereals such as wheat, barley or rye, whereby the cereals tolerance to such herbicides may optionally be a result of genetic modifications of the crop plants. Examples of such herbicides are the acetohydroxyacid synthase-inhibiting herbicides imazamethabenz, imazamox, imazapic, imazapyr, imazaquin, imazethapyr, amidosulfuron, chlorsulfuron, flucetosulfuron, flupyrsulfuron, iodosulfuron, mesosulfuron, metsulfuron, sulfosulfuron, thifensulfuron, triasulfuron, tribenuron, tritosulfuron, florasulam, pyroxsulam, pyrimisulfan, flucarbazone, propoxycarbazone or thiencarbazone, the EPSP synthase-inhibiting herbicides glyphosate or sulfosate, the glutamine synthase-inhibiting herbicides glufosinate, glufosinate-P or bialaphos, the lipid biosynthesis inhibitor herbicides prosulfocarb, the photosynthesis inhibitor herbicides bentazon, chlorotoluron, isoproturon, ioxynil, bromoxynil, the bleacher herbicides diflufenican, flurtamone, picolinafen or pyrasulfotole, the auxin herbicides aminocyclopyrachlor, aminopyralid, 2,4-D, dicamba, fluroxypyr, MCPA, clopyralid, MCPP, or MCPP-P, the microtubule inhibitor herbicides pendimethalin or trifluralin, the VLCFA inhibitor herbicide flufenacet, or the protoporphyrinogen-IX-oxidase inhibitor herbicides bencarbazone, carfentrazone or saflufenacil, or the herbicide difenzoquat.

In one embodiment of the invention, any of the above acetyl-Coenzyme A carboxylase-inhibiting herbicides are combined with herbicides which exhibit low damage to turf, whereby the turf tolerance to such herbicides may optionally be a result of genetic modifications of the crop plants. Examples of such herbicides are the acetohydroxyacid synthase-inhibiting herbicides imazamethabenz, imazamox, imazapic, imazapyr, imazaquin, imazethapyr, flazasulfuron, foramsulfuron, halosulfuron, trifloxysulfuron, bispyribac or thiencarbazone, the EPSP synthase-inhibiting herbicides glyphosate or sulfosate, the glutamine synthase-inhibiting herbicides glufosinate, glufosinate-P or bialaphos, the photosynthesis inhibitor herbicides atrazine or bentazon, the bleacher herbicides mesotrione, picolinafen, pyrasulfotole or topramezone, the auxin herbicides aminocyclopyrachlor, aminopyralid, 2,4-D, 2,4-DB, clopyralid, dicamba, dichlorprop, dichlorprop-P, fluroxypyr, MCPA, MCPB, MCPP, MCPP-P, quinclorac, quinmerac or trichlopyr, the microtubule inhibitor herbicide pendimethalin, the VLCFA inhibitor herbicides dimethenamide, dimethenamide-P or ipfencarbazone, the protoporphyrinogen-IX-oxidase inhibitor herbicides saflufenacil or sulfentrazone, or the herbicide indaziflam.

Furthermore, any of the above acetyl-Coenzyme A carboxylase-inhibiting herbicides can be combined with safeners. Safeners are chemical compounds which prevent or reduce damage on useful plants without having a major impact on the herbicidal action of the herbicides towards unwanted plants. They can be applied either before sowings (e. g. on seed treatments, shoots or seedlings) or in the pre-emergence application or post-emergence application of the useful plant. The safeners and the aforementioned herbicides can be applied simultaneously or in succession. Suitable safeners are e. g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates. Examples of saferners are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4).

In some embodiments, an herbicidal composition hereof can comprise, e.g., a combination of: auxinic herbicide(s), e.g., dicamba; AHAS-inhibitor(s), e.g., imidazolinone(s) and/or sulfonylurea(s); ACCase-inhibitor(s); EPSPS inhibitor(s), e.g., glyphosate; glutamine synthetase inhibitor(s), e.g., glufosinate; protoporphyrinogen-IX oxidase (PPO) inhibitor(s), e.g., saflufenacil; fungicide(s), e.g., strobilurin fungicide(s) such as pyraclostrobin; and the like. In some embodiments, an herbicidal composition hereof can comprise, e.g., a combination of auxinic herbicide(s), e.g., dicamba; a microtubule inhibitor herbicide, e.g., pendimethalin and strobilurin fungicide(s) such as pyraclostrobin(s). An herbicidal composition will be selected according to the tolerances of a plant hereof, and the plant can be selected from among those having stacked tolerance traits.

The herbicides individually and/or in combination as described in the present disclosure can be used as pre-mixes or tank mixes. Such herbicides can also be incorporated into agronomically acceptable compositions.

Those skilled in the art will recognize that some of the above mentioned herbicides and/or safeners are capable of forming geometrical isomers, for example E/Z isomers. It is possible to use both, the pure isomers and mixtures thereof, in the compositions according to the invention. Furthermore, some of the above mentioned herbicides and/or safeners have one or more centers of chirality and, as a consequence, are present as enantiomers or diastereomers. It is possible to use both, the pure enantiomers and diastereomers and their mixtures, in the compositions according to the invention. In particular, some of the aryloxyphenoxy propionate herbicides are chiral, and some of them are commonly used in enantiomerically enriched or enantiopure form, e. g. clodinafop, cyhalofop, fenoxaprop-P, fluazifop-P, haloxyfop-P, metamifop, propaquizafop or quizalofop-P. As a further example, glufosinate may be used in enantiomerically enriched or enantiopure form, also known as glufosinate-P.

Those skilled in the art will recognize that any derivative of the above mentioned herbicides and/or safeners can be used in the practice of the invention, for example agriculturally suitable salts and esters.

The herbicides and/or safeners, or the herbicidal compositions comprising them, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of at least one of the acetyl-Coenzyme A carboxylase-inhibiting herbicides and potentially other herbicides and/or safeners and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives. The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on diclorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers. Liquid carriers include e.g. non-ageuos solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or concomitant grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the herbicidal compositions, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

Rice-Non-Selective ACCase-Inhibitor Herbicides

Aspects of the present disclosure relate to methods for the treatment of rice comprising providing a domestic rice crop plant with at least one herbicide that is a rice-non-selective ACCase-inhibiting herbicide. The method comprises applying an effective amount (measured in g AI/Ha) of the at least one rice-non-selective ACCase-inhibiting herbicide to the domestic rice crop plant, post-emergence; thereby creating a treated rice plant; and growing the resulting treated rice plant. In some embodiments said rice-non-selective ACCase-inhibiting herbicide includes isomers, salts or esters of the rice-non-selective ACCase-inhibiting herbicide.

Some examples of rice-non-selective ACCase-inhibiting herbicides include, but are not limited to, those shown here in Table 2.

TABLE 2

| Herbicide Class (Synonyms) | Name of Active | Example Synonyms, Isomers, Salts, Esters | Example Products |
|---|---|---|---|
| Cyclohexene Oxime (Cyclohexanedione; Cyclohexanedione oxime; CHD; DIM) | alloxydim | alloxydim-sodium | Kusaguard; Fervin Clout |
| | butroxydim | butoxydim | Falcon; Factor; Fusion Super |
| | cethoxydim | CGA215684 | |
| | clethodim | | Select; Prism |
| | cloproxydim | | Selectone |
| | cycloxydim | | Focus 10 EC; Focus Ultra; Laser; Stratos Ultra |
| | sethoxydim | cyethoxydim; sethoxydime | Poast; Rezult; Vantage |
| | tepraloxydim | caloxydim | Aramo |
| | tralkoxydim | | Achieve |
| Aryloxyphenoxy Propionate (Aryloxyphenoxyalkanoate; APP; AOPP; FOP) | chlorazifop | chlorazifop-propargyl; chloroazifop-propynyl | |
| | clodinafop | clodinafop-propargyl | Discover; Cowboy; Dynofop; Topik |
| | clofop | clofop-isobutyl | Alopex |
| | diclofop | | Hoelon; Hoegrass |
| | fenthiaprop | fenthiaprop-ethyl | Joker |
| | fluazifop | fluazifop-P | Fusilade DX; Fusion |
| | baloxyfop | haloxyfop-P | Motsa: Verdict |
| | isoxapyrifop | | |
| | propaquizafop | | Correct; Agil 100EC; Falcon; Longhorn; Shogun; Zealot |
| | quizalofop | quizalofop-P; quizafop; quizafop-P; quizalofop-P-ethyl; quizalofop-P-tefuryl | Assure II; Targa |
| | trifop | trifop-methyl | |

Field Herbicide Application

Aspects of the present disclosure relate to methods for the treatment of rice comprising providing a domestic rice crop plant in a field and at least one ACCase-inhibiting FOP herbicide. The method comprises applying an effective amount (measured in g AI/Ha) of the at least one FOP herbicide to the domestic rice crop plant, post-emergence; thereby creating a treated rice plant; and growing the resulting treated rice plant.

In other embodiments, the FOP herbicide is quizalofop or an ester thereof quizalofop or an ester thereof (e.g., the ethyl ester thereof). In some further embodiments, the effective amount of quizalofop or an ester thereof is at least 14 g AI/Ha. In other further embodiments, the effective amount of quizalofop or an ester thereof is at least 16, 18, 20, 22, 24 or 26 g AI/Ha. In still other further embodiments, the effective amount of quizalofop or an ester thereof is at least 28 g AI/Ha. In yet other further embodiments, the effective amount of quizalofop or an ester thereof is at least 32, 36 or 40 g AI/Ha.

In some embodiments, the FOP herbicide is haloxyfop. In some further embodiments, the effective amount of haloxyfop is at least 38 g AI/Ha. In other further embodiments, the effective amount of haloxyfop is at least 44, 50, 56, 62, 66 or 72 g AI/Ha. In still other further embodiments, the effective amount of haloxyfop is at least 76 g AI/Ha. In yet other further embodiments, the effective amount of haloxyfop is at least 82, 88 or 94 g AI/Ha.

In other embodiments, the FOP herbicide is fluazifop or an ester thereof (e.g., the butyl ester thereof). In some further embodiments, the effective amount of fluazifop or an ester thereof is at least 56 g AI/Ha. In other further embodiments, the effective amount of fluazifop or an ester thereof is at least 65, 74, 83, 92 or 102 g AI/Ha. In still other further embodiments, the effective amount of fluazifop or an ester thereof is at least 112 g AI/Ha. In yet other further embodiments, the effective amount of fluazifop or an ester thereof is at least 120, 130 or 140 g AI/Ha.

In some embodiments, the FOP herbicide is clodinafop or clodinafop-propargyl. In some further embodiments, the effective amount of clodinafop or clodinafop-propargyl is at least 11 g AI/Ha. In other further embodiments, the effective amount of clodinafop or clodinafop-propargyl is at least 13, 15, 17, 19 or 20 g AI/Ha. In still other further embodiments, the effective amount of clodinafop or clodinafop-propargyl is at least 22 g AI/Ha. In yet other further embodiments, the effective amount of clodinafop or clodinafop-propargyl is at least 26, 30 or 34 g AI/Ha.

In some embodiments, the FOP herbicide is diclofop or diclofop-methyl. In some further embodiments, the effective amount of diclofop or diclofop-methyl is at least 226 g AI/Ha. In other further embodiments, the effective amount of diclofop or diclofop-methyl is at least 260, 295, 330, 395 or 426 g AI/Ha. In still other further embodiments, the effective amount of diclofop or diclofop-methyl is at least 452 g AI/Ha. In yet other further embodiments, the effective amount of diclofop or diclofop-methyl is at least 480, 510 or 540 g AI/Ha.

In some embodiments, providing a domestic rice crop plant relates to planting a seed for the domestic rice crop plant and allowing the domestic rice crop plant to emerge prior to applying an effective amount of the at least one FOP herbicide.

In other embodiments, providing a domestic rice crop plant relates to transplanting the domestic rice crop plant prior to applying an effective amount of the at least one FOP herbicide.

In still other embodiments, providing a domestic rice crop plant relates to the domestic rice crop plant being previously established pre-emergence or post-emergence in a field prior to applying an effective amount of the at least one FOP herbicide post-emergence.

In some embodiments, the domestic rice crop plant was further treated pre-emergence or post-emergence with at least one additional herbicide. In some further embodiments, the at least one additional herbicide is a FOP, DIM, or DEN herbicide. In other further embodiments, the pre-emergence treatment with at least one additional herbicide is a seed coating. In still other further embodiments, the post-emergence treatment with at least one additional herbicide is prior to, concurrent with, or following the applying an effective amount of the at least one FOP herbicide to the domestic rice crop plant, post-emergence. In even other further embodiments, the DIM herbicide is selected from the group consisting of cycloxydim, sethoxydim, tepraloxydim, clethodim, and tralkoxydim.

In some embodiments, the field was previously used for the growth of a previous domestic rice crop plant that was not treated with an herbicide.

In other embodiments, the field was previously used for the growth of a previous herbicide-treated domestic rice crop plant. In some further embodiments, the previous herbicide-treated domestic rice crop plant was treated with at least one FOP, DIM, or DEN herbicide. In even other further embodiments, the DIM herbicide is selected from the group consisting of cycloxydim, sethoxydim, tepraloxydim, clethodim, and tralkoxydim.

Problem Weed Species

There are a number of weed species that present problems to the commercial cultivation of rice and that can be controlled according to the methods of the present disclosure including, but not limited to, weeds of the genera *Echinochloa* and *Leptochloa*.

Exemplary of problem *Echinochloa* species include, but are not limited to *E. colona* (common name Jungle rice), *E. crus-galli* (Barnyard grass), *E. crus-pavonis* (Gulf barnyard grass, or Gulf cockspur), *E. oryzicola* (Late Watergrass, or Late Barnyard grass; a.k.a., *E. phyllopogon* or *E. crus-galli* var. *oryzicola*), and *E. oryzoides* (Early Watergrass, or Early Barnyard grass).

Exemplary of problem *Leptochloa* species include, but are not limited to *L. chinensis* (Red sprangletop, Chinese sprangletop, or Asian sprangletop), *L. fascicularis* (Bearded sprangletop; a.k.a., *L. fusca* subspecies *fascicularis*), *L. panacea* (Mucronate sprangletop; a.k.a., *L. mucronata, L. panacea* subspecies *mucronata*, and *L. filiformis*), and *L. panicoides* (Amazon sprangletop).

Methods of Controlling Weeds

Herbicide-tolerant plants of the disclosure may be used in conjunction with an herbicide to which they are tolerant. Herbicides may be applied to the plants of the disclosure using any techniques known to those skilled in the art. Herbicides may be applied at any point in the plant cultivation process. For example, herbicides may be applied pre-planting, at planting, pre-emergence, post-emergence or combinations thereof.

Herbicide compositions hereof can be applied, e.g., as foliar treatments, soil treatments, seed treatments, or soil drenches. Application can be made, e.g., by spraying, dusting, broadcasting, or any other mode known useful in the art.

In one embodiment, herbicides may be used to control the growth of weeds that may be found growing in the vicinity of the herbicide-tolerant plants invention. In embodiments of this type, an herbicide may be applied to a plot in which herbicide-tolerant plants of the disclosure are growing in vicinity to weeds. An herbicide to which the herbicide-tolerant plant of the disclosure is tolerant may then be applied to the plot at a concentration sufficient to kill or inhibit the growth of the weed. Concentrations of herbicide sufficient to kill or inhibit the growth of weeds are known in the art.

It will be readily apparent to one of ordinary skill in the relevant arts that other suitable modifications and adaptations to the methods and applications described herein are obvious and may be made without departing from the scope of the disclosure or any embodiment thereof. Having now described the present disclosure in detail, the same will be more clearly understood by reference to the following examples, which are included herewith for purposes of illustration only and are not intended to be limiting of the invention.

Use of Tissue Culture for Selection of Herbicide

Herbicide tolerant crops offer farmers additional options for weed management. Currently, there are genetically modified (GMO) solutions available in some crop systems. Additional, mutational techniques have been used to select for altered enzyme, activities or structures that confer herbicide resistance such as the current CLEARFIELD° solutions from BASF. In the US, CLEARFIELD Rice is the premier tool for managing red rice in infested areas (USDA-ARS, 2006); however, gene flow between red rice and CLEARFIELD Rice represents a considerable risk for the AHAS tolerance since out-crossing, has been reported at up to 170 F1 hybrids/ha (Shivrain et al, 2007). Stewardship guidelines including, amongst many other aspects, alternation non CLEARFIELD Rice can limit CLEARFIELD Rice market penetration. The generation of cultivated rice with tolerance to a different mode of action (MOA) graminicides would reduce these risks and provide more tools for weed management.

One enzyme that is already a target for many different graminaceous herbicides is acetyl CoA carboxylase (ACCase, EC 6.4.1.2), which catalyzes the first committed step in fatty acid (FA) biosynthesis. Aryloxyphenoxypropionate (APP or FOP) and cyclohexanedione (CHD or DIM) type herbicides are used post-emergence in dicot crops, with the exception of cyhalofop-butyl which is selective in rice to control grass weeds. Furthermore, most of these herbicides have relatively low persistence in soil and provide growers with flexibility for weed control and crop rotation. Mutations in this enzyme are known that confer tolerance to specific sets of FOPS and/or DIMS (Liu et al, 2007; Delye et al, 2003, 2005).

Tissue culture offers an alternative approach in that single clumps of callus represent hundreds or even thousands of cells, each of which can be selected for a novel trait such as herbicide resistance (Jain, 2001). Mutations arising spontaneously in tissue culture or upon some kind of induction can be directly selected in culture and mutated events selected.

The exploitation of somaclonal variation that is inherent to in vitro tissue culture techniques has been a successful approach to selectively generate mutations that confer DIM and FOP tolerance in corn (Somers, 1996; Somers et al., 1994; Marshal et al., 1992; Parker et al., 1990) and in seashore paspalum (Heckart et al, 2009). In the case of maize, the efficiencies of producing regenerable events can be calculated. In Somers et al, 1994, sethoxydim resistant maize plants were obtained using tissue culture selection. They utilized 100 g of callus and obtained 2 tolerant lines following stepwise selection at 0.5, 1.0, 2.0, 5.0 and 10 μM sethoxydim. A calculated mutation rate in their protocol would be 2 lines/100 g of callus or 0.02 lines/g.

In the case of seashore paspalum, Heckert directly utilized a high level of sethoxydim and recovered 3 regenerable lines in approx 10,000 callus pieces or, essentially, a 0.03% rate. While not comparable, these numbers will be later used for comparison with rice tissue culture mutagenesis. In the maize work, calli were constantly culled at each selection stage with only growing callus being transferred; however, in the case of seashore paspalum, all calli were transferred at each subculture. ACCase genes as selectable markers:

Plant transformation involves the use of selectable marker genes to identify the few transformed cells or individuals from the larger group of non-transformed cells or individuals Selectable marker genes exist, but they are limited in number and availability. Alternative marker genes are required for stacking traits. In addition, the use of a selectable marker gene that confers an agronomic trait (i.e. herbicide resistance) is often desirable. The present disclosure discloses ACCase genes as selectable markers that can be added to the current limited suite of available selectable marker genes. Any of the mutants described herein can be introduced into a plasmid with a gene of interest and transformed into the whole plant, plant tissue or plant cell for use as selectable markers. A detailed method is outlined in example 7 below. The selectable markers of the inventions may be utilized to produce events that confer field tolerance to a given group of herbicides and other where cross protection has been shown (i.e., FOP's).

Modern, high throughput plant transformation systems require an effective selectable marker system; however, there is a limited number available that are acceptable in the market. Therefore, selection systems which also convey a commercial trait are always valuable. The system described herein is an effective selection system in/for plant cells which also encode for an herbicide tolerance trait suitable for use in any monocotyledonous crop.

In one embodiment, the present disclosure provides a method for selecting a transformed plant comprising introducing a nucleic acid molecule encoding a gene of interest into a plant cell, wherein the nucleic acid molecule further encodes a mutant acetyl-Coenzyme A carboxylase (ACCase) in which the amino acid sequence differs from an amino acid sequence of an ACCase of a corresponding wild-type rice plant at one amino acid position; and contacting the plant cells with an ACCase inhibitor to obtain the transformed plant, wherein said mutant ACCase confers upon the transformed plant increased herbicide tolerance as compared to the corresponding wild-type variety of the plant when expressed therein.

In one embodiment, the present disclosure provides a method of marker-assisted breeding, the method comprising breeding any plant of the disclosure with a second plant; and contacting progeny of the breeding step with an ACCase inhibitor to obtain the progeny comprising said mutant ACCase; wherein said mutant ACCase confers upon the progeny plant increased herbicide tolerance as compared to the second plant.

In one embodiment, a single ACCase gene is linked to a single gene of interest. The ACCase gene may be linked upstream or downstream of the gene of interest.

In one embodiment, the present disclosure provides for the use of ACCase nucleic acid and protein as described above in diagnostic assays. The diagnostic uses for selectable markers described herein can be employed to identify ACCase gene. Diagnostic methods can include PCR methodologies, proteins assays, labeled probes, and any other standard diagnostic methods known in the art.

EXAMPLES

Example 1: Tissue Culture Conditions

An in vitro tissue culture mutagenesis assay has been developed to isolate and characterize plant tissue (e.g., rice tissue) that is tolerant to acetyl-Coenzyme A carboxylase inhibiting herbicides, e.g., tepraloxydim, cycloxydim, and sethoxydim. The assay utilizes the somaclonal variation that is found in in vitro tissue culture. Spontaneous mutations derived from somaclonal variation can be enhanced by chemical mutagenesis and subsequent selection in a stepwise manner, on increasing concentrations of herbicide.

The present disclosure provides tissue culture conditions for encouraging growth of friable, embryogenic rice callus that is regenerable. Calli were initiated from 4 different rice cultivars encompassing both *Japonica* (Taipei 309, Nipponbare, Koshihikari) and *Indica* (*Indica* 1) varieties. Dehusked seed were surface sterilized in 70% ethanol for approximately 1 min followed by 20% commercial Clorox bleach for 20 minutes. Seeds were rinsed with sterile water and plated on callus induction media. Various callus induction media were tested. The ingredient lists for the media tested are presented in Table 3.

TABLE 3

| Ingredient | Supplier | R001M | R025M | R026M | R327M | R008M | MS711R |
|---|---|---|---|---|---|---|---|
| B5 Vitamins | Sigma | | | | | 1.0 X | |
| MS salts | Sigma | | | 1.0 X | 1.0 X | 1.0 X | 1.0 X |
| MS Vitamins | Sigma | | | 1.0 X | 1.0 X | | |
| N6 salts | Phytotech | 4.0 g/L | 4.0 g/L | | | | |
| N6 vitamins | Phytotech | 1.0 X | 1.0 X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | 30 g/L | | | |
| Sucrose | VWR | | | | | 10 g/L | 30 g/L |
| NAA | Duchefa | | | | | 50 μg/L | |
| 2,4-D | Sigma | 2.0 mg/L | | | | | 1.0 mg/L |
| $MgCl_2 \cdot 6H_2O$ | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |

TABLE 3-continued

| Ingredient | Supplier | R001M | R025M | R026M | R327M | R008M | MS711R |
|---|---|---|---|---|---|---|---|
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001M callus induction media was selected after testing numerous variations. Cultures were kept in the dark at 30° C. Embryogenic callus was subcultured to fresh media after 10-14 days.

Example 2: Selection of Herbicide-Tolerant Calli

Once tissue culture conditions were determined, further establishment of selection conditions were established through the analysis of tissue survival in kill curves with cycloxydim, tepraloxydim, sethoxydim (FIG. 1) or haloxyfop (not shown). Careful consideration of accumulation of the herbicide in the tissue, as well as its persistence and stability in the cells and the culture media was performed. Through these experiments, a sub-lethal dose has been established for the initial selection of mutated material.

Figure 2:
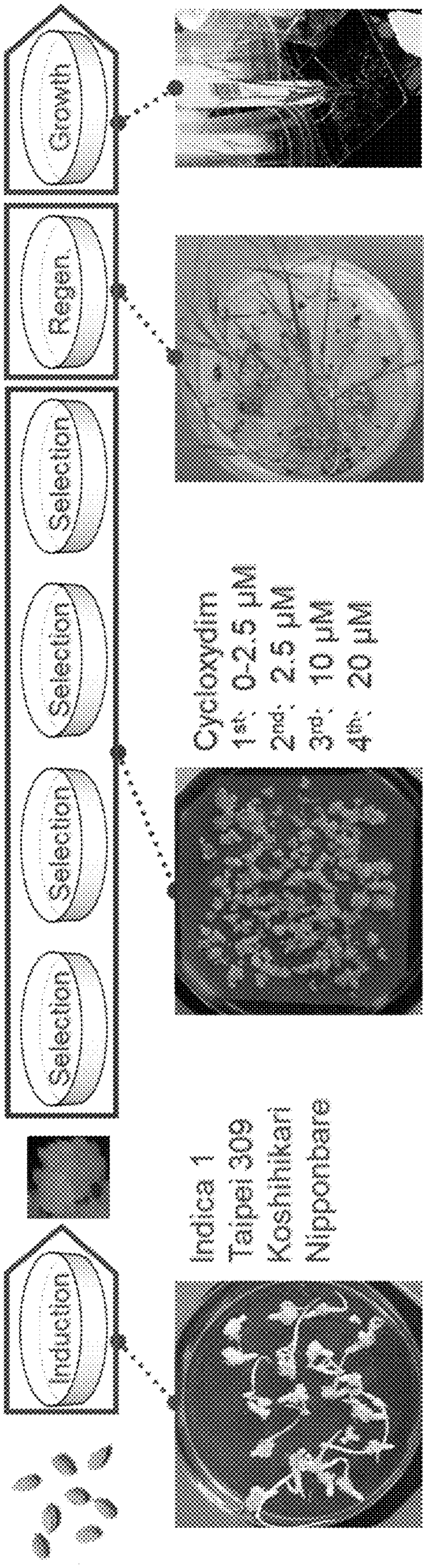
FIG. 2 is a diagram of the selection process used to produce herbicide-tolerant rice plants.

After the establishment of the starting dose of sethoxydim, cycloxydim, tepraloxydim, and haloxyfop in selection media, the tissues were selected in a step-wise fashion by increasing the concentration of the ACCase inhibitor with each transfer until cells are recovered that grew vigorously in the presence of toxic doses (see FIG. 2). The resulting calli were further subcultured every 3-4 weeks to R001M with selective agent. Over 26,000 calli were subjected to selection for 4-5 subcultures until the selective pressure was above toxic levels as determined by kill curves and observations of continued culture. Toxic levels were determined to be 50 μM sethoxydim, 20 μM cycloxydim, 2.5 μM tepraloxydim (FIG. 1) and 10 μM haloxyfop (not shown).

Alternatively, liquid cultures initiated from calli in MS711R (Table 2) with slow shaking and weekly subcultures. Once liquid cultures were established, selection agent was added directly to the flask at each subculture. Following 2-4 rounds of liquid selection, cultures were transferred to filters on solid R001M media for further growth.

Example 3: Regeneration of Plants

Tolerant tissue was regenerated and characterized molecularly for ACCase gene sequence mutations and/or biochemically for altered ACCase activity in the presence of the selective agent.

Following herbicide selection, calli were regenerated using a media regime of R025M for 10-14 days, R026M for ca. 2 weeks, R327M until well formed shoots were developed, and R008S until shoots were well rooted for transfer to the greenhouse (Table 2). Regeneration was carried out in the light. No selection agent was included during regeneration.

Once strong roots were established, M0 regenerants were transplant to the greenhouse in 4" square pots in a mixture of sand, NC Sandhills loamy soil, and Redi-earth (2:4:6) supplemented with gypsum. Transplants were maintained under a clear plastic cup until they were adapted to greenhouse conditions (ca. 1 week). The greenhouse was set to a day/night cycle of 27° C./21° C. (80° F./70° F.) with 600W high pressure sodium lights supplementing light to maintain a 14 hour day length. Plants were watered 2-3 times a day depending in the weather and fertilized daily. Rice plants selected for seed increase were transplanted into one gallon pots. As plants approached maturity and prepared to bolt, the pots were placed in small flood flats to better maintain water and nutrient delivery. Plants were monitored for insects and plant health and managed under standard Integrated Pest Management practices.

Example 4: Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368,800) as directed by the manufacturer. Isolated DNA was PCR amplified using one forward and one reverse primer.

Forward Primers:

OsACCpU5142: 5'-GCAAATGATATTACGTTCAGAGCTG-3' (SEQ ID NO:7)

OsACCpU5205: 5'-GTTACCAACCTAGCCTGTGAGAAG-3' (SEQ ID NO: 8)

Reverse Primers:

OsACCpL7100: 5'-GATTTCTTCAACAAGTTGAGCTCTTC-3' (SEQ ID NO: 9)

OsACCpL7054: 5'-AGTAACATGGAAAGACCCTGTGGC-3' (SEQ ID NO: 10)

PCR amplification was performed using Hotstar Taq DNA Polymerase (Qiagen) using touchdown thermocycling program as follows: 96° C. for 15 min, followed by 35 cycles (96° C., 30 sec; 58° C.-0.2° C. per cycle, 30 sec; 72° C., 3 min and 30 sec), 10 min at 72° C.

PCR products were verified for concentration and fragment size via agarose gel electrophoresis. Dephosphorylated PCR products were analyzed by direct sequence using the PCR primers (DNA Landmarks). Chromatogram trace files (.scf) were analyzed for mutation relative to Os05g0295300 using Vector NTI Advance 10T (Invitrogen). Based on sequence information, two mutations were identified in several individuals. I1,781(Am)L and D2,078(Am)G were present in the heterozygous state. Sequence analysis was performed on the representative chromatograms and corresponding AlignX alignment with default settings and edited to call secondary peaks.

Samples inconsistent with an ACCase mutation were spray tested for tolerance and discarded as escapes. Surprisingly, most of the recovered lines were heterozygous for the I1,781(Am)L mutation and resistant events were generated in all tested genotypes using cycloxydim or sethoxydim: *Indica*1 (≥18 lines), Taipei 309 (≥14 lines), Nipponbare (≥3 lines), and Koshihikare (?6 lines). One line was heterozygous for a D2,078(0.4m)G mutation. The D2,078(0.4m)G heterozygote line appeared stunted with narrow leaves, while the I1,781(Am)L heterozygotes varied in appearance, but most looked normal relative to their parental genotype. Several escapes were recovered and confirmed by sequencing and spray testing; however, sequencing results of the herbicide sensitive region of ACCase revealed that most tolerant mutants were heterozygous for an I1,781(Am)L, A to T mutation (See Table 4). One line, OsARWI010, was heterozygous for a D2,078(Am)G, A to G mutation. To date, all recovered plants lacking an ACCase mutation have been sensitive to herbicide application in the greenhouse.

TABLE 4

Genotype of Rice Lines Recovered via Tissue Culture Selection

| Line | Parental Genotype | Rice Type | Mutation Identified | ATCC ® Patent Deposit Designation |
|---|---|---|---|---|
| OsARWI1 | Indica 1 | *indica* | I1781(Am)L | PTA-10568 |
| OsARWI3 | Indica 1 | *indica* | I1781(Am)L | PTA-10569 |
| OsARWI8 | Indica 1 | *indica* | I1781(Am)L | PTA-10570 |
| OsARWI10 | Indica 1 | *indica* | D2078(Am)G | NA, sterile |
| OsARWI15 | Indica 1 | *indica* | I1781(Am)L | NA |
| OsHPHI2 | Indica 1 | *indica* | I1781(Am)L | PTA-10267 |
| OsHPHI3 | Indica 1 | *indica* | I1781(Am)L | NA |
| OsHPHI4 | Indica 1 | *indica* | I1781(Am)L | NA |
| OsHPHK1 | Koshihikari | *japonica* | I1781(Am)L | NA |
| OsHPHK2 | Koshihikari | *japonica* | I1781(Am)L | NA |
| OsHPHK3 | Koshihikari | *japonica* | I1781(Am)L | NA |
| OsHPHK4 | Koshihikari | *japonica* | I1781(Am)L | NA |
| OsHPHK6 | Koshihikari | *japonica* | I178](Am)L | NA |
| OsHPHN1 | Nipponbare | *japonica* | I1781(Am)L | PTA-10571 |
| OsHPHT1 | Taipei 309 | *japonica* | I1781(Am)L | NA |
| OsHPHT4 | Taipei 309 | *japonica* | I1781(Am)L | NA |
| OsHPHT6 | Taipei 309 | *japonica* | I1781(Am)L | NA |

Example 5: Demonstration of Herbicide-Tolerance

Selected mutants and escapes were transferred to small pots. Wild-type cultivars and 3 biovars of red rice were germinated from seed to serve as controls.

Figure 3:
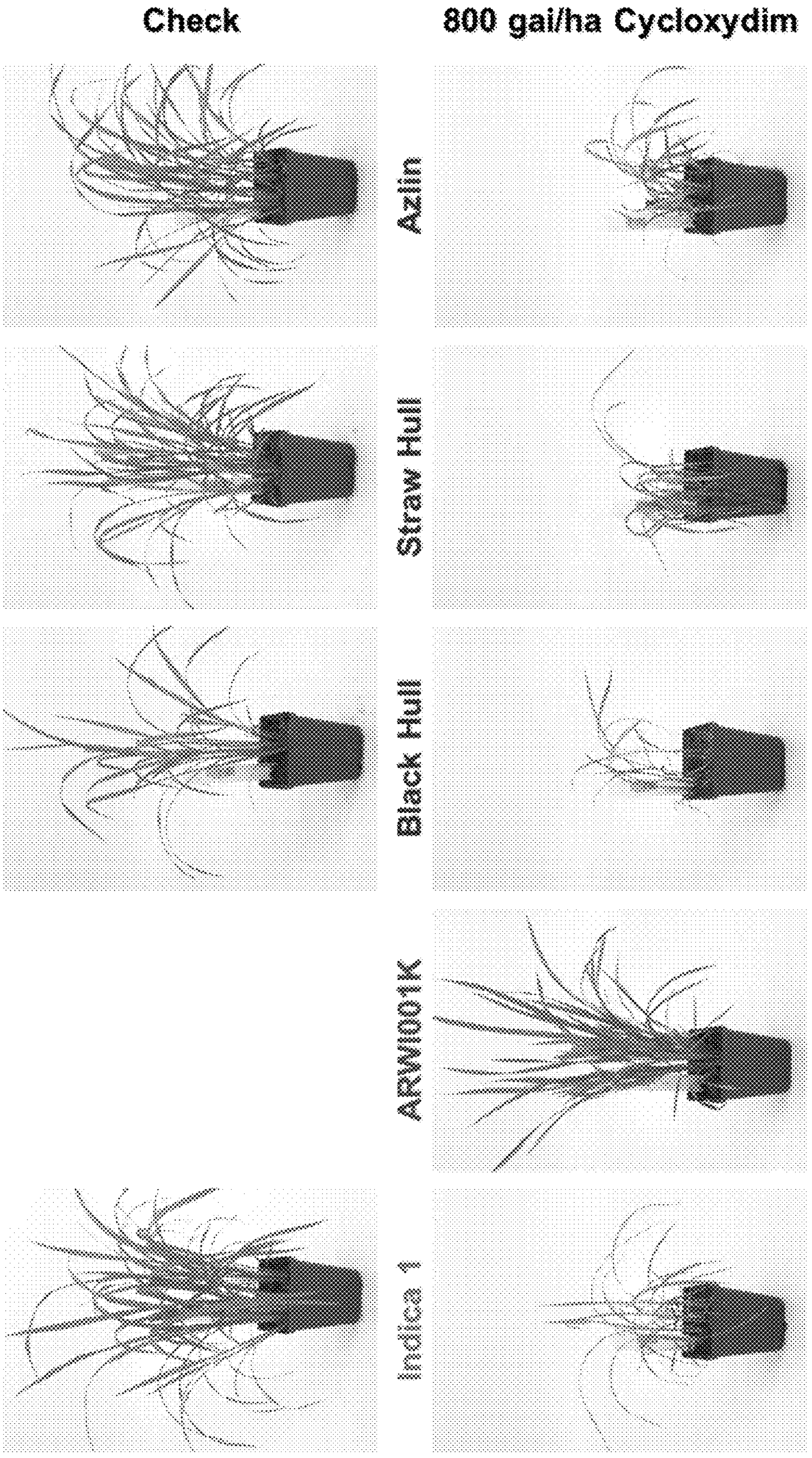
FIG. 3 shows photographs of plants taken one week after treatment with herbicide.
Figure 4:
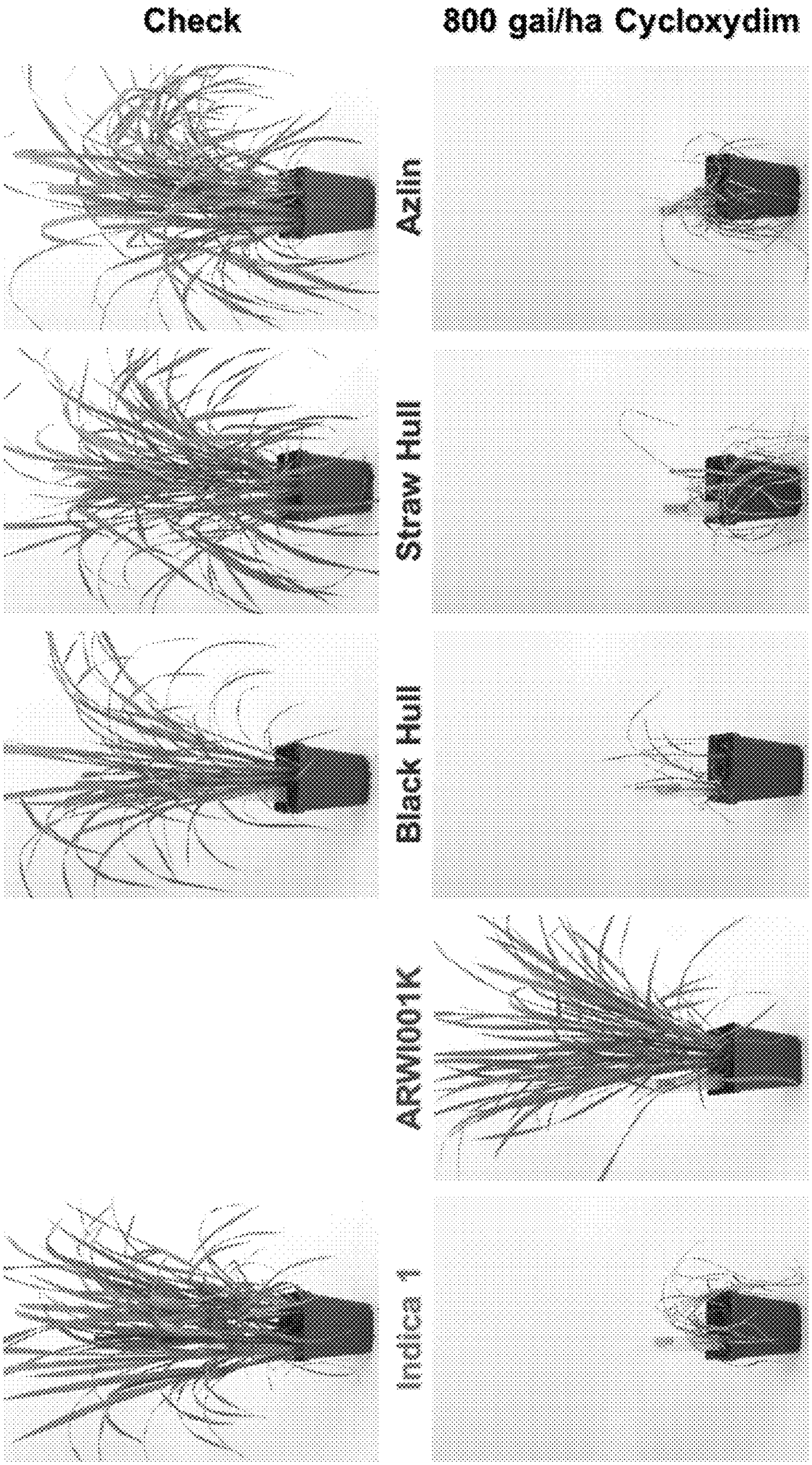
FIG. 4 shows photographs of plants taken two weeks after treatment with herbicide.
Figure 17:
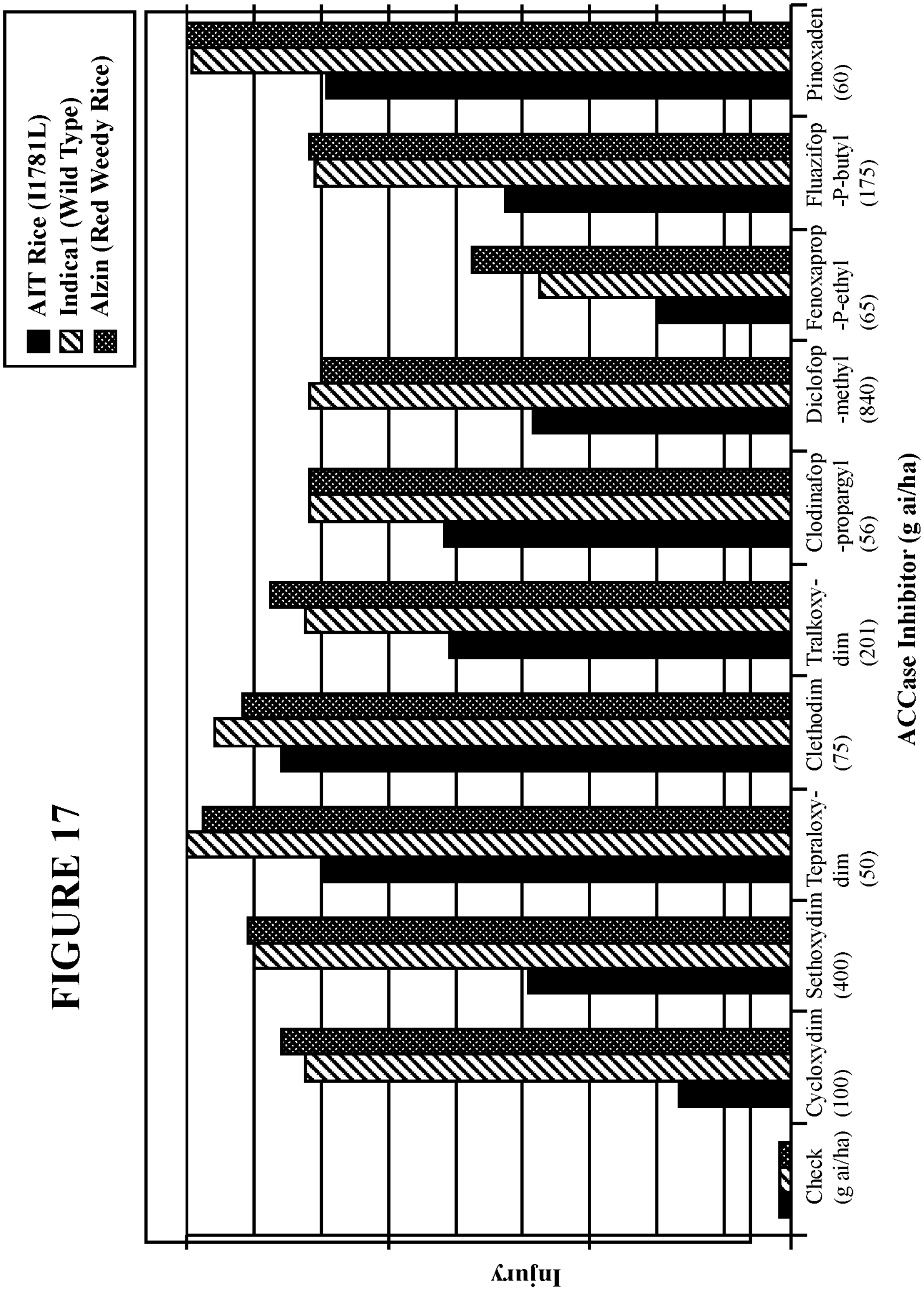
FIG. 17 provides a graph showing results for mutant rice versus various ACCase inhibitors.

After ca. 3 weeks post-transplant. M0 regenerants were sprayed using a track sprayer with 400-1600 g ai/ha cycloxydim (BAS 517H) supplemented with 0.1% methylated seed oil. After the plants had adapted to greenhouse conditions, a subset were sprayed with 800 g ai/ha cycloxydim. Once sprayed, plants were kept on drought conditions for 24 hours before being watered and fertilized again. Sprayed plants were photographed and rated for herbicide injury at 1 (FIG. 3) and 2 weeks after treatment (FIG. 4). No injury was observed on plants containing the I1,781(Am)L heterozygous mutation while control plants and tissue culture escapes (regenerated plants negative for the sequenced mutations) were heavily damaged after treatment (FIGS. 3 & 4). FIGS. 5-15 provide nucleic acid and/or amino acid sequences of acetyl-Coenzyme A carboxylase enzymes from various plants. FIG. 17 provides a graph showing results for mutant rice versus various ACCase inhibitors.

Example 6: Herbicide Selection Using Tissue Culture

Media was selected for use and kill curves developed as specified above. For selection, different techniques were utilized. Either a step wise selection was applied, or an immediate lethal level of herbicide was applied. In either case, all of the calli were transferred for each new round of selection. Selection was 4-5 cycles of culture with 3-5 weeks for each cycle. Cali were placed onto nylon membranes to: facilitate transfer (200 micron pore sheets, Biodesign, Saco, Maine). Membranes were cut to fit 100×20 mm Petri dishes and were autoclaved prior to use 25-35 calli (average weight/calli being 22 mg) were utilized in every plate. In addition, one set of calli were subjected to selection in liquid culture media with weekly subcultures followed by further selection on semi-solid media.

Mutant lines were selected using cycloxydim or sethoxydim in 4 different rice genotypes. Efficiencies of obtaining mutants was high either based on a percentage of calli that gave rise to a regenerable, mutant line or the number of lines as determined by the gram of tissue utilized. Overall, the mutation frequency compared to seashore paspalum is 5 fold and compared to maize is 2 fold. In some cases, this difference is much higher (>10 fold) as shown in Table 5 below.

TABLE 5

| Genotype | # Calli | Selection | Mutants | Rate | Weight (g) | #/gm callus |
|---|---|---|---|---|---|---|
| Indica 1 | 1865 | Cycloxidim | 3 | 0.161% | 41.04 | 0.07 |
| Indica 1 | 2640 | Sethoxydim | 3 | 0.114% | 58.08 | 0.05 |
| Koshi | 1800 | Cycloxidim | 6 | 0.333% | 39.6 | 0.15 |
| NB | 3400 | Cycloxidim | 1 | 0.029% | 74.8 | 0.01 |
| NB | 725 | Sethoxydim | 0 | 0.000% | 15.95 | 0.00 |
| T309 | 1800 | Cycloxidim | 8 | 0.444% | 36.9 | 0.20 |
| T309 | 1015 | Sethoxydim | 0 | 0.000% | 22.33 | 0.00 |
| Total | 13245 | | 21 | 0.159% | 291.39 | 0.07 |

If the data is analyzed using the criteria of selection, it is possible to see that cycloxydim selection contributes to a higher rate of mutants isolated than sethoxydim, as shown in Table 6.

TABLE 6

| Genotype | # Calli | Selection | Mutants | Rate | Weight (g) | #/gm callus |
|---|---|---|---|---|---|---|
| Indica 1 | 1865 | Cycloxidim | 3 | 0.161% | 41.03 | 0.07 |
| Koshi | 1800 | Cycloxidim | 6 | 0.333% | 39.6 | 0.15 |
| NB | 3400 | Cycloxidim | 1 | 0.029% | 74.8 | 0.01 |
| T309 | 1800 | Cycloxidim | 8 | 0.444% | 39.6 | 0.20 |
| Total | 8865 | | 18 | 0.203% | 195.03 | 0.09 |
| Indica 1 | 2640 | Sethoxydim | 3 | 0.114% | 58.08 | 0.05 |
| NB | 725 | Sethoxydim | 0 | 0.000% | 15.95 | 0.00 |
| T309 | 1015 | Sethoxydim | 0 | 0.000% | 22.33 | 0.00 |
| Total | 4380 | | 3 | 0.068% | 96.36 | 0.03 |

Using this analysis, the rate for cycloxydim is almost 10 fold higher than either of the previous reports using sethoxydim selection, whereas rates using sethoxydim selection are similar to those previously reported. Further, 68% of the lines were confirmed as mutants when selection was on cycloxydim compared to 21% of the lines when selection was on sethoxydim. Increases seem to come from using cycloxydim instead of sethoxydim as a selection agent. Further, the use of membranes made transfer of callus significantly easier than moving each piece individually during subcultures. Over 20 mutants were obtained. Fertility appears to be high with the exception of one mutant that has a mutation known to cause a fitness penalty (D2,078(Am) G).

Example 7: Use of Mutant Accase Genes as Selectable Markers in Plant Transformation Methods:

*Indica*1 and Nipponbare rice callus transformation was carried out essentially as described in Hiei and Komari (2008) with the exception of media substitutions as specified (see attached media table for details). Callus was induced on R001M media for 4-8 weeks prior to use in transformation. *Agrobacterium* utilized was LBA4404(pSB1) (Ishida et al. 1996) transformed with RLM185 (L. Mankin, unpublished: contains DsRed and a mutant AHAS for selection), ACC gene containing I1781(Am)L, ACC gene containing I1781 (Am)L and W2027C, ACC gene containing I1781(Am)L and I2041(Am)N, or ACC gene containing I1781(Am)A or wild type which also contains a mutant AHAS gene for selection. *Agrobacterium* grown for 1-3 days on solid media was suspended in M-LS-002 medium and the $OD_{660}$ adjusted to approximately 0.1. Callus was immersed in the *Agrobacterium* solution for approximately 30 minutes. Liquid was removed, and then callus was moved to filter paper for co-culture on semi-solid rice cc media. Co-culture was for 3 days in the dark at 24° C. Filters containing rice callus were directly transferred to R001M media containing Timentin for 1-2 weeks for recovery and cultured in the dark at 30° C. Callus was subdivided onto fresh R001M media with Timentin and supplemented with 100 μM Imazethapyr, 10 μM Cycloxydim or 2.5 μM Tepraloxydim. After 3-4 weeks, callus was transferred to fresh selection media. Following another 3-4 weeks, growing callus was transferred to fresh media and allowed to grow prior to Taqman analysis. Taqman analysis was for the Nos terminator and was conducted to provide for a molecular confirmation of the transgenic nature of the selected calli. Growth of transgenic calli was measured with various selection agents by subculturing calli on media containing either 10 μM Cycloxydim or Haloxyfop, 2.5 μM Tepraloxydim or 100 μM Imazethapry. Calli size was measured from scanned images following initial subculture and then after approximately 1 month of growth.

Transformation of maize immature embryos was carried out essentially as described by Lai et al (submitted). Briefly, immature embryos were co-cultured with the same *Agrobacterium* strains utilized for rice transformation suspended in M-LS-002 medium to an $OD_{660}$ of 1.0. Co-culture was on Maize CC medium for 3 days in the dark at 22° C. Embryos were removed from co-culture and transferred to M-MS-101 medium for 4-7 days at 27° C. Responding embryos were transferred to M-LS-202 medium for Imazethapyr selection or M-LS-213 media supplemented with either 1 μM Cycloxydim or 0.75 μM Tepraloxydim. Embryos were cultured for 2 weeks and growing callus was transferred to a second round of selection using the same media as previous except that Cycloxydim selection was increased to 5 μM. Selected calli were transferred to M-LS-504 or M-LS-513 media supplemented with either 5 μM Cycloxydim or 0.75 μM of Tepraloxydim for and moved to the light (16 hr/8 hr day/night) for regeneration. Shoots appeared between 2-3 weeks and were transferred to plantcon boxes containing either M-LS-618 or M-LS-613 supplemented with either 5 μM Cycloxydim or 0.75 μM of Tepraloxydim for further shoot development and rooting. Leaf samples were submitted for Taqman analysis. Positive plants were transferred to soil for growth and seed generation. In the second set of experiments, conditions were identical except that Tepraloxydim selection was decreased to 0.5 μM during regeneration and shoot and root formation. In the third set of experiments, Haloxyfop was also tested as a selection agent. In these experiments, 1 μM was used throughout for selection.

Results and Discussion:

Transgenic calli were obtained from *Indica*1 rice transformation experiments using ACC gene containing I1781 (Am)L and W2027(Am)C, and ACC gene containing I1781 (Am)L and I2041(Am)N. One callus was obtained from ACC gene containing I1781(Am)L and W2027(Am)C following Tepraloxydim selection and 3 calli were obtained from ACC gene containing I1781(Am)L and I2041(Am)N. One callus was obtained from ACC gene containing I1781 (Am)L and I2041(Am)N using Cycloxydim selection. Nos Taqman showed that all of these calli were transgenic. Calli were screened for growth under various selection agents including Imazethapry (Pursuit—P) for the mutant AHAS selectable marker.

As can be observed in Table 7, the double mutant constructs allowed for growth on both Cycloxydim and Tepraloxydim in addition to Haloxyfop. The levels utilized in these growth experiments are inhibitory for wild type material. Growth was measured as a % change in size following 1 month of culture on the selection media.

TABLE 7

Growth of transgenic Indical callus on various selection media.

| Construct | Selection μM | | | |
|---|---|---|---|---|
| | H10 | C10 | T2.5 | P100 |
| I1781(Am)L, W2027(Am)C | 1669% | 867% | 1416% | 739% |
| I1781(Am)L, I2041(Am)N | 1613% | 884% | 1360% | 634% |

Results from the first set of maize experiments reveal that both the single of the double mutant can be used to select for Cycloxydim resistance or both Cycloxydim or Tepraloxydim resistance at a relatively high efficiency (FIG. 16).

Efficiencies between selection agents was relatively comparable in these experiments with maybe a slight decrease in the overall efficiency with the single mutant on Cycloxydim compared to Pursuit selection. However, the double mutant may have a slight increased efficiency. The escape rate—the percentage of non-confirmed putative events—was lower for Cycloxydim or Tepraloxydim. Further, under the conditions described, it was possible to differentiate between the single and double mutants using Tepraloxydim selection.

Similar results have been obtained in the second set of experiments (not shown). In the third set of experiments, Haloxyfop is also an efficient selectable marker for use in transformation with either the single or the double mutant (not shown).

The single mutant is useful for high efficiency transformation using Cycloxydim or Haloxyfop selection. It should also be useful for other related compounds such as Sethoxydim. The double mutant is useful for these selection agents with the addition that Tepraloxydim can be used. The single and the double mutant can be used in a two stage transformation in that the single mutant can be differentiated from the double with Tepraloxydim selection. In combination with other current BASF selection markers, these give two more options for high efficiency transformations of monocots and maize in particular.

Herbicide tolerance phenotypes as described herein have also been exhibited by ACCase-inhibitor tolerant rice plants hereof, in the field under 600 g/ha cycloxydim treatment (data not shown).

Example 8: AIT Rice Tolerance to Herbicide Versus Red Rice

The tolerance of AIT rice to a variety of FOP, DIM and DEN herbicides was evaluated and compared to the tolerance of wild-type red rice to the same herbicides.

Methods:

Untreated AIT rice and red rice seeds were sown into fields in three separate locations and allowed to emerge. At the 3-4 leaf growth stage, plots at each location were treated with single applications of varying concentrations of herbicide. All herbicides were suspended in solutions comprising 1% methylated seed oil.

Cycloxydim was applied at a rate of 300 g AI/Ha.

Sethoxydim was applied at a rate of 600 g AI/Ha.

Tepraloxydim was applied at a rate of 50 g AI/Ha.

Clethodim was applied at a rate of 100 200 g AI/Ha.

Quizalofop-P-ethyl was applied at rates of 35, 70 and 140 g AI/Ha.

Pinoxaden was applied at rates of 30, 60 and 120 g AI/Ha.

Clodinafop-propargyl was applied at rates of 35, 70 and 140 g AI/Ha.

Percent injury to treated plants was evaluated two weeks after herbicide treatment according to procedures standard in the art.

Results:

Results are shown as the average percent injury of the three plots for each plant type treated with the given application rate of herbicide.

Figure 20A:
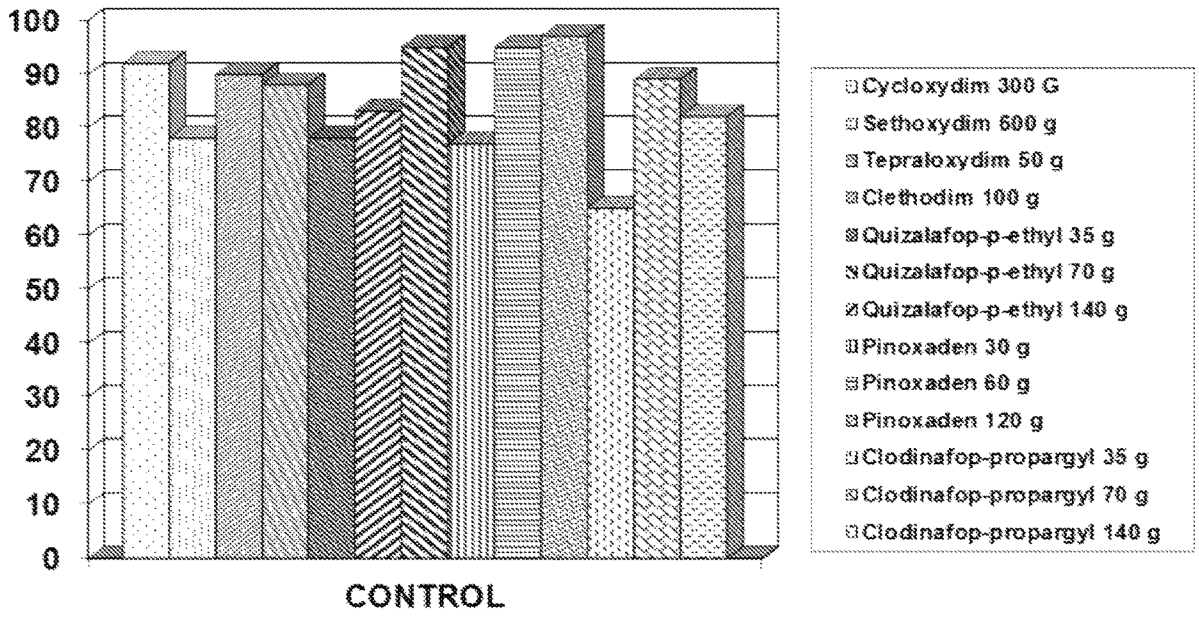
FIG. 20A shows the effect of post-emergent application of herbicides on Red rice.
Figure 20B:
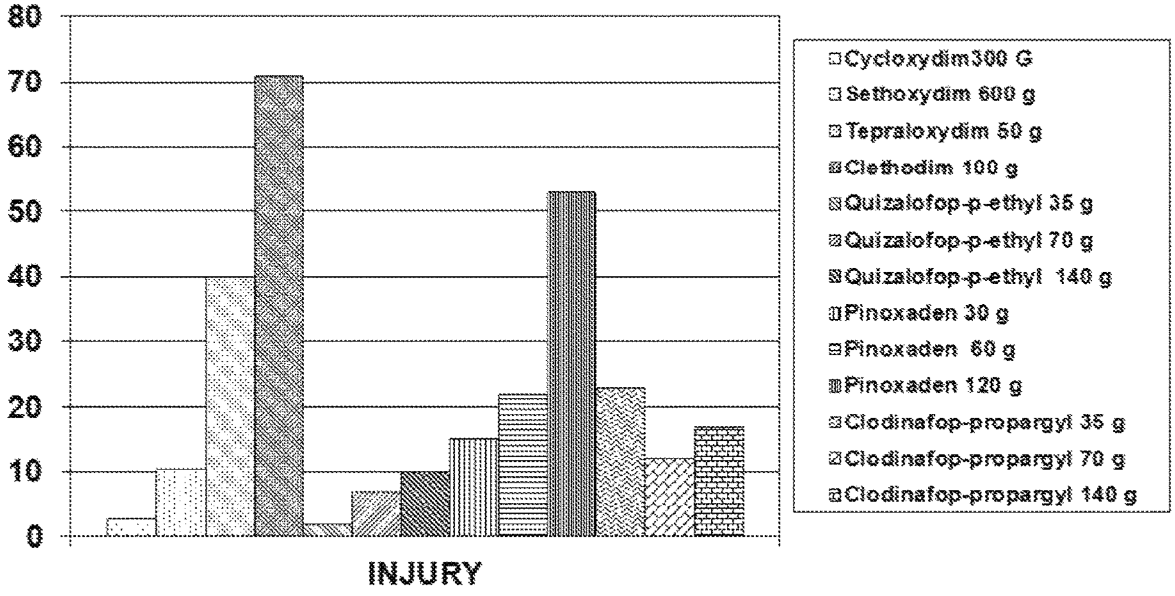
FIG. 20B shows the effect of post-emergent application of herbicides on AIT rice.

As shown in FIG. 20A, red rice suffered more injury to each herbicide at each concentration that the corresponding plots of AIT rice as shown in FIG. 20B.

The above description is for the purpose of teaching the person of ordinary skill in the art how to practice the claimed aspects of the disclosure and embodiments thereof, and it is not intended to detail all those obvious modifications and variations of it which will become apparent to the skilled worker upon reading the description. It is intended, however, that all such obvious modifications and variations be included within the scope of the present disclosure. The disclosure is intended to cover the components and steps in any sequence which is effective to meet the objectives there intended, unless the context specifically indicates the contrary. All patents and publications cited herein are entirely incorporated herein by reference.

What is claimed is:

1. A method for treating rice, comprising:

(A) providing (1) a domestic rice crop plant, the domestic rice crop plant (a) comprising and expressing an endogenous non-transfected mutant ACCase nucleic acid whose sequence encodes a multi-functional, plastidic ACCase containing an I1781(Am)L substitution; and (b) possessing a phenotype of tolerance to quizalofop or an ester thereof, wherein said plant exhibits less than 10% herbicide injury to a field application of at least 14 grams of active ingredient per hectare (g AI/ha) to 140 g AI/ha of quizalofop or an ester thereof; and (2) at least one ACCase-inhibiting aryloxyphenoxypropanoate herbicide composition comprising quizalofop or an ester thereof;

(B) applying an effective amount of the at least one aryloxyphenoxypropanoate herbicide composition to the domestic rice crop plant, post-emergence, thereby creating a treated rice plant; and (C) growing the treated rice plant;

wherein the effective amount of the at least one ACCase-inhibiting aryloxyphenoxypropanoate herbicide composition is at least 14 g AI/ha to 140 g AI/ha of quizalofop or an ester thereof.

2. The method of claim 1, further comprising harvesting seed from the treated rice plant.

3. The method of claim 1, wherein the effective amount is effective for killing a weed of the genus *Echinochloa* or of the genus *Leptochloa*.

4. The method of claim 1, wherein the effective amount is effective for killing red rice having tolerance to herbicides having a mode of action different from that of ACCase-inhibitors.

5. The method of claim 1, wherein said method is performed in a crop rotation in which said rice plant is provided in a rice field with other rice plants comprising and expressing said nucleic acid and possessing said phenotype of tolerance, the plants together composing a crop of rice plants, and said herbicide composition is applied to rice plants of said crop.

6. A method for treating rice, comprising:

(A) providing (1) a domestic rice crop plant, the domestic rice crop plant (a) comprising and expressing an endogenous non-transfected mutant ACCase nucleic acid whose sequence encodes a multi-functional, plastidic ACCase containing an I1781(Am)L substitution; and (b) possessing a phenotype of tolerance to fluazifop or an ester thereof, wherein said plant exhibits less than 10% herbicide injury to a field application of at least 56 g AI/la to 140 g AI/ha of fluazifop or an ester thereof; and (2) at least one ACCase-inhibiting aryloxyphenoxypropanoate herbicide composition comprising fluazifop or an ester thereof;

(B) applying an effective amount of the at least one aryloxyphenoxypropanoate herbicide composition to the domestic rice crop plant, post-emergence, thereby creating a treated rice plant; and (C) growing the treated rice plant;

wherein the effective amount of the at least one ACCase-inhibiting aryloxyphenoxypropanoate herbicide composition is at least 56 g AI/ha to 140 g AI/ha of fluazifop or an ester thereof.

7. The method of claim 6, further comprising harvesting seed from the treated rice plant.

8. The method of claim 6, wherein the effective amount is effective for killing a weed of the genus *Echinochloa* or of the genus *Leptochloa*.

9. The method of claim 6, wherein the effective amount is effective for killing red rice having tolerance to herbicides having a mode of action different from that of ACCase-inhibitors.

10. The method of claim 6, wherein said method is performed in a crop rotation in which said rice plant is provided in a rice field with other rice plants comprising and expressing said nucleic acid and possessing said phenotype of tolerance, the plants together composing a crop of rice plants, and said herbicide composition is applied to rice plants of said crop.

11. A method for treating rice, comprising:

(A) providing (1) a domestic rice crop plant, the domestic rice crop plant (a) comprising and expressing an endogenous non-transfected mutant ACCase nucleic acid whose sequence encodes a multi-functional, plastidic ACCase containing an I1781(Am)L substitution; and (b) possessing a phenotype of tolerance to clodinafop or clodinafop-propargyl, wherein said plant exhibits less than 10% herbicide injury to a field application of at least 70 g AI/ha to 140 g AI/ha of clodinafop-propargyl or at least 11 g AI/ha to 34 g AI/ha of clodinafop; and (2) at least one ACCase-inhibiting aryloxyphenoxypropanoate herbicide composition comprising clodinafop or clodinafop-propargyl;

(B) applying an effective amount of the at least one aryloxyphenoxypropanoate herbicide composition to the domestic rice crop plant, post-emergence, thereby creating a treated rice plant; and (C) growing the treated rice plant;

wherein the effective amount of the at least one ACCase-inhibiting aryloxyphenoxypropanoate herbicide composition is at least 70 g AI/ha to 140 g AI/ha of clodinafop-propargyl or at least 11 g AI/ha to 34 g AI/ha of clodinafop.

12. The method of claim 11, further comprising harvesting seed from the treated rice plant.

13. The method of claim 11, wherein the effective amount is effective for killing a weed of the genus *Echinochloa* or of the genus *Leptochloa*.

14. The method of claim 11, wherein the effective amount is effective for killing red rice having tolerance to herbicides having a mode of action different from that of ACCase-inhibitors.

15. The method of claim 11, wherein said method is performed in a crop rotation in which said rice plant is provided in a rice field with other rice plants comprising and expressing said nucleic acid and possessing said phenotype of tolerance, the plants together composing a crop of rice plants, and said herbicide composition is applied to rice plants of said crop.

16. A method for treating rice, comprising:

(A) providing (1) a domestic rice crop plant, the domestic rice crop plant (a) comprising and expressing an endogenous non-transfected mutant ACCase nucleic acid whose sequence encodes a multi-functional, plastidic ACCase containing an I1781(Am)L substitution; and (b) possessing a phenotype of tolerance to diclofop or diclofop-methyl, wherein said plant exhibits less than 10% herbicide injury to a field application of at least 226 g AI/ha to 540 g AI/ha of diclofop or diclofop-methyl; and (2) at least one ACCase-inhibiting aryloxyphenoxypropanoate herbicide composition comprising diclofop, or diclofop-methyl;

(B) applying an effective amount of the at least one aryloxyphenoxypropanoate herbicide composition to the domestic rice crop plant, post-emergence, thereby creating a treated rice plant; and (C) growing the treated rice plant;

wherein the effective amount of the at least one ACCase-inhibiting aryloxyphenoxypropanoate herbicide composition is at least 226 g AI/ha to 540 g AI/ha of diclofop or diclofop-methyl.

17. The method of claim 16, further comprising harvesting seed from the treated rice plant.

18. The method of claim 16, wherein the effective amount is effective for killing a weed of the genus *Echinochloa* or of the genus *Leptochloa*.

19. The method of claim 16, wherein the effective amount is effective for killing red rice having tolerance to herbicides having a mode of action different from that of ACCase-inhibitors.

20. The method of claim 16, wherein said method is performed in a crop rotation in which said rice plant is provided in a rice field with other rice plants comprising and expressing said nucleic acid and possessing said phenotype of tolerance, the plants together composing a crop of rice plants, and said herbicide composition is applied to rice plants of said crop.

* * * * *

SEQUENCE LISTING

<160> NUMBER OF SEQ ID NOS: 26

<210> SEQ ID NO 1
<211> LENGTH: 2320
<212> TYPE: PRT
<213> ORGANISM: Alopecurus myosuroides

<400> SEQUENCE: 1

Met Gly Ser Thr His Leu Pro Ile Val Gly Phe Asn Ala Ser Thr Thr
1 5 10 15

Pro Ser Leu Ser Thr Leu Arg Gln Ile Asn Ser Ala Ala Ala Ala Phe
20 25 30

Gln Ser Ser Ser Pro Ser Arg Ser Ser Lys Lys Lys Ser Arg Arg Val
35 40 45

Lys Ser Ile Arg Asp Asp Gly Asp Gly Ser Val Pro Asp Pro Ala Gly
50 55 60

His Gly Gln Ser Ile Arg Gln Gly Leu Ala Gly Ile Ile Asp Leu Pro
65 70 75 80

Lys Glu Gly Ala Ser Ala Pro Asp Val Asp Ile Ser His Gly Ser Glu
85 90 95

Asp His Lys Ala Ser Tyr Gln Met Asn Gly Ile Leu Asn Glu Ser His
100 105 110

Asn Gly Arg His Ala Ser Leu Ser Lys Val Tyr Glu Phe Cys Thr Glu
115 120 125

Leu Gly Gly Lys Thr Pro Ile His Ser Val Leu Val Ala Asn Asn Gly
130 135 140

Met Ala Ala Ala Lys Phe Met Arg Ser Val Arg Thr Trp Ala Asn Asp
145 150 155 160

Thr Phe Gly Ser Glu Lys Ala Ile Gln Leu Ile Ala Met Ala Thr Pro
165 170 175

Glu Asp Met Arg Ile Asn Ala Glu His Ile Arg Ile Ala Asp Gln Phe
180 185 190

Val Glu Val Pro Gly Gly Thr Asn Asn Asn Asn Tyr Ala Asn Val Gln

-continued

```
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
    290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Gly Lys Gly Ile Arg Lys Val
                325                 330                 335

Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
        355                 360                 365

His Leu Glu Val Gln Leu Leu Cys Asp Glu Tyr Gly Asn Val Ala Ala
    370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Ser
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
            500                 505                 510

Pro Phe Asn Phe Asp Glu Val Asp Ser Gln Trp Pro Lys Gly His Cys
        515                 520                 525

Val Ala Val Arg Ile Thr Ser Glu Asn Pro Asp Asp Gly Phe Lys Pro
    530                 535                 540

Thr Gly Gly Lys Val Lys Glu Ile Ser Phe Lys Ser Lys Pro Asn Val
545                 550                 555                 560

Trp Gly Tyr Phe Ser Val Lys Ser Gly Gly Gly Ile His Glu Phe Ala
                565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
        595                 600                 605

Glu Ile His Thr Asn Val Asp Tyr Thr Val Asp Leu Leu Asn Ala Pro
    610                 615                 620
```

```
Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
            645                 650                 655

Gly Gly Ala Leu Tyr Lys Thr Ile Thr Thr Asn Ala Glu Thr Val Ser
            660                 665                 670

Glu Tyr Val Ser Tyr Leu Ile Lys Gly Gln Ile Pro Pro Lys His Ile
        675                 680                 685

Ser Leu Val His Ser Thr Ile Ser Leu Asn Ile Glu Glu Ser Lys Tyr
    690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
            725                 730                 735

Leu Leu Met Gln Leu Asp Gly Asn Ser His Val Ile Tyr Ala Glu Glu
            740                 745                 750

Glu Ala Gly Gly Thr Arg Leu Leu Ile Asp Gly Lys Thr Cys Leu Leu
        755                 760                 765

Gln Asn Asp His Asp Pro Ser Arg Leu Leu Ala Glu Thr Pro Cys Lys
    770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
            805                 810                 815

Pro Ala Ala Gly Val Ile Asn Val Leu Leu Ser Glu Gly Gln Ala Met
            820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Gly Ser Phe Pro Glu Met Ser Leu
    850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
            885                 890                 895

Val Val Gln Asp Leu Val Trp Cys Leu Asp Thr Pro Ala Leu Pro Phe
            900                 905                 910

Leu Gln Trp Glu Glu Leu Met Ser Val Leu Ala Thr Arg Leu Pro Arg
        915                 920                 925

Arg Leu Lys Ser Glu Leu Glu Gly Lys Tyr Asn Glu Tyr Lys Leu Asn
    930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
            965                 970                 975

Ile Glu Arg Leu Val Asp Pro Leu Met Ser Leu Leu Lys Ser Tyr Glu
            980                 985                 990

Gly Gly Arg Glu Ser His Ala His  Phe Ile Val Lys Ser  Leu Phe Glu
        995                 1000                1005

Glu Tyr  Leu Ser Val Glu Glu  Leu Phe Ser Asp Gly  Ile Gln Ser
    1010                1015                1020

Asp Val  Ile Glu Arg Leu Arg  Leu Gln Tyr Ser Lys  Asp Leu Gln
    1025                1030                1035
```

Lys Val Val Asp Ile Val Leu Ser His Gln Gly Val Arg Asn Lys
1040 1045 1050

Thr Lys Leu Ile Leu Ala Leu Met Glu Lys Leu Val Tyr Pro Asn
1055 1060 1065

Pro Ala Ala Tyr Arg Asp Gln Leu Ile Arg Phe Ser Ser Leu Asn
1070 1075 1080

His Lys Arg Tyr Tyr Lys Leu Ala Leu Lys Ala Ser Glu Leu Leu
1085 1090 1095

Glu Gln Thr Lys Leu Ser Glu Leu Arg Thr Ser Ile Ala Arg Asn
1100 1105 1110

Leu Ser Ala Leu Asp Met Phe Thr Glu Glu Lys Ala Asp Phe Ser
1115 1120 1125

Leu Gln Asp Arg Lys Leu Ala Ile Asn Glu Ser Met Gly Asp Leu
1130 1135 1140

Val Thr Ala Pro Leu Pro Val Glu Asp Ala Leu Val Ser Leu Phe
1145 1150 1155

Asp Cys Thr Asp Gln Thr Leu Gln Gln Arg Val Ile Gln Thr Tyr
1160 1165 1170

Ile Ser Arg Leu Tyr Gln Pro Gln Leu Val Lys Asp Ser Ile Gln
1175 1180 1185

Leu Lys Tyr Gln Asp Ser Gly Val Ile Ala Leu Trp Glu Phe Thr
1190 1195 1200

Glu Gly Asn His Glu Lys Arg Leu Gly Ala Met Val Ile Leu Lys
1205 1210 1215

Ser Leu Glu Ser Val Ser Thr Ala Ile Gly Ala Ala Leu Lys Asp
1220 1225 1230

Ala Ser His Tyr Ala Ser Ser Ala Gly Asn Thr Val His Ile Ala
1235 1240 1245

Leu Leu Asp Ala Asp Thr Gln Leu Asn Thr Thr Glu Asp Ser Gly
1250 1255 1260

Asp Asn Asp Gln Ala Gln Asp Lys Met Asp Lys Leu Ser Phe Val
1265 1270 1275

Leu Lys Gln Asp Val Val Met Ala Asp Leu Arg Ala Ala Asp Val
1280 1285 1290

Lys Val Val Ser Cys Ile Val Gln Arg Asp Gly Ala Ile Met Pro
1295 1300 1305

Met Arg Arg Thr Phe Leu Leu Ser Glu Glu Lys Leu Cys Tyr Glu
1310 1315 1320

Glu Glu Pro Ile Leu Arg His Val Glu Pro Pro Leu Ser Ala Leu
1325 1330 1335

Leu Glu Leu Asp Lys Leu Lys Val Lys Gly Tyr Asn Glu Met Lys
1340 1345 1350

Tyr Thr Pro Ser Arg Asp Arg Gln Trp His Ile Tyr Thr Leu Arg
1355 1360 1365

Asn Thr Glu Asn Pro Lys Met Leu His Arg Val Phe Phe Arg Thr
1370 1375 1380

Leu Val Arg Gln Pro Ser Ala Gly Asn Arg Phe Thr Ser Asp His
1385 1390 1395

Ile Thr Asp Val Glu Val Gly His Ala Glu Glu Pro Leu Ser Phe
1400 1405 1410

Thr Ser Ser Ser Ile Leu Lys Ser Leu Lys Ile Ala Lys Glu Glu
1415 1420 1425

Leu Glu Leu His Ala Ile Arg Thr Gly His Ser His Met Tyr Leu

-continued

```
    1430                1435                1440

Cys Ile  Leu Lys Glu Gln Lys  Leu Leu Asp Leu Val  Pro Val Ser
    1445                1450                1455

Gly Asn  Thr Val Val Asp Val  Gly Gln Asp Glu Ala  Thr Ala Cys
    1460                1465                1470

Ser Leu  Leu Lys Glu Met Ala  Leu Lys Ile His Glu  Leu Val Gly
    1475                1480                1485

Ala Arg  Met His His Leu Ser  Val Cys Gln Trp Glu  Val Lys Leu
    1490                1495                1500

Lys Leu  Val Ser Asp Gly Pro  Ala Ser Gly Ser Trp  Arg Val Val
    1505                1510                1515

Thr Thr  Asn Val Thr Gly His  Thr Cys Thr Val Asp  Ile Tyr Arg
    1520                1525                1530

Glu Val  Glu Asp Thr Glu Ser  Gln Lys Leu Val Tyr  His Ser Thr
    1535                1540                1545

Ala Leu  Ser Ser Gly Pro Leu  His Gly Val Ala Leu  Asn Thr Ser
    1550                1555                1560

Tyr Gln  Pro Leu Ser Val Ile  Asp Leu Lys Arg Cys  Ser Ala Arg
    1565                1570                1575

Asn Asn  Lys Thr Thr Tyr Cys  Tyr Asp Phe Pro Leu  Thr Phe Glu
    1580                1585                1590

Ala Ala  Val Gln Lys Ser Trp  Ser Asn Ile Ser Ser  Glu Asn Asn
    1595                1600                1605

Gln Cys  Tyr Val Lys Ala Thr  Glu Leu Val Phe Ala  Glu Lys Asn
    1610                1615                1620

Gly Ser  Trp Gly Thr Pro Ile  Ile Pro Met Gln Arg  Ala Ala Gly
    1625                1630                1635

Leu Asn  Asp Ile Gly Met Val  Ala Trp Ile Leu Asp  Met Ser Thr
    1640                1645                1650

Pro Glu  Phe Pro Ser Gly Arg  Gln Ile Ile Val Ile  Ala Asn Asp
    1655                1660                1665

Ile Thr  Phe Arg Ala Gly Ser  Phe Gly Pro Arg Glu  Asp Ala Phe
    1670                1675                1680

Phe Glu  Ala Val Thr Asn Leu  Ala Cys Glu Lys Lys  Leu Pro Leu
    1685                1690                1695

Ile Tyr  Leu Ala Ala Asn Ser  Gly Ala Arg Ile Gly  Ile Ala Asp
    1700                1705                1710

Glu Val  Lys Ser Cys Phe Arg  Val Gly Trp Thr Asp  Asp Ser Ser
    1715                1720                1725

Pro Glu  Arg Gly Phe Arg Tyr  Ile Tyr Met Thr Asp  Glu Asp His
    1730                1735                1740

Asp Arg  Ile Gly Ser Ser Val  Ile Ala His Lys Met  Gln Leu Asp
    1745                1750                1755

Ser Gly  Glu Ile Arg Trp Val  Ile Asp Ser Val Val  Gly Lys Glu
    1760                1765                1770

Asp Gly  Leu Gly Val Glu Asn  Ile His Gly Ser Ala  Ala Ile Ala
    1775                1780                1785

Ser Ala  Tyr Ser Arg Ala Tyr  Glu Glu Thr Phe Thr  Leu Thr Phe
    1790                1795                1800

Val Thr  Gly Arg Thr Val Gly  Ile Gly Ala Tyr Leu  Ala Arg Leu
    1805                1810                1815

Gly Ile  Arg Cys Ile Gln Arg  Ile Asp Gln Pro Ile  Ile Leu Thr
    1820                1825                1830
```

```
Gly Phe  Ser Ala Leu Asn Lys  Leu Leu Gly Arg Glu  Val Tyr Ser
    1835                 1840                 1845

Ser His  Met Gln Leu Gly Gly  Pro Lys Ile Met Ala  Thr Asn Gly
    1850                 1855                 1860

Val Val  His Leu Thr Val Pro  Asp Asp Leu Glu Gly  Val Ser Asn
    1865                 1870                 1875

Ile Leu  Arg Trp Leu Ser Tyr  Val Pro Ala Asn Ile  Gly Gly Pro
    1880                 1885                 1890

Leu Pro  Ile Thr Lys Ser Leu  Asp Pro Ile Asp Arg  Pro Val Ala
    1895                 1900                 1905

Tyr Ile  Pro Glu Asn Thr Cys  Asp Pro Arg Ala Ala  Ile Ser Gly
    1910                 1915                 1920

Ile Asp  Asp Ser Gln Gly Lys  Trp Leu Gly Gly Met  Phe Asp Lys
    1925                 1930                 1935

Asp Ser  Phe Val Glu Thr Phe  Glu Gly Trp Ala Lys  Thr Val Val
    1940                 1945                 1950

Thr Gly  Arg Ala Lys Leu Gly  Gly Ile Pro Val Gly  Val Ile Ala
    1955                 1960                 1965

Val Glu  Thr Gln Thr Met Met  Gln Leu Val Pro Ala  Asp Pro Gly
    1970                 1975                 1980

Gln Pro  Asp Ser His Glu Arg  Ser Val Pro Arg Ala  Gly Gln Val
    1985                 1990                 1995

Trp Phe  Pro Asp Ser Ala Thr  Lys Thr Ala Gln Ala  Met Leu Asp
    2000                 2005                 2010

Phe Asn  Arg Glu Gly Leu Pro  Leu Phe Ile Leu Ala  Asn Trp Arg
    2015                 2020                 2025

Gly Phe  Ser Gly Gly Gln Arg  Asp Leu Phe Glu Gly  Ile Leu Gln
    2030                 2035                 2040

Ala Gly  Ser Thr Ile Val Glu  Asn Leu Arg Thr Tyr  Asn Gln Pro
    2045                 2050                 2055

Ala Phe  Val Tyr Ile Pro Lys  Ala Ala Glu Leu Arg  Gly Gly Ala
    2060                 2065                 2070

Trp Val  Val Ile Asp Ser Lys  Ile Asn Pro Asp Arg  Ile Glu Cys
    2075                 2080                 2085

Tyr Ala  Glu Arg Thr Ala Lys  Gly Asn Val Leu Glu  Pro Gln Gly
    2090                 2095                 2100

Leu Ile  Glu Ile Lys Phe Arg  Ser Glu Glu Leu Lys  Glu Cys Met
    2105                 2110                 2115

Gly Arg  Leu Asp Pro Glu Leu  Ile Asp Leu Lys Ala  Arg Leu Gln
    2120                 2125                 2130

Gly Ala  Asn Gly Ser Leu Ser  Asp Gly Glu Ser Leu  Gln Lys Ser
    2135                 2140                 2145

Ile Glu  Ala Arg Lys Lys Gln  Leu Leu Pro Leu Tyr  Thr Gln Ile
    2150                 2155                 2160

Ala Val  Arg Phe Ala Glu Leu  His Asp Thr Ser Leu  Arg Met Ala
    2165                 2170                 2175

Ala Lys  Gly Val Ile Arg Lys  Val Val Asp Trp Glu  Asp Ser Arg
    2180                 2185                 2190

Ser Phe  Phe Tyr Lys Arg Leu  Arg Arg Arg Leu Ser  Glu Asp Val
    2195                 2200                 2205

Leu Ala  Lys Glu Ile Arg Gly  Val Ile Gly Glu Lys  Phe Pro His
    2210                 2215                 2220
```

-continued

```
Lys Ser  Ala Ile Glu Leu Ile  Lys Lys Trp Tyr Leu  Ala Ser Glu
    2225                2230                2235

Ala Ala  Ala Ala Gly Ser Thr  Asp Trp Asp Asp Asp  Asp Ala Phe
    2240                2245                2250

Val Ala  Trp Arg Glu Asn Pro  Glu Asn Tyr Lys Glu  Tyr Ile Lys
    2255                2260                2265

Glu Leu  Arg Ala Gln Arg Val  Ser Arg Leu Leu Ser  Asp Val Ala
    2270                2275                2280

Gly Ser  Ser Ser Asp Leu Gln  Ala Leu Pro Gln Gly  Leu Ser Met
    2285                2290                2295

Leu Leu  Asp Lys Met Asp Pro  Ser Lys Arg Ala Gln  Phe Ile Glu
    2300                2305                2310

Glu Val  Met Lys Val Leu Lys
    2315                2320


<210> SEQ ID NO 2
<211> LENGTH: 2327
<212> TYPE: PRT
<213> ORGANISM: Oryza sativa

<400> SEQUENCE: 2

Met Thr Ser Thr His Val Ala Thr Leu Gly Val Gly Ala Gln Ala Pro
1               5                   10                  15

Pro Arg His Gln Lys Lys Ser Ala Gly Thr Ala Phe Val Ser Ser Gly
            20                  25                  30

Ser Ser Arg Pro Ser Tyr Arg Lys Asn Gly Gln Arg Thr Arg Ser Leu
        35                  40                  45

Arg Glu Glu Ser Asn Gly Gly Val Ser Asp Ser Lys Lys Leu Asn His
    50                  55                  60

Ser Ile Arg Gln Gly Leu Ala Gly Ile Ile Asp Leu Pro Asn Asp Ala
65                  70                  75                  80

Ala Ser Glu Val Asp Ile Ser His Gly Ser Glu Asp Pro Arg Gly Pro
                85                  90                  95

Thr Val Pro Gly Ser Tyr Gln Met Asn Gly Ile Ile Asn Glu Thr His
            100                 105                 110

Asn Gly Arg His Ala Ser Val Ser Lys Val Val Glu Phe Cys Thr Ala
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Leu Arg Ile Asn Ala Glu His Ile Arg Ile Ala Asp Gln Phe
            180                 185                 190

Val Glu Val Pro Gly Gly Thr Asn Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met His Ala
                245                 250                 255

Leu Gly Asp Lys Val Gly Ser Ala Leu Ile Ala Gln Ala Ala Gly Val
            260                 265                 270
```

-continued

```
Pro Thr Leu Ala Trp Ser Gly Ser His Val Glu Val Pro Leu Glu Cys
        275                 280                 285

Cys Leu Asp Ser Ile Pro Asp Glu Met Tyr Arg Lys Ala Cys Val Thr
    290                 295                 300

Thr Thr Glu Glu Ala Val Ala Ser Cys Gln Val Val Gly Tyr Pro Ala
305                 310                 315                 320

Met Ile Lys Ala Ser Trp Gly Gly Gly Gly Lys Gly Ile Arg Lys Val
                325                 330                 335

His Asn Asp Asp Glu Val Arg Thr Leu Phe Lys Gln Val Gln Gly Glu
            340                 345                 350

Val Pro Gly Ser Pro Ile Phe Ile Met Arg Leu Ala Ala Gln Ser Arg
        355                 360                 365

His Leu Glu Val Gln Leu Leu Cys Asp Gln Tyr Gly Asn Val Ala Ala
    370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Trp
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asn
                485                 490                 495

His Gly Gly Gly Tyr Asp Leu Trp Arg Lys Thr Ala Ala Leu Ala Thr
            500                 505                 510

Pro Phe Asn Phe Asp Glu Val Asp Ser Lys Trp Pro Lys Gly His Cys
        515                 520                 525

Val Ala Val Arg Ile Thr Ser Glu Asp Pro Asp Asp Gly Phe Lys Pro
    530                 535                 540

Thr Gly Gly Lys Val Lys Glu Ile Ser Phe Lys Ser Lys Pro Asn Val
545                 550                 555                 560

Trp Ala Tyr Phe Ser Val Lys Ser Gly Gly Gly Ile His Glu Phe Ala
                565                 570                 575

Asp Ser Gln Phe Gly His Val Phe Ala Tyr Gly Thr Thr Arg Ser Ala
            580                 585                 590

Ala Ile Thr Thr Met Ala Leu Ala Leu Lys Glu Val Gln Ile Arg Gly
        595                 600                 605

Glu Ile His Ser Asn Val Asp Tyr Thr Val Asp Leu Leu Asn Ala Ser
    610                 615                 620

Asp Phe Arg Glu Asn Lys Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Val Thr Ala Asn Thr Ala Thr Val Ser
            660                 665                 670

Asp Tyr Val Gly Tyr Leu Thr Lys Gly Gln Ile Pro Pro Lys His Ile
        675                 680                 685
```

-continued

```
Ser Leu Val Tyr Thr Thr Val Ala Leu Asn Ile Asp Gly Lys Lys Tyr
    690                 695                 700

Thr Ile Asp Thr Val Arg Ser Gly His Gly Ser Tyr Arg Leu Arg Met
705                 710                 715                 720

Asn Gly Ser Thr Val Asp Ala Asn Val Gln Ile Leu Cys Asp Gly Gly
                725                 730                 735

Leu Leu Met Gln Leu Asp Gly Asn Ser His Val Ile Tyr Ala Glu Glu
            740                 745                 750

Glu Ala Ser Gly Thr Arg Leu Leu Ile Asp Gly Lys Thr Cys Met Leu
        755                 760                 765

Gln Asn Asp His Asp Pro Ser Lys Leu Leu Ala Glu Thr Pro Cys Lys
    770                 775                 780

Leu Leu Arg Phe Leu Val Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ser Gly Val Ile His Val Val Met Ser Glu Gly Gln Ala Met
            820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Asp Thr Phe Pro Gln Met Gly Leu
    850                 855                 860

Pro Ile Ala Ala Ser Gly Gln Val His Lys Leu Cys Ala Ala Ser Leu
865                 870                 875                 880

Asn Ala Cys Arg Met Ile Leu Ala Gly Tyr Glu His Asp Ile Asp Lys
                885                 890                 895

Val Val Pro Glu Leu Val Tyr Cys Leu Asp Thr Pro Glu Leu Pro Phe
            900                 905                 910

Leu Gln Trp Glu Glu Leu Met Ser Val Leu Ala Thr Arg Leu Pro Arg
        915                 920                 925

Asn Leu Lys Ser Glu Leu Glu Gly Lys Tyr Glu Glu Tyr Lys Val Lys
    930                 935                 940

Phe Asp Ser Gly Ile Ile Asn Asp Phe Pro Ala Asn Met Leu Arg Val
945                 950                 955                 960

Ile Ile Glu Glu Asn Leu Ala Cys Gly Ser Glu Lys Glu Lys Ala Thr
                965                 970                 975

Asn Glu Arg Leu Val Glu Pro Leu Met Ser Leu Leu Lys Ser Tyr Glu
            980                 985                 990

Gly Gly Arg Glu Ser His Ala His  Phe Val Val Lys Ser  Leu Phe Glu
        995                 1000                1005

Glu Tyr  Leu Tyr Val Glu Glu  Leu Phe Ser Asp Gly  Ile Gln Ser
    1010                1015                1020

Asp Val  Ile Glu Arg Leu Arg  Leu Gln His Ser Lys  Asp Leu Gln
    1025                1030                1035

Lys Val  Val Asp Ile Val Leu  Ser His Gln Ser Val  Arg Asn Lys
    1040                1045                1050

Thr Lys  Leu Ile Leu Lys Leu  Met Glu Ser Leu Val  Tyr Pro Asn
    1055                1060                1065

Pro Ala  Ala Tyr Arg Asp Gln  Leu Ile Arg Phe Ser  Ser Leu Asn
    1070                1075                1080

His Lys  Ala Tyr Tyr Lys Leu  Ala Leu Lys Ala Ser  Glu Leu Leu
    1085                1090                1095

Glu Gln  Thr Lys Leu Ser Glu  Leu Arg Ala Arg Ile  Ala Arg Ser
```

```
    1100                1105                1110

Leu Ser  Glu Leu Glu Met Phe  Thr Glu Glu Ser Lys  Gly Leu Ser
    1115                1120                1125

Met His  Lys Arg Glu Ile Ala  Ile Lys Glu Ser Met  Glu Asp Leu
    1130                1135                1140

Val Thr  Ala Pro Leu Pro Val  Glu Asp Ala Leu Ile  Ser Leu Phe
    1145                1150                1155

Asp Cys  Ser Asp Thr Thr Val  Gln Gln Arg Val Ile  Glu Thr Tyr
    1160                1165                1170

Ile Ala  Arg Leu Tyr Gln Pro  His Leu Val Lys Asp  Ser Ile Lys
    1175                1180                1185

Met Lys  Trp Ile Glu Ser Gly  Val Ile Ala Leu Trp  Glu Phe Pro
    1190                1195                1200

Glu Gly  His Phe Asp Ala Arg  Asn Gly Gly Ala Val  Leu Gly Asp
    1205                1210                1215

Lys Arg  Trp Gly Ala Met Val  Ile Val Lys Ser Leu  Glu Ser Leu
    1220                1225                1230

Ser Met  Ala Ile Arg Phe Ala  Leu Lys Glu Thr Ser  His Tyr Thr
    1235                1240                1245

Ser Ser  Glu Gly Asn Met Met  His Ile Ala Leu Leu  Gly Ala Asp
    1250                1255                1260

Asn Lys  Met His Ile Ile Gln  Glu Ser Gly Asp Asp  Ala Asp Arg
    1265                1270                1275

Ile Ala  Lys Leu Pro Leu Ile  Leu Lys Asp Asn Val  Thr Asp Leu
    1280                1285                1290

His Ala  Ser Gly Val Lys Thr  Ile Ser Phe Ile Val  Gln Arg Asp
    1295                1300                1305

Glu Ala  Arg Met Thr Met Arg  Arg Thr Phe Leu Trp  Ser Asp Glu
    1310                1315                1320

Lys Leu  Ser Tyr Glu Glu Glu  Pro Ile Leu Arg His  Val Glu Pro
    1325                1330                1335

Pro Leu  Ser Ala Leu Leu Glu  Leu Asp Lys Leu Lys  Val Lys Gly
    1340                1345                1350

Tyr Asn  Glu Met Lys Tyr Thr  Pro Ser Arg Asp Arg  Gln Trp His
    1355                1360                1365

Ile Tyr  Thr Leu Arg Asn Thr  Glu Asn Pro Lys Met  Leu His Arg
    1370                1375                1380

Val Phe  Phe Arg Thr Leu Val  Arg Gln Pro Ser Val  Ser Asn Lys
    1385                1390                1395

Phe Ser  Ser Gly Gln Ile Gly  Asp Met Glu Val Gly  Ser Ala Glu
    1400                1405                1410

Glu Pro  Leu Ser Phe Thr Ser  Thr Ser Ile Leu Arg  Ser Leu Met
    1415                1420                1425

Thr Ala  Ile Glu Glu Leu Glu  Leu His Ala Ile Arg  Thr Gly His
    1430                1435                1440

Ser His  Met Tyr Leu His Val  Leu Lys Glu Gln Lys  Leu Leu Asp
    1445                1450                1455

Leu Val  Pro Val Ser Gly Asn  Thr Val Leu Asp Val  Gly Gln Asp
    1460                1465                1470

Glu Ala  Thr Ala Tyr Ser Leu  Leu Lys Glu Met Ala  Met Lys Ile
    1475                1480                1485

His Glu  Leu Val Gly Ala Arg  Met His His Leu Ser  Val Cys Gln
    1490                1495                1500
```

-continued

```
Trp Glu  Val Lys Leu Lys Leu  Asp Cys Asp Gly Pro  Ala Ser Gly
    1505                 1510                 1515

Thr Trp  Arg Ile Val Thr Thr  Asn Val Thr Ser His  Thr Cys Thr
    1520                 1525                 1530

Val Asp  Ile Tyr Arg Glu Met  Glu Asp Lys Glu Ser  Arg Lys Leu
    1535                 1540                 1545

Val Tyr  His Pro Ala Thr Pro  Ala Ala Gly Pro Leu  His Gly Val
    1550                 1555                 1560

Ala Leu  Asn Asn Pro Tyr Gln  Pro Leu Ser Val Ile  Asp Leu Lys
    1565                 1570                 1575

Arg Cys  Ser Ala Arg Asn Asn  Arg Thr Thr Tyr Cys  Tyr Asp Phe
    1580                 1585                 1590

Pro Leu  Ala Phe Glu Thr Ala  Val Arg Lys Ser Trp  Ser Ser Ser
    1595                 1600                 1605

Thr Ser  Gly Ala Ser Lys Gly  Val Glu Asn Ala Gln  Cys Tyr Val
    1610                 1615                 1620

Lys Ala  Thr Glu Leu Val Phe  Ala Asp Lys His Gly  Ser Trp Gly
    1625                 1630                 1635

Thr Pro  Leu Val Gln Met Asp  Arg Pro Ala Gly Leu  Asn Asp Ile
    1640                 1645                 1650

Gly Met  Val Ala Trp Thr Leu  Lys Met Ser Thr Pro  Glu Phe Pro
    1655                 1660                 1665

Ser Gly  Arg Glu Ile Ile Val  Val Ala Asn Asp Ile  Thr Phe Arg
    1670                 1675                 1680

Ala Gly  Ser Phe Gly Pro Arg  Glu Asp Ala Phe Phe  Glu Ala Val
    1685                 1690                 1695

Thr Asn  Leu Ala Cys Glu Lys  Lys Leu Pro Leu Ile  Tyr Leu Ala
    1700                 1705                 1710

Ala Asn  Ser Gly Ala Arg Ile  Gly Ile Ala Asp Glu  Val Lys Ser
    1715                 1720                 1725

Cys Phe  Arg Val Gly Trp Ser  Asp Asp Gly Ser Pro  Glu Arg Gly
    1730                 1735                 1740

Phe Gln  Tyr Ile Tyr Leu Ser  Glu Glu Asp Tyr Ala  Arg Ile Gly
    1745                 1750                 1755

Thr Ser  Val Ile Ala His Lys  Met Gln Leu Asp Ser  Gly Glu Ile
    1760                 1765                 1770

Arg Trp  Val Ile Asp Ser Val  Val Gly Lys Glu Asp  Gly Leu Gly
    1775                 1780                 1785

Val Glu  Asn Ile His Gly Ser  Ala Ala Ile Ala Ser  Ala Tyr Ser
    1790                 1795                 1800

Arg Ala  Tyr Lys Glu Thr Phe  Thr Leu Thr Phe Val  Thr Gly Arg
    1805                 1810                 1815

Thr Val  Gly Ile Gly Ala Tyr  Leu Ala Arg Leu Gly  Ile Arg Cys
    1820                 1825                 1830

Ile Gln  Arg Leu Asp Gln Pro  Ile Ile Leu Thr Gly  Tyr Ser Ala
    1835                 1840                 1845

Leu Asn  Lys Leu Leu Gly Arg  Glu Val Tyr Ser Ser  His Met Gln
    1850                 1855                 1860

Leu Gly  Gly Pro Lys Ile Met  Ala Thr Asn Gly Val  Val His Leu
    1865                 1870                 1875

Thr Val  Ser Asp Asp Leu Glu  Gly Val Ser Asn Ile  Leu Arg Trp
    1880                 1885                 1890
```

-continued

```
Leu Ser  Tyr Val Pro Ala Tyr  Ile Gly Gly Pro Leu  Pro Val Thr
    1895                 1900                 1905

Thr Pro  Leu Asp Pro Pro Asp  Arg Pro Val Ala Tyr  Ile Pro Glu
    1910                 1915                 1920

Asn Ser  Cys Asp Pro Arg Ala  Ala Ile Arg Gly Val  Asp Asp Ser
    1925                 1930                 1935

Gln Gly  Lys Trp Leu Gly Gly  Met Phe Asp Lys Asp  Ser Phe Val
    1940                 1945                 1950

Glu Thr  Phe Glu Gly Trp Ala  Lys Thr Val Val Thr  Gly Arg Ala
    1955                 1960                 1965

Lys Leu  Gly Gly Ile Pro Val  Gly Val Ile Ala Val  Glu Thr Gln
    1970                 1975                 1980

Thr Met  Met Gln Thr Ile Pro  Ala Asp Pro Gly Gln  Leu Asp Ser
    1985                 1990                 1995

Arg Glu  Gln Ser Val Pro Arg  Ala Gly Gln Val Trp  Phe Pro Asp
    2000                 2005                 2010

Ser Ala  Thr Lys Thr Ala Gln  Ala Leu Leu Asp Phe  Asn Arg Glu
    2015                 2020                 2025

Gly Leu  Pro Leu Phe Ile Leu  Ala Asn Trp Arg Gly  Phe Ser Gly
    2030                 2035                 2040

Gly Gln  Arg Asp Leu Phe Glu  Gly Ile Leu Gln Ala  Gly Ser Thr
    2045                 2050                 2055

Ile Val  Glu Asn Leu Arg Thr  Tyr Asn Gln Pro Ala  Phe Val Tyr
    2060                 2065                 2070

Ile Pro  Met Ala Ala Glu Leu  Arg Gly Gly Ala Trp  Val Val Val
    2075                 2080                 2085

Asp Ser  Lys Ile Asn Pro Asp  Arg Ile Glu Cys Tyr  Ala Glu Arg
    2090                 2095                 2100

Thr Ala  Lys Gly Asn Val Leu  Glu Pro Gln Gly Leu  Ile Glu Ile
    2105                 2110                 2115

Lys Phe  Arg Ser Glu Glu Leu  Gln Asp Cys Met Ser  Arg Leu Asp
    2120                 2125                 2130

Pro Thr  Leu Ile Asp Leu Lys  Ala Lys Leu Glu Val  Ala Asn Lys
    2135                 2140                 2145

Asn Gly  Ser Ala Asp Thr Lys  Ser Leu Gln Glu Asn  Ile Glu Ala
    2150                 2155                 2160

Arg Thr  Lys Gln Leu Met Pro  Leu Tyr Thr Gln Ile  Ala Ile Arg
    2165                 2170                 2175

Phe Ala  Glu Leu His Asp Thr  Ser Leu Arg Met Ala  Ala Lys Gly
    2180                 2185                 2190

Val Ile  Lys Lys Val Val Asp  Trp Glu Glu Ser Arg  Ser Phe Phe
    2195                 2200                 2205

Tyr Lys  Arg Leu Arg Arg Arg  Ile Ser Glu Asp Val  Leu Ala Lys
    2210                 2215                 2220

Glu Ile  Arg Ala Val Ala Gly  Glu Gln Phe Ser His  Gln Pro Ala
    2225                 2230                 2235

Ile Glu  Leu Ile Lys Lys Trp  Tyr Ser Ala Ser His  Ala Ala Glu
    2240                 2245                 2250

Trp Asp  Asp Asp Asp Ala Phe  Val Ala Trp Met Asp  Asn Pro Glu
    2255                 2260                 2265

Asn Tyr  Lys Asp Tyr Ile Gln  Tyr Leu Lys Ala Gln  Arg Val Ser
    2270                 2275                 2280

Gln Ser  Leu Ser Ser Leu Ser  Asp Ser Ser Ser Asp  Leu Gln Ala
```

```
    2285                2290                2295

Leu Pro  Gln Gly Leu Ser Met  Leu Leu Asp Lys Met  Asp Pro Ser
    2300                2305                2310

Arg Arg  Ala Gln Leu Val Glu  Glu Ile Arg Lys Val  Leu Gly
    2315                2320                2325


<210> SEQ ID NO 3
<211> LENGTH: 2327
<212> TYPE: PRT
<213> ORGANISM: Oryza sativa

<400> SEQUENCE: 3

Met Thr Ser Thr His Val Ala Thr Leu Gly Val Gly Ala Gln Ala Pro
1               5                   10                  15

Pro Arg His Gln Lys Lys Ser Ala Gly Thr Ala Phe Val Ser Ser Gly
            20                  25                  30

Ser Ser Arg Pro Ser Tyr Arg Lys Asn Gly Gln Arg Thr Arg Ser Leu
        35                  40                  45

Arg Glu Glu Ser Asn Gly Gly Val Ser Asp Ser Lys Lys Leu Asn His
    50                  55                  60

Ser Ile Arg Gln Gly Leu Ala Gly Ile Ile Asp Leu Pro Asn Asp Ala
65                  70                  75                  80

Ala Ser Glu Val Asp Ile Ser His Gly Ser Glu Asp Pro Arg Gly Pro
                85                  90                  95

Thr Val Pro Gly Ser Tyr Gln Met Asn Gly Ile Ile Asn Glu Thr His
            100                 105                 110

Asn Gly Arg His Ala Ser Val Ser Lys Val Val Glu Phe Cys Thr Ala
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Leu Arg Ile Asn Ala Glu His Ile Arg Ile Ala Asp Gln Phe
            180                 185                 190

Val Glu Val Pro Gly Gly Thr Asn Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met His Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Val Pro Leu Glu Cys
        275                 280                 285

Cys Leu Asp Ser Ile Pro Asp Glu Met Tyr Arg Lys Ala Cys Val Thr
    290                 295                 300

Thr Thr Glu Glu Ala Val Ala Ser Cys Gln Val Val Gly Tyr Pro Ala
305                 310                 315                 320

Met Ile Lys Ala Ser Trp Gly Gly Gly Gly Lys Gly Ile Arg Lys Val
                325                 330                 335
```

-continued

```
His Asn Asp Asp Glu Val Arg Thr Leu Phe Lys Gln Val Gln Gly Glu
            340                 345                 350

Val Pro Gly Ser Pro Ile Phe Ile Met Arg Leu Ala Ala Gln Ser Arg
        355                 360                 365

His Leu Glu Val Gln Leu Leu Cys Asp Gln Tyr Gly Asn Val Ala Ala
    370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Trp
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asn
                485                 490                 495

His Gly Gly Gly Tyr Asp Leu Trp Arg Lys Thr Ala Ala Leu Ala Thr
            500                 505                 510

Pro Phe Asn Phe Asp Glu Val Asp Ser Lys Trp Pro Lys Gly His Cys
        515                 520                 525

Val Ala Val Arg Ile Thr Ser Glu Asp Pro Asp Asp Gly Phe Lys Pro
    530                 535                 540

Thr Gly Gly Lys Val Lys Glu Ile Ser Phe Lys Ser Lys Pro Asn Val
545                 550                 555                 560

Trp Ala Tyr Phe Ser Val Lys Ser Gly Gly Gly Ile His Glu Phe Ala
                565                 570                 575

Asp Ser Gln Phe Gly His Val Phe Ala Tyr Gly Thr Thr Arg Ser Ala
            580                 585                 590

Ala Ile Thr Thr Met Ala Leu Ala Leu Lys Glu Val Gln Ile Arg Gly
        595                 600                 605

Glu Ile His Ser Asn Val Asp Tyr Thr Val Asp Leu Leu Asn Ala Ser
    610                 615                 620

Asp Phe Arg Glu Asn Lys Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Val Thr Ala Asn Thr Ala Thr Val Ser
            660                 665                 670

Asp Tyr Val Gly Tyr Leu Thr Lys Gly Gln Ile Pro Pro Lys His Ile
        675                 680                 685

Ser Leu Val Tyr Thr Thr Val Ala Leu Asn Ile Asp Gly Lys Lys Tyr
    690                 695                 700

Thr Ile Asp Thr Val Arg Ser Gly His Gly Ser Tyr Arg Leu Arg Met
705                 710                 715                 720

Asn Gly Ser Thr Val Asp Ala Asn Val Gln Ile Leu Cys Asp Gly Gly
                725                 730                 735

Leu Leu Met Gln Leu Asp Gly Asn Ser His Val Ile Tyr Ala Glu Glu
            740                 745                 750

Glu Ala Ser Gly Thr Arg Leu Leu Ile Asp Gly Lys Thr Cys Met Leu
```

-continued

```
        755                 760                 765

Gln Asn Asp His Asp Pro Ser Lys Leu Leu Ala Glu Thr Pro Cys Lys
    770                 775                 780

Leu Leu Arg Phe Leu Val Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ser Gly Val Ile His Val Val Met Ser Glu Gly Gln Ala Met
            820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Asp Thr Phe Pro Gln Met Gly Leu
    850                 855                 860

Pro Ile Ala Ala Ser Gly Gln Val His Lys Leu Cys Ala Ala Ser Leu
865                 870                 875                 880

Asn Ala Cys Arg Met Ile Leu Ala Gly Tyr Glu His Asp Ile Asp Lys
                885                 890                 895

Val Val Pro Glu Leu Val Tyr Cys Leu Asp Thr Pro Glu Leu Pro Phe
            900                 905                 910

Leu Gln Trp Glu Glu Leu Met Ser Val Leu Ala Thr Arg Leu Pro Arg
        915                 920                 925

Asn Leu Lys Ser Glu Leu Glu Gly Lys Tyr Glu Glu Tyr Lys Val Lys
    930                 935                 940

Phe Asp Ser Gly Ile Ile Asn Asp Phe Pro Ala Asn Met Leu Arg Val
945                 950                 955                 960

Ile Ile Glu Glu Asn Leu Ala Cys Gly Ser Glu Lys Glu Lys Ala Thr
                965                 970                 975

Asn Glu Arg Leu Val Glu Pro Leu Met Ser Leu Leu Lys Ser Tyr Glu
            980                 985                 990

Gly Gly Arg Glu Ser His Ala His  Phe Val Val Lys Ser  Leu Phe Glu
        995                 1000                1005

Glu Tyr  Leu Tyr Val Glu Glu  Leu Phe Ser Asp Gly  Ile Gln Ser
    1010                1015                1020

Asp Val  Ile Glu Arg Leu Arg  Leu Gln His Ser Lys  Asp Leu Gln
    1025                1030                1035

Lys Val  Val Asp Ile Val Leu  Ser His Gln Ser Val  Arg Asn Lys
    1040                1045                1050

Thr Lys  Leu Ile Leu Lys Leu  Met Glu Ser Leu Val  Tyr Pro Asn
    1055                1060                1065

Pro Ala  Ala Tyr Arg Asp Gln  Leu Ile Arg Phe Ser  Ser Leu Asn
    1070                1075                1080

His Lys  Ala Tyr Tyr Lys Leu  Ala Leu Lys Ala Ser  Glu Leu Leu
    1085                1090                1095

Glu Gln  Thr Lys Leu Ser Glu  Leu Arg Ala Arg Ile  Ala Arg Ser
    1100                1105                1110

Leu Ser  Glu Leu Glu Met Phe  Thr Glu Glu Ser Lys  Gly Leu Ser
    1115                1120                1125

Met His  Lys Arg Glu Ile Ala  Ile Lys Glu Ser Met  Glu Asp Leu
    1130                1135                1140

Val Thr  Ala Pro Leu Pro Val  Glu Asp Ala Leu Ile  Ser Leu Phe
    1145                1150                1155

Asp Cys  Ser Asp Thr Thr Val  Gln Gln Arg Val Ile  Glu Thr Tyr
    1160                1165                1170
```

Ile Ala Arg Leu Tyr Gln Pro His Leu Val Lys Asp Ser Ile Lys
1175 1180 1185

Met Lys Trp Ile Glu Ser Gly Val Ile Ala Leu Trp Glu Phe Pro
1190 1195 1200

Glu Gly His Phe Asp Ala Arg Asn Gly Gly Ala Val Leu Gly Asp
1205 1210 1215

Lys Arg Trp Gly Ala Met Val Ile Val Lys Ser Leu Glu Ser Leu
1220 1225 1230

Ser Met Ala Ile Arg Phe Ala Leu Lys Glu Thr Ser His Tyr Thr
1235 1240 1245

Ser Ser Glu Gly Asn Met Met His Ile Ala Leu Leu Gly Ala Asp
1250 1255 1260

Asn Lys Met His Ile Ile Gln Glu Ser Gly Asp Asp Ala Asp Arg
1265 1270 1275

Ile Ala Lys Leu Pro Leu Ile Leu Lys Asp Asn Val Thr Asp Leu
1280 1285 1290

His Ala Ser Gly Val Lys Thr Ile Ser Phe Ile Val Gln Arg Asp
1295 1300 1305

Glu Ala Arg Met Thr Met Arg Arg Thr Phe Leu Trp Ser Asp Glu
1310 1315 1320

Lys Leu Ser Tyr Glu Glu Glu Pro Ile Leu Arg His Val Glu Pro
1325 1330 1335

Pro Leu Ser Ala Leu Leu Glu Leu Asp Lys Leu Lys Val Lys Gly
1340 1345 1350

Tyr Asn Glu Met Lys Tyr Thr Pro Ser Arg Asp Arg Gln Trp His
1355 1360 1365

Ile Tyr Thr Leu Arg Asn Thr Glu Asn Pro Lys Met Leu His Arg
1370 1375 1380

Val Phe Phe Arg Thr Leu Val Arg Gln Pro Ser Val Ser Asn Lys
1385 1390 1395

Phe Ser Ser Gly Gln Ile Gly Asp Met Glu Val Gly Ser Ala Glu
1400 1405 1410

Glu Pro Leu Ser Phe Thr Ser Thr Ser Ile Leu Arg Ser Leu Met
1415 1420 1425

Thr Ala Ile Glu Glu Leu Glu Leu His Ala Ile Arg Thr Gly His
1430 1435 1440

Ser His Met Tyr Leu His Val Leu Lys Glu Gln Lys Leu Leu Asp
1445 1450 1455

Leu Val Pro Val Ser Gly Asn Thr Val Leu Asp Val Gly Gln Asp
1460 1465 1470

Glu Ala Thr Ala Tyr Ser Leu Leu Lys Glu Met Ala Met Lys Ile
1475 1480 1485

His Glu Leu Val Gly Ala Arg Met His His Leu Ser Val Cys Gln
1490 1495 1500

Trp Glu Val Lys Leu Lys Leu Asp Cys Asp Gly Pro Ala Ser Gly
1505 1510 1515

Thr Trp Arg Ile Val Thr Thr Asn Val Thr Ser His Thr Cys Thr
1520 1525 1530

Val Asp Ile Tyr Arg Glu Met Glu Asp Lys Glu Ser Arg Lys Leu
1535 1540 1545

Val Tyr His Pro Ala Thr Pro Ala Ala Gly Pro Leu His Gly Val
1550 1555 1560

```
Ala Leu Asn Asn Pro Tyr Gln Pro Leu Ser Val Ile Asp Leu Lys
    1565                1570                1575

Arg Cys Ser Ala Arg Asn Asn Arg Thr Thr Tyr Cys Tyr Asp Phe
    1580                1585                1590

Pro Leu Ala Phe Glu Thr Ala Val Arg Lys Ser Trp Ser Ser Ser
    1595                1600                1605

Thr Ser Gly Ala Ser Lys Gly Val Glu Asn Ala Gln Cys Tyr Val
    1610                1615                1620

Lys Ala Thr Glu Leu Val Phe Ala Asp Lys His Gly Ser Trp Gly
    1625                1630                1635

Thr Pro Leu Val Gln Met Asp Arg Pro Ala Gly Leu Asn Asp Ile
    1640                1645                1650

Gly Met Val Ala Trp Thr Leu Lys Met Ser Thr Pro Glu Phe Pro
    1655                1660                1665

Ser Gly Arg Glu Ile Ile Val Val Ala Asn Asp Ile Thr Phe Arg
    1670                1675                1680

Ala Gly Ser Phe Gly Pro Arg Glu Asp Ala Phe Phe Glu Ala Val
    1685                1690                1695

Thr Asn Leu Ala Cys Glu Lys Lys Leu Pro Leu Ile Tyr Leu Ala
    1700                1705                1710

Ala Asn Ser Gly Ala Arg Ile Gly Ile Ala Asp Glu Val Lys Ser
    1715                1720                1725

Cys Phe Arg Val Gly Trp Ser Asp Asp Gly Ser Pro Glu Arg Gly
    1730                1735                1740

Phe Gln Tyr Ile Tyr Leu Ser Glu Glu Asp Tyr Ala Arg Ile Gly
    1745                1750                1755

Thr Ser Val Ile Ala His Lys Met Gln Leu Asp Ser Gly Glu Ile
    1760                1765                1770

Arg Trp Val Ile Asp Ser Val Val Gly Lys Glu Asp Gly Leu Gly
    1775                1780                1785

Val Glu Asn Ile His Gly Ser Ala Ala Ile Ala Ser Ala Tyr Ser
    1790                1795                1800

Arg Ala Tyr Lys Glu Thr Phe Thr Leu Thr Phe Val Thr Gly Arg
    1805                1810                1815

Thr Val Gly Ile Gly Ala Tyr Leu Ala Arg Leu Gly Ile Arg Cys
    1820                1825                1830

Ile Gln Arg Leu Asp Gln Pro Ile Ile Leu Thr Gly Tyr Ser Ala
    1835                1840                1845

Leu Asn Lys Leu Leu Gly Arg Glu Val Tyr Ser Ser His Met Gln
    1850                1855                1860

Leu Gly Gly Pro Lys Ile Met Ala Thr Asn Gly Val Val His Leu
    1865                1870                1875

Thr Val Ser Asp Asp Leu Glu Gly Val Ser Asn Ile Leu Arg Trp
    1880                1885                1890

Leu Ser Tyr Val Pro Ala Tyr Ile Gly Gly Pro Leu Pro Val Thr
    1895                1900                1905

Thr Pro Leu Asp Pro Pro Asp Arg Pro Val Ala Tyr Ile Pro Glu
    1910                1915                1920

Asn Ser Cys Asp Pro Arg Ala Ala Ile Arg Gly Val Asp Asp Ser
    1925                1930                1935

Gln Gly Lys Trp Leu Gly Gly Met Phe Asp Lys Asp Ser Phe Val
    1940                1945                1950

Glu Thr Phe Glu Gly Trp Ala Lys Thr Val Val Thr Gly Arg Ala
```

```
    1955                1960                1965

Lys Leu  Gly Gly Ile Pro Val  Gly Val Ile Ala Val  Glu Thr Gln
    1970                1975                1980

Thr Met  Met Gln Thr Ile Pro  Ala Asp Pro Gly Gln  Leu Asp Ser
    1985                1990                1995

Arg Glu  Gln Ser Val Pro Arg  Ala Gly Gln Val Trp  Phe Pro Asp
    2000                2005                2010

Ser Ala  Thr Lys Thr Ala Gln  Ala Leu Leu Asp Phe  Asn Arg Glu
    2015                2020                2025

Gly Leu  Pro Leu Phe Ile Leu  Ala Asn Trp Arg Gly  Phe Ser Gly
    2030                2035                2040

Gly Gln  Arg Asp Leu Phe Glu  Gly Ile Leu Gln Ala  Gly Ser Thr
    2045                2050                2055

Ile Val  Glu Asn Leu Arg Thr  Tyr Asn Gln Pro Ala  Phe Val Tyr
    2060                2065                2070

Ile Pro  Met Ala Ala Glu Leu  Arg Gly Gly Ala Trp  Val Val Val
    2075                2080                2085

Asp Ser  Lys Ile Asn Pro Asp  Arg Ile Glu Cys Tyr  Ala Glu Arg
    2090                2095                2100

Thr Ala  Lys Gly Asn Val Leu  Glu Pro Gln Gly Leu  Ile Glu Ile
    2105                2110                2115

Lys Phe  Arg Ser Glu Glu Leu  Gln Asp Cys Met Ser  Arg Leu Asp
    2120                2125                2130

Pro Thr  Leu Ile Asp Leu Lys  Ala Lys Leu Glu Val  Ala Asn Lys
    2135                2140                2145

Asn Gly  Ser Ala Asp Thr Lys  Ser Leu Gln Glu Asn  Ile Glu Ala
    2150                2155                2160

Arg Thr  Lys Gln Leu Met Pro  Leu Tyr Thr Gln Ile  Ala Ile Arg
    2165                2170                2175

Phe Ala  Glu Leu His Asp Thr  Ser Leu Arg Met Ala  Ala Lys Gly
    2180                2185                2190

Val Ile  Lys Lys Val Val Asp  Trp Glu Glu Ser Arg  Ser Phe Phe
    2195                2200                2205

Tyr Lys  Arg Leu Arg Arg Arg  Ile Ser Glu Asp Val  Leu Ala Lys
    2210                2215                2220

Glu Ile  Arg Ala Val Ala Gly  Glu Gln Phe Ser His  Gln Pro Ala
    2225                2230                2235

Ile Glu  Leu Ile Lys Lys Trp  Tyr Ser Ala Ser His  Ala Ala Glu
    2240                2245                2250

Trp Asp  Asp Asp Asp Ala Phe  Val Ala Trp Met Asp  Asn Pro Glu
    2255                2260                2265

Asn Tyr  Lys Asp Tyr Ile Gln  Tyr Leu Lys Ala Gln  Arg Val Ser
    2270                2275                2280

Gln Ser  Leu Ser Ser Leu Ser  Asp Ser Ser Ser Asp  Leu Gln Ala
    2285                2290                2295

Leu Pro  Gln Gly Leu Ser Met  Leu Leu Asp Lys Met  Asp Pro Ser
    2300                2305                2310

Arg Arg  Ala Gln Leu Val Glu  Glu Ile Arg Lys Val  Leu Gly
    2315                2320                2325
```

<210> SEQ ID NO 4
<211> LENGTH: 6963
<212> TYPE: DNA
<213> ORGANISM: Alopecurus myosuroides

<400> SEQUENCE: 4
atgggatcca cacatctgcc cattgtcggg tttaatgcat ccacaacacc atcgctatcc 60
actcttcgcc agataaactc agctgctgct gcattccaat cttcgtcccc ttcaaggtca 120
tccaagaaga aaagccgacg tgttaagtca ataagggatg atggcgatgg aagcgtgcca 180
gaccctgcag gccatggcca gtctattcgc caaggtctcg ctggcatcat cgacctccca 240
aaggagggcg catcagctcc agatgtggac atttcacatg ggtctgaaga ccacaaggcc 300
tcctaccaaa tgaatgggat actgaatgaa tcacataacg ggaggcacgc ctctctgtct 360
aaagtttatg aattttgcac ggaattgggt ggaaaaacac caattcacag tgtattagtc 420
gccaacaatg gaatggcagc agctaagttc atgcggagtg tccggacatg ggctaatgat 480
acatttgggt cagagaaggc gattcagttg atagctatgg caactccgga agacatgaga 540
ataaatgcag agcacattag aattgctgat cagtttgttg aagtacctgg tggaacaaac 600
aataacaact atgcaaatgt ccaactcata gtggagatag cagagagaac tggtgtctcc 660
gccgtttggc ctggttgggg ccatgcatct gagaatcctg aacttccaga tgcactaact 720
gcaaaaggaa ttgtttttct tggccacca gcatcatcaa tgaacgcact aggcgacaag 780
gttggttcag ctctcattgc tcaagcagca ggggttccca ctcttgcttg gagtggatca 840
catgtggaaa ttccattaga actttgtttg gactcgatac ctgaggagat gtataggaaa 900
gcctgtgtta caaccgctga tgaagcagtt gcaagttgtc agatgattgg ttaccctgcc 960
atgatcaagg catcctgggg tggtggtggt aaagggatta gaaaggttaa taatgatgac 1020
gaggtgaaag cactgtttaa gcaagtacag ggtgaagttc ctggctcccc gatatttatc 1080
atgagacttg catctcagag tcgtcatctt gaagtccagc tgctttgtga tgaatatggc 1140
aatgtagcag cacttcacag tcgtgattgc agtgtgcaac gacgacacca aaagattatc 1200
gaggaaggac cagttactgt tgctcctcgt gaaacagtga aagagctaga gcaagcagca 1260
aggaggcttg ctaaggccgt gggttacgtc ggtgctgcta ctgttgaata tctctacagc 1320
atggagactg gtgaatacta ttttctggag cttaatccac ggttgcaggt tgagcaccca 1380
gtcaccgagt cgatagctga agtaaatttg cctgcagccc aagttgcagt tgggatgggt 1440
atacccctttt ggcagattcc agagatcaga cgtttctacg gaatggacaa tggaggaggc 1500
tatgatattt ggaggaaaac agcagctctc gctactccat tcaactttga tgaagtagat 1560
tctcaatggc cgaagggtca ttgtgtggca gttaggataa ccagtgagaa tccagatgat 1620
ggattcaagc ctactggtgg aaaagtaaag gagataagtt ttaaaagtaa gccaaatgtc 1680
tggggatatt tctcagttaa gtctggtgga ggcattcatg aatttgcgga ttctcagttt 1740
ggacacgttt ttgcctatgg agagactaga tcagcagcaa taaccagcat gtctcttgca 1800
ctaaaagaga ttcaaattcg tggagaaatt catacaaacg ttgattacac ggttgatctc 1860
ttgaatgccc cagacttcag agaaaacacg atccataccg gttggctgga taccagaata 1920
gctatgcgtg ttcaagctga gaggcctccc tggtatattt cagtggttgg aggagctcta 1980
tataaaacaa taaccaccaa tgcggagacc gtttctgaat atgttagcta tctcatcaag 2040
ggtcagattc caccaaagca catatccctt gtccattcaa ctatttcttt gaatatagag 2100
gaaagcaaat atacaattga gattgtgagg agtggacagg gtagctacag attgagactg 2160
aatggatcac ttattgaagc caatgtacaa acattatgtg atggaggcct tttaatgcag 2220
ctggatggaa atagccatgt tatttatgct gaagaagaag cgggtggtac acggcttctt 2280

```
attgatggaa aaacatgctt gctacagaat gaccatgatc cgtcaaggtt attagctgag   2340
acaccctgca aacttcttcg tttcttgatt gccgatggtg ctcatgttga tgctgatgta   2400
ccatacgcgg aagttgaggt tatgaagatg tgcatgcccc tcttgtcgcc tgctgctggt   2460
gtcattaatg ttttgttgtc tgagggccag gcgatgcagg ctggtgatct tatagcgaga   2520
cttgatctcg atgacccttc tgctgtgaag agagccgagc catttgaagg atcttttcca   2580
gaaatgagcc ttcctattgc tgcttctggc caagttcaca aaagatgtgc tgcaagtttg   2640
aacgctgctc gaatggtcct tgcaggatat gaccatgcgg ccaacaaagt tgtgcaagat   2700
ttggtatggt gccttgatac acctgctctt cctttcctac aatgggaaga gcttatgtct   2760
gttttagcaa ctagacttcc aagacgtctt aagagcgagt tggagggcaa atacaatgaa   2820
tacaagttaa atgttgacca tgtgaagatc aaggatttcc ctaccgagat gcttagagag   2880
acaatcgagg aaaatcttgc atgtgtttcc gagaaggaaa tggtgacaat tgagaggctt   2940
gttgaccctc tgatgagcct gctgaagtca tacgagggtg ggagagaaag ccatgcccac   3000
tttattgtca agtccctttt tgaggagtat ctctcggttg aggaactatt cagtgatggc   3060
attcagtctg acgtgattga acgcctgcgc ctacaatata gtaaagacct ccagaaggtt   3120
gtagacattg ttttgtctca ccagggtgtg agaaacaaaa caaagctgat actcgcgctc   3180
atggagaaac tggtctatcc aaaccctgct gcctacagag atcagttgat tcgcttttct   3240
tccctcaacc ataaaagata ttataagttg gctcttaaag ctagtgaact tcttgaacaa   3300
accaagctca gcgaactccg cacaagcatt gcaaggaacc tttcagcgct ggatatgttc   3360
accgaggaaa aggcagattt ctccttgcaa gacagaaaat tggccattaa tgagagcatg   3420
ggagatttag tcactgcccc actgccagtt gaagatgcac ttgtttcttt gtttgattgt   3480
actgatcaaa ctcttcagca gagagtgatt cagacataca tatctcgatt ataccagcct   3540
caacttgtga aggatagcat ccagctgaaa tatcaggatt ctggtgttat tgctttatgg   3600
gaattcactg aaggaaatca tgagaagaga ttgggtgcta tggttatcct gaagtcacta   3660
gaatctgtgt caacagccat tggagctgct ctaaaggatg catcacatta tgcaagctct   3720
gcgggcaaca cggtgcatat tgctttgttg gatgctgata cccaactgaa tacaactgaa   3780
gatagtggtg ataatgacca agctcaagac aagatggata aactttcttt tgtactgaaa   3840
caagatgttg tcatggctga tctacgtgct gctgatgtca aggttgttag ttgcattgtt   3900
caaagagatg gagcaatcat gcctatgcgc cgtaccttcc tcttgtcaga ggaaaaactt   3960
tgttacgagg aagagccgat tcttcggcat gtggagcctc cactttctgc acttcttgag   4020
ttggataaat tgaaagtgaa aggatacaat gagatgaagt atacaccgtc acgtgatcgt   4080
cagtggcata tatacacact tagaaatact gaaaatccaa aaatgctgca cagggtattt   4140
ttccgaacac ttgtcagaca acccagtgca ggcaacaggt ttacatcaga ccatatcact   4200
gatgttgaag taggacacgc agaggaacct ctttcattta cttcaagcag catattaaaa   4260
tcgttgaaga ttgctaaaga agaattggag cttcacgcga tcaggactgg ccattctcat   4320
atgtacttgt gcatattgaa agagcaaaag cttcttgacc ttgttcctgt ttcagggaac   4380
actgttgtgg atgttggtca agatgaagct actgcatgct ctcttttgaa agaaatggct   4440
ttaaagatac atgaacttgt tggtgcaaga atgcatcatc tttctgtatg ccagtgggaa   4500
gtgaaactta agttggtgag cgatgggcct gccagtggta gctggagagt tgtaacaacc   4560
aatgttactg gtcacacctg cactgtggat atctaccggg aggtcgaaga tacagaatca   4620
cagaaactag tataccactc caccgcattg tcatctggtc ctttgcatgg tgttgcactg   4680
```

-continued

```
aatacttcgt atcagccttt gagtgttatt gatttaaaac gttgctctgc caggaacaac   4740
aaaactacat actgctatga ttttccattg acatttgaag ctgcagtgca gaagtcgtgg   4800
tctaacattt ccagtgaaaa caaccaatgt tatgttaaag cgacagagct tgtgtttgct   4860
gaaaagaatg ggtcgtgggg cactcctata attcctatgc agcgtgctgc tgggctgaat   4920
gacattggta tggtagcctg gatcttggac atgtccactc ctgaatttcc cagcggcaga   4980
cagatcattg ttatcgcaaa tgatattaca tttagagctg gatcatttgg cccaagggaa   5040
gatgcatttt tcgaagctgt aaccaacctg gcttgtgaga agaagcttcc acttatctac   5100
ttggctgcaa actctggtgc tcggattggc attgctgatg aagtaaaatc ttgcttccgt   5160
gttggatgga ctgatgatag cagccctgaa cgtggattta ggtacattta tatgactgac   5220
gaagaccatg atcgtattgg ctcttcagtt atagcacaca agatgcagct agatagtggc   5280
gagatcaggt gggttattga ttctgttgtg ggaaaagagg atggactagg tgtggagaac   5340
atacatggaa gtgctgctat tgccagtgcc tattctaggg cgtacgagga gacatttaca   5400
cttacattcg ttactggacg aactgttgga atcggagcct atcttgctcg acttggcata   5460
cggtgcatac agcgtattga ccagcccatt attttgaccg ggttttctgc cctgaacaag   5520
cttcttgggc gggaggtgta cagctcccac atgcagttgg gtggtcccaa aatcatggcg   5580
acgaatggtg ttgtccatct gactgttcca gatgaccttg aaggtgtttc taatatattg   5640
aggtggctca gctatgttcc tgcaaacatt ggtggacctc ttcctattac aaaatctttg   5700
gacccaatag acagacccgt tgcatacatc cctgagaata catgtgatcc tcgtgcagcc   5760
atcagtggca ttgatgacag ccaagggaaa tggttgggtg gcatgtttga caaagacagt   5820
tttgtggaga catttgaagg atgggcgaag acagtagtta ctggcagagc aaaacttgga   5880
gggattcctg ttggtgttat agctgtggag acacagacca tgatgcagct cgtccccgct   5940
gatccaggcc agcctgattc ccacgagcgg tctgttcctc gtgctgggca agtttggttt   6000
ccagattctg ctaccaagac agcgcaggcg atgttggact tcaaccgtga aggattacct   6060
ctgttcatac ttgctaactg gagaggcttc tctggagggc aaagagatct tttgaagga    6120
attctgcagg ctgggtcaac aattgttgag aaccttagga catacaatca gcctgccttt   6180
gtatatatcc ccaaggctgc agagctacgt ggaggagcct gggtcgtgat tgatagcaag   6240
ataaacccag atcgcatcga gtgctatgct gagaggactg caaagggtaa tgttctcgaa   6300
cctcaagggt tgattgagat caagttcagg tcagaggaac tcaaagaatg catgggtagg   6360
cttgatccag aattgataga tctgaaagca agactccagg gagcaaatgg aagcctatct   6420
gatggagaat cccttcagaa gagcatagaa gctcggaaga aacagttgct gcctctgtac   6480
acccaaatcg cggtacgttt tgcggaattg cacgacactt cccttagaat ggctgctaaa   6540
ggtgtgatca ggaaagttgt agactgggaa gactctcggt ctttcttcta caagagatta   6600
cggaggaggc tatccgagga cgttctggca aaggagatta gaggtgtaat tggtgagaag   6660
tttcctcaca aatcagcgat cgagctgatc aagaaatggt acttggcttc tgaggcagct   6720
gcagcaggaa gcaccgactg ggatgacgac gatgcttttg tcgcctggag ggagaaccct   6780
gaaaactata aggagtatat caaagagctt agggctcaaa gggtatctcg gttgctctca   6840
gatgttgcag gctccagttc ggatttacaa gccttgccgc agggtctttc catgctacta   6900
gataagatgg atccctctaa gagagcacag tttatcgagg aggtcatgaa ggtcctgaaa   6960
tga                                                                 6963
```

<210> SEQ ID NO 5
<211> LENGTH: 11927
<212> TYPE: DNA
<213> ORGANISM: Oryza sativa

<400> SEQUENCE: 5
atgacatcca cacatgtggc gacattggga gttggtgccc aggcacctcc tcgtcaccag 60
aaaaagtcag ctggcactgc atttgtatca tctgggtcat caagaccctc ataccgaaag 120
aatggtcagc gtactcggtc acttagggaa gaaagcaatg gaggagtgtc tgattccaaa 180
aagcttaacc actctattcg ccaaggtgac cactagctac tttacatatg ctataatttg 240
tgccaaacat aaacatgcaa tggctgctat tatttaaacg ttaatgttga aatagctgct 300
ataggataca gcaaaaatat ataattgact gggcaagatg caacaattgt ttttcactaa 360
agttagttat cttttgctgt aaaagacaac tgttttttac ataaaatggt attaataacc 420
ttgtaatatt caatgcaaca tgttctcaag taaaaaaaaa cattgcctgg ttgtataagc 480
aaatgtgtcg ttgtagacat cttattaaac ctttttgtga tatctattac cgtagggaac 540
aggggagctg tttaaatctg ttatcataga gtaatatgag aaaagtggat tgtgcgactt 600
tggcatgtat acctgctcaa tttcaaatat atgtctatgt gcaggtcttg ctggcatcat 660
tgacctccca aatgacgcag cttcagaagt tgatatttca cagtaaggac tttatatttt 720
ataataatta ttatataatt ttctgacatg ttttgagaac ctcaaaacat gtgattgcac 780
cttccttttt tatgtctggt tcagaaactg ataagttttg acagtgttta ggatggatct 840
ttgatgcgca cagtgctttc taatgttttc atttttgaaa gtaatgtttt aggaagaaat 900
atctgattaa atttatactt tatctttaca aaagtcaaat gcgttctgta tcaattgcgg 960
tttgtaatat ggcaagaaca tgctttcaga atttgttcat acaatgcttt ctttctatta 1020
ttatgtagaa caaataccta atactttgtt caccttttat agtggacacc tctcacagct 1080
ttttcagtaa gtgatgcaat tttgtacatt tgtaagatgt gttccagaaa ccttttctcc 1140
tgcaattcta atgtacccac tcaaactggt atcaccaaag atctccatct gattgaaaaa 1200
aagctgcgtg aagtatgctt atttatgcta accatacatg atttatactg ttttatagta 1260
caatgcttat ttatgctaac catacataat tttattctgt tttctagtac attatttgtg 1320
cccctgacca taaatgatcc tttcttttac agtggttccg aagatcccag ggggcctacg 1380
gtcccaggtt cctaccaaat gaatgggatt atcaatgaaa cacataatgg gaggcatgct 1440
tcagtctcca aggttgttga gttttgtacg gcacttggtg gcaaaacacc aattcacagt 1500
gtattagtgg ccaacaatgg aatggcagca gctaagttca tgcggagtgt ccgaacatgg 1560
gctaatgata cttttggatc agagaaggca attcagctga tagctatggc aactccggag 1620
gatctgagga taaatgcaga gcacatcaga attgccgatc aatttgtaga ggtacctggt 1680
ggaacaaaca acaacaacta tgcaaatgtc caactcatag tggaggttag ttcagctcat 1740
ccctcaacac aacattttcg tttctattta agttagggaa aaatctctac gaccctccaa 1800
tttctgaaca tccaattttc accatcaact gcaatcacag atagcagaga gaacaggtgt 1860
ttctgctgtt tggcctggtt ggggtcatgc atctgagaat cctgaacttc cagatgcgct 1920
gactgcaaaa ggaattgttt ttcttgggcc accagcatca tcaatgcatg cattaggaga 1980
caaggttggc tcagctctca ttgctcaagc agctggagtt ccaacacttg cttggagtgg 2040
atcacatgtg agccttgtct tctctttttt agcttatcat cttatctttt cggtgatgca 2100
ttatcccaat gacactaaac cataggtgga agttcctctg gagtgttgct tggactcaat 2160

```
acctgatgag atgtatagaa aagcttgtgt tactaccaca gaggaagcag ttgcaagttg   2220
tcaggtggtt ggttatcctg ccatgattaa ggcatcttgg ggtggtggtg gtaaaggaat   2280
aaggaaggtt tgttcttctt gtagttatca agagattgtt tggattgcaa gtgtttagtg   2340
cccatagtta actctggtct ttctaacatg agtaactcaa ctttcttgca ggttcataat   2400
gatgatgagg ttaggacatt atttaagcaa gttcaaggcg aagtacctgg ttccccaata   2460
tttatcatga ggctagctgc tcaggtgggg ccttttatgg aagttacacc ttttccctta   2520
atgttgagtt attccggagt tattatggtt atgttctgta tgtttgatct gtaaattatt   2580
gaaattcacc tccattggtt ctccagatta gcagacctac aattctacat atggtttata   2640
ctttataaat actaggattt agggatcttc atatagttta tacatggtat ttagatttca   2700
tttgtaaccc tattgaagac atcctgattg ttgtcttatg tagagtcgac atcttgaagt   2760
tcagttgctt tgtgatcaat atggcaacgt agcagcactt cacagtcgag attgcagtgt   2820
acaacggcga caccaaaagg tctgctgtct cagttaaatc acccctctga atgatctact   2880
tcttgcctgc tgcgttggtc agaggaataa tggttgtatt ctactgaaca gataatcgag   2940
gaaggaccag ttactgttgc tcctcgtgag actgtgaaag agcttgagca ggcagcacgg   3000
aggcttgcta aagctgtggg ttatgttggt gctgctactg ttgaatacct ttacagcatg   3060
gaaactggtg aatattattt tctggaactt aatccacggc tacaggtcgg ctcctttgac   3120
attcttcagg aattaatttc tgttgaccac atgatttaca ttgtcaaatg gtctcacagg   3180
ttgagcatcc tgtcactgag tggatagctg aagtaaattt gcctgcggct caagttgctg   3240
ttggaatggg tataccctt tggcagattc caggtaatgc ttcttcattt agttcctgct   3300
ctttgttaat tgaatgagct cttatacaga ccatgagaca cattctactg ttaattcata   3360
gtatcccctg acttgttagt gttagagata cagagatgta tcacaaattc attgtatctc   3420
ctcaaggact gtaaaaatcc tataattaaa tttctgaaaa tttgttcttt taagcagaaa   3480
aaaaatctct aaattatctc cctgtataca gagatcaggc gcttctacgg aatgaaccat   3540
ggaggaggct atgacctttg gaggaaaaca gcagctctag cgactccatt taactttgat   3600
gaagtagatt ctaaatggcc aaaaggccac tgcgtagctg ttagaataac tagcgaggat   3660
ccagatgatg ggtttaagcc tactggtgga aaagtaaagg tgcggtttcc tgatgttagg   3720
tgtatgaatt gaacacattg ctatattgca gctagtgaaa tgactggatc atggttctct   3780
tattttcagg agataagttt caagagtaaa ccaaatgttt gggcctattt ctcagtaaag   3840
gtagtcctca atattgttgc actgccacat tatttgagtt gtcctaacaa ttgtgctgca   3900
attgttagtt ttcaactatt tgttgttctg tttggttgac tggtaccctc tctttgcagt   3960
ctggtggagg catccatgaa ttcgctgatt ctcagttcgg tatgtaaagt taaaagagta   4020
atattgtctt tgctatttat gtttgtcctc acttttaaaa gatattgcct tccattacag   4080
gacatgtttt tgcgtatgga actactagat cggcagcaat aactaccatg gctcttgcac   4140
taaaagaggt tcaaattcgt ggagaaattc attcaaacgt agactacaca gttgacctat   4200
taaatgtaag gactaaatat ctgcttattg aaccttgctt tttggttccc taatgccatt   4260
ttagtctggc tactgaagaa cttatccatc atgccatttc tgttatctta aattcaggcc   4320
tcagatttta gagaaaataa gattcatact ggttggctgg ataccaggat agccatgcgt   4380
gttcaagctg agaggcctcc atggtatatt tcagtcgttg gaggggcttt atatgtaaga   4440
caaactatgc cactcattag catttatgtg aagcaaatgc ggaaaacatg atcaatatgt   4500
```

-continued

```
cgtcttattt aaatttattt atttttgtgc tgcagaaaac agtaactgcc aacacggcca   4560
ctgtttctga ttatgttggt tatcttacca agggccagat tccaccaaag gtactattct   4620
gtttttttcag gatatgaatg ctgtttgaat gtgaaaacca ttgaccataa atccttgttt   4680
gcagcatata tcccttgtct atacgactgt tgctttgaat atagatggga aaaaatatac   4740
agtaagtgtg acattcttaa tggggaaact taatttgttg taaataatca atatcatatt   4800
gactcgtgta tgctgcatca tagatcgata ctgtgaggag tggacatggt agctacagat   4860
tgcgaatgaa tggatcaacg gttgacgcaa atgtacaaat attatgtgat ggtgggcttt   4920
taatgcaggt aatatcttct tcctagttaa agaagatata tcttgttcaa agaattctga   4980
ttattgatct tttaatgttt tcagctggat ggaaacagcc atgtaattta tgctgaagaa   5040
gaggccagtg gtacacgact tcttattgat ggaaagacat gcatgttaca ggtaatgata   5100
gccttgttct ttttagttct agtcacggtg tttgcttgct atttgttgta tctatttaat   5160
gcattcacta attactatat tagtttgcat catcaagtta aaatggaact tctttcttgc   5220
agaatgacca tgacccatca aagttattag ctgagacacc atgcaaactt cttcgtttct   5280
tggttgctga tggtgctcat gttgatgctg atgtaccata tgcggaagtt gaggttatga   5340
agatgtgcat gcccctctta tcacccgctt ctggtgtcat acatgttgta atgtctgagg   5400
gccaagcaat gcaggtacat tcctacattc cattcattgt gctgtgctga catgaacatt   5460
tcaagtaaat acctgtaact tgtttattat tctaggctgg tgatcttata gctaggctgg   5520
atcttgatga cccttctgct gttaagagag ctgagccgtt cgaagatact tttccacaaa   5580
tgggtctccc tattgctgct tctggccaag ttcacaaatt atgtgctgca agtctgaatg   5640
cttgtcgaat gatccttgcg gggtatgagc atgatattga caaggtaaac atcatgtcct   5700
cttgtttttt cttttgttta tcatgcattc ttatgttcat catgtcctct ggcaaatcta   5760
gattccgctg tcgtttcaca cagatttttc tcattctcat aatggtgcca aacataaata   5820
tgctgctata ttcatcaatg ttttcactcg atttctaatt ttgcttttga gttttaaact   5880
ttagtacaat ccatatctaa tctcctttgg caacagtgaa tccattatat atatttttat   5940
taaactgctt tctttttcag gttgtgccag agttggtata ctgcctagac actccggagc   6000
ttcctttcct gcagtgggag gagcttatgt ctgttttagc aactagactt ccaagaaatc   6060
ttaaaagtga ggtatattat ggttgacaag atagctagtc tcatgctcta aggacttgta   6120
catttcgcca cataggttaa ttttccatat caagttctaa tgtacgatat aaaagtagta   6180
ctggcctaaa acagtattgg tggttgacta tctttgttgt gtaagatcaa gtatttcttt   6240
ttcatgctta gtttgtcaat acttcacatt tatcactgac ttgtcgagct aaatgagatt   6300
ttatttgatt tctgtgctcc attatttttg tatatatata tatatattta actatgacta   6360
tatgttatgc ctcaaacgtt tcaaactctt tcagttggag ggcaaatatg aggaatacaa   6420
agtaaaattt gactctggga taatcaatga tttccctgcc aatatgctac gagtgataat   6480
tgaggtcagt tattcaattt gttgtgataa tcactgcctt aactgttcgt tcttttaaca   6540
agcggtttta taggaaaatc ttgcatgtgg ttctgagaag gagaaggcta caaatgagag   6600
gcttgttgag cctcttatga gcctactgaa gtcatatgag ggtgggagag aaagtcatgc   6660
tcactttgtt gtcaagtccc tttttgagga gtatctctat gttgaagaat tgttcagtga   6720
tggaattcag gttaacttac ctattcgcat taaacaaatc atcagttgtt ttatgataaa   6780
gtcaaaatgt ttatatttcc cattcttctg tggatcaaat atatcacgga catgatatag   6840
tttccttagg ctatataatg gttcttcatc aaataatatt gcaggaaaca gtatagcaaa   6900
```

```
ctatttgtat atactcgaga tggaaattgt tagaaacatc attgactaaa tctgtccttt   6960
gttacgctgt ttttgtagtc tgatgtgatt gagcgtctgc gccttcaaca tagtaaagac   7020
ctacagaagg tcgtagacat tgtgttgtcc caccaggtaa atttcttcat ggtctgatga   7080
cttcactgcg aatggttact gaactgtctt cttgttctga caatgtgact tttctttgta   7140
gagtgttaga aataaaacta agctgatact aaaactcatg gagagtctgg tctatccaaa   7200
tcctgctgcc tacagggatc aattgattcg cttttcttcc cttaatcaca aagcgtatta   7260
caaggtgacc aggataaaca taaataaacg tgaatttttc aatgaccttt tcttctgaca   7320
tctgaatctg atgaatttct tgcatattaa tacagttggc acttaaagct agtgaacttc   7380
ttgaacaaac aaaacttagt gagctccgtg caagaatagc aaggagcctt tcagagctgg   7440
agatgtttac tgaggaaagc aagggtctct ccatgcataa gcgagaaatt gccattaagg   7500
agagcatgga agatttagtc actgctccac tgccagttga agatgcgctc atttctttat   7560
ttgattgtag tgatacaact gttcaacaga gagtgattga gacttatata gctcgattat   7620
accaggtatg agaagaaaga ccttttgaaa ttatttatat taacatatcc tagtaaaaca   7680
gcatgctcat catttcttaa aaaaagttta cagcacctga tgtttggtta ctgaccgcat   7740
cattaaaata aagttacttg ttgtggagag atgtattttg gaacttgtgg cacatgcagt   7800
aacatgctac tgctcgatat gtttgctaac ttgacaacaa tatttttcag cctcatcttg   7860
taaaggacag tatcaaaatg aaatggatag aatcgggtgt tattgcttta tgggaatttc   7920
ctgaagggca ttttgatgca agaaatggag gagcggttct tggtgacaaa agatggggtg   7980
ccatggtcat tgtcaagtct cttgaatcac tttcaatggc cattagattt gcactaaagg   8040
agacatcaca ctacactagc tctgagggca atatgatgca tattgctttg ttgggtgctg   8100
ataataagat gcatataatt caagaaaggt atgttcatat gctatgttgg tgctgaaata   8160
gttatatatg tagttagctg gtggagttct ggtaattaac ctatcccatt gttcagtggt   8220
gatgatgctg acagaatagc caaacttccc ttgatactaa aggataatgt aaccgatctg   8280
catgcctctg gtgtgaaaac aataagtttc attgttcaaa gagatgaagc acggatgaca   8340
atgcgtcgta ccttcctttg gtctgatgaa aagctttctt atgaggaaga gccaattctc   8400
cggcatgtgg aacctcctct ttctgcactt cttgagttgg tacgtgatat catcaaaatg   8460
ataatgtttt ggtatggcat tgattatctt ctatgctctt tgtatttatt cagcctattg   8520
tggatacagg acaagttgaa agtgaaagga tacaatgaaa tgaagtatac cccatcacgg   8580
gatcgtcaat ggcatatcta cacacttaga aatactgaaa accccaaaat gttgcaccgg   8640
gtatttttcc gaacccttgt caggcaaccc agtgtatcca acaagttttc ttcgggccag   8700
attggtgaca tggaagttgg gagtgctgaa gaacctctgt catttacatc aaccagcata   8760
ttaagatctt tgatgactgc tatagaggaa ttggagcttc acgcaattag aactggccat   8820
tcacacatgt atttgcatgt attgaaagaa caaaagcttc ttgatcttgt tccagtttca   8880
gggtaagtgc gcatatttct ttttgggaac atatgcttgc ttatgaggtt ggtcttctca   8940
atgatcttct tatcttactc aggaatacag ttttggatgt tggtcaagat gaagctactg   9000
catattcact tttaaaagaa atggctatga agatacatga acttgttggt gcaagaatgc   9060
accatctttc tgtatgccaa tgggaagtga aacttaagtt ggactgcgat ggtcctgcca   9120
gtggtacctg gaggattgta acaaccaatg ttactagtca cacttgcact gtggatgtaa   9180
gtttaatcct ctagcatttt gttttctttg gaaaagcatg tgattttaag ccggctggtc   9240
```

-continued

```
ctcataccca gacctagtga tctttatata gtgtagacat ttttctaact gcttttaatt   9300
gttttagatc taccgtgaga tggaagataa agaatcacgg aagttagtat accatcccgc   9360
cactccggcg gctggtcctc tgcatggtgt ggcactgaat aatccatatc agcctttgag   9420
tgtcattgat ctcaaacgct gttctgctag gaataataga actacatact gctatgattt   9480
tccactggtg agttgactgc tcccttatat tcaatgcatt accatagcaa attcatattc   9540
gttcatgttg tcaaaataag ccgatgaaaa ttcaaaactg taggcatttg aaactgcagt   9600
gaggaagtca tggtcctcta gtacctctgg tgcttctaaa ggtgttgaaa atgcccaatg   9660
ttatgttaaa gctacagagt tggtatttgc ggacaaacat gggtcatggg gcactccttt   9720
agttcaaatg gaccggcctg ctgggctcaa tgacattggt atggtagctt ggaccttgaa   9780
gatgtccact cctgaatttc ctagtggtag ggagattatt gttgttgcaa atgatattac   9840
gttcagagct ggatcatttg gcccaaggga agatgcattt tttgaagctg ttaccaacct   9900
agcctgtgag aagaaacttc ctcttattta tttggcagca aattctggtg ctcgaattgg   9960
catagcagat gaagtgaaat cttgcttccg tgttgggtgg tctgatgatg gcagccctga  10020
acgtgggttt cagtacattt atctaagcga agaagactat gctcgtattg gcacttctgt  10080
catagcacat aagatgcagc tagacagtgg tgaaattagg tgggttattg attctgttgt  10140
gggcaaggaa gatggacttg gtgtggagaa tatacatgga agtgctgcta ttgccagtgc  10200
ttattctagg gcatataagg agacatttac acttacattt gtgactggaa gaactgttgg  10260
aataggagct tatcttgctc gacttggcat ccggtgcata cagcgtcttg accagcctat  10320
tattcttaca ggctattctg cactgaacaa gcttcttggg cgggaagtgt acagctccca  10380
catgcagttg ggtggtccca aaatcatggc aactaatggt gttgtccatc ttactgtttc  10440
agatgacctt gaaggcgttt ctaatatatt gaggtggctc agttatgttc ctgcctacat  10500
tggtggacca cttccagtaa caacaccgtt ggacccaccg gacagacctg ttgcatacat  10560
tcctgagaac tcgtgtgatc ctcgagcggc tatccgtggt gttgatgaca gccaagggaa  10620
atggttaggt ggtatgtttg ataaagacag ctttgtggaa acatttgaag gttgggctaa  10680
gacagtggtt actggcagag caaagcttgg tggaattcca gtgggtgtga tagctgtgga  10740
gactcagacc atgatgcaaa ctatccctgc tgaccctggt cagcttgatt cccgtgagca  10800
atctgttcct cgtgctggac aagtgtggtt tccagattct gcaaccaaga ctgcgcaggc  10860
attgctggac ttcaaccgtg aaggattacc tctgttcatc ctcgctaact ggagaggctt  10920
ctctggtgga caaagagatc tttttgaagg aattcttcag gctggctcga ctattgttga  10980
gaaccttagg acatacaatc agcctgcctt tgtctacatt cccatggctg cagagctacg  11040
aggaggggct tgggttgtgg ttgatagcaa gataaaccca gaccgcattg agtgctatgc  11100
tgagaggact gcaaaaggca atgttctgga accgcaaggg ttaattgaga tcaagttcag  11160
gtcagaggaa ctccaggatt gcatgagtcg gcttgaccca acattaattg atctgaaagc  11220
aaaactcgaa gtagcaaata aaaatggaag tgctgacaca aaatcgcttc aagaaaatat  11280
agaagctcga acaaaacagt tgatgcctct atatactcag attgcgatac ggtttgctga  11340
attgcatgat acatccctca gaatggctgc gaaaggtgtg attaagaaag ttgtggactg  11400
ggaagaatca cgatctttct tctataagag attacggagg aggatctctg aggatgttct  11460
tgcaaaagaa attagagctg tagcaggtga gcagttttcc caccaaccag caatcgagct  11520
gatcaagaaa tggtattcag cttcacatgc agctgaatgg gatgatgacg atgcttttgt  11580
tgcttggatg gataaccctg aaaactacaa ggattatatt caatatctta aggctcaaag  11640
```

agtatcccaa tccctctcaa gtctttcaga ttccagctca gatttgcaag ccctgccaca 11700
gggtctttcc atgttactag ataaggtaat tagcttactg atgcttatat aaattctttt 11760
tcattacata tggctggaga actatctaat caaataatga ttataattcc aatcgttctt 11820
tttatgccat tatgatcttc tgaaatttcc ttctttggac acttattcag atggatccct 11880
ctagaagagc tcaacttgtt gaagaaatca ggaaggtcct tggttga 11927

<210> SEQ ID NO 6
<211> LENGTH: 6984
<212> TYPE: DNA
<213> ORGANISM: Oryza sativa

<400> SEQUENCE: 6
atgacatcca cacatgtggc gacattggga gttggtgccc aggcacctcc tcgtcaccag 60
aaaaagtcag ctggcactgc atttgtatca tctgggtcat caagaccctc ataccgaaag 120
aatggtcagc gtactcggtc acttagggaa gaaagcaatg gaggagtgtc tgattccaaa 180
aagcttaacc actctattcg ccaaggtctt gctggcatca ttgacctccc aaatgacgca 240
gcttcagaag ttgatatttc acatggttcc gaagatccca gggggcctac ggtcccaggt 300
tcctaccaaa tgaatgggat tatcaatgaa acacataatg ggaggcatgc ttcagtctcc 360
aaggttgttg agttttgtac ggcacttggt ggcaaaacac caattcacag tgtattagtg 420
gccaacaatg gaatggcagc agctaagttc atgcggagtg tccgaacatg ggctaatgat 480
acttttggat cagagaaggc aattcagctg atagctatgg caactccgga ggatctgagg 540
ataaatgcag agcacatcag aattgccgat caatttgtag aggtacctgg tggaacaaac 600
aacaacaact atgcaaatgt ccaactcata gtggagatag cagagagaac aggtgtttct 660
gctgtttggc ctggttgggg tcatgcatct gagaatcctg aacttccaga tgcgctgact 720
gcaaaaggaa ttgtttttct tgggccacca gcatcatcaa tgcatgcatt aggagacaag 780
gttggctcag ctctcattgc tcaagcagct ggagttccaa cacttgcttg gagtggatca 840
catgtggaag ttcctctgga gtgttgcttg gactcaatac ctgatgagat gtatagaaaa 900
gcttgtgtta ctaccacaga ggaagcagtt gcaagttgtc aggtggttgg ttatcctgcc 960
atgattaagg catcttgggg tggtggtggt aaaggaataa ggaaggttca taatgatgat 1020
gaggttagga cattatttaa gcaagttcaa ggcgaagtac ctggttcccc aatatttatc 1080
atgaggctag ctgctcagag tcgacatctt gaagttcagt tgctttgtga tcaatatggc 1140
aacgtagcag cacttcacag tcgagattgc agtgtacaac ggcgacacca aaagataatc 1200
gaggaaggac cagttactgt tgctcctcgt gagactgtga aagagcttga gcaggcagca 1260
cggaggcttg ctaaagctgt gggttatgtt ggtgctgcta ctgttgaata cctttacagc 1320
atggaaactg gtgaatatta ttttctggaa cttaatccac ggctacaggt tgagcatcct 1380
gtcactgagt ggatagctga agtaaatttg cctgcggctc aagttgctgt tggaatgggt 1440
ataccccttt ggcagattcc agagatcagg cgcttctacg gaatgaacca tggaggaggc 1500
tatgaccttt ggaggaaaac agcagctcta gcgactccat ttaactttga tgaagtagat 1560
tctaaatggc caaaaggcca ctgcgtagct gttagaataa ctagcgagga tccagatgat 1620
gggtttaagc ctactggtgg aaaagtaaag gagataagtt tcaagagtaa accaaatgtt 1680
tgggcctatt tctcagtaaa gtctggtgga ggcatccatg aattcgctga ttctcagttc 1740
ggacatgttt ttgcgtatgg aactactaga tcggcagcaa taactaccat ggctcttgca 1800

-continued

```
ctaaaagagg ttcaaattcg tggagaaatt cattcaaacg tagactacac agttgaccta   1860
ttaaatgcct cagattttag agaaaataag attcatactg gttggctgga taccaggata   1920
gccatgcgtg ttcaagctga gaggcctcca tggtatattt cagtcgttgg aggggcttta   1980
tataaaacag taactgccaa cacggccact gtttctgatt atgttggtta tcttaccaag   2040
ggccagattc caccaaagca tatatccctt gtctatacga ctgttgcttt gaatatagat   2100
gggaaaaaat atacaatcga tactgtgagg agtggacatg gtagctacag attgcgaatg   2160
aatggatcaa cggttgacgc aaatgtacaa atattatgtg atggtgggct tttaatgcag   2220
ctggatggaa acagccatgt aatttatgct gaagaagagg ccagtggtac acgacttctt   2280
attgatggaa agacatgcat gttacagaat gaccatgacc catcaaagtt attagctgag   2340
acaccatgca aacttcttcg tttcttggtt gctgatggtg ctcatgttga tgctgatgta   2400
ccatatgcgg aagttgaggt tatgaagatg tgcatgcccc tcttatcacc cgcttctggt   2460
gtcatacatg ttgtaatgtc tgagggccaa gcaatgcagg ctggtgatct tatagctagg   2520
ctggatcttg atgacccttc tgctgttaag agagctgagc cgttcgaaga tacttttcca   2580
caaatgggtc tccctattgc tgcttctggc caagttcaca aattatgtgc tgcaagtctg   2640
aatgcttgtc gaatgatcct tgcggggtat gagcatgata ttgacaaggt tgtgccagag   2700
ttggtatact gcctagacac tccggagctt cctttcctgc agtgggagga gcttatgtct   2760
gttttagcaa ctagacttcc aagaaatctt aaaagtgagt tggagggcaa atatgaggaa   2820
tacaaagtaa aatttgactc tgggataatc aatgatttcc ctgccaatat gctacgagtg   2880
ataattgagg aaaatcttgc atgtggttct gagaaggaga aggctacaaa tgagaggctt   2940
gttgagcctc ttatgagcct actgaagtca tatgagggtg ggagagaaag tcatgctcac   3000
tttgttgtca agtccctttt tgaggagtat ctctatgttg aagaattgtt cagtgatgga   3060
attcagtctg atgtgattga gcgtctgcgc cttcaacata gtaaagacct acagaaggtc   3120
gtagacattg tgttgtccca ccagagtgtt agaaataaaa ctaagctgat actaaaactc   3180
atggagagtc tggtctatcc aaatcctgct gcctacaggg atcaattgat tcgcttttct   3240
tcccttaatc acaaagcgta ttacaagttg gcacttaaag ctagtgaact tcttgaacaa   3300
acaaaactta gtgagctccg tgcaagaata gcaaggagcc tttcagagct ggagatgttt   3360
actgaggaaa gcaagggtct ctccatgcat aagcgagaaa ttgccattaa ggagagcatg   3420
gaagatttag tcactgctcc actgccagtt gaagatgcgc tcatttcttt atttgattgt   3480
agtgatacaa ctgttcaaca gagagtgatt gagacttata tagctcgatt ataccagcct   3540
catcttgtaa aggacagtat caaaatgaaa tggatagaat cgggtgttat tgctttatgg   3600
gaatttcctg aagggcattt tgatgcaaga aatggaggag cggttcttgg tgacaaaaga   3660
tggggtgcca tggtcattgt caagtctctt gaatcacttt caatggccat tagatttgca   3720
ctaaaggaga catcacacta cactagctct gagggcaata tgatgcatat tgctttgttg   3780
ggtgctgata ataagatgca tataattcaa gaaagtggtg atgatgctga cagaatagcc   3840
aaacttccct tgatactaaa ggataatgta accgatctgc atgcctctgg tgtgaaaaca   3900
ataagtttca ttgttcaaag agatgaagca cggatgacaa tgcgtcgtac cttcctttgg   3960
tctgatgaaa agctttctta tgaggaagag ccaattctcc ggcatgtgga acctcctctt   4020
tctgcacttc ttgagttgga caagttgaaa gtgaaaggat acaatgaaat gaagtatacc   4080
ccatcacggg atcgtcaatg gcatatctac acacttagaa atactgaaaa ccccaaaatg   4140
ttgcaccggg tatttttccg aacccttgtc aggcaaccca gtgtatccaa caagttttct   4200
```

```
tcgggccaga ttggtgacat ggaagttggg agtgctgaag aacctctgtc atttacatca   4260
accagcatat taagatcttt gatgactgct atagaggaat tggagcttca cgcaattaga   4320
actggccatt cacacatgta tttgcatgta ttgaaagaac aaaagcttct tgatcttgtt   4380
ccagtttcag ggaatacagt tttggatgtt ggtcaagatg aagctactgc atattcactt   4440
ttaaaagaaa tggctatgaa gatacatgaa cttgttggtg caagaatgca ccatctttct   4500
gtatgccaat gggaagtgaa acttaagttg gactgcgatg gtcctgccag tggtacctgg   4560
aggattgtaa caaccaatgt tactagtcac acttgcactg tggatatcta ccgtgagatg   4620
gaagataaag aatcacggaa gttagtatac catcccgcca ctccggcggc tggtcctctg   4680
catggtgtgg cactgaataa tccatatcag cctttgagtg tcattgatct caaacgctgt   4740
tctgctagga ataatagaac tacatactgc tatgattttc cactggcatt tgaaactgca   4800
gtgaggaagt catggtcctc tagtacctct ggtgcttcta aaggtgttga aaatgcccaa   4860
tgttatgtta aagctacaga gttggtattt gcggacaaac atgggtcatg ggcactcct    4920
ttagttcaaa tggaccggcc tgctgggctc aatgacattg gtatggtagc ttggaccttg   4980
aagatgtcca ctcctgaatt tcctagtggt agggagatta ttgttgttgc aaatgatatt   5040
acgttcagag ctggatcatt tggcccaagg gaagatgcat tttttgaagc tgttaccaac   5100
ctagcctgtg agaagaaact tcctcttatt tatttggcag caaattctgg tgctcgaatt   5160
ggcatagcag atgaagtgaa atcttgcttc cgtgttgggt ggtctgatga tggcagccct   5220
gaacgtgggt ttcagtacat ttatctaagc gaagaagact atgctcgtat tggcacttct   5280
gtcatagcac ataagatgca gctagacagt ggtgaaatta ggtgggttat tgattctgtt   5340
gtgggcaagg aagatggact tggtgtggag aatatacatg gaagtgctgc tattgccagt   5400
gcttattcta gggcatataa ggagacattt acacttacat ttgtgactgg aagaactgtt   5460
ggaataggag cttatcttgc tcgacttggc atccggtgca tacagcgtct tgaccagcct   5520
attattctta caggctattc tgcactgaac aagcttcttg ggcgggaagt gtacagctcc   5580
cacatgcagt tgggtggtcc caaaatcatg gcaactaatg gtgttgtcca tcttactgtt   5640
tcagatgacc ttgaaggcgt ttctaatata ttgaggtggc tcagttatgt tcctgcctac   5700
attggtggac cacttccagt aacaacaccg ttggacccac cggacagacc tgttgcatac   5760
attcctgaga actcgtgtga tcctcgagcg gctatccgtg gtgttgatga cagccaaggg   5820
aaatggttag gtggtatgtt tgataaagac agctttgtgg aaacatttga aggttgggct   5880
aagacagtgg ttactggcag agcaaagctt ggtggaattc cagtgggtgt gatagctgtg   5940
gagactcaga ccatgatgca aactatccct gctgaccctg gtcagcttga ttcccgtgag   6000
caatctgttc ctcgtgctgg acaagtgtgg tttccagatt ctgcaaccaa gactgcgcag   6060
gcattgctgg acttcaaccg tgaaggatta cctctgttca tcctcgctaa ctggagaggc   6120
ttctctggtg gacaaagaga tctttttgaa ggaattcttc aggctggctc gactattgtt   6180
gagaacctta ggacatacaa tcagcctgcc tttgtctaca ttcccatggc tgcagagcta   6240
cgaggagggg cttgggttgt ggttgatagc aagataaacc cagaccgcat tgagtgctat   6300
gctgagagga ctgcaaaagg caatgttctg gaaccgcaag ggttaattga gatcaagttc   6360
aggtcagagg aactccagga ttgcatgagt cggcttgacc caacattaat tgatctgaaa   6420
gcaaaactcg aagtagcaaa taaaaatgga agtgctgaca caaaatcgct tcaagaaaat   6480
atagaagctc gaacaaaaca gttgatgcct ctatatactc agattgcgat acggtttgct   6540
```

```
gaattgcatg atacatccct cagaatggct gcgaaaggtg tgattaagaa agttgtggac   6600

tgggaagaat cacgatcttt cttctataag agattacgga ggaggatctc tgaggatgtt   6660

cttgcaaaag aaattagagc tgtagcaggt gagcagtttt cccaccaacc agcaatcgag   6720

ctgatcaaga aatggtattc agcttcacat gcagctgaat gggatgatga cgatgctttt   6780

gttgcttgga tggataaccc tgaaaactac aaggattata ttcaatatct taaggctcaa   6840

agagtatccc aatccctctc aagtctttca gattccagct cagatttgca agccctgcca   6900

cagggtcttt ccatgttact agataagatg gatccctcta gaagagctca acttgttgaa   6960

gaaatcagga aggtccttgg ttga                                          6984


<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

gcaaatgata ttacgttcag agctg                                           25


<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

gttaccaacc tagcctgtga gaag                                            24


<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

gatttcttca acaagttgag ctcttc                                          26


<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

agtaacatgg aaagaccctg tggc                                            24


<210> SEQ ID NO 11
<211> LENGTH: 6978
<212> TYPE: DNA
<213> ORGANISM: Zea mays

<400> SEQUENCE: 11

atgtcacagc ttggattagc cgcagctgcc tcaaaggcct tgccactact ccctaatcgc     60

cagagaagtt cagctgggac tacattctca tcatcttcat tatcgaggcc cttaaacaga    120
```

-continued

```
aggaaaagcc gtactcgttc actccgtgat ggcggagatg gggtatcaga tgccaaaaag    180
cacagccagt ctgttcgtca aggtcttgct ggcattatcg acctcccaag tgaggcacct    240
tccgaagtgg atatttcaca tggatctgag gatcctaggg ggccaacaga ttcttatcaa    300
atgaatggga ttatcaatga aacacataat ggaagacatg cctcagtgtc caaggttgtt    360
gaattttgtg cggcactagg tggcaaaaca ccaattcaca gtatattagt ggccaacaat    420
ggaatggcag cagcaaaatt tatgaggagt gtccggacat gggctaatga tactttgga     480
tctgagaagg caattcaact catagctatg gcaactccgg aagacatgag gataaatgca    540
gaacacatta gaattgctga ccaattcgta gaggtgcctg gtggaacaaa caataataac    600
tacgccaatg ttcaactcat agtggagatg gcacaaaaac taggtgtttc tgctgtttgg    660
cctggttggg gtcatgcttc tgagaatcct gaactgccag atgcattgac cgcaaaaggg    720
atcgtttttc ttggcccacc tgcatcatca atgaatgctt tgggagataa ggtcggctca    780
gctctcattg ctcaagcagc cggggtccca actcttgctc ggagtggatc acatgttgaa    840
gttccattag agtgctgctt agacgcgata cctgaggaga tgtatagaaa agcttgcgtt    900
actaccacag aggaagcagt tgcaagttgt caagtggttg gttatcctgc catgattaag    960
gcatcctggg gaggtggtgg taaaggaata agaaaggttc ataatgatga tgaggttaga   1020
gcgctgttta agcaagtaca aggtgaagtc cctggctccc caatatttgt catgaggctt   1080
gcatcccaga gtcggcatct tgaagttcag ttgctttgtg atcaatatgg taatgtagca   1140
gcacttcaca gtcgtgattg cagtgtgcaa cggcgacacc agaagattat tgaagaaggt   1200
ccagttactg ttgctcctcg tgagacagtt aaagcacttg agcaggcagc aaggaggctt   1260
gctaaggctg tgggttatgt tggtgctgct actgttgagt atctttacag catggaaact   1320
ggagactact attttctgga acttaatccc cgactacagg ttgagcatcc agtcaccgag   1380
tggatagctg aagtaaatct gcctgcagct caagttgctg ttggaatggg catacctctt   1440
tggcagattc cagaaatcag acgtttctat ggaatggact atggaggagg gtatgacatt   1500
tggaggaaaa cagcagctct tgctacacca tttaattttg atgaagtaga ttctcaatgg   1560
ccaaagggcc attgtgtagc agttagaatt actagtgagg acccagatga tggtttcaaa   1620
cctactggtg ggaaagtgaa ggagataagt tttaaaagca agcctaatgt ttgggcctac   1680
ttctcagtaa agtctggtgg aggcattcat gaatttgctg attctcagtt cggacatgtt   1740
tttgcatatg ggctctctag atcagcagca ataacaaaca tgactcttgc attaaaagag   1800
attcaaattc gtggagaaat tcattcaaat gttgattaca cagttgacct cttaaatgct   1860
tcagacttta gagaaaacaa gattcatact ggttggctcg acaccagaat agctatgcgt   1920
gttcaagctg agaggccccc atggtatatt tcagtggttg gaggtgcttt atataaaaca   1980
gtaaccacca atgcagccac tgtttctgaa tatgttagtt atctcaccaa gggccagatt   2040
ccaccaaagc atatatccct tgtcaattct acagttaatt tgaatataga agggagcaaa   2100
tacacaattg aaactgtaag gactggacat ggtagctaca ggttgagaat gaatgattca   2160
acagttgaag cgaatgtaca atctttatgt gatggtggcc tcttaatgca gttggatgga   2220
aacagccatg taatttatgc agaagaagaa gctggtggta cacggcttca gattgatgga   2280
aagacatgtt tattgcagaa tgaccatgat ccatcaaagt tattagctga gacaccctgc   2340
aaacttcttc gtttcttggt tgctgatggt gctcatgttg atgcggatgt accatacgcg   2400
gaagttgagg ttatgaagat gtgcatgcct ctcttgtcac ctgcttctgg tgtcattcat   2460
```

-continued

```
tgtatgatgt ctgagggcca ggcattgcag gctggtgatc ttatagcaag gttggatctt   2520
gatgaccctt ctgctgtgaa aagagctgag ccatttgatg gaatatttcc acaaatggag   2580
ctccctgttg ctgtctctag tcaagtacac aaaagatatg ctgcaagttt gaatgctgct   2640
cgaatggtcc ttgcaggata tgagcacaat attaatgaag tcgttcaaga tttggtatgc   2700
tgcctggaca accctgagct tcctttccta cagtgggatg aacttatgtc tgttctagca   2760
acgaggcttc caagaaatct caagagtgag ttagaggata aatacaagga atacaagttg   2820
aatttttacc atggaaaaaa cgaggacttt ccatccaagt tgctaagaga catcattgag   2880
gaaaatcttt cttatggttc agagaaggaa aaggctacaa atgagaggct tgttgagcct   2940
cttatgaacc tactgaagtc atatgagggt gggagagaga gccatgcaca ttttgttgtc   3000
aagtctcttt tcgaggagta tcttacagtg gaagaacttt ttagtgatgg cattcagtct   3060
gacgtgattg aaacattgcg gcatcagcac agtaaagacc tgcagaaggt tgtagacatt   3120
gtgttgtctc accagggtgt gaggaacaaa gctaagcttg taacggcact tatggaaaag   3180
ctggtttatc caaatcctgg tggttacagg gatctgttag ttcgcttttc ttccctcaat   3240
cataaaagat attataagtt ggcccttaaa gcaagtgaac ttcttgaaca aaccaaacta   3300
agtgaactcc gtgcaagcgt tgcaagaagc ctttcggatc tggggatgca taagggagaa   3360
atgagtatta aggataacat ggaagattta gtctctgccc cattacctgt tgaagatgct   3420
ctgatttctt tgtttgatta cagtgatcga actgttcagc agaaagtgat tgagacatac   3480
atatcacgat tgtaccagcc tcatcttgta aaggatagca tccaaatgaa attcaaggaa   3540
tctggtgcta ttacttttg ggaattttat gaagggcatg ttgatactag aaatggacat   3600
ggggctatta ttggtgggaa gcgatggggt gccatggtcg ttctcaaatc acttgaatct   3660
gcgtcaacag ccattgtggc tgcattaaag gattcggcac agttcaacag ctctgagggc   3720
aacatgatgc acattgcatt attgagtgct gaaaatgaaa gtaatataag tggaataagc   3780
agtgatgatc aagctcaaca taagatggaa aagcttagca agatactgaa ggatactagc   3840
gttgcaagtg atctccaagc tgctggtttg aaggttataa gttgcattgt tcaaagagat   3900
gaagctcgca tgccaatgcg ccacacattc ctctggttgg atgacaagag ttgttatgaa   3960
gaagagcaga ttctccggca tgtggagcct cccctctcta cacttcttga attggataag   4020
ttgaaggtga aaggatacaa tgaaatgaag tatactcctt cgcgtgaccg ccaatggcat   4080
atctacacac taagaaatac tgaaaacccc aaaatgttgc atagggtgtt tttccgaact   4140
attgtcaggc aacccaatgc aggcaacaag tttacatcgg ctcagatcag cgacgctgaa   4200
gtaggatgtc ccgaagaatc tctttcattt acatcaaata gcatcttaag atcattgatg   4260
actgctattg aagaattaga gcttcatgca attaggacag gtcattctca catgtatttg   4320
tgcatactga aagagcaaaa gcttcttgac ctcattccat tttcagggag tacaattgtt   4380
gatgttggcc aagatgaagc taccgcttgt tcacttttaa aatcaatggc tttgaagata   4440
catgagcttg ttggtgcaag gatgcatcat ctgtctgtat gccagtggga ggtgaaactc   4500
aagttggact gtgatggccc tgcaagtggt acctggagag ttgtaactac aaatgttact   4560
ggtcacacct gcaccattga tatataccga gaagtggagg aaatagaatc gcagaagtta   4620
gtgtaccatt cagccacttc gtcagctgga ccattgcatg gtgttgcact gaataatcca   4680
tatcaacctt tgagtgtgat tgatctaaag cgctgctctg ctaggaacaa cagaacaaca   4740
tattgctatg attttccgct ggcctttgaa actgcactgc agaagtcatg gcagtccaat   4800
ggctctactg tttctgaagg caatgaaaat agtaaatcct acgtgaaggc aactgagcta   4860
```

```
gtgtttgctg aaaaacatgg gtcctggggc actcctataa ttccgatgga acgccctgct   4920

gggctcaacg acattggtat ggtcgcttgg atcatggaga tgtcaacacc tgaatttccc   4980

aatggcaggc agattattgt tgtagcaaat gatatcactt tcagagctgg atcatttggc   5040

ccaagggaag atgcattttt tgaaactgtc actaacctgg cttgcgaaag gaaacttcct   5100

cttatatact tggcagcaaa ctctggtgct aggattggca tagctgatga agtaaaatct   5160

tgcttccgtg ttggatggtc tgacgaaggc agtcctgaac gagggtttca gtacatctat   5220

ctgactgaag aagactatgc tcgcattagc tcttctgtta tagcacataa gctggagcta   5280

gatagtggtg aaattaggtg gattattgac tctgttgtgg gcaaggagga tgggcttggt   5340

gtcgagaaca tacatggaag tgctgctatt gccagtgctt attctagggc atatgaggag   5400

acatttacac ttacatttgt gactgggcgg actgtaggaa taggagctta tcttgctcga   5460

cttggtatac ggtgcataca gcgtcttgac cagcctatta ttttaacagg gttttctgcc   5520

ctgaacaagc tccttgggcg ggaagtgtac agctcccaca tgcagcttgg tggtcctaag   5580

atcatggcga ctaatggtgt tgtccacctc actgttccag atgaccttga aggtgtttcc   5640

aatatattga ggtggctcag ctatgttcct gcaaacattg gtggacctct tcctattacc   5700

aaacctctgg accctccaga cagacctgtt gcttacatcc ctgagaacac atgcgatcca   5760

cgtgcagcta tctgtggtgt agatgacagc caagggaaat ggttgggtgg tatgtttgac   5820

aaagacagct ttgtggagac atttgaagga tgggcaaaaa cagtggttac tggcagagca   5880

aagcttggag gaattcctgt gggcgtcata gctgtggaga cacagaccat gatgcagatc   5940

atccctgctg atccaggtca gcttgattcc catgagcgat ctgtccctcg tgctggacaa   6000

gtgtggttcc cagattctgc aaccaagacc gctcaggcat tattagactt caaccgtgaa   6060

ggattgcctc tgttcatcct ggctaattgg agaggcttct ctggtggaca aagagatctc   6120

tttgaaggaa ttcttcaggc tgggtcaaca attgtcgaga accttaggac atctaatcag   6180

cctgcttttg tgtacattcc tatggctgga gagcttcgtg gaggagcttg ggttgtggtc   6240

gatagcaaaa taaatccaga ccgcattgag tgttatgctg aaaggactgc caaaggtaat   6300

gttctcgaac ctcaagggtt aattgaaatc aagttcaggt cagaggaact ccaagactgt   6360

atgggtaggc ttgacccaga gttgataaat ctgaaagcaa aactccaaga tgtaaatcat   6420

ggaaatggaa gtctaccaga catagaaggg attcggaaga gtatagaagc acgtacgaaa   6480

cagttgctgc ctttatatac ccagattgca atacggtttg ctgaattgca tgatacttcc   6540

ctaagaatgg cagctaaagg tgtgattaag aaagttgtag actgggaaga atcacgctcg   6600

ttcttctata aaaggctacg gaggaggatc gcagaagatg ttcttgcaaa agaaataagg   6660

cagatagtcg gtgataaatt tacgcaccaa ttagcaatgg agctcatcaa ggaatggtac   6720

cttgcttctc aggccacaac aggaagcact ggatgggatg acgatgatgc ttttgttgcc   6780

tggaaggaca gtcctgaaaa ctacaagggg catatccaaa agcttagggc tcaaaaagtg   6840

tctcattcgc tctctgatct tgctgactcc agttcagatc tgcaagcatt ctcgcagggt   6900

ctttctacgc tattagataa gatggatccc tctcagagag cgaagtttgt tcaggaagtc   6960

aagaaggtcc ttgattga                                                 6978
```

<210> SEQ ID NO 12
<211> LENGTH: 2325
<212> TYPE: PRT
<213> ORGANISM: Zea mays

<400> SEQUENCE: 12

Met Ser Gln Leu Gly Leu Ala Ala Ala Ala Ser Lys Ala Leu Pro Leu
1 5 10 15

Leu Pro Asn Arg Gln Arg Ser Ser Ala Gly Thr Thr Phe Ser Ser Ser
20 25 30

Ser Leu Ser Arg Pro Leu Asn Arg Arg Lys Ser Arg Thr Arg Ser Leu
35 40 45

Arg Asp Gly Gly Asp Gly Val Ser Asp Ala Lys Lys His Ser Gln Ser
50 55 60

Val Arg Gln Gly Leu Ala Gly Ile Ile Asp Leu Pro Ser Glu Ala Pro
65 70 75 80

Ser Glu Val Asp Ile Ser His Gly Ser Glu Asp Pro Arg Gly Pro Thr
85 90 95

Asp Ser Tyr Gln Met Asn Gly Ile Ile Asn Glu Thr His Asn Gly Arg
100 105 110

His Ala Ser Val Ser Lys Val Val Glu Phe Cys Ala Ala Leu Gly Gly
115 120 125

Lys Thr Pro Ile His Ser Ile Leu Val Ala Asn Asn Gly Met Ala Ala
130 135 140

Ala Lys Phe Met Arg Ser Val Arg Thr Trp Ala Asn Asp Thr Phe Gly
145 150 155 160

Ser Glu Lys Ala Ile Gln Leu Ile Ala Met Ala Thr Pro Glu Asp Met
165 170 175

Arg Ile Asn Ala Glu His Ile Arg Ile Ala Asp Gln Phe Val Glu Val
180 185 190

Pro Gly Gly Thr Asn Asn Asn Asn Tyr Ala Asn Val Gln Leu Ile Val
195 200 205

Glu Met Ala Gln Lys Leu Gly Val Ser Ala Val Trp Pro Gly Trp Gly
210 215 220

His Ala Ser Glu Asn Pro Glu Leu Pro Asp Ala Leu Thr Ala Lys Gly
225 230 235 240

Ile Val Phe Leu Gly Pro Pro Ala Ser Ser Met Asn Ala Leu Gly Asp
245 250 255

Lys Val Gly Ser Ala Leu Ile Ala Gln Ala Ala Gly Val Pro Thr Leu
260 265 270

Ala Arg Ser Gly Ser His Val Glu Val Pro Leu Glu Cys Cys Leu Asp
275 280 285

Ala Ile Pro Glu Glu Met Tyr Arg Lys Ala Cys Val Thr Thr Thr Glu
290 295 300

Glu Ala Val Ala Ser Cys Gln Val Val Gly Tyr Pro Ala Met Ile Lys
305 310 315 320

Ala Ser Trp Gly Gly Gly Gly Lys Gly Ile Arg Lys Val His Asn Asp
325 330 335

Asp Glu Val Arg Ala Leu Phe Lys Gln Val Gln Gly Glu Val Pro Gly
340 345 350

Ser Pro Ile Phe Val Met Arg Leu Ala Ser Gln Ser Arg His Leu Glu
355 360 365

Val Gln Leu Leu Cys Asp Gln Tyr Gly Asn Val Ala Ala Leu His Ser
370 375 380

Arg Asp Cys Ser Val Gln Arg Arg His Gln Lys Ile Ile Glu Glu Gly
385 390 395 400

Pro Val Thr Val Ala Pro Arg Glu Thr Val Lys Ala Leu Glu Gln Ala
405 410 415

```
Ala Arg Arg Leu Ala Lys Ala Val Gly Tyr Val Gly Ala Ala Thr Val
            420                 425                 430

Glu Tyr Leu Tyr Ser Met Glu Thr Gly Asp Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Ala Asp Ser Gln
                565                 570                 575

Phe Gly His Val Phe Ala Tyr Gly Leu Ser Arg Ser Ala Ala Ile Thr
            580                 585                 590

Asn Met Thr Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Arg
    610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Val Thr Thr Asn Ala Ala Thr Val Ser Glu Tyr Val
            660                 665                 670

Ser Tyr Leu Thr Lys Gly Gln Ile Pro Pro Lys His Ile Ser Leu Val
        675                 680                 685

Asn Ser Thr Val Asn Leu Asn Ile Glu Gly Ser Lys Tyr Thr Ile Glu
    690                 695                 700

Thr Val Arg Thr Gly His Gly Ser Tyr Arg Leu Arg Met Asn Asp Ser
705                 710                 715                 720

Thr Val Glu Ala Asn Val Gln Ser Leu Cys Asp Gly Gly Leu Leu Met
                725                 730                 735

Gln Leu Asp Gly Asn Ser His Val Ile Tyr Ala Glu Glu Glu Ala Gly
            740                 745                 750

Gly Thr Arg Leu Gln Ile Asp Gly Lys Thr Cys Leu Leu Gln Asn Asp
        755                 760                 765

His Asp Pro Ser Lys Leu Leu Ala Glu Thr Pro Cys Lys Leu Leu Arg
    770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Cys Met Met Ser Glu Gly Gln Ala Leu Gln Ala Gly
            820                 825                 830
```

-continued

```
Asp Leu Ile Ala Arg Leu Asp Leu Asp Asp Pro Ser Ala Val Lys Arg
        835                 840                 845

Ala Glu Pro Phe Asp Gly Ile Phe Pro Gln Met Glu Leu Pro Val Ala
    850                 855                 860

Val Ser Ser Gln Val His Lys Arg Tyr Ala Ala Ser Leu Asn Ala Ala
865                 870                 875                 880

Arg Met Val Leu Ala Gly Tyr Glu His Asn Ile Asn Glu Val Val Gln
                885                 890                 895

Asp Leu Val Cys Cys Leu Asp Asn Pro Glu Leu Pro Phe Leu Gln Trp
            900                 905                 910

Asp Glu Leu Met Ser Val Leu Ala Thr Arg Leu Pro Arg Asn Leu Lys
        915                 920                 925

Ser Glu Leu Glu Asp Lys Tyr Lys Glu Tyr Lys Leu Asn Phe Tyr His
    930                 935                 940

Gly Lys Asn Glu Asp Phe Pro Ser Lys Leu Leu Arg Asp Ile Ile Glu
945                 950                 955                 960

Glu Asn Leu Ser Tyr Gly Ser Glu Lys Glu Lys Ala Thr Asn Glu Arg
                965                 970                 975

Leu Val Glu Pro Leu Met Asn Leu Leu Lys Ser Tyr Glu Gly Gly Arg
            980                 985                 990

Glu Ser His Ala His Phe Val Val  Lys Ser Leu Phe Glu  Glu Tyr Leu
        995                 1000                 1005

Thr Val  Glu Glu Leu Phe Ser  Asp Gly Ile Gln Ser  Asp Val Ile
    1010                 1015                 1020

Glu Thr  Leu Arg His Gln His  Ser Lys Asp Leu Gln  Lys Val Val
    1025                 1030                 1035

Asp Ile  Val Leu Ser His Gln  Gly Val Arg Asn Lys  Ala Lys Leu
    1040                 1045                 1050

Val Thr  Ala Leu Met Glu Lys  Leu Val Tyr Pro Asn  Pro Gly Gly
    1055                 1060                 1065

Tyr Arg  Asp Leu Leu Val Arg  Phe Ser Ser Leu Asn  His Lys Arg
    1070                 1075                 1080

Tyr Tyr  Lys Leu Ala Leu Lys  Ala Ser Glu Leu Leu  Glu Gln Thr
    1085                 1090                 1095

Lys Leu  Ser Glu Leu Arg Ala  Ser Val Ala Arg Ser  Leu Ser Asp
    1100                 1105                 1110

Leu Gly  Met His Lys Gly Glu  Met Ser Ile Lys Asp  Asn Met Glu
    1115                 1120                 1125

Asp Leu  Val Ser Ala Pro Leu  Pro Val Glu Asp Ala  Leu Ile Ser
    1130                 1135                 1140

Leu Phe  Asp Tyr Ser Asp Arg  Thr Val Gln Gln Lys  Val Ile Glu
    1145                 1150                 1155

Thr Tyr  Ile Ser Arg Leu Tyr  Gln Pro His Leu Val  Lys Asp Ser
    1160                 1165                 1170

Ile Gln  Met Lys Phe Lys Glu  Ser Gly Ala Ile Thr  Phe Trp Glu
    1175                 1180                 1185

Phe Tyr  Glu Gly His Val Asp  Thr Arg Asn Gly His  Gly Ala Ile
    1190                 1195                 1200

Ile Gly  Gly Lys Arg Trp Gly  Ala Met Val Val Leu  Lys Ser Leu
    1205                 1210                 1215

Glu Ser  Ala Ser Thr Ala Ile  Val Ala Ala Leu Lys  Asp Ser Ala
    1220                 1225                 1230

Gln Phe  Asn Ser Ser Glu Gly  Asn Met Met His Ile  Ala Leu Leu
```

```
    1235                1240                1245

Ser Ala  Glu Asn Glu Ser Asn  Ile Ser Gly Ile Ser  Ser Asp Asp
    1250                1255                1260

Gln Ala  Gln His Lys Met Glu  Lys Leu Ser Lys Ile  Leu Lys Asp
    1265                1270                1275

Thr Ser  Val Ala Ser Asp Leu  Gln Ala Ala Gly Leu  Lys Val Ile
    1280                1285                1290

Ser Cys  Ile Val Gln Arg Asp  Glu Ala Arg Met Pro  Met Arg His
    1295                1300                1305

Thr Phe  Leu Trp Leu Asp Asp  Lys Ser Cys Tyr Glu  Glu Glu Gln
    1310                1315                1320

Ile Leu  Arg His Val Glu Pro  Pro Leu Ser Thr Leu  Leu Glu Leu
    1325                1330                1335

Asp Lys  Leu Lys Val Lys Gly  Tyr Asn Glu Met Lys  Tyr Thr Pro
    1340                1345                1350

Ser Arg  Asp Arg Gln Trp His  Ile Tyr Thr Leu Arg  Asn Thr Glu
    1355                1360                1365

Asn Pro  Lys Met Leu His Arg  Val Phe Phe Arg Thr  Ile Val Arg
    1370                1375                1380

Gln Pro  Asn Ala Gly Asn Lys  Phe Thr Ser Ala Gln  Ile Ser Asp
    1385                1390                1395

Ala Glu  Val Gly Cys Pro Glu  Glu Ser Leu Ser Phe  Thr Ser Asn
    1400                1405                1410

Ser Ile  Leu Arg Ser Leu Met  Thr Ala Ile Glu Glu  Leu Glu Leu
    1415                1420                1425

His Ala  Ile Arg Thr Gly His  Ser His Met Tyr Leu  Cys Ile Leu
    1430                1435                1440

Lys Glu  Gln Lys Leu Leu Asp  Leu Ile Pro Phe Ser  Gly Ser Thr
    1445                1450                1455

Ile Val  Asp Val Gly Gln Asp  Glu Ala Thr Ala Cys  Ser Leu Leu
    1460                1465                1470

Lys Ser  Met Ala Leu Lys Ile  His Glu Leu Val Gly  Ala Arg Met
    1475                1480                1485

His His  Leu Ser Val Cys Gln  Trp Glu Val Lys Leu  Lys Leu Asp
    1490                1495                1500

Cys Asp  Gly Pro Ala Ser Gly  Thr Trp Arg Val Val  Thr Thr Asn
    1505                1510                1515

Val Thr  Gly His Thr Cys Thr  Ile Asp Ile Tyr Arg  Glu Val Glu
    1520                1525                1530

Glu Ile  Glu Ser Gln Lys Leu  Val Tyr His Ser Ala  Thr Ser Ser
    1535                1540                1545

Ala Gly  Pro Leu His Gly Val  Ala Leu Asn Asn Pro  Tyr Gln Pro
    1550                1555                1560

Leu Ser  Val Ile Asp Leu Lys  Arg Cys Ser Ala Arg  Asn Asn Arg
    1565                1570                1575

Thr Thr  Tyr Cys Tyr Asp Phe  Pro Leu Ala Phe Glu  Thr Ala Leu
    1580                1585                1590

Gln Lys  Ser Trp Gln Ser Asn  Gly Ser Thr Val Ser  Glu Gly Asn
    1595                1600                1605

Glu Asn  Ser Lys Ser Tyr Val  Lys Ala Thr Glu Leu  Val Phe Ala
    1610                1615                1620

Glu Lys  His Gly Ser Trp Gly  Thr Pro Ile Ile Pro  Met Glu Arg
    1625                1630                1635
```

Pro Ala Gly Leu Asn Asp Ile Gly Met Val Ala Trp Ile Met Glu
1640 1645 1650

Met Ser Thr Pro Glu Phe Pro Asn Gly Arg Gln Ile Ile Val Val
1655 1660 1665

Ala Asn Asp Ile Thr Phe Arg Ala Gly Ser Phe Gly Pro Arg Glu
1670 1675 1680

Asp Ala Phe Phe Glu Thr Val Thr Asn Leu Ala Cys Glu Arg Lys
1685 1690 1695

Leu Pro Leu Ile Tyr Leu Ala Ala Asn Ser Gly Ala Arg Ile Gly
1700 1705 1710

Ile Ala Asp Glu Val Lys Ser Cys Phe Arg Val Gly Trp Ser Asp
1715 1720 1725

Glu Gly Ser Pro Glu Arg Gly Phe Gln Tyr Ile Tyr Leu Thr Glu
1730 1735 1740

Glu Asp Tyr Ala Arg Ile Ser Ser Ser Val Ile Ala His Lys Leu
1745 1750 1755

Glu Leu Asp Ser Gly Glu Ile Arg Trp Ile Ile Asp Ser Val Val
1760 1765 1770

Gly Lys Glu Asp Gly Leu Gly Val Glu Asn Ile His Gly Ser Ala
1775 1780 1785

Ala Ile Ala Ser Ala Tyr Ser Arg Ala Tyr Glu Glu Thr Phe Thr
1790 1795 1800

Leu Thr Phe Val Thr Gly Arg Thr Val Gly Ile Gly Ala Tyr Leu
1805 1810 1815

Ala Arg Leu Gly Ile Arg Cys Ile Gln Arg Leu Asp Gln Pro Ile
1820 1825 1830

Ile Leu Thr Gly Phe Ser Ala Leu Asn Lys Leu Leu Gly Arg Glu
1835 1840 1845

Val Tyr Ser Ser His Met Gln Leu Gly Gly Pro Lys Ile Met Ala
1850 1855 1860

Thr Asn Gly Val Val His Leu Thr Val Pro Asp Asp Leu Glu Gly
1865 1870 1875

Val Ser Asn Ile Leu Arg Trp Leu Ser Tyr Val Pro Ala Asn Ile
1880 1885 1890

Gly Gly Pro Leu Pro Ile Thr Lys Pro Leu Asp Pro Pro Asp Arg
1895 1900 1905

Pro Val Ala Tyr Ile Pro Glu Asn Thr Cys Asp Pro Arg Ala Ala
1910 1915 1920

Ile Cys Gly Val Asp Asp Ser Gln Gly Lys Trp Leu Gly Gly Met
1925 1930 1935

Phe Asp Lys Asp Ser Phe Val Glu Thr Phe Glu Gly Trp Ala Lys
1940 1945 1950

Thr Val Val Thr Gly Arg Ala Lys Leu Gly Gly Ile Pro Val Gly
1955 1960 1965

Val Ile Ala Val Glu Thr Gln Thr Met Met Gln Ile Ile Pro Ala
1970 1975 1980

Asp Pro Gly Gln Leu Asp Ser His Glu Arg Ser Val Pro Arg Ala
1985 1990 1995

Gly Gln Val Trp Phe Pro Asp Ser Ala Thr Lys Thr Ala Gln Ala
2000 2005 2010

Leu Leu Asp Phe Asn Arg Glu Gly Leu Pro Leu Phe Ile Leu Ala
2015 2020 2025

```
Asn Trp  Arg Gly Phe Ser Gly  Gly Gln Arg Asp Leu  Phe Glu Gly
    2030                 2035                 2040

Ile Leu  Gln Ala Gly Ser Thr  Ile Val Glu Asn Leu  Arg Thr Ser
    2045                 2050                 2055

Asn Gln  Pro Ala Phe Val Tyr  Ile Pro Met Ala Gly  Glu Leu Arg
    2060                 2065                 2070

Gly Gly  Ala Trp Val Val Val  Asp Ser Lys Ile Asn  Pro Asp Arg
    2075                 2080                 2085

Ile Glu  Cys Tyr Ala Glu Arg  Thr Ala Lys Gly Asn  Val Leu Glu
    2090                 2095                 2100

Pro Gln  Gly Leu Ile Glu Ile  Lys Phe Arg Ser Glu  Glu Leu Gln
    2105                 2110                 2115

Asp Cys  Met Gly Arg Leu Asp  Pro Glu Leu Ile Asn  Leu Lys Ala
    2120                 2125                 2130

Lys Leu  Gln Asp Val Asn His  Gly Asn Gly Ser Leu  Pro Asp Ile
    2135                 2140                 2145

Glu Gly  Ile Arg Lys Ser Ile  Glu Ala Arg Thr Lys  Gln Leu Leu
    2150                 2155                 2160

Pro Leu  Tyr Thr Gln Ile Ala  Ile Arg Phe Ala Glu  Leu His Asp
    2165                 2170                 2175

Thr Ser  Leu Arg Met Ala Ala  Lys Gly Val Ile Lys  Lys Val Val
    2180                 2185                 2190

Asp Trp  Glu Glu Ser Arg Ser  Phe Phe Tyr Lys Arg  Leu Arg Arg
    2195                 2200                 2205

Arg Ile  Ala Glu Asp Val Leu  Ala Lys Glu Ile Arg  Gln Ile Val
    2210                 2215                 2220

Gly Asp  Lys Phe Thr His Gln  Leu Ala Met Glu Leu  Ile Lys Glu
    2225                 2230                 2235

Trp Tyr  Leu Ala Ser Gln Ala  Thr Thr Gly Ser Thr  Gly Trp Asp
    2240                 2245                 2250

Asp Asp  Asp Ala Phe Val Ala  Trp Lys Asp Ser Pro  Glu Asn Tyr
    2255                 2260                 2265

Lys Gly  His Ile Gln Lys Leu  Arg Ala Gln Lys Val  Ser His Ser
    2270                 2275                 2280

Leu Ser  Asp Leu Ala Asp Ser  Ser Ser Asp Leu Gln  Ala Phe Ser
    2285                 2290                 2295

Gln Gly  Leu Ser Thr Leu Leu  Asp Lys Met Asp Pro  Ser Gln Arg
    2300                 2305                 2310

Ala Lys  Phe Val Gln Glu Val  Lys Lys Val Leu Asp
    2315                 2320                 2325


<210> SEQ ID NO 13
<211> LENGTH: 6975
<212> TYPE: DNA
<213> ORGANISM: Zea mays

<400> SEQUENCE: 13

atgtcacagc ttggattagc cgcagctgcc tcaaaggcct tgccactact ccctaatcgc     60

cagagaagtt cagctgggac tacattctca tcatcttcat tatcgaggcc cttaaacaga    120

aggaaaagcc gtactcgttc actccgtgat ggcggagatg ggtatcaga tgccaaaaag    180

cacagccagt ctgttcgtca aggtcttgct ggcattatcg acctcccaag tgaggcacct    240

tccgaagtgg atatttcaca tggatctgag gatcctaggg ggccaacaga ttcttatcaa    300

atgaatggga ttatcaatga aacacataat ggaagacatg cctcagtgtc caaggttgtt    360
```

```
gaattttgtg cggcactagg tggcaaaaca ccaattcaca gtatattagt ggccaacaat    420
ggaatggcag cagcaaaatt tatgaggagt gtccggacat gggctaatga tacttttgga    480
tctgagaagg caattcaact catagctatg gcaactccgg aagacatgag gataaatgca    540
gaacacatta gaattgctga ccaattcgta gaggtgcctg gtggaacaaa caataataac    600
tacgccaatg ttcaactcat agtggagatg gcacaaaaac taggtgtttc tgctgtttgg    660
cctggttggg gtcatgcttc tgagaatcct gaactgccag atgcattgac cgcaaaaggg    720
atcgtttttc ttggcccacc tgcatcatca atgaatgctt tgggagataa ggtcggctca    780
gctctcattg ctcaagcagc cggggtccca actcttgctt ggagtggatc acatgttgaa    840
gttccattag agtgctgctt agacgcgata cctgaggaga tgtatagaaa agcttgcgtt    900
actaccacag aggaagcagt tgcaagttgt caagtggttg gttatcctgc catgattaag    960
gcatcctggg gaggtggtgg taaaggaata agaaaggttc ataatgatga tgaggttaga   1020
gcgctgttta agcaagtaca aggtgaagtc cctggctccc caatatttgt catgaggctt   1080
gcatcccaga gtcggcatct tgaagttcag ttgctttgtg atcaatatgg taatgtagca   1140
gcacttcaca gtcgtgattg cagtgtgcaa cggcgacacc agaagattat tgaagaaggt   1200
ccagttactg ttgctcctcg tgagacagtt aaagcacttg agcaggcagc aaggaggctt   1260
gctaaggctg tgggttatgt tggtgctgct actgttgagt atctttacag catggaaact   1320
ggagactact attttctgga acttaatccc cgactacagg ttgagcatcc agtcaccgag   1380
tggatagctg aagtaaatct gcctgcagct caagttgctg ttggaatggg catacctctt   1440
tggcagattc cagaaatcag acgtttctat ggaatggact atggaggagg gtatgacatt   1500
tggaggaaaa cagcagctct tgctacacca tttaattttg atgaagtaga ttctcaatgg   1560
ccaaagggcc attgtgtagc agttagaatt actagtgagg acccagatga tggtttcaaa   1620
cctactggtg ggaaagtgaa ggagataagt tttaaaagca agcctaatgt ttgggcctac   1680
ttctcagtaa agtctggtgg aggcattcat gaatttgctg attctcagtt cggacatgtt   1740
tttgcatatg ggctctctag atcagcagca ataacaaaca tgactcttgc attaaaagag   1800
attcaaattc gtggagaaat tcattcaaat gttgattaca cagttgacct cttaaatgct   1860
tcagacttta gagaaaacaa gattcatact ggttggctcg acaccagaat agctatgcgt   1920
gttcaagctg agaggccccc atggtatatt tcagtggttg gggtgcttt atataaaaca    1980
gtaaccacca atgcagccac tgtttctgaa tatgttagtt atctcaccaa gggccagatt   2040
ccaccaaagc atatatccct tgtcaattct acagttaatt tgaatataga agggagcaaa   2100
tacacaattg aaactgtaag gactggacat ggtagctaca ggttgagaat gaatgattca   2160
acagttgaag cgaatgtaca atctttatgt gatggtggcc tcttaatgca gttggatgga   2220
aacagccatg taatttatgc agaagaagaa gctggtggta cacggcttca gattgatgga   2280
aagacatgtt tattgcagaa tgaccatgat ccatcaaagt tattagctga gacaccctgc   2340
aaacttcttc gtttcttggt tgctgatggt gctcatgttg atgcggatgt accatacgcg   2400
gaagttgagg ttatgaagat gtgcatgcct ctcttgtcgc ctgcttctgg tgtcattcat   2460
tgtatgatgt ctgagggcca ggcattgcag gctggtgatc ttatagcaag gttggatctt   2520
gatgaccctt ctgctgtgaa aagagctgag ccatttgatg gaatatttcc acaaatggag   2580
ctccctgttg ctgtctctag tcaagtacac aaaagatatg ctgcaagttt gaatgctgct   2640
cgaatggtcc ttgcaggata tgagcacaat attaatgaag tcgttcaaga tttggtatgc   2700
```

-continued

```
tgcctggaca accctgagct tcctttccta cagtgggatg aacttatgtc tgttctagca   2760
acgaggcttc caagaaatct caagagtgag ttagaggata aatacaagga atacaagttg   2820
aatttttacc atggaaaaaa cgaggacttt ccatccaagt tgctaagaga catcattgag   2880
gaaaatcttt cttatggttc agagaaggaa aaggctacaa atgagaggct tgttgagcct   2940
cttatgaacc tactgaagtc atatgagggt gggagagaga gccatgcaca ttttgttgtc   3000
aagtctcttt tcgaggagta tcttacagtg gaagaacttt ttagtgatgg cattcagtct   3060
gacgtgattg aaacattgcg gcatcagcac agtaaagacc tgcagaaggt tgtagacatt   3120
gtgttgtctc accagggtgt gaggaacaaa gctaagcttg taacggcact tatggaaaag   3180
ctggtttatc caaatcctgg tggttacagg gatctgttag ttcgcttttc ttccctcaat   3240
cataaaagat attataagtt ggcccttaaa gcaagtgaac ttcttgaaca aaccaaacta   3300
agtgaactcc gtgcaagcgt tgcaagaagc ctttcggatc tggggatgca taagggagaa   3360
atgagtatta aggataacat ggaagattta gtctctgccc cattacctgt tgaagatgct   3420
ctgatttctt tgtttgatta cagtgatcga actgttcagc agaaagtgat tgagacatac   3480
atatcacgat tgtaccagcc tcatcttgta aaggatagca tccaaatgaa attcaaggaa   3540
tctggtgcta ttactttttg ggaattttat gaagggcatg ttgatactag aaatggacat   3600
ggggctatta ttggtgggaa gcgatggggt gccatggtcg ttctcaaatc acttgaatct   3660
gcgtcaacag ccattgtggc tgcattaaag gattcggcac agttcaacag ctctgagggc   3720
aacatgatgc acattgcatt attgagtgct gaaaatgaaa gtaatataag tggaataagt   3780
gatgatcaag ctcaacataa gatggaaaag cttagcaaga tactgaagga tactagcgtt   3840
gcaagtgatc tccaagctgc tggtttgaag gttataagtt gcattgttca aagagatgaa   3900
gctcgcatgc caatgcgcca cacattcctc tggttggatg acaagagttg ttatgaagaa   3960
gagcagattc tccggcatgt ggagcctccc ctctctacac ttcttgaatt ggataagttg   4020
aaggtgaaag gatacaatga aatgaagtat actccttcgc gtgaccgcca atggcatatc   4080
tacacactaa gaaatactga aaaccccaaa atgttgcata gggtgttttt ccgaactatt   4140
gtcaggcaac ccaatgcagg caacaagttt acatcggctc agatcagcga cgctgaagta   4200
ggatgtcccg aagaatctct ttcatttaca tcaaatagca tcttaagatc attgatgact   4260
gctattgaag aattagagct tcatgcaatt aggacaggtc attctcacat gtatttgtgc   4320
atactgaaag agcaaaagct tcttgacctc attccatttt cagggagtac aattgttgat   4380
gttggccaag atgaagctac cgcttgttca cttttaaaat caatggcttt gaagatacat   4440
gagcttgttg gtgcaaggat gcatcatctg tctgtatgcc agtgggaggt gaaactcaag   4500
ttggactgtg atggccctgc aagtggtacc tggagagttg taactacaaa tgttactggt   4560
cacacctgca ccattgatat ataccgagaa gtggaggaaa tagaatcgca gaagttagtg   4620
taccattcag ccacttcgtc agctggacca ttgcatggtg ttgcactgaa taatccatat   4680
caacctttga gtgtgattga tctaaagcgc tgctctgcta ggaacaacag aacaacatat   4740
tgctatgatt ttccgctggc ctttgaaact gcactgcaga agtcatggca gaccaatggc   4800
tctactgttt ctgaaggcaa tgaaaatagt aaatcctacg tgaaggcaac tgagctagtg   4860
tttgctgaaa aacatgggtc ctggggcact cctataattc cgatggaacg ccctgctggg   4920
ctcaacgaca ttggtatggt cgcttggatc atggagatgt caacacctga atttcccaat   4980
ggcaggcaga ttattgttgt agcaaatgat atcactttca gagctggatc atttggccca   5040
agggaagatg catttttga aactgtcact aacctggctt gcgaaaggaa acttcctctt   5100
```

-continued

```
atatacttgg cagcaaactc tggtgctagg attggcatag ctgatgaagt aaaatcttgc   5160

ttccgtgttg gatggtctga cgaaggcagt cctgaacgag ggtttcagta catctatctg   5220

actgaagaag actatgctcg cattagctct tctgttatag cacataagct ggagctagat   5280

agtggtgaaa ttaggtggat tattgactct gttgtgggca aggaggatgg gcttggtgtc   5340

gagaacatac atggaagtgc tgctattgcc agtgcttatt ctagggcata tgaggagaca   5400

tttacactta catttgtgac tgggcggact gtaggaatag gagcttatct tgctcgactt   5460

ggtatacggt gcatacagcg tcttgaccag cctattattt taacagggtt ttctgccctg   5520

aacaagctcc ttgggcggga agtgtacagc tcccacatgc agcttggtgg tcctaagatc   5580

atggcgacta atggtgttgt ccacctcact gttccagatg accttgaagg tgtttccaat   5640

atattgaggt ggctcagcta tgttcctgca aacattggtg gacctcttcc tattaccaaa   5700

cctctggacc ctccagacag acctgttgct tacatccctg agaacacatg cgatccacgt   5760

gcagctatct gtggtgtaga tgacagccaa gggaaatggt tgggtggtat gtttgacaaa   5820

gacagctttg tggagacatt tgaaggatgg gcaaaaacag tggttactgg cagagcaaag   5880

cttggaggaa ttcctgtggg cgtcatagct gtggagacac agaccatgat gcagatcatc   5940

cctgctgatc caggtcagct tgattcccat gagcgatctg tccctcgtgc tggacaagtg   6000

tggttcccag attctgcaac caagaccgct caggcattat tagacttcaa ccgtgaagga   6060

ttgcctctgt tcatcctggc taattggaga ggcttctctg gtggacaaag agatctcttt   6120

gaaggaattc ttcaggctgg gtcaacaatt gtcgagaacc ttaggacata taatcagcct   6180

gcttttgtgt acattcctat ggctggagag cttcgtggag gagcttgggt tgtggtcgat   6240

agcaaaataa atccagaccg cattgagtgt tatgctgaaa ggactgccaa aggtaatgtt   6300

ctcgaacctc aagggttaat tgaaatcaag ttcaggtcag aggaactcca agactgtatg   6360

ggtaggcttg acccagagtt gataaatctg aaagcaaaac tccaagatgt aaatcatgga   6420

aatggaagtc taccagacat agaagggatt cggaagagta tagaagcacg tacgaaacag   6480

ttgctgcctt tatataccca gattgcaata cggtttgctg aattgcatga tacttcccta   6540

agaatggcag ctaaaggtgt gattaagaaa gttgtagact gggaagaatc acgctcgttc   6600

ttctataaaa ggctacggag gaggatcgca gaagatgttc ttgcaaaaga aataaggcag   6660

atagtcggtg ataaatttac gcaccaatta gcaatggagc tcatcaagga atggtacctt   6720

gcttctcagg ccacaacagg aagcactgga tgggatgacg atgatgcttt tgttgcctgg   6780

aaggacagtc ctgaaaacta caaggggcat atccaaaagc ttagggctca aaaagtgtct   6840

cattcgctct ctgatcttgc tgactccagt tcagatctgc aagcattctc gcagggtctt   6900

tctacgctat tagataagat ggatccctct cagagagcga agtttgttca ggaagtcaag   6960

aaggtccttg attga                                                    6975
```

<210> SEQ ID NO 14
<211> LENGTH: 2324
<212> TYPE: PRT
<213> ORGANISM: Zea mays

<400> SEQUENCE: 14

```
Met Ser Gln Leu Gly Leu Ala Ala Ala Ala Ser Lys Ala Leu Pro Leu
1               5                   10                  15

Leu Pro Asn Arg Gln Arg Ser Ser Ala Gly Thr Thr Phe Ser Ser Ser
            20                  25                  30
```

-continued

```
Ser Leu Ser Arg Pro Leu Asn Arg Arg Lys Ser Arg Thr Arg Ser Leu
        35                  40                  45

Arg Asp Gly Gly Asp Gly Val Ser Asp Ala Lys Lys His Ser Gln Ser
    50                  55                  60

Val Arg Gln Gly Leu Ala Gly Ile Ile Asp Leu Pro Ser Glu Ala Pro
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Ile Asn Glu Thr His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205

Glu Met Ala Gln Lys Leu Gly Val Ser Ala Val Trp Pro Gly Trp Gly
    210                 215                 220

His Ala Ser Glu Asn Pro Glu Leu Pro Asp Ala Leu Thr Ala Lys Gly
225                 230                 235                 240

Ile Val Phe Leu Gly Pro Pro Ala Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Ala Trp Ser Gly Ser His Val Glu Val Pro Leu Glu Cys Cys Leu Asp
        275                 280                 285

Ala Ile Pro Glu Glu Met Tyr Arg Lys Ala Cys Val Thr Thr Thr Glu
    290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
            340                 345                 350

Ser Pro Ile Phe Val Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Asp Tyr Tyr Phe Leu Glu Leu
        435                 440                 445

Asn Pro Arg Leu Gln Val Glu His Pro Val Thr Glu Trp Ile Ala Glu
```

```
    450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Ala Asp Ser Gln
                565                 570                 575

Phe Gly His Val Phe Ala Tyr Gly Leu Ser Arg Ser Ala Ala Ile Thr
            580                 585                 590

Asn Met Thr Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Arg
    610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Val Thr Thr Asn Ala Ala Thr Val Ser Glu Tyr Val
            660                 665                 670

Ser Tyr Leu Thr Lys Gly Gln Ile Pro Pro Lys His Ile Ser Leu Val
        675                 680                 685

Asn Ser Thr Val Asn Leu Asn Ile Glu Gly Ser Lys Tyr Thr Ile Glu
    690                 695                 700

Thr Val Arg Thr Gly His Gly Ser Tyr Arg Leu Arg Met Asn Asp Ser
705                 710                 715                 720

Thr Val Glu Ala Asn Val Gln Ser Leu Cys Asp Gly Gly Leu Leu Met
                725                 730                 735

Gln Leu Asp Gly Asn Ser His Val Ile Tyr Ala Glu Glu Glu Ala Gly
            740                 745                 750

Gly Thr Arg Leu Gln Ile Asp Gly Lys Thr Cys Leu Leu Gln Asn Asp
        755                 760                 765

His Asp Pro Ser Lys Leu Leu Ala Glu Thr Pro Cys Lys Leu Leu Arg
    770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Cys Met Met Ser Glu Gly Gln Ala Leu Gln Ala Gly
            820                 825                 830

Asp Leu Ile Ala Arg Leu Asp Leu Asp Asp Pro Ser Ala Val Lys Arg
        835                 840                 845

Ala Glu Pro Phe Asp Gly Ile Phe Pro Gln Met Glu Leu Pro Val Ala
    850                 855                 860

Val Ser Ser Gln Val His Lys Arg Tyr Ala Ala Ser Leu Asn Ala Ala
865                 870                 875                 880
```

-continued

```
Arg Met Val Leu Ala Gly Tyr Glu His Asn Ile Asn Glu Val Val Gln
                885                 890                 895

Asp Leu Val Cys Cys Leu Asp Asn Pro Glu Leu Pro Phe Leu Gln Trp
            900                 905                 910

Asp Glu Leu Met Ser Val Leu Ala Thr Arg Leu Pro Arg Asn Leu Lys
        915                 920                 925

Ser Glu Leu Glu Asp Lys Tyr Lys Glu Tyr Lys Leu Asn Phe Tyr His
    930                 935                 940

Gly Lys Asn Glu Asp Phe Pro Ser Lys Leu Leu Arg Asp Ile Ile Glu
945                 950                 955                 960

Glu Asn Leu Ser Tyr Gly Ser Glu Lys Glu Lys Ala Thr Asn Glu Arg
                965                 970                 975

Leu Val Glu Pro Leu Met Asn Leu Leu Lys Ser Tyr Glu Gly Gly Arg
            980                 985                 990

Glu Ser His Ala His Phe Val Val  Lys Ser Leu Phe Glu  Glu Tyr Leu
        995                 1000                1005

Thr Val  Glu Glu Leu Phe Ser  Asp Gly Ile Gln Ser  Asp Val Ile
    1010                1015                1020

Glu Thr  Leu Arg His Gln His  Ser Lys Asp Leu Gln  Lys Val Val
    1025                1030                1035

Asp Ile  Val Leu Ser His Gln  Gly Val Arg Asn Lys  Ala Lys Leu
    1040                1045                1050

Val Thr  Ala Leu Met Glu Lys  Leu Val Tyr Pro Asn  Pro Gly Gly
    1055                1060                1065

Tyr Arg  Asp Leu Leu Val Arg  Phe Ser Ser Leu Asn  His Lys Arg
    1070                1075                1080

Tyr Tyr  Lys Leu Ala Leu Lys  Ala Ser Glu Leu Leu  Glu Gln Thr
    1085                1090                1095

Lys Leu  Ser Glu Leu Arg Ala  Ser Val Ala Arg Ser  Leu Ser Asp
    1100                1105                1110

Leu Gly  Met His Lys Gly Glu  Met Ser Ile Lys Asp  Asn Met Glu
    1115                1120                1125

Asp Leu  Val Ser Ala Pro Leu  Pro Val Glu Asp Ala  Leu Ile Ser
    1130                1135                1140

Leu Phe  Asp Tyr Ser Asp Arg  Thr Val Gln Gln Lys  Val Ile Glu
    1145                1150                1155

Thr Tyr  Ile Ser Arg Leu Tyr  Gln Pro His Leu Val  Lys Asp Ser
    1160                1165                1170

Ile Gln  Met Lys Phe Lys Glu  Ser Gly Ala Ile Thr  Phe Trp Glu
    1175                1180                1185

Phe Tyr  Glu Gly His Val Asp  Thr Arg Asn Gly His  Gly Ala Ile
    1190                1195                1200

Ile Gly  Gly Lys Arg Trp Gly  Ala Met Val Val Leu  Lys Ser Leu
    1205                1210                1215

Glu Ser  Ala Ser Thr Ala Ile  Val Ala Ala Leu Lys  Asp Ser Ala
    1220                1225                1230

Gln Phe  Asn Ser Ser Glu Gly  Asn Met Met His Ile  Ala Leu Leu
    1235                1240                1245

Ser Ala  Glu Asn Glu Ser Asn  Ile Ser Gly Ile Ser  Asp Asp Gln
    1250                1255                1260

Ala Gln  His Lys Met Glu Lys  Leu Ser Lys Ile Leu  Lys Asp Thr
    1265                1270                1275
```

Ser Val Ala Ser Asp Leu Gln Ala Ala Gly Leu Lys Val Ile Ser
1280 1285 1290

Cys Ile Val Gln Arg Asp Glu Ala Arg Met Pro Met Arg His Thr
1295 1300 1305

Phe Leu Trp Leu Asp Asp Lys Ser Cys Tyr Glu Glu Glu Gln Ile
1310 1315 1320

Leu Arg His Val Glu Pro Pro Leu Ser Thr Leu Leu Glu Leu Asp
1325 1330 1335

Lys Leu Lys Val Lys Gly Tyr Asn Glu Met Lys Tyr Thr Pro Ser
1340 1345 1350

Arg Asp Arg Gln Trp His Ile Tyr Thr Leu Arg Asn Thr Glu Asn
1355 1360 1365

Pro Lys Met Leu His Arg Val Phe Phe Arg Thr Ile Val Arg Gln
1370 1375 1380

Pro Asn Ala Gly Asn Lys Phe Thr Ser Ala Gln Ile Ser Asp Ala
1385 1390 1395

Glu Val Gly Cys Pro Glu Glu Ser Leu Ser Phe Thr Ser Asn Ser
1400 1405 1410

Ile Leu Arg Ser Leu Met Thr Ala Ile Glu Glu Leu Glu Leu His
1415 1420 1425

Ala Ile Arg Thr Gly His Ser His Met Tyr Leu Cys Ile Leu Lys
1430 1435 1440

Glu Gln Lys Leu Leu Asp Leu Ile Pro Phe Ser Gly Ser Thr Ile
1445 1450 1455

Val Asp Val Gly Gln Asp Glu Ala Thr Ala Cys Ser Leu Leu Lys
1460 1465 1470

Ser Met Ala Leu Lys Ile His Glu Leu Val Gly Ala Arg Met His
1475 1480 1485

His Leu Ser Val Cys Gln Trp Glu Val Lys Leu Lys Leu Asp Cys
1490 1495 1500

Asp Gly Pro Ala Ser Gly Thr Trp Arg Val Val Thr Thr Asn Val
1505 1510 1515

Thr Gly His Thr Cys Thr Ile Asp Ile Tyr Arg Glu Val Glu Glu
1520 1525 1530

Ile Glu Ser Gln Lys Leu Val Tyr His Ser Ala Thr Ser Ser Ala
1535 1540 1545

Gly Pro Leu His Gly Val Ala Leu Asn Asn Pro Tyr Gln Pro Leu
1550 1555 1560

Ser Val Ile Asp Leu Lys Arg Cys Ser Ala Arg Asn Asn Arg Thr
1565 1570 1575

Thr Tyr Cys Tyr Asp Phe Pro Leu Ala Phe Glu Thr Ala Leu Gln
1580 1585 1590

Lys Ser Trp Gln Thr Asn Gly Ser Thr Val Ser Glu Gly Asn Glu
1595 1600 1605

Asn Ser Lys Ser Tyr Val Lys Ala Thr Glu Leu Val Phe Ala Glu
1610 1615 1620

Lys His Gly Ser Trp Gly Thr Pro Ile Ile Pro Met Glu Arg Pro
1625 1630 1635

Ala Gly Leu Asn Asp Ile Gly Met Val Ala Trp Ile Met Glu Met
1640 1645 1650

Ser Thr Pro Glu Phe Pro Asn Gly Arg Gln Ile Ile Val Val Ala
1655 1660 1665

Asn Asp Ile Thr Phe Arg Ala Gly Ser Phe Gly Pro Arg Glu Asp

```
    1670                1675                1680

Ala Phe  Phe Glu Thr Val Thr  Asn Leu Ala Cys Glu  Arg Lys Leu
    1685                1690                1695

Pro Leu  Ile Tyr Leu Ala Ala  Asn Ser Gly Ala Arg  Ile Gly Ile
    1700                1705                1710

Ala Asp  Glu Val Lys Ser Cys  Phe Arg Val Gly Trp  Ser Asp Glu
    1715                1720                1725

Gly Ser  Pro Glu Arg Gly Phe  Gln Tyr Ile Tyr Leu  Thr Glu Glu
    1730                1735                1740

Asp Tyr  Ala Arg Ile Ser Ser  Ser Val Ile Ala His  Lys Leu Glu
    1745                1750                1755

Leu Asp  Ser Gly Glu Ile Arg  Trp Ile Ile Asp Ser  Val Val Gly
    1760                1765                1770

Lys Glu  Asp Gly Leu Gly Val  Glu Asn Ile His Gly  Ser Ala Ala
    1775                1780                1785

Ile Ala  Ser Ala Tyr Ser Arg  Ala Tyr Glu Glu Thr  Phe Thr Leu
    1790                1795                1800

Thr Phe  Val Thr Gly Arg Thr  Val Gly Ile Gly Ala  Tyr Leu Ala
    1805                1810                1815

Arg Leu  Gly Ile Arg Cys Ile  Gln Arg Leu Asp Gln  Pro Ile Ile
    1820                1825                1830

Leu Thr  Gly Phe Ser Ala Leu  Asn Lys Leu Leu Gly  Arg Glu Val
    1835                1840                1845

Tyr Ser  Ser His Met Gln Leu  Gly Gly Pro Lys Ile  Met Ala Thr
    1850                1855                1860

Asn Gly  Val Val His Leu Thr  Val Pro Asp Asp Leu  Glu Gly Val
    1865                1870                1875

Ser Asn  Ile Leu Arg Trp Leu  Ser Tyr Val Pro Ala  Asn Ile Gly
    1880                1885                1890

Gly Pro  Leu Pro Ile Thr Lys  Pro Leu Asp Pro Pro  Asp Arg Pro
    1895                1900                1905

Val Ala  Tyr Ile Pro Glu Asn  Thr Cys Asp Pro Arg  Ala Ala Ile
    1910                1915                1920

Cys Gly  Val Asp Asp Ser Gln  Gly Lys Trp Leu Gly  Gly Met Phe
    1925                1930                1935

Asp Lys  Asp Ser Phe Val Glu  Thr Phe Glu Gly Trp  Ala Lys Thr
    1940                1945                1950

Val Val  Thr Gly Arg Ala Lys  Leu Gly Gly Ile Pro  Val Gly Val
    1955                1960                1965

Ile Ala  Val Glu Thr Gln Thr  Met Met Gln Ile Ile  Pro Ala Asp
    1970                1975                1980

Pro Gly  Gln Leu Asp Ser His  Glu Arg Ser Val Pro  Arg Ala Gly
    1985                1990                1995

Gln Val  Trp Phe Pro Asp Ser  Ala Thr Lys Thr Ala  Gln Ala Leu
    2000                2005                2010

Leu Asp  Phe Asn Arg Glu Gly  Leu Pro Leu Phe Ile  Leu Ala Asn
    2015                2020                2025

Trp Arg  Gly Phe Ser Gly Gly  Gln Arg Asp Leu Phe  Glu Gly Ile
    2030                2035                2040

Leu Gln  Ala Gly Ser Thr Ile  Val Glu Asn Leu Arg  Thr Tyr Asn
    2045                2050                2055

Gln Pro  Ala Phe Val Tyr Ile  Pro Met Ala Gly Glu  Leu Arg Gly
    2060                2065                2070
```

```
Gly Ala  Trp Val Val Val Asp  Ser Lys Ile Asn Pro  Asp Arg Ile
    2075                 2080                 2085

Glu Cys  Tyr Ala Glu Arg Thr  Ala Lys Gly Asn Val  Leu Glu Pro
    2090                 2095                 2100

Gln Gly  Leu Ile Glu Ile Lys  Phe Arg Ser Glu Glu  Leu Gln Asp
    2105                 2110                 2115

Cys Met  Gly Arg Leu Asp Pro  Glu Leu Ile Asn Leu  Lys Ala Lys
    2120                 2125                 2130

Leu Gln  Asp Val Asn His Gly  Asn Gly Ser Leu Pro  Asp Ile Glu
    2135                 2140                 2145

Gly Ile  Arg Lys Ser Ile Glu  Ala Arg Thr Lys Gln  Leu Leu Pro
    2150                 2155                 2160

Leu Tyr  Thr Gln Ile Ala Ile  Arg Phe Ala Glu Leu  His Asp Thr
    2165                 2170                 2175

Ser Leu  Arg Met Ala Ala Lys  Gly Val Ile Lys Lys  Val Val Asp
    2180                 2185                 2190

Trp Glu  Glu Ser Arg Ser Phe  Phe Tyr Lys Arg Leu  Arg Arg Arg
    2195                 2200                 2205

Ile Ala  Glu Asp Val Leu Ala  Lys Glu Ile Arg Gln  Ile Val Gly
    2210                 2215                 2220

Asp Lys  Phe Thr His Gln Leu  Ala Met Glu Leu Ile  Lys Glu Trp
    2225                 2230                 2235

Tyr Leu  Ala Ser Gln Ala Thr  Thr Gly Ser Thr Gly  Trp Asp Asp
    2240                 2245                 2250

Asp Asp  Ala Phe Val Ala Trp  Lys Asp Ser Pro Glu  Asn Tyr Lys
    2255                 2260                 2265

Gly His  Ile Gln Lys Leu Arg  Ala Gln Lys Val Ser  His Ser Leu
    2270                 2275                 2280

Ser Asp  Leu Ala Asp Ser Ser  Ser Asp Leu Gln Ala  Phe Ser Gln
    2285                 2290                 2295

Gly Leu  Ser Thr Leu Leu Asp  Lys Met Asp Pro Ser  Gln Arg Ala
    2300                 2305                 2310

Lys Phe  Val Gln Glu Val Lys  Lys Val Leu Asp
    2315                 2320
```

<210> SEQ ID NO 15
<211> LENGTH: 6936
<212> TYPE: DNA
<213> ORGANISM: Triticum aestivum

<400> SEQUENCE: 15

```
atgggatcca cacatttgcc cattgtcggc cttaatgcct cgacaacacc atcgctatcc     60

actattcgcc cggtaaattc agccggtgct gcattccaac catctgcccc ttctagaacc    120

tccaagaaga aaagtcgtcg tgttcagtca ttaagggatg gaggcgatgg aggcgtgtca    180

gaccctaacc agtctattcg ccaaggtctt gccggcatca ttgacctccc aaaggagggc    240

acatcagctc cggaagtgga tatttcacat gggtccgaag aacccagggg ctcctaccaa    300

atgaatggga tactgaatga agcacataat gggaggcatg cttcgctgtc taaggttgtc    360

gaattttgta tggcattggg cggcaaaaca ccaattcaca gtgtattagt tgcgaacaat    420

ggaatggcag cagctaagtt catgcggagt gtccgaacat gggctaatga aacatttggg    480

tcagagaagg caattcagtt gatagctatg gctactccag aagacatgag gataaatgca    540

gagcacatta gaattgctga tcaatttgtt gaagtacccg gtggaacaaa caataacaac    600
```

-continued

```
tatgcaaatg tccaactcat agtggagata gcagtgagaa ccggtgtttc tgctgtttgg    660
cctggttggg gccatgcatc tgagaatcct gaacttccag atgcactaaa tgcaaacgga    720
attgtttttc ttgggccacc atcatcatca atgaacgcac taggtgacaa ggttggttca    780
gctctcattg ctcaagcagc aggggttccg actcttcctt ggagtggatc acaggtggaa    840
attccattag aagtttgttt ggactcgata cccgcggaga tgtataggaa agcttgtgtt    900
agtactacgg aggaagcact tgcgagttgt cagatgattg ggtatcccgc catgattaaa    960
gcatcatggg gtggtggtgg taaagggatc cgaaaggtta ataatgacga tgatgtcaga   1020
gcactgttta agcaagtgca aggtgaagtt cctggctccc caatatttat catgagactt   1080
gcatctcaga gtcgacatct tgaagttcag ttgctttgtg atcaatatgg caatgtagct   1140
gcgcttcaca gtcgtgactg cagtgtgcaa cggcgacacc aaaagattat tgaggaagga   1200
ccagttactg ttgctcctcg cgagacagtg aaagagctag agcaagcagc aaggaggctt   1260
gctaaggctg tgggttatgt tggtgctgct actgttgaat atctctacag catggagact   1320
ggtgaatact attttctgga acttaatcca cggttgcagg ttgagcatcc agtcaccgag   1380
tggatagctg aagtaaactt gcctgcagct caagttgcag ttggaatggg tataccccctt   1440
tggcaggttc cagagatcag acgtttctat ggaatggaca atggaggagg ctatgacatt   1500
tggaggaaaa cagcagctct tgctactcca tttaacttcg atgaagtgga ttctcaatgg   1560
ccaaagggtc attgtgtagc agttaggata accagtgagg atccagatga cggattcaag   1620
cctaccggtg gaaaagtaaa ggagatcagt tttaaaagca agccaaatgt ttgggcctat   1680
ttctctgtta agtccggtgg aggcattcat gaatttgctg attctcagtt tggacatgtt   1740
tttgcatatg gagtgtctag agcagcagca ataaccaaca tgtctcttgc gctaaaagag   1800
attcaaattc gtggagaaat tcattcaaat gttgattaca cagttgatct cttgaatgcc   1860
tcagacttca aagaaaacag gattcatact ggctggctgg ataacagaat agcaatgcga   1920
gtccaagctg agagacctcc gtggtatatt tcagtggttg gaggagctct atataaaaca   1980
ataacgagca acacagacac tgtttctgaa tatgttagct atctcgtcaa gggtcagatt   2040
ccaccgaagc atatatccct tgtccattca actgtttctt tgaatataga ggaaagcaaa   2100
tatacaattg aaactataag gagcggacag ggtagctaca gattgcgaat gaatggatca   2160
gttattgaag caaatgtcca aacattatgt gatggtggac ttttaatgca gttggatgga   2220
aacagccatg taatttatgc tgaagaagag gccggtggta cacggcttct aattgatgga   2280
aagacatgct tgttacagaa tgatcacgat ccttcaaggt tattagctga gacaccctgc   2340
aaacttcttc gtttcttggt tgccgatggt gctcatgttg aagctgatgt accatatgcg   2400
gaagttgagg ttatgaagat gtgcatgccc ctcttgtcac ctgctgctgg tgtcattaat   2460
gttttgttgt ctgagggcca gcctatgcag gctggtgatc ttatagcaag acttgatctt   2520
gatgaccctt ctgctgtgaa gagagctgag ccatttaacg gatctttccc agaaatgagc   2580
cttcctattg ctgcttctgg ccaagttcac aaaagatgtg ccacaagctt gaatgctgct   2640
cggatggtcc ttgcaggata tgatcacccg atcaacaaag ttgtacaaga tctggtatcc   2700
tgtctagatg ctcctgagct tcctttccta caatgggaag agcttatgtc tgttttagca   2760
actagacttc caaggcttct taagagcgag ttggagggta aatacagtga atataagtta   2820
aatgttggcc atgggaagag caaggatttc ccttccaaga tgctaagaga gataatcgag   2880
gaaaatcttg cacatggttc tgagaaggaa attgctacaa atgagaggct tgttgagcct   2940
```

```
cttatgagcc tactgaagtc atatgagggt ggcagagaaa gccatgcaca ctttattgtg   3000
aagtcccttt tcgaggacta tctctcggtt gaggaactat tcagtgatgg cattcagtct   3060
gatgtgattg aacgcctgcg ccaacaacat agtaaagatc tccagaaggt tgtagacatt   3120
gtgttgtctc accagggtgt gagaaacaaa actaagctga tactaacact catggagaaa   3180
ctggtctatc caaaccctgc tgtctacaag gatcagttga ctcgcttttc ctccctcaat   3240
cacaaaagat attataagtt ggcccttaaa gctagcgagc ttcttgaaca aaccaagctt   3300
agtgagctcc gcacaagcat tgcaaggagc ctttcagaac ttgagatgtt tactgaagaa   3360
aggacggcca ttagtgagat catgggagat ttagtgactg ccccactgcc agttgaagat   3420
gcactggttt ctttgtttga ttgtagtgat caaactcttc agcagagggt gatcgagacg   3480
tacatatctc gattatacca gcctcatctt gtcaaggata gtatccagct gaaatatcag   3540
gaatctggtg ttattgcttt atgggaattc gctgaagcgc attcagagaa gagattgggt   3600
gctatggtta ttgtgaagtc gttagaatct gtatcagcag caattggagc tgcactaaag   3660
ggtacatcac gctatgcaag ctctgagggt aacataatgc atattgcttt attgggtgct   3720
gataatcaaa tgcatggaac tgaagacagt ggtgataacg atcaagctca agtcaggata   3780
gacaaacttt ctgcgacact ggaacaaaat actgtcacag ctgatctccg tgctgctggt   3840
gtgaaggtta ttagttgcat tgttcaaagg gatggagcac tcatgcctat gcgccatacc   3900
ttcctcttgt cggatgaaaa gctttgttat gaggaagagc cggttctccg gcatgtggag   3960
cctcctcttt ctgctcttct tgagttgggt aagttgaaag tgaaaggata caatgaggtg   4020
aagtatacac cgtcacgtga tcgtcagtgg aacatataca cacttagaaa tacagagaac   4080
cccaaaatgt tgcacagggt gtttttccga actcttgtca ggcaacccgg tgcttccaac   4140
aaattcacat caggcaacat cagtgatgtt gaagtgggag gagctgagga atctctttca   4200
tttacatcga gcagcatatt aagatcgctg atgactgcta tagaagagtt ggagcttcac   4260
gcgattagga caggtcactc tcatatgttt ttgtgcatat tgaaagagca aaagcttctt   4320
gatcttgttc ccgtttcagg gaacaaagtt gtggatattg gccaagatga agctactgca   4380
tgcttgcttc tgaaagaaat ggctctacag atacatgaac ttgtgggtgc aaggatgcat   4440
catctttctg tatgccaatg ggaggtgaaa cttaagttgg acagcgatgg gcctgccagt   4500
ggtacctgga gagttgtaac aaccaatgtt actagtcaca cctgcactgt ggatatctac   4560
cgtgaggtcg aagatacaga atcacagaaa ctagtgtacc actctgctcc atcgtcatct   4620
ggtcctttgc atggcgttgc actgaatact ccatatcagc ctttgagtgt tattgatctg   4680
aaacgttgct ccgctagaaa taacagaact acatactgct atgattttcc gttggcattt   4740
gaaactgcag tgcagaagtc atggtctaac atttctagtg acactaaccg atgttatgtt   4800
aaagcgacgg agctggtgtt tgctcacaag aacgggtcat ggggcactcc tgtaattcct   4860
atggagcgtc ctgctgggct caatgacatt ggtatggtag cttggatctt ggacatgtcc   4920
actcctgaat atcccaatgg caggcagatt gttgtcatcg caaatgatat tacttttaga   4980
gctggatcgt ttggtccaag ggaagatgca ttttttgaaa ctgttaccaa cctagcttgt   5040
gagaggaagc ttcctctcat ctacttggca gcaaactctg gtgctcggat cggcatagca   5100
gatgaagtaa aatcttgctt ccgtgttgga tggtctgatg atggcagccc tgaacgtggg   5160
tttcaatata tttatctgac tgaagaagac catgctcgta ttagcgcttc tgttatagcg   5220
cacaagatgc agcttgataa tggtgaaatt aggtgggtta ttgattctgt tgtagggaag   5280
gaggatgggc taggtgtgga gaacatacat ggaagtgctg ctattgccag tgcctattct   5340
```

-continued agggcctatg aggagacatt tacgcttaca tttgtgactg gaaggactgt tggaatagga 5400
gcatatcttg ctcgacttgg catacggtgc atacagcgta ctgaccagcc cattatccta 5460
actgggttct ctgccttgaa caagcttctt ggccgggaag tttacagctc ccacatgcag 5520
ttgggtggcc ccaaaattat ggcgacaaac ggtgttgtcc atctgacagt ttcagatgac 5580
cttgaaggtg tatctaatat attgaggtgg ctcagctatg ttcctgccaa cattggtgga 5640
cctcttccta ttacaaaatc tttggaccca cctgacagac ccgttgctta catccctgag 5700
aatacatgcg atcctcgtgc tgccatcagt ggcattgatg atagccaagg gaaatggttg 5760
gggggcatgt tcgacaaaga cagttttgtg gagacatttg aaggatgggc gaagtcagtt 5820
gttactggca gagcgaaact cggagggatt ccggtgggtg ttatagctgt ggagacacag 5880
actatgatgc agctcatccc tgctgatcca ggccagcttg attcccatga gcgatctgtt 5940
cctcgtgctg ggcaagtctg gtttccagat tcagctacta agacagcgca ggcaatgctg 6000
gacttcaacc gtgaaggatt acctctgttc atccttgcta actggagagg cttctctggt 6060
ggacaaagag atctttttga aggaatcctt caggctgggt caacaattgt tgagaacctt 6120
aggacataca atcagcctgc ctttgtatat atccccaagg ctgcagagct acgtggaggg 6180
gcttgggtcg tgattgatag caagataaat ccagatcgca ttgagttcta tgctgagagg 6240
actgcaaagg gcaatgttct cgaacctcaa gggttgatcg agatcaagtt caggtcagag 6300
gaactccaag agtgcatggg taggcttgat ccagaattga taaatctgaa ggcaaagctc 6360
cagggagtaa agcatgaaaa tggaagtcta cctgagtcag aatcccttca gaagagcata 6420
gaagcccgga agaaacagtt gttgcctttg tatactcaaa ttgcggtacg gttcgctgaa 6480
ttgcatgaca cttcccttag aatggctgct aagggtgtga ttaagaaggt tgtagactgg 6540
gaagattcta ggtcgttctt ctacaagaga ttacggagga ggatatccga ggatgttctt 6600
gcgaaggaaa ttagaggtgt aagtggcaag cagttttctc accaatcggc aatcgagctg 6660
atccagaaat ggtacttggc ctctaaggga gctgaaacag gaagcactga atgggatgat 6720
gacgatgctt ttgttgcctg gagggaaaac cctgaaaact accaggagta tatcaaagaa 6780
ctcagggctc aaagggtatc tcagttgctc tcagatgttg cagactccag tccagatcta 6840
gaagccttgc cacagggtct ttctatgcta ttagagaaga tggatccctc aaggagagca 6900
cagtttgttg aggaagtcaa gaaagtcctt aaatga 6936

<210> SEQ ID NO 16
<211> LENGTH: 2311
<212> TYPE: PRT
<213> ORGANISM: Triticum aestivum

<400> SEQUENCE: 16

Met Gly Ser Thr His Leu Pro Ile Val Gly Leu Asn Ala Ser Thr Thr
1 5 10 15

Pro Ser Leu Ser Thr Ile Arg Pro Val Asn Ser Ala Gly Ala Ala Phe
20 25 30

Gln Pro Ser Ala Pro Ser Arg Thr Ser Lys Lys Lys Ser Arg Arg Val
35 40 45

Gln Ser Leu Arg Asp Gly Gly Asp Gly Gly Val Ser Asp Pro Asn Gln
50 55 60

Ser Ile Arg Gln Gly Leu Ala Gly Ile Ile Asp Leu Pro Lys Glu Gly
65 70 75 80

Thr Ser Ala Pro Glu Val Asp Ile Ser His Gly Ser Glu Glu Pro Arg

```
                85                  90                  95

Gly Ser Tyr Gln Met Asn Gly Ile Leu Asn Glu Ala His Asn Gly Arg
            100                 105                 110

His Ala Ser Leu Ser Lys Val Val Glu Phe Cys Met Ala Leu Gly Gly
        115                 120                 125

Lys Thr Pro Ile His Ser Val Leu Val Ala Asn Asn Gly Met Ala Ala
    130                 135                 140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205

Glu Ile Ala Val Arg Thr Gly Val Ser Ala Val Trp Pro Gly Trp Gly
    210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Pro Trp Ser Gly Ser Gln Val Glu Ile Pro Leu Glu Val Cys Leu Asp
        275                 280                 285

Ser Ile Pro Ala Glu Met Tyr Arg Lys Ala Cys Val Ser Thr Thr Glu
    290                 295                 300

Glu Ala Leu Ala Ser Cys Gln Met Ile Gly Tyr Pro Ala Met Ile Lys
305                 310                 315                 320

Ala Ser Trp Gly Gly Gly Gly Lys Gly Ile Arg Lys Val Asn Asn Asp
                325                 330                 335

Asp Asp Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Glu Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
                485                 490                 495

Gly Tyr Asp Ile Trp Arg Lys Thr Ala Ala Leu Ala Thr Pro Phe Asn
            500                 505                 510
```

```
Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Ala Asp Ser Gln
                565                 570                 575

Phe Gly His Val Phe Ala Tyr Gly Val Ser Arg Ala Ala Ala Ile Thr
            580                 585                 590

Asn Met Ser Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Lys
    610                 615                 620

Glu Asn Arg Ile His Thr Gly Trp Leu Asp Asn Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Ile Thr Ser Asn Thr Asp Thr Val Ser Glu Tyr Val
            660                 665                 670

Ser Tyr Leu Val Lys Gly Gln Ile Pro Pro Lys His Ile Ser Leu Val
        675                 680                 685

His Ser Thr Val Ser Leu Asn Ile Glu Glu Ser Lys Tyr Thr Ile Glu
    690                 695                 700

Thr Ile Arg Ser Gly Gln Gly Ser Tyr Arg Leu Arg Met Asn Gly Ser
705                 710                 715                 720

Val Ile Glu Ala Asn Val Gln Thr Leu Cys Asp Gly Gly Leu Leu Met
                725                 730                 735

Gln Leu Asp Gly Asn Ser His Val Ile Tyr Ala Glu Glu Glu Ala Gly
            740                 745                 750

Gly Thr Arg Leu Leu Ile Asp Gly Lys Thr Cys Leu Leu Gln Asn Asp
        755                 760                 765

His Asp Pro Ser Arg Leu Leu Ala Glu Thr Pro Cys Lys Leu Leu Arg
    770                 775                 780

Phe Leu Val Ala Asp Gly Ala His Val Glu Ala Asp Val Pro Tyr Ala
785                 790                 795                 800

Glu Val Glu Val Met Lys Met Cys Met Pro Leu Leu Ser Pro Ala Ala
                805                 810                 815

Gly Val Ile Asn Val Leu Leu Ser Glu Gly Gln Pro Met Gln Ala Gly
            820                 825                 830

Asp Leu Ile Ala Arg Leu Asp Leu Asp Asp Pro Ser Ala Val Lys Arg
        835                 840                 845

Ala Glu Pro Phe Asn Gly Ser Phe Pro Glu Met Ser Leu Pro Ile Ala
    850                 855                 860

Ala Ser Gly Gln Val His Lys Arg Cys Ala Thr Ser Leu Asn Ala Ala
865                 870                 875                 880

Arg Met Val Leu Ala Gly Tyr Asp His Pro Ile Asn Lys Val Val Gln
                885                 890                 895

Asp Leu Val Ser Cys Leu Asp Ala Pro Glu Leu Pro Phe Leu Gln Trp
            900                 905                 910

Glu Glu Leu Met Ser Val Leu Ala Thr Arg Leu Pro Arg Leu Leu Lys
        915                 920                 925
```

-continued

```
Ser Glu Leu Glu Gly Lys Tyr Ser Glu Tyr Lys Leu Asn Val Gly His
    930                 935                 940

Gly Lys Ser Lys Asp Phe Pro Ser Lys Met Leu Arg Glu Ile Ile Glu
945                 950                 955                 960

Glu Asn Leu Ala His Gly Ser Glu Lys Glu Ile Ala Thr Asn Glu Arg
                965                 970                 975

Leu Val Glu Pro Leu Met Ser Leu Leu Lys Ser Tyr Glu Gly Gly Arg
            980                 985                 990

Glu Ser His Ala His Phe Ile Val  Lys Ser Leu Phe Glu  Asp Tyr Leu
        995                 1000                1005

Ser Val  Glu Glu Leu Phe Ser  Asp Gly Ile Gln Ser  Asp Val Ile
    1010                 1015                1020

Glu Arg  Leu Arg Gln Gln His  Ser Lys Asp Leu Gln  Lys Val Val
    1025                 1030                1035

Asp Ile  Val Leu Ser His Gln  Gly Val Arg Asn Lys  Thr Lys Leu
    1040                 1045                1050

Ile Leu  Thr Leu Met Glu Lys  Leu Val Tyr Pro Asn  Pro Ala Val
    1055                 1060                1065

Tyr Lys  Asp Gln Leu Thr Arg  Phe Ser Ser Leu Asn  His Lys Arg
    1070                 1075                1080

Tyr Tyr  Lys Leu Ala Leu Lys  Ala Ser Glu Leu Leu  Glu Gln Thr
    1085                 1090                1095

Lys Leu  Ser Glu Leu Arg Thr  Ser Ile Ala Arg Ser  Leu Ser Glu
    1100                 1105                1110

Leu Glu  Met Phe Thr Glu Glu  Arg Thr Ala Ile Ser  Glu Ile Met
    1115                 1120                1125

Gly Asp  Leu Val Thr Ala Pro  Leu Pro Val Glu Asp  Ala Leu Val
    1130                 1135                1140

Ser Leu  Phe Asp Cys Ser Asp  Gln Thr Leu Gln Gln  Arg Val Ile
    1145                 1150                1155

Glu Thr  Tyr Ile Ser Arg Leu  Tyr Gln Pro His Leu  Val Lys Asp
    1160                 1165                1170

Ser Ile  Gln Leu Lys Tyr Gln  Glu Ser Gly Val Ile  Ala Leu Trp
    1175                 1180                1185

Glu Phe  Ala Glu Ala His Ser  Glu Lys Arg Leu Gly  Ala Met Val
    1190                 1195                1200

Ile Val  Lys Ser Leu Glu Ser  Val Ser Ala Ala Ile  Gly Ala Ala
    1205                 1210                1215

Leu Lys  Gly Thr Ser Arg Tyr  Ala Ser Ser Glu Gly  Asn Ile Met
    1220                 1225                1230

His Ile  Ala Leu Leu Gly Ala  Asp Asn Gln Met His  Gly Thr Glu
    1235                 1240                1245

Asp Ser  Gly Asp Asn Asp Gln  Ala Gln Val Arg Ile  Asp Lys Leu
    1250                 1255                1260

Ser Ala  Thr Leu Glu Gln Asn  Thr Val Thr Ala Asp  Leu Arg Ala
    1265                 1270                1275

Ala Gly  Val Lys Val Ile Ser  Cys Ile Val Gln Arg  Asp Gly Ala
    1280                 1285                1290

Leu Met  Pro Met Arg His Thr  Phe Leu Leu Ser Asp  Glu Lys Leu
    1295                 1300                1305

Cys Tyr  Glu Glu Glu Pro Val  Leu Arg His Val Glu  Pro Pro Leu
    1310                 1315                1320

Ser Ala  Leu Leu Glu Leu Gly  Lys Leu Lys Val Lys  Gly Tyr Asn
```

1325 1330 1335

Glu Val Lys Tyr Thr Pro Ser Arg Asp Arg Gln Trp Asn Ile Tyr
1340 1345 1350

Thr Leu Arg Asn Thr Glu Asn Pro Lys Met Leu His Arg Val Phe
1355 1360 1365

Phe Arg Thr Leu Val Arg Gln Pro Gly Ala Ser Asn Lys Phe Thr
1370 1375 1380

Ser Gly Asn Ile Ser Asp Val Glu Val Gly Gly Ala Glu Glu Ser
1385 1390 1395

Leu Ser Phe Thr Ser Ser Ser Ile Leu Arg Ser Leu Met Thr Ala
1400 1405 1410

Ile Glu Glu Leu Glu Leu His Ala Ile Arg Thr Gly His Ser His
1415 1420 1425

Met Phe Leu Cys Ile Leu Lys Glu Gln Lys Leu Leu Asp Leu Val
1430 1435 1440

Pro Val Ser Gly Asn Lys Val Val Asp Ile Gly Gln Asp Glu Ala
1445 1450 1455

Thr Ala Cys Leu Leu Leu Lys Glu Met Ala Leu Gln Ile His Glu
1460 1465 1470

Leu Val Gly Ala Arg Met His His Leu Ser Val Cys Gln Trp Glu
1475 1480 1485

Val Lys Leu Lys Leu Asp Ser Asp Gly Pro Ala Ser Gly Thr Trp
1490 1495 1500

Arg Val Val Thr Thr Asn Val Thr Ser His Thr Cys Thr Val Asp
1505 1510 1515

Ile Tyr Arg Glu Val Glu Asp Thr Glu Ser Gln Lys Leu Val Tyr
1520 1525 1530

His Ser Ala Pro Ser Ser Ser Gly Pro Leu His Gly Val Ala Leu
1535 1540 1545

Asn Thr Pro Tyr Gln Pro Leu Ser Val Ile Asp Leu Lys Arg Cys
1550 1555 1560

Ser Ala Arg Asn Asn Arg Thr Thr Tyr Cys Tyr Asp Phe Pro Leu
1565 1570 1575

Ala Phe Glu Thr Ala Val Gln Lys Ser Trp Ser Asn Ile Ser Ser
1580 1585 1590

Asp Thr Asn Arg Cys Tyr Val Lys Ala Thr Glu Leu Val Phe Ala
1595 1600 1605

His Lys Asn Gly Ser Trp Gly Thr Pro Val Ile Pro Met Glu Arg
1610 1615 1620

Pro Ala Gly Leu Asn Asp Ile Gly Met Val Ala Trp Ile Leu Asp
1625 1630 1635

Met Ser Thr Pro Glu Tyr Pro Asn Gly Arg Gln Ile Val Val Ile
1640 1645 1650

Ala Asn Asp Ile Thr Phe Arg Ala Gly Ser Phe Gly Pro Arg Glu
1655 1660 1665

Asp Ala Phe Phe Glu Thr Val Thr Asn Leu Ala Cys Glu Arg Lys
1670 1675 1680

Leu Pro Leu Ile Tyr Leu Ala Ala Asn Ser Gly Ala Arg Ile Gly
1685 1690 1695

Ile Ala Asp Glu Val Lys Ser Cys Phe Arg Val Gly Trp Ser Asp
1700 1705 1710

Asp Gly Ser Pro Glu Arg Gly Phe Gln Tyr Ile Tyr Leu Thr Glu
1715 1720 1725

```
Glu Asp  His Ala Arg Ile Ser  Ala Ser Val Ile Ala  His Lys Met
    1730                 1735                 1740

Gln Leu  Asp Asn Gly Glu Ile  Arg Trp Val Ile Asp  Ser Val Val
    1745                 1750                 1755

Gly Lys  Glu Asp Gly Leu Gly  Val Glu Asn Ile His  Gly Ser Ala
    1760                 1765                 1770

Ala Ile  Ala Ser Ala Tyr Ser  Arg Ala Tyr Glu Glu  Thr Phe Thr
    1775                 1780                 1785

Leu Thr  Phe Val Thr Gly Arg  Thr Val Gly Ile Gly  Ala Tyr Leu
    1790                 1795                 1800

Ala Arg  Leu Gly Ile Arg Cys  Ile Gln Arg Thr Asp  Gln Pro Ile
    1805                 1810                 1815

Ile Leu  Thr Gly Phe Ser Ala  Leu Asn Lys Leu Leu  Gly Arg Glu
    1820                 1825                 1830

Val Tyr  Ser Ser His Met Gln  Leu Gly Gly Pro Lys  Ile Met Ala
    1835                 1840                 1845

Thr Asn  Gly Val Val His Leu  Thr Val Ser Asp Asp  Leu Glu Gly
    1850                 1855                 1860

Val Ser  Asn Ile Leu Arg Trp  Leu Ser Tyr Val Pro  Ala Asn Ile
    1865                 1870                 1875

Gly Gly  Pro Leu Pro Ile Thr  Lys Ser Leu Asp Pro  Pro Asp Arg
    1880                 1885                 1890

Pro Val  Ala Tyr Ile Pro Glu  Asn Thr Cys Asp Pro  Arg Ala Ala
    1895                 1900                 1905

Ile Ser  Gly Ile Asp Asp Ser  Gln Gly Lys Trp Leu  Gly Gly Met
    1910                 1915                 1920

Phe Asp  Lys Asp Ser Phe Val  Glu Thr Phe Glu Gly  Trp Ala Lys
    1925                 1930                 1935

Ser Val  Val Thr Gly Arg Ala  Lys Leu Gly Gly Ile  Pro Val Gly
    1940                 1945                 1950

Val Ile  Ala Val Glu Thr Gln  Thr Met Met Gln Leu  Ile Pro Ala
    1955                 1960                 1965

Asp Pro  Gly Gln Leu Asp Ser  His Glu Arg Ser Val  Pro Arg Ala
    1970                 1975                 1980

Gly Gln  Val Trp Phe Pro Asp  Ser Ala Thr Lys Thr  Ala Gln Ala
    1985                 1990                 1995

Met Leu  Asp Phe Asn Arg Glu  Gly Leu Pro Leu Phe  Ile Leu Ala
    2000                 2005                 2010

Asn Trp  Arg Gly Phe Ser Gly  Gly Gln Arg Asp Leu  Phe Glu Gly
    2015                 2020                 2025

Ile Leu  Gln Ala Gly Ser Thr  Ile Val Glu Asn Leu  Arg Thr Tyr
    2030                 2035                 2040

Asn Gln  Pro Ala Phe Val Tyr  Ile Pro Lys Ala Ala  Glu Leu Arg
    2045                 2050                 2055

Gly Gly  Ala Trp Val Val Ile  Asp Ser Lys Ile Asn  Pro Asp Arg
    2060                 2065                 2070

Ile Glu  Phe Tyr Ala Glu Arg  Thr Ala Lys Gly Asn  Val Leu Glu
    2075                 2080                 2085

Pro Gln  Gly Leu Ile Glu Ile  Lys Phe Arg Ser Glu  Glu Leu Gln
    2090                 2095                 2100

Glu Cys  Met Gly Arg Leu Asp  Pro Glu Leu Ile Asn  Leu Lys Ala
    2105                 2110                 2115
```

-continued

```
Lys Leu  Gln Gly Val Lys His  Glu Asn Gly Ser Leu  Pro Glu Ser
    2120                 2125                 2130

Glu Ser  Leu Gln Lys Ser Ile  Glu Ala Arg Lys Lys  Gln Leu Leu
    2135                 2140                 2145

Pro Leu  Tyr Thr Gln Ile Ala  Val Arg Phe Ala Glu  Leu His Asp
    2150                 2155                 2160

Thr Ser  Leu Arg Met Ala Ala  Lys Gly Val Ile Lys  Lys Val Val
    2165                 2170                 2175

Asp Trp  Glu Asp Ser Arg Ser  Phe Phe Tyr Lys Arg  Leu Arg Arg
    2180                 2185                 2190

Arg Ile  Ser Glu Asp Val Leu  Ala Lys Glu Ile Arg  Gly Val Ser
    2195                 2200                 2205

Gly Lys  Gln Phe Ser His Gln  Ser Ala Ile Glu Leu  Ile Gln Lys
    2210                 2215                 2220

Trp Tyr  Leu Ala Ser Lys Gly  Ala Glu Thr Gly Ser  Thr Glu Trp
    2225                 2230                 2235

Asp Asp  Asp Asp Ala Phe Val  Ala Trp Arg Glu Asn  Pro Glu Asn
    2240                 2245                 2250

Tyr Gln  Glu Tyr Ile Lys Glu  Leu Arg Ala Gln Arg  Val Ser Gln
    2255                 2260                 2265

Leu Leu  Ser Asp Val Ala Asp  Ser Ser Pro Asp Leu  Glu Ala Leu
    2270                 2275                 2280

Pro Gln  Gly Leu Ser Met Leu  Leu Glu Lys Met Asp  Pro Ser Arg
    2285                 2290                 2295

Arg Ala  Gln Phe Val Glu Glu  Val Lys Lys Val Leu  Lys
    2300                 2305                 2310
```

<210> SEQ ID NO 17
<211> LENGTH: 6966
<212> TYPE: DNA
<213> ORGANISM: Setaria italica

<400> SEQUENCE: 17

```
atgtcgcaac ttggattagc tgcagctgcc tcaaaggcgc tgccactact tcctaatcgc      60

catagaactt cagctggaac tacattccca tcacctgtat catcgcggcc ctcaaaccga     120

aggaaaagcc gcactcgttc acttcgtgat ggaggagatg gggtatcaga tgccaaaaag     180

cacaaccagt ctgtccgtca aggtcttgct ggcatcatcg acctcccaaa tgaggcaaca     240

tcggaagtgg atatttctca tggatccgag gatcccaggg ggccaaccga ttcatatcaa     300

atgaatggga ttgtaagtga agcacataat ggcagacatg cctcagtgtc caaggttgtt     360

gaattttgtg cggcgctagg tggcaaaaca ccaattcaca gtatactagt ggccaacaat     420

ggaatggcag cagcaaagtt catgaggagt gtccggacat gggctaatga tacttttgga     480

tcggagaagg cgattcagct catagctatg gcaactccag aagacatgag gataaatgca     540

gaacacatta gaattgctga tcaatttgtg gaggtgcctg gtggaacaaa caataacaac     600

tatgcaaatg ttcaactcat agtggaggta gcagaaagaa taggtgtttc tgctgtttgg     660

cctggttggg gtcatgcttc tgagaatcct gaacttccag atgcattgac cgcaaaagga     720

gttgttttcc ttgggccacc tgcggcatca atgaatgcat tgggagataa ggtcggttca     780

gctctcattg ctcaagcagc tggggtcccg accctttcgt ggagtggatc acatgttgaa     840

gttccattag agtgctgctt agatgcgata cctgaggaaa tgtatagaaa agcttgtgtt     900

actaccacag aagaagctgt tgcgagttgt caggtggttg gttatcctgc catgattaag     960
```

```
gcatcctggg gaggtggtgg taaaggaata agaaaggttc ataatgacga tgaggttaga   1020
gcactgttta agcaagtaca aggtgaagtc cctggctccc caatatttat catgaggctt   1080
gcatcccaga gtcgtcatct tgaagttcag ttgctttgtg atcaatatgg caatgtggca   1140
gcacttcaca gtcgtgattg cagtgtgcaa cggcgacacc aaaagattat tgaggaaggc   1200
ccagttactg ttgctcctcg tgagacagtt aaagcgcttg agcaggcagc aaggaggctt   1260
gctaaggctg tgggttatgt tggtgctgct actgttgaat acctttacag catggagact   1320
ggggaatact attttctgga gcttaatccc agattacagg tcgagcatcc agtcactgag   1380
tggattgctg aagtaaatct tcctgcagct caagttgcag ttggaatggg catacctctt   1440
tggcagattc cagaaatcag acgtttcgat ggaatggact atggaggagg atatgacatt   1500
tggaggaaaa cagcagctct tgccacacca tttaattttg atgaagtaga ttctcaatgg   1560
ccaaagggcc attgtgtagc agttagaatt actagcgagg atccagatga tggtttcaaa   1620
cctactggtg ggaaagtgaa ggagataagt tttaaaagca agcctaatgt ttgggcctac   1680
ttctcagtaa agtctggtgg aggcattcat gaatttgttg attctcagtt tgggcatgtt   1740
tttgcatatg ggctctctag atcagcagca ataacgaaca tggctcttgc attaaaagag   1800
attcaaattc gtggagaaat tcattcaaat gttgattaca cagttgatct cttaaatgct   1860
tcagacttca gagaaaataa gattcatact ggctggcttg ataccagaat agctatgcgt   1920
gttcaagctg agaggccccc atggtatatt tcagtggttg gaggagctct atataaaaca   1980
gtaactgcca atgcagccac tgtttctgat tatgtcagtt atctcaccaa gggccagatt   2040
ccaccaaagc atatatccct tgtcagttca acagttaatc tgaatatcga agggagcaaa   2100
tacacagttg aaactgtaag gactggacat ggtagctaca gattacgaat gaatgattca   2160
gcaattgaag cgaatgtaca atccttatgt gatggaggcc tcttaatgca gttggatgga   2220
aatagccatg taatttacgc ggaagaagaa gctggtggta cacgacttct gattgatgga   2280
aagacatgct tgttacagaa tgatcatgat ccatcaaagt tattagctga gacaccctgc   2340
aaacttcttc ggttcttggt tgctgatggt gcccatgttg atgctgatgt accatatgcg   2400
gaagttgagg ttatgaaaat gtgcatgcct ctcttgtcgc ctgcttctgg tgtcattcat   2460
gttatgatgt ctgagggcca ggcattgcag gctggtgatc ttatagcaag gctggatctt   2520
gatgaccctt ctgctgtgaa aagagctgaa ccatttcatg gaatatttcc acaaatggac   2580
cttcctgttg ctgcctctag ccaagtacac aaaagatatg ctgcaagttg gaatgctgct   2640
cgaatggtcc ttgcaggata cgagcataat atcaatgaag ttgtacaaga tttggtatgc   2700
tgcctggatg atcccgagct tcccttccta cagtgggatg aacttatgtc agttctagca   2760
actaggcttc caagaaatct taagagtgag ttagaggata aatacatgga atacaagttg   2820
aacttttacc atgggaaaaa caaggacttc ccgtccaagc tgctgagaga catcattgag   2880
gcaaatcttg catatggttc agagaaggaa aaagctacga atgagaggct tattgagcct   2940
cttatgagcc tacttaagtc atatgagggt gggagagaaa gccatgctca ttttgttgtc   3000
aagtcccttt tcaaggagta ccttgctgtg gaagaacttt tcagtgatgg gattcagtct   3060
gatgtgattg aaaccctgcg tcatcagcac agtaaagact tgcagaaggt tgtagacatt   3120
gtgttgtctc accagggtgt gaggaacaaa gctaagcttg taacagcact tatggaaaag   3180
ctggtttatc caaatcctgc tgcttacagg gatctgttgg ttcgcttttc ttcactcaat   3240
cataaaagat attataagtt ggcccttaaa gcaagcgaac ttcttgaaca aactaaacta   3300
agtgaactcc gtgcaagcat cgcaagaagc ctttctgatc tggggatgca taagggagaa   3360
```

atgactattg aagatagcat ggaagattta gtctctgccc cattacctgt cgaagatgca 3420
cttatttctt tgtttgatta cagtgatcca actgttcagc agaaagtgat cgagacatac 3480
atatctcgat tgtatcagcc tcttcttgtg aaagatagca tccaagtgaa atttaaggaa 3540
tctggtgcct ttgctttatg ggaattttct gaagggcatg ttgatactaa aaatggacaa 3600
gggaccgttc ttggtcgaac aagatggggt gccatggtag ctgtcaaatc agttgaatct 3660
gcacgaacag ccattgtagc tgcattaaag gattcggcac agcatgccag ctctgagggc 3720
aacatgatgc acattgcctt attgagtgct gaaaatgaaa ataatatcag tgatgatcaa 3780
gctcaacata ggatggaaaa acttaacaag atactcaagg atactagtgt cgcaaatgat 3840
cttcgagctg ctggtttgaa ggttataagt tgcattgttc aaagagatga agcacgcatg 3900
ccaatgcgcc acacattact ctggtcagat gaaaagagtt gttatgagga agagcagatt 3960
cttcggcatg tggagcctcc cctctccatg cttcttgaaa tggataagtt gaaagtgaaa 4020
ggatacaatg aaatgaagta tactccatca cgtgatcgtc aatggcatat ctacacacta 4080
agaaatactg aaaaccccaa aatgttgcat agggtatttt tccgaactat tgtcaggcaa 4140
cccaatgcag gcaacaagtt tatatcagcc caaattggcg acactgaagt aggaggtcct 4200
gaggaatctt tgtcatttac atctaatagc attttaagag ccttgatgac tgctattgaa 4260
gaattagagc ttcatgcaat taggactgat cattctcaca tgtatttgtg catattgaaa 4320
gaacaaaagc ttcttgatct cattccgttt tcagggagca caatcgtcga tgttgtccaa 4380
gacgaagcta ctgcttgttc acttttaaaa tcaatggctt tgaagataca cgaacttgtt 4440
ggtgcacaga tgcatcatct ttctgtatgc cagtgggagg tgaaactcaa gttgtactgc 4500
gatgggcctg ccagtggcac ctggagagtt gtaactacaa atgttactag tcacacttgc 4560
accgttgata tctaccggga agtggaagat actgaatcgc agaagttagt ataccattca 4620
gcttctccgt cagctagtcc tttgcatggt gtggccctgg ataatccgta tcaacctttg 4680
agtgtcattg atctaaaaca ctgctctgct aggaacaaca gaactacata ttgctatgat 4740
tttccactgg catttgaaac tgccctgcag aagtcatggc agtccaatgg ctccagtgtt 4800
tctgaaggca gtgaaaatag taggtcttat gtgaaagcaa cagagctggt gtttgctgaa 4860
aaacatgggt cctggggcac tcctataatt tccatggagc gtcccgctgg gctcaatgac 4920
attggcatgg tagcttggat cttagagatg tccactcctg aatttcccaa tggcaggcag 4980
attattgtca tagcaaatga tattactttc agagctggat catttggccc aagggaagat 5040
gcgtttttttg aagctgtcac gaacctggcc tgcgagagga agcttcctct tatatacttg 5100
gcagcaaact ccggtgctag gattggcata gccgatgaag tgaaatcttg cttccgtgtt 5160
gggtggtccg atgaaggcag ccctgaacgg ggttttcagt acatttatct gactgacgaa 5220
gactatgccc gtattagctt gtctgttata gcacacaagc tgcagctgga taatggtgaa 5280
attaggtgga ttattgactc tgttgtgggc aaggaggatg ggcttggtgt tgagaatata 5340
catggaagtg ctgctattgc cagtgcttat tctagggcat atgaggagac atttacactt 5400
acatttgtga ctgggcggac tgttggaata ggagcatatc ttgctcggct cggtatacgg 5460
tgcatacagc gtcttgacca gcctattatt ttaactgggt tttctgccct gaacaagctt 5520
cttgggcggg aagtgtacag ctcccacatg cagttgggtg gtcctaagat catggcgacc 5580
aatggtgttg tccacttgac tgtttcagat gaccttgaag gtgtttccaa tatattgagg 5640
tggctcagct atgttcctgc caacattggt ggacctcttc ctattacaaa acctttggac 5700

```
ccaccagaca gacctgttgc atacatccct gagaacacat gtgatccgcg cgcagccatt   5760

cgtggtgtag atgacagcca agggaaatgg ttgggtggta tgtttgacaa agacagcttt   5820

gtcgagacat ttgaaggatg ggcgaaaaca gtggttacgg gcagagcaaa gcttggagga   5880

attcctgttg gcgtcatagc tgtggagaca caaaccatga tgcagcttat ccctgctgat   5940

ccaggccagc ttgattccca tgagcgatct gttcctcggg ctggacaagt gtggttccca   6000

gattctgcaa ccaagacagc tcaggcattg ttggacttca accgtgaagg attgccgctg   6060

ttcatccttg ctaactggag aggattctct ggtggacaaa gagatctgtt tgaaggaatt   6120

cttcaggctg ggtcaacaat tgttgagaac cttaggacat acaatcagcc tgcttttgtc   6180

tacattccta tggctggaga gctgcgtgga ggagcttggg ttgtggttga tagcaaaata   6240

aatccagacc gaattgagtg ttatgctgag aggactgcta aaggcaatgt tctggaacct   6300

caagggttaa ttgaaatcaa attcagatca gaggagctcc aagactgtat gggtaggctt   6360

gacccagggt tgataaatct gaaagcaaaa ctccaaggtg caaagcttgg aaatggaagc   6420

ctaacagatg tagaatccct tcagaagagt atagatgctc gtacgaaaca gttgttgcct   6480

ttatacaccc agattgcaat acggtttgct gaattgcatg atacttccct cagaatggca   6540

gctaaaggtg tgattaagaa agttgtagat tgggaagaat cacgttcttt cttctacaga   6600

aggctacgga ggaggatctc tgaagatgtt cttgcaaaag aaataagagg aatagctggt   6660

gaccacttca ctcaccaatc agcagttgag ctgatcaagg aatggtactt ggcttctcaa   6720

gccacaacag gaagcactga atgggatgat gatgatgctt ttgttgcctg gaaggagaat   6780

cctgaaaact ataagggata tatccaagag ttaagggctc aaaaggtgtc tcagtcgctc   6840

tccgatcttg cagactccag ttcagatcta gaagcattct cacagggtct ttccacatta   6900

ttagataaga tggatccctc tcagagagcc aagttcattc aggaagtcaa gaaggtcctg   6960

ggttga                                                              6966
```

<210> SEQ ID NO 18
<211> LENGTH: 2321
<212> TYPE: PRT
<213> ORGANISM: Setaria italica

<400> SEQUENCE: 18

```
Met Ser Gln Leu Gly Leu Ala Ala Ala Ala Ser Lys Ala Leu Pro Leu
1               5                   10                  15

Leu Pro Asn Arg His Arg Thr Ser Ala Gly Thr Thr Phe Pro Ser Pro
            20                  25                  30

Val Ser Ser Arg Pro Ser Asn Arg Arg Lys Ser Arg Thr Arg Ser Leu
        35                  40                  45

Arg Asp Gly Gly Asp Gly Val Ser Asp Ala Lys Lys His Asn Gln Ser
    50                  55                  60

Val Arg Gln Gly Leu Ala Gly Ile Ile Asp Leu Pro Asn Glu Ala Thr
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Val Ser Glu Ala His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140
```

-continued

```
Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205

Glu Val Ala Glu Arg Ile Gly Val Ser Ala Val Trp Pro Gly Trp Gly
    210                 215                 220

His Ala Ser Glu Asn Pro Glu Leu Pro Asp Ala Leu Thr Ala Lys Gly
225                 230                 235                 240

Val Val Phe Leu Gly Pro Pro Ala Ala Ser Met Asn Ala Leu Gly Asp
                245                 250                 255

Lys Val Gly Ser Ala Leu Ile Ala Gln Ala Ala Gly Val Pro Thr Leu
            260                 265                 270

Ser Trp Ser Gly Ser His Val Glu Val Pro Leu Glu Cys Cys Leu Asp
        275                 280                 285

Ala Ile Pro Glu Glu Met Tyr Arg Lys Ala Cys Val Thr Thr Thr Glu
    290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Asp Gly Met Asp Tyr Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Val Asp Ser Gln
```

-continued

```
                565                 570                 575

Phe Gly His Val Phe Ala Tyr Gly Leu Ser Arg Ser Ala Ala Ile Thr
            580                 585                 590

Asn Met Ala Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Arg
    610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Val Thr Ala Asn Ala Ala Thr Val Ser Asp Tyr Val
            660                 665                 670

Ser Tyr Leu Thr Lys Gly Gln Ile Pro Pro Lys His Ile Ser Leu Val
        675                 680                 685

Ser Ser Thr Val Asn Leu Asn Ile Glu Gly Ser Lys Tyr Thr Val Glu
    690                 695                 700

Thr Val Arg Thr Gly His Gly Ser Tyr Arg Leu Arg Met Asn Asp Ser
705                 710                 715                 720

Ala Ile Glu Ala Asn Val Gln Ser Leu Cys Asp Gly Gly Leu Leu Met
                725                 730                 735

Gln Leu Asp Gly Asn Ser His Val Ile Tyr Ala Glu Glu Glu Ala Gly
            740                 745                 750

Gly Thr Arg Leu Leu Ile Asp Gly Lys Thr Cys Leu Leu Gln Asn Asp
        755                 760                 765

His Asp Pro Ser Lys Leu Leu Ala Glu Thr Pro Cys Lys Leu Leu Arg
    770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Val Met Met Ser Glu Gly Gln Ala Leu Gln Ala Gly
            820                 825                 830

Asp Leu Ile Ala Arg Leu Asp Leu Asp Asp Pro Ser Ala Val Lys Arg
        835                 840                 845

Ala Glu Pro Phe His Gly Ile Phe Pro Gln Met Asp Leu Pro Val Ala
    850                 855                 860

Ala Ser Ser Gln Val His Lys Arg Tyr Ala Ala Ser Trp Asn Ala Ala
865                 870                 875                 880

Arg Met Val Leu Ala Gly Tyr Glu His Asn Ile Asn Glu Val Val Gln
                885                 890                 895

Asp Leu Val Cys Cys Leu Asp Asp Pro Glu Leu Pro Phe Leu Gln Trp
            900                 905                 910

Asp Glu Leu Met Ser Val Leu Ala Thr Arg Leu Pro Arg Asn Leu Lys
        915                 920                 925

Ser Glu Leu Glu Asp Lys Tyr Met Glu Tyr Lys Leu Asn Phe Tyr His
    930                 935                 940

Gly Lys Asn Lys Asp Phe Pro Ser Lys Leu Leu Arg Asp Ile Ile Glu
945                 950                 955                 960

Ala Asn Leu Ala Tyr Gly Ser Glu Lys Glu Lys Ala Thr Asn Glu Arg
                965                 970                 975

Leu Ile Glu Pro Leu Met Ser Leu Leu Lys Ser Tyr Glu Gly Gly Arg
            980                 985                 990
```

Glu Ser His Ala His Phe Val Val Lys Ser Leu Phe Lys Glu Tyr Leu
995 1000 1005

Ala Val Glu Glu Leu Phe Ser Asp Gly Ile Gln Ser Asp Val Ile
1010 1015 1020

Glu Thr Leu Arg His Gln His Ser Lys Asp Leu Gln Lys Val Val
1025 1030 1035

Asp Ile Val Leu Ser His Gln Gly Val Arg Asn Lys Ala Lys Leu
1040 1045 1050

Val Thr Ala Leu Met Glu Lys Leu Val Tyr Pro Asn Pro Ala Ala
1055 1060 1065

Tyr Arg Asp Leu Leu Val Arg Phe Ser Ser Leu Asn His Lys Arg
1070 1075 1080

Tyr Tyr Lys Leu Ala Leu Lys Ala Ser Glu Leu Leu Glu Gln Thr
1085 1090 1095

Lys Leu Ser Glu Leu Arg Ala Ser Ile Ala Arg Ser Leu Ser Asp
1100 1105 1110

Leu Gly Met His Lys Gly Glu Met Thr Ile Glu Asp Ser Met Glu
1115 1120 1125

Asp Leu Val Ser Ala Pro Leu Pro Val Glu Asp Ala Leu Ile Ser
1130 1135 1140

Leu Phe Asp Tyr Ser Asp Pro Thr Val Gln Gln Lys Val Ile Glu
1145 1150 1155

Thr Tyr Ile Ser Arg Leu Tyr Gln Pro Leu Leu Val Lys Asp Ser
1160 1165 1170

Ile Gln Val Lys Phe Lys Glu Ser Gly Ala Phe Ala Leu Trp Glu
1175 1180 1185

Phe Ser Glu Gly His Val Asp Thr Lys Asn Gly Gln Gly Thr Val
1190 1195 1200

Leu Gly Arg Thr Arg Trp Gly Ala Met Val Ala Val Lys Ser Val
1205 1210 1215

Glu Ser Ala Arg Thr Ala Ile Val Ala Ala Leu Lys Asp Ser Ala
1220 1225 1230

Gln His Ala Ser Ser Glu Gly Asn Met Met His Ile Ala Leu Leu
1235 1240 1245

Ser Ala Glu Asn Glu Asn Asn Ile Ser Asp Asp Gln Ala Gln His
1250 1255 1260

Arg Met Glu Lys Leu Asn Lys Ile Leu Lys Asp Thr Ser Val Ala
1265 1270 1275

Asn Asp Leu Arg Ala Ala Gly Leu Lys Val Ile Ser Cys Ile Val
1280 1285 1290

Gln Arg Asp Glu Ala Arg Met Pro Met Arg His Thr Leu Leu Trp
1295 1300 1305

Ser Asp Glu Lys Ser Cys Tyr Glu Glu Glu Gln Ile Leu Arg His
1310 1315 1320

Val Glu Pro Pro Leu Ser Met Leu Leu Glu Met Asp Lys Leu Lys
1325 1330 1335

Val Lys Gly Tyr Asn Glu Met Lys Tyr Thr Pro Ser Arg Asp Arg
1340 1345 1350

Gln Trp His Ile Tyr Thr Leu Arg Asn Thr Glu Asn Pro Lys Met
1355 1360 1365

Leu His Arg Val Phe Phe Arg Thr Ile Val Arg Gln Pro Asn Ala
1370 1375 1380

-continued

```
Gly Asn  Lys Phe Ile Ser Ala  Gln Ile Gly Asp Thr  Glu Val Gly
    1385                1390                1395

Gly Pro  Glu Glu Ser Leu Ser  Phe Thr Ser Asn Ser  Ile Leu Arg
    1400                1405                1410

Ala Leu  Met Thr Ala Ile Glu  Glu Leu Glu Leu His  Ala Ile Arg
    1415                1420                1425

Thr Asp  His Ser His Met Tyr  Leu Cys Ile Leu Lys  Glu Gln Lys
    1430                1435                1440

Leu Leu  Asp Leu Ile Pro Phe  Ser Gly Ser Thr Ile  Val Asp Val
    1445                1450                1455

Val Gln  Asp Glu Ala Thr Ala  Cys Ser Leu Leu Lys  Ser Met Ala
    1460                1465                1470

Leu Lys  Ile His Glu Leu Val  Gly Ala Gln Met His  His Leu Ser
    1475                1480                1485

Val Cys  Gln Trp Glu Val Lys  Leu Lys Leu Tyr Cys  Asp Gly Pro
    1490                1495                1500

Ala Ser  Gly Thr Trp Arg Val  Val Thr Thr Asn Val  Thr Ser His
    1505                1510                1515

Thr Cys  Thr Val Asp Ile Tyr  Arg Glu Val Glu Asp  Thr Glu Ser
    1520                1525                1530

Gln Lys  Leu Val Tyr His Ser  Ala Ser Pro Ser Ala  Ser Pro Leu
    1535                1540                1545

His Gly  Val Ala Leu Asp Asn  Pro Tyr Gln Pro Leu  Ser Val Ile
    1550                1555                1560

Asp Leu  Lys His Cys Ser Ala  Arg Asn Asn Arg Thr  Thr Tyr Cys
    1565                1570                1575

Tyr Asp  Phe Pro Leu Ala Phe  Glu Thr Ala Leu Gln  Lys Ser Trp
    1580                1585                1590

Gln Ser  Asn Gly Ser Ser Val  Ser Glu Gly Ser Glu  Asn Ser Arg
    1595                1600                1605

Ser Tyr  Val Lys Ala Thr Glu  Leu Val Phe Ala Glu  Lys His Gly
    1610                1615                1620

Ser Trp  Gly Thr Pro Ile Ile  Ser Met Glu Arg Pro  Ala Gly Leu
    1625                1630                1635

Asn Asp  Ile Gly Met Val Ala  Trp Ile Leu Glu Met  Ser Thr Pro
    1640                1645                1650

Glu Phe  Pro Asn Gly Arg Gln  Ile Ile Val Ile Ala  Asn Asp Ile
    1655                1660                1665

Thr Phe  Arg Ala Gly Ser Phe  Gly Pro Arg Glu Asp  Ala Phe Phe
    1670                1675                1680

Glu Ala  Val Thr Asn Leu Ala  Cys Glu Arg Lys Leu  Pro Leu Ile
    1685                1690                1695

Tyr Leu  Ala Ala Asn Ser Gly  Ala Arg Ile Gly Ile  Ala Asp Glu
    1700                1705                1710

Val Lys  Ser Cys Phe Arg Val  Gly Trp Ser Asp Glu  Gly Ser Pro
    1715                1720                1725

Glu Arg  Gly Phe Gln Tyr Ile  Tyr Leu Thr Asp Glu  Asp Tyr Ala
    1730                1735                1740

Arg Ile  Ser Leu Ser Val Ile  Ala His Lys Leu Gln  Leu Asp Asn
    1745                1750                1755

Gly Glu  Ile Arg Trp Ile Ile  Asp Ser Val Val Gly  Lys Glu Asp
    1760                1765                1770

Gly Leu  Gly Val Glu Asn Ile  His Gly Ser Ala Ala  Ile Ala Ser
```

```
1775 1780 1785

Ala Tyr Ser Arg Ala Tyr Glu Glu Thr Phe Thr Leu Thr Phe Val
1790 1795 1800

Thr Gly Arg Thr Val Gly Ile Gly Ala Tyr Leu Ala Arg Leu Gly
1805 1810 1815

Ile Arg Cys Ile Gln Arg Leu Asp Gln Pro Ile Ile Leu Thr Gly
1820 1825 1830

Phe Ser Ala Leu Asn Lys Leu Leu Gly Arg Glu Val Tyr Ser Ser
1835 1840 1845

His Met Gln Leu Gly Gly Pro Lys Ile Met Ala Thr Asn Gly Val
1850 1855 1860

Val His Leu Thr Val Ser Asp Asp Leu Glu Gly Val Ser Asn Ile
1865 1870 1875

Leu Arg Trp Leu Ser Tyr Val Pro Ala Asn Ile Gly Gly Pro Leu
1880 1885 1890

Pro Ile Thr Lys Pro Leu Asp Pro Pro Asp Arg Pro Val Ala Tyr
1895 1900 1905

Ile Pro Glu Asn Thr Cys Asp Pro Arg Ala Ala Ile Arg Gly Val
1910 1915 1920

Asp Asp Ser Gln Gly Lys Trp Leu Gly Gly Met Phe Asp Lys Asp
1925 1930 1935

Ser Phe Val Glu Thr Phe Glu Gly Trp Ala Lys Thr Val Val Thr
1940 1945 1950

Gly Arg Ala Lys Leu Gly Gly Ile Pro Val Gly Val Ile Ala Val
1955 1960 1965

Glu Thr Gln Thr Met Met Gln Leu Ile Pro Ala Asp Pro Gly Gln
1970 1975 1980

Leu Asp Ser His Glu Arg Ser Val Pro Arg Ala Gly Gln Val Trp
1985 1990 1995

Phe Pro Asp Ser Ala Thr Lys Thr Ala Gln Ala Leu Leu Asp Phe
2000 2005 2010

Asn Arg Glu Gly Leu Pro Leu Phe Ile Leu Ala Asn Trp Arg Gly
2015 2020 2025

Phe Ser Gly Gly Gln Arg Asp Leu Phe Glu Gly Ile Leu Gln Ala
2030 2035 2040

Gly Ser Thr Ile Val Glu Asn Leu Arg Thr Tyr Asn Gln Pro Ala
2045 2050 2055

Phe Val Tyr Ile Pro Met Ala Gly Glu Leu Arg Gly Gly Ala Trp
2060 2065 2070

Val Val Val Asp Ser Lys Ile Asn Pro Asp Arg Ile Glu Cys Tyr
2075 2080 2085

Ala Glu Arg Thr Ala Lys Gly Asn Val Leu Glu Pro Gln Gly Leu
2090 2095 2100

Ile Glu Ile Lys Phe Arg Ser Glu Glu Leu Gln Asp Cys Met Gly
2105 2110 2115

Arg Leu Asp Pro Gly Leu Ile Asn Leu Lys Ala Lys Leu Gln Gly
2120 2125 2130

Ala Lys Leu Gly Asn Gly Ser Leu Thr Asp Val Glu Ser Leu Gln
2135 2140 2145

Lys Ser Ile Asp Ala Arg Thr Lys Gln Leu Leu Pro Leu Tyr Thr
2150 2155 2160

Gln Ile Ala Ile Arg Phe Ala Glu Leu His Asp Thr Ser Leu Arg
2165 2170 2175
```

```
Met Ala Ala Lys Gly Val Ile Lys Lys Val Val Asp Trp Glu Glu
    2180                2185                2190

Ser Arg Ser Phe Phe Tyr Arg Arg Leu Arg Arg Arg Ile Ser Glu
    2195                2200                2205

Asp Val Leu Ala Lys Glu Ile Arg Gly Ile Ala Gly Asp His Phe
    2210                2215                2220

Thr His Gln Ser Ala Val Glu Leu Ile Lys Glu Trp Tyr Leu Ala
    2225                2230                2235

Ser Gln Ala Thr Thr Gly Ser Thr Glu Trp Asp Asp Asp Asp Ala
    2240                2245                2250

Phe Val Ala Trp Lys Glu Asn Pro Glu Asn Tyr Lys Gly Tyr Ile
    2255                2260                2265

Gln Glu Leu Arg Ala Gln Lys Val Ser Gln Ser Leu Ser Asp Leu
    2270                2275                2280

Ala Asp Ser Ser Ser Asp Leu Glu Ala Phe Ser Gln Gly Leu Ser
    2285                2290                2295

Thr Leu Leu Asp Lys Met Asp Pro Ser Gln Arg Ala Lys Phe Ile
    2300                2305                2310

Gln Glu Val Lys Lys Val Leu Gly
    2315                2320
```

<210> SEQ ID NO 19
<211> LENGTH: 6966
<212> TYPE: DNA
<213> ORGANISM: Setaria italica

<400> SEQUENCE: 19

```
atgtcgcaac ttggattagc tgcagctgcc tcaaaggcgc tgccactact tcctaatcgc     60

catagaactt cagctggaac tacattccca tcacctgtat catcgcggcc ctcaaaccga    120

aggaaaagcc gcactcgttc acttcgtgat ggaggagatg gggtatcaga tgccaaaaag    180

cacaaccagt ctgtccgtca aggtcttgct ggcatcatcg acctcccaaa tgaggcaaca    240

tcggaagtgg atatttctca tggatccgag gatcccaggg ggccaaccga ttcatatcaa    300

atgaatggga ttgtaaatga agcacataat ggcagacatg cctcagtgtc caaggttgtt    360

gaattttgtg cggcgctagg tggcaaaaca ccaattcaca gtatactagt ggccaacaat    420

ggaatggcag cagcaaagtt catgaggagt gtccggacat gggctaatga tacttttgga    480

tcggagaagg cgattcagct catagctatg gcaactccag aagacatgag gataaatgca    540

gaacacatta gaattgctga tcaatttgta gaggtgcctg gtggaacaaa caataacaac    600

tatgcaaatg ttcaactcat agtggaggta gcagaaagaa taggtgtttc tgctgtttgg    660

cctggttggg gtcatgcttc tgagaatcct gaacttccag atgcattgac cgcaaaagga    720

attgttttcc ttgggccacc tgcggcatca atgaatgcat tgggagataa ggtcggttca    780

gctctcattg ctcaagcagc tggggtcccg accctttcgt ggagtggatc acatgttgaa    840

gttccattag agtgctgctt agatgcgata cctgaggaaa tgtatagaaa agcttgtgtt    900

actaccacag aagaagctgt tgcgagttgt caggtggttg gttatcctgc catgattaag    960

gcatcctggg gaggtggtgg taaaggaata agaaaggttc ataatgacga tgaggttaga   1020

gcactgttta agcaagtaca aggtgaagtc cctggctccc caatatttat catgaggctt   1080

gcatcccaga gtcgtcatct tgaagttcag ttgctttgtg atcaatatgg caatgtggca   1140

gcacttcaca gtcgtgattg cagtgtgcaa cggcgacacc aaaagattat tgaggaaggc   1200
```

-continued

```
ccagttactg ttgctcctcg tgagacagtt aaagcgcttg agcaggcagc aaggaggctt   1260
gctaaggctg tgggttatgt tggtgctgct actgttgaat acctttacag catggagact   1320
ggggaatact attttctgga gcttaatccc agattacagg tcgagcatcc agtcactgag   1380
tggattgctg aagtaaatct tcctgcagct caagttgcag ttggaatggg catacctctt   1440
tggcagattc cagaaatcag acgtttctat ggaatggact atggaggagg atatgacatt   1500
tggaggaaaa cagcagctct tgccacacca tttaattttg atgaagtaga ttctcaatgg   1560
ccaaagggcc attgtgtagc agttagaatt actagcgagg atccagatga tggtttcaaa   1620
cctactggtg ggaaagtgaa ggagataagt tttaaaagca agcctaatgt ttgggcctac   1680
ttctcagtaa agtctggtgg aggcattcat gaatttgctg attctcagtt tgggcatgtt   1740
tttgcatatg ggctctctag atcagcagca ataacgaaca tggctcttgc attaaaagag   1800
attcaaattc gtggagaaat tcattcaaat gttgattaca cagttgatct cttaaatgct   1860
tcagacttca gagaaaataa gattcatact ggctggcttg ataccagaat agctatgcgt   1920
gttcaagctg agaggccccc atggtatatt tcagtggttg gaggagctct atataaaaca   1980
gtaactgcca atgcagccac tgtttctgat tatgtcagtt atctcaccaa gggccagatt   2040
ccaccaaagc atatatccct tgtcagttca acagttaatc tgaatatcga agggagcaaa   2100
tacacagttg aaactgtaag gactggacat ggtagctaca gattacgaat gaatgattca   2160
gcaattgaag cgaatgtaca atctttatgt gatggaggcc tcttaatgca gttggatgga   2220
aatagccatg taatttacgc ggaagaagaa gctggtggta cacgacttct gattgatgga   2280
aagacatgct tgttacagaa tgatcatgat ccatcaaagt tattagctga gacaccctgc   2340
aaacttcttc ggttcttggt tgctgatggt gctcatgttg atgctgatgt accatatgcg   2400
gaagttgagg ttatgaaaat gtgcatgcct ctcttgtcgc ctgcttctgg tgtcattcat   2460
gttatgatgt ctgagggcca ggcattgcag gctggtgatc ttatagcaag gctggatctt   2520
gatgaccctt ctgctgtgaa aagagctgaa ccatttcatg gaatatttcc acaaatggac   2580
cttcctgttg ctgcctctag ccaagtacac aaaagatatg ctgcaagttt gaatgctgct   2640
cgaatggtcc ttgcaggata cgagcataat atcaatgaag ttgtacaaga tttggtatgc   2700
tgcctggatg atcccgagct tcccttccta cagtgggatg aacttatgtc agttctagca   2760
actaggcttc caagaaatct taagagtgag ttagaggata aatacatgga atacaagttg   2820
aacttttacc atgggaaaaa caaggacttc ccgtccaagc tgctgagaga catcattgag   2880
gcaaatcttg catatggttc agagaaggaa aaagctacga atgagaggct tattgagcct   2940
cttatgagcc tacttaagtc atatgagggt gggagagaaa gccatgctca ttttgttgtc   3000
aagtcccttt tcaaggagta ccttgctgtg gaagaacttt tcagtgatgg gattcagtct   3060
gatgtgattg aaaccctgcg tcatcagcac agtaaagact tgcagaaggt tgtagacatt   3120
gtgttgtctc accagggtgt gaggaacaaa gctaagcttg taacagcact tatggaaaag   3180
ctggtttatc caaatcctgc tgcttacagg gatctgttgg ttcgcttttc ttcactcaat   3240
cataaaagat attataagtt ggcccttaaa gcaagcgaac ttcttgaaca aactaaacta   3300
agtgaactcc gtgcaagcat cgcaagaagc ctttctgatc tggggatgca taagggagaa   3360
atgactattg aagatagcat ggaagattta gtctctgccc cattacctgt cgaagatgca   3420
cttatttctt tgtttgatta cagtgatcca actgttcagc agaaagtgat cgagacatac   3480
atatctcgat tgtatcagcc tcttcttgtg aaagatagca tccaagtgaa atttaaggaa   3540
tctggtgcct ttgctttatg ggaattttct gaagggcatg ttgatactaa aaatggacaa   3600
```

-continued

```
gggaccgttc ttggtcgaac aagatggggt gccatggtag ctgtcaaatc agttgaatct   3660
gcacgaacag ccattgtagc tgcattaaag gattcggcac agcatgccag ctctgagggc   3720
aacatgatgc acattgcctt attgagtgct gaaaatgaaa ataatatcag tgatgatcaa   3780
gctcaacata ggatggaaaa acttaacaag atactcaagg atactagtgt cgcaaatgat   3840
cttcgagctg ctggtttgaa ggttataagt tgcattgttc aaagagatga agcacgcatg   3900
ccaatgcgcc acacattact ctggtcagat gaaaagagtt gttatgagga agagcagatt   3960
cttcggcatg tggagcctcc cctctccatg cttcttgaaa tggataagtt gaaagtgaaa   4020
ggatacaatg aaatgaagta tactccatca cgtgatcgtc aatggcatat ctacacacta   4080
agaaatactg aaaaccccaa aatgttgcat agggtatttt tccgaactat tgtcaggcaa   4140
cccaatgcag gcaacaagtt tatatcagcc caaattggcg acactgaagt aggaggtcct   4200
gaggaatctt tgtcatttac atctaatagc attttaagag ccttgatgac tgctattgaa   4260
gaattagagc ttcatgcaat taggactggt cattctcaca tgtatttgtg catattgaaa   4320
gaacaaaagc ttcttgatct cattccgttt tcagggagca caatcgtcga tgttggccaa   4380
gacgaagcta ctgcttgttc acttttaaaa tcaatggctt tgaagataca cgaacttgtt   4440
ggtgcacaga tgcatcatct ttctgtatgc cagtgggagg tgaaactcaa gttgtactgc   4500
gatgggcctg ccagtggcac ctggagagtt gtaactacaa atgttactag tcacacttgc   4560
accattgata tctaccggga agtggaagat actgaatcgc agaagttagt ataccattca   4620
gcttctccgt cagctagtcc tttgcatggt gtggccctgg ataatccgta tcaacctttg   4680
agtgtcattg atctaaaacg ctgctctgct aggaacaaca gaactacata ttgctatgat   4740
tttccactgg catttgaaac tgccctgcag aagtcatggc agtccaatgg ctccagtgtt   4800
tctgaaggca gtgaaaatag taggtcttat gtgaaagcaa cagagctggt gtttgctgaa   4860
aaacatgggt cctggggcac tcctataatt tccatggagc gtcccgctgg gctcaatgac   4920
attggcatgg tagcttggat cttagagatg tccactcctg aatttcccaa tggcaggcag   4980
attattgtca tagcaaatga tattactttc agagctggat catttggccc aagggaagat   5040
gcgtttttg aagctgtcac gaacctggcc tgcgagagga agcttcctct tatatacttg   5100
gcagcaaact ccggtgctag gattggcata gccgatgaag tgaaatcttg cttccgtgtt   5160
gggtggtccg atgaaggcag ccctgaacgg ggttttcagt acatttatct gactgacgaa   5220
gactatgccc gtattagctt gtctgttata gcacacaagc tgcagctgga taatggtgaa   5280
attaggtgga ttattgactc tgttgtgggc aaggaggatg ggcttggtgt tgagaatcta   5340
catggaagtg ctgctattgc cagtgcttat tctagggcat atgaggagac atttacactt   5400
acatttgtga ctgggcggac tgttggaata ggagcatatc tcgctcggct cggtatacgg   5460
tgcatacagc gtcttgacca gcctattatt ttaactgggt tttctgccct gaacaagctt   5520
cttgggcggg aagtgtacag ctcccacatg cagttgggtg gtcctaagat catggcgacc   5580
aatggtgttg tccacttgac tgtttcagat gaccttgaag gtgtttccaa tatattgagg   5640
tggctcagct atgttcctgc caacattggt ggacctcttc ctattacaaa acctttggac   5700
ccaccagaca gacctgttgc atacatccct gagaacacat gtgatccgcg cgcagccatt   5760
cgtggtgtag atgacagcca agggaaatgg ttgggtggta tgtttgacaa agacagcttt   5820
gtcgagacat ttgaaggatg ggcgaaaaca gtggttacgg gcagagcaaa gcttggagga   5880
attcctgttg gtgtcatagc tgtggagaca caaaccatga tgcagcttat ccctgctgat   5940
```

```
ccaggccagc ttgattccca tgagcgatct gttcctcggg ctggacaagt gtggttccca   6000

gattctgcaa ccaagacagc tcaggcattg ttggacttca accgtgaagg attgccgctg   6060

ttcatccttg ctaactggag aggattctct ggtggacaaa gagatctgtt tgaaggaatt   6120

cttcaggctg ggtcaacaat tgttgagaac cttaggacat acaatcagcc tgcttttgtc   6180

tacattccta tggctggaga gctgcgtgga ggagcttggg ttgtggttga tagcaaaata   6240

aatccagacc gaattgagtg ttatgctgag aggactgcta aaggcaatgt tcttgaacct   6300

caagggttaa ttgaaatcaa attcagatca gaggagctcc aagactgtat gggtaggctt   6360

gacccagagt tgataaatct gaaagcaaaa ctccaaggtg caaagcttgg aaatggaagc   6420

ctaacagatg tagaatccct tcagaagagt atagatgctc gtacgaaaca gttgttgcct   6480

ttatacaccc agattgcaat acggtttgct gaattgcatg atacttccct cagaatggca   6540

gctaaaggtg tgattaagaa agttgtagat tgggaagaat cacgttcttt cttctacaga   6600

aggctacgga ggaggatctc tgaagatgtt cttgcaaaag aaataagagg aatagctggt   6660

gaccacttca ctcaccaatc agcagttgag ctgatcaagg aatggtactt ggcttctcaa   6720

gccacaacag gaagcactga atgggatgat gatgatgctt ttgttgcctg gaaggagaat   6780

cctgaaaact ataagggata tatccaagag ttaagggctc aaaaggtgtc tcagtcgctc   6840

tccgatcttg cagactccag ttcagatcta gaagcattct cacagggtct ttccacatta   6900

ttagataaga tggatccctc tcagagagcc aagttcattc aggaagtcaa gaaggtcctg   6960

ggttga                                                              6966
```

```
<210> SEQ ID NO 20
<211> LENGTH: 2321
<212> TYPE: PRT
<213> ORGANISM: Setaria italica

<400> SEQUENCE: 20

Met Ser Gln Leu Gly Leu Ala Ala Ala Ala Ser Lys Ala Leu Pro Leu
1               5                   10                  15

Leu Pro Asn Arg His Arg Thr Ser Ala Gly Thr Thr Phe Pro Ser Pro
            20                  25                  30

Val Ser Ser Arg Pro Ser Asn Arg Arg Lys Ser Arg Thr Arg Ser Leu
        35                  40                  45

Arg Asp Gly Gly Asp Gly Val Ser Asp Ala Lys Lys His Asn Gln Ser
    50                  55                  60

Val Arg Gln Gly Leu Ala Gly Ile Ile Asp Leu Pro Asn Glu Ala Thr
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Val Asn Glu Ala His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190
```

```
Pro Gly Gly Thr Asn Asn Asn Asn Tyr Ala Asn Val Gln Leu Ile Val
        195                 200                 205

Glu Val Ala Glu Arg Ile Gly Val Ser Ala Val Trp Pro Gly Trp Gly
    210                 215                 220

His Ala Ser Glu Asn Pro Glu Leu Pro Asp Ala Leu Thr Ala Lys Gly
225                 230                 235                 240

Ile Val Phe Leu Gly Pro Pro Ala Ala Ser Met Asn Ala Leu Gly Asp
                245                 250                 255

Lys Val Gly Ser Ala Leu Ile Ala Gln Ala Ala Gly Val Pro Thr Leu
            260                 265                 270

Ser Trp Ser Gly Ser His Val Glu Val Pro Leu Glu Cys Cys Leu Asp
        275                 280                 285

Ala Ile Pro Glu Glu Met Tyr Arg Lys Ala Cys Val Thr Thr Thr Glu
    290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Ala Asp Ser Gln
                565                 570                 575

Phe Gly His Val Phe Ala Tyr Gly Leu Ser Arg Ser Ala Ala Ile Thr
            580                 585                 590

Asn Met Ala Leu Ala Leu Lys Glu Ile Gln Ile Arg Gly Glu Ile His
        595                 600                 605
```

-continued

```
Ser Asn Val Asp Tyr Thr Val Asp Leu Leu Asn Ala Ser Asp Phe Arg
    610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Val Thr Ala Asn Ala Ala Thr Val Ser Asp Tyr Val
            660                 665                 670

Ser Tyr Leu Thr Lys Gly Gln Ile Pro Pro Lys His Ile Ser Leu Val
        675                 680                 685

Ser Ser Thr Val Asn Leu Asn Ile Glu Gly Ser Lys Tyr Thr Val Glu
    690                 695                 700

Thr Val Arg Thr Gly His Gly Ser Tyr Arg Leu Arg Met Asn Asp Ser
705                 710                 715                 720

Ala Ile Glu Ala Asn Val Gln Ser Leu Cys Asp Gly Gly Leu Leu Met
                725                 730                 735

Gln Leu Asp Gly Asn Ser His Val Ile Tyr Ala Glu Glu Glu Ala Gly
            740                 745                 750

Gly Thr Arg Leu Leu Ile Asp Gly Lys Thr Cys Leu Leu Gln Asn Asp
        755                 760                 765

His Asp Pro Ser Lys Leu Leu Ala Glu Thr Pro Cys Lys Leu Leu Arg
    770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Val Met Met Ser Glu Gly Gln Ala Leu Gln Ala Gly
            820                 825                 830

Asp Leu Ile Ala Arg Leu Asp Leu Asp Asp Pro Ser Ala Val Lys Arg
        835                 840                 845

Ala Glu Pro Phe His Gly Ile Phe Pro Gln Met Asp Leu Pro Val Ala
    850                 855                 860

Ala Ser Ser Gln Val His Lys Arg Tyr Ala Ala Ser Leu Asn Ala Ala
865                 870                 875                 880

Arg Met Val Leu Ala Gly Tyr Glu His Asn Ile Asn Glu Val Val Gln
                885                 890                 895

Asp Leu Val Cys Cys Leu Asp Asp Pro Glu Leu Pro Phe Leu Gln Trp
            900                 905                 910

Asp Glu Leu Met Ser Val Leu Ala Thr Arg Leu Pro Arg Asn Leu Lys
        915                 920                 925

Ser Glu Leu Glu Asp Lys Tyr Met Glu Tyr Lys Leu Asn Phe Tyr His
    930                 935                 940

Gly Lys Asn Lys Asp Phe Pro Ser Lys Leu Leu Arg Asp Ile Ile Glu
945                 950                 955                 960

Ala Asn Leu Ala Tyr Gly Ser Glu Lys Glu Lys Ala Thr Asn Glu Arg
                965                 970                 975

Leu Ile Glu Pro Leu Met Ser Leu Leu Lys Ser Tyr Glu Gly Gly Arg
            980                 985                 990

Glu Ser His Ala His Phe Val Val  Lys Ser Leu Phe Lys  Glu Tyr Leu
        995                 1000                1005

Ala Val  Glu Glu Leu Phe Ser  Asp Gly Ile Gln Ser  Asp Val Ile
    1010                1015                1020

Glu Thr  Leu Arg His Gln His  Ser Lys Asp Leu Gln  Lys Val Val
```

```
    1025                1030                1035

Asp Ile  Val Leu Ser His Gln  Gly Val Arg Asn Lys  Ala Lys Leu
    1040                1045                1050

Val Thr  Ala Leu Met Glu Lys  Leu Val Tyr Pro Asn  Pro Ala Ala
    1055                1060                1065

Tyr Arg  Asp Leu Leu Val Arg  Phe Ser Ser Leu Asn  His Lys Arg
    1070                1075                1080

Tyr Tyr  Lys Leu Ala Leu Lys  Ala Ser Glu Leu Leu  Glu Gln Thr
    1085                1090                1095

Lys Leu  Ser Glu Leu Arg Ala  Ser Ile Ala Arg Ser  Leu Ser Asp
    1100                1105                1110

Leu Gly  Met His Lys Gly Glu  Met Thr Ile Glu Asp  Ser Met Glu
    1115                1120                1125

Asp Leu  Val Ser Ala Pro Leu  Pro Val Glu Asp Ala  Leu Ile Ser
    1130                1135                1140

Leu Phe  Asp Tyr Ser Asp Pro  Thr Val Gln Gln Lys  Val Ile Glu
    1145                1150                1155

Thr Tyr  Ile Ser Arg Leu Tyr  Gln Pro Leu Leu Val  Lys Asp Ser
    1160                1165                1170

Ile Gln  Val Lys Phe Lys Glu  Ser Gly Ala Phe Ala  Leu Trp Glu
    1175                1180                1185

Phe Ser  Glu Gly His Val Asp  Thr Lys Asn Gly Gln  Gly Thr Val
    1190                1195                1200

Leu Gly  Arg Thr Arg Trp Gly  Ala Met Val Ala Val  Lys Ser Val
    1205                1210                1215

Glu Ser  Ala Arg Thr Ala Ile  Val Ala Ala Leu Lys  Asp Ser Ala
    1220                1225                1230

Gln His  Ala Ser Ser Glu Gly  Asn Met Met His Ile  Ala Leu Leu
    1235                1240                1245

Ser Ala  Glu Asn Glu Asn Asn  Ile Ser Asp Asp Gln  Ala Gln His
    1250                1255                1260

Arg Met  Glu Lys Leu Asn Lys  Ile Leu Lys Asp Thr  Ser Val Ala
    1265                1270                1275

Asn Asp  Leu Arg Ala Ala Gly  Leu Lys Val Ile Ser  Cys Ile Val
    1280                1285                1290

Gln Arg  Asp Glu Ala Arg Met  Pro Met Arg His Thr  Leu Leu Trp
    1295                1300                1305

Ser Asp  Glu Lys Ser Cys Tyr  Glu Glu Glu Gln Ile  Leu Arg His
    1310                1315                1320

Val Glu  Pro Pro Leu Ser Met  Leu Leu Glu Met Asp  Lys Leu Lys
    1325                1330                1335

Val Lys  Gly Tyr Asn Glu Met  Lys Tyr Thr Pro Ser  Arg Asp Arg
    1340                1345                1350

Gln Trp  His Ile Tyr Thr Leu  Arg Asn Thr Glu Asn  Pro Lys Met
    1355                1360                1365

Leu His  Arg Val Phe Phe Arg  Thr Ile Val Arg Gln  Pro Asn Ala
    1370                1375                1380

Gly Asn  Lys Phe Ile Ser Ala  Gln Ile Gly Asp Thr  Glu Val Gly
    1385                1390                1395

Gly Pro  Glu Glu Ser Leu Ser  Phe Thr Ser Asn Ser  Ile Leu Arg
    1400                1405                1410

Ala Leu  Met Thr Ala Ile Glu  Glu Leu Glu Leu His  Ala Ile Arg
    1415                1420                1425
```

```
Thr Gly  His Ser His Met Tyr  Leu Cys Ile Leu Lys  Glu Gln Lys
    1430                 1435                 1440

Leu Leu  Asp Leu Ile Pro Phe  Ser Gly Ser Thr Ile  Val Asp Val
    1445                 1450                 1455

Gly Gln  Asp Glu Ala Thr Ala  Cys Ser Leu Leu Lys  Ser Met Ala
    1460                 1465                 1470

Leu Lys  Ile His Glu Leu Val  Gly Ala Gln Met His  His Leu Ser
    1475                 1480                 1485

Val Cys  Gln Trp Glu Val Lys  Leu Lys Leu Tyr Cys  Asp Gly Pro
    1490                 1495                 1500

Ala Ser  Gly Thr Trp Arg Val  Val Thr Thr Asn Val  Thr Ser His
    1505                 1510                 1515

Thr Cys  Thr Ile Asp Ile Tyr  Arg Glu Val Glu Asp  Thr Glu Ser
    1520                 1525                 1530

Gln Lys  Leu Val Tyr His Ser  Ala Ser Pro Ser Ala  Ser Pro Leu
    1535                 1540                 1545

His Gly  Val Ala Leu Asp Asn  Pro Tyr Gln Pro Leu  Ser Val Ile
    1550                 1555                 1560

Asp Leu  Lys Arg Cys Ser Ala  Arg Asn Asn Arg Thr  Thr Tyr Cys
    1565                 1570                 1575

Tyr Asp  Phe Pro Leu Ala Phe  Glu Thr Ala Leu Gln  Lys Ser Trp
    1580                 1585                 1590

Gln Ser  Asn Gly Ser Ser Val  Ser Glu Gly Ser Glu  Asn Ser Arg
    1595                 1600                 1605

Ser Tyr  Val Lys Ala Thr Glu  Leu Val Phe Ala Glu  Lys His Gly
    1610                 1615                 1620

Ser Trp  Gly Thr Pro Ile Ile  Ser Met Glu Arg Pro  Ala Gly Leu
    1625                 1630                 1635

Asn Asp  Ile Gly Met Val Ala  Trp Ile Leu Glu Met  Ser Thr Pro
    1640                 1645                 1650

Glu Phe  Pro Asn Gly Arg Gln  Ile Ile Val Ile Ala  Asn Asp Ile
    1655                 1660                 1665

Thr Phe  Arg Ala Gly Ser Phe  Gly Pro Arg Glu Asp  Ala Phe Phe
    1670                 1675                 1680

Glu Ala  Val Thr Asn Leu Ala  Cys Glu Arg Lys Leu  Pro Leu Ile
    1685                 1690                 1695

Tyr Leu  Ala Ala Asn Ser Gly  Ala Arg Ile Gly Ile  Ala Asp Glu
    1700                 1705                 1710

Val Lys  Ser Cys Phe Arg Val  Gly Trp Ser Asp Glu  Gly Ser Pro
    1715                 1720                 1725

Glu Arg  Gly Phe Gln Tyr Ile  Tyr Leu Thr Asp Glu  Asp Tyr Ala
    1730                 1735                 1740

Arg Ile  Ser Leu Ser Val Ile  Ala His Lys Leu Gln  Leu Asp Asn
    1745                 1750                 1755

Gly Glu  Ile Arg Trp Ile Ile  Asp Ser Val Val Gly  Lys Glu Asp
    1760                 1765                 1770

Gly Leu  Gly Val Glu Asn Leu  His Gly Ser Ala Ala  Ile Ala Ser
    1775                 1780                 1785

Ala Tyr  Ser Arg Ala Tyr Glu  Glu Thr Phe Thr Leu  Thr Phe Val
    1790                 1795                 1800

Thr Gly  Arg Thr Val Gly Ile  Gly Ala Tyr Leu Ala  Arg Leu Gly
    1805                 1810                 1815
```

```
Ile Arg  Cys Ile Gln Arg Leu  Asp Gln Pro Ile Ile  Leu Thr Gly
    1820                 1825                 1830

Phe Ser  Ala Leu Asn Lys Leu  Leu Gly Arg Glu Val  Tyr Ser Ser
    1835                 1840                 1845

His Met  Gln Leu Gly Gly Pro  Lys Ile Met Ala Thr  Asn Gly Val
    1850                 1855                 1860

Val His  Leu Thr Val Ser Asp  Asp Leu Glu Gly Val  Ser Asn Ile
    1865                 1870                 1875

Leu Arg  Trp Leu Ser Tyr Val  Pro Ala Asn Ile Gly  Gly Pro Leu
    1880                 1885                 1890

Pro Ile  Thr Lys Pro Leu Asp  Pro Pro Asp Arg Pro  Val Ala Tyr
    1895                 1900                 1905

Ile Pro  Glu Asn Thr Cys Asp  Pro Arg Ala Ala Ile  Arg Gly Val
    1910                 1915                 1920

Asp Asp  Ser Gln Gly Lys Trp  Leu Gly Gly Met Phe  Asp Lys Asp
    1925                 1930                 1935

Ser Phe  Val Glu Thr Phe Glu  Gly Trp Ala Lys Thr  Val Val Thr
    1940                 1945                 1950

Gly Arg  Ala Lys Leu Gly Gly  Ile Pro Val Gly Val  Ile Ala Val
    1955                 1960                 1965

Glu Thr  Gln Thr Met Met Gln  Leu Ile Pro Ala Asp  Pro Gly Gln
    1970                 1975                 1980

Leu Asp  Ser His Glu Arg Ser  Val Pro Arg Ala Gly  Gln Val Trp
    1985                 1990                 1995

Phe Pro  Asp Ser Ala Thr Lys  Thr Ala Gln Ala Leu  Leu Asp Phe
    2000                 2005                 2010

Asn Arg  Glu Gly Leu Pro Leu  Phe Ile Leu Ala Asn  Trp Arg Gly
    2015                 2020                 2025

Phe Ser  Gly Gly Gln Arg Asp  Leu Phe Glu Gly Ile  Leu Gln Ala
    2030                 2035                 2040

Gly Ser  Thr Ile Val Glu Asn  Leu Arg Thr Tyr Asn  Gln Pro Ala
    2045                 2050                 2055

Phe Val  Tyr Ile Pro Met Ala  Gly Glu Leu Arg Gly  Gly Ala Trp
    2060                 2065                 2070

Val Val  Val Asp Ser Lys Ile  Asn Pro Asp Arg Ile  Glu Cys Tyr
    2075                 2080                 2085

Ala Glu  Arg Thr Ala Lys Gly  Asn Val Leu Glu Pro  Gln Gly Leu
    2090                 2095                 2100

Ile Glu  Ile Lys Phe Arg Ser  Glu Glu Leu Gln Asp  Cys Met Gly
    2105                 2110                 2115

Arg Leu  Asp Pro Glu Leu Ile  Asn Leu Lys Ala Lys  Leu Gln Gly
    2120                 2125                 2130

Ala Lys  Leu Gly Asn Gly Ser  Leu Thr Asp Val Glu  Ser Leu Gln
    2135                 2140                 2145

Lys Ser  Ile Asp Ala Arg Thr  Lys Gln Leu Leu Pro  Leu Tyr Thr
    2150                 2155                 2160

Gln Ile  Ala Ile Arg Phe Ala  Glu Leu His Asp Thr  Ser Leu Arg
    2165                 2170                 2175

Met Ala  Ala Lys Gly Val Ile  Lys Lys Val Val Asp  Trp Glu Glu
    2180                 2185                 2190

Ser Arg  Ser Phe Phe Tyr Arg  Arg Leu Arg Arg Arg  Ile Ser Glu
    2195                 2200                 2205

Asp Val  Leu Ala Lys Glu Ile  Arg Gly Ile Ala Gly  Asp His Phe
```

2210 2215 2220

Thr His Gln Ser Ala Val Glu Leu Ile Lys Glu Trp Tyr Leu Ala
2225 2230 2235

Ser Gln Ala Thr Thr Gly Ser Thr Glu Trp Asp Asp Asp Asp Ala
2240 2245 2250

Phe Val Ala Trp Lys Glu Asn Pro Glu Asn Tyr Lys Gly Tyr Ile
2255 2260 2265

Gln Glu Leu Arg Ala Gln Lys Val Ser Gln Ser Leu Ser Asp Leu
2270 2275 2280

Ala Asp Ser Ser Ser Asp Leu Glu Ala Phe Ser Gln Gly Leu Ser
2285 2290 2295

Thr Leu Leu Asp Lys Met Asp Pro Ser Gln Arg Ala Lys Phe Ile
2300 2305 2310

Gln Glu Val Lys Lys Val Leu Gly
2315 2320

<210> SEQ ID NO 21
<211> LENGTH: 6966
<212> TYPE: DNA
<213> ORGANISM: Setaria italica

<400> SEQUENCE: 21
atgtcgcaac ttggattagc tgcagctgcc tcaaaggcgc tgccactact tcctaatcgc 60
catagaactt cagctggaac tacattccca tcacctgtat catcgcggcc ctcaaaccga 120
aggaaaagcc gcactcgttc acttcgtgat ggaggagatg ggtatcaga tgccaaaaag 180 cacaaccagt ctgtccgtca aggtcttgct ggcatcatcg acctcccaaa tgaggcaaca 240
tcggaagtgg atatttctca tggatccgag gatcccaggg ggccaaccga ttcatatcaa 300
atgaatggga ttgtaaatga agcacataat ggcagacatg cctcagtgtc caaggttgtt 360
gaattttgtg cggcgctagg tggcaaaaca ccaattcaca gtatactagt ggccaacaat 420
ggaatggcag cagcaaagtt catgaggagt gtccggacat gggctaatga tacttttgga 480
tcggagaagg cgattcagct catagctatg gcaactccag aagacatgag gataaatgca 540
gaacacatta gaattgctga tcaatttgta gaggtgcctg gtggaacaaa caataacaac 600
tatgcaaatg ttcaactcat agtggaggta gcagaaagaa taggtgtttc tgctgtttgg 660
cctggttggg gtcatgcttc tgagaatcct gaacttccag atgcattgac cgcaaaagga 720
attgttttcc ttgggccacc tgcggcatca atgaatgcat tgggagataa ggtcggttca 780
gctctcattg ctcaagcagc tggggtcccg accctttcgt ggagtggatc acatgttgaa 840
gttccattag agtgctgctt agatgcgata cctgaggaaa tgtatagaaa agcttgtgtt 900
actaccacag aagaagctgt tgcgagttgt caggtggttg gttatcctgc catgattaag 960
gcatcctggg gaggtggtgg taaaggaata agaaaggttc ataatgacga tgaggttaga 1020
gcactgttta agcaagtaca aggtgaagtc cctggctccc caatatttat catgaggctt 1080
gcatcccaga gtcgtcatct tgaagttcag ttgctttgtg atcaatatgg caatgtggca 1140
gcacttcaca gtcgtgattg cagtgtgcaa cggcgacacc aaaagattat tgaggaaggc 1200
ccagttactg ttgctcctcg tgagacagtt aaagcgcttg agcaggcagc aaggaggctt 1260
gctaaggctg tgggttatgt tggtgctgct actgttgaat acctttacag catggagact 1320
ggggaatact attttctgga gcttaatccc agattacagg tcgagcatcc agtcactgag 1380
tggattgctg aagtaaatct tcctgcagct caagttgcag ttggaatggg catacctctt 1440

-continued

```
tggcagattc cagaaatcag acgtttctat ggaatggact atggaggagg atatgacatt   1500
tggaggaaaa cagcagctct tgccacacca tttaattttg atgaagtaga ttctcaatgg   1560
ccaaagggcc attgtgtagc agttagaatt actagcgagg atccagatga tggtttcaaa   1620
cctactggtg ggaaagtgaa ggagataagt tttaaaagca agcctaatgt ttgggcctac   1680
ttctcagtaa agtctggtgg aggcattcat gaatttgctg attctcagtt tgggcatgtt   1740
tttgcatatg ggctctctag atcagcagca ataacgaaca tggctcttgc attaaaagag   1800
attcaaattc gtggagaaat tcattcaaat gttgattaca cagttgatct cttaaatgct   1860
tcagacttca gagaaaataa gattcatact ggctggcttg ataccagaat agctatgcgt   1920
gttcaagctg agaggccccc atggtatatt tcagtggttg gaggagctct atataaaaca   1980
gtaactgcca atgcagccac tgtttctgat tatgtcagtt atctcaccaa gggccagatt   2040
ccaccaaagc atatatccct tgtcagttca acagttaatc tgaatatcga agggagcaaa   2100
tacacagttg aaactgtaag gactggacat ggtagctaca gattacgaat gaatgattca   2160
gcaattgaag cgaatgtaca atctttatgt gatggaggcc tcttaatgca gttggatgga   2220
aatagccatg taatttacgc ggaagaagaa gctggtggta cacgacttct gattgatgga   2280
aagacatgct tgttacagaa tgatcatgat ccatcaaagt tattagctga gacaccctgc   2340
aaacttcttc ggttcttggt tgctgatggt gctcatgttg atgctgatgt accatatgcg   2400
gaagttgagg ttatgaaaat gtgcatgcct ctcttgtcgc ctgcttctgg tgtcattcat   2460
gttatgatgt ctgagggcca ggcattgcag gctggtgatc ttatagcaag gctggatctt   2520
gatgaccctt ctgctgtgaa aagagctgaa ccatttcatg gaatatttcc acaaatggac   2580
cttcctgttg ctgcctctag ccaagtacac aaaagatatg ctgcaagttt gaatgctgct   2640
cgaatggtcc ttgcaggata cgagcataat atcaatgaag ttgtacaaga tttggtatgc   2700
tgcctggatg atcccgagct tcccttccta cagtgggatg aacttatgtc agttctagca   2760
actaggcttc caagaaatct taagagtgag ttagaggata aatacatgga atacaagttg   2820
aacttttacc atgggaaaaa caaggacttc ccgtccaagc tgctgagaga catcattgag   2880
gcaaatcttg catatggttc agagaaggaa aaagctacga atgagaggct tattgagcct   2940
cttatgagcc tacttaagtc atatgagggt gggagagaaa gccatgctca ttttgttgtc   3000
aagtcccttt tcaaggagta ccttgctgtg gaagaacttt tcagtgatgg gattcagtct   3060
gatgtgattg aaaccctgcg tcatcagcac agtaaagact tgcagaaggt tgtagacatt   3120
gtgttgtctc accagggtgt gaggaacaaa gctaagcttg taacagcact tatggaaaag   3180
ctggtttatc caaatcctgc tgcttacagg gatctgttgg ttcgcttttc ttcactcaat   3240
cataaaagat attataagtt ggcccttaaa gcaagcgaac ttcttgaaca aactaaacta   3300
agtgaactcc gtgcaagcat cgcaagaagc ctttctgatc tggggatgca taagggagaa   3360
atgactattg aagatagcat ggaagattta gtctctgccc cattacctgt cgaagatgca   3420
cttatttctt tgtttgatta cagtgatcca actgttcagc agaaagtgat cgagacatac   3480
atatctcgat tgtatcagcc tcttcttgtg aaagatagca tccaagtgaa atttaaggaa   3540
tctggtgcct ttgctttatg ggaattttct gaagggcatg ttgatactaa aaatggacaa   3600
gggaccgttc ttggtcgaac aagatggggt gccatggtag ctgtcaaatc agttgaatct   3660
gcacgaacag ccattgtagc tgcattaaag gattcggcac agcatgccag ctctgagggc   3720
aacatgatgc acattgcctt attgagtgct gaaaatgaaa ataatatcag tgatgatcaa   3780
gctcaacata ggatggaaaa acttaacaag atactcaagg atactagtgt cgcaaatgat   3840
```

cttcgagctg ctggtttgaa ggttataagt tgcattgttc aaagagatga agcacgcatg 3900
ccaatgcgcc acacattact ctggtcagat gaaaagagtt gttatgagga agagcagatt 3960
cttcggcatg tggagcctcc cctctccatg cttcttgaaa tggataagtt gaaagtgaaa 4020
ggatacaatg aaatgaagta tactccatca cgtgatcgtc aatggcatat ctacacacta 4080
agaaatactg aaaaccccaa aatgttgcat agggtatttt tccgaactat tgtcaggcaa 4140
cccaatgcag gcaacaagtt tatatcagcc caaattggcg acactgaagt aggaggtcct 4200
gaggaatctt tgtcatttac atctaatagc attttaagag ccttgatgac tgctattgaa 4260
gaattagagc ttcatgcaat taggactggt cattctcaca tgtatttgtg catattgaaa 4320
gaacaaaagc ttcttgatct cattccgttt tcagggagca caatcgtcga tgttggccaa 4380
gacgaagcta ctgcttgttc acttttaaaa tcaatggctt tgaagataca cgaacttgtt 4440
ggtgcacaga tgcatcatct ttctgtatgc cagtgggagg tgaaactcaa gttgtactgc 4500
gatgggcctg ccagtggcac ctggagagtt gtaactacaa atgttactag tcacacttgc 4560
accgttgata tctaccggga agtggaagat actgaatcgc agaagttagt ataccattca 4620
gcttctccgt cagctagtcc tttgcatggt gtggccctgg ataatccgta tcaacctttg 4680
agtgtcattg atctaaaacg ctgctctgct aggaacaaca gaactacata ttgctatgat 4740
tttccactgg catttgaaac tgccctgcag aagtcatggc agtccaatgg ctccagtgtt 4800
tctgaaggca gtgaaaatag taggtcttat gtgaaagcaa cagagctggt gtttgctgaa 4860
aaacatgggt cctggggcac tcctataatt tccatggagc gtcccgctgg gctcaatgac 4920
attggcatgg tagcttggat cttagagatg tccactcctg aatttcccaa tggcaggcag 4980
attattgtca tagcaaatga tattactttc agagctggat catttggccc aagggaagat 5040
gcgtttttttg aagctgtcac gaacctggcc tgcgagagga agcttcctct tatatacttg 5100
gcagcaaact ccggtgctag gattggcata gccgatgaag tgaaatcttg cttccgtgtt 5160
gggtggtccg atgaaggcag ccctgaacgg ggttttcagt acatttatct gactgacgaa 5220
gactatgccc gtattagctt gtctgttata gcacacaagc tgcagctgga taatggtgaa 5280
attaggtgga ttattgactc tgttgtgggc aaggaggatg ggcttggtgt tgagaatata 5340
catggaagtg ctgctattgc cagtgcttat tctagggcat atgaggagac atttacactt 5400
acatttgtga ctgggcggac tgttggaata ggagcatatc ttgctcggct cggtatacgg 5460
tgcatacagc gtcttgacca gcctattatt ttaactgggt tttctgccct gaacaagctt 5520
cttgggcggg aagtgtacag ctcccacatg cagttgggtg gtcctaagat catggcgacc 5580
aatggtgttg tccacttgac tgtttcagat gaccttgaag gtgtttccaa tatattgagg 5640
tggctcagct atgttcctgc caacattggt ggacctcttc ctattacaaa acctttggac 5700
ccaccagaca gacctgttgc atacatccct gagaacacat gtgatccgcg cgcagccatt 5760
cgtggtgtag atgacagcca agggaaatgg ttgggtggta tgtttgacaa agacagcttt 5820
gtcgagacat ttgaaggatg ggcgaaaaca gtggttacgg gcagagcaaa gcttggagga 5880
attcctgttg gtgtcatagc tgtggagaca caaaccatga tgcagcttat ccctgctgat 5940
ccaggccagc ttgattccca tgagcgatct gttcctcggg ctggacaagt gtggttccca 6000
gattctgcaa ccaagacagc tcaggcattg ttggacttca accgtgaagg attgccgctg 6060
ttcatccttg ctaactggag aggattctct ggtggacaaa gagatctgtt tgaaggaatt 6120
cttcaggctg ggtcaacaat tgttgagaac cttaggacat acaatcagcc tgcttttgtc 6180

-continued

```
tacattccta tggctggaga gctgcgtgga ggagcttggg ttgtggttga tagcaaaata   6240

aatccagacc gaattgagtg ttatgctgag aggactgcta aaggcaatgt tctggaacct   6300

caagggttaa ttgaaatcaa attcagatca gaggagctcc aagactgtat gggtaggctt   6360

gacccagagt tgataaatct gaaagcaaaa ctccaaggtg caaagcttgg aaatggaagc   6420

ctaacagatg tagaatccct tcagaagagt atagatgctc gtacgaaaca gttgttgcct   6480

ttatacaccc agattgcaat acggtttgct gaattgcatg atacttccct cagaatggca   6540

gctaaaggtg tgattaagaa agttgtagat tgggaagaat tacgttcttt cttctacaga   6600

aggctacgga ggaggatctc tgaagatgtt cttgcaaaag aaataagagg aatagctggt   6660

gaccacttca ctcaccaatc agcagttgag ctgatcaagg aatggtactt ggcttctcaa   6720

gccacaacag gaagcactga atgggatgat gatgatgctt ttgttgcctg gaaggagaat   6780

cctgaaaact ataagggata tatccaagag ttaagggctc aaaaggtgtc tcagtcgctc   6840

tccgatcttg cagactccag ttcagatcta gaagcattct cacagggtct ttccacatta   6900

ttagataaga tggatccctc tcagagagcc aagttcattc aggaagtcaa gaaggtcctg   6960

ggttga                                                              6966
```

<210> SEQ ID NO 22
<211> LENGTH: 2321
<212> TYPE: PRT
<213> ORGANISM: Setaria italica

<400> SEQUENCE: 22

```
Met Ser Gln Leu Gly Leu Ala Ala Ala Ala Ser Lys Ala Leu Pro Leu
1               5                   10                  15

Leu Pro Asn Arg His Arg Thr Ser Ala Gly Thr Thr Phe Pro Ser Pro
            20                  25                  30

Val Ser Ser Arg Pro Ser Asn Arg Arg Lys Ser Arg Thr Arg Ser Leu
        35                  40                  45

Arg Asp Gly Gly Asp Gly Val Ser Asp Ala Lys Lys His Asn Gln Ser
    50                  55                  60

Val Arg Gln Gly Leu Ala Gly Ile Ile Asp Leu Pro Asn Glu Ala Thr
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Val Asn Glu Ala His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205

Glu Val Ala Glu Arg Ile Gly Val Ser Ala Val Trp Pro Gly Trp Gly
    210                 215                 220

His Ala Ser Glu Asn Pro Glu Leu Pro Asp Ala Leu Thr Ala Lys Gly
```

-continued

```
225                 230                 235                 240

Ile Val Phe Leu Gly Pro Pro Ala Ala Ser Met Asn Ala Leu Gly Asp
                245                 250                 255

Lys Val Gly Ser Ala Leu Ile Ala Gln Ala Ala Gly Val Pro Thr Leu
            260                 265                 270

Ser Trp Ser Gly Ser His Val Glu Val Pro Leu Glu Cys Cys Leu Asp
        275                 280                 285

Ala Ile Pro Glu Glu Met Tyr Arg Lys Ala Cys Val Thr Thr Thr Glu
    290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Ala Asp Ser Gln
                565                 570                 575

Phe Gly His Val Phe Ala Tyr Gly Leu Ser Arg Ser Ala Ala Ile Thr
            580                 585                 590

Asn Met Ala Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Arg
    610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655
```

-continued

```
Leu Tyr Lys Thr Val Thr Ala Asn Ala Ala Thr Val Ser Asp Tyr Val
            660                 665                 670

Ser Tyr Leu Thr Lys Gly Gln Ile Pro Pro Lys His Ile Ser Leu Val
        675                 680                 685

Ser Ser Thr Val Asn Leu Asn Ile Glu Gly Ser Lys Tyr Thr Val Glu
    690                 695                 700

Thr Val Arg Thr Gly His Gly Ser Tyr Arg Leu Arg Met Asn Asp Ser
705                 710                 715                 720

Ala Ile Glu Ala Asn Val Gln Ser Leu Cys Asp Gly Gly Leu Leu Met
                725                 730                 735

Gln Leu Asp Gly Asn Ser His Val Ile Tyr Ala Glu Glu Glu Ala Gly
            740                 745                 750

Gly Thr Arg Leu Leu Ile Asp Gly Lys Thr Cys Leu Leu Gln Asn Asp
        755                 760                 765

His Asp Pro Ser Lys Leu Leu Ala Glu Thr Pro Cys Lys Leu Leu Arg
    770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Val Met Met Ser Glu Gly Gln Ala Leu Gln Ala Gly
            820                 825                 830

Asp Leu Ile Ala Arg Leu Asp Leu Asp Asp Pro Ser Ala Val Lys Arg
        835                 840                 845

Ala Glu Pro Phe His Gly Ile Phe Pro Gln Met Asp Leu Pro Val Ala
    850                 855                 860

Ala Ser Ser Gln Val His Lys Arg Tyr Ala Ala Ser Leu Asn Ala Ala
865                 870                 875                 880

Arg Met Val Leu Ala Gly Tyr Glu His Asn Ile Asn Glu Val Val Gln
                885                 890                 895

Asp Leu Val Cys Cys Leu Asp Asp Pro Glu Leu Pro Phe Leu Gln Trp
            900                 905                 910

Asp Glu Leu Met Ser Val Leu Ala Thr Arg Leu Pro Arg Asn Leu Lys
        915                 920                 925

Ser Glu Leu Glu Asp Lys Tyr Met Glu Tyr Lys Leu Asn Phe Tyr His
    930                 935                 940

Gly Lys Asn Lys Asp Phe Pro Ser Lys Leu Leu Arg Asp Ile Ile Glu
945                 950                 955                 960

Ala Asn Leu Ala Tyr Gly Ser Glu Lys Glu Lys Ala Thr Asn Glu Arg
                965                 970                 975

Leu Ile Glu Pro Leu Met Ser Leu Leu Lys Ser Tyr Glu Gly Gly Arg
            980                 985                 990

Glu Ser His Ala His Phe Val Val  Lys Ser Leu Phe Lys  Glu Tyr Leu
        995                 1000                1005

Ala Val  Glu Glu Leu Phe Ser  Asp Gly Ile Gln Ser  Asp Val Ile
    1010                1015                1020

Glu Thr  Leu Arg His Gln His  Ser Lys Asp Leu Gln  Lys Val Val
    1025                1030                1035

Asp Ile  Val Leu Ser His Gln  Gly Val Arg Asn Lys  Ala Lys Leu
    1040                1045                1050

Val Thr  Ala Leu Met Glu Lys  Leu Val Tyr Pro Asn  Pro Ala Ala
    1055                1060                1065
```

```
Tyr Arg  Asp Leu Leu Val Arg  Phe Ser Ser Leu Asn  His Lys Arg
    1070                 1075                 1080

Tyr Tyr  Lys Leu Ala Leu Lys  Ala Ser Glu Leu Leu  Glu Gln Thr
    1085                 1090                 1095

Lys Leu  Ser Glu Leu Arg Ala  Ser Ile Ala Arg Ser  Leu Ser Asp
    1100                 1105                 1110

Leu Gly  Met His Lys Gly Glu  Met Thr Ile Glu Asp  Ser Met Glu
    1115                 1120                 1125

Asp Leu  Val Ser Ala Pro Leu  Pro Val Glu Asp Ala  Leu Ile Ser
    1130                 1135                 1140

Leu Phe  Asp Tyr Ser Asp Pro  Thr Val Gln Gln Lys  Val Ile Glu
    1145                 1150                 1155

Thr Tyr  Ile Ser Arg Leu Tyr  Gln Pro Leu Leu Val  Lys Asp Ser
    1160                 1165                 1170

Ile Gln  Val Lys Phe Lys Glu  Ser Gly Ala Phe Ala  Leu Trp Glu
    1175                 1180                 1185

Phe Ser  Glu Gly His Val Asp  Thr Lys Asn Gly Gln  Gly Thr Val
    1190                 1195                 1200

Leu Gly  Arg Thr Arg Trp Gly  Ala Met Val Ala Val  Lys Ser Val
    1205                 1210                 1215

Glu Ser  Ala Arg Thr Ala Ile  Val Ala Ala Leu Lys  Asp Ser Ala
    1220                 1225                 1230

Gln His  Ala Ser Ser Glu Gly  Asn Met Met His Ile  Ala Leu Leu
    1235                 1240                 1245

Ser Ala  Glu Asn Glu Asn Asn  Ile Ser Asp Asp Gln  Ala Gln His
    1250                 1255                 1260

Arg Met  Glu Lys Leu Asn Lys  Ile Leu Lys Asp Thr  Ser Val Ala
    1265                 1270                 1275

Asn Asp  Leu Arg Ala Ala Gly  Leu Lys Val Ile Ser  Cys Ile Val
    1280                 1285                 1290

Gln Arg  Asp Glu Ala Arg Met  Pro Met Arg His Thr  Leu Leu Trp
    1295                 1300                 1305

Ser Asp  Glu Lys Ser Cys Tyr  Glu Glu Glu Gln Ile  Leu Arg His
    1310                 1315                 1320

Val Glu  Pro Pro Leu Ser Met  Leu Leu Glu Met Asp  Lys Leu Lys
    1325                 1330                 1335

Val Lys  Gly Tyr Asn Glu Met  Lys Tyr Thr Pro Ser  Arg Asp Arg
    1340                 1345                 1350

Gln Trp  His Ile Tyr Thr Leu  Arg Asn Thr Glu Asn  Pro Lys Met
    1355                 1360                 1365

Leu His  Arg Val Phe Phe Arg  Thr Ile Val Arg Gln  Pro Asn Ala
    1370                 1375                 1380

Gly Asn  Lys Phe Ile Ser Ala  Gln Ile Gly Asp Thr  Glu Val Gly
    1385                 1390                 1395

Gly Pro  Glu Glu Ser Leu Ser  Phe Thr Ser Asn Ser  Ile Leu Arg
    1400                 1405                 1410

Ala Leu  Met Thr Ala Ile Glu  Glu Leu Glu Leu His  Ala Ile Arg
    1415                 1420                 1425

Thr Gly  His Ser His Met Tyr  Leu Cys Ile Leu Lys  Glu Gln Lys
    1430                 1435                 1440

Leu Leu  Asp Leu Ile Pro Phe  Ser Gly Ser Thr Ile  Val Asp Val
    1445                 1450                 1455

Gly Gln  Asp Glu Ala Thr Ala  Cys Ser Leu Leu Lys  Ser Met Ala
```

-continued

```
    1460                1465                1470

Leu Lys  Ile His Glu Leu Val  Gly Ala Gln Met His  His Leu Ser
    1475                1480                1485

Val Cys  Gln Trp Glu Val Lys  Leu Lys Leu Tyr Cys  Asp Gly Pro
    1490                1495                1500

Ala Ser  Gly Thr Trp Arg Val  Val Thr Thr Asn Val  Thr Ser His
    1505                1510                1515

Thr Cys  Thr Val Asp Ile Tyr  Arg Glu Val Glu Asp  Thr Glu Ser
    1520                1525                1530

Gln Lys  Leu Val Tyr His Ser  Ala Ser Pro Ser Ala  Ser Pro Leu
    1535                1540                1545

His Gly  Val Ala Leu Asp Asn  Pro Tyr Gln Pro Leu  Ser Val Ile
    1550                1555                1560

Asp Leu  Lys Arg Cys Ser Ala  Arg Asn Asn Arg Thr  Thr Tyr Cys
    1565                1570                1575

Tyr Asp  Phe Pro Leu Ala Phe  Glu Thr Ala Leu Gln  Lys Ser Trp
    1580                1585                1590

Gln Ser  Asn Gly Ser Ser Val  Ser Glu Gly Ser Glu  Asn Ser Arg
    1595                1600                1605

Ser Tyr  Val Lys Ala Thr Glu  Leu Val Phe Ala Glu  Lys His Gly
    1610                1615                1620

Ser Trp  Gly Thr Pro Ile Ile  Ser Met Glu Arg Pro  Ala Gly Leu
    1625                1630                1635

Asn Asp  Ile Gly Met Val Ala  Trp Ile Leu Glu Met  Ser Thr Pro
    1640                1645                1650

Glu Phe  Pro Asn Gly Arg Gln  Ile Ile Val Ile Ala  Asn Asp Ile
    1655                1660                1665

Thr Phe  Arg Ala Gly Ser Phe  Gly Pro Arg Glu Asp  Ala Phe Phe
    1670                1675                1680

Glu Ala  Val Thr Asn Leu Ala  Cys Glu Arg Lys Leu  Pro Leu Ile
    1685                1690                1695

Tyr Leu  Ala Ala Asn Ser Gly  Ala Arg Ile Gly Ile  Ala Asp Glu
    1700                1705                1710

Val Lys  Ser Cys Phe Arg Val  Gly Trp Ser Asp Glu  Gly Ser Pro
    1715                1720                1725

Glu Arg  Gly Phe Gln Tyr Ile  Tyr Leu Thr Asp Glu  Asp Tyr Ala
    1730                1735                1740

Arg Ile  Ser Leu Ser Val Ile  Ala His Lys Leu Gln  Leu Asp Asn
    1745                1750                1755

Gly Glu  Ile Arg Trp Ile Ile  Asp Ser Val Val Gly  Lys Glu Asp
    1760                1765                1770

Gly Leu  Gly Val Glu Asn Ile  His Gly Ser Ala Ala  Ile Ala Ser
    1775                1780                1785

Ala Tyr  Ser Arg Ala Tyr Glu  Glu Thr Phe Thr Leu  Thr Phe Val
    1790                1795                1800

Thr Gly  Arg Thr Val Gly Ile  Gly Ala Tyr Leu Ala  Arg Leu Gly
    1805                1810                1815

Ile Arg  Cys Ile Gln Arg Leu  Asp Gln Pro Ile Ile  Leu Thr Gly
    1820                1825                1830

Phe Ser  Ala Leu Asn Lys Leu  Leu Gly Arg Glu Val  Tyr Ser Ser
    1835                1840                1845

His Met  Gln Leu Gly Gly Pro  Lys Ile Met Ala Thr  Asn Gly Val
    1850                1855                1860
```

Val His Leu Thr Val Ser Asp Asp Leu Glu Gly Val Ser Asn Ile
1865 1870 1875

Leu Arg Trp Leu Ser Tyr Val Pro Ala Asn Ile Gly Gly Pro Leu
1880 1885 1890

Pro Ile Thr Lys Pro Leu Asp Pro Pro Asp Arg Pro Val Ala Tyr
1895 1900 1905

Ile Pro Glu Asn Thr Cys Asp Pro Arg Ala Ala Ile Arg Gly Val
1910 1915 1920

Asp Asp Ser Gln Gly Lys Trp Leu Gly Gly Met Phe Asp Lys Asp
1925 1930 1935

Ser Phe Val Glu Thr Phe Glu Gly Trp Ala Lys Thr Val Val Thr
1940 1945 1950

Gly Arg Ala Lys Leu Gly Gly Ile Pro Val Gly Val Ile Ala Val
1955 1960 1965

Glu Thr Gln Thr Met Met Gln Leu Ile Pro Ala Asp Pro Gly Gln
1970 1975 1980

Leu Asp Ser His Glu Arg Ser Val Pro Arg Ala Gly Gln Val Trp
1985 1990 1995

Phe Pro Asp Ser Ala Thr Lys Thr Ala Gln Ala Leu Leu Asp Phe
2000 2005 2010

Asn Arg Glu Gly Leu Pro Leu Phe Ile Leu Ala Asn Trp Arg Gly
2015 2020 2025

Phe Ser Gly Gly Gln Arg Asp Leu Phe Glu Gly Ile Leu Gln Ala
2030 2035 2040

Gly Ser Thr Ile Val Glu Asn Leu Arg Thr Tyr Asn Gln Pro Ala
2045 2050 2055

Phe Val Tyr Ile Pro Met Ala Gly Glu Leu Arg Gly Gly Ala Trp
2060 2065 2070

Val Val Val Asp Ser Lys Ile Asn Pro Asp Arg Ile Glu Cys Tyr
2075 2080 2085

Ala Glu Arg Thr Ala Lys Gly Asn Val Leu Glu Pro Gln Gly Leu
2090 2095 2100

Ile Glu Ile Lys Phe Arg Ser Glu Glu Leu Gln Asp Cys Met Gly
2105 2110 2115

Arg Leu Asp Pro Glu Leu Ile Asn Leu Lys Ala Lys Leu Gln Gly
2120 2125 2130

Ala Lys Leu Gly Asn Gly Ser Leu Thr Asp Val Glu Ser Leu Gln
2135 2140 2145

Lys Ser Ile Asp Ala Arg Thr Lys Gln Leu Leu Pro Leu Tyr Thr
2150 2155 2160

Gln Ile Ala Ile Arg Phe Ala Glu Leu His Asp Thr Ser Leu Arg
2165 2170 2175

Met Ala Ala Lys Gly Val Ile Lys Lys Val Val Asp Trp Glu Glu
2180 2185 2190

Leu Arg Ser Phe Phe Tyr Arg Arg Leu Arg Arg Arg Ile Ser Glu
2195 2200 2205

Asp Val Leu Ala Lys Glu Ile Arg Gly Ile Ala Gly Asp His Phe
2210 2215 2220

Thr His Gln Ser Ala Val Glu Leu Ile Lys Glu Trp Tyr Leu Ala
2225 2230 2235

Ser Gln Ala Thr Thr Gly Ser Thr Glu Trp Asp Asp Asp Asp Ala
2240 2245 2250

-continued

```
Phe Val  Ala Trp Lys Glu Asn  Pro Glu Asn Tyr Lys  Gly Tyr Ile
    2255                 2260                 2265

Gln Glu  Leu Arg Ala Gln Lys  Val Ser Gln Ser Leu  Ser Asp Leu
    2270                 2275                 2280

Ala Asp  Ser Ser Ser Asp Leu  Glu Ala Phe Ser Gln  Gly Leu Ser
    2285                 2290                 2295

Thr Leu  Leu Asp Lys Met Asp  Pro Ser Gln Arg Ala  Lys Phe Ile
    2300                 2305                 2310

Gln Glu  Val Lys Lys Val Leu  Gly
    2315                 2320
```

<210> SEQ ID NO 23
<211> LENGTH: 6963
<212> TYPE: DNA
<213> ORGANISM: Alopecurus myosuroides

<400> SEQUENCE: 23

```
atgggatcca cacatctgcc cattgtcggg tttaatgcat ccacaacacc atcgctatcc     60

actcttcgcc agataaactc agctgctgct gcattccaat cttcgtcccc ttcaaggtca    120

tccaagaaga aaagccgacg tgttaagtca ataagggatg atggcgatgg aagcgtgcca    180

gaccctgcag gccatggcca gtctattcgc caaggtctcg ctggcatcat cgacctccca    240

aaggagggcg catcagctcc agatgtggac atttcacatg ggtctgaaga ccacaaggcc    300

tcctaccaaa tgaatgggat actgaatgaa tcacataacg ggaggcacgc ctctctgtct    360

aaagtttatg aattttgcac ggaattgggt ggaaaaacac caattcacag tgtattagtc    420

gccaacaatg gaatggcagc agctaagttc atgcggagtg tccggacatg ggctaatgat    480

acatttgggt cagagaaggc gattcagttg atagctatgg caactccgga agacatgaga    540

ataaatgcag agcacattag aattgctgat cagtttgttg aagtacctgg tggaacaaac    600

aataacaact atgcaaatgt ccaactcata gtggagatag cagagagaac tggtgtctcc    660

gccgtttggc ctggttgggg ccatgcatct gagaatcctg aacttccaga tgcactaact    720

gcaaaaggaa ttgtttttct tgggccacca gcatcatcaa tgaacgcact aggcgacaag    780

gttggttcag ctctcattgc tcaagcagca ggggttccca ctcttgcttg gagtggatca    840

catgtggaaa ttccattaga actttgtttg gactcgatac ctgaggagat gtataggaaa    900

gcctgtgtta caaccgctga tgaagcagtt gcaagttgtc agatgattgg ttaccctgcc    960

atgatcaagg catcctgggg tggtggtggt aaagggatta gaaaggttaa taatgatgac   1020

gaggtgaaag cactgtttaa gcaagtacag ggtgaagttc ctggctcccc gatatttatc   1080

atgagacttg catctcagag tcgtcatctt gaagtccagc tgctttgtga tgaatatggc   1140

aatgtagcag cacttcacag tcgtgattgc agtgtgcaac gacgacacca aaagattatc   1200

gaggaaggac cagttactgt tgctcctcgt gaaacagtga aagagctaga gcaagcagca   1260

aggaggcttg ctaaggccgt gggttacgtc ggtgctgcta ctgttgaata tctctacagc   1320

atggagactg gtgaatacta ttttctggag cttaatccac ggttgcaggt tgagcaccca   1380

gtcaccgagt cgatagctga agtaaatttg cctgcagccc aagttgcagt tgggatgggt   1440

ataccccttt ggcagattcc agagatcaga cgtttctacg gaatggacaa tggaggaggc   1500

tatgatattt ggaggaaaac agcagctctc gctactccat tcaactttga tgaagtagat   1560

tctcaatggc cgaagggtca ttgtgtggca gttaggataa ccagtgagaa tccagatgat   1620

ggattcaagc ctactggtgg aaaagtaaag gagataagtt ttaaaagtaa gccaaatgtc   1680
```

tggggatatt tctcagttaa gtctggtgga ggcattcatg aatttgcgga ttctcagttt 1740
ggacacgttt ttgcctatgg agagactaga tcagcagcaa taaccagcat gtctcttgca 1800
ctaaaagaga ttcaaattcg tggagaaatt catacaaacg ttgattacac ggttgatctc 1860
ttgaatgccc cagacttcag agaaaacacg atccataccg gttggctgga taccagaata 1920
gctatgcgtg ttcaagctga gaggcctccc tggtatattt cagtggttgg aggagctcta 1980
tataaaacaa taaccaccaa tgcggagacc gtttctgaat atgttagcta tctcatcaag 2040
ggtcagattc caccaaagca catatccctt gtccattcaa ctatttcttt gaatatagag 2100
gaaagcaaat atacaattga gattgtgagg agtggacagg gtagctacag attgagactg 2160
aatggatcac ttattgaagc caatgtacaa acattatgtg atggaggcct tttaatgcag 2220
ctggatggaa atagccatgt tatttatgct gaagaagaag cgggtggtac acggcttctt 2280
attgatggaa aaacatgctt gctacagaat gaccatgatc cgtcaaggtt attagctgag 2340
acaccctgca aacttcttcg tttcttgatt gccgatggtg ctcatgttga tgctgatgta 2400
ccatacgcgg aagttgaggt tatgaagatg tgcatgcccc tcttgtcgcc tgctgctggt 2460
gtcattaatg ttttgttgtc tgagggccag gcgatgcagg ctggtgatct tatagcgaga 2520
cttgatctcg atgacccttc tgctgtgaag agagccgagc catttgaagg atcttttcca 2580
gaaatgagcc ttcctattgc tgcttctggc caagttcaca aaagatgtgc tgcaagtttg 2640
aacgctgctc gaatggtcct tgcaggatat gaccatgcgg ccaacaaagt tgtgcaagat 2700
ttggtatggt gccttgatac acctgctctt cctttcctac aatgggaaga gcttatgtct 2760
gttttagcaa ctagacttcc aagacgtctt aagagcgagt tggagggcaa atacaatgaa 2820
tacaagttaa atgttgacca tgtgaagatc aaggatttcc ctaccgagat gcttagagag 2880
acaatcgagg aaaatcttgc atgtgtttcc gagaaggaaa tggtgacaat tgagaggctt 2940
gttgaccctc tgatgagcct gctgaagtca tacgagggtg ggagagaaag ccatgcccac 3000
tttattgtca agtccctttt tgaggagtat ctctcggttg aggaactatt cagtgatggc 3060
attcagtctg acgtgattga acgcctgcgc ctacaatata gtaaagacct ccagaaggtt 3120
gtagacattg ttttgtctca ccagggtgtg agaaacaaaa caaagctgat actcgcgctc 3180
atggagaaac tggtctatcc aaaccctgct gcctacagag atcagttgat tcgcttttct 3240
tccctcaacc ataaaagata ttataagttg gctcttaaag ctagtgaact tcttgaacaa 3300
accaagctca gcgaactccg cacaagcatt gcaaggaacc tttcagcgct ggatatgttc 3360
accgaggaaa aggcagattt ctccttgcaa gacagaaaat tggccattaa tgagagcatg 3420
ggagatttag tcactgcccc actgccagtt gaagatgcac ttgtttcttt gtttgattgt 3480
actgatcaaa ctcttcagca gagagtgatt cagacataca tatctcgatt ataccagcct 3540
caacttgtga aggatagcat ccagctgaaa tatcaggatt ctggtgttat tgctttatgg 3600
gaattcactg aaggaaatca tgagaagaga ttgggtgcta tggttatcct gaagtcacta 3660
gaatctgtgt caacagccat tggagctgct ctaaaggatg catcacatta tgcaagctct 3720
gcgggcaaca cggtgcatat tgctttgttg gatgctgata cccaactgaa tacaactgaa 3780
gatagtggtg ataatgacca agctcaagac aagatggata aactttcttt tgtactgaaa 3840
caagatgttg tcatggctga tctacgtgct gctgatgtca aggttgttag ttgcattgtt 3900
caaagagatg gagcaatcat gcctatgcgc cgtaccttcc tcttgtcaga ggaaaaactt 3960
tgttacgagg aagagccgat tcttcggcat gtggagcctc cactttctgc acttcttgag 4020
ttggataaat tgaaagtgaa aggatacaat gagatgaagt atacaccgtc acgtgatcgt 4080

```
cagtggcata tatacacact tagaaatact gaaaatccaa aaatgctgca cagggtattt   4140
ttccgaacac ttgtcagaca acccagtgca ggcaacaggt ttacatcaga ccatatcact   4200
gatgttgaag taggacacgc agaggaacct ctttcattta cttcaagcag catattaaaa   4260
tcgttgaaga ttgctaaaga agaattggag cttcacgcga tcaggactgg ccattctcat   4320
atgtacttgt gcatattgaa agagcaaaag cttcttgacc ttgttcctgt ttcagggaac   4380
actgttgtgg atgttggtca agatgaagct actgcatgct ctcttttgaa agaaatggct   4440
ttaaagatac atgaacttgt tggtgcaaga atgcatcatc tttctgtatg ccagtgggaa   4500
gtgaaactta agttggtgag cgatgggcct gccagtggta gctggagagt tgtaacaacc   4560
aatgttactg gtcacacctg cactgtggat atctaccggg aggtcgaaga tacagaatca   4620
cagaaactag tataccactc caccgcattg tcatctggtc ctttgcatgg tgttgcactg   4680
aatacttcgt atcagccttt gagtgttatt gatttaaaac gttgctctgc caggaacaac   4740
aaaactacat actgctatga ttttccattg acatttgaag ctgcagtgca gaagtcgtgg   4800
tctaacattt ccagtgaaaa caaccaatgt tatgttaaag cgacagagct tgtgtttgct   4860
gaaaagaatg ggtcgtgggg cactcctata attcctatgc agcgtgctgc tgggctgaat   4920
gacattggta tggtagcctg gatcttggac atgtccactc ctgaatttcc cagcggcaga   4980
cagatcattg ttatcgcaaa tgatattaca tttagagctg gatcatttgg cccaagggaa   5040
gatgcatttt tcgaagctgt aaccaacctg gcttgtgaga agaagcttcc acttatctac   5100
ttggctgcaa actctggtgc tcggattggc attgctgatg aagtaaaatc ttgcttccgt   5160
gttggatgga ctgatgatag cagccctgaa cgtggattta ggtacattta tatgactgac   5220
gaagaccatg atcgtattgg ctcttcagtt atagcacaca agatgcagct agatagtggc   5280
gagatcaggt gggttattga ttctgttgtg ggaaaagagg atggactagg tgtggagaac   5340
atacatggaa gtgctgctat tgccagtgcc tattctaggg cgtacgagga gacatttaca   5400
cttacattcg ttactggacg aactgttgga atcggagcct atcttgctcg acttggcata   5460
cggtgcatac agcgtattga ccagcccatt attttgaccg ggttttctgc cctgaacaag   5520
cttcttgggc gggaggtgta cagctcccac atgcagttgg gtggtcccaa aatcatggcg   5580
acgaatggtg ttgtccatct gactgttcca gatgaccttg aaggtgtttc taatatattg   5640
aggtggctca gctatgttcc tgcaaacatt ggtggacctc ttcctattac aaaatctttg   5700
gacccaatag acagacccgt tgcatacatc cctgagaata catgtgatcc tcgtgcagcc   5760
atcagtggca ttgatgacag ccaagggaaa tggttgggtg gcatgtttga caaagacagt   5820
tttgtggaga catttgaagg atgggcgaag acagtagtta ctggcagagc aaaacttgga   5880
gggattcctg ttggtgttat agctgtggag acacagacca tgatgcagct cgtccccgct   5940
gatccaggcc agcctgattc ccacgagcgg tctgttcctc gtgctgggca agtttggttt   6000
ccagattctg ctaccaagac agcgcaggcg atgttggact tcaaccgtga aggattacct   6060
ctgttcatac ttgctaactg gagaggcttc tctggagggc aaagagatct tttgaagga    6120
attctgcagg ctgggtcaac aattgttgag aaccttagga catacaatca gcctgccttt   6180
gtatatatcc ccaaggctgc agagctacgt ggaggagcct gggtcgtgat tgatagcaag   6240
ataaacccag atcgcatcga gtgctatgct gagaggactg caaagggtaa tgttctcgaa   6300
cctcaagggt tgattgagat caagttcagg tcagaggaac tcaaagaatg catgggtagg   6360
cttgatccag aattgataga tctgaaagca agactccagg gagcaaatgg aagcctatct   6420
```

```
gatggagaat cccttcagaa gagcatagaa gctcggaaga aacagttgct gcctctgtac   6480

acccaaatcg cggtacgttt tgcggaattg cacgacactt cccttagaat ggctgctaaa   6540

ggtgtgatca ggaaagttgt agactgggaa gactctcggt ctttcttcta caagagatta   6600

cggaggaggc tatccgagga cgttctggca aaggagatta gaggtgtaat tggtgagaag   6660

tttcctcaca aatcagcgat cgagctgatc aagaaatggt acttggcttc tgaggcagct   6720

gcagcaggaa gcaccgactg ggatgacgac gatgcttttg tcgcctggag ggagaaccct   6780

gaaaactata aggagtatat caaagagctt agggctcaaa gggtatctcg gttgctctca   6840

gatgttgcag gctccagttc ggatttacaa gccttgccgc agggtctttc catgctacta   6900

gataagatgg atccctctaa gagagcacag tttatcgagg aggtcatgaa ggtcctgaaa   6960

tga                                                                 6963
```

<210> SEQ ID NO 24
<211> LENGTH: 2320
<212> TYPE: PRT
<213> ORGANISM: Alopecurus myosuroides

<400> SEQUENCE: 24

```
Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Lys Ser Arg Arg Val
        35                  40                  45

Lys Ser Ile Arg Asp Asp Gly Asp Gly Ser Val Pro Asp Pro Ala Gly
    50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
                85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270
```

```
Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
    290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Gly Lys Gly Ile Arg Lys Val
                325                 330                 335

Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
        355                 360                 365

His Leu Glu Val Gln Leu Leu Cys Asp Glu Tyr Gly Asn Val Ala Ala
    370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Ser
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
            500                 505                 510

Pro Phe Asn Phe Asp Glu Val Asp Ser Gln Trp Pro Lys Gly His Cys
        515                 520                 525

Val Ala Val Arg Ile Thr Ser Glu Asn Pro Asp Asp Gly Phe Lys Pro
    530                 535                 540

Thr Gly Gly Lys Val Lys Glu Ile Ser Phe Lys Ser Lys Pro Asn Val
545                 550                 555                 560

Trp Gly Tyr Phe Ser Val Lys Ser Gly Gly Gly Ile His Glu Phe Ala
                565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
        595                 600                 605

Glu Ile His Thr Asn Val Asp Tyr Thr Val Asp Leu Leu Asn Ala Pro
    610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Glu Thr Val Ser
            660                 665                 670

Glu Tyr Val Ser Tyr Leu Ile Lys Gly Gln Ile Pro Pro Lys His Ile
        675                 680                 685

Ser Leu Val His Ser Thr Ile Ser Leu Asn Ile Glu Glu Ser Lys Tyr
```

```
    690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
            740                 745                 750

Glu Ala Gly Gly Thr Arg Leu Leu Ile Asp Gly Lys Thr Cys Leu Leu
        755                 760                 765

Gln Asn Asp His Asp Pro Ser Arg Leu Leu Ala Glu Thr Pro Cys Lys
    770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
            820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Gly Ser Phe Pro Glu Met Ser Leu
    850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
            900                 905                 910

Leu Gln Trp Glu Glu Leu Met Ser Val Leu Ala Thr Arg Leu Pro Arg
        915                 920                 925

Arg Leu Lys Ser Glu Leu Glu Gly Lys Tyr Asn Glu Tyr Lys Leu Asn
    930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
                965                 970                 975

Ile Glu Arg Leu Val Asp Pro Leu Met Ser Leu Leu Lys Ser Tyr Glu
            980                 985                 990

Gly Gly Arg Glu Ser His Ala His  Phe Ile Val Lys Ser  Leu Phe Glu
        995                 1000                1005

Glu Tyr  Leu Ser Val Glu Glu  Leu Phe Ser Asp Gly  Ile Gln Ser
    1010                1015                1020

Asp Val  Ile Glu Arg Leu Arg  Leu Gln Tyr Ser Lys  Asp Leu Gln
    1025                1030                1035

Lys Val  Val Asp Ile Val Leu  Ser His Gln Gly Val  Arg Asn Lys
    1040                1045                1050

Thr Lys  Leu Ile Leu Ala Leu  Met Glu Lys Leu Val  Tyr Pro Asn
    1055                1060                1065

Pro Ala  Ala Tyr Arg Asp Gln  Leu Ile Arg Phe Ser  Ser Leu Asn
    1070                1075                1080

His Lys  Arg Tyr Tyr Lys Leu  Ala Leu Lys Ala Ser  Glu Leu Leu
    1085                1090                1095

Glu Gln  Thr Lys Leu Ser Glu  Leu Arg Thr Ser Ile  Ala Arg Asn
    1100                1105                1110
```

```
Leu Ser  Ala Leu Asp Met Phe  Thr Glu Glu Lys Ala  Asp Phe Ser
    1115                 1120                 1125

Leu Gln  Asp Arg Lys Leu Ala  Ile Asn Glu Ser Met  Gly Asp Leu
    1130                 1135                 1140

Val Thr  Ala Pro Leu Pro Val  Glu Asp Ala Leu Val  Ser Leu Phe
    1145                 1150                 1155

Asp Cys  Thr Asp Gln Thr Leu  Gln Gln Arg Val Ile  Gln Thr Tyr
    1160                 1165                 1170

Ile Ser  Arg Leu Tyr Gln Pro  Gln Leu Val Lys Asp  Ser Ile Gln
    1175                 1180                 1185

Leu Lys  Tyr Gln Asp Ser Gly  Val Ile Ala Leu Trp  Glu Phe Thr
    1190                 1195                 1200

Glu Gly  Asn His Glu Lys Arg  Leu Gly Ala Met Val  Ile Leu Lys
    1205                 1210                 1215

Ser Leu  Glu Ser Val Ser Thr  Ala Ile Gly Ala Ala  Leu Lys Asp
    1220                 1225                 1230

Ala Ser  His Tyr Ala Ser Ser  Ala Gly Asn Thr Val  His Ile Ala
    1235                 1240                 1245

Leu Leu  Asp Ala Asp Thr Gln  Leu Asn Thr Thr Glu  Asp Ser Gly
    1250                 1255                 1260

Asp Asn  Asp Gln Ala Gln Asp  Lys Met Asp Lys Leu  Ser Phe Val
    1265                 1270                 1275

Leu Lys  Gln Asp Val Val Met  Ala Asp Leu Arg Ala  Ala Asp Val
    1280                 1285                 1290

Lys Val  Val Ser Cys Ile Val  Gln Arg Asp Gly Ala  Ile Met Pro
    1295                 1300                 1305

Met Arg  Arg Thr Phe Leu Leu  Ser Glu Glu Lys Leu  Cys Tyr Glu
    1310                 1315                 1320

Glu Glu  Pro Ile Leu Arg His  Val Glu Pro Pro Leu  Ser Ala Leu
    1325                 1330                 1335

Leu Glu  Leu Asp Lys Leu Lys  Val Lys Gly Tyr Asn  Glu Met Lys
    1340                 1345                 1350

Tyr Thr  Pro Ser Arg Asp Arg  Gln Trp His Ile Tyr  Thr Leu Arg
    1355                 1360                 1365

Asn Thr  Glu Asn Pro Lys Met  Leu His Arg Val Phe  Phe Arg Thr
    1370                 1375                 1380

Leu Val  Arg Gln Pro Ser Ala  Gly Asn Arg Phe Thr  Ser Asp His
    1385                 1390                 1395

Ile Thr  Asp Val Glu Val Gly  His Ala Glu Glu Pro  Leu Ser Phe
    1400                 1405                 1410

Thr Ser  Ser Ser Ile Leu Lys  Ser Leu Lys Ile Ala  Lys Glu Glu
    1415                 1420                 1425

Leu Glu  Leu His Ala Ile Arg  Thr Gly His Ser His  Met Tyr Leu
    1430                 1435                 1440

Cys Ile  Leu Lys Glu Gln Lys  Leu Leu Asp Leu Val  Pro Val Ser
    1445                 1450                 1455

Gly Asn  Thr Val Val Asp Val  Gly Gln Asp Glu Ala  Thr Ala Cys
    1460                 1465                 1470

Ser Leu  Leu Lys Glu Met Ala  Leu Lys Ile His Glu  Leu Val Gly
    1475                 1480                 1485

Ala Arg  Met His His Leu Ser  Val Cys Gln Trp Glu  Val Lys Leu
    1490                 1495                 1500
```

```
Lys Leu  Val Ser Asp Gly Pro  Ala Ser Gly Ser Trp  Arg Val Val
    1505                 1510                 1515

Thr Thr  Asn Val Thr Gly His  Thr Cys Thr Val Asp  Ile Tyr Arg
    1520                 1525                 1530

Glu Val  Glu Asp Thr Glu Ser  Gln Lys Leu Val Tyr  His Ser Thr
    1535                 1540                 1545

Ala Leu  Ser Ser Gly Pro Leu  His Gly Val Ala Leu  Asn Thr Ser
    1550                 1555                 1560

Tyr Gln  Pro Leu Ser Val Ile  Asp Leu Lys Arg Cys  Ser Ala Arg
    1565                 1570                 1575

Asn Asn  Lys Thr Thr Tyr Cys  Tyr Asp Phe Pro Leu  Thr Phe Glu
    1580                 1585                 1590

Ala Ala  Val Gln Lys Ser Trp  Ser Asn Ile Ser Ser  Glu Asn Asn
    1595                 1600                 1605

Gln Cys  Tyr Val Lys Ala Thr  Glu Leu Val Phe Ala  Glu Lys Asn
    1610                 1615                 1620

Gly Ser  Trp Gly Thr Pro Ile  Ile Pro Met Gln Arg  Ala Ala Gly
    1625                 1630                 1635

Leu Asn  Asp Ile Gly Met Val  Ala Trp Ile Leu Asp  Met Ser Thr
    1640                 1645                 1650

Pro Glu  Phe Pro Ser Gly Arg  Gln Ile Ile Val Ile  Ala Asn Asp
    1655                 1660                 1665

Ile Thr  Phe Arg Ala Gly Ser  Phe Gly Pro Arg Glu  Asp Ala Phe
    1670                 1675                 1680

Phe Glu  Ala Val Thr Asn Leu  Ala Cys Glu Lys Lys  Leu Pro Leu
    1685                 1690                 1695

Ile Tyr  Leu Ala Ala Asn Ser  Gly Ala Arg Ile Gly  Ile Ala Asp
    1700                 1705                 1710

Glu Val  Lys Ser Cys Phe Arg  Val Gly Trp Thr Asp  Asp Ser Ser
    1715                 1720                 1725

Pro Glu  Arg Gly Phe Arg Tyr  Ile Tyr Met Thr Asp  Glu Asp His
    1730                 1735                 1740

Asp Arg  Ile Gly Ser Ser Val  Ile Ala His Lys Met  Gln Leu Asp
    1745                 1750                 1755

Ser Gly  Glu Ile Arg Trp Val  Ile Asp Ser Val Val  Gly Lys Glu
    1760                 1765                 1770

Asp Gly  Leu Gly Val Glu Asn  Ile His Gly Ser Ala  Ala Ile Ala
    1775                 1780                 1785

Ser Ala  Tyr Ser Arg Ala Tyr  Glu Glu Thr Phe Thr  Leu Thr Phe
    1790                 1795                 1800

Val Thr  Gly Arg Thr Val Gly  Ile Gly Ala Tyr Leu  Ala Arg Leu
    1805                 1810                 1815

Gly Ile  Arg Cys Ile Gln Arg  Ile Asp Gln Pro Ile  Ile Leu Thr
    1820                 1825                 1830

Gly Phe  Ser Ala Leu Asn Lys  Leu Leu Gly Arg Glu  Val Tyr Ser
    1835                 1840                 1845

Ser His  Met Gln Leu Gly Gly  Pro Lys Ile Met Ala  Thr Asn Gly
    1850                 1855                 1860

Val Val  His Leu Thr Val Pro  Asp Asp Leu Glu Gly  Val Ser Asn
    1865                 1870                 1875

Ile Leu  Arg Trp Leu Ser Tyr  Val Pro Ala Asn Ile  Gly Gly Pro
    1880                 1885                 1890

Leu Pro  Ile Thr Lys Ser Leu  Asp Pro Ile Asp Arg  Pro Val Ala
```

```
    1895                1900                1905

Tyr Ile  Pro Glu Asn Thr Cys  Asp Pro Arg Ala Ala  Ile Ser Gly
    1910                1915                1920

Ile Asp  Asp Ser Gln Gly Lys  Trp Leu Gly Gly Met  Phe Asp Lys
    1925                1930                1935

Asp Ser  Phe Val Glu Thr Phe  Glu Gly Trp Ala Lys  Thr Val Val
    1940                1945                1950

Thr Gly  Arg Ala Lys Leu Gly  Gly Ile Pro Val Gly  Val Ile Ala
    1955                1960                1965

Val Glu  Thr Gln Thr Met Met  Gln Leu Val Pro Ala  Asp Pro Gly
    1970                1975                1980

Gln Pro  Asp Ser His Glu Arg  Ser Val Pro Arg Ala  Gly Gln Val
    1985                1990                1995

Trp Phe  Pro Asp Ser Ala Thr  Lys Thr Ala Gln Ala  Met Leu Asp
    2000                2005                2010

Phe Asn  Arg Glu Gly Leu Pro  Leu Phe Ile Leu Ala  Asn Trp Arg
    2015                2020                2025

Gly Phe  Ser Gly Gly Gln Arg  Asp Leu Phe Glu Gly  Ile Leu Gln
    2030                2035                2040

Ala Gly  Ser Thr Ile Val Glu  Asn Leu Arg Thr Tyr  Asn Gln Pro
    2045                2050                2055

Ala Phe  Val Tyr Ile Pro Lys  Ala Ala Glu Leu Arg  Gly Gly Ala
    2060                2065                2070

Trp Val  Val Ile Asp Ser Lys  Ile Asn Pro Asp Arg  Ile Glu Cys
    2075                2080                2085

Tyr Ala  Glu Arg Thr Ala Lys  Gly Asn Val Leu Glu  Pro Gln Gly
    2090                2095                2100

Leu Ile  Glu Ile Lys Phe Arg  Ser Glu Glu Leu Lys  Glu Cys Met
    2105                2110                2115

Gly Arg  Leu Asp Pro Glu Leu  Ile Asp Leu Lys Ala  Arg Leu Gln
    2120                2125                2130

Gly Ala  Asn Gly Ser Leu Ser  Asp Gly Glu Ser Leu  Gln Lys Ser
    2135                2140                2145

Ile Glu  Ala Arg Lys Lys Gln  Leu Leu Pro Leu Tyr  Thr Gln Ile
    2150                2155                2160

Ala Val  Arg Phe Ala Glu Leu  His Asp Thr Ser Leu  Arg Met Ala
    2165                2170                2175

Ala Lys  Gly Val Ile Arg Lys  Val Val Asp Trp Glu  Asp Ser Arg
    2180                2185                2190

Ser Phe  Phe Tyr Lys Arg Leu  Arg Arg Arg Leu Ser  Glu Asp Val
    2195                2200                2205

Leu Ala  Lys Glu Ile Arg Gly  Val Ile Gly Glu Lys  Phe Pro His
    2210                2215                2220

Lys Ser  Ala Ile Glu Leu Ile  Lys Lys Trp Tyr Leu  Ala Ser Glu
    2225                2230                2235

Ala Ala  Ala Ala Gly Ser Thr  Asp Trp Asp Asp Asp  Asp Ala Phe
    2240                2245                2250

Val Ala  Trp Arg Glu Asn Pro  Glu Asn Tyr Lys Glu  Tyr Ile Lys
    2255                2260                2265

Glu Leu  Arg Ala Gln Arg Val  Ser Arg Leu Leu Ser  Asp Val Ala
    2270                2275                2280

Gly Ser  Ser Ser Asp Leu Gln  Ala Leu Pro Gln Gly  Leu Ser Met
    2285                2290                2295
```

```
Leu Leu  Asp Lys Met Asp Pro  Ser Lys Arg Ala Gln  Phe Ile Glu
    2300                 2305                 2310

Glu Val  Met Lys Val Leu Lys
    2315                 2320


<210> SEQ ID NO 25
<211> LENGTH: 6936
<212> TYPE: DNA
<213> ORGANISM: Aegilops tauschii

<400> SEQUENCE: 25

atgggatcca cacatttgcc cattgtcggc cttaatgcct cgacaacacc atcgctatcc     60

actattcgcc cggtaaattc agccggtgct gcattccaac catctgcccc ttctagaacc    120

tccaagaaga aaagtcgtcg tgttcagtca ttaagggatg gaggcgatgg aggcgtgtca    180

gaccctaacc agtctattcg ccaaggtctt gccggcatca ttgacctccc aaaggagggc    240

acatcagctc cggaagtgga tatttcacat gggtccgaag aacccagggg ctcctaccaa    300

atgaatggga tactgaatga agcacataat gggaggcatg cttcgctgtc taaggttgtc    360

gaattttgta tggcattggg cggcaaaaca ccaattcata gtgtattagt tgcgaacaat    420

ggaatggcag cagctaagtt catgcggagt gtccgaacat gggctaatga aacatttggg    480

tcagagaagg caattcagtt gatagctatg gctactccag aagacatgag gataaatgca    540

gagcacatta gaattgctga tcaatttgtt gaagtacccg gtggaacaaa caataacaac    600

tatgcaaatg tccaactcat agtggagata gcagtgagaa ccggtgtttc tgctgtttgg    660

cctggttggg gccatgcatc tgagaatcct gaacttccag atgcactaaa tgcaaacgga    720

attgtttttc ttgggccacc atcatcatca atgaacgcac taggtgacaa ggttggttca    780

gctctcattg ctcaagcagc aggggttccg actcttcctt ggagtggatc acaggtggaa    840

attccattag aagtttgttt ggactcgata cctgcggata tgtataggaa agcttgtgtt    900

agtactacgg aggaagcact tgcgagttgt cagatgattg ggtatccagc catgattaaa    960

gcatcatggg gtggtggtgg taaagggatc cgaaaggtta ataacgacga tgatgtcaga   1020

gcactgttta agcaagtgca aggtgaagtt cctggctccc caatatttat catgagactt   1080

gcatctcaga gtcgacatct tgaagttcag ttgctttgtg atcaatatgg caatgtagct   1140

gcgcttcaca gtcgtgactg cagtgtgcaa cggcgacacc aaaagattat tgaggaagga   1200

ccagttactg ttgctcctcg cgagacagtg aaagagctag agcaagcagc aaggaggctt   1260

gctaaggctg tgggttatgt tggtgctgct actgttgaat atctctacag catggagact   1320

ggtgaatact attttctgga acttaatcca cggttgcagg ttgagcatcc agtcaccgag   1380

tggatagctg aagtaaactt gcctgcagct caagttgcag ttggaatggg tataccccctt   1440

tggcaggttc cagagatcag acgtttctat ggaatggaca atggaggagg ctatgacatt   1500

tggaggaaaa cagcagctct tgctacccca tttaactttg atgaagtgga ttctcaatgg   1560

ccaaagggtc attgtgtagc agttaggata accagtgagg atccagatga cggattcaag   1620

cctaccggtg gaaaagtaaa ggagatcagt tttaaaagca agccaaatgt ttgggcctat   1680

ttctctgtta agtccggtgg aggcattcat gaatttgctg attctcagtt tggacatgtt   1740

tttgcatatg gagtgtctag agcagcagca ataaccaaca tgtctcttgc gctaaaagag   1800

attcaaattc gtggagaaat tcattcaaat gttgattaca cagttgatct cttgaatgcc   1860

tcagacttca aagaaaacag gattcatact ggctggctgg ataacagaat agcaatgcga   1920
```

-continued

```
gtccaagctg agagacctcc gtggtatatt tcagtggttg gaggagctct atataaaaca   1980
ataacgagca acacagacac tgtttctgaa tatgttagct atctcgtcaa gggtcagatt   2040
ccaccgaagc atatatccct tgtccattca actgtttctt tgaatataga ggaaagcaaa   2100
tatacaattg aaactataag gagcggacag ggtagctaca gattgcgaat gaatggatca   2160
gttattgaag caaatgtcca aacattatgt gatggtggac ttttaatgca gttggatgga   2220
aacagccatg taatttatgc tgaagaagag gccggtggta cacggcttct aattgatgga   2280
aagacatgct tgttacagaa tgatcacgat ccttcaaggt tattagctga gacaccctgc   2340
aaacttcttc gtttcttggt tgccgatggt gctcatgttg aagctgatgt accatatgcg   2400
gaagttgagg ttatgaagat gtgcatgccc ctcttgtcac ctgctgctgg tgtcattaat   2460
gttttgttgt ctgagggcca gcctatgcag gctggtgatc ttatagcaag acttgatctt   2520
gatgaccctt ctgctgtgaa gagagctgag ccgtttaacg gatctttccc agaaatgagc   2580
cttcctattg ctgcttctgg ccaagttcac aaaagatgtg ccacaagctt gaatgctgct   2640
cggatggtcc ttgcaggata tgatcacccg atcaacaaag ttgtacaaga tctggtatcc   2700
tgtctagatg ctcctgagct tcctttccta caatgggaag agcttatgtc tgttttagca   2760
actagacttc caaggcttct taagagcgag ttggagggta aatacagtga atataagtta   2820
aatgttggcc atggaaagag caaggatttc ccttccaaga tgctaagaga gataatcgag   2880
gaaaatcttg cacatggttc tgagaaggaa attgctacaa atgagaggct tgttgagcct   2940
cttatgagcc tactgaagtc atatgagggt ggcagagaaa gccatgcaca ctttattgtg   3000
aagtcccttt tcgaggacta tctctcggtt gaggaactat tcagtgatgg cattcagtct   3060
gatgtgattg aacgcctgcg ccaacaacat agtaaagatc tccagaaggt tgtagacatt   3120
gtgttgtctc accagggtgt gagaaacaaa actaagctga tactaacact catggagaaa   3180
ctggtctatc caaaccctgc tgcctacaag gatcagttga ctcgcttttc ctccctcaat   3240
cacaaaagat attataagtt ggcccttaaa gctagcgagc ttcttgaaca aaccaagctt   3300
agtgagctcc gcacaagcat tgcaaggagc ctttcagaac ttgagatgtt tactgaagaa   3360
aggacggcca ttagtgagat catgggagat ttagtgactg ccccactgcc agttgaagat   3420
gcactggttt ctttgtttga ttgtagtgat caaactcttc agcagagggt gatcgagacg   3480
tacatatctc gattatacca gcctcatctt gtcaaggata gtatccagct gaaatatcag   3540
gaatctggtg ttattgcttt atgggaattc gctgaagcgc attcagagaa gagattgggt   3600
gctatggtta ttgtgaagtc gttagaatct gtatcagcag caattggagc tgcactaaag   3660
ggtacatcac gctatgcaag ctctgagggt aacataatgc atattgcttt attgggtgct   3720
gataatcaaa tgcatggaac tgaagacagt ggtgataacg atcaagctca agtcaggata   3780
gacaaacttt ctgcgacact ggaacaaaat actgtcacag ctgatctccg tgctgctggt   3840
gtgaaggtta ttagttgcat tgttcaaagg gatggagcac tcatgcctat gcgccatacc   3900
ttcctcttgt cggatgaaaa gctttgttat gaggaagagc cggttctccg gcatgtggag   3960
cctcctcttt ctgctcttct tgagttgggt aagttgaaag tgaaaggata caatgaggtg   4020
aagtatacac cgtcacgtga tcgtcagtgg aacatataca cacttagaaa tacagagaac   4080
cccaaaatgt tgcacagggt gtttttccga actcttgtca ggcaacccgg tgcttccaac   4140
aaattcacat caggcaacat cagtgatgtt gaagtgggag gagctgagga atctctttca   4200
tttacatcga gcagcatatt aagatcgctg atgactgcta tagaagagtt ggagcttcac   4260
gcgattagga caggtcactc tcatatgttt ttgtgcatat tgaaagagca aaagcttctt   4320
```

```
gatcttgttc ccgtttcagg gaacaaagtt gtggatattg gccaagatga agctactgca   4380
tgcttgcttc tgaaagaaat ggctctacag atacatgaac ttgtgggtgc aaggatgcat   4440
catctttctg tatgccaatg ggaggtgaaa cttaagttgg acagcgatgg gcctgccagt   4500
ggtacctgga gagttgtaac aaccaatgtt actagtcaca cctgcactgt ggatatctac   4560
cgtgaggttg aagatacaga atcacagaaa ctagtgtacc actctgctcc atcgtcatct   4620
ggtcctttgc atggcgttgc actgaatact ccatatcagc ctttgagtgt tattgatctg   4680
aaacgttgct ccgctagaaa taacagaact acatactgct atgattttcc gttggcattt   4740
gaaactgcag tgcagaagtc atggtctaac atttctagtg acactaaccg atgttatgtt   4800
aaagcgacgg agctggtgtt tgctcacaag aacgggtcat ggggcactcc tgtaattcct   4860
atggagcgtc ctgctgggct caatgacatt ggtatggtag cttggatctt ggacatgtcc   4920
actcctgaat atcccaatgg caggcagatt gttgtcatcg caaatgatat tacttttaga   4980
gctggatcgt ttggtccaag ggaagatgca ttttttgaaa ctgttaccaa cctagcttgt   5040
gagaggaagc ttcctctcat ctacttggca gcaaactctg gtgctcggat cggcatagca   5100
gatgaagtaa aatcttgctt ccgtgttgga tggtctgatg atggcagccc tgaacgtggg   5160
tttcaatata tttatctgac tgaagaagac catgctcgta ttagcgcttc tgttatagcg   5220
cacaagatgc agcttgataa tggtgaaatt aggtgggtta ttgattctgt tgtagggaag   5280
gaggatgggc taggtgtgga gaacatacat ggaagtgctg ctattgccag tgcctattct   5340
agggcctatg aggagacatt tacgcttaca tttgtgactg gaaggactgt tggaatagga   5400
gcatatcttg ctcgacttgg catacggtgc attcagcgta ctgaccagcc cattatccta   5460
actgggttct ctgccttgaa caagcttctt ggccgggaag tgtacagctc ccacatgcag   5520
ttgggtggcc ccaaaattat ggccacaaac ggtgttgtcc atctgacagt ttcagatgac   5580
cttgaaggtg tatctaatat attgaggtgg ctcagctatg ttcctgccaa cattggtgga   5640
cctcttccta ttacaaaatc tttggaccca cctgacagac ccgttgctta catccctgag   5700
aatacatgtg atcctcgtgc agccatcagt ggcattgatg atagccaagg gaaatggttg   5760
gggggtatgt tcgacaaaga cagttttgtg gagacatttg aaggatgggc gaagtcagta   5820
gttactggca gagcgaaact cggagggatt ccggtgggtg ttatagctgt ggagacacag   5880
actatgatgc agctcatccc tgctgatcca ggtcagcttg attcccatga gcggtctgtt   5940
cctcgtgctg ggcaagtctg gtttccagat tcagctacta agacagcgca ggcaatgctg   6000
gacttcaacc gtgaaggatt acctctgttc atccttgcta actggagagg cttctctggt   6060
gggcaaagag atctttttga aggaatcctt caggctgggt caacaattgt tgagaacctt   6120
aggacataca atcagcctgc ctttgtatat atccccaagg ctgcagagct acgtggaggg   6180
gcttgggtcg tgattgatag caagataaat ccagatcgca ttgagttcta tgctgagagg   6240
actgcaaagg gcaatgttct tgaacctcaa gggttgattg agatcaagtt caggtcagag   6300
gaactccaag agtgcatggg caggcttgac ccagaattga taaatttgaa ggcaaaactc   6360
ctgggagcaa agcatgaaaa tggaagtcta tctgagtcag aatcccttca gaagagcata   6420
gaagcccgga agaaacagtt gttgcctttg tatactcaaa ttgcggtacg gttcgctgaa   6480
ttgcatgaca cttcccttag aatggctgct aagggtgtga ttaagaaggt tgtagactgg   6540
gaagattcta ggtctttctt ctacaagaga ttacggagga ggatatccga ggatgttctt   6600
gcaaaggaaa ttagaggtgt aagtggcaag cagttttctc accaatcggc aatcgagctg   6660
```

-continued atccagaaat ggtacttggc ctctaaggga gctgaaacgg gaaacactga atgggatgat 6720
gacgatgctt ttgttgcctg gagggaaaac cctgaaaact accaggagta tatcaaagaa 6780
ctcagggctc aaagggtatc tcagttgctc tcagatgttg cagactccag tccagatcta 6840
gaagccttgc cacagggtct ttctatgcta ctagagaaga tggatccctc aaggagagca 6900
cagtttgttg aggaagtcaa gaaggccctt aaatga 6936

<210> SEQ ID NO 26
<211> LENGTH: 2311
<212> TYPE: PRT
<213> ORGANISM: Aegilops tauschii

<400> SEQUENCE: 26

Met Gly Ser Thr His Leu Pro Ile Val Gly Leu Asn Ala Ser Thr Thr
1 5 10 15

Pro Ser Leu Ser Thr Ile Arg Pro Val Asn Ser Ala Gly Ala Ala Phe
20 25 30

Gln Pro Ser Ala Pro Ser Arg Thr Ser Lys Lys Lys Ser Arg Arg Val
35 40 45

Gln Ser Leu Arg Asp Gly Gly Asp Gly Gly Val Ser Asp Pro Asn Gln
50 55 60

Ser Ile Arg Gln Gly Leu Ala Gly Ile Ile Asp Leu Pro Lys Glu Gly
65 70 75 80

Thr Ser Ala Pro Glu Val Asp Ile Ser His Gly Ser Glu Glu Pro Arg
85 90 95

Gly Ser Tyr Gln Met Asn Gly Ile Leu Asn Glu Ala His Asn Gly Arg
100 105 110

His Ala Ser Leu Ser Lys Val Val Glu Phe Cys Met Ala Leu Gly Gly
115 120 125

Lys Thr Pro Ile His Ser Val Leu Val Ala Asn Asn Gly Met Ala Ala
130 135 140

Ala Lys Phe Met Arg Ser Val Arg Thr Trp Ala Asn Glu Thr Phe Gly
145 150 155 160

Ser Glu Lys Ala Ile Gln Leu Ile Ala Met Ala Thr Pro Glu Asp Met
165 170 175

Arg Ile Asn Ala Glu His Ile Arg Ile Ala Asp Gln Phe Val Glu Val
180 185 190

Pro Gly Gly Thr Asn Asn Asn Asn Tyr Ala Asn Val Gln Leu Ile Val
195 200 205

Glu Ile Ala Val Arg Thr Gly Val Ser Ala Val Trp Pro Gly Trp Gly
210 215 220

His Ala Ser Glu Asn Pro Glu Leu Pro Asp Ala Leu Asn Ala Asn Gly
225 230 235 240

Ile Val Phe Leu Gly Pro Pro Ser Ser Ser Met Asn Ala Leu Gly Asp
245 250 255

Lys Val Gly Ser Ala Leu Ile Ala Gln Ala Ala Gly Val Pro Thr Leu
260 265 270

Pro Trp Ser Gly Ser Gln Val Glu Ile Pro Leu Glu Val Cys Leu Asp
275 280 285

Ser Ile Pro Ala Asp Met Tyr Arg Lys Ala Cys Val Ser Thr Thr Glu
290 295 300

Glu Ala Leu Ala Ser Cys Gln Met Ile Gly Tyr Pro Ala Met Ile Lys
305 310 315 320

Ala Ser Trp Gly Gly Gly Gly Lys Gly Ile Arg Lys Val Asn Asn Asp

```
                325                 330                 335

Asp Asp Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Glu Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Ala Asp Ser Gln
                565                 570                 575

Phe Gly His Val Phe Ala Tyr Gly Val Ser Arg Ala Ala Ala Ile Thr
            580                 585                 590

Asn Met Ser Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Lys
    610                 615                 620

Glu Asn Arg Ile His Thr Gly Trp Leu Asp Asn Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Ile Thr Ser Asn Thr Asp Thr Val Ser Glu Tyr Val
            660                 665                 670

Ser Tyr Leu Val Lys Gly Gln Ile Pro Pro Lys His Ile Ser Leu Val
        675                 680                 685

His Ser Thr Val Ser Leu Asn Ile Glu Glu Ser Lys Tyr Thr Ile Glu
    690                 695                 700

Thr Ile Arg Ser Gly Gln Gly Ser Tyr Arg Leu Arg Met Asn Gly Ser
705                 710                 715                 720

Val Ile Glu Ala Asn Val Gln Thr Leu Cys Asp Gly Gly Leu Leu Met
                725                 730                 735

Gln Leu Asp Gly Asn Ser His Val Ile Tyr Ala Glu Glu Glu Ala Gly
            740                 745                 750
```

Gly Thr Arg Leu Leu Ile Asp Gly Lys Thr Cys Leu Leu Gln Asn Asp
755 760 765

His Asp Pro Ser Arg Leu Leu Ala Glu Thr Pro Cys Lys Leu Leu Arg
770 775 780

Phe Leu Val Ala Asp Gly Ala His Val Glu Ala Asp Val Pro Tyr Ala
785 790 795 800

Glu Val Glu Val Met Lys Met Cys Met Pro Leu Leu Ser Pro Ala Ala
805 810 815

Gly Val Ile Asn Val Leu Leu Ser Glu Gly Gln Pro Met Gln Ala Gly
820 825 830

Asp Leu Ile Ala Arg Leu Asp Leu Asp Asp Pro Ser Ala Val Lys Arg
835 840 845

Ala Glu Pro Phe Asn Gly Ser Phe Pro Glu Met Ser Leu Pro Ile Ala
850 855 860

Ala Ser Gly Gln Val His Lys Arg Cys Ala Thr Ser Leu Asn Ala Ala
865 870 875 880

Arg Met Val Leu Ala Gly Tyr Asp His Pro Ile Asn Lys Val Val Gln
885 890 895

Asp Leu Val Ser Cys Leu Asp Ala Pro Glu Leu Pro Phe Leu Gln Trp
900 905 910

Glu Glu Leu Met Ser Val Leu Ala Thr Arg Leu Pro Arg Leu Leu Lys
915 920 925

Ser Glu Leu Glu Gly Lys Tyr Ser Glu Tyr Lys Leu Asn Val Gly His
930 935 940

Gly Lys Ser Lys Asp Phe Pro Ser Lys Met Leu Arg Glu Ile Ile Glu
945 950 955 960

Glu Asn Leu Ala His Gly Ser Glu Lys Glu Ile Ala Thr Asn Glu Arg
965 970 975

Leu Val Glu Pro Leu Met Ser Leu Leu Lys Ser Tyr Glu Gly Gly Arg
980 985 990

Glu Ser His Ala His Phe Ile Val Lys Ser Leu Phe Glu Asp Tyr Leu
995 1000 1005

Ser Val Glu Glu Leu Phe Ser Asp Gly Ile Gln Ser Asp Val Ile
1010 1015 1020

Glu Arg Leu Arg Gln Gln His Ser Lys Asp Leu Gln Lys Val Val
1025 1030 1035

Asp Ile Val Leu Ser His Gln Gly Val Arg Asn Lys Thr Lys Leu
1040 1045 1050

Ile Leu Thr Leu Met Glu Lys Leu Val Tyr Pro Asn Pro Ala Ala
1055 1060 1065

Tyr Lys Asp Gln Leu Thr Arg Phe Ser Ser Leu Asn His Lys Arg
1070 1075 1080

Tyr Tyr Lys Leu Ala Leu Lys Ala Ser Glu Leu Leu Glu Gln Thr
1085 1090 1095

Lys Leu Ser Glu Leu Arg Thr Ser Ile Ala Arg Ser Leu Ser Glu
1100 1105 1110

Leu Glu Met Phe Thr Glu Glu Arg Thr Ala Ile Ser Glu Ile Met
1115 1120 1125

Gly Asp Leu Val Thr Ala Pro Leu Pro Val Glu Asp Ala Leu Val
1130 1135 1140

Ser Leu Phe Asp Cys Ser Asp Gln Thr Leu Gln Gln Arg Val Ile
1145 1150 1155

```
Glu Thr  Tyr Ile Ser Arg Leu  Tyr Gln Pro His Leu  Val Lys Asp
    1160                 1165                 1170

Ser Ile  Gln Leu Lys Tyr Gln  Glu Ser Gly Val Ile  Ala Leu Trp
    1175                 1180                 1185

Glu Phe  Ala Glu Ala His Ser  Glu Lys Arg Leu Gly  Ala Met Val
    1190                 1195                 1200

Ile Val  Lys Ser Leu Glu Ser  Val Ser Ala Ala Ile  Gly Ala Ala
    1205                 1210                 1215

Leu Lys  Gly Thr Ser Arg Tyr  Ala Ser Ser Glu Gly  Asn Ile Met
    1220                 1225                 1230

His Ile  Ala Leu Leu Gly Ala  Asp Asn Gln Met His  Gly Thr Glu
    1235                 1240                 1245

Asp Ser  Gly Asp Asn Asp Gln  Ala Gln Val Arg Ile  Asp Lys Leu
    1250                 1255                 1260

Ser Ala  Thr Leu Glu Gln Asn  Thr Val Thr Ala Asp  Leu Arg Ala
    1265                 1270                 1275

Ala Gly  Val Lys Val Ile Ser  Cys Ile Val Gln Arg  Asp Gly Ala
    1280                 1285                 1290

Leu Met  Pro Met Arg His Thr  Phe Leu Leu Ser Asp  Glu Lys Leu
    1295                 1300                 1305

Cys Tyr  Glu Glu Glu Pro Val  Leu Arg His Val Glu  Pro Pro Leu
    1310                 1315                 1320

Ser Ala  Leu Leu Glu Leu Gly  Lys Leu Lys Val Lys  Gly Tyr Asn
    1325                 1330                 1335

Glu Val  Lys Tyr Thr Pro Ser  Arg Asp Arg Gln Trp  Asn Ile Tyr
    1340                 1345                 1350

Thr Leu  Arg Asn Thr Glu Asn  Pro Lys Met Leu His  Arg Val Phe
    1355                 1360                 1365

Phe Arg  Thr Leu Val Arg Gln  Pro Gly Ala Ser Asn  Lys Phe Thr
    1370                 1375                 1380

Ser Gly  Asn Ile Ser Asp Val  Glu Val Gly Gly Ala  Glu Glu Ser
    1385                 1390                 1395

Leu Ser  Phe Thr Ser Ser Ser  Ile Leu Arg Ser Leu  Met Thr Ala
    1400                 1405                 1410

Ile Glu  Glu Leu Glu Leu His  Ala Ile Arg Thr Gly  His Ser His
    1415                 1420                 1425

Met Phe  Leu Cys Ile Leu Lys  Glu Gln Lys Leu Leu  Asp Leu Val
    1430                 1435                 1440

Pro Val  Ser Gly Asn Lys Val  Val Asp Ile Gly Gln  Asp Glu Ala
    1445                 1450                 1455

Thr Ala  Cys Leu Leu Leu Lys  Glu Met Ala Leu Gln  Ile His Glu
    1460                 1465                 1470

Leu Val  Gly Ala Arg Met His  His Leu Ser Val Cys  Gln Trp Glu
    1475                 1480                 1485

Val Lys  Leu Lys Leu Asp Ser  Asp Gly Pro Ala Ser  Gly Thr Trp
    1490                 1495                 1500

Arg Val  Val Thr Thr Asn Val  Thr Ser His Thr Cys  Thr Val Asp
    1505                 1510                 1515

Ile Tyr  Arg Glu Val Glu Asp  Thr Glu Ser Gln Lys  Leu Val Tyr
    1520                 1525                 1530

His Ser  Ala Pro Ser Ser Ser  Gly Pro Leu His Gly  Val Ala Leu
    1535                 1540                 1545

Asn Thr  Pro Tyr Gln Pro Leu  Ser Val Ile Asp Leu  Lys Arg Cys
```

-continued

```
    1550                1555                1560

Ser Ala  Arg Asn Asn Arg Thr  Thr Tyr Cys Tyr Asp  Phe Pro Leu
    1565                1570                1575

Ala Phe  Glu Thr Ala Val Gln  Lys Ser Trp Ser Asn  Ile Ser Ser
    1580                1585                1590

Asp Thr  Asn Arg Cys Tyr Val  Lys Ala Thr Glu Leu  Val Phe Ala
    1595                1600                1605

His Lys  Asn Gly Ser Trp Gly  Thr Pro Val Ile Pro  Met Glu Arg
    1610                1615                1620

Pro Ala  Gly Leu Asn Asp Ile  Gly Met Val Ala Trp  Ile Leu Asp
    1625                1630                1635

Met Ser  Thr Pro Glu Tyr Pro  Asn Gly Arg Gln Ile  Val Val Ile
    1640                1645                1650

Ala Asn  Asp Ile Thr Phe Arg  Ala Gly Ser Phe Gly  Pro Arg Glu
    1655                1660                1665

Asp Ala  Phe Phe Glu Thr Val  Thr Asn Leu Ala Cys  Glu Arg Lys
    1670                1675                1680

Leu Pro  Leu Ile Tyr Leu Ala  Ala Asn Ser Gly Ala  Arg Ile Gly
    1685                1690                1695

Ile Ala  Asp Glu Val Lys Ser  Cys Phe Arg Val Gly  Trp Ser Asp
    1700                1705                1710

Asp Gly  Ser Pro Glu Arg Gly  Phe Gln Tyr Ile Tyr  Leu Thr Glu
    1715                1720                1725

Glu Asp  His Ala Arg Ile Ser  Ala Ser Val Ile Ala  His Lys Met
    1730                1735                1740

Gln Leu  Asp Asn Gly Glu Ile  Arg Trp Val Ile Asp  Ser Val Val
    1745                1750                1755

Gly Lys  Glu Asp Gly Leu Gly  Val Glu Asn Ile His  Gly Ser Ala
    1760                1765                1770

Ala Ile  Ala Ser Ala Tyr Ser  Arg Ala Tyr Glu Glu  Thr Phe Thr
    1775                1780                1785

Leu Thr  Phe Val Thr Gly Arg  Thr Val Gly Ile Gly  Ala Tyr Leu
    1790                1795                1800

Ala Arg  Leu Gly Ile Arg Cys  Ile Gln Arg Thr Asp  Gln Pro Ile
    1805                1810                1815

Ile Leu  Thr Gly Phe Ser Ala  Leu Asn Lys Leu Leu  Gly Arg Glu
    1820                1825                1830

Val Tyr  Ser Ser His Met Gln  Leu Gly Gly Pro Lys  Ile Met Ala
    1835                1840                1845

Thr Asn  Gly Val Val His Leu  Thr Val Ser Asp Asp  Leu Glu Gly
    1850                1855                1860

Val Ser  Asn Ile Leu Arg Trp  Leu Ser Tyr Val Pro  Ala Asn Ile
    1865                1870                1875

Gly Gly  Pro Leu Pro Ile Thr  Lys Ser Leu Asp Pro  Pro Asp Arg
    1880                1885                1890

Pro Val  Ala Tyr Ile Pro Glu  Asn Thr Cys Asp Pro  Arg Ala Ala
    1895                1900                1905

Ile Ser  Gly Ile Asp Asp Ser  Gln Gly Lys Trp Leu  Gly Gly Met
    1910                1915                1920

Phe Asp  Lys Asp Ser Phe Val  Glu Thr Phe Glu Gly  Trp Ala Lys
    1925                1930                1935

Ser Val  Val Thr Gly Arg Ala  Lys Leu Gly Gly Ile  Pro Val Gly
    1940                1945                1950
```

-continued

```
Val Ile Ala Val Glu Thr Gln Thr Met Met Gln Leu Ile Pro Ala
    1955                1960                1965

Asp Pro Gly Gln Leu Asp Ser His Glu Arg Ser Val Pro Arg Ala
    1970                1975                1980

Gly Gln Val Trp Phe Pro Asp Ser Ala Thr Lys Thr Ala Gln Ala
    1985                1990                1995

Met Leu Asp Phe Asn Arg Glu Gly Leu Pro Leu Phe Ile Leu Ala
    2000                2005                2010

Asn Trp Arg Gly Phe Ser Gly Gly Gln Arg Asp Leu Phe Glu Gly
    2015                2020                2025

Ile Leu Gln Ala Gly Ser Thr Ile Val Glu Asn Leu Arg Thr Tyr
    2030                2035                2040

Asn Gln Pro Ala Phe Val Tyr Ile Pro Lys Ala Ala Glu Leu Arg
    2045                2050                2055

Gly Gly Ala Trp Val Val Ile Asp Ser Lys Ile Asn Pro Asp Arg
    2060                2065                2070

Ile Glu Phe Tyr Ala Glu Arg Thr Ala Lys Gly Asn Val Leu Glu
    2075                2080                2085

Pro Gln Gly Leu Ile Glu Ile Lys Phe Arg Ser Glu Glu Leu Gln
    2090                2095                2100

Glu Cys Met Gly Arg Leu Asp Pro Glu Leu Ile Asn Leu Lys Ala
    2105                2110                2115

Lys Leu Leu Gly Ala Lys His Glu Asn Gly Ser Leu Ser Glu Ser
    2120                2125                2130

Glu Ser Leu Gln Lys Ser Ile Glu Ala Arg Lys Lys Gln Leu Leu
    2135                2140                2145

Pro Leu Tyr Thr Gln Ile Ala Val Arg Phe Ala Glu Leu His Asp
    2150                2155                2160

Thr Ser Leu Arg Met Ala Ala Lys Gly Val Ile Lys Lys Val Val
    2165                2170                2175

Asp Trp Glu Asp Ser Arg Ser Phe Phe Tyr Lys Arg Leu Arg Arg
    2180                2185                2190

Arg Ile Ser Glu Asp Val Leu Ala Lys Glu Ile Arg Gly Val Ser
    2195                2200                2205

Gly Lys Gln Phe Ser His Gln Ser Ala Ile Glu Leu Ile Gln Lys
    2210                2215                2220

Trp Tyr Leu Ala Ser Lys Gly Ala Glu Thr Gly Asn Thr Glu Trp
    2225                2230                2235

Asp Asp Asp Asp Ala Phe Val Ala Trp Arg Glu Asn Pro Glu Asn
    2240                2245                2250

Tyr Gln Glu Tyr Ile Lys Glu Leu Arg Ala Gln Arg Val Ser Gln
    2255                2260                2265

Leu Leu Ser Asp Val Ala Asp Ser Ser Pro Asp Leu Glu Ala Leu
    2270                2275                2280

Pro Gln Gly Leu Ser Met Leu Leu Glu Lys Met Asp Pro Ser Arg
    2285                2290                2295

Arg Ala Gln Phe Val Glu Glu Val Lys Lys Ala Leu Lys
    2300                2305                2310
```